United States Patent
Korber et al.

(10) Patent No.: US 11,773,144 B2
(45) Date of Patent: Oct. 3, 2023

(54) MOSAIC HIV-1 ENVELOPES TO INDUCE ADCC RESPONSES

(71) Applicants: DUKE UNIVERSITY, Durham, NC (US); LOS ALAMOS NATIONAL SECURITY, LLC, Los Alamos, NM (US)

(72) Inventors: Bette Korber, Los Alamos, NM (US); Sandrasegaram Gnanakaran, Los Alamos, NM (US); Guido Ferrari, Durham, NC (US); Barton F. Haynes, Durham, NC (US)

(73) Assignees: DUKE UNIVERSITY, Durham, NC (US); LOS ALAMOS NATIONAL SECURITY, LLC, Los Alamos, NM (US)

( * ) Notice: Subject to any disclaimer, the term of this patent is extended or adjusted under 35 U.S.C. 154(b) by 0 days.

(21) Appl. No.: 16/753,303

(22) PCT Filed: Oct. 2, 2018

(86) PCT No.: PCT/US2018/053994
§ 371 (c)(1),
(2) Date: Apr. 2, 2020

(87) PCT Pub. No.: WO2019/070730
PCT Pub. Date: Apr. 11, 2019

(65) Prior Publication Data
US 2021/0139544 A1    May 13, 2021

Related U.S. Application Data

(60) Provisional application No. 62/566,928, filed on Oct. 2, 2017, provisional application No. 62/672,158, filed on May 16, 2018.

(51) Int. Cl.
C07K 14/16  (2006.01)
A61K 39/12  (2006.01)
A61K 39/00  (2006.01)

(52) U.S. Cl.
CPC ............ C07K 14/162 (2013.01); A61K 39/12 (2013.01); A61K 2039/53 (2013.01); A61K 2039/70 (2013.01)

(58) Field of Classification Search
None
See application file for complete search history.

(56) References Cited

U.S. PATENT DOCUMENTS

2009/0286852 A1   11/2009   Katalin et al.
2010/0080818 A1    4/2010   Quinnan, Jr. et al.
(Continued)

FOREIGN PATENT DOCUMENTS

WO   WO2013006688 A2    1/2013
WO   WO2015164674 A1   10/2015

OTHER PUBLICATIONS

Acharya, Priyamvada, et al. "Structural definition of an antibody-dependent cellular cytotoxicity response implicated in reduced risk for HIV-1 infection." Journal of virology 88.21 (2014): 12895-12906.
(Continued)

*Primary Examiner* — Shanon A. Foley
(74) *Attorney, Agent, or Firm* — Baker Donelson

(57) ABSTRACT

The invention is directed to mosaic HIV-1 envelopes, and methods of using the same to induce ADCC responses.

15 Claims, 124 Drawing Sheets

Specification includes a Sequence Listing.

| SEQ ID | HV Number | Protein Name | SEQ ID NO without signal peptide |
|---|---|---|---|
| 1. | HV1301523 | ADCC-StrMos.B.1+1.1Δ11gp120 | 12 |
| 2. | HV1301524 | ADCC-StrMos.B.1+1.2delta11gp120 | 13 |
| 3. | HV1301525 | ADCC-StrNat.B1delta11gp120 | 14 |
| 4. | HV1301529 | ADCC-StrNat.B5delta11gp120 | 15 |
| 5. | HV1301526_CD5ss | ADCC-StrNat.B2delta11gp120_CD5ss | 16 |
| 6. | HV1301527 | ADCC-StrNat.B3delta11gp120 | 17 |
| 7. | HV1301528 | ADCC-StrNat.B4delta11gp120 | 18 |
| 8. | HV1301536 | ADCC-StrMos.M.3+2.4 | 19 |
| 9. | HV1301537_TPAss | ADCC-StrMos.M.3+2.5_TPAss | 20 |
| 10. | HV1301532_TPAss | ADCC.StrMos.C.1+1.1delta11gp120_TPAss | 21 |
| 11. | HV1301534 | ADCC.StrMos.AE.1+1.1delta11gp120 | 22 |

Signal sequences in red/underlined. Provided are also SEQ ID Nos. without the signal peptide: SEQ ID Nos. 12-22 in order of appearance.

>HV1301523

MRVKGIRKNYQHLWRWGTMLLGMLMICSAVPVWKEATTTLFCASDAKAYDTEVHNVWATHACVPTDPNPQ
EVVLENVTENFNMWKNNMVEQMHEDIISLWDQSLKPCVKLTPLCVTLNCTDVSSNSTSVNITSEKGEIKN
CSFNITTSIRDKVQKEYALFYKLDVVPIEDDSRNNSYRLISCNTSVITQACPKVSFEPIPIHYCAPAGFA
ILKCNDKKFNGTGPCTNVSTVQCTHGIRPVVSTQLLLNGSLAEEEVVIRSENFTNNAKTIIVQLNESVEI
NCTRPNNNTRKSIHIGPGRAFYATGDIIGDIRQAHCNISREKWNNTLKQIVKKLREQFGNKTIVFNQSSG
GDPEIVMHSFNCGGEFFYCNTTQLFNSTWSINGTWNGTTESNDTITLPCRIKQIINMWQEVGKAMYAPPI
RGQIRCSSNITGLLLTRDGGNSSNNETFRPGGGDMRDNWRSELYKYKVVKIEPLGVAPTKAKERVVQRE
KE.

(56) References Cited

U.S. PATENT DOCUMENTS

| | | | |
|---|---|---|---|
| 2013/0111615 A1 | 5/2013 | Katalin et al. | |
| 2013/0197068 A1 | 8/2013 | Katalin et al. | |
| 2013/0261172 A1 | 10/2013 | Katalin et al. | |
| 2014/0248311 A1 | 9/2014 | Kim et al. | |
| 2015/0038558 A1 | 2/2015 | Katalin et al. | |
| 2016/0032316 A1 | 2/2016 | Weissman et al. | |
| 2016/0339051 A1 | 11/2016 | Haynes et al. | |
| 2017/0043037 A1 | 2/2017 | Katalin et al. | |
| 2017/0327842 A1 | 11/2017 | Weissman et al. | |
| 2017/0369532 A1 | 12/2017 | Carfi et al. | |
| 2018/0028645 A1 | 2/2018 | Ciaramella et al. | |
| 2021/0139544 A1* | 5/2021 | Korber | C07K 16/1063 |

OTHER PUBLICATIONS

Alam, S. Munir, et al. "Human immunodeficiency virus type 1 gp41 antibodies that mask membrane proximal region epitopes: antibody binding kinetics, induction, and potential for regulation in acute infection." Journal of virology 82.1 (2008): 115-125.

Alam, S. Munir, et al. "Role of HIV membrane in neutralization by two broadly neutralizing antibodies." Proceedings of the National Academy of Sciences 106.48 (2009): 20234-20239.

Alam, S. Munir, et al. "The role of antibody polyspecificity and lipid reactivity in binding of broadly neutralizing anti-HIV-1 envelope human monoclonal antibodies 2F5 and 4E10 to glycoprotein 41 membrane proximal envelope epitopes." The Journal of Immunology 178.7 (2007): 4424-4435.

Alving, Carl R., et al. "Adjuvants for human vaccines." Current opinion in immunology 24.3 (2012): 310-315.

Amaoty, Ahmed, et al. "Novel approach for the development of new antibodies directed against transposase-derived proteins encoded by human neogenes." Mobile Genetic Elements. Humana Press, 2012. 293-305.

Amaoty, Ahmed, et al. "Reliability of the nanopheres-DNA immunization technology to produce polyclonal antibodies directed against human neogenic proteins." Molecular genetics and genomics 288.7 (2013): 347-363.

Barouch, Dan H., et al. "Mosaic HIV-1 vaccines expand the breadth and depth of cellular immune responses in rhesus monkeys." Nature medicine 16.3 (2010): 319-323.

Binley, James M., et al. "Enhancing the proteolytic maturation of human immunodeficiency virus type 1 envelope glycoproteins " Journal of virology 76.6 (2002): 2606-2616.

Bosch, Valerie, and M. Pawlita. "Mutational analysis of the human immunodeficiency virus type 1 env gene product proteolytic cleavage site." Journal of virology 64.5 (1990): 2337-2344.

Bradley, Todd, et al. "Pentavalent HIV-1 vaccine protects against simian-human immunodeficiency virus challenge." Nature communications 8.1 (2017): 1-15.

Cany, Jeannette, et al. "AFP-specific immunotherapy impairs growth of autochthonous hepatocellular carcinoma in mice." Journal of hepatology 54.1 (2011): 115-121.

Chakrabarti, Bimal K., et al. "Modifications of the human immunodeficiency virus envelope glycoprotein enhance immunogenicity for genetic immunization." Journal of virology 76.11 (2002): 5357-5368.

Churchyard, Gavin J., et al. "A phase IIA randomized clinical trial of a multiclade HIV-1 DNA prime followed by a multiclade rAd5 HIV-1 vaccine boost in healthy adults (HVTN204)." PloS one 6.8 (2011): e21225.

Dennison, S. Moses, et al. "Induction of antibodies in rhesus macaques that recognize a fusion-intermediate conformation of HIV-1 gp41" PloS one 6.11 (2011): e27824.

Dennison, S. Moses, et al. "Stable docking of neutralizing human immunodeficiency virus type 1 gp41 membrane-proximal external region monoclonal antibodies 2F5 and 4E10 is dependent on the membrane immersion depth of their epitope regions." Journal of virology 83.19 (2009): 10211-10223.

Gao, Feng, et al. "Antigenicity and immunogenicity of a synthetic human immunodeficiency virus type 1 group m consensus envelope glycoprotein." Journal of virology 79.2 (2005): 1154-1163.

Gohain, Neelakshi, et al. "Cocrystal structures of antibody N60-i3 and antibody JR4 in complex with gp120 define more cluster A epitopes involved in effective antibody-dependent effector function against HIV-1." Journal of virology 89.17 (2015): 8840-8854.

Guo, Hong-Guang, et al. "Characterization of an HIV-1 point mutant blocked in envelope glycoprotein cleavage." Virology 174.1 (1990): 217-224.

IAS presentation on Jul. 24, 2017 in Paris, France, entitled "Evaluation of lead HIV-1 vaccine regimen in APPROACH: Phase 1/2a study testing heterologous prime boost regimens using mosaic Ad26 and MVA vectors combined with Env protein" and an IAS presentation on Jul. 25, 2017 entitled The Ad26/Ad26+gp140 HIV Vaccine Regimen Provided Significant Protection against SHIV Challenges in NHP sn62p3 (study 13-19*).

International search report for PCT/US2018/053994 dated Jan. 4, 2019.

Li, Yan, et al. "Control of expression, glycosylation, and secretion of HIV-1 gp120 by homologous and heterologous signal sequences." Virology 204.1 (1994): 266-278.

Li, Yan, et al. "Effects of inefficient cleavage of the signal sequence of HIV-1 gp 120 on its association with calnexin, folding, and intracellular transport." Proceedings of the National Academy of Sciences 93.18 (1996): 9606-9611.

Liao, Hua-Xin, et al. "A group M consensus envelope glycoprotein induces antibodies that neutralize subsets of subtype B and C HIV-1 primary viruses." Virology 353.2 (2006): 268-282.

Liao, Hua-Xin, et al. "Antigenicity and immunogenicity of transmitted/founder, consensus, and chronic envelope glycoproteins of human immunodeficiency virus type 1." Journal of virology 87.8 (2013): 4185-4201.

McCune, Joseph M., et al. "Endoproteolytic cleavage of gp160 is required for the activation of human immunodeficiency virus." Cell 53.1 (1988): 55-67.

Moody, M. Anthony, et al. "Toll-like receptor 7/8 (TLR7/8) and TLR9 agonists cooperate to enhance HIV-1 envelope antibody responses in rhesus macaques " Journal of virology 88.6 (2014): 3329-3339.

Pardi, Norbert, et al. "Zika virus protection by a single low-dose nucleoside-modified mRNA vaccination " Nature 543.7644 (2017): 248-251.

Pollara, Justin, et al. "HIV-1 vaccine-induced C1 and V2 Env-specific antibodies synergize for increased antiviral activities." Journal of virology 88.14 (2014): 7715-7726.

Prévost, Jérémie, et al. "Influence of the envelope gp120 Phe 43 cavity on HIV-1 sensitivity to antibody-dependent cell-mediated cytotoxicity responses." Journal of virology 91.7 (2017): e02452-16.

Santra, Sampa, et al. "Mosaic vaccines elicit CD8+ T lymphocyte responses that confer enhanced immune coverage of diverse HIV strains in monkeys." Nature medicine 16.3 (2010): 324-328.

Tolbert, William D., et al. "Paring down HIV Env: design and crystal structure of a stabilized inner domain of HIV-1 gp120 displaying a major ADCC target of the A32 region." Structure 24.5 (2016): 697-709.

Written Opinion of the ISA for PCT/US2018/053994 dated Jan. 4, 2019.

Yu, Jae-Sung, et al. "Recombinant Mycobacterium bovis bacillus Calmette-Guerin elicits human immunodeficiency virus type 1 envelope-specific T lymphocytes at mucosal sites." Clinical and Vaccine Immunology 14.7 (2007) 886-893.

* cited by examiner

| SEQ ID | HV Number | Protein Name | SEQ ID NO without signal peptide |
|---|---|---|---|
| 1. | HV1301523 | ADCC-StrMos.B.1+1.1 Δ 11gp120 | 12 |
| 2. | HV1301524 | ADCC-StrMos.B.1+1.2delta11gp120 | 13 |
| 3. | HV1301525 | ADCC-StrNat.B1delta11gp120 | 14 |
| 4. | HV1301529 | ADCC-StrNat.B5delta11gp120 | 15 |
| 5. | HV1301526_CD5ss | ADCC-StrNat.B2delta11gp120_CD5ss | 16 |
| 6. | HV1301527 | ADCC-StrNat.B3delta11gp120 | 17 |
| 7. | HV1301528 | ADCC-StrNat.B4delta11gp120 | 18 |
| 8. | HV1301536 | ADCC-StrMos.M.3+2.4 | 19 |
| 9. | HV1301537_TPAss | ADCC-StrMos.M.3+2.5_TPAss | 20 |
| 10. | HV1301532_TPAss | ADCC.StrMos.C.1+1.1delta11gp120_TPAss | 21 |
| 11. | HV1301534 | ADCC.StrMos.AE.1+1.1delta11gp120 | 22 |

Signal sequences in red/underlined. Provided are also SEQ ID Nos. without the signal peptide: SEQ ID Nos. 12-22 in order of appearance.

>HV1301523

MRVKGIRKNYQHLWRWGTMLLGMLMICSAVPVWKEATTTLFCASDAKAYDTEVHNVWATHACVPTDPNPQ
EVVLENVTENFNMWKNNMVEQMHEDIISLWDQSLKPCVKLTPLCVTLNCTDVSSNSTSVNITSEKGEIKN
CSFNITTSIRDKVQKEYALFYKLDVVPIEDDSRNNSYRLISCNTSVITQACPKVSFEPIPIHYCAPAGFA
ILKCNDKKFNGTGPCTNVSTVQCTHGIRPVVSTQLLLNGSLAEEEVVIRSENFTNNAKTIIVQLNESVEI
NCTRPNNNTRKSIHIGPGRAFYATGDIIGDIRQAHCNISREKWNNTLKQIVKKLREQFGNKTIVFNQSSG
GDPEIVMHSFNCGGEFFYCNTTQLFNSTWSINGTWNGTTESNDTITLPCRIKQIINMWQEVGKAMYAPPI
RGQIRCSSNITGLLLTRDGGNSSSNNETFRPGGGDMRDNWRSELYKYKVVKIEPLGVAPTKAKERVVQRE
KE.

MKVKGIRKNCQHLWRWGIMLLGMLMICSAVPVWKEATTTLFCASDAKAYDTEAHNVWATHACVPTDPNPQ
EIVLENVTENFNMWKNDMVEQMHEDIISLWDESLKPCVELTPLCVTLNCTNVNATNTNNSSGIEGGEMKN
CSFNVTTSIRDKMQKEYALFYSLDVVQIDNDTNYRLINCNTSVITQACPKISFEPIPIHYCTPAGFAILK
CNDKKFNGSGPCKNVSTVQCTHGIKPVVSTQLLLNGSLAEEEIVIRSENFSDNAKTIIVQLNESVVINCT
RPNNNTRKSISIGPGRAFYATGDIIGNIRQAHCNLSRAEWNNTLRQIVTKLREQFKNKTIAFNHSSGGDP
EIVMHTFNCGGEFFYCNSTQLFNSTWIANKTGNDTGGSNGTITLQCRIKQIVNRWQEVGKAMYAPPISGQ
ISCSSNITGLILTRDGGTNNTNGTEIFRPGGGNMKDNWRSELYKYKVVRIEPLGIAPTKARERVVQREKE

MKAKETRKNYQHLWRWGITLLGMLMICSAVPVWKEATTTLFCASDAKAYDTEVHNVWATHACVPTDPNPQ
EVVLENVTENFNMWKNNMVEQMHEDIISLWDQSLKPCVKLTPLCVTLNCTDDLKNATVKNATNTNNSSWG
GMERGEIKNCSFNITTSIRDKVQKEYALFYKLDVVPIDNADNNNITTNYTSYRLISCNTSVITQACPKVS
FEPIPIHYCAPAGFAILKCNDKKFNGTGPCTNVSTVQCTHGIRPVVSTQLLLNGSLAEKEVVIRSENFTN
NAKTIIVQLDESVVINCTRPNNNTRKSIHIGPGRAFYTTGEIIGDIRQAHCTLNRTEWNNTLAKITEKLR
EQFGNNITIVFNHSSGGDPEIVMHSFICGGEFFYCNTSQLFNSTWNSTGNNISESDNTERNITLPCRIKQ
IINLWQEVGKAMYAPPIRGQIRCSSNITGLLLTRDGGSNTDENRTEIFRPGGGDMRDNWRSELYKYKVVK
IEPLGVAPTKAKERVVQREKE.

MRAKETRKKYQHLWAWGTLLLGMLMICSAVPVWKDANTTLFCASDAKAYDTEVHNVWATHACVPTDPSPQ
EIVLKNVTENFNMWKNNMVEQMHKDIISLWDESLKPCVKLTPLCVTLNCSNYNSTNSTIDPNMEGAIKNC
SFNATTGIQNKMKKEYALFYSLDIVQIESENKSNKSYMLRSCNTSVITQACPKVTFEPIPIHYCAPAGFA
ILKCNDKKFNGTGPCKNVSTVQCTHGIRPVVSTQLLLNGSLAEEETIIRSENITNNAKTIIIQLNRSIEI
NCTRPNNNTRKSIHMGWGRAFYATGDIIGDIRQAHCNLSGTKWNNTLYQIARKLREHFNNTIVFNQSSGG
DPEIVMHTFNCGGEFFYCNTTQLFNSTWHANSTWNETTGSGSNDTISLPCRIKQIINRWQEVGKAMYAPP
IGGQIRCSSNITGILLTRDGGTENNTSETFRPGGGNMKDNWRSELYKYKVVRIEPLGVAPTKAKERVVQR
EKE.

MPMGSLQPLATLYLLGMLVASCLGVPVWKEATTTLFCASDAKAYDTEVHNVWATHACVPTDPNPQEVVLG
NVTENFNMWKNNMVEQMHEDVISLWDQSLKPCVKLTPLCVTLNCTDVLGKGTSANATSANVTSEKGEIKN
CSFNITTTLRDKVQKAHALFYRLDVVPIDDNNDNSSSSYRLINCNTSVITQACPKVSFEPIPIHFCTPAG
FALLKCNNKKFNGTGPCTNVSTVQCTHGIKPVVSTQLLLNGSLAEEEVVIRSENFTDNAKTIIVQLNDSV
VINCTRPNNNTRKGITIGPGSVFYTGEIIGDIRQAHCNLSSAKWNNTLKQIVIKLREQFGNKTIVFNQSS
GGDPEIVLHSFNCGGEFFYCNTTQLFNSTWNINDTRNGTTESSKTITLPCRIKQIINMWQEVGKAMYAPP
IRGQIRCSSNITGLLLTRDGGNQNTSGTEIFRPGGGNMRDNWRSELYKYKVVKIEPLGIAPTKAKERVVQ
REKE.

MRVKGIRKNCQHLWRWGTMLLGMLMICSAVPVWKEATTTLFCASDAKAYDTEAHNVWATHACVPTDPNPQ
EVVLGNVTENFNMWKNDMVEQMHEDIISLWDQSLKPCVKLTPICVALNCTDVKDTNNTSNNTNNTSSNNS
SMTEGGEMKNCSFNITTSIKTKVKDYALFYKLDIVPIDNDGDNTSYRLISCNTSVITQACPKISFEPIPI
HYCTPAGYALLKCNNKKFNGTGPCKNVSTVQCTHGIRPVVSTQLLLNGSLAEEEVVIRSSNFTNNAKVII
VQLKEAVEINCTRPNNNTRKSIHIGPGKAWYTTGEIIGNIRQAHCNISRTKWNNTLHQIVKKLRIQFGNK
TIIFNQSAGGDPEIVVHSFNCGGEFFYCNTSQLFNSTWRNDTWNDTSPQIATTGNDTITLPCRIRQIVNM
WQQVGKAMYAPPIAGQIRCSSNITGVLLTRDGGNNESKANANETFRPAGGDMRDNWRSELYKYKVVKIEP
LGVAPTKAKERVVQREKE.

MKVKGIRKNYQHLWRWGNMLLGMLMICSAVPVWRDATTTLFCASDAKAYETELHNVWATHACVPTDPNPQ
EVVLGNVTENFNMWKNDMVEQMNEDIISLWDESLKPCVKLTPLCVTLNCTNYNETTTNSTTTNATVVSPG
EIKNCSFNVTTGIRDKVRKDHALFYALDIVPIDNTIDNTSYRLVSCNTSVLTQACPKVSFEPIPIHFCAP
AGYAIIKCNNKTFNGSGPCRNVSTVQCTHGIRPVVSTQLLLNGSLAEEEIVIRSANFSDNTKTIIVQLNE
AVKINCTRPNNNTRRSVHMGPGSAFYTTGGIIGDIRQAHCNISERDWNGALKQIVEKLGEQFQNKTIVFK
QSSGGDPEVVMHTFNCRGEFFYCNTTKLFNSTWVNGTKNDTKGGNGTITLQCRIKQIINMWQQVGKAMYA
PPISGPISCSSNITGLILTRDGGTNTTNETFRPGGDMRDNWRSELYKYKVVKIEPIGVAPTKARERVVQ
REKE.

Fig. 1G

\>HV1301536
MRVMGIQRNCQHLWRWGIMLLGMLMICNAVPVWRDAETTLFCASDAKGYDTEAHNVWATHACVPTDPSPQ
EIHLENVTEEFNMWKNNMVEQMHTDIISLWDQSLKPCVKLTPLCVTLDCTLDCNNVTNNGTSDMREEIKN
CSFNITTELRDKKKKVYSLFYKLDIVPINGDNSTNTYMLINCNTSAITQACPKVTFEPIPIHFCAPAGYA
ILKCKDKEFNGTGPCKNVSTVQCTHGIKPVVSTQLLLNGSLAEEEIMIRSENITNNAKIIIVQLNQSVVI
NCTRPGNNTRKSVRIGPGQTFYATGDIIGDIRQAHCNVSRIKWNTALQKVAKQLRKYFRNKTITFNQSSG
GDPEITTHTFNCGGEFFYCNTSNLFNSTWGNGNGTDNMQGSNSTNITLQCRIKQIINMWQEVGRAIYAPP
IEGNISCSSNITGLLLTRDGGNSKNSTTEEIFRPGGGNMRDNWRSELYKYKVVKIEPIGVAPTKARERVV
EREKE.

Fig. 1H

>HV1301537_TPAss

MDAMKRGLCCVLLLCGAVFVSPVPVWREANTTLFCASDAKAYDTEVHNIWATHACVPTDPNPQEIVLGNV
TENFNMWKNNMVDQMHEDVISLWDESLKPCVKLTPLCVTLECNDAKLNSTKTNSTTNSTDPNNSNLGIEG
EIKNCSFNTTTEIRDKKKRAYALFYRPDVVPLNENSSSYILINCNSSTITQACPKVSFEPIPIHYCTPAG
FALLKCNNKTFNGSGPCTNVSTVQCTHGIRPVVSTQLLLNGSLAEEEIVIRSENFTDNAKTIIVQLNESV
EINCTRPNNNTRKSIRIGPGQAFYATGEIIGNIRQAYCNINESLWNETLYKVSEKLKEYFNTTIEFQQPA
GGDLEITTHSFNCRGEFFYCNTTKLFNGTYSQPNSTGNTPHSNITLPCKIKQIINMWQGVGRAMYAPPIA
GNITCISNITGLILTRDGGDKNGSKPEIFRPGGGNMKDNWRSELYKYKVVEIKPLGLAPTEAKREVVERE
KE.

Fig. 1I

>HV1301532_TPAss

MDAMKRGLCCVLLLCGAVFVSPVPVWKEAKTTLFCASDAKAYEKEVHNVWATHACVPTDPNPQEMVLENV
TENFNMWKNDMVDQMHEDIISLWDQSLKPCVKLTPLCVTLNCVNITNSTTSNGDGTVTHINSIKEEIKNC
SFNATTELRDKKSKEYALFYRLDIVPLSSGNSSSNSSKYRLINCNTSTITQACPKVSFDPIPIHYCAPAG
YAILKCNNKTFNGTGPCNNVSTVQCTHGIKPVVSTQLLLNGSLAEEEIIIRSENLTDNVKTIIVHLNESV
EIVCTRPNNNTRKSIRIGPGQTFYATGDIIGDIRQAHCNISKGAWNETLQWVGKKLKEHFPNKTIKFNSS
SGGDLEITTHSFNCRGEFFYCNTSGLFNSTYRNNSTGDNSTITLPCRIKQIINMWQEVGRAMYAPPIAGN
ITCKSNITGLLLTRDGGTRDRNDTETFRPGGGDMRDNWRSELYKYKVVEIKPLGIAPTKAKERVVEREKE
.

MRVKETQMNWPNLWKWGTLILGLVIICSAVPVWRDADTTLFCASDAKAHETEVHNVWATHACVPTDPNPQEIHLE
NVTENFNMWKNNMVEQMQEDVISLWDQSLKPCVKLTPLCVTLNCTKANLTNINETTASNGIGNITDEVRNCSFNMT
TELRDKKQKVHALFYKLDIVPIRNESKMGNVSSEYRLINCNTSVIKQACPKISFDPIPIHYCTPAGYAILKCNDKNFNGTGP
CKNVSSVQCTHGIKPVVSTQLLLNGSLAEEEIIRSENLTNNAKTIIVHLNKSVEINCTRPSNNTRTSITIGPGQVFYRTGDII
GDIRKAYCEINGTKWNETLKQVAGKLKEHFNKTIIFQPPSGGDLEITMHHFNCRGEFFYCNTTKLFNSTWNGTMEGRN
GTIILPCRIKQIINMWQGVGQAMYAPPISGIINCVSNITGILLTRDGGNNNATNETFRPGGGNIKDNWRSELYKYKVVQI
EPLGIAPTRAKERVVEREKE.

Fig. 1K

>ADCC-StrMos.B.1+1.1

MRVKGIRKNYQHLWRWGTMLLGMLMICSAAEQLWVTVYYGVPVWKEATTTLFCASDAKAYDTEVHNVWATHACV
PTDPNPQEVVLENVTENFNMWKNDMVEQMHEDIISLWDQSLKPCVKLTPLCVTLNCTDVSSNSTSVNITSEKG
EIKNCSFNITTSIRDKVQKEYALFYKLDVVPIEDDSRNNSYRLISCNTSVITQACPKVSFEPIPIHYCAPAGF
AILKCNDKKFNGTGPCTNVSTVQCTHGIRPVVSTQLLLNGSLAEEEVVIRSENFTNNAKTIIVQLNESVEINCT
RPNNNTRKSIHIGPGRAFYATGDIIGDIRQAHCNISREKWNNTLKQIVKKLREQFGNKTIVFNQSSGGDPEIVM
HSFNCGGEFFYCNTTQLFNSTWSINGTWNGTTESNDTITLPCRIKQIINMWQEVGKAMYAPPIRGQIRCSSNIT
GLLLTRDGGNSSSNNETFRPGGGDMRDNWRSELYKYKVVKIEPLGVAPTKAKRRVVQREKR

Fig. 2A

>ADCC-StrMos.B.1+1.2

MKVKGIRKNCQHLWRWGIMLLGMLMICSATEKLWVTVYYGVPVWKEATTTLFCASDAKAYDTEAHNVWATHACV
PTDPNPQEIVLENVTENFNMWKNDMVEQMHEDIISLWDESLKPCVELTPLCVTLNCTNVNATNTNNSSGIEGGE
MKNCSFNVTTSIRDKMQKEYALFYSLDVVQIDNDTNYRLINCNTSVITQACPKISFEPIPIHYCTPAGFAIIKC
NDKKFNGSGPCKNVSTVQCTEGIKPVVSTQLLLNGSLAEEEIVIRSENFSDNAKTIIVQLNESVVINCTRPNNN
TRKSISIGPGRAFYATGDIIGNIRQAHCNLSRAEWNNTLRQIVTKLREQFKNKTIAFNHSSGGDPEIVMHTFNC
GGEFFYCNSTQLFNSTWIANKTGNDTGGSNGTITLQCRIKQIVNRWQEVGKAMYAPPISGQISCSSNITGLILT
RDGGTNNTNGTEIFRPGGGNMKDNWRSELYKYKVVRIEPLGIAPTKARRRVVQREKR

Fig. 2B

>ADCC-StrNat.B1

MKAKETRKNYQHLWRWGITLLGMLMICSAAEQLWVTVYYGVPVWKEATTTLFCASDAKAYDTEVHNVWAT
HACVPTDPNPQEVVLENVTENFNMWKNNMVEQMHEDIISLWDQSLKPCVKLTPLCVTLNCTDDLKNATVK
NATNTNNSSWGGMERGEIKNCSFNITTSIRDKVQKEYALFYKLDVVPIDNADNNIPTNYTSYRLISCNT
SVITQACPKVSFEPIPIHYCAPAGFAILKCNDKKFNGTGPCTNVSTVQCTHGIRPVVSTQLLLNGSLAEK
EVVIRSENFTNNAKTIIVQLDESVVINCTRPNNNTRKSIHIGPGRAFYTTGEIIGDIRQAHCTLNRTEWN
NTLAKITEKLREQFGNNITIVFNHSSGGDPEIVMHSFICGGEFFYCNTSQLFNSTWNSTGNNISESDNTE
RNITLPCRIKQIINLWQEVGKAMYAPPIRGQIRCSSNITGLLLTRDGGSNTDENRTEIFRPGGGDMRDNW
RSELYKYKVVKIEPLGVAPTKAKRRVVQREKR

Fig. 2C

\>ADCC-StrNat.B2

MRVKETRRIWQHLWKWGTMLLGMLMIYSAAENLWVTVYYGVPVWKEATTTLFCASDAKAYDTEVHNVWAT
HACVPTDPNPQEVVLGNVTENFNMWKNNMVEQMHEDVISLWDQSLKPCVKLTPLCVTLNCTDVLGKGTSA
NATSANVTSEKGEIKNCSFNITTTLRDKVQKAHALFYRLDVVPIDNNNONSSSSYRLINCNTSVITQACP
KVSFEPIPIHFCTPAGFALLKCNNKKFNGTGPCTNVSTVQCTHGIKPVVSTQLLLNGSLAEEEVVIRSEN
FTDNAKTIIVQLNDSVVINCTRPNNNTRKGITIGPGSVFYTGEIIGDIRQAHCNLSSAKWNNTLKQIVIK
LREQFGNKTIVFNQSSGGDPEIVLHSFNCGGEFFYCNTTQLFNSTWNINDTKNGTFESSKTITLPCRIKQ
IINMWQEVGKAMYAPPIRGQIRCSSNITGLLLTRDGGWQNTSGTEIFRPGGGNMRDNWRSELYKYKVVKI
EPLGIAPTKAKRRVVQREKR

Fig. 2D

\>ADCC-StrNat.B3

MRVKGIRKNCQHLWRWGTMLLGMLMICSAAENLWVTVYYGVPVWKEATTTLFCASDAKAYDTEAHNVWATHACV
PTDPNPQEVVLGNVTENFNMWKNDMVEQMHEDIISLWDQSLKPCVKLTPICVALNCTDVKDTNNTSNNTNNTRS
NNSSMTRGGEMKNCSFNITTSIKTKVKDYALFYKLDIVPIDNDGUNTSYRLISCNTSVITQACPKISFEPIPIH
YCTPAGYALLKCNNKKFNGTGPCKNVSTVQCTHGIRPVVSTQLLLNGSLAEEEVVIRSSNFTNNAKVIIVQLKE
AVEINCTRPNNNTRKSIHIGPGKAWYTTGEIIGNIRQAHCNISRTKWNNTLHQIVKKLRIQFGNKTIIFNQSAG
GDPEIVVHSFNCGGEFFYCNTSQLFNSTWRNDTWNOTSPQIATTGNDTITLPCRIRQIVNMWQQVGKAMYAPPI
AGQIRCSSNITGVLLTRDGGNDESKANANETFRPAGGDMRDNWRSELYKYKVVKIEPLGVAPTKAKRRVVQREK
R

Fig. 2E

\>ADCC-StrNat.B4

MKVKGIRKNYQHLWRWGMMLLGMLMICSATEKLWVTVYYGVPVWRDATTTLFCASDAKAYETELHNVWATHACV
PTDPNPQEVVLGNVTENFNMWKNDMVEQMNEDIISLWDESLKPCVKLTPLCVTLNCTNYMETTTNSTTTNATVV
SPGEIKNCSFNVTTGIRDKVRKDHALFYALDIVPIDNTIDNTSYRLVSCNTSVLTQACPKVSFEPIPIHFCAPA
GYAIIKCNNKTFNGSGPCRNVSTVQCTHGIRPVVSTQLLLNGSLAEEEIVIRSANFSDNTKTIIVQLNEAVKIN
CTRPNNNTRRSVHMGPGSAFYTTGGIIGDIRQAHCNISERDWNGALKQIVEKLGEQFQNKTIVFKQSSGGDPEV
VMHTFNCPGEFFYCNTTKLFNSTWVNGTKNDTKGGNGTITLQCRIKQIINMWQQVGKAMYAPPISGPISCSSNI
TGLILTRDGGTNTTNETFRPGGGDMRDNWRSELYKYKVVKIEPIGVAPTKARRRVVQREKR

Fig. 2F

>ADCC-StrNat.B5

MRAKETRKKYQHLWAWGTLLLGMLMICSATEQLWVTVYYGVPVWKDANTTLFCASDAKAYDTEVHNVWATHA
CVPTDPSPQEIVLKNVTENFNMWKNNMVEQMHKDIISLWDESLKPCVKLTPLCVTLNCSNYNSTNSTIDPNMEG
AIKNCSFNATTGIQNKMKKEYALFYSLDIVQIESSNKSNKSYMLRSCNTSVITQACPKVTFEPIPIHYCAPAGF
AILKCNDKKFNGTGPCKNVSTVQCTHGIRPVVSTQLLLNGSLAEEEIIRSENITNNAKTIIIQLNRSIEINCT
RPNNNTRKSIHMGWGRAFYATGDIIGDIRQAHCNLSGTKWNNTLYQIARKLREHFNNTIVFNQSSGGDPEIVMH
TFNCGGEFFYCNTTQLFNSTWBANSTWNETTGSGSNDTTISLPCRIKQIINRWQEVGKAMYAPPIGGQIRCSSNI
TGILLTRDGGTSNNTSETFRPGGGNMKDNWRSELYKYKVVRIEPLGVAPTKAKRRVVQREKR

Fig. 2G

>ADCC-StrMos-Modified.B.1+1.1

MRVKGIRKNYQHLWRWGTMLLGMLMICSAAEQLWVTVYYGVPVWKEATTTLFCASDAKANDTEVHNVWATHACV
PTDPNPQEVVLENVTENFNMWKNNMVEQMQEDVISLWDQSLKPCVKLTPLCVTLNCTDVSSNSTSVNITSEKG
EIKNCSFNVTTSIKDKVQKEYALFYKLDVVPIEDDSRNNSYRLISCNTSVITQACPKVSFEPIPIHYCTPAGF
AILKCNDKKFNGTGPCTNVSTVQCTHGIRPVVSTQLLLNGSLAEEEVVIRSENFTNNAKTIIVQLNESVEINCT
RPNNNTRKSIHIGPGRAFYATGDIIGDIRQAHCNISREKWNNTLKQIVKKLREQFGNKTIVFNQSSGGDPEIVM
HSFNCGGEFFYCNTTQLFNSTWSINGTWNGTTRSNDTITLPCRIKQIINMWQEVGKAMYAPPIRGQIPCSSNIT
GLLLTRDGGNSSSNNETFRPGGGDMRDNWRSELYKYKVVKIEPLGVAPTKAKRRVVQREKR

Fig. 2H

>ADCC-StrMos-Modified.B.1+1.2

MKVKGIRKNCQHLWRWGIMLLGMLMICSATEKLWVTVYYGVPVWKEATTTLFCASDAKANDTEAHNVWATHACV
PTDPNPQEIVLENVTENFNMWKNDMVEQMQEDVISLWDESLKPCVELTPLCVTLNCTNVNATNTNNSSGIEGGE
MKNCSFNVTTSIKDKMQKEYALFYSLDVVQIDNDTNYRLINCNTSVITQACPKISFEPIPIHYCTPAGFAIIKC
NDKKFNGSGPCKNVSTVQCTHGIKPVVSTQLLLNGSLAEEEIVIRSENFSDNAKTIIVQLNESVVINCTRPNNN
TRKSISIGPGRAFYATGDIIGNIRQAHCNLSRAKWNNTLPQIVTKLREQFKNKTIAFNHSSGGDPEIVMHTFNC
GGEFFYCNSTQLFNSTWIANKTGNDTGSSNGTITLQCRIKQIVNRWQEVGKAMYAPPISGQISCSSNITGLILT
RDGGTNNTNGTEIFRPGGGNMKDNWRSELYKYKVVRIEPLGIAPTKARRRVVQREKR

Fig. 2I

>ADCC.StrMos.C.1+1.1

MRVRGILRNYQQWWIWGILGFWMLMICNVVGNLWVTVYYGVPVWKEAKTTLFCASDAKAYEKEVHNVWAT
HACVPTDPNPQEMVLENVTENFNMWKNDMVDQMHEDIISLWDQSLKPCVKLTPLCVTLNCVNITNSTTSN
GDGTVTNINSIKEEIKNCSFNATTELRDKKSKEYALFYRLDIVPLSSGNSSSNSSKYRLINCNTSTITQA
CPKVSFDPIPIHYCAPAGYAILKCNNKTFNGTGPCNNVSTVQCTHGIKPVVSTQLLLNGSLAEEEIIIRS
ENLTDNVKTIIVHLNESVEIVCTRPNNNTRKSIRIGPGQTFYATGDIIGDIRQAHCNISKGAWNETLQWV
GKKLKEHFPNKTIKFNSSSGGDLEITTHSFNCRGEFFYCNTSGLFNSTYRNNSTGDNSTITLPCRIKQII
NMWQEVGRAMYAPPIAGNITCKSNITGLLLTRDGGTRDRNDTETFRPGGGDMRDNWRSELYKYKVVEIKP
LGIAPTKAKRRVVEREKR

Fig. 2J

>ADCC.StrMos.C.1+1.2

MRVMGIQRNWPQWWIWGILGFWMIIICRVVGNLWVTVYYGVPVWREAKTTLFCASDAKAYEREVHNVWAT
HACVPTDPNPQELVLENVTENFNMWENDMVDQMHEDVISLWDQSLKPCVKLTPLCVTLKCTNTTYYNVSS
NEFTNGEIKNCSFNTTTELRDKKQKVSALFYRLDVVPLSKKDKTNNDSGEYILINCNTSAITQACPKVSF
DPIPIHYCTPAGYAILKCNNKTFNGTGPCHNVSTVQCTHGIKPVVSTQLLLNGSLTEGEIIIRSENLTNN
AKTIIVHLNQSVAIVCTRPGNNTRKSVRIGPGQAFYATGEIIGDIRQAYCNLTNWQETLKNVSKKLQERF
NKTIRFAPSSGGDLEITTHSFNCGGEFFYCNTSSLFNSAYNPNGTKDNSNSSITIQCKIKQIINMWQGVGR
AIYAPPIAGNITCNSNITGILLTRDGGSKNNTREIFRPGGGNMKDNWRSELYRYKVVEIKPLGVAPTEAK
RRVVEREKR

Fig. 2K

>ADCC.StrMos.AE.1+1.1

MRVKETQMNWPNLWKWGTLILGLVIICSASDNLWVTVYYGVPVWRDADTTLFCASDAKAHETEVHNVWAT
HACVPTDPNPQEIHLENVTENFNMWKNNMVEQMQEDVISLWDQSLKPCVKLTPLCVTLNCTKANLTNINS
TTASNGIGNITDEVRNCSFNMTTELRDKKQKVHALFYKLDIVPIRNESKNNVSSEYRLINCNTSVIKQA
CPKISFDPIPIHYCTPAGYAILKCNDKNFNGTGPCKNVSSVQCTHGIKPVVSTQLLLNGSLAEEEIIIRS
ENLTNNAKTIIVHLNKSVEINCTRPSNNTRTSITIGPGQVFYRTGDIIGDIRKAYCEINGTKWNETLKQV
AGKLKEHFNKTIIFQPPSGGDLEITMHHFNCRGEFFYCNTTKLFNSTWNGTNEGRNGTIILPCRIKQIIN
MWQGVGQAMYAPPISGIINCVSNITGILLTRDGGNNNATNETFRPGGGNIKDNWRSELYKYKVVQIEPLG
IAPTRAKRRVVEREKR

Fig. 2L

\>ADCC.StrMos.AE.1+1.2

MRVKGTQMNWPNLWRWGTLILGLVIMCSASDNLWVTVYYGVPVWKDADTTLFCASDAKAHETEVHNIWAT
HACVPTDPNPQEIPLENVTENFNMWKNNMAEQMQEDVISLWDESLKPCVKLTPLCVTLHCTNANLTNNTT
NDKNGTGNITDEVKIGNITDEVKNCSFNMTTEIRDKKQKVYALFYKLDIVQIGENGSEYRLINCNTSVIK
QACPKVSFDPIPIHYCAPAGYALLKCNDKKFNGTGPCRNVSSVQCTHGIKPVVSTQLLLNGSLAEEEIII
RSENLTDNAKTIIVHLNESVVINCTRPSNNVRISTRIGPGQVFYRTGEIIGDIRKAYCEINGTKWNKVLK
EVTEKLKEHFNKTIIFQPPSGGDLEITTHHFNCRGEFFYCNTTKLFNNTCNGTNEGWCNNITLPCKIKQI
INMWQGAGQAIYAPPISGSIKCVSNITGIILTRDGGNDTGTSEIFRPGGGNMKDNWRNELYKYKVVQIEP
LGVAPTKAKRRVVDREKR

Fig. 2M

\>ADCC.StrMos.C.1+1.1

MRVRGILRNYQQWWIWGILGFWMLMICNVVGNLWVTVYYGVPVWKEAKTTLFCASDAKAYEKEVHNVWAT
HACVPTDPNPQEMVLENVTENFNMWKNDMVDQMHEDIISLWDQSLKPCVKLTPLCVTLNCVNITNSTTSN
GDGTVTNINSIKEEIKNCSFNATTELRDKKSKEYALFYRLDIVPLSSGNSSSNSSKYRLINCNTSTITQA
CPKVSFDPIPIHYCAPAGYAILKCNNKTFNGTGPCNNVSTVQCTHGIKPVVSTQLLLNGSLAEEEIIRS
ENLTDNVKTIIVHLNESVEIVCTRPNNNTRKSIRIGPGQTFYATGDIIGDIRQAHCNISKGAWNETLQWV
GKKLKEHFPNKTIKFNSSSGGDLEITTHSFNCRGEFFYCNTSGLFNSTYNNSTGDNSTITLPCRIKQII
NMWQEVGRAMYAPPIAGNITCKSNITGLLLTRDGGTRDRNDTETFRPGGGDMRDNWRSELYKYKVVEIKP
LGIAPTKAKRRVVEREKR

Fig. 2N

\>ADCC.StrMos.C.1+1.2

MRVMGIQRNWPQWWIWGILGFWMIIICRVVGNLWVTVYYGVPVWREAKTTLFCASDAKAYEREVHNVWAT
HACVPTDPNPQELVLENVTENFNMWENDMVDQMHEDVISLWDQSLKPCVKLTPLCVTLKCTNTTYNVSS
KRPTNGEIKNCSFNTTTELRDKKQKVSALFYRLDVVPLSKKDKTNNDSGEYILINCNTSAITQACPKVSF
DPIPIHYCTPAGYAILKCNNKTFNGTGPCHNVSTVQCTHGIKPVVSTQLLLNGSLTEGEIIIRSENLTNN
AKTIIVHLNQSVAIVCTRPGNNTRKSVRIGPGQAFYATGEIIGDIRQAYCNLTNWQETLKNVSKKLQERF
NKTIRFAPSSGGDLEITTHSFNCGGEFFYCNTSSLFNSAYNPNSTKDNSNSSITIQCKIKQIINMWQGVGR
AIYAPPIAGNITCNSNITGILLTRDGGSKNNTREIFRPGGGNMKDNWRSELYRYKVVEIKPLGVAPTEAK
RRVVEREKR

Fig. 2O

>ADCC.StrMos.AE.1+1.1

MRVKETQMNWPNLWKWGTLILGLVIICSASDNLWVTVYYGVPVWRDADTTLFCASDAKAHETEVHNVWAT
HACVPTDPNPQEIHLENVTENFNMWKNNMVEQMQEDVISLWDQSLKPCVKLTPLCVTLNCTKANLTNINE
TTASNGIGNITDEVRNCSFNMTTELRDKKQKVHALFYKLDIVPIRNESKNGNVSSEYRLINCNTSVIKQA
CPKISFDPIPIHYCTPAGYAILKCNDKNFNGTGPCKNVSSVQCTHGIKPVVSTQLLLNGSLAEEEIIIRS
ENLTNNAKTIIVHLNKSVEINCTRPSNNTRTSITIGPGQVFYRTGDIIGDIRKAYCEINGTKWNETLKQV
AGKLKEHFNKTIIFQPPSGGDLEITMHHFNCRGEFFYCNTTKLFNSTWNGTMEGRNGTIILPCRIKQIIN
MWQGVGQAMYAPPISGIINCVSNITGILLTRDGGNNATNETFRPGGGNIKDNWRSELYKYKVVQIEPLG
IAPTRAKRRVVEREKR

Fig. 2P

>ADCC.StrMos.AE.1+1.2

MRVKGTQMNWPNLWRWGTLILGLVIMCSASDNLWVTVYYGVPVWKDADTTLFCASDAKAHETEVHNIWAT
HACVPTDPNPQEIPLENVTENFNMWKNNMAEQMQEDVISLWDESLKPCVKLTPLCVTLHCTKANLTNNTT
NDKNSTGNITDEVKIGNITDEVKNCSFNMTTEIRDKKQKVYALFYKLDIVQIGENGSEYRLINCNTSVIK
QACPKVSFDPIPIHYCAPAGYALLKCNDKKFNGTGPCRNVSSVQCTHGIKPVVSTQLLLNGSLAEEEIII
RSENLTDNAKTIIVHLNESVVINCTRPSNNVRISTRIGPGQVFYRTGEIIGDIRKAYCEINGTKWNKVLK
EVTEKLKEHFNKTIIFQPPSGGDLEITTHHFNCRGEFFYCNTTKLFNNTCNGTMEGPCNNITLPCKIKQI
INMWQGAGQAIYAPPISGSIKCVSNITGIILTRDGGNDTGTSEIFRPGGGNMKDNWRNELYKYKVVQIEP
LGVAPTKAKRRVVDREKR

Fig. 2Q

>ADCC-StrMos.M.3+2.4

MRVMGIQRNCQHLWRWGIMLLGMLMICNATDKLWVTVYYGVPVWRDAETTLFCASDAKGYDTEAHNVWAT
HACVPTDPSPQEIHLENVTEEFNMWKNNMVEQMHTDIISLWDQSLKPCVKLTPLCVTLDCTLDCNNVTNN
GTSDNREEIKNCSFNITTELRDKKKKVYSLFYKLDIVPINGDNSTNTYMLINCNTSAITQACPKVTFEPI
PIHFCAPAGYAILKCKDKEFNGTGPCKNVSTVQCTHGIKPVVSTQLLLNGSLAEEEIMIRSENITNNAKI
IIVQLNQSVVINCTRPGNNTRKSVRIGPGQTFYATGDIIGDIRQAHCNVSRIKWNTALQKVAKQLRKYFR
NKTITFNQSSGGDPEITTHTFNCGGEFFYCNTSNLFNSTWGNGNGTDNNQGSNSTNITLQCRIKQIINMW
QEVGRAIYAPPIEGNISCSSNITGLLLTRDGGNSKNSTTSEIFRPGGGNMRDNWRSELYKYKVVKIEPIG
VAPTKARRRVVEREKRI

Fig. 2R

```
>ADCC-StrMos.M.3+2.5
```

MKVKGIQRNWPQWWIWGILGFWMLMICNVGGNLWVTVYYGVPVWREANTTLFCASDAKAYDTEVHNIWAT
HACVPTDPNPQEIVLGNVTENFNMWKNNMVDQMHEDVISLWDESLKPCVKLTPLCVTLECNDAKLNSTRT
NSTTNSTDPNNSNLGIEGEIKNCSFNTTTEIRDKKKRAYALFYRPDVVPLNKNSSSYILINCNSSTITQA
CPKVSFEPIPIHYCTPAGFALLKCNNKTFNGSGPCTNVSTVQCTHGIRPVVSTQLLLNGSLAEEEIVIRS
ENFTDNAKTIIVQLNESVEINCTRPNNNTRKSIRIGPGQAFYATGEIIGNIRQAYCNINESLWNETLYKV
SEKLKEYFNTTIEFQQPAGGDLEITTHSFNCRGEFFYCNTTKLFNGTYSQPNSTGNTPHSNITLPCKIKQI
INMWQGVGRAMYAPPIAGNITCISNITGLILTRDGGDKNGSKPEIFRPGGGNMKDNWRSELYKYKVVEIKP
LGLAPTEAKRRVVEREKRA

Fig. 2S

>ADCC-StrMos.B.1+1.1

MRVKGIRKNYQHLWRWGTMLLGMLMICSAAEQLWVTVYYGVPVWKEATTTLFCASDAKAYDTEVHNVWATHACV
PTDPNPQEVVLENVTENFNMWKNNMVEQMHEDIISLWDQSLKPCVKLTPLCVTLNCTDVSSNSTSVNITSEKG
EIKNCSFNITTSIRDKVQKEYALFYKLDVVPIEDDSNNSYRLISCNTSVITQACPKVSFEPIPIHYCAPAGF
AILKCNDKKFNGTGPCTNVSTVQCTHGIRPVVSTQLLLNGSLAEEEVVIRSENFTNNAKTIIVQLNESVEINCT
RPNNNTRKSIHIGPGRAFYATGDIIGDIRQAHCNISREKWNNTLKQIVKKLREQFGNKTIVFNQSSGGDPEIVM
HSFNCGGEFFYCNTTQLFNSTWSINGTWNGTTESNDTITLPCRIKQIINMWQEVGKAMYAPPIRGQIRCSSNIT
GLLLTRDGGNSSNNETFRPGGGDMRDNWRSELYKYKVVKIEPLGVAPTKAKRRVVQREKR

Fig. 3A

>ADCC-StrMos.B.1+1.2

MKVKGIRKNCQHLWRWGIMLLGMLMICSATEKLWVTVYYGVPVWKEATTTLFCASDAKAYDTEAHNVWATHACV
PTDPNPQEIVLENVTENFNMWKNDMVEQMHEDIISLWDESLKPCVELTPLCVTLNCTNVNATNTNNSSGIEGGE
MKNCSFNVTTSIRDKMQKEYALFYSLDVVQIDNDTNYRLINCNTSVITQACPKISFEPIPIHYCTPAGFAIIKC
NDKKFNGSGPCKNVSTVQCTHGIKPVVSTQLLLNGSLAEEEIVIRSENFSDNAKTIIVQLNESVVINCTRPNNN
TRKSISIGPGRAFYATGDIIGNIRQAHCNLSRAEWNNTLRQIVTELREQFKNKTIAFNHSSGGDPEIVMHTFNC
GGEFFYCNSTQLFNSTWIANKTGNDTGGSNGTITLQCRIKQIVNRWQEVGKAMYAPPISGQISCSSNITGLILT
RDGGTNNTNGTEIFRPGGGNMKDNWRSELYKYKVVRIEPLGIAPTKARRRVVQREKR

Fig. 3B

>ADCC-StrNat.B1

MKAKETRKNYQHLWRWGITLLGMLMICSAAEQLWVTVYYGVPVWKEATTTLFCASDAKAYDTEVHNVWAT
HACVPTDPNPQEVVLENVTENFNMWKNNMVEQMHEDIISLWDQSLKPCVKLTPLCVTLNCTDDLKNATVK
NATNTNNSSWGGMERGEIKNCSFNITTSIRDKVQKEYALFYKLDVVPIDNADNNNITTNYTSYRLISCNT
SVITQACPKVSFEPIPIHYCAPAGFAILKCNDKKFNGTGPCTNVSTVQCTHGIRPVVSTQLLLNGSLAEK
EVVIRSENFTNNAKTIIVQLDESVVINCTRPNNNTRKSIHIGPGRAFYTTGEIIGDIRQAHCTLNRTEWN
NTLAKITEKLREQFGNNITIVFNHSSGGDPEIVMHSFICGGEFFYCNTSQLFNSTWNSTGNNISESDNTE
RNITLPCRIKQIINLWQEVGKAMYAPPIRGQIRCSSNITGLLLTRDGGSNTDRNRTEIFRPGGGDMRDNW
RSELYKYKVVKIEPLGVAPTKAKRRVVQREKR

Fig. 3C

>ADCC-StrNat.B2

MRVKETRRIWQHLWKWGTMLLGMLMIYSAAENLWVTVYYGVPVWKEATTTLFCASDAKAYDTEVHNVWAT
HACVPTDPNPQEVVLGNVTENFNMWKNNMVEQMHEDVISLWDQSLKPCVKLTPLCVTLNCTDVLGKGTSA
NATSANVTSEKGEIKNCSFNITTTLRDKVQKAHALFYRLDVVPIDNNNONSSSSYRLINCNTSVITQACP
KVSFEPIPIHFCTPAGFALLKCNNKKFNGTGPCTNVSTVQCTHGIKPVVSTQLLLNGSLAEEEVVIRSEN
FTDNAKTIIVQLNDSVVINCTRPNNNTRKGITIGPGSVFYTGEIIGDIRQAHCNLSSAKWNNTLKQIVIK
LREQFGNKTIVFNQSSGGDPEIVLHSFNCGGEFFYCNTTQLFNSTWNINDTRNGTTESSKTITLPCRIKQ
IINMWQEVGKAMYAPPIRGQIRCSSNITGLLLTRDGGWQNFSGTEIFRPGGGNMRDNWRSELYKYKVVKI
EPLGIAPTKAKRRVVQREKR

Fig. 3D

>ADCC-StrNat.B3

MRVKGIRKNCQHLWRWGTMLLGMLMICSAAENLWVTVYYGVPVWKEATTTLFCASDAKAYDTEAHNVWATHACV
PTDPNPQEVVLGNVTENFNMWKNDMVEQMHEDIISLWDQSLKPCVKLTPICVALNCTDVRDTNNTSNNTNNTSS
NNSSMTEGGEMKNCSFNITTSIKTKVKDYALFYKLDIVPIDNDGDNTSYRLISCNTSVITQACPKISFEPIPIH
YCTPAGYALLKCNNKKFNGTGPCKNVSTVQCTHGIRPVVSTQLLLNGSLAEEEVVIRSSNFTNNAKVIIVQLKE
AVEINCTRPNNNTRKSIHIGPGKAWYTTGEIIGNIRQAHCNISRTKWNNTLHQIVKKLRIQFGNKTIIFNQSAG
GDPEIVVHSFNCGGEFFYCNTSQLFNSTWRNDTWNGTSPQIATTGNDTITLPCRIRQIVNMWQQVGKAMYAPPI
AGQIRCSSNITGVLLTRDGGNNESKANANETFRPAGGDMRDNWRSELYKYKVVKIEPLGVAPTKAKRRVVQREK
R

Fig. 3E

>ADCC-StrNat.B4

MKVKGIRKNYQHLWRWGMMLLGMLMICSAAEKLWVTVYYGVPVWRDATTTLFCASDAKAYETELHNVWATHACV
PTDPNPQEVVLGNVTENFNMWKNDMVEQMNEDIISLWDESLKPCVKLTPLCVTLNCTNYNETTTNSTTTNATVV
SPGEIKNCSFNVTTGIRDKVRKDHALFYALDIVPIDNTIDNTSYRLVSCNTSVLTQACPKVSFEPIPIHFCAPA
GYAIIKCNNKTFNGSGPCRNVSTVQCTHGIRPVVSTQLLLNGSLAEEEIVIRSANFSDNTKTIIVQLNEAVKIN
CTRPNNNTRRSVHMGPGSAFYTTGGIIGDIRQAHCNISERDWNGALKQIVEKLGEQFQNKTIVFKQSSGGDPEV
VMHTFNCRGEFFYCNTTKLFNSTWVNGTKNDTKGGNGTITLQCRIKQIINMWQQVGKAMYAPPISGPISCSSNI
TGLILTRDGGTNTTNETFRPGGGDMRDNWRSELYKYKVVKIEPIGVAPTKARRRVVQREKR

Fig. 3F

>ADCC-StrNat.B5

MRAKETRKKYQHLWRWGTLLLGMLMICSATEQLWVTVYYGVPVWKDANTTLFCASDAKAYDTEVHNVWATHA
CVPTDPSPQEIVLKNVTENFNMWKNNMVEQMHKDIISLWDESLKPCVKLTPLCVTLNCSNYNSTNSTIDPNMEG
AIKNCSFNATTGIQNKMKKEYALFYSLDIVQIESSNKSNKSYMLRSCNTSVITQACPKVTFEPIPIHYCAPAGF
AILKCNDKKFNGTGPCKNVSTVQCTHGIRPVVSTQLLLNGSLAEEEIIIRSENITNNAKTIIIQLNRSIEINCT
RPNNNTRKSIHMGWGRAFYATGDIIGDIRQAHCNLSGTKWNNTLYQIARKLREHFNNTIVFNQSSGGDPEIVMH
TFNCGGEFFYCNTTQLFNSTWSANSTWNETTGSGSNDTTSLPCRIKQIINRWQEVGKAMYAPPIGGQIRCSSNI
TGILLTRDGGTNNNTSETFRPGGGNMKDNWRSELYKYKVVRIEPLGVAPTKAKRRVVQREKR

Fig. 3G

>ADCC-StrMos-Modified.B.1+1.1

MRVKGIRKNYQHLWRWGTMLLGMLMICSAAEQLWVTVYYGVPVWKEATTTLFCASDAKANDTEVHNVWATHACV
PTDPNPQEVVLENVTENFNMWKNNMVEQMQEDVISLWDQSLKPCVKLTPLCVTLNCTDVSSNSTSVNITSEKG
EIKNCSFNVTTSIKDKVQKEYALFYKLDVVPIEDDSRNNSYRLISCNTSVITQACPKVSFEPIPIHYCTPAGF
AILKCNDKKFNGTGPCTNVSTVQCTHGIRPVVSTQLLLNGSLAEEEVVIRSENFTNNAKTIIVQLNESVEINCT
RPNNNTRKSIHIGPGRAFYATGDIIGDIRQAHCNISREKWNNTLKQIVKKLREQFGNKTIVFNQSSGGDPEIVM
HSFNCGGEFFYCNTTQLFNSTWSINGTWNGTTESNDTITLPCRIKQIINMWQEVGKAMYAPPIRGQIPCSSNIT
GLLLTRDGGNSSNWETFRPGGGDMRDNWRSELYKYKVVKIEPLGVAPTKAKRRVVQREKR

Fig. 3H

>ADCC-StrMos-Modified.B.1+1.2

MKVKGIRKNCQHLWRWGIMLLGMLMICSATEKLWVTVYYGVPVWKEATTTLFCASDAKANDTEAHNVWATHACV
PTDPNPQEIVLENVTENFNMWKNDMVEQMQEDVISLWDESLKPCVELTPLCVTLNCTNVNATNTNNSSGIEGGE
MKNCSFNVTTSIKDKMQKEYALFYSLDVVQIDNDTNYRLINCNTSVITQACPKISFEPIPIHYCTPAGFAIIKC
NDKKFNGSGPCKNVSTVQCTSGIKPVVSTQLLLNGSLAEEEIVIRSENFSDNAKTIIVQLNESVVINCTRPNNN
TRKSISIGPGRAFYATGDIIGNIRQAHCNLSRAKWNNTLRQIVTKLREQFKNKTIAFNHSSGGDPEIVMHTFNC
GGEFFYCNSTQLFNSTWIANKTGNDTGGSNGTITLQCRIKQIVNRWQEVGKAMYAPPISGQISCSSNITGLILT
RDGGTNNTNGTEIFRPGGGNMKDNWRSELYKYKVVRIEPLGIAPTKARRRVVQREKR

Fig. 3I

>ADCC.StrMos.C.1+1.1

MRVRGILRNYQQWWIWGILGFWMLMICNVVGNLWVTVYYGVPVWKEAKTTLFCASDAKAYEKEVHNVWAT
HACVPTDPNPQEMVLENVTENFNMWKNDMVDQMHEDIISLWDQSLKPCVKLTPLCVTLNCVNITNSTTSN
GDGTVTNINSIKEEIKNCSFNATTELRDKKSKEYALFYRLDIVPLSSGNSSSNSSKYRLINCNTSTITQA
CPKVSFDPIPIHYCAPAGYAILKCNNKTFNGTGPCNNVSTVQCTHGIKPVVSTQLLLNGSLAEEEIIIRS
ENLTDNVKTIIVHLNESVEIVCTRPNNNTRKSIRIGPGQTFYATGDIIGDIRQAHCNISKGAWNETLQWV
GKKLKEHFPNKTIKFNSSSGGDLEITTHSFNCRGEFFYCNTSGLFNSTYRNNSTGDNSTITLPCRIKQII
NMWQEVGRAMYAPPIAGNITCKSNITGLLLTRDGGTRDKNDTETFRPGGGDMRDNWRSELYKYKVVEIKP
LGIAPTKAKRRVVEREKR

Fig. 3J

>ADCC.StrMos.C.1+1.2

MRVMGIQRNWPQWWIWGILGFWMIIICRVVGNLWVTVYYGVPVWREAKTTLFCASDAKAYEREVHNVWAT
HACVPTDPNPQELVLENVTENFNMWENDMVDQMHEDVISLWDQSLKPCVKLTPLCVTLKCTNTTYYNVSS
KFTNGEIKNCSFNTTTELRDKKQKVSALFYRLDVVPLSKKDKTNNDSGEYILINCNTSAITQACPKVSF
DPIPIHYCTPAGYAILKCNNKTFNGTGPCHNVSTVQCTHGIKPVVSTQLLLNGSLTEGEIIIRSENLTNN
AKTIIVHLNQSVAIVCTRPGNNTRKSVRIGPGQAFYATGEIIGDIRQAYCNLTNWQETLKNVSKKLQERF
NKTIRFAPSSGGDLEITTHSFNCGGEFFYCNTSSLFNSAYNPNGTKDNSNSSITIQCKIKQIINMWQGVGR
AIYAPPIAGNITCNSNITGILLTRDGGSKNNTREIFRPGGGNMKDNWRSELYRYKVVEIKPLGVAPTEAK
RRVVEREKR

Fig. 3K

>ADCC.StrMos.AE.1+1.1

MRVKETQMNWPNLWKWGTLILGLVIICSASDNLWVTVYYGVPVWRDADTTLFCASDAKAHETEVHNVWAT
HACVPTDPNPQEIHLENVTENFNMWKNNMVEQMQEDVISLWDQSLKPCVKLTPLCVTLNCTANLTNINS
TTASNGIGNITDEVRNCSFNMTTELRDKKQKVHALFYKLDIVPIRNESKNVSSEYRLINCNTSVIKQA
CPKISFDPIPIHYCTPAGYAILKCNDKNFNGTGPCKNVSSVQCTHGIKPVVSTQLLLNGSLAEEEIIIRS
ENLTNNAKTIIVHLNKSVEINCTRPSNNTRTSITIGPGQVFYRTGDIIGDIRKAYCEINGTKWNETLKQV
AGKLKEHFNKTIIFQPPSSGGDLEITMHHFNCRGEFFYCNTTKLFNSTWNGTMSGRNGTIILPCRIKQIIN
MWQGVGQAMYAPPISGIINCVSNITGILLTRDGGNNNATNETFRPGGGNIKDNWRSELYKYKVVQIEPLG
IAPTRAKRRVVEREKR

Fig. 3L

>ADCC.StrMos.AE.1+1.2

MRVKGTQMNWPNLWRWGTLILGLVIMCSASDNLWVTVYYGVPVWKDADTTLFCASDAKAHETEVHNIWAT
HACVPTDPNPQEIPLENVTENFNMWKNNMAEQMQEDVISLWDESLKPCVKLTPLCVTLHCTNANLTNNTT
NDKNGTGNITDEVKIGNITDEVKNCSFNMTTEIRDKKQKVYALFYKLDIVQIGENGSEYRLINCNTSVIK
QACPKVSFDPIPIHYCAPAGYALLKCNDKKFNGTPCRNVSSVQCTHGIKPVVSTQLLLNGSLAEEEIII
RSENLTDNAKTIIVHLNESVVINCTRPSNNVRISTRIGPGQVFYRTGEIIGDIRKAYCEINGTKWNKVLK
EVTEKLKEHFNKTIIFQPPSGGDLEITTHHFNCRGEFFYCNTTKLFNNTCNGTNEGPCNNITLPCKIKQI
INMWQGAGQAIYAPPISGSIKCVSNITGIILTRDGGNDTGTSEIFRPGGGNMKDNWRNELYKYKVVQIEP
LGVAPTKAKRRVVDREKR

Fig. 3M

>ADCC.StrMos.C.1+1.1

MRVRGILRNYQQWWIWGILGFWMLMICNVVGNLWVTVYYGVPVWKEAKTTLFCASDAKAYEKEVHNVWAT
HACVPTDPNPQEMVLENVTENFNMWKNDMVDQMHEDIISLWDQSLKPCVKLTPLCVTLNCVNITNSTTSN
GDGTVTNINSIKEEIKNCSFNATTELRDKKSKEYALFYRLDIVPLSSGNSSSNSSKYRLINCNTSTITQA
CPKVSFDPIPIHYCAPAGYAILKCNNKTFNGTGPCNNVSTVQCTHGIKPVVSTQLLLNGSLAEEEIIRS
ENLTDNVKTIIVHLNESVEIVCTRPNNNTRKSIRIGPGQTFYATGDIIGDIRQAHCNISKGAWNETLQWV
GKKLKEHFPNKTIKFNSSSGGDLEITTHSFNCRGEFFYCNTSGLFNSTYRNNSTGDNSTITLPCRIKQII
NMWQEVGRAMYAPPIAGNITCKSNITGLLLTRDGGTRDRNDTETFRPGGGDMRDNWRSELYKYKVVEIKP
LGIAPTKAKRRVVEREKR

Fig. 3N

>ADCC.StrMos.C.1+1.2

MRVMGIQRNWPQWWIWGILGFWMIIICRVVGNLWVTVYYGVPVWREAKTTLFCASDAKAYEREVHNVWAT
HACVPTDPNPQELVLENVTENFNMWENDMVDQMHEDVISLWDQSLKPCVKLTPLCVTLKCTNTTYYNVSS
KRPTNGEIKNCSFNTTTELRDKKQKVSALFYRLDVVPLSKKDKTNNDSGEYILINCNTSAITQACPKVSF
DPIPIHYCTPAGYAILKCNNKTFNGTGPCHNVSTVQCTHGIKPVVSTQLLLNGSLTEGEIIIRSENLTNN
AKTIIVHLNQSVAIVCTRPGNNTRKSVRIGPGQAFYATGEIIGDIRQAYCNLTNWQETLKNVSKKLQERF
NKTIRFAPSSGGDLEITTHSFNCGGEFFYCNTSSLFNSAYNPNSTKDNSNSSITIQCKIKQIINMWQGVGR
AIYAPPIAGNITCNSNITGILLTRDGGSKNNTREIFRPGGGNMKDNWRSELYRYKVVEIKPLGVAPTEAK
RRVVEREKR

Fig. 3O

>ADCC.StrMos.AE.1+1.1

MRVKETQMNWPNLWKWGTLILGLVIICSASDNLWVTVYYGVPVWRDADTTLFCASDAKAHETEVHNVWAT
HACVPTDPNPQEIHLENVTENFNMWKNNMVEQMQEDVISLWDQSLKPCVKLTPLCVTLNCTKANLTNINE
TTASNGIGNITDEVRNCSFNMTTELRDKKQKVHALFYKLDIVPIRNESNMGNVSSEYRLINCNTSVIKQA
CPKISFDPIPIHYCTPAGYAILKCNDKNFNGTGPCKNVSSVQCTHGIKPVVSTQLLLNGSLAEEEIIIRS
ENLTNNAKTIIVHLNKSVEINCTRPSNNTRTSITIGPGQVFYRTGDIIGDIRKAYCEINGTKWNETLKQV
AGKLKEHFNKTIIFQPPSGGDLEITMHHFNCRGEFFYCNTTKLFNSTWNGTMEGRNGTIILPCRIKQIIN
MWQGVGQAMYAPPISGIINCVSNITGILLTRDGGNNNATNETFRPGGGNIKDNWRSELYKYKVVQIEPLG
IAPTRAKRRVVEREKR

Fig. 3P

>ADCC.StrMos.AE.1+1.2

MRVKGTQMNWPNLWRWGTLILGLVIMCSASDNLWVTVYYGVPVWKDADTTLFCASDAKAHETEVHNIWAT
HACVPTDPNPQEIPLENVTENFNMWKNNMAEQMQEDVISLWDESLKPCVKLTPLCVTLHCTKANLTNNTT
NDKNSTGNITDEVKIGNITDEVKNCSFNMTTEIRDKKQKVYALFYKLDIVQIGENGSEYRLINCNTSVIK
QACPKVSFDPIPIHYCAPAGYALLKCNDKKFNGTGPCRNVSSVQCTHGIKPVVSTQLLLNGSLAEEEIII
RSENLTDNAKTIIVHLNESVVINCTRPSNNVRISTRIGPGQVFYRTGEIIGDIRKAYCEINGTKWNKVLK
EVTEKLKEHFNKTIIFQPPSGGDLEITTHHFNCRGEFFYCNTTKLFNNTCNGTMEGFCNNITLPCKIKQI
INMWQGAGQAIYAPPISGSIKCVSNITGIILTRDGGNDTQTSEIFRPGGGNMKDNWRNELYKYKVVQIEP
LGVAPTKAKRRVVDREKR

Fig. 3Q

>ADCC-StrMos.M.3+2.4

MRVMGIQRNCQHLWRWGIMLLGMLMICNATDKLWVTVYYGVPVWRDAETTLFCASDAKGYDTEAHNVWAT
HACVPTDPSPQEIHLENVTEEFNMWKNNMVEQMHTDIISLWDQSLKPCVKLTPLCVTLDCTLDCNNVTNN
GTSDMREEIKNCSFNITTELRDKKKVYSLFYKLDIVPINGDNSTNTYMLINCNTSAITQACPKVTFEPI
PIHFCAPAGYAILKCKDKEFNGTGPCKNVSTVQCTHGIKPVVSTQLLLNGSLAEEEIMIRSENITNNAKI
IIVQLNQSVVINCTRPGNNTRKSVRIGPGQTFYATGDIIGDIRQAHCNVSRIKWNTALQKVAKQLRKYFR
NKTITFNQSSGGDPEITTHTFNCGGEFFYCNTSNLFNSTWGNGNGTDNNQGSNSTNITLQCRIKQIINMW
QEVGRAIYAPPIEGNISCSSNITGLLLTRDGGNSKNSTTEEIFRPGGGNMRDNWRSELYKYKVVKIEPIG
VAPTKARRRVVEREKR

Fig. 3R

>ADCC-StrMos.M.3+2.5

MKVKGIQRNWPQWWIWGILGFWMLMICNVGGNLWVTVYYGVPVWREANTTLFCASDAKAYDTEVHNIWAT
HACVPTDPNPQEIVLGNVTENFNMWKNNMVDQMHEDVISLWDESLKPCVKLTPLCVTLECNDAKLNSTKT
NSTTNSTDPNNSNLGIEGEIKNCSFNTTTEIRDKKKRAYALFYRPDVVPLNNSSSYILINCNSSTITQA
CPKVSFEPIPIHYCTPAGFALLKCNNKTFNGSGPCTNVSTVQCTHGIRPVVSTQLLLNGSLAEEEIVIRS
ENFTDNAKTIIVQLNESVEINCTRPNNNTRKSIRIGPGQAFYATGEIIGNIRQAYCNINESLWNETLYKV
SEKLKEYFNTTIEFQQPAGGDLEITTHSFNCRGEFFYCNPTKLFNGTYSQPNSTGNTPHSNITLPCKIKQI
INMWQGVGRAMYAPPIAGNITCTSNITGLILTRDGGDNNGSKPEIFRPGGGNMKDNWRSELYKYKVVEIKP
LGLAPTEAKRRVVEREKR

Fig. 3S

**To DELETE the N-terminus

Mutate furin cleavage site (in the first two sequences the mutated residues are underlined—in the rest of the sequences the "E"s are readily identifiable

\>ADCC-StrMos.B.1+1.1deltallgp120

MRVKGIRKNYQHLWRWGTMLLGMLMICSAVPVWKEATTTLFCASDAKAYDTEVHNVWATHACVPTDPNPQEVVL
ENVTENFNMWKNNMVEQMHEDIISLWDQSLKPCVKLTPLCVTLNCTDVSSNSTSVNTTSEKGEIKNCSFNITT
SIRDKVQKEYALFYKLDVVPIEDDSRNNSYRLISCNTSVITQACPKVSFEPIPIHYCAPAGFAILKCNDKKFN
GTGPCTNVSTVQCTHGIRPVVSTQLLLNGSLAEEEVVIRSENFTNNAKTIIVQLNESVEINCTRPNNNTRKSIH
IGPGRAFYATGDIIGDIRQAHCNISREKWNNTLKQIVKKLREQFGNKTIVFNQSSGGDPEIVMHSFNCGGEFFY
CNTTQLFNSTWSINGTWNGTTESNDTITLPCRIKQIINMWQEVGKAMYAPPIRGQIRCSSNITGLLLTRDGGNS
SSNNETFRPGGGDMRDNWRSELYKYKVVKIEPLGVAPTKAKERVVQREKE

Fig. 4A

\>ADCC-StrMos.B.1+1.2deltallgp120

MKVKGIRKNCQHLWRWGIMLLGMLMICSAVPVWKEATTTLFCASDAKAYDTEAHNVWATHACVPTDPNPQEIVL
ENVTENFNMWKNDMVEQMHEDIISLWDESLKPCVELTPLCVTLNCTNVNATNTNNSSGIEGGEMKNCSFNVTTS
IRDKMQKEYALFYSLDVVQIDNDTNYRLINCNTSVITQACPKISFEPIPIHYCTPAGFAIIKCNDKKFNGSGPC
KNVSTVQCTHGIKPVVSTQLLLNGSLAEEEIVIRSENFSDNAKTIIVQLNESVVINCTRPNNNTRKSISIGPGR
AFYATGDIIGNIRQAHCNLSRAEWNNTLRQIVTKLREQFKNKTIAFNESSGGDPEIVMHTFNCGGEFFYCNSTQ
LFNSTWIANKTGNDTGSSNGTITLQCRIKQIVNRWQEVGKAMYAPPISGQISCSSNITGLILTRDGGTNNTNGT
EIFRPGGGNMKDNWRSELYKYKVVRIEPLGIAPTKARERVVQREKE

Fig. 4B

\>ADCC-StrNat.B1deltallgp120

MKAKETRKNYQHLWRWGITLLGMLMICSAVPVWKEATTTLFCASDAKAYDTEVHNVWATHACVPTDPNPQ
EVVLENVTENFNMWKNNMVEQMHEDIISLWDQSLKPCVKLTPLCVTLNCTDELKNATVKNATNTNNSSWG
GMERGEIKNCSFNITTSIRDKVQKEYALFYKLDVVPIDNADNNNITTNYTSYRLISCNTSVITQACPKVS
FEPIPIHYCAPAGFAILKCNDKKFNGTGPCTNVSTVQCTHGIRPVVSTQLLLNGSLAEKEVVIRSENFTN
NAKTIIVQLDESVVINCTRPNNNTRKSIHIGPGRAFYTTGEIIGDIRQAHCTLNRTEWNNTLAKITEKLR
EQFGNNITIVFNHSSGGDPEIVMHSFICGGEFFYCNTQLFNSTWNSTGNNISESINTERNITLPCRIKQ
IINLWQEVGKAMYAPPIRGQIRCSSNITGLLLTRDGGSNTDENRTEIFRPGGGDMRDNWRSELYKYKVVK
IEPLGVAPTKAKERVVQREKE

Fig. 4C

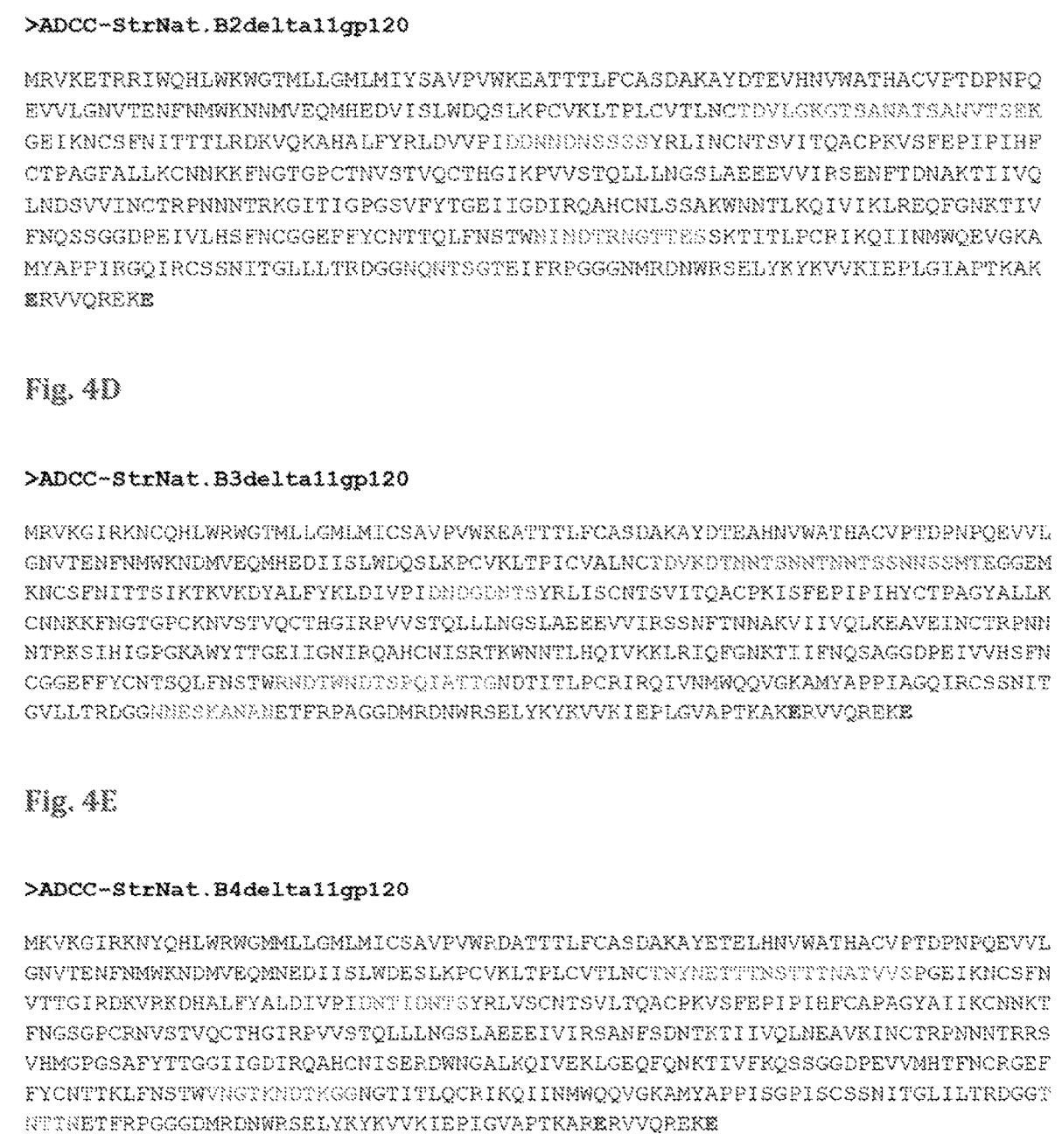

>ADCC-StrNat.B2deltallgp120

MRVKETRRIWQHLWKWGTMLLGMLMIYSAVPVWKEATTTLFCASDAKAYDTEVHNVWATHACVPTDPNPQ
EVVLGNVTENFNMWKNNMVEQMHEDVISLWDQSLKPCVKLTPLCVTLNCTDVLGKGTSANATSANVTSEK
GEIKNCSFNITTTLRDKVQKAHALFYRLDVVPIDDNNDNSSSSYRLINCNTSVITQACPKVSFEPIPIHF
CTPAGFALLKCNNKKFNGTGPCTNVSTVQCTHGIKPVVSTQLLLNGSLAEEEVVIRSENFTDNAKTIIVQ
LNDSVVINCTRPNNNTRKGITIGPGSVFYTGEIIGDIRQAHCNLSSAKWNNTLKQIVIKLREQFGNKTIV
FNQSSGGDPEIVLHSFNCGGEFFYCNTTQLFNSTWNINDTRNGTTESSKTITLPCRIKQIINMWQEVGKA
MYAPPIRGQIRCSSNITGLLLTRDGGNQNTSGTEIFRPGGGNMRDNWRSELYKYKVVKIEPLGIAPTKAK
RRVVQREKR

Fig. 4D

>ADCC-StrNat.B3deltallgp120

MRVKGIRKNCQHLWRWGTMLLGMLMICSAVPVWKEATTTLFCASDAKAYDTEAHNVWATHACVPTDPNPQEVVL
GNVTENFNMWKNDMVEQMHEDIISLWDQSLKPCVKLTPICVALNCTDVKDTNNTSNNTNNTSSNNSSMTEGGEM
KNCSFNITTSIKTKVKDYALFYKLDIVPIDNDGLNTSYRLISCNTSVITQACPKISFEPIPIHYCTPAGYALLK
CNNKKFNGTGPCKNVSTVQCTHGIRPVVSTQLLLNGSLAEEEVVIRSSNFTNNAKVIIVQLKEAVEINCTRPNN
NTRKSIHIGPGKAWYTTGEIIGNIRQAHCNISRTKWNNTLHQIVKKLRIQFGNKTIIFNQSAGGDPEIVVHSFN
CGGEFFYCNTSQLFNSTWRNDTWNDTSPQIATTGNDTITLPCRIRQIVNMWQQVGKAMYAPPIAGQIRCSSNIT
GVLLTRDGGNNESKANANETFRPAGGDMRDNWRSELYKYKVVKIEPLGVAPTKAKRRVVQREKR

Fig. 4E

>ADCC-StrNat.B4deltallgp120

MKVKGIRKNYQHLWRWGMMLLGMLMICSAVPVWRDATTTLFCASDAKAYETELHNVWATHACVPTDPNPQEVVL
GNVTENFNMWKNDMVEQMNEDIISLWDESLKPCVKLTPLCVTLNCTNYNETTTNSTTTNATVVSPGEIKNCSFN
VTTGIRDKVRKDHALFYALDIVPIDNTIDNTSYRLVSCNTSVLTQACPKVSFEPIPIHFCAPAGYAIIKCNNKT
FNGSGPCRNVSTVQCTHGIRPVVSTQLLLNGSLAEEEIVIRSANFSDNTKTIIVQLNEAVKINCTRPNNNTRRS
VHMGPGSAFYTTGGIIGDIRQAHCNISERDWNGALKQIVEKLGEQFQNKTIVFKQSSGGDPEVVMHTFNCRGEF
FYCNTTKLFNSTWVNGTKNDTKGGNGTITLQCRIKQIINMWQQVGKAMYAPPISGPISCSSNITGLILTRDGGT
NTTNETFRPGGGDMRDNWRSELYKYKVVKIEPIGVAPTKARRRVVQREKR

Fig. 4F

>ADCC-StrNat.B5delta11gp120

MRAKETRKKYQHLWAWGTLLLGMLMICSAVPVWKDANTTLFCASDAKAYDTEVHNVWATHACVPTDPSPQEI
VLKNVTENFNMWKNNMVEQMHKDIISLWDESLKPCVKLTPLCVTLNCSNYNSTNSTIDPNMEGAIKNCSFNATT
GIQNKMKKEYALFYSLDIVQIESENKSNKSYMLRSCNTSVITQACPKVTFEPIPIHYCAPAGFAILKCNDKKFN
GTGPCKNVSTVQCTHGIRPVVSTQLLLNGSLAEEEIIIRSENITNNAKTIIIQLNRSIEINCTRPNNNTRKSIH
MGWGRAFYATGDIIGDIRQAHCNLSGTKWNNTLYQIARKLREHFNNTIVFNQSSGGDPEIVMHTFNCGGEFFYC
NTTQLFNSTWHANSTWNETTGSGSNDTISLPCRIKQIINRWQEVGKAMYAPPIGGQIRCSSNITGILLTRDGGT
ENNTSETFRPGGGNMKDNWRSELYKYKVVRIEPLGVAPTKAKERVVQREKE

Fig. 4G

>ADCC-StrMos-Modified.B.1+1.1delta11gp120

MRVKGIRKNYQHLWRWGTMLLGMLMICSAVPVWKEATTTLFCASDAKANDTEVHNVWATHACVPTDPNPQEVVL
ENVTENFNMWKNNMVEQMQEDVISLWDQSLKPCVKLTPLCVTLNCTDVSSNSTSVNITSEKGEIKNCSFNVTT
SIKDKVQKEYALFYKLDVVPIEDDSRNNSYRLISCNTSVITQACPKVSFEPIPIHYCTPAGFAILKCNDKKFN
GTGPCTNVSTVQCTHGIRPVVSTQLLLNGSLAEEEVVIRSENFTNNAKTIIVQLNESVEINCTRPNNNTRKSIH
IGPGRAFYATGDIIGDIRQAHCNISREKWNNTLKQIVKKLREQFGNKTIVFNQSSGGDPEIVMHSFNCGGEFFY
CNTTQLFNSTWSINGTWNGTTESNDTITLPCRIKQIINMWQEVGKAMYAPPIRGQIRCSSNITGLLLTRDGGNS
SSNNETFRPGGGDMRDNWRSELYKYKVVKIEPLGVAPTKAKERVVQREKE

Fig. 4H

>ADCC-StrMos-Modified.B.1+1.2delta11gp120

MKVKGIRKNCQHLWRWGIMLLGMLMICSAVPVWKEATTTLFCASDAKANDTEAHNVWATHACVPTDPNPQEIVL
ENVTENFNMWKNDMVEQMQEDVISLWDESLKPCVELTPLCVTLNCTNVNATNTNNSSGIEGGEMKNCSFNVTTS
IKDKMQKEYALFYSLDVVQIDNDTNYRLINCNTSVITQACPKISFEPIPIHYCTPAGFAIIKCNDKKFNGSGPC
KNVSTVQCTHGIKPVVSTQLLLNGSLAEEEIVIRSENFSDNAKTIIVQLNESVVINCTRPNNNTRKSISIGPGR
AFYATGDIIGNIRQAHCNLSRAKWNNTLRQIVTKLREQFKNKTIAFNHSSGGDPEIVMHTFNCGGEFFYCNSTQ
LFNSTWIANKTGNDTGGSNGTITLQCRIKQIVNRWQEVGKAMYAPPISGQISCSSNITGLILTRDGGTNNTNGT
EIFRPGGGNMKDNWRSELYKYKVVRIEPLGIAPTKARERVVQREKE

Fig. 4I

>ADCC.StrMos.C.1+1.1deltal1gp120

MRVRGILRNYQQWWIWGILGFWMLMICNVVPVWKEAKTTLFCASDAKAYEKEVHNVWATHACVPTDPNPQ
EMVLENVTENFNMWKNDMVDQMHEDIISLWDQSLKPCVKLTPLCVTLNCVNITNSFTSNGDGTVTHINSI
KEEIKNCSFNATTELRDKKSKEYALFYRLDIVPLSSGNSSSNSSKYRLINCNTSTITQACPKVSFDPIPI
HYCAPAGYAILKCNNKTFNGTGPCNNVSTVQCTHGIKPVVSTQLLLNGSLAEEEIIIRSENLTDNVKTII
VHLNESVEIVCTRPNNNTRKSIRIGPGQTFYATGDIIGDIRQAHCNISKGAWNETLQWVGKKLKEHFPNK
TIKFNSSSGGDLEITTHSFNCRGEFFYCNTSGLFNSTYRNNS

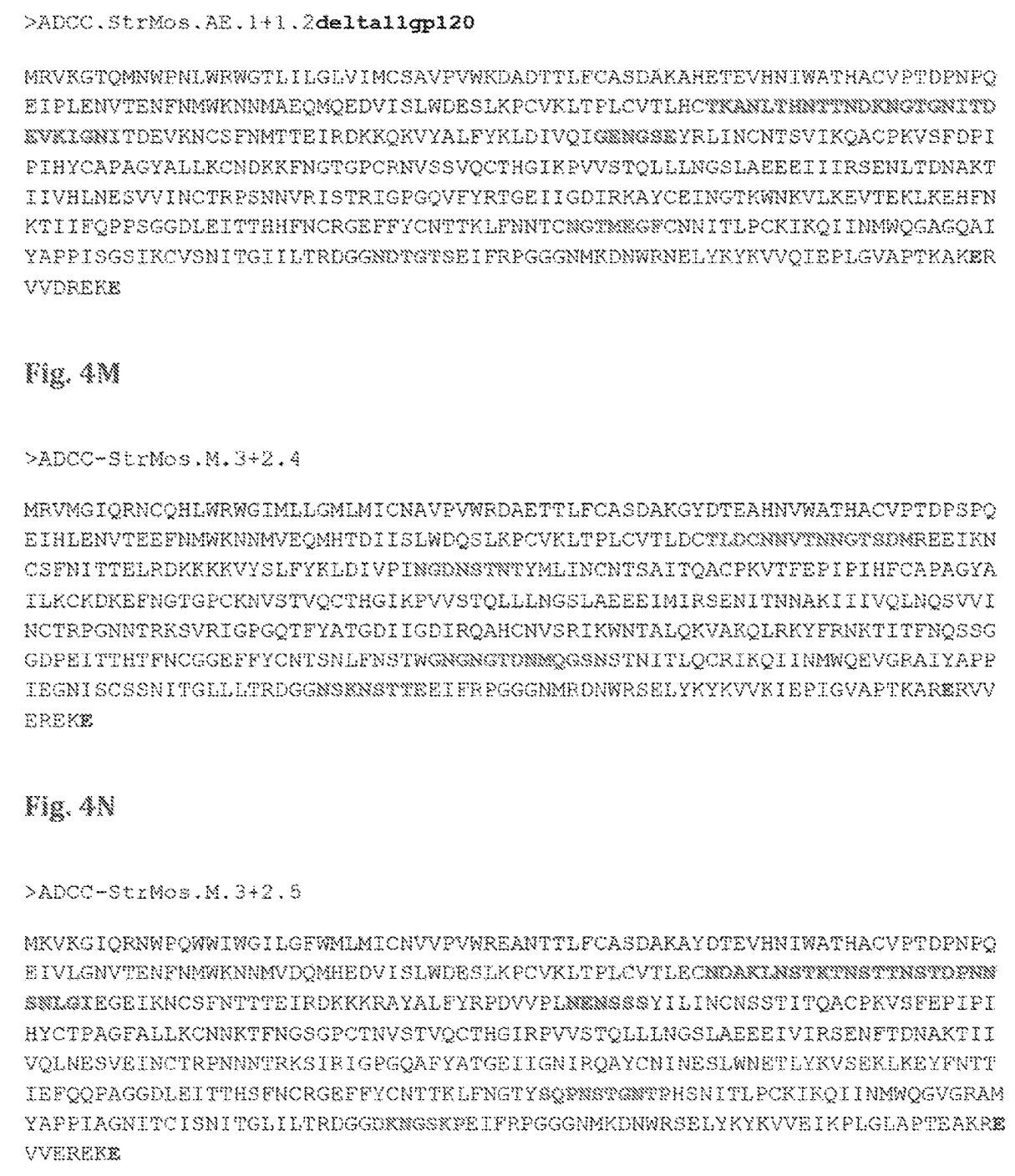

>ADCC.StrMos.AE.1+1.2delta11gp120

MRVKGTQMNWPNLWRWGTLILGLVIMCSAVPVWKDADTTLFCASDAKAHETEVHNIWATHACVPTDPNPQ
EIPLENVTENFNMWKNNMAEQMQEDVISLWDESLKPCVKLTPLCVTLHCTKANLTHNTTNDKNGTGNITD
EVKIGNITDEVKNCSFNMTTEIRDKKQKVYALFYKLDIVQIGENGSEYRLINCNTSVIKQACPKVSFDPI
PIHYCAPAGYALLKCNDKKFNGTGPCRNVSSVQCTHGIKPVVSTQLLLNGSLAEEEIIIRSENLTDNAKT
IIVHLNESVVINCTRPSNNVRISTRIGPGQVFYRTGEIIGDIRKAYCEINGTKWNKVLKEVTEKLKEHFN
KTIIFQPPSGGDLEITTHHFNCRGEFFYCNTTKLFNNTCNGTMEGFCNNITLPCKIKQIINMWQGAGQAI
YAPPISGSIKCVSNITGIILTRDGGNDTGTSEIFRPGGGNMKDNWRNELYKYKVVQIEPLGVAPTKAKER
VVDREKE

Fig. 4M

>ADCC-StrMos.M.3+2.4

MRVMGIQRNCQHLWRWGIMLLGMLMICNAVPVWRDAETTLFCASDAKGYDTEAHNVWATHACVPTDPSPQ
EIHLENVTEEFNMWKNNMVEQMHTDIISLWDQSLKPCVKLTPLCVTLDCTLDCNNVTNNGTSDMREEIKN
CSFNITTELRDKKKKVYSLFYKLDIVPINGDNSTNTYMLINCNTSAITQACPKVTFEPIPIHFCAPAGYA
ILKCKDKEFNGTGPCKNVSTVQCTHGIKPVVSTQLLLNGSLAEEEIMIRSENITNNAKIIIVQLNQSVVI
NCTRPGNNTRKSVRIGPGQTFYATGDIIGDIRQAHCNVSRIKWNTALQKVAKQLRKYFRNKTITFNQSSG
GDPEITTHTFNCGGEFFYCNTSNLFNSTWGNGNGTDNMQGSNSTNITLQCRIKQIINMWQEVGRAIYAPP
IEGNISCSSNITGLLLTRDGGNSENSTTEEIFRPGGGNMRDNWRSELYKYKVVKIEPIGVAPTKARERVV
EREKE

Fig. 4N

>ADCC-StrMos.M.3+2.5

MKVKGIQRNWPQWWIWGILGFWMLMICNVVPVWREANTTLFCASDAKAYDTEVHNIWATHACVPTDPNPQ
EIVLGNVTENFNMWKNNMVDQMHEDVISLWDESLKPCVKLTPLCVTLECNDAKLNSTKTNSTTNSTDPNN
SNLGIEGEIKNCSFNTTTEIRDKKKRAYALFYRPDVVPLNENSSSYILINCNSSTITQACPKVSFEPIPI
HYCTPAGFALLKCNNKTFNGSGPCTNVSTVQCTHGIRPVVSTQLLLNGSLAEEEIVIRSENFTDNAKTII
VQLNESVEINCTRPNNNTRKSIRIGPGQAFYATGEIIGNIRQAYCNINESLWNETLYKVSEKLKEYFNTT
IEFQQPAGGDLEITTHSFNCRGEFFYCNTTKLFNGTYSQPNSTGNTPHSNITLPCKIKQIINMWQGVGRAM
YAPPIAGNITCISNITGLILTRDGGDKNGSKPEIFRPGGGNMKDNWRSELYKYKVVEIKPLGLAPTEAKRE
VVEREKE

Fig. 4O

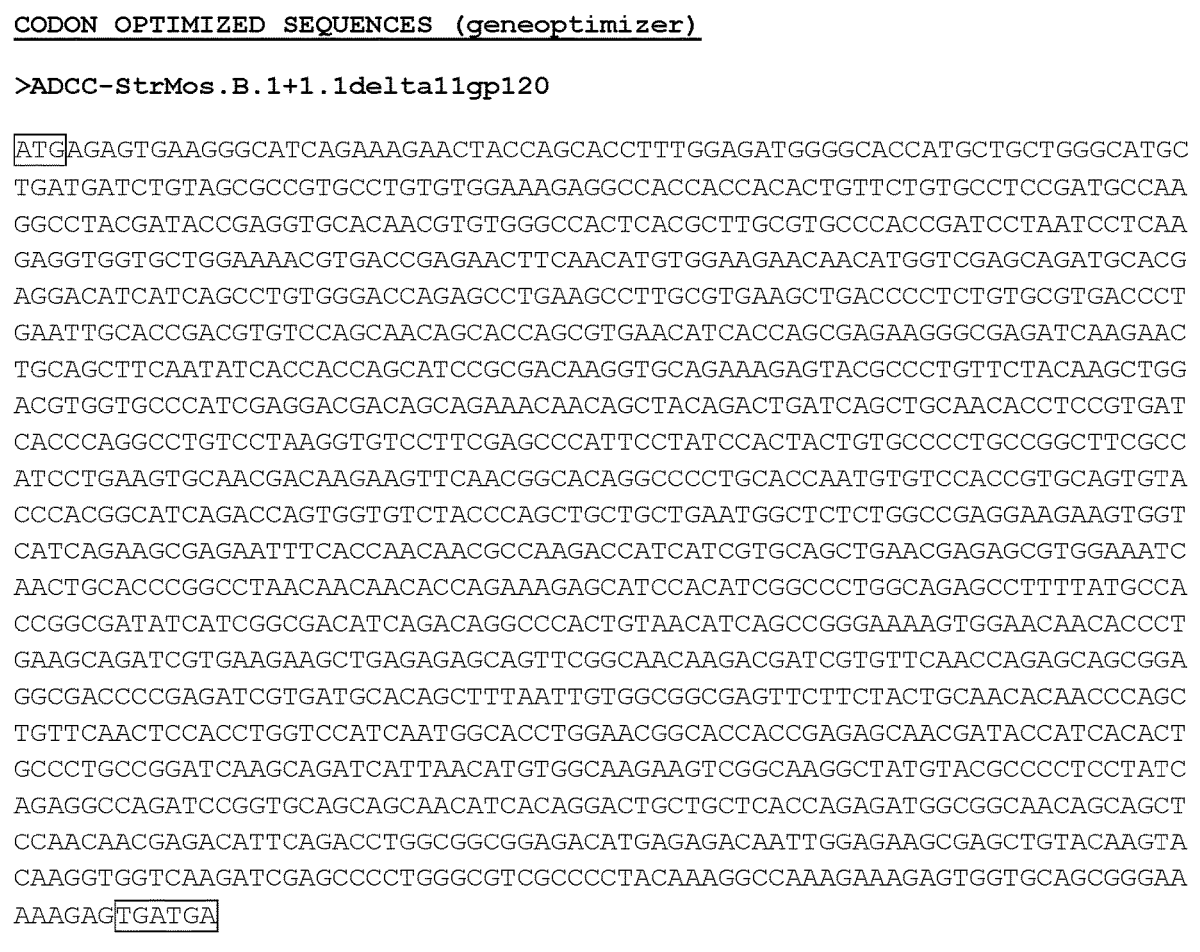

CODON OPTIMIZED SEQUENCES (geneoptimizer)

>ADCC-StrMos.B.1+1.1delta11gp120

ATGAGAGTGAAGGGCATCAGAAAGAACTACCAGCACCTTTGGAGATGGGGCACCATGCTGCTGGGCATGC
TGATGATCTGTAGCGCCGTGCCTGTGTGGAAAGAGGCCACCACCACACTGTTCTGTGCCTCCGATGCCAA
GGCCTACGATACCGAGGTGCACAACGTGTGGGCCACTCACGCTTGCGTGCCCACCGATCCTAATCCTCAA
GAGGTGGTGCTGGAAAACGTGACCGAGAACTTCAACATGTGGAAGAACAACATGGTCGAGCAGATGCACG
AGGACATCATCAGCCTGTGGGACCAGAGCCTGAAGCCTTGCGTGAAGCTGACCCCTCTGTGCGTGACCCT
GAATTGCACCGACGTGTCCAGCAACAGCACCAGCGTGAACATCACCAGCGAGAAGGGCGAGATCAAGAAC
TGCAGCTTCAATATCACCACCAGCATCCGCGACAAGGTGCAGAAAGAGTACGCCCTGTTCTACAAGCTGG
ACGTGGTGCCCATCGAGGACGACAGCAGAAACAACAGCTACAGACTGATCAGCTGCAACACCTCCGTGAT
CACCCAGGCCTGTCCTAAGGTGTCCTTCGAGCCCATTCCTATCCACTACTGTGCCCCTGCCGGCTTCGCC
ATCCTGAAGTGCAACGACAAGAAGTTCAACGGCACAGGCCCCTGCACCAATGTGTCCACCGTGCAGTGTA
CCCACGGCATCAGACCAGTGGTGTCTACCCAGCTGCTGCTGAATGGCTCTCTGGCCGAGGAAGAAGTGGT
CATCAGAAGCGAGAATTTCACCAACAACGCCAAGACCATCATCGTGCAGCTGAACGAGAGCGTGGAAATC
AACTGCACCCGGCCTAACAACAACACCAGAAAGAGCATCCACATCGGCCCTGGCAGAGCCTTTTATGCCA
CCGGCGATATCATCGGCGACATCAGACAGGCCCACTGTAACATCAGCCGGGAAAAGTGGAACAACACCCT
GAAGCAGATCGTGAAGAAGCTGAGAGAGCAGTTCGGCAACAAGACGATCGTGTTCAACCAGAGCAGCGGA
GGCGACCCCGAGATCGTGATGCACAGCTTTAATTGTGGCGGCGAGTTCTTCTACTGCAACACAACCCAGC
TGTTCAACTCCACCTGGTCCATCAATGGCACCTGGAACGGCACCACCGAGAGCAACGATACCATCACACT
GCCCTGCCGGATCAAGCAGATCATTAACATGTGGCAAGAAGTCGGCAAGGCTATGTACGCCCCTCCTATC
AGAGGCCAGATCCGGTGCAGCAGCAACATCACAGGACTGCTGCTCACCAGAGATGGCGGCAACAGCAGCT
CCAACAACGAGACATTCAGACCTGGCGGCGGAGACATGAGAGACAATTGGAGAAGCGAGCTGTACAAGTA
CAAGGTGGTCAAGATCGAGCCCCTGGGCGTCGCCCCTACAAAGGCCAAAGAAAGAGTGGTGCAGCGGGAA
AAAGAGTGATGA

Fig. 5A

\>ADCC-StrMos.B.1+1.2delta11gp120

ATGAAAGTGAAGGGCATCAGAAAGAACTGCCAGCACCTTTGGAGATGGGGCATCATGCTGCTGGGCATGC
TGATGATCTGTAGCGCCGTGCCTGTGTGGAAAGAGGCCACCACCACACTGTTCTGTGCCTCCGATGCCAA
GGCCTACGATACAGAGGCCCATAACGTGTGGGCCACTCACGCCTGTGTGCCCACCGATCCTAATCCTCAA
GAGATCGTGCTGGAAAACGTGACCGAGAACTTCAACATGTGGAAGAACGACATGGTCGAGCAGATGCACG
AGGACATCATCAGCCTGTGGGACGAGAGCCTGAAGCCTTGCGTGGAACTGACCCCTCTGTGCGTGACCCT
GAACTGCACCAATGTGAACGCCACCAACACCAACAACAGCAGCGGCATCGAAGGCGGCGAGATGAAGAAC
TGCAGCTTCAACGTGACCACCAGCATCCGGGACAAGATGCAGAAAGAGTACGCCCTGTTCTACAGCCTGG
ACGTGGTGCAGATCGACAACGACACCAACTACCGGCTGATCAACTGCAACACCAGCGTGATCACCCAGGC
CTGTCCTAAGATCAGCTTCGAGCCCATTCCTATCCACTACTGCACCCCTGCCGGCTTCGCCATCATCAAG
TGCAACGACAAGAAGTTCAACGGCAGCGGCCCCTGCAAGAACGTGTCCACAGTGCAGTGTACCCACGGCA
TCAAGCCCGTGGTGTCTACACAGCTGCTGCTGAATGGCAGCCTGGCCGAAGAGGAAATCGTGATCAGAAG
CGAGAATTTCAGCGACAACGCCAAGACCATCATCGTGCAGCTGAACGAGAGCGTGGTCATCAATTGCACC
CGGCCTAACAACAACACCCGGAAGTCCATCAGCATCGGCCCTGGCAGAGCCTTTTATGCCACCGGCGACA
TCATCGGCAACATCAGACAGGCCCACTGCAACCTGTCTCGGGCCGAGTGGAACAATACCCTGAGACAGAT
CGTGACCAAGCTGCGCGAGCAGTTCAAGAACAAGACAATCGCCTTCAACCACAGCTCTGGCGGCGACCCT
GAGATCGTGATGCACACCTTTAACTGTGGCGGCGAGTTCTTCTACTGCAACAGCACCCAGCTGTTCAACT
CCACCTGGATCGCCAACAAGACCGGCAATGATACCGGCGGCAGCAACGGCACAATCACCCTGCAGTGCCG
GATCAAGCAGATTGTGAACCGGTGGCAAGAAGTGGGCAAAGCTATGTACGCCCCTCCTATCAGCGGCCAG
ATCAGCTGCAGCAGCAATATCACCGGCCTGATCCTGACCAGAGATGGCGGCACCAACAATACCAACGGCA
CCGAGATCTTCAGACCCGGCGGAGGCAACATGAAGGACAATTGGAGAAGCGAGCTGTACAAGTACAAGGT
CGTGCGGATCGAGCCCCTGGGAATCGCCCCTACAAAGGCCAGAGAAAGAGTGGTGCAGCGGGAAAAAGAG
TGATGA

Fig. 5B

\>ADCC-StrNat.B1delta11gp120

ATGAAGGCCAAAGAGACACGGAAGAACTACCAGCACCTTTGGAGATGGGGCATCACCCTGCTGGGCATGCTGATG
ATCTGTAGCGCTGTGCCCGTGTGGAAAGAGGCCACCACCACACTGTTTTGTGCCAGCGACGCCAAGGCCTACGAT
ACCGAGGTGCACAATGTGTGGGCCACTCACGCCTGCGTGCCCACCGATCCTAATCCTCAAGAGGTGGTGCTGGAA
AACGTGACCGAGAACTTCAACATGTGGAAGAACAACATGGTCGAGCAGATGCACGAGGACATCATCAGCCTGTGG
GACCAGAGCCTGAAGCCTTGCGTGAAGCTGACCCCTCTGTGCGTGACCCTGAACTGCACCGACGACCTGAAGAAT
GCCACCGTGAAGAACGCCACAAACACCAACAACAGCAGCTGGGGCGGCATGGAAAGGGGCGAGATCAAGAACTGC
AGCTTCAACATCACCACCAGCATCAGAGACAAGGTGCAGAAAGAGTACGCCCTGTTCTACAAGCTGGACGTGGTG
CCCATCGACAACGCCGACAACAACAATATCACCACGAACTACACCAGCTACCGGCTGATCTCCTGCAACACCAGC
GTGATCACTCAGGCCTGTCCTAAGGTGTCCTTCGAGCCCATTCCTATCCACTACTGTGCCCCTGCCGGCTTCGCC
ATCCTGAAGTGCAACGACAAGAAGTTCAACGGCACAGGCCCCTGCACCAACGTGTCCACAGTGCAGTGTACCCAC
GGCATCAGACCCGTGGTGTCTACACAGCTGCTGCTGAATGGAAGCCTGGCCGAGAAGAAGTGGTCATCAGAAGC
GAGAACTTTACCAACAACGCCAAGACCATCATCGTGCAGCTGGACGAGAGCGTCGTGATCAACTGCACCCGGCCT
AACAACAACACCAGAAAGAGCATCCACATCGGCCCTGGCAGAGCCTTTTACACCACCGGCGAGATTATCGGCGAC
ATCAGACAGGCCCACTGTACCCTGAACCGGACCGAGTGGAACAACACCCTGGCCAAGATCACCGAGAAGCTGAGA
GAGCAGTTCGGCAACAACATCACAATCGTGTTCAACCACAGCTCTGGCGGCGACCCCGAAATCGTGATGCACAGC
TTTATCTGTGGCGGCGAGTTCTTCTACTGCAATACCAGCCAGCTGTTCAACAGCACCTGGAACAGCACCGGCAAC
AATATTAGCGAGAGCGACAACACCGAGCGGAACATCACACTGCCCTGCCGGATCAAGCAGATCATTAACCTGTGG
CAAGAAGTCGGCAAGGCTATGTACGCCCCTCCTATCAGAGGCCAGATCCGGTGCAGCAGCAACATTACAGGCCTG
CTGCTCACCAGAGATGGCGGCAGCAACACCGACGAGAATCGGACCGAGATCTTTAGACCCGGCGGAGGCGACATG
AGAGACAATTGGAGAAGCGAGCTGTACAAGTACAAGGTGGTCAAGATCGAGCCCCTGGGCGTCGCCCCTACCAAA
GCCAAAGAAAGAGTGGTGCAGCGGGAAAAAGAGTGATGA

Fig. 5C

>ADCC-StrNat.B2delta11gp120

ATGAGAGTGAAAGAGACACGGCGGATCTGGCAGCACCTGTGGAAGTGGGGAACAATGCTGCTGGGCATGC
TGATGATCTACAGCGCCGTGCCTGTGTGGAAAGAGGCCACCACCACACTGTTCTGTGCCTCCGATGCCAA
GGCCTACGATACCGAGGTGCACAACGTGTGGGCCACTCACGCTTGCGTGCCCACCGATCCTAATCCTCAA
GAGGTGGTGCTGGGCAACGTGACCGAGAACTTCAACATGTGGAAGAACAACATGGTCGAGCAGATGCACG
AGGACGTGATCAGCCTGTGGGACCAGAGCCTGAAGCCTTGCGTGAAGCTGACCCCTCTGTGCGTGACCCT
GAACTGCACAGATGTGCTCGGCAAGGGCACAAGCGCCAATGCCACATCTGCCAATGTGACCAGCGAGAAG
GGCGAGATCAAGAACTGCAGCTTCAACATCACCACCACTCTGAGAGACAAGGTGCAGAAGGCCCACGCTC
TGTTCTACAGACTGGACGTGGTGCCCATCGACGACAACAACGACAACTCCAGCAGCAGCTACCGGCTGAT
CAACTGCAACACCAGCGTGATCACCCAGGCCTGTCCTAAGGTGTCCTTCGAGCCTATTCCTATCCACTTC
TGTACCCCTGCCGGCTTCGCCCTGCTGAAGTGCAACAACAAGAAGTTCAACGGCACAGGCCCCTGCACCA
ACGTGTCCACAGTGCAGTGTACCCACGGCATCAAGCCCGTGGTGTCTACACAGCTCCTGCTGAATGGCAG
CCTGGCCGAGGAAGAAGTGGTCATCAGAAGCGAGAATTTCACCGACAACGCCAAGACCATCATCGTGCAG
CTGAACGACAGCGTCGTGATCAATTGCACCCGGCCTAACAACAACACCCGGAAGGGCATCACAATCGGCC
CTGGCTCCGTGTTTTACACCGGGGAGATCATCGGCGACATCAGACAGGCCCACTGTAACCTGTCTAGCGC
CAAGTGGAACAATACCCTGAAGCAGATCGTCATCAAGCTGAGAGAGCAGTTCGGCAACAAGACGATCGTG
TTCAACCAGAGCAGCGGAGGCGACCCTGAGATCGTGCTGCACAGCTTTAATTGTGGCGGCGAGTTCTTCT
ACTGCAATACCACACAGCTGTTCAACAGCACCTGGAACATCAACGACACCAGAAACGGCACCACCGAGAG
CAGCAAGACAATCACCCTGCCTTGCCGGATCAAGCAGATCATCAATATGTGGCAAGAAGTCGGCAAGGCT
ATGTACGCCCCTCCTATCAGAGGCCAGATCAGATGCAGCAGCAATATCACCGGCCTGCTGCTGACAAGAG
ATGGCGGCAACCAGAATACCAGCGGCACCGAGATCTTCAGACCCGGCGGAGGCAACATGCGGGACAATTG
GAGAAGCGAGCTGTACAAGTACAAGGTGGTCAAGATCGAGCCCCTGGGAATCGCCCCTACCAAGGCCAAA
GAAAGAGTGGTGCAGCGGGAAAAAGAGTGATGA

Fig. 5D

>ADCC-StrNat.B3delta11gp120

ATGAGAGTGAAGGGCATCAGAAAGAACTGCCAGCACCTTTGGAGATGGGGCACCATGCTGCTGGGCATGC
TGATGATCTGTAGCGCCGTGCCTGTGTGGAAAGAGGCCACCACCACACTGTTCTGTGCCTCCGATGCCAA
GGCCTACGATACAGAGGCCCATAACGTGTGGGCCACTCACGCCTGTGTGCCCACCGATCCTAATCCTCAA
GAGGTGGTGCTGGGCAACGTGACCGAGAACTTCAACATGTGGAAGAACGACATGGTCGAGCAGATGCACG
AGGACATCATCAGCCTGTGGGACCAGAGCCTGAAGCCTTGCGTGAAGCTGACCCCTATCTGCGTGGCCCT
GAACTGCACCGACGTGAAGGACACCAACAACACCAGCAACAACACGAACAATACCAGCTCCAACAACAGC
TCCATGACCGAAGGCGGCGAGATGAAGAACTGCAGCTTCAACATCACCACCAGCATCAAGACCAAAGTGA
AGGACTACGCCCTGTTCTACAAGCTGGACATCGTGCCCATCGACAACGACGGCGACAACACCTCCTACAG
ACTGATCAGCTGCAATACCTCCGTGATCACCCAGGCCTGTCCTAAGATCAGCTTCGAGCCCATTCCTATC
CACTACTGCACCCCTGCCGGATACGCCCTGCTGAAGTGCAACAACAAGAAGTTCAACGGCACAGGCCCCT
GCAAGAACGTGTCCACCGTGCAGTGTACCCACGGCATCAGACCAGTGGTGTCTACCCAGCTGCTGCTGAA
TGGCTCTCTGGCCGAGGAAGAAGTGGTCATCAGAAGCAGCAACTTCACCAACAATGCCAAAGTGATCATC
GTGCAGCTGAAAGAAGCCGTCGAGATCAACTGCACCCGGCCTAACAACAATACCCGGAAGTCCATCCACA
TCGGCCCTGGCAAGGCCTGGTATACAACCGGCGAGATCATCGGCAACATCAGACAGGCCCACTGTAACAT
CAGCCGGACCAAGTGGAACAACACCCTGCACCAGATTGTGAAGAAGCTGAGAATCCAGTTCGGCAACAAG
ACCATCATCTTCAACCAGAGCGCTGGCGGCGACCCTGAGATTGTGGTGCACAGCTTTAACTGTGGCGGCG
AGTTCTTCTACTGCAACACAAGCCAGCTGTTCAACAGCACCTGGCGGAACGACACCTGGAACGATACAAG
CCCTCAGATCGCCACCACCGGCAACGACACAATCACCCTGCCTTGCCGGATCAGACAGATCGTGAACATG
TGGCAGCAAGTGGGCAAAGCTATGTACGCCCCTCCTATCGCCGGCCAGATCAGATGCAGCAGCAATATCA
CTGGCGTGCTGCTGACCAGAGATGGCGGCAACAATGAGAGCAAGGCCAACGCCAACGAGACATTCAGACC
TGCCGGCGGAGACATGAGAGACAATTGGAGAAGCGAGCTGTACAAGTACAAGGTGGTCAAGATCGAGCCC
CTGGGCGTCGCCCCTACAAAGGCCAAAGAAAGAGTGGTGCAGCGGGAAAAAGAGTGATGA

Fig. 5E

>ADCC-StrNat.B4delta11gp120

ATGAAAGTGAAGGGCATCAGAAAGAACTACCAGCACCTTTGGAGATGGGGCATGATGCTGCTGGGCATGC
TGATGATCTGTAGCGCCGTGCCTGTTTGGCGGGATGCCACCACCACACTGTTTTGTGCCTCTGACGCCAA
GGCCTACGAGACAGAGCTGCACAATGTGTGGGCCACTCACGCCTGCGTGCCCACCGATCCTAATCCTCAA
GAAGTGGTGCTGGGCAACGTGACCGAGAACTTCAACATGTGGAAGAACGACATGGTCGAGCAGATGAACG
AGGACATCATCAGCCTGTGGGACGAGAGCCTGAAGCCTTGCGTGAAGCTGACCCCTCTGTGCGTGACCCT
GAACTGCACCAACTACAACGAGACAACCACCAACAGCACCACCACCAACGCCACAGTGGTGTCTCCAGGC
GAGATCAAGAACTGCAGCTTCAATGTGACCACCGGCATCCGGGACAAAGTGCGGAAAGATCACGCCCTGT
TCTACGCCCTGGACATCGTGCCCATCGACAACACCATCGATAATACCAGCTACCGGCTGGTGTCCTGCAA
CACCAGTGTGCTGACACAGGCTTGCCCCAAGGTGTCCTTCGAGCCTATTCCTATCCACTTCTGTGCCCCT
GCCGGCTACGCCATCATCAAGTGCAACAACAAGACCTTCAACGGCAGCGGCCCCTGCAGAAATGTGTCCA
CCGTGCAGTGTACCCACGGCATCAGACCCGTGGTGTCTACACAGCTGCTGCTGAATGGCAGCCTGGCCGA
AGAGGAAATCGTGATCAGAAGCGCCAACTTCAGCGACAATACCAAGACCATCATCGTGCAGCTGAATGAG
GCCGTGAAGATCAACTGCACCCGGCCTAACAACAACACCAGGCGGAGTGTGCACATGGGCCCTGGCTCTG
CCTTCTATACAACCGGCGGCATCATCGGCGACATCAGACAGGCCCACTGCAACATCAGCGAGAGAGATTG
GAACGGCGCCCTGAAGCAGATCGTGGAAAAGCTGGGCGAGCAGTTCCAGAACAAGACAATCGTGTTCAAG
CAGAGCAGCGGAGGCGACCCTGAGGTGGTCATGCACACCTTCAATTGCAGAGGCGAGTTCTTCTACTGCA
ATACCACCAAGCTGTTCAACTCCACCTGGGTCAACGGCACCAAGAACGATACCAAAGGCGGCAACGGCAC
AATCACCCTGCAGTGCAGAATCAAGCAGATCATTAACATGTGGCAGCAAGTCGGCAAGGCTATGTACGCC
CCTCCTATCAGCGGCCCTATCAGCTGCAGCAGCAATATCACCGGCCTGATCCTGACCAGAGATGGCGGCA
CCAACACCACAAACGAGACATTCAGACCTGGCGGCGGAGACATGAGAGACAATTGGAGAAGCGAGCTGTA
CAAGTACAAGGTGGTCAAGATCGAGCCCATCGGCGTGGCCCCTACAAAGGCCAGAGAAAGAGTGGTGCAG
CGCGAGAAAGAGTGATGA

Fig. 5F

>ADCC-StrNat.B5delta11gp120

ATGAGAGCCAAAGAGACACGGAAGAAATACCAGCACCTGTGGGCCTGGGGAACACTGCTGCTGGGAATGC
TGATGATCTGCAGCGCTGTGCCCGTGTGGAAGGACGCCAATACCACACTGTTCTGTGCCAGCGACGCCAA
GGCCTACGATACCGAGGTGCACAATGTGTGGGCCACTCACGCCTGCGTGCCAACCGATCCATCTCCTCAA
GAGATCGTGCTGAAGAACGTGACCGAGAACTTCAACATGTGGAAGAACAACATGGTCGAGCAGATGCACA
AGGACATCATCAGCCTGTGGGACGAGAGCCTGAAGCCTTGCGTGAAGCTGACCCCTCTGTGCGTGACCCT
GAACTGCAGCAACTACAACAGCACCAACTCCACCATCGATCCCAACATGGAAGGCGCCATCAAGAATTGC
AGCTTCAACGCCACCACCGGCATCCAGAACAAGATGAAGAAAGAGTACGCCCTGTTCTACAGCCTGGACA
TCGTGCAGATCGAGAGCGAGAACAAGAGCAACAAGTCCTACATGCTGCGGAGCTGCAACACCAGCGTGAT
CACTCAGGCCTGTCCTAAAGTGACCTTCGAGCCCATTCCTATCCACTACTGTGCCCCTGCCGGCTTCGCC
ATCCTGAAGTGCAACGACAAGAAGTTCAACGGCACAGGCCCCTGCAAGAACGTGTCCACCGTGCAGTGTA
CCCACGGCATCAGACCAGTGGTGTCTACCCAGCTGCTGCTGAATGGCTCTCTGGCCGAGGAAGAGATCAT
CATCAGATCCGAGAACATCACCAACAACGCCAAGACCATCATCATCCAGCTGAACCGGTCCATCGAGATC
AACTGCACCCGGCCTAACAACAACACCCGGAAGTCCATCCACATGGGCTGGGGCAGAGCCTTTTATGCCA
CCGGCGATATCATCGGCGACATCAGACAGGCCCACTGTAACCTGAGCGGCACCAAGTGGAACAATACCCT
GTACCAGATCGCCCGGAAGCTGAGAGAGCACTTCAACAATACCATCGTGTTCAACCAGAGCAGCGGAGGC
GACCCCGAGATCGTGATGCACACCTTTAATTGTGGCGGCGAGTTCTTCTACTGCAACACAACCCAGCTGT
TCAATAGCACCTGGCACGCCAATTCCACCTGGAACGAGACAACAGGCAGCGGCAGCAACGATACCATCTC
TCTGCCCTGCCGGATCAAGCAGATCATTAACCGGTGGCAAGAAGTCGGCAAGGCTATGTACGCCCCTCCT
ATCGGCGGCCAGATCAGATGCAGCAGCAACATCACAGGCATCCTGCTGACCAGAGATGGCGGCACCGAGA
ACAACACAAGCGAGACATTCAGACCCGGCGGAGGCAACATGAAGGACAATTGGAGAAGCGAGCTGTACAA
GTACAAGGTTGTGCGGATCGAGCCCCTGGGCGTTGCCCCTACAAAGGCCAAAGAAAGGGTCGTGCAGCGC
GAGAAAGAGTGATGA

Fig. 5G

\>ADCC-StrMos-Modified.B.1+1.1delta11gp120

ATGAGAGTGAAGGGCATCAGAAAGAACTACCAGCACCTTTGGAGATGGGGCACCATGCTGCTGGGCATGC
TGATGATCTGTAGCGCCGTGCCTGTGTGGAAAGAGGCCACCACCACACTGTTCTGTGCCAGCGACGCCAA
GGCTCACGATACCGAGGTGCACAATGTGTGGGCCACTCACGCCTGCGTGCCCACCGATCCTAATCCTCAA
GAGGTGGTGCTGGAAAACGTGACCGAGAACTTCAACATGTGGAAGAACAACATGGTCGAGCAGATGCAAG
AGGACGTGATCAGCCTGTGGGACCAGAGCCTGAAGCCTTGCGTGAAGCTGACCCCTCTGTGCGTGACCCT
GAATTGCACCGACGTGTCCAGCAACAGCACCAGCGTGAACATCACCAGCGAGAAGGGCGAGATCAAGAAC
TGCAGCTTCAACGTGACCACCAGCATCAAGGACAAGGTGCAGAAAGAGTACGCCCTGTTCTACAAGCTGG
ACGTGGTGCCCATCGAGGACGACAGCAGAAACAACAGCTACAGACTGATCAGCTGCAACACCTCCGTGAT
CACCCAGGCCTGTCCTAAGGTGTCCTTCGAGCCCATTCCTATCCACTACTGTACCCCTGCCGGCTTCGCC
ATCCTGAAGTGCAACGACAAGAAGTTCAACGGCACAGGCCCCTGCACCAATGTGTCCACCGTGCAGTGTA
CCCACGGCATCAGACCTGTGGTGTCTACCCAGCTGCTGCTGAATGGCTCTCTGGCCGAGGAAGAAGTGGT
CATCAGAAGCGAGAATTTCACCAACAACGCCAAGACCATCATCGTGCAGCTGAACGAGAGCGTGGAAATC
AACTGCACCCGGCCTAACAACAACACCAGAAAGAGCATCCACATCGGCCCTGGCAGAGCCTTTTATGCCA
CCGGCGATATCATCGGCGACATCAGACAGGCCCACTGTAACATCAGCCGGGAAAAGTGGAACAACACCCT
GAAGCAGATCGTGAAGAAGCTGAGAGAGCAGTTCGGCAACAAGACGATCGTGTTCAACCAGAGCAGCGGA
GGCGACCCCGAGATCGTGATGCACAGCTTTAATTGTGGCGGCGAGTTCTTCTACTGCAACACAACCCAGC
TGTTCAACTCCACCTGGTCCATCAATGGCACCTGGAACGGCACCACCGAGAGCAACGATACCATCACACT
GCCCTGCCGGATCAAGCAGATCATTAACATGTGGCAAGAAGTCGGCAAGGCTATGTACGCCCCTCCTATC
AGAGGCCAGATCCGGTGCAGCAGCAATATCACAGGCCTGCTGCTCACCAGAGATGGCGGCAATAGCAGCT
CCAACAACGAGACATTCAGACCTGGCGGCGGAGACATGAGAGACAATTGGAGAAGCGAGCTGTACAAGTA
CAAGGTGGTCAAGATCGAGCCCCTGGGCGTCGCCCCTACAAAGGCCAAAGAAAGAGTGGTGCAGCGGGAA
AAAGAGTGATGA

Fig. 5H

>ADCC-StrMos-Modified.B.1+1.2delta11gp120

ATGAAAGTGAAGGGCATCAGAAAGAACTGCCAGCACCTTTGGAGATGGGGCATCATGCTGCTGGGCATGC
TGATGATCTGTAGCGCCGTGCCTGTGTGGAAAGAGGCCACCACCACACTGTTCTGTGCCAGCGACGCCAA
GGCTCACGATACAGAGGCCCATAACGTGTGGGCCACTCACGCCTGTGTGCCCACCGATCCTAATCCTCAA
GAGATCGTGCTGGAAAACGTGACCGAGAACTTCAACATGTGGAAGAACGACATGGTCGAGCAGATGCAAG
AGGACGTGATCAGCCTGTGGGACGAGAGCCTGAAGCCTTGCGTGGAACTGACCCCTCTGTGCGTGACCCT
GAACTGCACCAATGTGAACGCCACCAACACCAACAACAGCAGCGGCATCGAAGGCGGCGAGATGAAGAAC
TGCAGCTTCAACGTGACCACCAGCATCAAGGACAAGATGCAGAAAGAGTACGCCCTGTTCTACAGCCTGG
ACGTGGTGCAGATCGACAACGACACCAACTACCGGCTGATCAACTGCAACACCAGCGTGATCACCCAGGC
CTGTCCTAAGATCAGCTTCGAGCCCATTCCTATCCACTACTGCACCCCTGCCGGCTTCGCCATCATCAAG
TGCAACGACAAGAAGTTCAACGGCAGCGGCCCCTGCAAGAACGTGTCCACAGTGCAGTGTACCCACGGCA
TCAAGCCCGTGGTGTCTACACAGCTGCTGCTGAATGGCAGCCTGGCCGAAGAGGAAATCGTGATCAGAAG
CGAGAATTTCAGCGACAACGCCAAGACCATCATCGTGCAGCTGAACGAGAGCGTGGTCATCAATTGCACC
CGGCCTAACAACAACACCCGGAAGTCCATCAGCATCGGCCCTGGCAGAGCCTTTTATGCCACCGGCGACA
TCATCGGCAACATCAGACAGGCCCACTGCAACCTGAGCCGGGCCAAGTGGAACAATACCCTGAGACAGAT
CGTGACCAAGCTGCGCGAGCAGTTCAAGAACAAGACAATCGCCTTCAACCACAGCTCTGGCGGCGACCCT
GAGATCGTGATGCACACCTTTAACTGTGGCGGCGAGTTCTTCTACTGCAACAGCACCCAGCTGTTCAACT
CCACCTGGATCGCCAACAAGACCGGCAATGATACCGGCGGCAGCAACGGCACAATCACCCTGCAGTGCCG
GATCAAGCAGATTGTGAACCGGTGGCAAGAAGTGGGCAAAGCTATGTACGCCCCTCCTATCAGCGGCCAG
ATCAGCTGCAGCAGCAATATCACCGGCCTGATCCTGACCAGAGATGGCGGCACCAACAATACCAACGGCA
CCGAGATCTTCAGACCCGGCGGAGGCAACATGAAGGACAATTGGAGAAGCGAGCTGTACAAGTACAAGGT
CGTGCGGATCGAGCCCCTGGGAATCGCCCCTACAAAGGCCAGAGAAAGAGTGGTGCAGCGGGAAAAAGAG
TGATGA

Fig. SI

>ADCC.StrMos.C.1+1.1delta11gp120

ATGAGAGTTAGAGGCATCCTGCGGAACTACCAGCAGTGGTGGATCTGGGGCATCCTCGGCTTTTGGATGC
TGATGATCTGCAACGTGGTGCCCGTGTGGAAAGAGGCCAAGACCACACTGTTCTGTGCCAGCGACGCCAA
GGCCTACGAGAAAGAGGTGCACAACGTCTGGGCCACACACGCCTGTGTGCCCACCGATCCTAATCCTCAA
GAGATGGTGCTGGAAAACGTGACCGAGAACTTCAACATGTGGAAGAACGACATGGTGGACCAGATGCACG
AGGACATCATCAGCCTGTGGGACCAGAGCCTGAAGCCTTGCGTGAAGCTGACCCCTCTGTGCGTGACCCT
GAACTGCGTGAACATCACCAACAGCACCACCAGCAACGGCGACGGCACAGTGACCCACATCAACAGCATC
AAAGAGGAAATCAAGAACTGCAGCTTCAACGCCACCACCGAGCTGCGGGACAAGAAGTCCAAAGAGTACG
CCCTGTTCTACCGGCTGGACATCGTGCCTCTGAGCAGCGGCAATAGCAGCAGCAACAGCTCCAAGTACCG
GCTGATCAACTGCAACACCAGCACAATCACCCAGGCCTGTCCTAAGGTGTCCTTCGATCCCATTCCTATC
CACTACTGTGCCCCTGCCGGCTACGCCATCCTGAAGTGCAACAACAAGACCTTCAACGGCACAGGCCCCT
GCAACAACGTGTCCACCGTGCAGTGTACCCACGGCATCAAGCCAGTGGTGTCTACCCAGCTGCTGCTGAA
TGGCTCTCTGGCCGAGGAAGAGATCATCATCAGAAGCGAGAACCTGACCGACAACGTCAAGACCATCATC
GTGCACCTGAACGAGAGCGTGGAAATCGTGTGCACCCGGCCTAACAACAACACCAGAAAGAGCATCCGGA
TCGGCCCTGGCCAGACCTTTTATGCCACCGGCGATATCATCGGCGACATCAGACAGGCCCACTGTAACAT
CAGCAAAGGCGCCTGGAACGAAACCCTGCAGTGGGTCGGAAAGAAGCTGAAAGAGCACTTCCCCAACAAG
ACGATCAAGTTCAACAGCAGCTCTGGCGGCGACCTGGAAATCACCACACACAGCTTCAATTGCAGAGGCG
AGTTCTTCTACTGCAATACCTCCGGCCTGTTCAACTCCACCTACCGGAACAATAGCACCGGCGACAATTC
CACCATCACACTGCCCTGCCGGATCAAGCAGATCATTAACATGTGGCAAGAAGTCGGCAGGGCTATGTAC
GCCCCTCCTATCGCCGGCAACATCACATGCAAGTCCAACATCACCGGCCTGCTGCTCACCAGAGATGGCG
GCACCAGAGACAGAAACGACACCGAGACATTCAGACCCGGCGGAGGCGACATGAGAGACAATTGGAGAAG
CGAGCTGTACAAGTACAAGGTGGTCGAGATCAAGCCCCTGGGAATCGCCCCTACCAAGGCCAAAGAAAGA
GTGGTGGAACGGGAAAAAGAGTGATGA

Fig. 5J

>ADCC.StrMos.C.1+1.2delta11gp120

ATGAGAGTGATGGGCATCCAGAGAAACTGGCCCCAGTGGTGGATCTGGGGCATCCTCGGCTTTTGGATGA
TCATTATCTGCAGAGTGGTGCCCGTGTGGCGCGAGGCCAAGACCACACTGTTTTGTGCCTCTGACGCCAA
GGCCTACGAGCGCGAAGTGCACAATGTGTGGGCTACCCATGCCTGCGTGCCCACCGATCCTAATCCTCAA
GAGCTGGTGCTGGAAAACGTGACCGAGAACTTCAACATGTGGGAGAACGACATGGTGGACCAGATGCACG
AGGACGTGATCAGCCTGTGGGACCAGAGCCTGAAGCCTTGCGTGAAGCTGACCCCTCTGTGCGTGACCCT
GAAGTGCACCAACACCACCTACTACAACGTGTCCAGCAAAGAGTTCACCAACGGCGAGATCAAGAACTGC
AGCTTCAATACCACCACCGAGCTGCGGGACAAGAAACAGAAGGTGTCAGCCCTGTTCTACCGGCTGGATG
TGGTGCCCCTGAGCAAGAAGGACAAGACCAACAACGACAGCGGCGAGTACATCCTGATCAACTGCAACAC
CAGCGCCATCACACAGGCTTGCCCCAAGGTGTCCTTCGATCCCATTCCTATCCACTACTGCACCCCTGCC
GGCTACGCCATCCTGAAGTGTAACAACAAGACCTTCAACGGCACAGGCCCCTGCCATAATGTGTCCACCG
TGCAGTGTACCCACGGCATCAAGCCAGTGGTGTCTACCCAGCTGCTGCTGAATGGCTCTCTGACCGAGGG
CGAGATTATCATCAGAAGCGAGAACCTGACCAACAATGCCAAGACAATCATCGTGCACCTGAACCAGAGC
GTGGCCATCGTGTGTACCAGACCTGGCAACAACACCAGAAAGAGCGTGCGGATCGGACCCGGCCAGGCCT
TTTATGCCACCGGCGAAATCATCGGCGACATCAGACAGGCCTACTGCAATCTGACCAACTGGCAAGAGAC
ACTGAAGAATGTCTCCAAGAAGCTGCAAGAGCGGTTTAACAAGACCATCAGATTCGCCCCTAGCTCTGGC
GGCGACCTGGAAATCACCACACACAGCTTTAACTGTGGCGGCGAGTTCTTCTACTGTAACACCTCCAGCC
TGTTCAACAGCGCCTACAATCCCAACGGCACCAAGGACAACAGCAACAGCAGCATCACCATCCAGTGCAA
GATCAAGCAGATCATCAATATGTGGCAAGGCGTGGGCAGAGCCATCTACGCCCCTCCAATCGCCGGCAAC
ATCACCTGTAACAGCAATATCACCGGCATCCTGCTGACCAGAGATGGCGGCAGCAAGAACAACACCGAGG
AAATCTTCAGACCCGGCGGAGGCAACATGAAGGACAATTGGAGAAGCGAGCTGTACCGCTACAAGGTGGT
GGAAATCAAGCCCCTGGGAGTCGCCCCTACCGAGGCCAAAGAAAGAGTGGTGGAACGGAAAAAGAGTGA
TGA

Fig. 5K

>ADCC.StrMos.AE.1+1.1delta11gp120

ATGAGAGTGAAAGAAACCCAGATGAACTGGCCCAACCTGTGGAAGTGGGGCACACTGATTCTGGGCCTCG
TGATCATCTGTAGCGCCGTGCCTGTTTGGAGGGACGCCGATACCACACTGTTCTGTGCCAGCGACGCCAA
GGCTCACGAAACCGAGGTGCACAATGTGTGGGCCACTCACGCCTGCGTGCCCACCGATCCTAATCCTCAA
GAGATCCACCTGGAAAACGTGACCGAGAACTTCAACATGTGGAAGAACAACATGGTCGAGCAGATGCAAG
AGGACGTGATCAGCCTGTGGGACCAGAGCCTGAAGCCTTGCGTGAAGCTGACCCCTCTGTGCGTGACCCT
GAATTGCACCAAGGCCAACCTGACCAACATCAACGAGACAACCGCCAGCAACGGCATCGGCAACATCACC
GACGAAGTGCGGAACTGCAGCTTCAATATGACCACCGAGCTGCGGGACAAGAAACAGAAGGTGCACGCCC
TGTTCTACAAGCTGGACATCGTGCCCATCCGGAACGAGAGCAAGATGGGCAATGTGTCCAGCGAGTACCG
GCTGATCAACTGCAACACCAGCGTGATCAAGCAGGCCTGTCCTAAGATCAGCTTCGACCCCATTCCTATC
CACTACTGCACCCCTGCCGGCTACGCCATCCTGAAGTGCAACGACAAGAATTTCAACGGCACAGGCCCCT
GCAAGAACGTGTCCTCTGTGCAGTGTACACACGGCATCAAGCCCGTGGTGTCTACCCAGCTGCTGCTGAA
TGGAAGCCTGGCCGAGGAAGAGATCATCATCAGAAGCGAGAACCTGACGAACAACGCCAAGACCATCATC
GTGCACCTGAACAAGAGCGTGGAAATCAATTGCACCCGGCCTAGCAACAACACCCGGACCAGCATCACAA
TCGGCCCAGGCCAGGTGTTCTACAGAACCGGCGATATCATCGGCGACATCCGGAAGGCCTACTGCGAGAT
CAATGGCACCAAGTGGAACGAGACACTGAAACAGGTGGCCGGCAAGCTGAAAGAGCACTTCAACAAGACG
ATCATCTTCCAGCCTCCATCTGGCGGCGACCTGGAAATCACCATGCACCACTTCAACTGCAGAGGCGAGT
TCTTCTACTGCAATACCACCAAGCTGTTCAACAGCACCTGGAACGGCACCATGGAAGGCAGAAACGGCAC
AATCATCCTGCCTTGCAGAATCAAGCAGATCATCAATATGTGGCAAGGCGTTGGCCAGGCTATGTACGCC
CCTCCTATCAGCGGCATCATCAACTGCGTGTCCAATATCACCGGCATCCTGCTGACCAGAGATGGCGGCA
ACAACAATGCCACCAACGAAACCTTCAGACCCGGCGGAGGCAATATCAAGGACAACTGGCGGAGCGAGCT
GTACAAGTACAAGGTGGTGCAGATCGAGCCCCTGGGAATCGCCCCTACCAGAGCCAAAGAAAGAGTGGTG
GAACGGGAAAAAGAGTGATGA

Fig. 5L

>ADCC.StrMos.AE.1+1.2delta11gp120

ATGAGAGTGAAGGGCACCCAGATGAACTGGCCCAACCTTTGGAGATGGGGCACCCTGATTCTGGGCCTCG
TGATCATGTGTAGCGCCGTGCCTGTGTGGAAGGACGCCGATACCACACTGTTCTGTGCCAGCGACGCCAA
GGCTCACGAGACAGAGGTGCACAACATCTGGGCCACACACGCCTGCGTGCCCACCGATCCTAATCCTCAA
GAGATCCCTCTGGAAAACGTGACCGAGAACTTCAACATGTGGAAGAACAACATGGCCGAGCAGATGCAAG
AGGACGTGATCAGCCTGTGGGACGAGAGCCTGAAGCCTTGCGTGAAGCTGACCCCTCTGTGTGTGACCCT
GCACTGCACCAAGGCCAATCTGACCCACAACACCACCAACGACAAGAACGGCACCGGCAACATCACCGAC
GAAGTGAAGATCGGCAATATCACGGATGAAGTCAAAAACTGCAGCTTCAATATGACCACCGAGATCCGGG
ACAAGAAGCAGAAGGTCTACGCCCTGTTCTACAAGCTGGACATCGTGCAGATCGGCGAGAACGGCAGCGA
GTACAGACTGATCAACTGCAACACCAGCGTGATCAAGCAGGCCTGTCCTAAGGTGTCCTTCGATCCCATT
CCTATCCACTACTGTGCCCCTGCCGGATACGCCCTGCTGAAGTGCAACGATAAGAAGTTCAACGGCACAG
GCCCCTGCAGAAACGTGTCCAGCGTGCAGTGTACCCACGGCATCAAGCCTGTGGTGTCTACCCAGCTGCT
GCTGAATGGCTCTCTGGCCGAGGAAGAGATCATCATCAGAAGCGAGAACCTGACCGACAACGCCAAGACC
ATCATCGTGCACCTGAACGAGAGCGTGGTCATCAATTGCACCCGGCCTAGCAACAACGTGCGGATCAGCA
CAAGAATCGGCCCAGGCCAGGTGTTCTACAGAACCGGCGAGATCATCGGCGACATCCGGAAGGCCTACTG
CGAGATCAATGGCACCAAGTGGAACAAGGTGCTGAAAGAAGTGACAGAGAAGCTGAAAGAGCACTTCAAC
AAGACGATCATCTTCCAGCCTCCATCTGGCGGCGACCTGGAAATCACCACACACCACTTCAACTGCAGAG
GCGAGTTCTTCTACTGCAATACCACCAAGCTGTTCAACAATACCTGCAACGGCACCATGGAAGGGTTCTG
CAACAACATCACACTGCCCTGCAAGATTAAGCAGATCATCAATATGTGGCAAGGCGCCGGACAGGCCATC
TACGCCCCTCCAATCAGCGGCAGCATTAAGTGCGTGTCCAATATCACCGGCATCATCCTGACCAGAGATG
GCGGCAATGATACCGGCACCAGCGAGATCTTTAGACCCGGCGGAGGCAACATGAAGGACAACTGGCGGAA
CGAGCTGTACAAGTACAAGGTGGTGCAGATTGAGCCCCTGGGCGTCGCCCCTACAAAGGCCAAAGAAAGA
GTGGTGGACCGGGAAAAAGAGTGATGA

Fig. 5M

\>ADCC-StrMos.M.3+2.4
ATGAGAGTGATGGGCATCCAGAGAAACTGCCAGCACCTTTGGAGATGGGGCATCATGCTGCTGGGCATGC
TGATGATCTGCAACGCCGTGCCTGTTTGGAGGGACGCCGAGACAACACTGTTCTGTGCCTCTGACGCCAA
GGGCTACGATACAGAGGCCCATAACGTGTGGGCCACTCACGCCTGTGTGCCCACAGATCCATCTCCACAA
GAGATCCACCTGGAAAACGTGACCGAGGAATTCAACATGTGGAAGAACAACATGGTCGAGCAGATGCACA
CCGACATCATCAGCCTGTGGGACCAGAGCCTGAAGCCTTGCGTGAAGCTGACCCCTCTGTGCGTGACCCT
GGACTGTACCCTGGATTGCAACAACGTGACCAACAACGGCACCAGCGACATGCGGGAAGAGATCAAGAAC
TGCAGCTTCAACATCACCACCGAGCTGCGGGACAAGAAAAAGAAGGTGTACAGCCTGTTCTACAAGCTGG
ACATCGTGCCCATCAACGGCGACAACAGCACCAACACCTACATGCTGATCAATTGCAACACCAGCGCCAT
CACACAGGCTTGCCCCAAAGTGACCTTCGAGCCTATTCCTATCCACTTCTGTGCCCCTGCCGGCTACGCC
ATCCTGAAGTGCAAGGACAAAGAGTTCAACGGCACAGGCCCCTGCAAGAACGTGTCCACCGTGCAGTGTA
CCCACGGCATCAAGCCAGTGGTGTCTACCCAGCTGCTGCTGAATGGCTCTCTGGCCGAAGAGGAAATCAT
GATCAGAAGCGAGAATATCACGAACAACGCCAAGATCATCATCGTGCAGCTGAACCAGAGCGTGGTCATC
AACTGCACCCGGCCTGGCAACAACACCAGAAAGTCTGTGCGGATCGGCCCTGGCCAGACCTTTTATGCCA
CCGGCGATATCATCGGCGACATCAGACAGGCCCACTGTAACGTGTCCCGGATCAAGTGGAACACAGCCCT
GCAGAAGGTGGCCAAGCAGCTGAGAAAGTACTTCCGGAACAAGACCATCACCTTCAACCAGAGCAGCGGA
GGCGACCCCGAGATCACCACACACACCTTTAATTGTGGCGGCGAGTTCTTCTACTGCAACACCTCCAACC
TGTTCAACTCCACCTGGGGCAACGGCAATGGCACCGACAATATGCAGGGCAGCAATAGCACCAATATCAC
CCTGCAGTGCCGCATCAAGCAGATCATTAACATGTGGCAAGAAGTCGGCAGGGCCATCTACGCCCCTCCA
ATCGAGGGCAATATCAGCTGCAGCAGCAACATTACCGGCCTGCTGCTCACCAGAGATGGCGGCAACAGCA
AGAACTCCACCACCGAAGAGATCTTCAGACCCGGCGGAGGCAACATGAGAGACAATTGGAGAAGCGAGCT
GTACAAGTACAAGGTGGTCAAGATCGAGCCCATCGGCGTGGCCCCTACAAAGGCCAGAGAAAGAGTGGTG
GAACGGGAAAAAGAGTGATGA

Fig. 5N

```
>ADCC-StrMos.M.3+2.5
ATGAAAGTGAAGGGCATCCAGAGAAACTGGCCCCAGTGGTGGATCTGGGGCATCCTCGGATTCTGGATGC
TGATGATCTGCAACGTGGTGCCCGTGTGGCGGGAAGCCAATACCACACTGTTTTGTGCCAGCGACGCCAA
GGCCTACGATACCGAGGTGCACAACATCTGGGCCACACACGCCTGCGTGCCCACCGATCCTAATCCTCAA
GAGATCGTGCTGGGCAACGTGACCGAGAACTTCAACATGTGGAAGAACAACATGGTGGACCAGATGCACG
AGGACGTGATCAGCCTGTGGGACGAGAGCCTGAAGCCTTGCGTGAAGCTGACCCCTCTGTGCGTGACCCT
GGAATGCAACGATGCCAAGCTGAACAGCACCAAGACCAACTCCACCACCAACAGCACAGACCCCAACAAC
AGCAACCTGGGCATCGAGGGCGAGATCAAGAACTGCAGCTTCAACACCACCACCGAGATCCGGGACAAGA
AGAAGAGAGCCTACGCTCTGTTCTACAGACCCGATGTGGTGCCCCTGAACGAGAACAGCAGCAGCTACAT
CCTGATCAACTGCAACAGCTCCACCATCACACAGGCTTGCCCCAAGGTGTCCTTCGAGCCCATTCCTATC
CACTACTGTACCCCTGCCGGCTTCGCCCTGCTGAAGTGCAACAACAAGACCTTCAACGGCAGCGGCCCCT
GCACCAATGTGTCTACCGTGCAGTGTACCCACGGCATCAGACCCGTGGTGTCTACACAGCTCCTGCTGAA
TGGCAGCCTGGCCGAAGAGGAAATCGTGATCAGAAGCGAGAATTTCACCGACAACGCCAAGACCATCATC
GTGCAGCTGAACGAGTCCGTGGAAATCAATTGCACCCGGCCTAACAACAACACCAGAAAGAGCATCCGGA
TCGGCCCAGGCCAGGCCTTTTATGCCACCGGCGAGATTATCGGCAACATCCGGCAGGCCTACTGCAACAT
CAACGAGTCCCTGTGGAACGAAACCCTGTATAAGGTGTCCGAGAAGCTGAAAGAGTACTTTAATACCACC
ATCGAGTTCCAGCAGCCTGCCGGCGGAGATCTGGAAATCACCACACACAGCTTCAATTGCAGGGGCGAGT
TCTTCTACTGTAACACGACCAAGCTGTTCAACGGGACCTACAGCCAGCCTAACAGCACCGGCAATACCCC
TCACAGCAACATCACCCTGCCTTGCAAGATCAAGCAGATCATTAACATGTGGCAAGGCGTGGGCAGAGCT
ATGTACGCCCCTCCTATCGCCGGCAACATTACCTGCATCAGCAATATCACCGGCCTGATCCTGACCAGAG
ATGGCGGCGACAAGAACGGCAGCAAGCCCGAGATTTTCAGACCCGGCGGAGGCAACATGAAGGACAATTG
GAGAAGCGAGCTGTACAAGTACAAGGTGGTCGAGATTAAGCCCCTGGGGCTCGCTCCTACAGAGGCCAAG
AGAGAAGTGGTCGAGCGCGAGAAGAGTGATGA
```

Fig. 50

>ADCC-StrMos.B.1+1.1delta11gp120
MRVKGIRKNYQHLWRWGTMLLGMLMICSAVPVWKEATTTLFCASDAKAYDTEVHNVWATH
ACVPTDPNPQEVVLENVTENFNMWKNNMVEQMHEDIISLWDQSLKPCVKLTPLCVTLNCT
DVSSNSTSVNITSEKGEIKNCSFNITTSIRDKVQKEYALFYKLDVVPIEDDSRNNSYRLI
SCNTSVITQACPKVSFEPIPIHYCAPAGFAILKCNDKKFNGTGPCTNVSTVQCTHGIRPV
VSTQLLLNGSLAEEEVVIRSENFTNNAKTIIVQLNESVEINCTRPNNNTRKSIHIGPGRA
FYATGDIIGDIRQAHCNISREKWNNTLKQIVKKLREQFGNKTIVFNQSSGGDPEIVMHSF
NCGGEFFYCNTTQLFNSTWSINGTWNGTTESNDTITLPCRIKQIINMWQEVGKAMYAPPI
RGQIRCSSNITGLLLTRDGGNSSSNNETFRPGGGDMRDNWRSELYKYKVVKIEPLGVAPT
KAKERVVQREKE**

Fig. 6A

>ADCC-StrMos.B.1+1.2delta11gp120
MKVKGIRKNCQHLWRWGIMLLGMLMICSAVPVWKEATTTLFCASDAKAYDTEAHNVWATH
ACVPTDPNPQEIVLENVTENFNMWKNDMVEQMHEDIISLWDESLKPCVELTPLCVTLNCT
NVNATNTNNSSGIEGGEMKNCSFNVTTSIRDKMQKEYALFYSLDVVQIDNDTNYRLINCN
TSVITQACPKISFEPIPIHYCTPAGFAIIKCNDKKFNGSGPCKNVSTVQCTHGIKPVVST
QLLLNGSLAEEEIVIRSENFSDNAKTIIVQLNESVVINCTRPNNNTRKSISIGPGRAFYA
TGDIIGNIRQAHCNLSRAEWNNTLRQIVTKLREQFKNKTIAFNHSSGGDPEIVMHTFNCG
GEFFYCNSTQLFNSTWIANKTGNDTGGSNGTITLQCRIKQIVNRWQEVGKAMYAPPISGQ
ISCSSNITGLILTRDGGTNNTNGTEIFRPGGGNMKDNWRSELYKYKVVRIEPLGIAPTKA
RERVVQREKE**

Fig. 6B

>ADCC-StrNat.B1delta11gp120
MKAKETRKNYQHLWRWGITLLGMLMICSAVPVWKEATTTLFCASDAKAYDTEVHNVWATH
ACVPTDPNPQEVVLENVTENFNMWKNNMVEQMHEDIISLWDQSLKPCVKLTPLCVTLNCT
DDLKNATVKNATNTNNSSWGGMERGEIKNCSFNITTSIRDKVQKEYALFYKLDVVPIDNA
DNNNITTNYTSYRLISCNTSVITQACPKVSFEPIPIHYCAPAGFAILKCNDKKFNGTGPC
TNVSTVQCTHGIRPVVSTQLLLNGSLAEKEVVIRSENFTNNAKTIIVQLDESVVINCTRP
NNNTRKSIHIGPGRAFYTTGEIIGDIRQAHCTLNRTEWNNTLAKITEKLREQFGNNITIV
FNHSSGGDPEIVMHSFICGGEFFYCNTSQLFNSTWNSTGNNISESDNTERNITLPCRIKQ
IINLWQEVGKAMYAPPIRGQIRCSSNITGLLLTRDGGSNTDENRTEIFRPGGGDMRDNWR
SELYKYKVVKIEPLGVAPTKAKERVVQREKE**

Fig. 6C

\>ADCC-StrNat.B2delta11gp120
MRVKETRRIWQHLWKWGTMLLGMLMIYSAVPVWKEATTTLFCASDAKAYDTEVHNVWATH
ACVPTDPNPQEVVLGNVTENFNMWKNNMVEQMHEDVISLWDQSLKPCVKLTPLCVTLNCT
DVLGKGTSANATSANVTSEKGEIKNCSFNITTTLRDKVQKAHALFYRLDVVPIDDNNDNS
SSSYRLINCNTSVITQACPKVSFEPIPIHFCTPAGFALLKCNNKKFNGTGPCTNVSTVQC
THGIKPVVSTQLLLNGSLAEEEVVIRSENFTDNAKTIIVQLNDSVVINCTRPNNNTRKGI
TIGPGSVFYTGEIIGDIRQAHCNLSSAKWNNTLKQIVIKLREQFGNKTIVFNQSSGGDPE
IVLHSFNCGGEFFYCNTTQLFNSTWNINDTRNGTTESSKTITLPCRIKQIINMWQEVGKA
MYAPPIRGQIRCSSNITGLLLTRDGGNQNTSGTEIFRPGGGNMRDNWRSELYKYKVVKIE
PLGIAPTKAKERVVQREKE**

Fig. 6D

\>ADCC-StrNat.B3delta11gp120
MRVKGIRKNCQHLWRWGTMLLGMLMICSAVPVWKEATTTLFCASDAKAYDTEAHNVWATH
ACVPTDPNPQEVVLGNVTENFNMWKNDMVEQMHEDIISLWDQSLKPCVKLTPICVALNCT
DVKDTNNTSNNTNNTSSNNSSMTEGGEMKNCSFNITTSIKTKVKDYALFYKLDIVPIDND
GDNTSYRLISCNTSVITQACPKISFEPIPIHYCTPAGYALLKCNNKKFNGTGPCKNVSTV
QCTHGIRPVVSTQLLLNGSLAEEEVVIRSSNFTNNAKVIIVQLKEAVEINCTRPNNNTRK
SIHIGPGKAWYTTGEIIGNIRQAHCNISRTKWNNTLHQIVKKLRIQFGNKTIIFNQSAGG
DPEIVVHSFNCGGEFFYCNTSQLFNSTWRNDTWNDTSPQIATTGNDTITLPCRIRQIVNM
WQQVGKAMYAPPIAGQIRCSSNITGVLLTRDGGNNESKANANETFRPAGGDMRDNWRSEL
YKYKVVKIEPLGVAPTKAKERVVQREKE**

Fig. 6E

\>ADCC-StrNat.B4delta11gp120
MKVKGIRKNYQHLWRWGMMLLGMLMICSAVPVWRDATTTLFCASDAKAYETELHNVWATH
ACVPTDPNPQEVVLGNVTENFNMWKNDMVEQMNEDIISLWDESLKPCVKLTPLCVTLNCT
NYNETTTNSTTTNATVVSPGEIKNCSFNVTTGIRDKVRKDHALFYALDIVPIDNTIDNTS
YRLVSCNTSVLTQACPKVSFEPIPIHFCAPAGYAIIKCNNKTFNGSGPCRNVSTVQCTHG
IRPVVSTQLLLNGSLAEEEIVIRSANFSDNTKTIIVQLNEAVKINCTRPNNNTRRSVHMG
PGSAFYTTGGIIGDIRQAHCNISERDWNGALKQIVEKLGEQFQNKTIVFKQSSGGDPEVV
MHTFNCRGEFFYCNTTKLFNSTWVNGTKNDTKGGNGTITLQCRIKQIINMWQQVGKAMYA
PPISGPISCSSNITGLILTRDGGTNTTNETFRPGGGDMRDNWRSELYKYKVVKIEPIGVA
PTKARERVVQREKE**

Fig. 6F

>ADCC-StrNat.B5delta11gp120
MRAKETRKKYQHLWAWGTLLLGMLMICSAVPVWKDANTTLFCASDAKAYDTEVHNVWATH
ACVPTDPSPQEIVLKNVTENFNMWKNNMVEQMHKDIISLWDESLKPCVKLTPLCVTLNCS
NYNSTNSTIDPNMEGAIKNCSFNATTGIQNKMKKEYALFYSLDIVQIESENKSNKSYMLR
SCNTSVITQACPKVTFEPIPIHYCAPAGFAILKCNDKKFNGTGPCKNVSTVQCTHGIRPV
VSTQLLLNGSLAEEEIIRSENITNNAKTIIQLNRSIEINCTRPNNNTRKSIHMGWGRA
FYATGDIIGDIRQAHCNLSGTKWNNTLYQIARKLREHFNNTIVFNQSSGGDPEIVMHTFN
CGGEFFYCNTTQLFNSTWHANSTWNETTGSGSNDTISLPCRIKQIINRWQEVGKAMYAPP
IGGQIRCSSNITGILLTRDGGTENNTSETFRPGGGNMKDNWRSELYKYKVVRIEPLGVAP
TKAKERVVQREKE**

Fig. 6G

>ADCC-StrMos-Modified.B.1+1.1delta11gp120
MRVKGIRKNYQHLWRWGTMLLGMLMICSAVPVWKEATTTLFCASDAKAHDTEVHNVWATH
ACVPTDPNPQEVVLENVTENFNMWKNNMVEQMQEDVISLWDQSLKPCVKLTPLCVTLNCT
DVSSNSTSVNITSEKGEIKNCSFNVTTSIKDKVQKEYALFYKLDVVPIEDDSRNNSYRLI
SCNTSVITQACPKVSFEPIPIHYCTPAGFAILKCNDKKFNGTGPCTNVSTVQCTHGIRPV
VSTQLLLNGSLAEEEVVIRSENFTNNAKTIIVQLNESVEINCTRPNNNTRKSIHIGPGRA
FYATGDIIGDIRQAHCNISREKWNNTLKQIVKKLREQFGNKTIVFNQSSGGDPEIVMHSF
NCGGEFFYCNTTQLFNSTWSINGTWNGTTESNDTITLPCRIKQIINMWQEVGKAMYAPPI
RGQIRCSSNITGLLLTRDGGNSSSNNETFRPGGGDMRDNWRSELYKYKVVKIEPLGVAPT
KAKERVVQREKE**

Fig. 6H

>ADCC-StrMos-Modified.B.1+1.2delta11gp120
MKVKGIRKNCQHLWRWGIMLLGMLMICSAVPVWKEATTTLFCASDAKAHDTEAHNVWATH
ACVPTDPNPQEIVLENVTENFNMWKNDMVEQMQEDVISLWDESLKPCVELTPLCVTLNCT
NVNATNTNNSSGIEGGEMKNCSFNVTTSIKDKMQKEYALFYSLDVVQIDNDTNYRLINCN
TSVITQACPKISFEPIPIHYCTPAGFAIIKCNDKKFNGSGPCKNVSTVQCTHGIKPVVST
QLLLNGSLAEEEIVIRSENFSDNAKTIIVQLNESVVINCTRPNNNTRKSISIGPGRAFYA
TGDIIGNIRQAHCNLSRAKWNNTLRQIVTKLREQFKNKTIAFNHSSGGDPEIVMHTFNCG
GEFFYCNSTQLFNSTWIANKTGNDTGGSNGTITLQCRIKQIVNRWQEVGKAMYAPPISGQ
ISCSSNITGLILTRDGGTNNTNGTEIFRPGGGNMKDNWRSELYKYKVVRIEPLGIAPTKA
RERVVQREKE**

Fig. 6I

>ADCC.StrMos.C.1+1.1delta11gp120
MRVRGILRNYQQWWIWGILGFWMLMICNVVPVWKEAKTTLFCASDAKAYEKEVHNVWATH
ACVPTDPNPQEMVLENVTENFNMWKNDMVDQMHEDIISLWDQSLKPCVKLTPLCVTLNCV
NITNSTTSNGDGTVTHINSIKEEIKNCSFNATTELRDKKSKEYALFYRLDIVPLSSGNSS
SNSSKYRLINCNTSTITQACPKVSFDPIPIHYCAPAGYAILKCNNKTFNGTGPCNNVSTV
QCTHGIKPVVSTQLLLNGSLAEEEIIRSENLTDNVKTIIVHLNESVEIVCTRPNNNTRK
SIRIGPGQTFYATGDIIGDIRQAHCNISKGAWNETLQWVGKKLKEHFPNKTIKFNSSSGG
DLEITTHSFNCRGEFFYCNTSGLFNSTYRNNSTGDNSTITLPCRIKQIINMWQEVGRAMY
APPIAGNITCKSNITGLLLTRDGGTRDRNDTETFRPG >ADCC.StrMos.AE.1+1.2delta11gp120
MRVKGTQMNWPNLWRWGTLILGLVIMCSAVPVWKDADTTLFCASDAKAHETEVHNIWATH
ACVPTDPNPQEIPLENVTENFNMWKNNMAEQMQEDVISLWDESLKPCVKLTPLCVTLHCT
KANLTHNTTNDKNGTGNITDEVKIGNITDEVKNCSFNMTTEIRDKKQKVYALFYKLDIVQ
IGENGSEYRLINCNTSVIKQACPKVSFDPIPIHYCAPAGYALLKCNDKKFNGTGPCRNVS
SVQCTHGIKPVVSTQLLLNGSLAEEEIIRSENLTDNAKTIIVHLNESVVINCTRPSNNV
RISTRIGPGQVFYRTGEIIGDIRKAYCEINGTKWNKVLKEVTEKLKEHFNKTIIFQPPSG
GDLEITTHHFNCRGEFFYCNTTKLFNNTCNGTMEGFCNNITLPCKIKQIINMWQGAGQAI
YAPPISGSIKCVSNITGIILTRDGGNDTGTSEIFRPGGGNMKDNWRNELYKYKVVQIEPL
GVAPTKAKERVVDREKE**

Fig. 6M

>ADCC-StrMos.M.3+2.4
MRVMGIQRNCQHLWRWGIMLLGMLMICNAVPVWRDAETTLFCASDAKGYDTEAHNVWATH
ACVPTDPSPQEIHLENVTEEFNMWKNNMVEQMHTDIISLWDQSLKPCVKLTPLCVTLDCT
LDCNNVTNNGTSDMREEIKNCSFNITTELRDKKKKVYSLFYKLDIVPINGDNSTNTYMLI
NCNTSAITQACPKVTFEPIPIHFCAPAGYAILKCKDKEFNGTGPCKNVSTVQCTHGIKPV
VSTQLLLNGSLAEEEIMIRSENITNNAKIIIVQLNQSVVINCTRPGNNTRKSVRIGPGQT
FYATGDIIGDIRQAHCNVSRIKWNTALQKVAKQLRKYFRNKTITFNQSSGGDPEITTHTF
NCGGEFFYCNTSNLFNSTWGNGNGTDNMQGSNSTNITLQCRIKQIINMWQEVGRAIYAPP
IEGNISCSSNITGLLLTRDGGNSKNSTTEEIFRPGGGNMRDNWRSELYKYKVVKIEPIGV
APTKARERVVEREKE**

Fig. 6N

>ADCC-StrMos.M.3+2.5
MKVKGIQRNWPQWWIWGILGFWMLMICNVVPVWREANTTLFCASDAKAYDTEVHNIWATH
ACVPTDPNPQEIVLGNVTENFNMWKNNMVDQMHEDVISLWDESLKPCVKLTPLCVTLECN
DAKLNSTKTNSTTNSTDPNNSNLGIEGEIKNCSFNTTTEIRDKKKRAYALFYRPDVVPLN
ENSSSYILINCNSSTITQACPKVSFEPIPIHYCTPAGFALLKCNNKTFNGSGPCTNVSTV
QCTHGIRPVVSTQLLLNGSLAEEEIVIRSENFTDNAKTIIVQLNESVEINCTRPNNNTRK
SIRIGPGQAFYATGEIIGNIRQAYCNINESLWNETLYKVSEKLKEYFNTTIEFQQPAGGD
LEITTHSFNCRGEFFYCNTTKLFNGTYSQPNSTGNTPHSNITLPCKIKQIINMWQGVGRA
MYAPPIAGNITCISNITGLILTRDGGDKNGSKPEIFRPGGGNMKDNWRSELYKYKVVEIK
PLGLAPTEAKREVVEREKE**

Phylogenetically corrected CH59 signatures, not in contacts

CH59 associations in the A32 contacts

V2 ADCC binding region in gp120, between hypervariable loops

ADCC-StrMos.B.1+1.1
MRVKGIRKNYQHLWRWGTMLLGMLMICSAAEQLWVTVYYGVPVWKEATTTLFCASDAKAYDTEVHNVWATHACVPTDPNPQEVVLE
NVTENFNMWKNNMVEQMHEDIISLWDQSLKPCVKLTPLCVTLNCTDVSSNSTSVNITSEKGEIKNCSFNITTSIRDKVQKEYALFY
KLDVVPIEDDSRNNSYRLISCNTSVITQACPKVSFEPIPIHYCAPAGFAILKCNDKKFNGTGPCTNVSTVQCTHGIRPVVSTQLLL
NGSLAEEEVVIRSENFTNNAKTIIVQLNESVEINCTRPNNNTRKSIHIGPGRAFYATGDIIGDIRQAHCNISREKWNNTLKQIVKK
LREQFGNKTIVFNQSSGGDPEIVMHSFNCGGEFFYCNTTQLFNSTWSINGTWNGTTESNDTITLPCRIKQIINMWQEVGKAMYAPP
IRGQIRCSSNITGLLLTRDGGNSSSNNETFRPGGGDMRDNWRSELYKYKVVKIEPLGVAPTKAKRRVVQREKRV

V1 B_acute_Con_SC31 TDVSSNSTSVNITSE
V2 B_acute_Con_9077 EDDSRNNS
V4 B_acute_Con_TT31P SINGTWNGTTES
V5 B_acute_Con_6247 NSSSNN ADCC-StrMos.B.1+1.2
MKVKGIRKNCQHLWRWGIMLLGMLMICSATEKLWVTVYYGVPVWKEATTTLFCASDAKAYDTEAHNVWATHACVPTDPNPQEIVLE
NVTENFNMWKNDMVEQMHEDIISLWDESLKPCVELTPLCVTLNCTNVNATNTNNSSGIEGGEMKNCSFNVTTSIRDKMQKEYALFY
SLDVVQIDNDTNYRLINCNTSVITQACPKISFEPIPIHYCTPAGFAIIKCNDKKFNGSGPCKNVSTVQCTHGIKPVVSTQLLLNGS
LAEEEIVIRSENFSDNAKTIIVQLNESVVINCTRPNNNTRKSISIGPGRAFYATGDIIGNIRQAHCNLSRAEWNNTLRQIVTKLRE
QFKNKTIAFNHSSGGDPEIVMHTFNCGGEFFYCNSTQLFNSTWIANKTGNDTGGSNGTITLQCRIKQIVNRWQEVGKAMYAPPISG
QISCSSNITGLILTRDGGTNNTNGTEIFRPGGGNMKDNWRSELYKYKVVRIEPLGIAPTKARRRVVQREKRI
Which has coverage: 0.509261

V1 B_acute_Con_63215 TNVNATNTNNSSGIE
V2 B_acute_Con_Z85 DNDTN
V4 B_acute_Con_61792 IANKTGNDTGGS
V5 B_acute_Con_SC20 TNNTNGT

```
ADCC-StrMos-Modified.B.1+1.1deltallgp120  (283)  TRPNNNTRKSIHIGPGRAFYATGDIIGDIRQAH
         ADCC-StrMos.B.1+1.1deltallgp120  (283)  TRPNNNTRKSIHIGPGRAFYATGDIIGDIPQAH
ADCC-StrMos-Modified.B.1+1.2deltallgp120  (280)  TRPNNNTRKSISIGPGRAFYATGDIIGNIRQAH
         ADCC-StrMos.B.1+1.2deltallgp120  (280)  TRPNNNTRKSISIGPGRAFYATGDIIGNIRQAH
                ADCC-StrNat.B4deltallgp120 (287) TRPNNNTPRSVHMGPGSAFYTTGDIIGDIRQAH
                ADCC-StrNat.B5deltallgp120 (283) TRPNNNTRKSIHMGWGRAFYATGDIIGDIPQAH
          ADCC.StrMos.AE.1+1.1deltallgp120 (292) TRPSNNTPTSITIGPSQVFYRTGDIIGDIRKKY
          ADCC.StrMos.AE.1+1.2deltallgp120 (294) TPPSNNVKISTRIGPGQVFYRTGEIIGDIPFAY
           ADCC.StrMos.C.1+1.1deltallgp120 (292) TRPNNNTPKSIRIGPGQTFYATGDIIGDIRKAH
           ADCC.StrMos.C.1+1.2deltallgp120 (286) TRPGNNTRKSVRIGPGQAFYATGEIIGDIRQAY
                ADCC-StrNat.B3deltallgp120 (292) TRPNNNTPKSIRIGPGKAWYTTGEIIGNIRQAH
                ADCC-StrNat.B1deltallgp120 (293) TRPNNNTRKSIHIGPGRAFYTTGEIIGDIRQAH
                ADCC-StrNat.B2deltallgp120 (290) TRPNNNTRKGITIGPG-SVFYTGEIIGDIRQAH
                                 Consensus (302) TRPNNNTRKSI IGPGRAFYATGDIIGDIRQAH
```

Fig. 17B

```
                             1                                  33
    C.1086WT    (1)  TRPNNNTRKSIRIGPGQTFYATGDIIGNIRQAH
  B.6240mutC    (1)  TRPNNNTRKSIRIGPGQTFYATGDIIGDIRQAH
    B.6240WT    (1)  TRPNNNTRKGIHIGLGRALYATGDIIGDIRQAH C.1086WT    (1)  TRPNNNTRKSIRIGPGQTFYATGDIIGNIRQAH
 B.63521mutC    (1)  TRPNNNTRKSIRIGPGQTFYATGEIIGNIRQAH
   B.63521WT    (1)  TRPNNNTRKSIHIGPGRAFYATGETIGNIRQAH C.1086WT    (1)  TRPNNNTRKSIRIGPGQTFYATGDIIGNIRQAH
  B.9021mutC    (1)  TRPNNNTRKSM-IGPGQTFYATGETIGDIRRAH
    B.9021WT    (1)  TRPGNNTRKSIHIAPGRTFYATGEH-GDIRRAH Consensus    (1)  TRPNNNTRKSI IGPGQTFYATGEIIGDIRQAH
```

Fig. 17C

- Group 1. Bivalent clade B structural mosaic Envs
- Group 2. Bivalent clade B natural Envs
- Group 3. Pentavalent clade B natural Envs
  - new pentavalent not in Bradley et al Nature Com (2017):8:15711-
  - that comparison pending)
- Group 4. Bivalent group M structural mosaic Envs
- Group 5. Trivalent clades AE, B, C structural mosaic Envs

See Table 1 immunogens in Groups 1-5. Study in Hartley outbred guinea pigs.

Adjuvant: Rehydragel (same as used in RV144 trial).

Immunizations: 100 ug of each protein, IM X5

Preliminary analyses after bleeds 2 and 4.

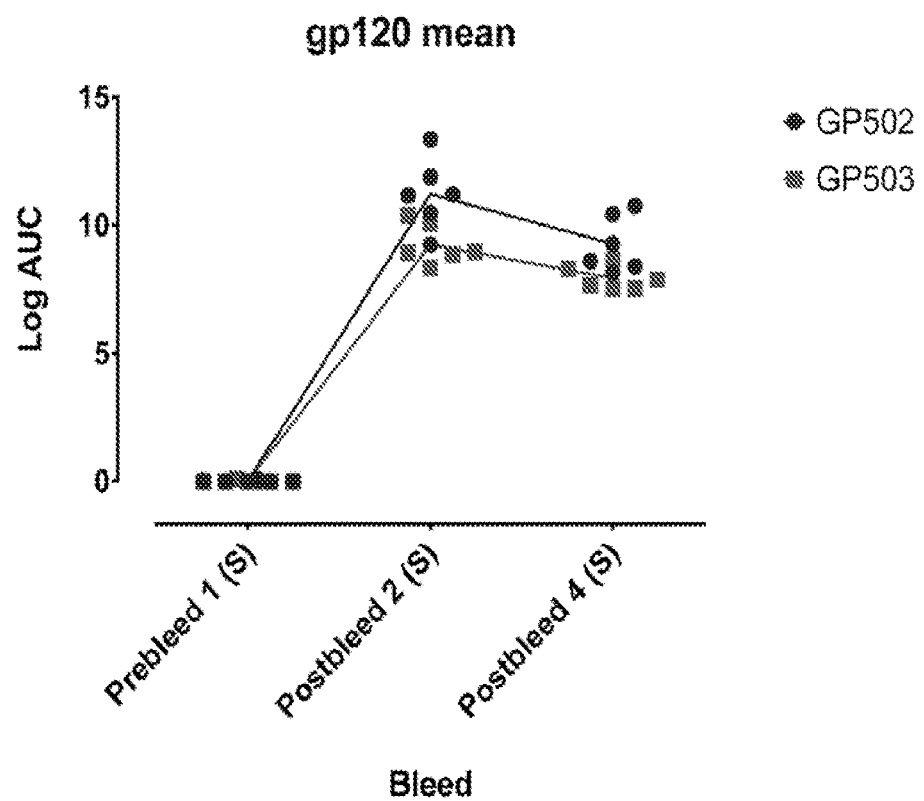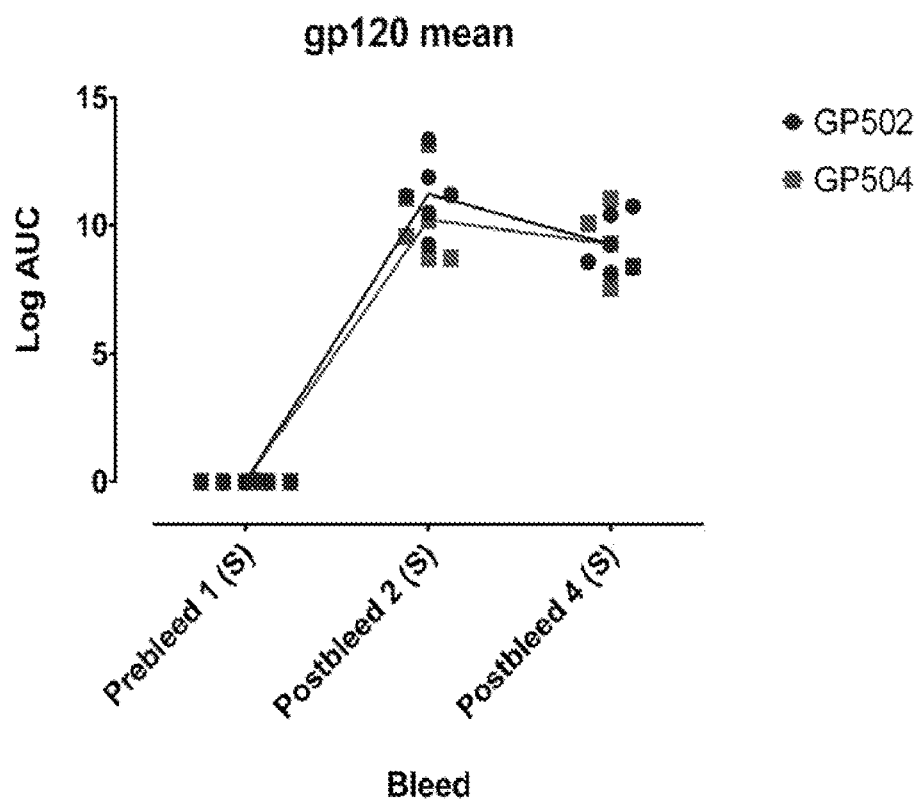
Fig. 19

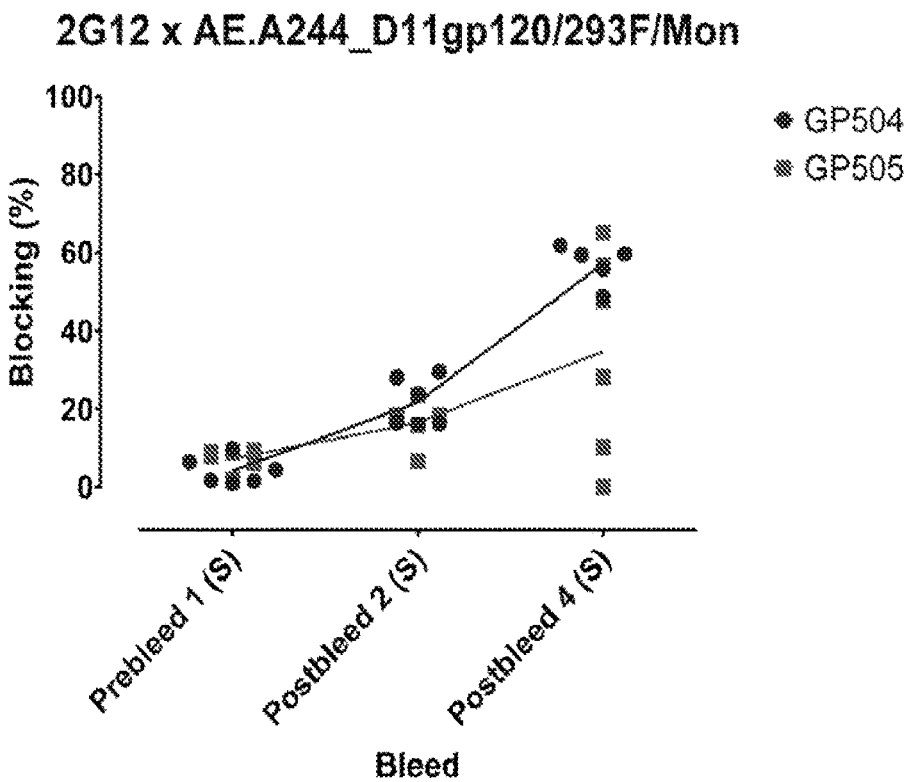
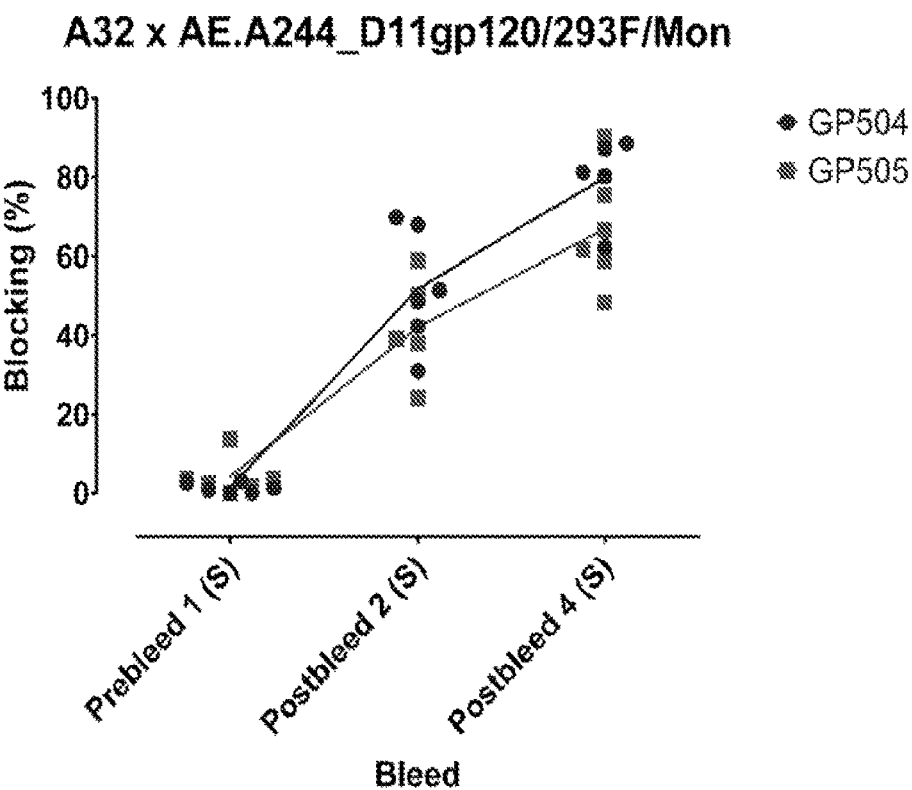
Fig. 29K Continued

```
                        SEQUENCE LISTING

<160> NUMBER OF SEQ ID NOS: 219

<210> SEQ ID NO 1
<211> LENGTH: 492
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Met Arg Val Lys Gly Ile Arg Lys Asn Tyr Gln His Leu Trp Arg Trp
1               5                   10                  15

Gly Thr Met Leu Leu Gly Met Leu Met Ile Cys Ser Ala Val Pro Val
                20                  25                  30

Trp Lys Glu Ala Thr Thr Thr Leu Phe Cys Ala Ser Asp Ala Lys Ala
            35                  40                  45

Tyr Asp Thr Glu Val His Asn Val Trp Ala Thr His Ala Cys Val Pro
    50                  55                  60

Thr Asp Pro Asn Pro Gln Glu Val Val Leu Glu Asn Val Thr Glu Asn
65                  70                  75                  80

Phe Asn Met Trp Lys Asn Asn Met Val Glu Gln Met His Glu Asp Ile
                85                  90                  95

Ile Ser Leu Trp Asp Gln Ser Leu Lys Pro Cys Val Lys Leu Thr Pro
            100                 105                 110

Leu Cys Val Thr Leu Asn Cys Thr Asp Val Ser Ser Asn Ser Thr Ser
        115                 120                 125

Val Asn Ile Thr Ser Glu Lys Gly Glu Ile Lys Asn Cys Ser Phe Asn
130                 135                 140

Ile Thr Thr Ser Ile Arg Asp Lys Val Gln Lys Glu Tyr Ala Leu Phe
145                 150                 155                 160

Tyr Lys Leu Asp Val Val Pro Ile Glu Asp Asp Ser Arg Asn Asn Ser
                165                 170                 175

Tyr Arg Leu Ile Ser Cys Asn Thr Ser Val Ile Thr Gln Ala Cys Pro
            180                 185                 190

Lys Val Ser Phe Glu Pro Ile Pro Ile His Tyr Cys Ala Pro Ala Gly
        195                 200                 205

Phe Ala Ile Leu Lys Cys Asn Asp Lys Lys Phe Asn Gly Thr Gly Pro
    210                 215                 220

Cys Thr Asn Val Ser Thr Val Gln Cys Thr His Gly Ile Arg Pro Val
225                 230                 235                 240

Val Ser Thr Gln Leu Leu Leu Asn Gly Ser Leu Ala Glu Glu Glu Val
                245                 250                 255

Val Ile Arg Ser Glu Asn Phe Thr Asn Asn Ala Lys Thr Ile Ile Val
            260                 265                 270

Gln Leu Asn Glu Ser Val Glu Ile Asn Cys Thr Arg Pro Asn Asn Asn
        275                 280                 285

Thr Arg Lys Ser Ile His Ile Gly Pro Gly Arg Ala Phe Tyr Ala Thr
    290                 295                 300

Gly Asp Ile Ile Gly Asp Ile Arg Gln Ala His Cys Asn Ile Ser Arg
305                 310                 315                 320
```

```
Glu Lys Trp Asn Asn Thr Leu Lys Gln Ile Val Lys Leu Arg Glu
            325                 330                 335

Gln Phe Gly Asn Lys Thr Ile Val Phe Asn Gln Ser Ser Gly Gly Asp
        340                 345                 350

Pro Glu Ile Val Met His Ser Phe Asn Cys Gly Gly Glu Phe Phe Tyr
            355                 360                 365

Cys Asn Thr Thr Gln Leu Phe Asn Ser Thr Trp Ser Ile Asn Gly Thr
370                 375                 380

Trp Asn Gly Thr Thr Glu Ser Asn Asp Thr Ile Thr Leu Pro Cys Arg
385                 390                 395                 400

Ile Lys Gln Ile Ile Asn Met Trp Gln Glu Val Gly Lys Ala Met Tyr
            405                 410                 415

Ala Pro Pro Ile Arg Gly Gln Ile Arg Cys Ser Ser Asn Ile Thr Gly
            420                 425                 430

Leu Leu Leu Thr Arg Asp Gly Gly Asn Ser Ser Ser Asn Asn Glu Thr
            435                 440                 445

Phe Arg Pro Gly Gly Gly Asp Met Arg Asp Asn Trp Arg Ser Glu Leu
        450                 455                 460

Tyr Lys Tyr Lys Val Val Lys Ile Glu Pro Leu Gly Val Ala Pro Thr
465                 470                 475                 480

Lys Ala Lys Glu Arg Val Val Gln Arg Glu Lys Glu
            485                 490

<210> SEQ ID NO 2
<211> LENGTH: 490
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Met Lys Val Lys Gly Ile Arg Lys Asn Cys Gln His Leu Trp Arg Trp
1               5                   10                  15

Gly Ile Met Leu Leu Gly Met Leu Met Ile Cys Ser Ala Val Pro Val
            20                  25                  30

Trp Lys Glu Ala Thr Thr Thr Leu Phe Cys Ala Ser Asp Ala Lys Ala
        35                  40                  45

Tyr Asp Thr Glu Ala His Asn Val Trp Ala Thr His Ala Cys Val Pro
    50                  55                  60

Thr Asp Pro Asn Pro Gln Glu Ile Val Leu Glu Asn Val Thr Glu Asn
65                  70                  75                  80

Phe Asn Met Trp Lys Asn Asp Met Val Glu Gln Met His Glu Asp Ile
                85                  90                  95

Ile Ser Leu Trp Asp Glu Ser Leu Lys Pro Cys Val Glu Leu Thr Pro
            100                 105                 110

Leu Cys Val Thr Leu Asn Cys Thr Asn Val Asn Ala Thr Asn Thr Asn
        115                 120                 125

Asn Ser Ser Gly Ile Glu Gly Gly Glu Met Lys Asn Cys Ser Phe Asn
    130                 135                 140

Val Thr Thr Ser Ile Arg Asp Lys Met Gln Lys Glu Tyr Ala Leu Phe
145                 150                 155                 160

Tyr Ser Leu Asp Val Val Gln Ile Asp Asn Asp Thr Asn Tyr Arg Leu
                165                 170                 175

Ile Asn Cys Asn Thr Ser Val Ile Thr Gln Ala Cys Pro Lys Ile Ser
            180                 185                 190
```

```
Phe Glu Pro Ile Pro Ile His Tyr Cys Thr Pro Ala Gly Phe Ala Ile
            195                 200                 205

Ile Lys Cys Asn Asp Lys Lys Phe Asn Gly Ser Gly Pro Cys Lys Asn
            210                 215                 220

Val Ser Thr Val Gln Cys Thr His Gly Ile Lys Pro Val Val Ser Thr
225                 230                 235                 240

Gln Leu Leu Leu Asn Gly Ser Leu Ala Glu Glu Ile Val Ile Arg
            245                 250                 255

Ser Glu Asn Phe Ser Asp Asn Ala Lys Thr Ile Ile Val Gln Leu Asn
            260                 265                 270

Glu Ser Val Val Ile Asn Cys Thr Arg Pro Asn Asn Thr Arg Lys
            275                 280                 285

Ser Ile Ser Ile Gly Pro Gly Arg Ala Phe Tyr Ala Thr Gly Asp Ile
            290                 295                 300

Ile Gly Asn Ile Arg Gln Ala His Cys Asn Leu Ser Arg Ala Glu Trp
305                 310                 315                 320

Asn Asn Thr Leu Arg Gln Ile Val Thr Lys Leu Arg Glu Gln Phe Lys
            325                 330                 335

Asn Lys Thr Ile Ala Phe Asn His Ser Ser Gly Gly Asp Pro Glu Ile
            340                 345                 350

Val Met His Thr Phe Asn Cys Gly Gly Glu Phe Phe Tyr Cys Asn Ser
            355                 360                 365

Thr Gln Leu Phe Asn Ser Thr Trp Ile Ala Asn Lys Thr Gly Asn Asp
            370                 375                 380

Thr Gly Gly Ser Asn Gly Thr Ile Thr Leu Gln Cys Arg Ile Lys Gln
385                 390                 395                 400

Ile Val Asn Arg Trp Gln Glu Val Gly Lys Ala Met Tyr Ala Pro Pro
            405                 410                 415

Ile Ser Gly Gln Ile Ser Cys Ser Ser Asn Ile Thr Gly Leu Ile Leu
            420                 425                 430

Thr Arg Asp Gly Gly Thr Asn Asn Thr Asn Gly Thr Glu Ile Phe Arg
            435                 440                 445

Pro Gly Gly Gly Asn Met Lys Asp Asn Trp Arg Ser Glu Leu Tyr Lys
            450                 455                 460

Tyr Lys Val Val Arg Ile Glu Pro Leu Gly Ile Ala Pro Thr Lys Ala
465                 470                 475                 480

Arg Glu Arg Val Val Gln Arg Glu Lys Glu
            485                 490

<210> SEQ ID NO 3
<211> LENGTH: 511
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Met Lys Ala Lys Glu Thr Arg Lys Asn Tyr Gln His Leu Trp Arg Trp
1               5                   10                  15

Gly Ile Thr Leu Leu Gly Met Leu Met Ile Cys Ser Ala Val Pro Val
            20                  25                  30

Trp Lys Glu Ala Thr Thr Thr Leu Phe Cys Ala Ser Asp Ala Lys Ala
            35                  40                  45

Tyr Asp Thr Glu Val His Asn Val Trp Ala Thr His Ala Cys Val Pro
```

```
                50                  55                  60
Thr Asp Pro Asn Pro Gln Glu Val Val Leu Glu Asn Val Thr Glu Asn
65                  70                  75                  80

Phe Asn Met Trp Lys Asn Asn Met Val Glu Gln Met His Glu Asp Ile
                85                  90                  95

Ile Ser Leu Trp Asp Gln Ser Leu Lys Pro Cys Val Lys Leu Thr Pro
                100                 105                 110

Leu Cys Val Thr Leu Asn Cys Thr Asp Asp Leu Lys Asn Ala Thr Val
                115                 120                 125

Lys Asn Ala Thr Asn Thr Asn Asn Ser Ser Trp Gly Gly Met Glu Arg
                130                 135                 140

Gly Glu Ile Lys Asn Cys Ser Phe Asn Ile Thr Thr Ser Ile Arg Asp
145                 150                 155                 160

Lys Val Gln Lys Glu Tyr Ala Leu Phe Tyr Lys Leu Asp Val Val Pro
                165                 170                 175

Ile Asp Asn Ala Asp Asn Asn Ile Thr Thr Asn Tyr Thr Ser Tyr
                180                 185                 190

Arg Leu Ile Ser Cys Asn Thr Ser Val Ile Thr Gln Ala Cys Pro Lys
                195                 200                 205

Val Ser Phe Glu Pro Ile Pro Ile His Tyr Cys Ala Pro Ala Gly Phe
210                 215                 220

Ala Ile Leu Lys Cys Asn Asp Lys Lys Phe Asn Gly Thr Gly Pro Cys
225                 230                 235                 240

Thr Asn Val Ser Thr Val Gln Cys Thr His Gly Ile Arg Pro Val Val
                245                 250                 255

Ser Thr Gln Leu Leu Leu Asn Gly Ser Leu Ala Glu Lys Glu Val Val
                260                 265                 270

Ile Arg Ser Glu Asn Phe Thr Asn Asn Ala Lys Thr Ile Ile Val Gln
                275                 280                 285

Leu Asp Glu Ser Val Val Ile Asn Cys Thr Arg Pro Asn Asn Asn Thr
290                 295                 300

Arg Lys Ser Ile His Ile Gly Pro Gly Arg Ala Phe Tyr Thr Thr Gly
305                 310                 315                 320

Glu Ile Ile Gly Asp Ile Arg Gln Ala His Cys Thr Leu Asn Arg Thr
                325                 330                 335

Glu Trp Asn Asn Thr Leu Ala Lys Ile Thr Glu Lys Leu Arg Glu Gln
                340                 345                 350

Phe Gly Asn Asn Ile Thr Ile Val Phe Asn His Ser Ser Gly Gly Asp
                355                 360                 365

Pro Glu Ile Val Met His Ser Phe Ile Cys Gly Gly Glu Phe Phe Tyr
                370                 375                 380

Cys Asn Thr Ser Gln Leu Phe Asn Ser Thr Trp Asn Ser Thr Gly Asn
385                 390                 395                 400

Asn Ile Ser Glu Ser Asp Asn Thr Glu Arg Asn Ile Thr Leu Pro Cys
                405                 410                 415

Arg Ile Lys Gln Ile Ile Asn Leu Trp Gln Glu Val Gly Lys Ala Met
                420                 425                 430

Tyr Ala Pro Pro Ile Arg Gly Gln Ile Arg Cys Ser Ser Asn Ile Thr
                435                 440                 445

Gly Leu Leu Leu Thr Arg Asp Gly Ser Asn Thr Asp Glu Asn Arg
                450                 455                 460

Thr Glu Ile Phe Arg Pro Gly Gly Gly Asp Met Arg Asp Asn Trp Arg
465                 470                 475                 480
```

Ser Glu Leu Tyr Lys Tyr Lys Val Val Lys Ile Glu Pro Leu Gly Val
            485                 490                 495

Ala Pro Thr Lys Ala Lys Glu Arg Val Val Gln Arg Glu Lys Glu
            500                 505                 510

<210> SEQ ID NO 4
<211> LENGTH: 493
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Met Arg Ala Lys Glu Thr Arg Lys Lys Tyr Gln His Leu Trp Ala Trp
1               5                   10                  15

Gly Thr Leu Leu Leu Gly Met Leu Met Ile Cys Ser Ala Val Pro Val
            20                  25                  30

Trp Lys Asp Ala Asn Thr Thr Leu Phe Cys Ala Ser Asp Ala Lys Ala
        35                  40                  45

Tyr Asp Thr Glu Val His Asn Val Trp Ala Thr His Ala Cys Val Pro
    50                  55                  60

Thr Asp Pro Ser Pro Gln Glu Ile Val Leu Lys Asn Val Thr Glu Asn
65                  70                  75                  80

Phe Asn Met Trp Lys Asn Asn Met Val Glu Gln Met His Lys Asp Ile
                85                  90                  95

Ile Ser Leu Trp Asp Glu Ser Leu Lys Pro Cys Val Lys Leu Thr Pro
            100                 105                 110

Leu Cys Val Thr Leu Asn Cys Ser Asn Tyr Asn Ser Thr Asn Ser Thr
        115                 120                 125

Ile Asp Pro Asn Met Glu Gly Ala Ile Lys Asn Cys Ser Phe Asn Ala
    130                 135                 140

Thr Thr Gly Ile Gln Asn Lys Met Lys Lys Glu Tyr Ala Leu Phe Tyr
145                 150                 155                 160

Ser Leu Asp Ile Val Gln Ile Glu Ser Glu Asn Lys Ser Asn Lys Ser
                165                 170                 175

Tyr Met Leu Arg Ser Cys Asn Thr Ser Val Ile Thr Gln Ala Cys Pro
            180                 185                 190

Lys Val Thr Phe Glu Pro Ile Pro Ile His Tyr Cys Ala Pro Ala Gly
        195                 200                 205

Phe Ala Ile Leu Lys Cys Asn Asp Lys Lys Phe Asn Gly Thr Gly Pro
    210                 215                 220

Cys Lys Asn Val Ser Thr Val Gln Cys Thr His Gly Ile Arg Pro Val
225                 230                 235                 240

Val Ser Thr Gln Leu Leu Leu Asn Gly Ser Leu Ala Glu Glu Glu Ile
                245                 250                 255

Ile Ile Arg Ser Glu Asn Ile Thr Asn Asn Ala Lys Thr Ile Ile Ile
            260                 265                 270

Gln Leu Asn Arg Ser Ile Glu Ile Asn Cys Thr Arg Pro Asn Asn Asn
        275                 280                 285

Thr Arg Lys Ser Ile His Met Gly Trp Gly Arg Ala Phe Tyr Ala Thr
    290                 295                 300

Gly Asp Ile Ile Gly Asp Ile Arg Gln Ala His Cys Asn Leu Ser Gly
305                 310                 315                 320

Thr Lys Trp Asn Asn Thr Leu Tyr Gln Ile Ala Arg Lys Leu Arg Glu

```
                325                 330                 335
His Phe Asn Asn Thr Ile Val Phe Asn Gln Ser Ser Gly Gly Asp Pro
            340                 345                 350

Glu Ile Val Met His Thr Phe Asn Cys Gly Gly Glu Phe Phe Tyr Cys
            355                 360                 365

Asn Thr Thr Gln Leu Phe Asn Ser Thr Trp His Ala Asn Ser Thr Trp
370                 375                 380

Asn Glu Thr Thr Gly Ser Gly Ser Asn Asp Thr Ile Ser Leu Pro Cys
385                 390                 395                 400

Arg Ile Lys Gln Ile Ile Asn Arg Trp Gln Glu Val Gly Lys Ala Met
                405                 410                 415

Tyr Ala Pro Pro Ile Gly Gly Gln Ile Arg Cys Ser Ser Asn Ile Thr
            420                 425                 430

Gly Ile Leu Leu Thr Arg Asp Gly Gly Thr Glu Asn Asn Thr Ser Glu
            435                 440                 445

Thr Phe Arg Pro Gly Gly Gly Asn Met Lys Asp Asn Trp Arg Ser Glu
450                 455                 460

Leu Tyr Lys Tyr Lys Val Val Arg Ile Glu Pro Leu Gly Val Ala Pro
465                 470                 475                 480

Thr Lys Ala Lys Glu Arg Val Val Gln Arg Glu Lys Glu
                485                 490

<210> SEQ ID NO 5
<211> LENGTH: 494
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Met Pro Met Gly Ser Leu Gln Pro Leu Ala Thr Leu Tyr Leu Leu Gly
1               5                   10                  15

Met Leu Val Ala Ser Cys Leu Gly Val Pro Val Trp Lys Glu Ala Thr
            20                  25                  30

Thr Thr Leu Phe Cys Ala Ser Asp Ala Lys Ala Tyr Asp Thr Glu Val
        35                  40                  45

His Asn Val Trp Ala Thr His Ala Cys Val Pro Thr Asp Pro Asn Pro
    50                  55                  60

Gln Glu Val Val Leu Gly Asn Val Thr Glu Asn Phe Asn Met Trp Lys
65                  70                  75                  80

Asn Asn Met Val Glu Gln Met His Glu Asp Val Ile Ser Leu Trp Asp
                85                  90                  95

Gln Ser Leu Lys Pro Cys Val Lys Leu Thr Pro Leu Cys Val Thr Leu
            100                 105                 110

Asn Cys Thr Asp Val Leu Gly Lys Gly Thr Ser Ala Asn Ala Thr Ser
        115                 120                 125

Ala Asn Val Thr Ser Glu Lys Gly Glu Ile Lys Asn Cys Ser Phe Asn
    130                 135                 140

Ile Thr Thr Thr Leu Arg Asp Lys Val Gln Lys Ala His Ala Leu Phe
145                 150                 155                 160

Tyr Arg Leu Asp Val Val Pro Ile Asp Asp Asn Asp Asn Ser Ser
                165                 170                 175

Ser Ser Tyr Arg Leu Ile Asn Cys Asn Thr Ser Val Ile Thr Gln Ala
            180                 185                 190
```

```
Cys Pro Lys Val Ser Phe Glu Pro Ile Pro Ile His Phe Cys Thr Pro
            195                 200                 205

Ala Gly Phe Ala Leu Leu Lys Cys Asn Lys Lys Phe Asn Gly Thr
    210                 215                 220

Gly Pro Cys Thr Asn Val Ser Thr Val Gln Cys Thr His Gly Ile Lys
225                 230                 235                 240

Pro Val Val Ser Thr Gln Leu Leu Leu Asn Gly Ser Leu Ala Glu Glu
                245                 250                 255

Glu Val Val Ile Arg Ser Glu Asn Phe Thr Asp Asn Ala Lys Thr Ile
            260                 265                 270

Ile Val Gln Leu Asn Asp Ser Val Val Ile Asn Cys Thr Arg Pro Asn
        275                 280                 285

Asn Asn Thr Arg Lys Gly Ile Thr Ile Gly Pro Gly Ser Val Phe Tyr
    290                 295                 300

Thr Gly Glu Ile Ile Gly Asp Ile Arg Gln Ala His Cys Asn Leu Ser
305                 310                 315                 320

Ser Ala Lys Trp Asn Asn Thr Leu Lys Gln Ile Val Ile Lys Leu Arg
                325                 330                 335

Glu Gln Phe Gly Asn Lys Thr Ile Val Phe Asn Gln Ser Ser Gly Gly
            340                 345                 350

Asp Pro Glu Ile Val Leu His Ser Phe Asn Cys Gly Gly Glu Phe Phe
        355                 360                 365

Tyr Cys Asn Thr Thr Gln Leu Phe Asn Ser Thr Trp Asn Ile Asn Asp
    370                 375                 380

Thr Arg Asn Gly Thr Thr Glu Ser Ser Lys Thr Ile Thr Leu Pro Cys
385                 390                 395                 400

Arg Ile Lys Gln Ile Ile Asn Met Trp Gln Glu Val Gly Lys Ala Met
                405                 410                 415

Tyr Ala Pro Pro Ile Arg Gly Gln Ile Arg Cys Ser Ser Asn Ile Thr
            420                 425                 430

Gly Leu Leu Leu Thr Arg Asp Gly Gly Asn Gln Asn Thr Ser Gly Thr
        435                 440                 445

Glu Ile Phe Arg Pro Gly Gly Gly Asn Met Arg Asp Asn Trp Arg Ser
    450                 455                 460

Glu Leu Tyr Lys Tyr Lys Val Val Lys Ile Glu Pro Leu Gly Ile Ala
465                 470                 475                 480

Pro Thr Lys Ala Lys Glu Arg Val Val Gln Arg Glu Lys Glu
                485                 490

<210> SEQ ID NO 6
<211> LENGTH: 508
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Met Arg Val Lys Gly Ile Arg Lys Asn Cys Gln His Leu Trp Arg Trp
1               5                   10                  15

Gly Thr Met Leu Leu Gly Met Leu Met Ile Cys Ser Ala Val Pro Val
            20                  25                  30

Trp Lys Glu Ala Thr Thr Thr Leu Phe Cys Ala Ser Asp Ala Lys Ala
        35                  40                  45

Tyr Asp Thr Glu Ala His Asn Val Trp Ala Thr His Ala Cys Val Pro
    50                  55                  60
```

```
Thr Asp Pro Asn Pro Gln Glu Val Val Leu Gly Asn Val Thr Glu Asn
 65                  70                  75                  80

Phe Asn Met Trp Lys Asn Asp Met Val Glu Gln Met His Glu Asp Ile
                 85                  90                  95

Ile Ser Leu Trp Asp Gln Ser Leu Lys Pro Cys Val Lys Leu Thr Pro
            100                 105                 110

Ile Cys Val Ala Leu Asn Cys Thr Asp Val Lys Asp Thr Asn Asn Thr
        115                 120                 125

Ser Asn Asn Thr Asn Asn Thr Ser Ser Asn Asn Ser Ser Met Thr Glu
130                 135                 140

Gly Gly Glu Met Lys Asn Cys Ser Phe Asn Ile Thr Thr Ser Ile Lys
145                 150                 155                 160

Thr Lys Val Lys Asp Tyr Ala Leu Phe Tyr Lys Leu Asp Ile Val Pro
                165                 170                 175

Ile Asp Asn Asp Gly Asp Asn Thr Ser Tyr Arg Leu Ile Ser Cys Asn
            180                 185                 190

Thr Ser Val Ile Thr Gln Ala Cys Pro Lys Ile Ser Phe Glu Pro Ile
        195                 200                 205

Pro Ile His Tyr Cys Thr Pro Ala Gly Tyr Ala Leu Leu Lys Cys Asn
210                 215                 220

Asn Lys Lys Phe Asn Gly Thr Gly Pro Cys Lys Asn Val Ser Thr Val
225                 230                 235                 240

Gln Cys Thr His Gly Ile Arg Pro Val Val Ser Thr Gln Leu Leu Leu
                245                 250                 255

Asn Gly Ser Leu Ala Glu Glu Val Val Ile Arg Ser Ser Asn Phe
            260                 265                 270

Thr Asn Asn Ala Lys Val Ile Ile Val Gln Leu Lys Glu Ala Val Glu
        275                 280                 285

Ile Asn Cys Thr Arg Pro Asn Asn Thr Arg Lys Ser Ile His Ile
290                 295                 300

Gly Pro Gly Lys Ala Trp Tyr Thr Thr Gly Glu Ile Ile Gly Asn Ile
305                 310                 315                 320

Arg Gln Ala His Cys Asn Ile Ser Arg Thr Lys Trp Asn Asn Thr Leu
                325                 330                 335

His Gln Ile Val Lys Lys Leu Arg Ile Gln Phe Gly Asn Lys Thr Ile
            340                 345                 350

Ile Phe Asn Gln Ser Ala Gly Gly Asp Pro Glu Ile Val Val His Ser
        355                 360                 365

Phe Asn Cys Gly Gly Glu Phe Phe Tyr Cys Asn Thr Ser Gln Leu Phe
370                 375                 380

Asn Ser Thr Trp Arg Asn Asp Thr Trp Asn Asp Thr Ser Pro Gln Ile
385                 390                 395                 400

Ala Thr Thr Gly Asn Asp Thr Ile Thr Leu Pro Cys Arg Ile Arg Gln
                405                 410                 415

Ile Val Asn Met Trp Gln Val Gly Lys Ala Met Tyr Ala Pro Pro
            420                 425                 430

Ile Ala Gly Gln Ile Arg Cys Ser Ser Asn Ile Thr Gly Val Leu Leu
        435                 440                 445

Thr Arg Asp Gly Gly Asn Asn Glu Ser Lys Ala Asn Ala Asn Glu Thr
450                 455                 460

Phe Arg Pro Ala Gly Gly Asp Met Arg Asp Asn Trp Arg Ser Glu Leu
465                 470                 475                 480
```

Tyr Lys Tyr Lys Val Val Lys Ile Glu Pro Leu Gly Val Ala Pro Thr
            485                 490                 495

Lys Ala Lys Glu Arg Val Val Gln Arg Glu Lys Glu
        500                 505

<210> SEQ ID NO 7
<211> LENGTH: 494
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Met Lys Val Lys Gly Ile Arg Lys Asn Tyr Gln His Leu Trp Arg Trp
1               5                   10                  15

Gly Met Met Leu Leu Gly Met Leu Met Ile Cys Ser Ala Val Pro Val
            20                  25                  30

Trp Arg Asp Ala Thr Thr Thr Leu Phe Cys Ala Ser Asp Ala Lys Ala
        35                  40                  45

Tyr Glu Thr Glu Leu His Asn Val Trp Ala Thr His Ala Cys Val Pro
    50                  55                  60

Thr Asp Pro Asn Pro Gln Glu Val Val Leu Gly Asn Val Thr Glu Asn
65                  70                  75                  80

Phe Asn Met Trp Lys Asn Asp Met Val Glu Gln Met Asn Glu Asp Ile
                85                  90                  95

Ile Ser Leu Trp Asp Glu Ser Leu Lys Pro Cys Val Lys Leu Thr Pro
            100                 105                 110

Leu Cys Val Thr Leu Asn Cys Thr Asn Tyr Asn Glu Thr Thr Thr Asn
        115                 120                 125

Ser Thr Thr Thr Asn Ala Thr Val Val Ser Pro Gly Glu Ile Lys Asn
    130                 135                 140

Cys Ser Phe Asn Val Thr Thr Gly Ile Arg Asp Lys Val Arg Lys Asp
145                 150                 155                 160

His Ala Leu Phe Tyr Ala Leu Asp Ile Val Pro Ile Asp Asn Thr Ile
                165                 170                 175

Asp Asn Thr Ser Tyr Arg Leu Val Ser Cys Asn Thr Ser Val Leu Thr
            180                 185                 190

Gln Ala Cys Pro Lys Val Ser Phe Glu Pro Ile Pro Ile His Phe Cys
        195                 200                 205

Ala Pro Ala Gly Tyr Ala Ile Ile Lys Cys Asn Asn Lys Thr Phe Asn
    210                 215                 220

Gly Ser Gly Pro Cys Arg Asn Val Ser Thr Val Gln Cys Thr His Gly
225                 230                 235                 240

Ile Arg Pro Val Val Ser Thr Gln Leu Leu Leu Asn Gly Ser Leu Ala
                245                 250                 255

Glu Glu Glu Ile Val Ile Arg Ser Ala Asn Phe Ser Asp Asn Thr Lys
            260                 265                 270

Thr Ile Ile Val Gln Leu Asn Glu Ala Val Lys Ile Asn Cys Thr Arg
        275                 280                 285

Pro Asn Asn Asn Thr Arg Arg Ser Val His Met Gly Pro Gly Ser Ala
    290                 295                 300

Phe Tyr Thr Thr Gly Gly Ile Ile Gly Asp Ile Arg Gln Ala His Cys
305                 310                 315                 320

Asn Ile Ser Glu Arg Asp Trp Asn Gly Ala Leu Lys Gln Ile Val Glu
                325                 330                 335

```
Lys Leu Gly Glu Gln Phe Gln Asn Lys Thr Ile Val Phe Lys Gln Ser
                340                 345                 350

Ser Gly Gly Asp Pro Glu Val Val Met His Thr Phe Asn Cys Arg Gly
            355                 360                 365

Glu Phe Phe Tyr Cys Asn Thr Thr Lys Leu Phe Asn Ser Thr Trp Val
        370                 375                 380

Asn Gly Thr Lys Asn Asp Thr Lys Gly Gly Asn Gly Thr Ile Thr Leu
385                 390                 395                 400

Gln Cys Arg Ile Lys Gln Ile Ile Asn Met Trp Gln Val Gly Lys
            405                 410                 415

Ala Met Tyr Ala Pro Pro Ile Ser Gly Pro Ile Ser Cys Ser Ser Asn
            420                 425                 430

Ile Thr Gly Leu Ile Leu Thr Arg Asp Gly Gly Thr Asn Thr Thr Asn
            435                 440                 445

Glu Thr Phe Arg Pro Gly Gly Gly Asp Met Arg Asp Asn Trp Arg Ser
450                 455                 460

Glu Leu Tyr Lys Tyr Lys Val Val Lys Ile Glu Pro Ile Gly Val Ala
465                 470                 475                 480

Pro Thr Lys Ala Arg Glu Arg Val Val Gln Arg Glu Lys Glu
                485                 490

<210> SEQ ID NO 8
<211> LENGTH: 495
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Met Arg Val Met Gly Ile Gln Arg Asn Cys Gln His Leu Trp Arg Trp
1               5                   10                  15

Gly Ile Met Leu Leu Gly Met Leu Met Ile Cys Asn Ala Val Pro Val
            20                  25                  30

Trp Arg Asp Ala Glu Thr Thr Leu Phe Cys Ala Ser Asp Ala Lys Gly
        35                  40                  45

Tyr Asp Thr Glu Ala His Asn Val Trp Ala Thr His Ala Cys Val Pro
    50                  55                  60

Thr Asp Pro Ser Pro Gln Glu Ile His Leu Glu Asn Val Thr Glu Glu
65                  70                  75                  80

Phe Asn Met Trp Lys Asn Asn Met Val Glu Gln Met His Thr Asp Ile
                85                  90                  95

Ile Ser Leu Trp Asp Gln Ser Leu Lys Pro Cys Val Lys Leu Thr Pro
            100                 105                 110

Leu Cys Val Thr Leu Asp Cys Thr Leu Asp Cys Asn Asn Val Thr Asn
        115                 120                 125

Asn Gly Thr Ser Asp Met Arg Glu Glu Ile Lys Asn Cys Ser Phe Asn
    130                 135                 140

Ile Thr Thr Glu Leu Arg Asp Lys Lys Lys Val Tyr Ser Leu Phe
145                 150                 155                 160

Tyr Lys Leu Asp Ile Val Pro Ile Asn Gly Asp Asn Ser Thr Asn Thr
                165                 170                 175

Tyr Met Leu Ile Asn Cys Asn Thr Ser Ala Ile Thr Gln Ala Cys Pro
            180                 185                 190

Lys Val Thr Phe Glu Pro Ile Pro Ile His Phe Cys Ala Pro Ala Gly
```

```
            195                 200                 205
Tyr Ala Ile Leu Lys Cys Lys Asp Lys Glu Phe Asn Gly Thr Gly Pro
210                 215                 220

Cys Lys Asn Val Ser Thr Val Gln Cys Thr His Gly Ile Lys Pro Val
225                 230                 235                 240

Val Ser Thr Gln Leu Leu Asn Gly Ser Leu Ala Glu Glu Ile
                    245                 250                 255

Met Ile Arg Ser Glu Asn Ile Thr Asn Asn Ala Lys Ile Ile Val
            260                 265                 270

Gln Leu Asn Gln Ser Val Val Ile Asn Cys Thr Arg Pro Gly Asn Asn
            275                 280                 285

Thr Arg Lys Ser Val Arg Ile Gly Pro Gly Gln Thr Phe Tyr Ala Thr
290                 295                 300

Gly Asp Ile Ile Gly Asp Ile Arg Gln Ala His Cys Asn Val Ser Arg
305                 310                 315                 320

Ile Lys Trp Asn Thr Ala Leu Gln Lys Val Ala Lys Gln Leu Arg Lys
                    325                 330                 335

Tyr Phe Arg Asn Lys Thr Ile Thr Phe Asn Gln Ser Ser Gly Gly Asp
            340                 345                 350

Pro Glu Ile Thr Thr His Thr Phe Asn Cys Gly Gly Glu Phe Phe Tyr
            355                 360                 365

Cys Asn Thr Ser Asn Leu Phe Asn Ser Thr Trp Gly Asn Gly Asn Gly
370                 375                 380

Thr Asp Asn Met Gln Gly Ser Asn Ser Thr Asn Ile Thr Leu Gln Cys
385                 390                 395                 400

Arg Ile Lys Gln Ile Ile Asn Met Trp Gln Glu Val Gly Arg Ala Ile
                    405                 410                 415

Tyr Ala Pro Pro Ile Glu Gly Asn Ile Ser Cys Ser Ser Asn Ile Thr
            420                 425                 430

Gly Leu Leu Leu Thr Arg Asp Gly Gly Asn Ser Lys Asn Ser Thr Thr
            435                 440                 445

Glu Glu Ile Phe Arg Pro Gly Gly Gly Asn Met Arg Asp Asn Trp Arg
450                 455                 460

Ser Glu Leu Tyr Lys Tyr Lys Val Val Lys Ile Glu Pro Ile Gly Val
465                 470                 475                 480

Ala Pro Thr Lys Ala Arg Glu Arg Val Val Glu Arg Glu Lys Glu
                    485                 490                 495

<210> SEQ ID NO 9
<211> LENGTH: 492
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Met Asp Ala Met Lys Arg Gly Leu Cys Cys Val Leu Leu Leu Cys Gly
1               5                   10                  15

Ala Val Phe Val Ser Pro Val Pro Val Trp Arg Glu Ala Asn Thr Thr
            20                  25                  30

Leu Phe Cys Ala Ser Asp Ala Lys Ala Tyr Asp Thr Glu Val His Asn
        35                  40                  45

Ile Trp Ala Thr His Ala Cys Val Pro Thr Asp Pro Asn Pro Gln Glu
    50                  55                  60
```

-continued

Ile Val Leu Gly Asn Val Thr Glu Asn Phe Asn Met Trp Lys Asn Asn
 65                  70                  75                  80

Met Val Asp Gln Met His Glu Asp Val Ile Ser Leu Trp Asp Glu Ser
                 85                  90                  95

Leu Lys Pro Cys Val Lys Leu Thr Pro Leu Cys Val Thr Leu Glu Cys
            100                 105                 110

Asn Asp Ala Lys Leu Asn Ser Thr Lys Thr Asn Ser Thr Asn Ser
        115                 120                 125

Thr Asp Pro Asn Asn Ser Asn Leu Gly Ile Glu Gly Glu Ile Lys Asn
    130                 135                 140

Cys Ser Phe Asn Thr Thr Thr Glu Ile Arg Asp Lys Lys Arg Ala
145                 150                 155                 160

Tyr Ala Leu Phe Tyr Arg Pro Asp Val Val Pro Leu Asn Glu Asn Ser
                165                 170                 175

Ser Ser Tyr Ile Leu Ile Asn Cys Asn Ser Ser Thr Ile Thr Gln Ala
            180                 185                 190

Cys Pro Lys Val Ser Phe Glu Pro Ile Pro Ile His Tyr Cys Thr Pro
        195                 200                 205

Ala Gly Phe Ala Leu Leu Lys Cys Asn Asn Lys Thr Phe Asn Gly Ser
210                 215                 220

Gly Pro Cys Thr Asn Val Ser Thr Val Gln Cys Thr His Gly Ile Arg
225                 230                 235                 240

Pro Val Val Ser Thr Gln Leu Leu Leu Asn Gly Ser Leu Ala Glu Glu
                245                 250                 255

Glu Ile Val Ile Arg Ser Glu Asn Phe Thr Asp Asn Ala Lys Thr Ile
            260                 265                 270

Ile Val Gln Leu Asn Glu Ser Val Glu Ile Asn Cys Thr Arg Pro Asn
        275                 280                 285

Asn Asn Thr Arg Lys Ser Ile Arg Ile Gly Pro Gly Gln Ala Phe Tyr
    290                 295                 300

Ala Thr Gly Glu Ile Ile Gly Asn Ile Arg Gln Ala Tyr Cys Asn Ile
305                 310                 315                 320

Asn Glu Ser Leu Trp Asn Glu Thr Leu Tyr Lys Val Ser Glu Lys Leu
                325                 330                 335

Lys Glu Tyr Phe Asn Thr Thr Ile Glu Phe Gln Gln Pro Ala Gly Gly
            340                 345                 350

Asp Leu Glu Ile Thr Thr His Ser Phe Asn Cys Arg Gly Glu Phe Phe
        355                 360                 365

Tyr Cys Asn Thr Thr Lys Leu Phe Asn Gly Thr Tyr Ser Gln Pro Asn
    370                 375                 380

Ser Thr Gly Asn Thr Pro His Ser Asn Ile Thr Leu Pro Cys Lys Ile
385                 390                 395                 400

Lys Gln Ile Ile Asn Met Trp Gln Gly Val Gly Arg Ala Met Tyr Ala
                405                 410                 415

Pro Pro Ile Ala Gly Asn Ile Thr Cys Ile Ser Asn Ile Thr Gly Leu
            420                 425                 430

Ile Leu Thr Arg Asp Gly Gly Asp Lys Asn Gly Ser Lys Pro Glu Ile
        435                 440                 445

Phe Arg Pro Gly Gly Gly Asn Met Lys Asp Asn Trp Arg Ser Glu Leu
    450                 455                 460

Tyr Lys Tyr Lys Val Val Glu Ile Lys Pro Leu Gly Leu Ala Pro Thr
465                 470                 475                 480

Glu Ala Lys Arg Glu Val Val Glu Arg Glu Lys Glu

-continued

```
                485                 490

<210> SEQ ID NO 10
<211> LENGTH: 490
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Met Asp Ala Met Lys Arg Gly Leu Cys Cys Val Leu Leu Leu Cys Gly
1               5                   10                  15

Ala Val Phe Val Ser Pro Val Pro Trp Lys Glu Ala Lys Thr Thr
            20                  25                  30

Leu Phe Cys Ala Ser Asp Ala Lys Ala Tyr Glu Lys Glu Val His Asn
        35                  40                  45

Val Trp Ala Thr His Ala Cys Val Pro Thr Asp Pro Asn Pro Gln Glu
    50                  55                  60

Met Val Leu Glu Asn Val Thr Glu Asn Phe Asn Met Trp Lys Asn Asp
65                  70                  75                  80

Met Val Asp Gln Met His Glu Asp Ile Ile Ser Leu Trp Asp Gln Ser
                85                  90                  95

Leu Lys Pro Cys Val Lys Leu Thr Pro Leu Cys Val Thr Leu Asn Cys
            100                 105                 110

Val Asn Ile Thr Asn Ser Thr Thr Ser Asn Gly Asp Gly Thr Val Thr
        115                 120                 125

His Ile Asn Ser Ile Lys Glu Glu Ile Lys Asn Cys Ser Phe Asn Ala
    130                 135                 140

Thr Thr Glu Leu Arg Asp Lys Lys Ser Lys Glu Tyr Ala Leu Phe Tyr
145                 150                 155                 160

Arg Leu Asp Ile Val Pro Leu Ser Ser Gly Asn Ser Ser Ser Asn Ser
                165                 170                 175

Ser Lys Tyr Arg Leu Ile Asn Cys Asn Thr Ser Thr Ile Thr Gln Ala
            180                 185                 190

Cys Pro Lys Val Ser Phe Asp Pro Ile Pro Ile His Tyr Cys Ala Pro
        195                 200                 205

Ala Gly Tyr Ala Ile Leu Lys Cys Asn Asn Lys Thr Phe Asn Gly Thr
    210                 215                 220

Gly Pro Cys Asn Asn Val Ser Thr Val Gln Cys Thr His Gly Ile Lys
225                 230                 235                 240

Pro Val Val Ser Thr Gln Leu Leu Leu Asn Gly Ser Leu Ala Glu Glu
                245                 250                 255

Glu Ile Ile Ile Arg Ser Glu Asn Leu Thr Asp Asn Val Lys Thr Ile
            260                 265                 270

Ile Val His Leu Asn Glu Ser Val Glu Ile Val Cys Thr Arg Pro Asn
        275                 280                 285

Asn Asn Thr Arg Lys Ser Ile Arg Ile Gly Pro Gly Gln Thr Phe Tyr
    290                 295                 300

Ala Thr Gly Asp Ile Ile Gly Asp Ile Arg Gln Ala His Cys Asn Ile
305                 310                 315                 320

Ser Lys Gly Ala Trp Asn Glu Thr Leu Gln Trp Val Gly Lys Lys Leu
                325                 330                 335

Lys Glu His Phe Pro Asn Lys Thr Ile Lys Phe Asn Ser Ser Ser Gly
            340                 345                 350
```

```
Gly Asp Leu Glu Ile Thr Thr His Ser Phe Asn Cys Arg Gly Glu Phe
            355                 360                 365

Phe Tyr Cys Asn Thr Ser Gly Leu Phe Asn Ser Thr Tyr Arg Asn Asn
370                 375                 380

Ser Thr Gly Asp Asn Ser Thr Ile Thr Leu Pro Cys Arg Ile Lys Gln
385                 390                 395                 400

Ile Ile Asn Met Trp Gln Glu Val Gly Arg Ala Met Tyr Ala Pro Pro
                405                 410                 415

Ile Ala Gly Asn Ile Thr Cys Lys Ser Asn Ile Thr Gly Leu Leu Leu
            420                 425                 430

Thr Arg Asp Gly Gly Thr Arg Asp Arg Asn Asp Thr Glu Thr Phe Arg
        435                 440                 445

Pro Gly Gly Gly Asp Met Arg Asp Asn Trp Arg Ser Glu Leu Tyr Lys
    450                 455                 460

Tyr Lys Val Val Glu Ile Lys Pro Leu Gly Ile Ala Pro Thr Lys Ala
465                 470                 475                 480

Lys Glu Arg Val Val Glu Arg Glu Lys Glu
                485                 490

<210> SEQ ID NO 11
<211> LENGTH: 495
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Met Arg Val Lys Glu Thr Gln Met Asn Trp Pro Asn Leu Trp Lys Trp
1               5                   10                  15

Gly Thr Leu Ile Leu Gly Leu Val Ile Ile Cys Ser Ala Val Pro Val
            20                  25                  30

Trp Arg Asp Ala Asp Thr Thr Leu Phe Cys Ala Ser Asp Ala Lys Ala
        35                  40                  45

His Glu Thr Glu Val His Asn Val Trp Ala Thr His Ala Cys Val Pro
    50                  55                  60

Thr Asp Pro Asn Pro Gln Glu Ile His Leu Glu Asn Val Thr Glu Asn
65                  70                  75                  80

Phe Asn Met Trp Lys Asn Asn Met Val Glu Gln Met Gln Glu Asp Val
                85                  90                  95

Ile Ser Leu Trp Asp Gln Ser Leu Lys Pro Cys Val Lys Leu Thr Pro
            100                 105                 110

Leu Cys Val Thr Leu Asn Cys Thr Lys Ala Asn Leu Thr Asn Ile Asn
        115                 120                 125

Glu Thr Thr Ala Ser Asn Gly Ile Gly Asn Ile Thr Asp Glu Val Arg
    130                 135                 140

Asn Cys Ser Phe Asn Met Thr Thr Glu Leu Arg Asp Lys Lys Gln Lys
145                 150                 155                 160

Val His Ala Leu Phe Tyr Lys Leu Asp Ile Val Pro Ile Arg Asn Glu
                165                 170                 175

Ser Lys Met Gly Asn Val Ser Ser Glu Tyr Arg Leu Ile Asn Cys Asn
            180                 185                 190

Thr Ser Val Ile Lys Gln Ala Cys Pro Lys Ile Ser Phe Asp Pro Ile
        195                 200                 205

Pro Ile His Tyr Cys Thr Pro Ala Gly Tyr Ala Ile Leu Lys Cys Asn
    210                 215                 220
```

-continued

Asp Lys Asn Phe Asn Gly Thr Gly Pro Cys Lys Asn Val Ser Ser Val
225                 230                 235                 240

Gln Cys Thr His Gly Ile Lys Pro Val Val Ser Thr Gln Leu Leu Leu
            245                 250                 255

Asn Gly Ser Leu Ala Glu Glu Ile Ile Arg Ser Glu Asn Leu
        260                 265                 270

Thr Asn Asn Ala Lys Thr Ile Ile Val His Leu Asn Lys Ser Val Glu
        275                 280                 285

Ile Asn Cys Thr Arg Pro Ser Asn Asn Thr Arg Thr Ser Ile Thr Ile
290                 295                 300

Gly Pro Gly Gln Val Phe Tyr Arg Thr Gly Asp Ile Ile Gly Asp Ile
305                 310                 315                 320

Arg Lys Ala Tyr Cys Glu Ile Asn Gly Thr Lys Trp Asn Glu Thr Leu
                325                 330                 335

Lys Gln Val Ala Gly Lys Leu Lys Glu His Phe Asn Lys Thr Ile Ile
            340                 345                 350

Phe Gln Pro Pro Ser Gly Gly Asp Leu Glu Ile Thr Met His His Phe
        355                 360                 365

Asn Cys Arg Gly Glu Phe Phe Tyr Cys Asn Thr Thr Lys Leu Phe Asn
    370                 375                 380

Ser Thr Trp Asn Gly Thr Met Glu Gly Arg Asn Gly Thr Ile Ile Leu
385                 390                 395                 400

Pro Cys Arg Ile Lys Gln Ile Ile Asn Met Trp Gln Gly Val Gly Gln
                405                 410                 415

Ala Met Tyr Ala Pro Pro Ile Ser Gly Ile Ile Asn Cys Val Ser Asn
            420                 425                 430

Ile Thr Gly Ile Leu Leu Thr Arg Asp Gly Gly Asn Asn Asn Ala Thr
        435                 440                 445

Asn Glu Thr Phe Arg Pro Gly Gly Gly Asn Ile Lys Asp Asn Trp Arg
    450                 455                 460

Ser Glu Leu Tyr Lys Tyr Lys Val Val Gln Ile Glu Pro Leu Gly Ile
465                 470                 475                 480

Ala Pro Thr Arg Ala Lys Glu Arg Val Val Glu Arg Glu Lys Glu
                485                 490                 495

<210> SEQ ID NO 12
<211> LENGTH: 463
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Val Pro Val Trp Lys Glu Ala Thr Thr Thr Leu Phe Cys Ala Ser Asp
1               5                   10                  15

Ala Lys Ala Tyr Asp Thr Glu Val His Asn Val Trp Ala Thr His Ala
            20                  25                  30

Cys Val Pro Thr Asp Pro Asn Pro Gln Glu Val Val Leu Glu Asn Val
        35                  40                  45

Thr Glu Asn Phe Asn Met Trp Lys Asn Asn Met Val Glu Gln Met His
    50                  55                  60

Glu Asp Ile Ile Ser Leu Trp Asp Gln Ser Leu Lys Pro Cys Val Lys
65                  70                  75                  80

Leu Thr Pro Leu Cys Val Thr Leu Asn Cys Thr Asp Val Ser Ser Asn

```
                        85                  90                  95
Ser Thr Ser Val Asn Ile Thr Ser Glu Lys Gly Glu Ile Lys Asn Cys
                100                 105                 110

Ser Phe Asn Ile Thr Thr Ser Ile Arg Asp Lys Val Gln Lys Glu Tyr
            115                 120                 125

Ala Leu Phe Tyr Lys Leu Asp Val Val Pro Ile Glu Asp Asp Ser Arg
        130                 135                 140

Asn Asn Ser Tyr Arg Leu Ile Ser Cys Asn Thr Ser Val Ile Thr Gln
145                 150                 155                 160

Ala Cys Pro Lys Val Ser Phe Glu Pro Ile Pro Ile His Tyr Cys Ala
                165                 170                 175

Pro Ala Gly Phe Ala Ile Leu Lys Cys Asn Asp Lys Lys Phe Asn Gly
            180                 185                 190

Thr Gly Pro Cys Thr Asn Val Ser Thr Val Gln Cys Thr His Gly Ile
        195                 200                 205

Arg Pro Val Val Ser Thr Gln Leu Leu Leu Asn Gly Ser Leu Ala Glu
    210                 215                 220

Glu Val Val Ile Arg Ser Glu Asn Phe Thr Asn Asn Ala Lys Thr
225                 230                 235                 240

Ile Ile Val Gln Leu Asn Glu Ser Val Glu Ile Asn Cys Thr Arg Pro
                245                 250                 255

Asn Asn Asn Thr Arg Lys Ser Ile His Ile Gly Pro Gly Arg Ala Phe
            260                 265                 270

Tyr Ala Thr Gly Asp Ile Ile Gly Asp Ile Arg Gln Ala His Cys Asn
        275                 280                 285

Ile Ser Arg Glu Lys Trp Asn Asn Thr Leu Lys Gln Ile Val Lys Lys
    290                 295                 300

Leu Arg Glu Gln Phe Gly Asn Lys Thr Ile Val Phe Asn Gln Ser Ser
305                 310                 315                 320

Gly Gly Asp Pro Glu Ile Val Met His Ser Phe Asn Cys Gly Gly Glu
                325                 330                 335

Phe Phe Tyr Cys Asn Thr Thr Gln Leu Phe Asn Ser Thr Trp Ser Ile
            340                 345                 350

Asn Gly Thr Trp Asn Gly Thr Thr Glu Ser Asn Asp Thr Ile Thr Leu
        355                 360                 365

Pro Cys Arg Ile Lys Gln Ile Ile Asn Met Trp Gln Glu Val Gly Lys
    370                 375                 380

Ala Met Tyr Ala Pro Pro Ile Arg Gly Gln Ile Arg Cys Ser Ser Asn
385                 390                 395                 400

Ile Thr Gly Leu Leu Leu Thr Arg Asp Gly Gly Asn Ser Ser Ser Asn
                405                 410                 415

Asn Glu Thr Phe Arg Pro Gly Gly Gly Asp Met Arg Asp Asn Trp Arg
            420                 425                 430

Ser Glu Leu Tyr Lys Tyr Lys Val Val Lys Ile Glu Pro Leu Gly Val
        435                 440                 445

Ala Pro Thr Lys Ala Lys Glu Arg Val Val Gln Arg Glu Lys Glu
    450                 455                 460
```

<210> SEQ ID NO 13
<211> LENGTH: 461
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 13

```
Val Pro Val Trp Lys Glu Ala Thr Thr Thr Leu Phe Cys Ala Ser Asp
1               5                   10                  15

Ala Lys Ala Tyr Asp Thr Glu Ala His Asn Val Trp Ala Thr His Ala
            20                  25                  30

Cys Val Pro Thr Asp Pro Asn Pro Gln Glu Ile Val Leu Glu Asn Val
        35                  40                  45

Thr Glu Asn Phe Asn Met Trp Lys Asn Asp Met Val Glu Gln Met His
    50                  55                  60

Glu Asp Ile Ile Ser Leu Trp Asp Glu Ser Leu Lys Pro Cys Val Glu
65                  70                  75                  80

Leu Thr Pro Leu Cys Val Thr Leu Asn Cys Thr Asn Val Asn Ala Thr
                85                  90                  95

Asn Thr Asn Asn Ser Ser Gly Ile Glu Gly Gly Glu Met Lys Asn Cys
            100                 105                 110

Ser Phe Asn Val Thr Thr Ser Ile Arg Asp Lys Met Gln Lys Glu Tyr
        115                 120                 125

Ala Leu Phe Tyr Ser Leu Asp Val Val Gln Ile Asp Asn Asp Thr Asn
    130                 135                 140

Tyr Arg Leu Ile Asn Cys Asn Thr Ser Val Ile Thr Gln Ala Cys Pro
145                 150                 155                 160

Lys Ile Ser Phe Glu Pro Ile Pro Ile His Tyr Cys Thr Pro Ala Gly
                165                 170                 175

Phe Ala Ile Ile Lys Cys Asn Asp Lys Lys Phe Asn Gly Ser Gly Pro
            180                 185                 190

Cys Lys Asn Val Ser Thr Val Gln Cys Thr His Gly Ile Lys Pro Val
        195                 200                 205

Val Ser Thr Gln Leu Leu Asn Gly Ser Leu Ala Glu Glu Glu Ile
    210                 215                 220

Val Ile Arg Ser Glu Asn Phe Ser Asp Asn Ala Lys Thr Ile Ile Val
225                 230                 235                 240

Gln Leu Asn Glu Ser Val Val Ile Asn Cys Thr Arg Pro Asn Asn Asn
                245                 250                 255

Thr Arg Lys Ser Ile Ser Ile Gly Pro Gly Arg Ala Phe Tyr Ala Thr
            260                 265                 270

Gly Asp Ile Ile Gly Asn Ile Arg Gln Ala His Cys Asn Leu Ser Arg
        275                 280                 285

Ala Glu Trp Asn Asn Thr Leu Arg Gln Ile Val Thr Lys Leu Arg Glu
    290                 295                 300

Gln Phe Lys Asn Lys Thr Ile Ala Phe Asn His Ser Ser Gly Gly Asp
305                 310                 315                 320

Pro Glu Ile Val Met His Thr Phe Asn Cys Gly Gly Glu Phe Phe Tyr
                325                 330                 335

Cys Asn Ser Thr Gln Leu Phe Asn Ser Thr Trp Ile Ala Asn Lys Thr
            340                 345                 350

Gly Asn Asp Thr Gly Gly Ser Asn Gly Thr Ile Thr Leu Gln Cys Arg
        355                 360                 365

Ile Lys Gln Ile Val Asn Arg Trp Gln Glu Val Gly Lys Ala Met Tyr
    370                 375                 380

Ala Pro Pro Ile Ser Gly Gln Ile Ser Cys Ser Ser Asn Ile Thr Gly
385                 390                 395                 400

Leu Ile Leu Thr Arg Asp Gly Gly Thr Asn Asn Thr Asn Gly Thr Glu
```

```
                 405                 410                 415
Ile Phe Arg Pro Gly Gly Gly Asn Met Lys Asp Asn Trp Arg Ser Glu
            420                 425                 430

Leu Tyr Lys Tyr Lys Val Val Arg Ile Glu Pro Leu Gly Ile Ala Pro
        435                 440                 445

Thr Lys Ala Arg Glu Arg Val Val Gln Arg Glu Lys Glu
    450                 455                 460

<210> SEQ ID NO 14
<211> LENGTH: 482
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Val Pro Val Trp Lys Glu Ala Thr Thr Thr Leu Phe Cys Ala Ser Asp
1               5                   10                  15

Ala Lys Ala Tyr Asp Thr Glu Val His Asn Val Trp Ala Thr His Ala
            20                  25                  30

Cys Val Pro Thr Asp Pro Asn Pro Gln Glu Val Val Leu Glu Asn Val
        35                  40                  45

Thr Glu Asn Phe Asn Met Trp Lys Asn Met Val Glu Gln Met His
    50                  55                  60

Glu Asp Ile Ile Ser Leu Trp Asp Gln Ser Leu Lys Pro Cys Val Lys
65                  70                  75                  80

Leu Thr Pro Leu Cys Val Thr Leu Asn Cys Thr Asp Asp Leu Lys Asn
                85                  90                  95

Ala Thr Val Lys Asn Ala Thr Asn Thr Asn Asn Ser Ser Trp Gly Gly
            100                 105                 110

Met Glu Arg Gly Glu Ile Lys Asn Cys Ser Phe Asn Ile Thr Thr Ser
        115                 120                 125

Ile Arg Asp Lys Val Gln Lys Glu Tyr Ala Leu Phe Tyr Lys Leu Asp
    130                 135                 140

Val Val Pro Ile Asp Asn Ala Asp Asn Asn Ile Thr Thr Asn Tyr
145                 150                 155                 160

Thr Ser Tyr Arg Leu Ile Ser Cys Asn Thr Ser Val Ile Thr Gln Ala
                165                 170                 175

Cys Pro Lys Val Ser Phe Glu Pro Ile Pro Ile His Tyr Cys Ala Pro
            180                 185                 190

Ala Gly Phe Ala Ile Leu Lys Cys Asn Asp Lys Lys Phe Asn Gly Thr
        195                 200                 205

Gly Pro Cys Thr Asn Val Ser Thr Val Gln Cys Thr His Gly Ile Arg
    210                 215                 220

Pro Val Val Ser Thr Gln Leu Leu Asn Gly Ser Leu Ala Glu Lys
225                 230                 235                 240

Glu Val Val Ile Arg Ser Glu Asn Phe Thr Asn Ala Lys Thr Ile
                245                 250                 255

Ile Val Gln Leu Asp Glu Ser Val Val Ile Asn Cys Thr Arg Pro Asn
            260                 265                 270

Asn Asn Thr Arg Lys Ser Ile His Ile Gly Pro Gly Arg Ala Phe Tyr
        275                 280                 285

Thr Thr Gly Glu Ile Ile Gly Asp Ile Arg Gln Ala His Cys Thr Leu
    290                 295                 300
```

```
Asn Arg Thr Glu Trp Asn Asn Thr Leu Ala Lys Ile Thr Glu Lys Leu
305                 310                 315                 320

Arg Glu Gln Phe Gly Asn Asn Ile Thr Ile Val Phe Asn His Ser Ser
            325                 330                 335

Gly Gly Asp Pro Glu Ile Val Met His Ser Phe Ile Cys Gly Gly Glu
            340                 345                 350

Phe Phe Tyr Cys Asn Thr Ser Gln Leu Phe Asn Ser Thr Trp Asn Ser
            355                 360                 365

Thr Gly Asn Asn Ile Ser Glu Ser Asp Asn Thr Glu Arg Asn Ile Thr
        370                 375                 380

Leu Pro Cys Arg Ile Lys Gln Ile Ile Asn Leu Trp Gln Glu Val Gly
385                 390                 395                 400

Lys Ala Met Tyr Ala Pro Pro Ile Arg Gly Gln Ile Arg Cys Ser Ser
                405                 410                 415

Asn Ile Thr Gly Leu Leu Leu Thr Arg Asp Gly Gly Ser Asn Thr Asp
            420                 425                 430

Glu Asn Arg Thr Glu Ile Phe Arg Pro Gly Gly Gly Asp Met Arg Asp
            435                 440                 445

Asn Trp Arg Ser Glu Leu Tyr Lys Tyr Lys Val Val Lys Ile Glu Pro
        450                 455                 460

Leu Gly Val Ala Pro Thr Lys Ala Lys Glu Arg Val Val Gln Arg Glu
465                 470                 475                 480

Lys Glu

<210> SEQ ID NO 15
<211> LENGTH: 464
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Val Pro Val Trp Lys Asp Ala Asn Thr Thr Leu Phe Cys Ala Ser Asp
1               5                   10                  15

Ala Lys Ala Tyr Asp Thr Glu Val His Asn Val Trp Ala Thr His Ala
            20                  25                  30

Cys Val Pro Thr Asp Pro Ser Pro Gln Glu Ile Val Leu Lys Asn Val
        35                  40                  45

Thr Glu Asn Phe Asn Met Trp Lys Asn Asn Met Val Glu Gln Met His
50                  55                  60

Lys Asp Ile Ile Ser Leu Trp Asp Glu Ser Leu Lys Pro Cys Val Lys
65                  70                  75                  80

Leu Thr Pro Leu Cys Val Thr Leu Asn Cys Ser Asn Tyr Asn Ser Thr
                85                  90                  95

Asn Ser Thr Ile Asp Pro Asn Met Glu Gly Ala Ile Lys Asn Cys Ser
            100                 105                 110

Phe Asn Ala Thr Thr Gly Ile Gln Asn Lys Met Lys Lys Glu Tyr Ala
        115                 120                 125

Leu Phe Tyr Ser Leu Asp Ile Val Gln Ile Glu Ser Glu Asn Lys Ser
130                 135                 140

Asn Lys Ser Tyr Met Leu Arg Ser Cys Asn Thr Ser Val Ile Thr Gln
145                 150                 155                 160

Ala Cys Pro Lys Val Thr Phe Glu Pro Ile Pro Ile His Tyr Cys Ala
                165                 170                 175
```

Pro Ala Gly Phe Ala Ile Leu Lys Cys Asn Asp Lys Lys Phe Asn Gly
              180                 185                 190

Thr Gly Pro Cys Lys Asn Val Ser Thr Val Gln Cys Thr His Gly Ile
          195                 200                 205

Arg Pro Val Val Ser Thr Gln Leu Leu Leu Asn Gly Ser Leu Ala Glu
      210                 215                 220

Glu Glu Ile Ile Ile Arg Ser Glu Asn Ile Thr Asn Asn Ala Lys Thr
225                 230                 235                 240

Ile Ile Ile Gln Leu Asn Arg Ser Ile Glu Ile Asn Cys Thr Arg Pro
              245                 250                 255

Asn Asn Asn Thr Arg Lys Ser Ile His Met Gly Trp Gly Arg Ala Phe
          260                 265                 270

Tyr Ala Thr Gly Asp Ile Ile Gly Asp Ile Arg Gln Ala His Cys Asn
      275                 280                 285

Leu Ser Gly Thr Lys Trp Asn Asn Thr Leu Tyr Gln Ile Ala Arg Lys
290                 295                 300

Leu Arg Glu His Phe Asn Asn Thr Ile Val Phe Asn Gln Ser Ser Gly
305                 310                 315                 320

Gly Asp Pro Glu Ile Val Met His Thr Phe Asn Cys Gly Gly Glu Phe
              325                 330                 335

Phe Tyr Cys Asn Thr Thr Gln Leu Phe Asn Ser Thr Trp His Ala Asn
          340                 345                 350

Ser Thr Trp Asn Glu Thr Thr Gly Ser Gly Ser Asn Asp Thr Ile Ser
      355                 360                 365

Leu Pro Cys Arg Ile Lys Gln Ile Ile Asn Arg Trp Gln Glu Val Gly
370                 375                 380

Lys Ala Met Tyr Ala Pro Pro Ile Gly Gly Gln Ile Arg Cys Ser Ser
385                 390                 395                 400

Asn Ile Thr Gly Ile Leu Leu Thr Arg Asp Gly Gly Thr Glu Asn Asn
              405                 410                 415

Thr Ser Glu Thr Phe Arg Pro Gly Gly Gly Asn Met Lys Asp Asn Trp
          420                 425                 430

Arg Ser Glu Leu Tyr Lys Tyr Lys Val Val Arg Ile Glu Pro Leu Gly
      435                 440                 445

Val Ala Pro Thr Lys Ala Lys Glu Arg Val Val Gln Arg Glu Lys Glu
450                 455                 460

<210> SEQ ID NO 16
<211> LENGTH: 470
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Val Pro Val Trp Lys Glu Ala Thr Thr Thr Leu Phe Cys Ala Ser Asp
1               5                   10                  15

Ala Lys Ala Tyr Asp Thr Glu Val His Asn Val Trp Ala Thr His Ala
              20                  25                  30

Cys Val Pro Thr Asp Pro Asn Pro Gln Glu Val Val Leu Gly Asn Val
          35                  40                  45

Thr Glu Asn Phe Asn Met Trp Lys Asn Asn Met Val Glu Gln Met His
      50                  55                  60

Glu Asp Val Ile Ser Leu Trp Asp Gln Ser Leu Lys Pro Cys Val Lys
65                  70                  75                  80

```
Leu Thr Pro Leu Cys Val Thr Leu Asn Cys Thr Asp Val Leu Gly Lys
                85                  90                  95
Gly Thr Ser Ala Asn Ala Thr Ser Ala Asn Val Thr Ser Glu Lys Gly
                100                 105                 110
Glu Ile Lys Asn Cys Ser Phe Asn Ile Thr Thr Thr Leu Arg Asp Lys
                115                 120                 125
Val Gln Lys Ala His Ala Leu Phe Tyr Arg Leu Asp Val Val Pro Ile
            130                 135                 140
Asp Asp Asn Asn Asp Asn Ser Ser Ser Tyr Arg Leu Ile Asn Cys
145                 150                 155                 160
Asn Thr Ser Val Ile Thr Gln Ala Cys Pro Lys Val Ser Phe Glu Pro
                165                 170                 175
Ile Pro Ile His Phe Cys Thr Pro Ala Gly Phe Ala Leu Leu Lys Cys
                180                 185                 190
Asn Asn Lys Lys Phe Asn Gly Thr Gly Pro Cys Thr Asn Val Ser Thr
                195                 200                 205
Val Gln Cys Thr His Gly Ile Lys Pro Val Val Ser Thr Gln Leu Leu
            210                 215                 220
Leu Asn Gly Ser Leu Ala Glu Glu Val Val Ile Arg Ser Glu Asn
225                 230                 235                 240
Phe Thr Asp Asn Ala Lys Thr Ile Ile Val Gln Leu Asn Asp Ser Val
                245                 250                 255
Val Ile Asn Cys Thr Arg Pro Asn Asn Asn Thr Arg Lys Gly Ile Thr
                260                 265                 270
Ile Gly Pro Gly Ser Val Phe Tyr Thr Gly Glu Ile Ile Gly Asp Ile
                275                 280                 285
Arg Gln Ala His Cys Asn Leu Ser Ser Ala Lys Trp Asn Asn Thr Leu
            290                 295                 300
Lys Gln Ile Val Ile Lys Leu Arg Glu Gln Phe Gly Asn Lys Thr Ile
305                 310                 315                 320
Val Phe Asn Gln Ser Ser Gly Gly Asp Pro Glu Ile Val Leu His Ser
                325                 330                 335
Phe Asn Cys Gly Gly Glu Phe Phe Tyr Cys Asn Thr Thr Gln Leu Phe
                340                 345                 350
Asn Ser Thr Trp Asn Ile Asn Asp Thr Arg Asn Gly Thr Thr Glu Ser
                355                 360                 365
Ser Lys Thr Ile Thr Leu Pro Cys Arg Ile Lys Gln Ile Ile Asn Met
                370                 375                 380
Trp Gln Glu Val Gly Lys Ala Met Tyr Ala Pro Pro Ile Arg Gly Gln
385                 390                 395                 400
Ile Arg Cys Ser Ser Asn Ile Thr Gly Leu Leu Leu Thr Arg Asp Gly
                405                 410                 415
Gly Asn Gln Asn Thr Ser Gly Thr Glu Ile Phe Arg Pro Gly Gly Gly
                420                 425                 430
Asn Met Arg Asp Asn Trp Arg Ser Glu Leu Tyr Lys Tyr Lys Val Val
            435                 440                 445
Lys Ile Glu Pro Leu Gly Ile Ala Pro Thr Lys Ala Lys Glu Arg Val
450                 455                 460
Val Gln Arg Glu Lys Glu
465                 470

<210> SEQ ID NO 17
<211> LENGTH: 479
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Val Pro Val Trp Lys Glu Ala Thr Thr Thr Leu Phe Cys Ala Ser Asp
1               5                   10                  15

Ala Lys Ala Tyr Asp Thr Glu Ala His Asn Val Trp Ala Thr His Ala
            20                  25                  30

Cys Val Pro Thr Asp Pro Asn Pro Gln Glu Val Val Leu Gly Asn Val
        35                  40                  45

Thr Glu Asn Phe Asn Met Trp Lys Asn Asp Met Val Glu Gln Met His
50                  55                  60

Glu Asp Ile Ile Ser Leu Trp Asp Gln Ser Leu Lys Pro Cys Val Lys
65                  70                  75                  80

Leu Thr Pro Ile Cys Val Ala Leu Asn Cys Thr Asp Val Lys Asp Thr
                85                  90                  95

Asn Asn Thr Ser Asn Asn Thr Asn Asn Thr Ser Ser Asn Asn Ser Ser
            100                 105                 110

Met Thr Glu Gly Gly Glu Met Lys Asn Cys Ser Phe Asn Ile Thr Thr
        115                 120                 125

Ser Ile Lys Thr Lys Val Lys Asp Tyr Ala Leu Phe Tyr Lys Leu Asp
130                 135                 140

Ile Val Pro Ile Asp Asn Asp Gly Asp Asn Thr Ser Tyr Arg Leu Ile
145                 150                 155                 160

Ser Cys Asn Thr Ser Val Ile Thr Gln Ala Cys Pro Lys Ile Ser Phe
                165                 170                 175

Glu Pro Ile Pro Ile His Tyr Cys Thr Pro Ala Gly Tyr Ala Leu Leu
            180                 185                 190

Lys Cys Asn Asn Lys Lys Phe Asn Gly Thr Gly Pro Cys Lys Asn Val
        195                 200                 205

Ser Thr Val Gln Cys Thr His Gly Ile Arg Pro Val Val Ser Thr Gln
210                 215                 220

Leu Leu Leu Asn Gly Ser Leu Ala Glu Glu Val Val Ile Arg Ser
225                 230                 235                 240

Ser Asn Phe Thr Asn Asn Ala Lys Val Ile Ile Val Gln Leu Lys Glu
                245                 250                 255

Ala Val Glu Ile Asn Cys Thr Arg Pro Asn Asn Asn Thr Arg Lys Ser
            260                 265                 270

Ile His Ile Gly Pro Gly Lys Ala Trp Tyr Thr Thr Gly Glu Ile Ile
        275                 280                 285

Gly Asn Ile Arg Gln Ala His Cys Asn Ile Ser Arg Thr Lys Trp Asn
290                 295                 300

Asn Thr Leu His Gln Ile Val Lys Lys Leu Arg Ile Gln Phe Gly Asn
305                 310                 315                 320

Lys Thr Ile Ile Phe Asn Gln Ser Ala Gly Gly Asp Pro Glu Ile Val
                325                 330                 335

Val His Ser Phe Asn Cys Gly Gly Glu Phe Phe Tyr Cys Asn Thr Ser
            340                 345                 350

Gln Leu Phe Asn Ser Thr Trp Arg Asn Asp Thr Trp Asn Asp Thr Ser
        355                 360                 365

Pro Gln Ile Ala Thr Thr Gly Asn Asp Thr Ile Thr Leu Pro Cys Arg
370                 375                 380
```

Ile Arg Gln Ile Val Asn Met Trp Gln Gln Val Gly Lys Ala Met Tyr
385                 390                 395                 400

Ala Pro Pro Ile Ala Gly Gln Ile Arg Cys Ser Ser Asn Ile Thr Gly
            405                 410                 415

Val Leu Leu Thr Arg Asp Gly Gly Asn Asn Glu Ser Lys Ala Asn Ala
        420                 425                 430

Asn Glu Thr Phe Arg Pro Ala Gly Gly Asp Met Arg Asp Asn Trp Arg
    435                 440                 445

Ser Glu Leu Tyr Lys Tyr Lys Val Val Lys Ile Glu Pro Leu Gly Val
450                 455                 460

Ala Pro Thr Lys Ala Lys Glu Arg Val Val Gln Arg Glu Lys Glu
465                 470                 475

<210> SEQ ID NO 18
<211> LENGTH: 465
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Val Pro Val Trp Arg Asp Ala Thr Thr Thr Leu Phe Cys Ala Ser Asp
1               5                   10                  15

Ala Lys Ala Tyr Glu Thr Glu Leu His Asn Val Trp Ala Thr His Ala
            20                  25                  30

Cys Val Pro Thr Asp Pro Asn Pro Gln Glu Val Val Leu Gly Asn Val
        35                  40                  45

Thr Glu Asn Phe Asn Met Trp Lys Asn Asp Met Val Glu Gln Met Asn
    50                  55                  60

Glu Asp Ile Ile Ser Leu Trp Asp Glu Ser Leu Lys Pro Cys Val Lys
65                  70                  75                  80

Leu Thr Pro Leu Cys Val Thr Leu Asn Cys Thr Asn Tyr Asn Glu Thr
                85                  90                  95

Thr Thr Asn Ser Thr Thr Thr Asn Ala Thr Val Val Ser Pro Gly Glu
            100                 105                 110

Ile Lys Asn Cys Ser Phe Asn Val Thr Thr Gly Ile Arg Asp Lys Val
        115                 120                 125

Arg Lys Asp His Ala Leu Phe Tyr Ala Leu Asp Ile Val Pro Ile Asp
    130                 135                 140

Asn Thr Ile Asp Asn Thr Ser Tyr Arg Leu Val Ser Cys Asn Thr Ser
145                 150                 155                 160

Val Leu Thr Gln Ala Cys Pro Lys Val Ser Phe Glu Pro Ile Pro Ile
                165                 170                 175

His Phe Cys Ala Pro Ala Gly Tyr Ala Ile Ile Lys Cys Asn Asn Lys
            180                 185                 190

Thr Phe Asn Gly Ser Gly Pro Cys Arg Asn Val Ser Thr Val Gln Cys
        195                 200                 205

Thr His Gly Ile Arg Pro Val Val Ser Thr Gln Leu Leu Leu Asn Gly
    210                 215                 220

Ser Leu Ala Glu Glu Ile Val Ile Arg Ser Ala Asn Phe Ser Asp
225                 230                 235                 240

Asn Thr Lys Thr Ile Ile Val Gln Leu Asn Glu Ala Val Lys Ile Asn
                245                 250                 255

Cys Thr Arg Pro Asn Asn Asn Thr Arg Arg Ser Val His Met Gly Pro

```
            260                 265                 270
Gly Ser Ala Phe Tyr Thr Thr Gly Gly Ile Ile Gly Asp Ile Arg Gln
        275                 280                 285
Ala His Cys Asn Ile Ser Glu Arg Asp Trp Asn Gly Ala Leu Lys Gln
    290                 295                 300
Ile Val Glu Lys Leu Gly Glu Gln Phe Gln Asn Lys Thr Ile Val Phe
305                 310                 315                 320
Lys Gln Ser Ser Gly Gly Asp Pro Glu Val Val Met His Thr Phe Asn
                325                 330                 335
Cys Arg Gly Glu Phe Phe Tyr Cys Asn Thr Thr Lys Leu Phe Asn Ser
            340                 345                 350
Thr Trp Val Asn Gly Thr Lys Asn Asp Thr Lys Gly Asn Gly Thr
        355                 360                 365
Ile Thr Leu Gln Cys Arg Ile Lys Gln Ile Ile Asn Met Trp Gln Gln
    370                 375                 380
Val Gly Lys Ala Met Tyr Ala Pro Pro Ile Ser Gly Pro Ile Ser Cys
385                 390                 395                 400
Ser Ser Asn Ile Thr Gly Leu Ile Leu Thr Arg Asp Gly Gly Thr Asn
                405                 410                 415
Thr Thr Asn Glu Thr Phe Arg Pro Gly Gly Gly Asp Met Arg Asp Asn
            420                 425                 430
Trp Arg Ser Glu Leu Tyr Lys Tyr Lys Val Val Lys Ile Glu Pro Ile
        435                 440                 445
Gly Val Ala Pro Thr Lys Ala Arg Glu Arg Val Gln Arg Glu Lys
    450                 455                 460
Glu
465

<210> SEQ ID NO 19
<211> LENGTH: 466
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Val Pro Val Trp Arg Asp Ala Glu Thr Thr Leu Phe Cys Ala Ser Asp
1               5                   10                  15
Ala Lys Gly Tyr Asp Thr Glu Ala His Asn Val Trp Ala Thr His Ala
            20                  25                  30
Cys Val Pro Thr Asp Pro Ser Pro Gln Glu Ile His Leu Glu Asn Val
        35                  40                  45
Thr Glu Glu Phe Asn Met Trp Lys Asn Asn Met Val Glu Gln Met His
    50                  55                  60
Thr Asp Ile Ile Ser Leu Trp Asp Gln Ser Leu Lys Pro Cys Val Lys
65                  70                  75                  80
Leu Thr Pro Leu Cys Val Thr Leu Asp Cys Thr Leu Asp Cys Asn Asn
                85                  90                  95
Val Thr Asn Asn Gly Thr Ser Asp Met Arg Glu Glu Ile Lys Asn Cys
            100                 105                 110
Ser Phe Asn Ile Thr Thr Glu Leu Arg Asp Lys Lys Lys Val Tyr
        115                 120                 125
Ser Leu Phe Tyr Lys Leu Asp Ile Val Pro Ile Asn Gly Asp Asn Ser
    130                 135                 140
```

```
Thr Asn Thr Tyr Met Leu Ile Asn Cys Asn Thr Ser Ala Ile Thr Gln
145                 150                 155                 160

Ala Cys Pro Lys Val Thr Phe Glu Pro Ile Pro Ile His Phe Cys Ala
                165                 170                 175

Pro Ala Gly Tyr Ala Ile Leu Lys Cys Lys Asp Lys Glu Phe Asn Gly
            180                 185                 190

Thr Gly Pro Cys Lys Asn Val Ser Thr Val Gln Cys Thr His Gly Ile
        195                 200                 205

Lys Pro Val Val Ser Thr Gln Leu Leu Leu Asn Gly Ser Leu Ala Glu
    210                 215                 220

Glu Glu Ile Met Ile Arg Ser Glu Asn Ile Thr Asn Asn Ala Lys Ile
225                 230                 235                 240

Ile Ile Val Gln Leu Asn Gln Ser Val Val Ile Asn Cys Thr Arg Pro
                245                 250                 255

Gly Asn Asn Thr Arg Lys Ser Val Arg Ile Gly Pro Gly Gln Thr Phe
            260                 265                 270

Tyr Ala Thr Gly Asp Ile Ile Gly Asp Ile Arg Gln Ala His Cys Asn
        275                 280                 285

Val Ser Arg Ile Lys Trp Asn Thr Ala Leu Gln Lys Val Ala Lys Gln
    290                 295                 300

Leu Arg Lys Tyr Phe Arg Asn Lys Thr Ile Thr Phe Asn Gln Ser Ser
305                 310                 315                 320

Gly Gly Asp Pro Glu Ile Thr Thr His Thr Phe Asn Cys Gly Gly Glu
                325                 330                 335

Phe Phe Tyr Cys Asn Thr Ser Asn Leu Phe Asn Ser Thr Trp Gly Asn
            340                 345                 350

Gly Asn Gly Thr Asp Asn Met Gln Gly Ser Asn Ser Thr Asn Ile Thr
        355                 360                 365

Leu Gln Cys Arg Ile Lys Gln Ile Ile Asn Met Trp Gln Glu Val Gly
    370                 375                 380

Arg Ala Ile Tyr Ala Pro Pro Ile Glu Gly Asn Ile Ser Cys Ser Ser
385                 390                 395                 400

Asn Ile Thr Gly Leu Leu Leu Thr Arg Asp Gly Gly Asn Ser Lys Asn
                405                 410                 415

Ser Thr Thr Glu Glu Ile Phe Arg Pro Gly Gly Gly Asn Met Arg Asp
            420                 425                 430

Asn Trp Arg Ser Glu Leu Tyr Lys Tyr Lys Val Val Lys Ile Glu Pro
        435                 440                 445

Ile Gly Val Ala Pro Thr Lys Ala Arg Glu Arg Val Val Glu Arg Glu
    450                 455                 460

Lys Glu
465

<210> SEQ ID NO 20
<211> LENGTH: 470
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Val Pro Val Trp Arg Glu Ala Asn Thr Thr Leu Phe Cys Ala Ser Asp
1               5                   10                  15

Ala Lys Ala Tyr Asp Thr Glu Val His Asn Ile Trp Ala Thr His Ala
            20                  25                  30
```

```
Cys Val Pro Thr Asp Pro Asn Pro Gln Glu Ile Val Leu Gly Asn Val
         35                  40                  45

Thr Glu Asn Phe Asn Met Trp Lys Asn Asn Met Val Asp Gln Met His
 50                  55                  60

Glu Asp Val Ile Ser Leu Trp Asp Glu Ser Leu Lys Pro Cys Val Lys
 65                  70                  75                  80

Leu Thr Pro Leu Cys Val Thr Leu Glu Cys Asn Asp Ala Lys Leu Asn
                 85                  90                  95

Ser Thr Lys Thr Asn Ser Thr Asn Ser Thr Asp Pro Asn Asn Ser
             100                 105                 110

Asn Leu Gly Ile Glu Gly Glu Ile Lys Asn Cys Ser Phe Asn Thr Thr
             115                 120                 125

Thr Glu Ile Arg Asp Lys Lys Lys Arg Ala Tyr Ala Leu Phe Tyr Arg
 130                 135                 140

Pro Asp Val Val Pro Leu Asn Glu Asn Ser Ser Ser Tyr Ile Leu Ile
145                 150                 155                 160

Asn Cys Asn Ser Ser Thr Ile Thr Gln Ala Cys Pro Lys Val Ser Phe
                 165                 170                 175

Glu Pro Ile Pro Ile His Tyr Cys Thr Pro Ala Gly Phe Ala Leu Leu
             180                 185                 190

Lys Cys Asn Asn Lys Thr Phe Asn Gly Ser Gly Pro Cys Thr Asn Val
             195                 200                 205

Ser Thr Val Gln Cys Thr His Gly Ile Arg Pro Val Val Ser Thr Gln
210                 215                 220

Leu Leu Leu Asn Gly Ser Leu Ala Glu Glu Ile Val Ile Arg Ser
225                 230                 235                 240

Glu Asn Phe Thr Asp Asn Ala Lys Thr Ile Ile Val Gln Leu Asn Glu
                 245                 250                 255

Ser Val Glu Ile Asn Cys Thr Arg Pro Asn Asn Asn Thr Arg Lys Ser
             260                 265                 270

Ile Arg Ile Gly Pro Gly Gln Ala Phe Tyr Ala Thr Gly Glu Ile Ile
             275                 280                 285

Gly Asn Ile Arg Gln Ala Tyr Cys Asn Ile Asn Glu Ser Leu Trp Asn
 290                 295                 300

Glu Thr Leu Tyr Lys Val Ser Glu Lys Leu Lys Glu Tyr Phe Asn Thr
305                 310                 315                 320

Thr Ile Glu Phe Gln Gln Pro Ala Gly Gly Asp Leu Glu Ile Thr Thr
                 325                 330                 335

His Ser Phe Asn Cys Arg Gly Glu Phe Phe Tyr Cys Asn Thr Thr Lys
             340                 345                 350

Leu Phe Asn Gly Thr Tyr Ser Gln Pro Asn Ser Thr Gly Asn Thr Pro
             355                 360                 365

His Ser Asn Ile Thr Leu Pro Cys Lys Ile Lys Gln Ile Ile Asn Met
 370                 375                 380

Trp Gln Gly Val Gly Arg Ala Met Tyr Ala Pro Ile Ala Gly Asn
385                 390                 395                 400

Ile Thr Cys Ile Ser Asn Ile Thr Gly Leu Ile Leu Thr Arg Asp Gly
                 405                 410                 415

Gly Asp Lys Asn Gly Ser Lys Pro Glu Ile Phe Arg Pro Gly Gly Gly
             420                 425                 430

Asn Met Lys Asp Asn Trp Arg Ser Glu Leu Tyr Lys Tyr Lys Val Val
             435                 440                 445
```

Glu Ile Lys Pro Leu Gly Leu Ala Pro Thr Glu Ala Lys Arg Glu Val
450                 455                 460

Val Glu Arg Glu Lys Glu
465                 470

<210> SEQ ID NO 21
<211> LENGTH: 468
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Val Pro Val Trp Lys Glu Ala Lys Thr Thr Leu Phe Cys Ala Ser Asp
1               5                   10                  15

Ala Lys Ala Tyr Glu Lys Glu Val His Asn Val Trp Ala Thr His Ala
                20                  25                  30

Cys Val Pro Thr Asp Pro Asn Pro Gln Glu Met Val Leu Glu Asn Val
            35                  40                  45

Thr Glu Asn Phe Asn Met Trp Lys Asn Asp Met Val Asp Gln Met His
    50                  55                  60

Glu Asp Ile Ile Ser Leu Trp Asp Gln Ser Leu Lys Pro Cys Val Lys
65                  70                  75                  80

Leu Thr Pro Leu Cys Val Thr Leu Asn Cys Val Asn Ile Thr Asn Ser
                85                  90                  95

Thr Thr Ser Asn Gly Asp Gly Thr Val Thr His Ile Asn Ser Ile Lys
            100                 105                 110

Glu Glu Ile Lys Asn Cys Ser Phe Asn Ala Thr Thr Glu Leu Arg Asp
        115                 120                 125

Lys Lys Ser Lys Glu Tyr Ala Leu Phe Tyr Arg Leu Asp Ile Val Pro
    130                 135                 140

Leu Ser Ser Gly Asn Ser Ser Asn Ser Ser Lys Tyr Arg Leu Ile
145                 150                 155                 160

Asn Cys Asn Thr Ser Thr Ile Thr Gln Ala Cys Pro Lys Val Ser Phe
                165                 170                 175

Asp Pro Ile Pro Ile His Tyr Cys Ala Pro Ala Gly Tyr Ala Ile Leu
            180                 185                 190

Lys Cys Asn Asn Lys Thr Phe Asn Gly Thr Gly Pro Cys Asn Asn Val
        195                 200                 205

Ser Thr Val Gln Cys Thr His Gly Ile Lys Pro Val Val Ser Thr Gln
    210                 215                 220

Leu Leu Leu Asn Gly Ser Leu Ala Glu Glu Ile Ile Arg Ser
225                 230                 235                 240

Glu Asn Leu Thr Asp Asn Val Lys Thr Ile Val His Leu Asn Glu
                245                 250                 255

Ser Val Glu Ile Val Cys Thr Arg Pro Asn Asn Asn Thr Arg Lys Ser
            260                 265                 270

Ile Arg Ile Gly Pro Gly Gln Thr Phe Tyr Ala Thr Gly Asp Ile Ile
        275                 280                 285

Gly Asp Ile Arg Gln Ala His Cys Asn Ile Ser Lys Gly Ala Trp Asn
    290                 295                 300

Glu Thr Leu Gln Trp Val Gly Lys Lys Leu Lys Glu His Phe Pro Asn
305                 310                 315                 320

Lys Thr Ile Lys Phe Asn Ser Ser Ser Gly Gly Asp Leu Glu Ile Thr
                325                 330                 335

```
Thr His Ser Phe Asn Cys Arg Gly Glu Phe Tyr Cys Asn Thr Ser
            340                 345                 350

Gly Leu Phe Asn Ser Thr Tyr Arg Asn Asn Ser Thr Gly Asp Asn Ser
                355                 360                 365

Thr Ile Thr Leu Pro Cys Arg Ile Lys Gln Ile Ile Asn Met Trp Gln
370                 375                 380

Glu Val Gly Arg Ala Met Tyr Ala Pro Pro Ile Ala Gly Asn Ile Thr
385                 390                 395                 400

Cys Lys Ser Asn Ile Thr Gly Leu Leu Leu Thr Arg Asp Gly Gly Thr
                405                 410                 415

Arg Asp Arg Asn Asp Thr Glu Thr Phe Arg Pro Gly Gly Gly Asp Met
                420                 425                 430

Arg Asp Asn Trp Arg Ser Glu Leu Tyr Lys Tyr Lys Val Val Glu Ile
                435                 440                 445

Lys Pro Leu Gly Ile Ala Pro Thr Lys Ala Lys Glu Arg Val Val Glu
                450                 455                 460

Arg Glu Lys Glu
465

<210> SEQ ID NO 22
<211> LENGTH: 466
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Val Pro Val Trp Arg Asp Ala Asp Thr Thr Leu Phe Cys Ala Ser Asp
1               5                   10                  15

Ala Lys Ala His Glu Thr Glu Val His Asn Val Trp Ala Thr His Ala
                20                  25                  30

Cys Val Pro Thr Asp Pro Asn Pro Gln Glu Ile His Leu Glu Asn Val
                35                  40                  45

Thr Glu Asn Phe Asn Met Trp Lys Asn Asn Met Val Glu Gln Met Gln
50                  55                  60

Glu Asp Val Ile Ser Leu Trp Asp Gln Ser Leu Lys Pro Cys Val Lys
65                  70                  75                  80

Leu Thr Pro Leu Cys Val Thr Leu Asn Cys Thr Lys Ala Asn Leu Thr
                85                  90                  95

Asn Ile Asn Glu Thr Thr Ala Ser Asn Gly Ile Gly Asn Ile Thr Asp
                100                 105                 110

Glu Val Arg Asn Cys Ser Phe Asn Met Thr Thr Glu Leu Arg Asp Lys
                115                 120                 125

Lys Gln Lys Val His Ala Leu Phe Tyr Lys Leu Asp Ile Val Pro Ile
130                 135                 140

Arg Asn Glu Ser Lys Met Gly Asn Val Ser Ser Glu Tyr Arg Leu Ile
145                 150                 155                 160

Asn Cys Asn Thr Ser Val Ile Lys Gln Ala Cys Pro Lys Ile Ser Phe
                165                 170                 175

Asp Pro Ile Pro Ile His Tyr Cys Thr Pro Ala Gly Tyr Ala Ile Leu
                180                 185                 190

Lys Cys Asn Asp Lys Asn Phe Asn Gly Thr Gly Pro Cys Lys Asn Val
                195                 200                 205

Ser Ser Val Gln Cys Thr His Gly Ile Lys Pro Val Val Ser Thr Gln
```

Leu Leu Leu Asn Gly Ser Leu Ala Glu Glu Ile Ile Arg Ser
225                 230                 235                 240

Glu Asn Leu Thr Asn Asn Ala Lys Thr Ile Ile Val His Leu Asn Lys
            245                 250                 255

Ser Val Glu Ile Asn Cys Thr Arg Pro Ser Asn Asn Thr Arg Thr Ser
                260                 265                 270

Ile Thr Ile Gly Pro Gly Gln Val Phe Tyr Arg Thr Gly Asp Ile Ile
            275                 280                 285

Gly Asp Ile Arg Lys Ala Tyr Cys Glu Ile Asn Gly Thr Lys Trp Asn
290                 295                 300

Glu Thr Leu Lys Gln Val Ala Gly Lys Leu Lys Glu His Phe Asn Lys
305                 310                 315                 320

Thr Ile Ile Phe Gln Pro Pro Ser Gly Gly Asp Leu Glu Ile Thr Met
                325                 330                 335

His His Phe Asn Cys Arg Gly Glu Phe Phe Tyr Cys Asn Thr Thr Lys
            340                 345                 350

Leu Phe Asn Ser Thr Trp Asn Gly Thr Met Glu Gly Arg Asn Gly Thr
                355                 360                 365

Ile Ile Leu Pro Cys Arg Ile Lys Gln Ile Ile Asn Met Trp Gln Gly
            370                 375                 380

Val Gly Gln Ala Met Tyr Ala Pro Pro Ile Ser Gly Ile Ile Asn Cys
385                 390                 395                 400

Val Ser Asn Ile Thr Gly Ile Leu Leu Thr Arg Asp Gly Gly Asn Asn
                405                 410                 415

Asn Ala Thr Asn Glu Thr Phe Arg Pro Gly Gly Asn Ile Lys Asp
            420                 425                 430

Asn Trp Arg Ser Glu Leu Tyr Lys Tyr Lys Val Val Gln Ile Glu Pro
                435                 440                 445

Leu Gly Ile Ala Pro Thr Arg Ala Lys Glu Arg Val Val Glu Arg Glu
            450                 455                 460

Lys Glu
465

<210> SEQ ID NO 23
<211> LENGTH: 503
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Met Arg Val Lys Gly Ile Arg Lys Asn Tyr Gln His Leu Trp Arg Trp
1               5                   10                  15

Gly Thr Met Leu Leu Gly Met Leu Met Ile Cys Ser Ala Ala Glu Gln
            20                  25                  30

Leu Trp Val Thr Val Tyr Tyr Gly Val Pro Val Trp Lys Glu Ala Thr
        35                  40                  45

Thr Thr Leu Phe Cys Ala Ser Asp Ala Lys Ala Tyr Asp Thr Glu Val
    50                  55                  60

His Asn Val Trp Ala Thr His Ala Cys Val Pro Thr Asp Pro Asn Pro
65                  70                  75                  80

Gln Glu Val Val Leu Glu Asn Val Thr Glu Asn Phe Asn Met Trp Lys
                85                  90                  95

```
Asn Asn Met Val Glu Gln Met His Glu Asp Ile Ile Ser Leu Trp Asp
            100                 105                 110
Gln Ser Leu Lys Pro Cys Val Lys Leu Thr Pro Leu Cys Val Thr Leu
        115                 120                 125
Asn Cys Thr Asp Val Ser Ser Asn Ser Thr Ser Val Asn Ile Thr Ser
    130                 135                 140
Glu Lys Gly Glu Ile Lys Asn Cys Ser Phe Asn Ile Thr Thr Ser Ile
145                 150                 155                 160
Arg Asp Lys Val Gln Lys Glu Tyr Ala Leu Phe Tyr Lys Leu Asp Val
                165                 170                 175
Val Pro Ile Glu Asp Asp Ser Arg Asn Asn Ser Tyr Arg Leu Ile Ser
            180                 185                 190
Cys Asn Thr Ser Val Ile Thr Gln Ala Cys Pro Lys Val Ser Phe Glu
        195                 200                 205
Pro Ile Pro Ile His Tyr Cys Ala Pro Ala Gly Phe Ala Ile Leu Lys
    210                 215                 220
Cys Asn Asp Lys Lys Phe Asn Gly Thr Gly Pro Cys Thr Asn Val Ser
225                 230                 235                 240
Thr Val Gln Cys Thr His Gly Ile Arg Pro Val Val Ser Thr Gln Leu
                245                 250                 255
Leu Leu Asn Gly Ser Leu Ala Glu Glu Val Val Ile Arg Ser Glu
            260                 265                 270
Asn Phe Thr Asn Asn Ala Lys Thr Ile Ile Val Gln Leu Asn Glu Ser
        275                 280                 285
Val Glu Ile Asn Cys Thr Arg Pro Asn Asn Thr Arg Lys Ser Ile
    290                 295                 300
His Ile Gly Pro Gly Arg Ala Phe Tyr Ala Thr Gly Asp Ile Ile Gly
305                 310                 315                 320
Asp Ile Arg Gln Ala His Cys Asn Ile Ser Arg Glu Lys Trp Asn Asn
                325                 330                 335
Thr Leu Lys Gln Ile Val Lys Lys Leu Arg Glu Gln Phe Gly Asn Lys
            340                 345                 350
Thr Ile Val Phe Asn Gln Ser Ser Gly Gly Asp Pro Glu Ile Val Met
        355                 360                 365
His Ser Phe Asn Cys Gly Gly Glu Phe Phe Tyr Cys Asn Thr Thr Gln
    370                 375                 380
Leu Phe Asn Ser Thr Trp Ser Ile Asn Gly Thr Trp Asn Gly Thr Thr
385                 390                 395                 400
Glu Ser Asn Asp Thr Ile Thr Leu Pro Cys Arg Ile Lys Gln Ile Ile
                405                 410                 415
Asn Met Trp Gln Glu Val Gly Lys Ala Met Tyr Ala Pro Pro Ile Arg
            420                 425                 430
Gly Gln Ile Arg Cys Ser Ser Asn Ile Thr Gly Leu Leu Leu Thr Arg
        435                 440                 445
Asp Gly Gly Asn Ser Ser Asn Asn Glu Thr Phe Arg Pro Gly Gly
    450                 455                 460
Gly Asp Met Arg Asp Asn Trp Arg Ser Glu Leu Tyr Lys Tyr Lys Val
465                 470                 475                 480
Val Lys Ile Glu Pro Leu Gly Val Ala Pro Thr Lys Ala Lys Arg Arg
                485                 490                 495
Val Val Gln Arg Glu Lys Arg
            500
```

```
<210> SEQ ID NO 24
<211> LENGTH: 501
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Met Lys Val Lys Gly Ile Arg Lys Asn Cys Gln His Leu Trp Arg Trp
1               5                   10                  15

Gly Ile Met Leu Leu Gly Met Leu Met Ile Cys Ser Ala Thr Glu Lys
            20                  25                  30

Leu Trp Val Thr Val Tyr Tyr Gly Val Pro Val Trp Lys Glu Ala Thr
        35                  40                  45

Thr Thr Leu Phe Cys Ala Ser Asp Ala Lys Ala Tyr Asp Thr Glu Ala
    50                  55                  60

His Asn Val Trp Ala Thr His Ala Cys Val Pro Thr Asp Pro Asn Pro
65                  70                  75                  80

Gln Glu Ile Val Leu Glu Asn Val Thr Glu Asn Phe Asn Met Trp Lys
                85                  90                  95

Asn Asp Met Val Glu Gln Met His Glu Asp Ile Ile Ser Leu Trp Asp
            100                 105                 110

Glu Ser Leu Lys Pro Cys Val Glu Leu Thr Pro Leu Cys Val Thr Leu
        115                 120                 125

Asn Cys Thr Asn Val Asn Ala Thr Asn Thr Asn Asn Ser Ser Gly Ile
    130                 135                 140

Glu Gly Gly Glu Met Lys Asn Cys Ser Phe Asn Val Thr Thr Ser Ile
145                 150                 155                 160

Arg Asp Lys Met Gln Lys Glu Tyr Ala Leu Phe Tyr Ser Leu Asp Val
                165                 170                 175

Val Gln Ile Asp Asn Asp Thr Asn Tyr Arg Leu Ile Asn Cys Asn Thr
            180                 185                 190

Ser Val Ile Thr Gln Ala Cys Pro Lys Ile Ser Phe Glu Pro Ile Pro
        195                 200                 205

Ile His Tyr Cys Thr Pro Ala Gly Phe Ala Ile Ile Lys Cys Asn Asp
    210                 215                 220

Lys Lys Phe Asn Gly Ser Gly Pro Cys Lys Asn Val Ser Thr Val Gln
225                 230                 235                 240

Cys Thr His Gly Ile Lys Pro Val Val Ser Thr Gln Leu Leu Leu Asn
                245                 250                 255

Gly Ser Leu Ala Glu Glu Glu Ile Val Ile Arg Ser Glu Asn Phe Ser
            260                 265                 270

Asp Asn Ala Lys Thr Ile Ile Val Gln Leu Asn Glu Ser Val Val Ile
        275                 280                 285

Asn Cys Thr Arg Pro Asn Asn Asn Thr Arg Lys Ser Ile Ser Ile Gly
    290                 295                 300

Pro Gly Arg Ala Phe Tyr Ala Thr Gly Asp Ile Ile Gly Asn Ile Arg
305                 310                 315                 320

Gln Ala His Cys Asn Leu Ser Arg Ala Glu Trp Asn Asn Thr Leu Arg
                325                 330                 335

Gln Ile Val Thr Lys Leu Arg Glu Gln Phe Lys Asn Lys Thr Ile Ala
            340                 345                 350

Phe Asn His Ser Ser Gly Gly Asp Pro Glu Ile Val Met His Thr Phe
        355                 360                 365
```

```
Asn Cys Gly Gly Glu Phe Phe Tyr Cys Asn Ser Thr Gln Leu Phe Asn
    370                 375                 380

Ser Thr Trp Ile Ala Asn Lys Thr Gly Asn Asp Thr Gly Gly Ser Asn
385                 390                 395                 400

Gly Thr Ile Thr Leu Gln Cys Arg Ile Lys Gln Ile Val Asn Arg Trp
                405                 410                 415

Gln Glu Val Gly Lys Ala Met Tyr Ala Pro Pro Ile Ser Gly Gln Ile
            420                 425                 430

Ser Cys Ser Ser Asn Ile Thr Gly Leu Ile Leu Thr Arg Asp Gly Gly
        435                 440                 445

Thr Asn Asn Thr Asn Gly Thr Glu Ile Phe Arg Pro Gly Gly Gly Asn
450                 455                 460

Met Lys Asp Asn Trp Arg Ser Glu Leu Tyr Lys Tyr Lys Val Val Arg
465                 470                 475                 480

Ile Glu Pro Leu Gly Ile Ala Pro Thr Lys Ala Arg Arg Arg Val Val
                485                 490                 495

Gln Arg Glu Lys Arg
            500
```

<210> SEQ ID NO 25
<211> LENGTH: 522
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

```
Met Lys Ala Lys Glu Thr Arg Lys Asn Tyr Gln His Leu Trp Arg Trp
1               5                   10                  15

Gly Ile Thr Leu Leu Gly Met Leu Met Ile Cys Ser Ala Ala Glu Gln
                20                  25                  30

Leu Trp Val Thr Val Tyr Tyr Gly Val Pro Val Trp Lys Glu Ala Thr
            35                  40                  45

Thr Thr Leu Phe Cys Ala Ser Asp Ala Lys Ala Tyr Asp Thr Glu Val
        50                  55                  60

His Asn Val Trp Ala Thr His Ala Cys Val Pro Thr Asp Pro Asn Pro
65                  70                  75                  80

Gln Glu Val Val Leu Glu Asn Val Thr Glu Asn Phe Asn Met Trp Lys
                85                  90                  95

Asn Asn Met Val Glu Gln Met His Glu Asp Ile Ile Ser Leu Trp Asp
                100                 105                 110

Gln Ser Leu Lys Pro Cys Val Lys Leu Thr Pro Leu Cys Val Thr Leu
            115                 120                 125

Asn Cys Thr Asp Asp Leu Lys Asn Ala Thr Val Lys Asn Ala Thr Asn
        130                 135                 140

Thr Asn Asn Ser Ser Trp Gly Gly Met Glu Arg Gly Glu Ile Lys Asn
145                 150                 155                 160

Cys Ser Phe Asn Ile Thr Thr Ser Ile Arg Asp Lys Val Gln Lys Glu
                165                 170                 175

Tyr Ala Leu Phe Tyr Lys Leu Asp Val Val Pro Ile Asp Asn Ala Asp
            180                 185                 190

Asn Asn Asn Ile Thr Thr Asn Tyr Thr Ser Tyr Arg Leu Ile Ser Cys
        195                 200                 205

Asn Thr Ser Val Ile Thr Gln Ala Cys Pro Lys Val Ser Phe Glu Pro
    210                 215                 220
```

```
Ile Pro Ile His Tyr Cys Ala Pro Ala Gly Phe Ala Ile Leu Lys Cys
225                 230                 235                 240

Asn Asp Lys Lys Phe Asn Gly Thr Gly Pro Cys Thr Asn Val Ser Thr
            245                 250                 255

Val Gln Cys Thr His Gly Ile Arg Pro Val Val Ser Thr Gln Leu Leu
        260                 265                 270

Leu Asn Gly Ser Leu Ala Glu Lys Glu Val Val Ile Arg Ser Glu Asn
    275                 280                 285

Phe Thr Asn Asn Ala Lys Thr Ile Ile Val Gln Leu Asp Glu Ser Val
290                 295                 300

Val Ile Asn Cys Thr Arg Pro Asn Asn Asn Thr Arg Lys Ser Ile His
305                 310                 315                 320

Ile Gly Pro Gly Arg Ala Phe Tyr Thr Thr Gly Glu Ile Ile Gly Asp
                325                 330                 335

Ile Arg Gln Ala His Cys Thr Leu Asn Arg Thr Glu Trp Asn Asn Thr
            340                 345                 350

Leu Ala Lys Ile Thr Glu Lys Leu Arg Glu Gln Phe Gly Asn Asn Ile
        355                 360                 365

Thr Ile Val Phe Asn His Ser Ser Gly Gly Asp Pro Glu Ile Val Met
370                 375                 380

His Ser Phe Ile Cys Gly Gly Glu Phe Phe Tyr Cys Asn Thr Ser Gln
385                 390                 395                 400

Leu Phe Asn Ser Thr Trp Asn Ser Thr Gly Asn Asn Ile Ser Glu Ser
                405                 410                 415

Asp Asn Thr Glu Arg Asn Ile Thr Leu Pro Cys Arg Ile Lys Gln Ile
            420                 425                 430

Ile Asn Leu Trp Gln Glu Val Gly Lys Ala Met Tyr Ala Pro Pro Ile
        435                 440                 445

Arg Gly Gln Ile Arg Cys Ser Ser Asn Ile Thr Gly Leu Leu Leu Thr
450                 455                 460

Arg Asp Gly Gly Ser Asn Thr Asp Glu Asn Arg Thr Glu Ile Phe Arg
465                 470                 475                 480

Pro Gly Gly Gly Asp Met Arg Asp Asn Trp Arg Ser Glu Leu Tyr Lys
                485                 490                 495

Tyr Lys Val Val Lys Ile Glu Pro Leu Gly Val Ala Pro Thr Lys Ala
            500                 505                 510

Lys Arg Arg Val Val Gln Arg Glu Lys Arg
        515                 520

<210> SEQ ID NO 26
<211> LENGTH: 510
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Met Arg Val Lys Glu Thr Arg Arg Ile Trp Gln His Leu Trp Lys Trp
1               5                   10                  15

Gly Thr Met Leu Leu Gly Met Leu Met Ile Tyr Ser Ala Ala Glu Asn
                20                  25                  30

Leu Trp Val Thr Val Tyr Tyr Gly Val Pro Val Trp Lys Glu Ala Thr
            35                  40                  45

Thr Thr Leu Phe Cys Ala Ser Asp Ala Lys Ala Tyr Asp Thr Glu Val
```

-continued

```
                50                  55                  60
His Asn Val Trp Ala Thr His Ala Cys Val Pro Thr Asp Pro Asn Pro
 65                  70                  75                  80

Gln Glu Val Val Leu Gly Asn Val Thr Glu Asn Phe Asn Met Trp Lys
                     85                  90                  95

Asn Asn Met Val Glu Gln Met His Glu Asp Val Ile Ser Leu Trp Asp
                    100                 105                 110

Gln Ser Leu Lys Pro Cys Val Lys Leu Thr Pro Leu Cys Val Thr Leu
                115                 120                 125

Asn Cys Thr Asp Val Leu Gly Lys Gly Thr Ser Ala Asn Ala Thr Ser
130                 135                 140

Ala Asn Val Thr Ser Glu Lys Gly Glu Ile Lys Asn Cys Ser Phe Asn
145                 150                 155                 160

Ile Thr Thr Thr Leu Arg Asp Lys Val Gln Lys Ala His Ala Leu Phe
                165                 170                 175

Tyr Arg Leu Asp Val Val Pro Ile Asp Asp Asn Asn Asp Asn Ser Ser
                180                 185                 190

Ser Ser Tyr Arg Leu Ile Asn Cys Asn Thr Ser Val Ile Thr Gln Ala
                195                 200                 205

Cys Pro Lys Val Ser Phe Glu Pro Ile Pro Ile His Phe Cys Thr Pro
    210                 215                 220

Ala Gly Phe Ala Leu Leu Lys Cys Asn Asn Lys Lys Phe Asn Gly Thr
225                 230                 235                 240

Gly Pro Cys Thr Asn Val Ser Thr Val Gln Cys Thr His Gly Ile Lys
                245                 250                 255

Pro Val Val Ser Thr Gln Leu Leu Leu Asn Gly Ser Leu Ala Glu Glu
                260                 265                 270

Glu Val Val Ile Arg Ser Glu Asn Phe Thr Asp Asn Ala Lys Thr Ile
                275                 280                 285

Ile Val Gln Leu Asn Asp Ser Val Val Ile Asn Cys Thr Arg Pro Asn
290                 295                 300

Asn Asn Thr Arg Lys Gly Ile Thr Ile Gly Pro Gly Ser Val Phe Tyr
305                 310                 315                 320

Thr Gly Glu Ile Ile Gly Asp Ile Arg Gln Ala His Cys Asn Leu Ser
                325                 330                 335

Ser Ala Lys Trp Asn Asn Thr Leu Lys Gln Ile Val Ile Lys Leu Arg
                340                 345                 350

Glu Gln Phe Gly Asn Lys Thr Ile Val Phe Asn Gln Ser Ser Gly Gly
                355                 360                 365

Asp Pro Glu Ile Val Leu His Ser Phe Asn Cys Gly Gly Glu Phe Phe
                370                 375                 380

Tyr Cys Asn Thr Thr Gln Leu Phe Asn Ser Thr Trp Asn Ile Asn Asp
385                 390                 395                 400

Thr Arg Asn Gly Thr Thr Glu Ser Ser Lys Thr Ile Thr Leu Pro Cys
                405                 410                 415

Arg Ile Lys Gln Ile Ile Asn Met Trp Gln Glu Val Gly Lys Ala Met
                420                 425                 430

Tyr Ala Pro Pro Ile Arg Gly Gln Ile Arg Cys Ser Ser Asn Ile Thr
                435                 440                 445

Gly Leu Leu Leu Thr Arg Asp Gly Gly Asn Gln Asn Thr Ser Gly Thr
450                 455                 460

Glu Ile Phe Arg Pro Gly Gly Gly Asn Met Arg Asp Asn Trp Arg Ser
465                 470                 475                 480
```

```
Glu Leu Tyr Lys Tyr Lys Val Val Lys Ile Glu Pro Leu Gly Ile Ala
            485                 490                 495

Pro Thr Lys Ala Lys Arg Arg Val Val Gln Arg Glu Lys Arg
        500                 505                 510

<210> SEQ ID NO 27
<211> LENGTH: 519
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Met Arg Val Lys Gly Ile Arg Lys Asn Cys Gln His Leu Trp Arg Trp
1               5                   10                  15

Gly Thr Met Leu Leu Gly Met Leu Met Ile Cys Ser Ala Ala Glu Asn
            20                  25                  30

Leu Trp Val Thr Val Tyr Tyr Gly Val Pro Val Trp Lys Glu Ala Thr
        35                  40                  45

Thr Thr Leu Phe Cys Ala Ser Asp Ala Lys Ala Tyr Asp Thr Glu Ala
50                  55                  60

His Asn Val Trp Ala Thr His Ala Cys Val Pro Thr Asp Pro Asn Pro
65                  70                  75                  80

Gln Glu Val Val Leu Gly Asn Val Thr Glu Asn Phe Asn Met Trp Lys
                85                  90                  95

Asn Asp Met Val Glu Gln Met His Glu Asp Ile Ile Ser Leu Trp Asp
            100                 105                 110

Gln Ser Leu Lys Pro Cys Val Lys Leu Thr Pro Ile Cys Val Ala Leu
        115                 120                 125

Asn Cys Thr Asp Val Lys Asp Thr Asn Asn Thr Ser Asn Asn Thr Asn
130                 135                 140

Asn Thr Ser Ser Asn Asn Ser Ser Met Thr Glu Gly Gly Glu Met Lys
145                 150                 155                 160

Asn Cys Ser Phe Asn Ile Thr Thr Ser Ile Lys Thr Lys Val Lys Asp
                165                 170                 175

Tyr Ala Leu Phe Tyr Lys Leu Asp Ile Val Pro Ile Asp Asn Asp Gly
            180                 185                 190

Asp Asn Thr Ser Tyr Arg Leu Ile Ser Cys Asn Thr Ser Val Ile Thr
        195                 200                 205

Gln Ala Cys Pro Lys Ile Ser Phe Glu Pro Ile Pro Ile His Tyr Cys
    210                 215                 220

Thr Pro Ala Gly Tyr Ala Leu Leu Lys Cys Asn Asn Lys Lys Phe Asn
225                 230                 235                 240

Gly Thr Gly Pro Cys Lys Asn Val Ser Thr Val Gln Cys Thr His Gly
                245                 250                 255

Ile Arg Pro Val Val Ser Thr Gln Leu Leu Leu Asn Gly Ser Leu Ala
            260                 265                 270

Glu Glu Glu Val Val Ile Arg Ser Ser Asn Phe Thr Asn Asn Ala Lys
        275                 280                 285

Val Ile Ile Val Gln Leu Lys Glu Ala Val Glu Ile Asn Cys Thr Arg
    290                 295                 300

Pro Asn Asn Asn Thr Arg Lys Ser Ile His Ile Gly Pro Gly Lys Ala
305                 310                 315                 320

Trp Tyr Thr Thr Gly Glu Ile Ile Gly Asn Ile Arg Gln Ala His Cys
```

```
                    325                 330                 335
Asn Ile Ser Arg Thr Lys Trp Asn Asn Thr Leu His Gln Ile Val Lys
                340                 345                 350
Lys Leu Arg Ile Gln Phe Gly Asn Lys Thr Ile Ile Phe Asn Gln Ser
            355                 360                 365
Ala Gly Gly Asp Pro Glu Ile Val Val His Ser Phe Asn Cys Gly Gly
        370                 375                 380
Glu Phe Phe Tyr Cys Asn Thr Ser Gln Leu Phe Asn Ser Thr Trp Arg
385                 390                 395                 400
Asn Asp Thr Trp Asn Asp Thr Ser Pro Gln Ile Ala Thr Thr Gly Asn
                405                 410                 415
Asp Thr Ile Thr Leu Pro Cys Arg Ile Arg Gln Ile Val Asn Met Trp
                420                 425                 430
Gln Gln Val Gly Lys Ala Met Tyr Ala Pro Pro Ile Ala Gly Gln Ile
            435                 440                 445
Arg Cys Ser Ser Asn Ile Thr Gly Val Leu Leu Thr Arg Asp Gly Gly
        450                 455                 460
Asn Asn Glu Ser Lys Ala Asn Ala Asn Glu Thr Phe Arg Pro Ala Gly
465                 470                 475                 480
Gly Asp Met Arg Asp Asn Trp Arg Ser Glu Leu Tyr Lys Tyr Lys Val
                485                 490                 495
Val Lys Ile Glu Pro Leu Gly Val Ala Pro Thr Lys Ala Lys Arg Arg
                500                 505                 510
Val Val Gln Arg Glu Lys Arg
            515
```

<210> SEQ ID NO 28
<211> LENGTH: 505
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 28

```
Met Lys Val Lys Gly Ile Arg Lys Asn Tyr Gln His Leu Trp Arg Trp
1               5                   10                  15
Gly Met Met Leu Leu Gly Met Leu Met Ile Cys Ser Ala Thr Glu Lys
            20                  25                  30
Leu Trp Val Thr Val Tyr Tyr Gly Val Pro Val Trp Arg Asp Ala Thr
        35                  40                  45
Thr Thr Leu Phe Cys Ala Ser Asp Ala Lys Ala Tyr Glu Thr Glu Leu
    50                  55                  60
His Asn Val Trp Ala Thr His Ala Cys Val Pro Thr Asp Pro Asn Pro
65                  70                  75                  80
Gln Glu Val Val Leu Gly Asn Val Thr Glu Asn Phe Asn Met Trp Lys
                85                  90                  95
Asn Asp Met Val Glu Gln Met Asn Glu Asp Ile Ile Ser Leu Trp Asp
            100                 105                 110
Glu Ser Leu Lys Pro Cys Val Lys Leu Thr Pro Leu Cys Val Thr Leu
        115                 120                 125
Asn Cys Thr Asn Tyr Asn Glu Thr Thr Thr Asn Ser Thr Thr Thr Asn
    130                 135                 140
Ala Thr Val Val Ser Pro Gly Glu Ile Lys Asn Cys Ser Phe Asn Val
145                 150                 155                 160
```

Thr Thr Gly Ile Arg Asp Lys Val Arg Lys Asp His Ala Leu Phe Tyr
            165                 170                 175

Ala Leu Asp Ile Val Pro Ile Asp Asn Thr Ile Asp Asn Thr Ser Tyr
            180                 185                 190

Arg Leu Val Ser Cys Asn Thr Ser Val Leu Thr Gln Ala Cys Pro Lys
            195                 200                 205

Val Ser Phe Glu Pro Ile Pro Ile His Phe Cys Ala Pro Ala Gly Tyr
            210                 215                 220

Ala Ile Ile Lys Cys Asn Asn Lys Thr Phe Asn Gly Ser Gly Pro Cys
225                 230                 235                 240

Arg Asn Val Ser Thr Val Gln Cys Thr His Gly Ile Arg Pro Val Val
            245                 250                 255

Ser Thr Gln Leu Leu Leu Asn Gly Ser Leu Ala Glu Glu Ile Val
            260                 265                 270

Ile Arg Ser Ala Asn Phe Ser Asp Asn Thr Lys Thr Ile Ile Val Gln
            275                 280                 285

Leu Asn Glu Ala Val Lys Ile Asn Cys Thr Arg Pro Asn Asn Asn Thr
            290                 295                 300

Arg Arg Ser Val His Met Gly Pro Gly Ser Ala Phe Tyr Thr Thr Gly
305                 310                 315                 320

Gly Ile Ile Gly Asp Ile Arg Gln Ala His Cys Asn Ile Ser Glu Arg
            325                 330                 335

Asp Trp Asn Gly Ala Leu Lys Gln Ile Val Glu Lys Leu Gly Glu Gln
            340                 345                 350

Phe Gln Asn Lys Thr Ile Val Phe Lys Gln Ser Ser Gly Gly Asp Pro
            355                 360                 365

Glu Val Val Met His Thr Phe Asn Cys Arg Gly Glu Phe Phe Tyr Cys
            370                 375                 380

Asn Thr Thr Lys Leu Phe Asn Ser Thr Trp Val Asn Gly Thr Lys Asn
385                 390                 395                 400

Asp Thr Lys Gly Gly Asn Gly Thr Ile Thr Leu Gln Cys Arg Ile Lys
            405                 410                 415

Gln Ile Ile Asn Met Trp Gln Gln Val Gly Lys Ala Met Tyr Ala Pro
            420                 425                 430

Pro Ile Ser Gly Pro Ile Ser Cys Ser Ser Asn Ile Thr Gly Leu Ile
            435                 440                 445

Leu Thr Arg Asp Gly Gly Thr Asn Thr Thr Asn Glu Thr Phe Arg Pro
            450                 455                 460

Gly Gly Gly Asp Met Arg Asp Asn Trp Arg Ser Glu Leu Tyr Lys Tyr
465                 470                 475                 480

Lys Val Val Lys Ile Glu Pro Ile Gly Val Ala Pro Thr Lys Ala Arg
            485                 490                 495

Arg Arg Val Val Gln Arg Glu Lys Arg
            500                 505

<210> SEQ ID NO 29
<211> LENGTH: 504
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Met Arg Ala Lys Glu Thr Arg Lys Lys Tyr Gln His Leu Trp Ala Trp
1               5                   10                  15

```
Gly Thr Leu Leu Leu Gly Met Leu Met Ile Cys Ser Ala Thr Glu Gln
            20                  25                  30

Leu Trp Val Thr Val Tyr Tyr Gly Val Pro Val Trp Lys Asp Ala Asn
        35                  40                  45

Thr Thr Leu Phe Cys Ala Ser Asp Ala Lys Ala Tyr Asp Thr Glu Val
    50                  55                  60

His Asn Val Trp Ala Thr His Ala Cys Val Pro Thr Asp Pro Ser Pro
65                  70                  75                  80

Gln Glu Ile Val Leu Lys Asn Val Thr Glu Asn Phe Asn Met Trp Lys
                85                  90                  95

Asn Asn Met Val Glu Gln Met His Lys Asp Ile Ser Leu Trp Asp
            100                 105                 110

Glu Ser Leu Lys Pro Cys Val Lys Leu Thr Pro Leu Cys Val Thr Leu
        115                 120                 125

Asn Cys Ser Asn Tyr Asn Ser Thr Asn Ser Thr Ile Asp Pro Asn Met
130                 135                 140

Glu Gly Ala Ile Lys Asn Cys Ser Phe Asn Ala Thr Thr Gly Ile Gln
145                 150                 155                 160

Asn Lys Met Lys Lys Glu Tyr Ala Leu Phe Tyr Ser Leu Asp Ile Val
                165                 170                 175

Gln Ile Glu Ser Glu Asn Lys Ser Asn Lys Ser Tyr Met Leu Arg Ser
            180                 185                 190

Cys Asn Thr Ser Val Ile Thr Gln Ala Cys Pro Lys Val Thr Phe Glu
        195                 200                 205

Pro Ile Pro Ile His Tyr Cys Ala Pro Ala Gly Phe Ala Ile Leu Lys
    210                 215                 220

Cys Asn Asp Lys Lys Phe Asn Gly Thr Gly Pro Cys Lys Asn Val Ser
225                 230                 235                 240

Thr Val Gln Cys Thr His Gly Ile Arg Pro Val Val Ser Thr Gln Leu
                245                 250                 255

Leu Leu Asn Gly Ser Leu Ala Glu Glu Ile Ile Ile Arg Ser Glu
            260                 265                 270

Asn Ile Thr Asn Asn Ala Lys Thr Ile Ile Ile Gln Leu Asn Arg Ser
        275                 280                 285

Ile Glu Ile Asn Cys Thr Arg Pro Asn Asn Asn Thr Arg Lys Ser Ile
    290                 295                 300

His Met Gly Trp Gly Arg Ala Phe Tyr Ala Thr Gly Asp Ile Ile Gly
305                 310                 315                 320

Asp Ile Arg Gln Ala His Cys Asn Leu Ser Gly Thr Lys Trp Asn Asn
                325                 330                 335

Thr Leu Tyr Gln Ile Ala Arg Lys Leu Arg Glu His Phe Asn Asn Thr
            340                 345                 350

Ile Val Phe Asn Gln Ser Ser Gly Gly Asp Pro Glu Ile Val Met His
        355                 360                 365

Thr Phe Asn Cys Gly Gly Glu Phe Phe Tyr Cys Asn Thr Thr Gln Leu
    370                 375                 380

Phe Asn Ser Thr Trp His Ala Asn Ser Thr Trp Asn Glu Thr Thr Gly
385                 390                 395                 400

Ser Gly Ser Asn Asp Thr Ile Ser Leu Pro Cys Arg Ile Lys Gln Ile
                405                 410                 415

Ile Asn Arg Trp Gln Glu Val Gly Lys Ala Met Tyr Ala Pro Pro Ile
            420                 425                 430
```

```
Gly Gly Gln Ile Arg Cys Ser Ser Asn Ile Thr Gly Ile Leu Leu Thr
            435                 440                 445

Arg Asp Gly Gly Thr Glu Asn Asn Thr Ser Glu Thr Phe Arg Pro Gly
450                 455                 460

Gly Gly Asn Met Lys Asp Asn Trp Arg Ser Glu Leu Tyr Lys Tyr Lys
465                 470                 475                 480

Val Val Arg Ile Glu Pro Leu Gly Val Ala Pro Thr Lys Ala Lys Arg
                485                 490                 495

Arg Val Val Gln Arg Glu Lys Arg
            500

<210> SEQ ID NO 30
<211> LENGTH: 503
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Met Arg Val Lys Gly Ile Arg Lys Asn Tyr Gln His Leu Trp Arg Trp
1               5                   10                  15

Gly Thr Met Leu Leu Gly Met Leu Met Ile Cys Ser Ala Ala Glu Gln
            20                  25                  30

Leu Trp Val Thr Val Tyr Tyr Gly Val Pro Val Trp Lys Glu Ala Thr
        35                  40                  45

Thr Thr Leu Phe Cys Ala Ser Asp Ala Lys Ala His Asp Thr Glu Val
    50                  55                  60

His Asn Val Trp Ala Thr His Ala Cys Val Pro Thr Asp Pro Asn Pro
65                  70                  75                  80

Gln Glu Val Val Leu Glu Asn Val Thr Glu Asn Phe Asn Met Trp Lys
                85                  90                  95

Asn Asn Met Val Glu Gln Met Gln Glu Asp Val Ile Ser Leu Trp Asp
            100                 105                 110

Gln Ser Leu Lys Pro Cys Val Lys Leu Thr Pro Leu Cys Val Thr Leu
        115                 120                 125

Asn Cys Thr Asp Val Ser Ser Asn Ser Thr Ser Val Asn Ile Thr Ser
    130                 135                 140

Glu Lys Gly Glu Ile Lys Asn Cys Ser Phe Asn Val Thr Thr Ser Ile
145                 150                 155                 160

Lys Asp Lys Val Gln Lys Glu Tyr Ala Leu Phe Tyr Lys Leu Asp Val
                165                 170                 175

Val Pro Ile Glu Asp Asp Ser Arg Asn Asn Ser Tyr Arg Leu Ile Ser
            180                 185                 190

Cys Asn Thr Ser Val Ile Thr Gln Ala Cys Pro Lys Val Ser Phe Glu
        195                 200                 205

Pro Ile Pro Ile His Tyr Cys Thr Pro Ala Gly Phe Ala Ile Leu Lys
    210                 215                 220

Cys Asn Asp Lys Lys Phe Asn Gly Thr Gly Pro Cys Thr Asn Val Ser
225                 230                 235                 240

Thr Val Gln Cys Thr His Gly Ile Arg Pro Val Val Ser Thr Gln Leu
                245                 250                 255

Leu Leu Asn Gly Ser Leu Ala Glu Glu Glu Val Val Ile Arg Ser Glu
            260                 265                 270

Asn Phe Thr Asn Asn Ala Lys Thr Ile Ile Val Gln Leu Asn Glu Ser
        275                 280                 285
```

```
Val Glu Ile Asn Cys Thr Arg Pro Asn Asn Thr Arg Lys Ser Ile
    290                 295                 300

His Ile Gly Pro Gly Arg Ala Phe Tyr Ala Thr Gly Asp Ile Ile Gly
305                 310                 315                 320

Asp Ile Arg Gln Ala His Cys Asn Ile Ser Arg Glu Lys Trp Asn Asn
                325                 330                 335

Thr Leu Lys Gln Ile Val Lys Lys Leu Arg Glu Gln Phe Gly Asn Lys
            340                 345                 350

Thr Ile Val Phe Asn Gln Ser Ser Gly Gly Asp Pro Glu Ile Val Met
            355                 360                 365

His Ser Phe Asn Cys Gly Gly Glu Phe Phe Tyr Cys Asn Thr Thr Gln
        370                 375                 380

Leu Phe Asn Ser Thr Trp Ser Ile Asn Gly Thr Trp Asn Gly Thr Thr
385                 390                 395                 400

Glu Ser Asn Asp Thr Ile Thr Leu Pro Cys Arg Ile Lys Gln Ile Ile
                405                 410                 415

Asn Met Trp Gln Glu Val Gly Lys Ala Met Tyr Ala Pro Pro Ile Arg
            420                 425                 430

Gly Gln Ile Arg Cys Ser Ser Asn Ile Thr Gly Leu Leu Leu Thr Arg
            435                 440                 445

Asp Gly Gly Asn Ser Ser Ser Asn Asn Glu Thr Phe Arg Pro Gly Gly
        450                 455                 460

Gly Asp Met Arg Asp Asn Trp Arg Ser Glu Leu Tyr Lys Tyr Lys Val
465                 470                 475                 480

Val Lys Ile Glu Pro Leu Gly Val Ala Pro Thr Lys Ala Lys Arg Arg
                485                 490                 495

Val Val Gln Arg Glu Lys Arg
            500

<210> SEQ ID NO 31
<211> LENGTH: 501
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Met Lys Val Lys Gly Ile Arg Lys Asn Cys Gln His Leu Trp Arg Trp
1               5                   10                  15

Gly Ile Met Leu Leu Gly Met Leu Met Ile Cys Ser Ala Thr Glu Lys
            20                  25                  30

Leu Trp Val Thr Val Tyr Tyr Gly Val Pro Val Trp Lys Glu Ala Thr
        35                  40                  45

Thr Thr Leu Phe Cys Ala Ser Asp Ala Lys Ala His Asp Thr Glu Ala
    50                  55                  60

His Asn Val Trp Ala Thr His Ala Cys Val Pro Thr Asp Pro Asn Pro
65                  70                  75                  80

Gln Glu Ile Val Leu Glu Asn Val Thr Glu Asn Phe Asn Met Trp Lys
                85                  90                  95

Asn Asp Met Val Glu Gln Met Gln Glu Asp Val Ile Ser Leu Trp Asp
            100                 105                 110

Glu Ser Leu Lys Pro Cys Val Glu Leu Thr Pro Leu Cys Val Thr Leu
        115                 120                 125

Asn Cys Thr Asn Val Asn Ala Thr Asn Thr Asn Asn Ser Ser Gly Ile
```

```
                130             135             140
Glu Gly Gly Glu Met Lys Asn Cys Ser Phe Asn Val Thr Thr Ser Ile
145             150                 155                 160

Lys Asp Lys Met Gln Lys Glu Tyr Ala Leu Phe Tyr Ser Leu Asp Val
                165                 170                 175

Val Gln Ile Asp Asn Asp Thr Asn Tyr Arg Leu Ile Asn Cys Asn Thr
            180                 185                 190

Ser Val Ile Thr Gln Ala Cys Pro Lys Ile Ser Phe Glu Pro Ile Pro
        195                 200                 205

Ile His Tyr Cys Thr Pro Ala Gly Phe Ala Ile Ile Lys Cys Asn Asp
    210                 215                 220

Lys Lys Phe Asn Gly Ser Gly Pro Cys Lys Asn Val Ser Thr Val Gln
225                 230                 235                 240

Cys Thr His Gly Ile Lys Pro Val Val Ser Thr Gln Leu Leu Leu Asn
                245                 250                 255

Gly Ser Leu Ala Glu Glu Glu Ile Val Ile Arg Ser Glu Asn Phe Ser
                260                 265                 270

Asp Asn Ala Lys Thr Ile Ile Val Gln Leu Asn Glu Ser Val Val Ile
            275                 280                 285

Asn Cys Thr Arg Pro Asn Asn Asn Thr Arg Lys Ser Ile Ser Ile Gly
        290                 295                 300

Pro Gly Arg Ala Phe Tyr Ala Thr Gly Asp Ile Ile Gly Asn Ile Arg
305                 310                 315                 320

Gln Ala His Cys Asn Leu Ser Arg Ala Lys Trp Asn Asn Thr Leu Arg
                325                 330                 335

Gln Ile Val Thr Lys Leu Arg Glu Gln Phe Lys Asn Lys Thr Ile Ala
                340                 345                 350

Phe Asn His Ser Ser Gly Gly Asp Pro Glu Ile Val Met His Thr Phe
            355                 360                 365

Asn Cys Gly Gly Glu Phe Phe Tyr Cys Asn Ser Thr Gln Leu Phe Asn
        370                 375                 380

Ser Thr Trp Ile Ala Asn Lys Thr Gly Asn Asp Thr Gly Gly Ser Asn
385                 390                 395                 400

Gly Thr Ile Thr Leu Gln Cys Arg Ile Lys Gln Ile Val Asn Arg Trp
                405                 410                 415

Gln Glu Val Gly Lys Ala Met Tyr Ala Pro Pro Ile Ser Gly Gln Ile
                420                 425                 430

Ser Cys Ser Ser Asn Ile Thr Gly Leu Ile Leu Thr Arg Asp Gly Gly
            435                 440                 445

Thr Asn Asn Thr Asn Gly Thr Glu Ile Phe Arg Pro Gly Gly Gly Asn
450                 455                 460

Met Lys Asp Asn Trp Arg Ser Glu Leu Tyr Lys Tyr Lys Val Val Arg
465                 470                 475                 480

Ile Glu Pro Leu Gly Ile Ala Pro Thr Lys Ala Arg Arg Arg Val Val
                485                 490                 495

Gln Arg Glu Lys Arg
                500
```

<210> SEQ ID NO 32
<211> LENGTH: 508
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 32

```
Met Arg Val Arg Gly Ile Leu Arg Asn Tyr Gln Gln Trp Trp Ile Trp
1               5                   10                  15

Gly Ile Leu Gly Phe Trp Met Leu Met Ile Cys Asn Val Val Gly Asn
            20                  25                  30

Leu Trp Val Thr Val Tyr Tyr Gly Val Pro Val Trp Lys Glu Ala Lys
        35                  40                  45

Thr Thr Leu Phe Cys Ala Ser Asp Ala Lys Ala Tyr Glu Lys Glu Val
50                  55                  60

His Asn Val Trp Ala Thr His Ala Cys Val Pro Thr Asp Pro Asn Pro
65                  70                  75                  80

Gln Glu Met Val Leu Glu Asn Val Thr Glu Asn Phe Asn Met Trp Lys
                85                  90                  95

Asn Asp Met Val Asp Gln Met His Glu Asp Ile Ile Ser Leu Trp Asp
            100                 105                 110

Gln Ser Leu Lys Pro Cys Val Lys Leu Thr Pro Leu Cys Val Thr Leu
        115                 120                 125

Asn Cys Val Asn Ile Thr Asn Ser Thr Thr Ser Asn Gly Asp Gly Thr
130                 135                 140

Val Thr His Ile Asn Ser Ile Lys Glu Glu Ile Lys Asn Cys Ser Phe
145                 150                 155                 160

Asn Ala Thr Thr Glu Leu Arg Asp Lys Lys Ser Lys Glu Tyr Ala Leu
                165                 170                 175

Phe Tyr Arg Leu Asp Ile Val Pro Leu Ser Ser Gly Asn Ser Ser Ser
            180                 185                 190

Asn Ser Ser Lys Tyr Arg Leu Ile Asn Cys Asn Thr Ser Thr Ile Thr
        195                 200                 205

Gln Ala Cys Pro Lys Val Ser Phe Asp Pro Ile Pro Ile His Tyr Cys
210                 215                 220

Ala Pro Ala Gly Tyr Ala Ile Leu Lys Cys Asn Asn Lys Thr Phe Asn
225                 230                 235                 240

Gly Thr Gly Pro Cys Asn Asn Val Ser Thr Val Gln Cys Thr His Gly
                245                 250                 255

Ile Lys Pro Val Val Ser Thr Gln Leu Leu Leu Asn Gly Ser Leu Ala
            260                 265                 270

Glu Glu Glu Ile Ile Ile Arg Ser Glu Asn Leu Thr Asp Asn Val Lys
        275                 280                 285

Thr Ile Ile Val His Leu Asn Glu Ser Val Gly Ile Val Cys Thr Arg
290                 295                 300

Pro Asn Asn Asn Thr Arg Lys Ser Ile Arg Ile Gly Pro Gly Gln Thr
305                 310                 315                 320

Phe Tyr Ala Thr Gly Asp Ile Ile Gly Asp Ile Arg Gln Ala His Cys
                325                 330                 335

Asn Ile Ser Lys Gly Ala Trp Asn Glu Thr Leu Gln Trp Val Gly Lys
            340                 345                 350

Lys Leu Lys Glu His Phe Pro Asn Lys Thr Ile Lys Phe Asn Ser Ser
        355                 360                 365

Ser Gly Gly Asp Leu Glu Ile Thr Thr His Ser Phe Asn Cys Arg Gly
370                 375                 380

Glu Phe Phe Tyr Cys Asn Thr Ser Gly Leu Phe Asn Ser Thr Tyr Arg
385                 390                 395                 400

Asn Asn Ser Thr Gly Asp Asn Ser Thr Ile Thr Leu Pro Cys Arg Ile
```

```
                    405                 410                 415

Lys Gln Ile Ile Asn Met Trp Gln Glu Val Gly Arg Ala Met Tyr Ala
                420                 425                 430

Pro Pro Ile Ala Gly Asn Ile Thr Cys Lys Ser Asn Ile Thr Gly Leu
            435                 440                 445

Leu Leu Thr Arg Asp Gly Gly Thr Arg Asp Arg Asn Asp Thr Glu Thr
        450                 455                 460

Phe Arg Pro Gly Gly Gly Asp Met Arg Asp Asn Trp Arg Ser Glu Leu
465                 470                 475                 480

Tyr Lys Tyr Lys Val Val Glu Ile Lys Pro Leu Gly Ile Ala Pro Thr
                485                 490                 495

Lys Ala Lys Arg Arg Val Val Glu Arg Glu Lys Arg
                500                 505

<210> SEQ ID NO 33
<211> LENGTH: 500
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Met Arg Val Met Gly Ile Gln Arg Asn Trp Pro Gln Trp Trp Ile Trp
1               5                   10                  15

Gly Ile Leu Gly Phe Trp Met Ile Ile Cys Arg Val Val Gly Asn
            20                  25                  30

Leu Trp Val Thr Val Tyr Tyr Gly Val Pro Val Trp Arg Glu Ala Lys
        35                  40                  45

Thr Thr Leu Phe Cys Ala Ser Asp Ala Lys Ala Tyr Glu Arg Glu Val
    50                  55                  60

His Asn Val Trp Ala Thr His Ala Cys Val Pro Thr Asp Pro Asn Pro
65                  70                  75                  80

Gln Glu Leu Val Leu Glu Asn Val Thr Glu Asn Phe Asn Met Trp Glu
                85                  90                  95

Asn Asp Met Val Asp Gln Met His Glu Asp Val Ile Ser Leu Trp Asp
            100                 105                 110

Gln Ser Leu Lys Pro Cys Val Lys Leu Thr Pro Leu Cys Val Thr Leu
        115                 120                 125

Lys Cys Thr Asn Thr Thr Tyr Tyr Asn Val Ser Ser Lys Glu Phe Thr
    130                 135                 140

Asn Gly Glu Ile Lys Asn Cys Ser Phe Asn Thr Thr Thr Glu Leu Arg
145                 150                 155                 160

Asp Lys Lys Gln Lys Val Ser Ala Leu Phe Tyr Arg Leu Asp Val Val
                165                 170                 175

Pro Leu Ser Lys Lys Asp Lys Thr Asn Asn Asp Ser Gly Glu Tyr Ile
            180                 185                 190

Leu Ile Asn Cys Asn Thr Ser Ala Ile Thr Gln Ala Cys Pro Lys Val
        195                 200                 205

Ser Phe Asp Pro Ile Pro Ile His Tyr Cys Thr Pro Ala Gly Tyr Ala
    210                 215                 220

Ile Leu Lys Cys Asn Asn Lys Thr Phe Asn Gly Thr Gly Pro Cys His
225                 230                 235                 240

Asn Val Ser Thr Val Gln Cys Thr His Gly Ile Lys Pro Val Val Ser
                245                 250                 255
```

Thr Gln Leu Leu Leu Asn Gly Ser Leu Thr Glu Gly Glu Ile Ile Ile
            260                 265                 270

Arg Ser Glu Asn Leu Thr Asn Asn Ala Lys Thr Ile Ile Val His Leu
        275                 280                 285

Asn Gln Ser Val Ala Ile Val Cys Thr Arg Pro Gly Asn Asn Thr Arg
    290                 295                 300

Lys Ser Val Arg Ile Gly Pro Gly Gln Ala Phe Tyr Ala Thr Gly Glu
305                 310                 315                 320

Ile Ile Gly Asp Ile Arg Gln Ala Tyr Cys Asn Leu Thr Asn Trp Gln
                325                 330                 335

Glu Thr Leu Lys Asn Val Ser Lys Lys Leu Gln Glu Arg Phe Asn Lys
            340                 345                 350

Thr Ile Arg Phe Ala Pro Ser Ser Gly Gly Asp Leu Glu Ile Thr Thr
        355                 360                 365

His Ser Phe Asn Cys Gly Gly Glu Phe Phe Tyr Cys Asn Thr Ser Ser
    370                 375                 380

Leu Phe Asn Ser Ala Tyr Asn Pro Asn Gly Thr Lys Asp Asn Ser Asn
385                 390                 395                 400

Ser Ser Ile Thr Ile Gln Cys Lys Ile Lys Gln Ile Ile Asn Met Trp
                405                 410                 415

Gln Gly Val Gly Arg Ala Ile Tyr Ala Pro Pro Ile Ala Gly Asn Ile
            420                 425                 430

Thr Cys Asn Ser Asn Ile Thr Gly Ile Leu Leu Thr Arg Asp Gly Gly
        435                 440                 445

Ser Lys Asn Asn Thr Glu Glu Ile Phe Arg Pro Gly Gly Gly Asn Met
    450                 455                 460

Lys Asp Asn Trp Arg Ser Glu Leu Tyr Arg Tyr Lys Val Val Glu Ile
465                 470                 475                 480

Lys Pro Leu Gly Val Ala Pro Thr Glu Ala Lys Arg Arg Val Val Glu
                485                 490                 495

Arg Glu Lys Arg
            500

<210> SEQ ID NO 34
<211> LENGTH: 506
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Met Arg Val Lys Glu Thr Gln Met Asn Trp Pro Asn Leu Trp Lys Trp
1               5                   10                  15

Gly Thr Leu Ile Leu Gly Leu Val Ile Ile Cys Ser Ala Ser Asp Asn
            20                  25                  30

Leu Trp Val Thr Val Tyr Tyr Gly Val Pro Val Trp Arg Asp Ala Asp
        35                  40                  45

Thr Thr Leu Phe Cys Ala Ser Asp Ala Lys Ala His Glu Thr Glu Val
    50                  55                  60

His Asn Val Trp Ala Thr His Ala Cys Val Pro Thr Asp Pro Asn Pro
65                  70                  75                  80

Gln Glu Ile His Leu Glu Asn Val Thr Glu Asn Phe Asn Met Trp Lys
                85                  90                  95

Asn Asn Met Val Glu Gln Met Gln Glu Asp Val Ile Ser Leu Trp Asp
            100                 105                 110

```
Gln Ser Leu Lys Pro Cys Val Lys Leu Thr Pro Leu Cys Val Thr Leu
    115                 120                 125

Asn Cys Thr Lys Ala Asn Leu Thr Asn Ile Asn Glu Thr Thr Ala Ser
    130                 135                 140

Asn Gly Ile Gly Asn Ile Thr Asp Glu Val Arg Asn Cys Ser Phe Asn
145                 150                 155                 160

Met Thr Thr Glu Leu Arg Asp Lys Lys Gln Lys Val His Ala Leu Phe
                165                 170                 175

Tyr Lys Leu Asp Ile Val Pro Ile Arg Asn Glu Ser Lys Met Gly Asn
                180                 185                 190

Val Ser Ser Glu Tyr Arg Leu Ile Asn Cys Asn Thr Ser Val Ile Lys
            195                 200                 205

Gln Ala Cys Pro Lys Ile Ser Phe Asp Pro Ile Pro Ile His Tyr Cys
        210                 215                 220

Thr Pro Ala Gly Tyr Ala Ile Leu Lys Cys Asn Asp Lys Asn Phe Asn
225                 230                 235                 240

Gly Thr Gly Pro Cys Lys Asn Val Ser Ser Val Gln Cys Thr His Gly
                245                 250                 255

Ile Lys Pro Val Val Ser Thr Gln Leu Leu Leu Asn Gly Ser Leu Ala
                260                 265                 270

Glu Glu Glu Ile Ile Ile Arg Ser Glu Asn Leu Thr Asn Asn Ala Lys
            275                 280                 285

Thr Ile Ile Val His Leu Asn Lys Ser Val Glu Ile Asn Cys Thr Arg
        290                 295                 300

Pro Ser Asn Asn Thr Arg Thr Ser Ile Thr Ile Gly Pro Gly Gln Val
305                 310                 315                 320

Phe Tyr Arg Thr Gly Asp Ile Ile Gly Asp Ile Arg Lys Ala Tyr Cys
                325                 330                 335

Glu Ile Asn Gly Thr Lys Trp Asn Glu Thr Leu Lys Gln Val Ala Gly
                340                 345                 350

Lys Leu Lys Glu His Phe Asn Lys Thr Ile Ile Phe Gln Pro Pro Ser
            355                 360                 365

Gly Gly Asp Leu Glu Ile Thr Met His His Phe Asn Cys Arg Gly Glu
        370                 375                 380

Phe Phe Tyr Cys Asn Thr Thr Lys Leu Phe Asn Ser Thr Trp Asn Gly
385                 390                 395                 400

Thr Met Glu Gly Arg Asn Gly Thr Ile Ile Leu Pro Cys Arg Ile Lys
                405                 410                 415

Gln Ile Ile Asn Met Trp Gln Gly Val Gly Gln Ala Met Tyr Ala Pro
                420                 425                 430

Pro Ile Ser Gly Ile Ile Asn Cys Val Ser Asn Ile Thr Gly Ile Leu
            435                 440                 445

Leu Thr Arg Asp Gly Gly Asn Asn Asn Ala Thr Asn Glu Thr Phe Arg
        450                 455                 460

Pro Gly Gly Gly Asn Ile Lys Asp Asn Trp Arg Ser Glu Leu Tyr Lys
465                 470                 475                 480

Tyr Lys Val Val Gln Ile Glu Pro Leu Gly Ile Ala Pro Thr Arg Ala
                485                 490                 495

Lys Arg Arg Val Val Glu Arg Glu Lys Arg
                500                 505

<210> SEQ ID NO 35
<211> LENGTH: 508
```

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

```
Met Arg Val Lys Gly Thr Gln Met Asn Trp Pro Asn Leu Trp Arg Trp
1               5                   10                  15

Gly Thr Leu Ile Leu Gly Leu Val Ile Met Cys Ser Ala Ser Asp Asn
            20                  25                  30

Leu Trp Val Thr Val Tyr Tyr Gly Val Pro Val Trp Lys Asp Ala Asp
        35                  40                  45

Thr Thr Leu Phe Cys Ala Ser Asp Ala Lys Ala His Glu Thr Glu Val
    50                  55                  60

His Asn Ile Trp Ala Thr His Ala Cys Val Pro Thr Asp Pro Asn Pro
65                  70                  75                  80

Gln Glu Ile Pro Leu Glu Asn Val Thr Glu Asn Phe Asn Met Trp Lys
                85                  90                  95

Asn Asn Met Ala Glu Gln Met Gln Glu Asp Val Ile Ser Leu Trp Asp
            100                 105                 110

Glu Ser Leu Lys Pro Cys Val Lys Leu Thr Pro Leu Cys Val Thr Leu
        115                 120                 125

His Cys Thr Lys Ala Asn Leu Thr His Asn Thr Thr Asn Asp Lys Asn
    130                 135                 140

Gly Thr Gly Asn Ile Thr Asp Glu Val Lys Ile Gly Asn Ile Thr Asp
145                 150                 155                 160

Glu Val Lys Asn Cys Ser Phe Asn Met Thr Thr Glu Ile Arg Asp Lys
                165                 170                 175

Lys Gln Lys Val Tyr Ala Leu Phe Tyr Lys Leu Asp Ile Val Gln Ile
            180                 185                 190

Gly Glu Asn Gly Ser Glu Tyr Arg Leu Ile Asn Cys Asn Thr Ser Val
        195                 200                 205

Ile Lys Gln Ala Cys Pro Lys Val Ser Phe Asp Pro Ile Pro Ile His
    210                 215                 220

Tyr Cys Ala Pro Ala Gly Tyr Ala Leu Leu Lys Cys Asn Asp Lys Lys
225                 230                 235                 240

Phe Asn Gly Thr Gly Pro Cys Arg Asn Val Ser Ser Val Gln Cys Thr
                245                 250                 255

His Gly Ile Lys Pro Val Val Ser Thr Gln Leu Leu Leu Asn Gly Ser
            260                 265                 270

Leu Ala Glu Glu Glu Ile Ile Ile Arg Ser Glu Asn Leu Thr Asp Asn
        275                 280                 285

Ala Lys Thr Ile Ile Val His Leu Asn Glu Ser Val Ile Asn Cys
    290                 295                 300

Thr Arg Pro Ser Asn Asn Val Arg Ile Ser Thr Arg Ile Gly Pro Gly
305                 310                 315                 320

Gln Val Phe Tyr Arg Thr Gly Glu Ile Gly Asp Ile Arg Lys Ala
                325                 330                 335

Tyr Cys Glu Ile Asn Gly Thr Lys Trp Asn Lys Val Leu Lys Glu Val
            340                 345                 350

Thr Glu Lys Leu Lys Glu His Phe Asn Lys Thr Ile Ile Phe Gln Pro
        355                 360                 365

Pro Ser Gly Gly Asp Leu Glu Ile Thr Thr His His Phe Asn Cys Arg
    370                 375                 380
```

```
Gly Glu Phe Phe Tyr Cys Asn Thr Thr Lys Leu Phe Asn Asn Thr Cys
385                 390                 395                 400

Asn Gly Thr Met Glu Gly Phe Cys Asn Asn Ile Thr Leu Pro Cys Lys
            405                 410                 415

Ile Lys Gln Ile Ile Asn Met Trp Gln Gly Ala Gly Gln Ala Ile Tyr
        420                 425                 430

Ala Pro Pro Ile Ser Gly Ser Ile Lys Cys Val Ser Asn Ile Thr Gly
            435                 440                 445

Ile Ile Leu Thr Arg Asp Gly Gly Asn Asp Thr Gly Thr Ser Glu Ile
        450                 455                 460

Phe Arg Pro Gly Gly Asn Met Lys Asp Asn Trp Arg Asn Glu Leu
465                 470                 475                 480

Tyr Lys Tyr Lys Val Val Gln Ile Glu Pro Leu Gly Val Ala Pro Thr
                485                 490                 495

Lys Ala Lys Arg Arg Val Val Asp Arg Glu Lys Arg
            500                 505

<210> SEQ ID NO 36
<211> LENGTH: 507
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Met Arg Val Met Gly Ile Gln Arg Asn Cys Gln His Leu Trp Arg Trp
1               5                   10                  15

Gly Ile Met Leu Leu Gly Met Leu Met Ile Cys Asn Ala Thr Asp Lys
            20                  25                  30

Leu Trp Val Thr Val Tyr Tyr Gly Val Pro Val Trp Arg Asp Ala Glu
        35                  40                  45

Thr Thr Leu Phe Cys Ala Ser Asp Ala Lys Gly Tyr Asp Thr Glu Ala
    50                  55                  60

His Asn Val Trp Ala Thr His Ala Cys Val Pro Thr Asp Pro Ser Pro
65                  70                  75                  80

Gln Glu Ile His Leu Glu Asn Val Thr Glu Glu Phe Asn Met Trp Lys
                85                  90                  95

Asn Asn Met Val Glu Gln Met His Thr Asp Ile Ile Ser Leu Trp Asp
            100                 105                 110

Gln Ser Leu Lys Pro Cys Val Lys Leu Thr Pro Leu Cys Val Thr Leu
        115                 120                 125

Asp Cys Thr Leu Asp Cys Asn Asn Val Thr Asn Asn Gly Thr Ser Asp
    130                 135                 140

Met Arg Glu Glu Ile Lys Asn Cys Ser Phe Asn Ile Thr Thr Glu Leu
145                 150                 155                 160

Arg Asp Lys Lys Lys Val Tyr Ser Leu Phe Tyr Lys Leu Asp Ile
                165                 170                 175

Val Pro Ile Asn Gly Asp Asn Ser Thr Asn Thr Tyr Met Leu Ile Asn
            180                 185                 190

Cys Asn Thr Ser Ala Ile Thr Gln Ala Cys Pro Lys Val Thr Phe Glu
        195                 200                 205

Pro Ile Pro Ile His Phe Cys Ala Pro Ala Gly Tyr Ala Ile Leu Lys
    210                 215                 220

Cys Lys Asp Lys Glu Phe Asn Gly Thr Gly Pro Cys Lys Asn Val Ser
```

```
                225                 230                 235                 240

Thr Val Gln Cys Thr His Gly Ile Lys Pro Val Val Ser Thr Gln Leu
                    245                 250                 255

Leu Leu Asn Gly Ser Leu Ala Glu Glu Ile Met Ile Arg Ser Glu
                260                 265                 270

Asn Ile Thr Asn Asn Ala Lys Ile Ile Val Gln Leu Asn Gln Ser
                275                 280                 285

Val Val Ile Asn Cys Thr Arg Pro Gly Asn Asn Thr Arg Lys Ser Val
            290                 295                 300

Arg Ile Gly Pro Gly Gln Thr Phe Tyr Ala Thr Gly Asp Ile Ile Gly
305                 310                 315                 320

Asp Ile Arg Gln Ala His Cys Asn Val Ser Arg Ile Lys Trp Asn Thr
                    325                 330                 335

Ala Leu Gln Lys Val Ala Lys Gln Leu Arg Lys Tyr Phe Arg Asn Lys
                340                 345                 350

Thr Ile Thr Phe Asn Gln Ser Ser Gly Gly Asp Pro Glu Ile Thr Thr
                355                 360                 365

His Thr Phe Asn Cys Gly Gly Glu Phe Phe Tyr Cys Asn Thr Ser Asn
                370                 375                 380

Leu Phe Asn Ser Thr Trp Gly Asn Gly Asn Gly Thr Asp Asn Met Gln
385                 390                 395                 400

Gly Ser Asn Ser Thr Asn Ile Thr Leu Gln Cys Arg Ile Lys Gln Ile
                405                 410                 415

Ile Asn Met Trp Gln Glu Val Gly Arg Ala Ile Tyr Ala Pro Pro Ile
                420                 425                 430

Glu Gly Asn Ile Ser Cys Ser Ser Asn Ile Thr Gly Leu Leu Leu Thr
                435                 440                 445

Arg Asp Gly Gly Asn Ser Lys Asn Ser Thr Thr Glu Glu Ile Phe Arg
                450                 455                 460

Pro Gly Gly Gly Asn Met Arg Asp Asn Trp Arg Ser Glu Leu Tyr Lys
465                 470                 475                 480

Tyr Lys Val Val Lys Ile Glu Pro Ile Gly Val Ala Pro Thr Lys Ala
                485                 490                 495

Arg Arg Arg Val Val Glu Arg Glu Lys Arg Ile
                500                 505

<210> SEQ ID NO 37
<211> LENGTH: 511
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Met Lys Val Lys Gly Ile Gln Arg Asn Trp Pro Gln Trp Trp Ile Trp
1               5                   10                  15

Gly Ile Leu Gly Phe Trp Met Leu Met Ile Cys Asn Val Gly Gly Asn
                20                  25                  30

Leu Trp Val Thr Val Tyr Tyr Gly Val Pro Val Trp Arg Glu Ala Asn
            35                  40                  45

Thr Thr Leu Phe Cys Ala Ser Asp Ala Lys Ala Tyr Asp Thr Glu Val
        50                  55                  60

His Asn Ile Trp Ala Thr His Ala Cys Val Pro Thr Asp Pro Asn Pro
65              70                  75                  80
```

-continued

```
Gln Glu Ile Val Leu Gly Asn Val Thr Glu Asn Phe Asn Met Trp Lys
                85                  90                  95
Asn Asn Met Val Asp Gln Met His Glu Asp Val Ile Ser Leu Trp Asp
            100                 105                 110
Glu Ser Leu Lys Pro Cys Val Lys Leu Thr Pro Leu Cys Val Thr Leu
        115                 120                 125
Glu Cys Asn Asp Ala Lys Leu Asn Ser Thr Lys Thr Asn Ser Thr Thr
    130                 135                 140
Asn Ser Thr Asp Pro Asn Asn Ser Asn Leu Gly Ile Glu Gly Glu Ile
145                 150                 155                 160
Lys Asn Cys Ser Phe Asn Thr Thr Thr Glu Ile Arg Asp Lys Lys Lys
                165                 170                 175
Arg Ala Tyr Ala Leu Phe Tyr Arg Pro Asp Val Val Pro Leu Asn Glu
            180                 185                 190
Asn Ser Ser Ser Tyr Ile Leu Ile Asn Cys Asn Ser Ser Thr Ile Thr
        195                 200                 205
Gln Ala Cys Pro Lys Val Ser Phe Glu Pro Ile Pro Ile His Tyr Cys
    210                 215                 220
Thr Pro Ala Gly Phe Ala Leu Leu Lys Cys Asn Asn Lys Thr Phe Asn
225                 230                 235                 240
Gly Ser Gly Pro Cys Thr Asn Val Ser Thr Val Gln Cys Thr His Gly
                245                 250                 255
Ile Arg Pro Val Val Ser Thr Gln Leu Leu Leu Asn Gly Ser Leu Ala
            260                 265                 270
Glu Glu Glu Ile Val Ile Arg Ser Glu Asn Phe Thr Asp Asn Ala Lys
        275                 280                 285
Thr Ile Ile Val Gln Leu Asn Glu Ser Val Glu Ile Asn Cys Thr Arg
    290                 295                 300
Pro Asn Asn Asn Thr Arg Lys Ser Ile Arg Ile Gly Pro Gly Gln Ala
305                 310                 315                 320
Phe Tyr Ala Thr Gly Glu Ile Ile Gly Asn Ile Arg Gln Ala Tyr Cys
                325                 330                 335
Asn Ile Asn Glu Ser Leu Trp Asn Glu Thr Leu Tyr Lys Val Ser Glu
            340                 345                 350
Lys Leu Lys Glu Tyr Phe Asn Thr Thr Ile Glu Phe Gln Gln Pro Ala
        355                 360                 365
Gly Gly Asp Leu Glu Ile Thr Thr His Ser Phe Asn Cys Arg Gly Glu
    370                 375                 380
Phe Phe Tyr Cys Asn Thr Thr Lys Leu Phe Asn Gly Thr Tyr Ser Gln
385                 390                 395                 400
Pro Asn Ser Thr Gly Asn Thr Pro His Ser Asn Ile Thr Leu Pro Cys
                405                 410                 415
Lys Ile Lys Gln Ile Ile Asn Met Trp Gln Gly Val Gly Arg Ala Met
            420                 425                 430
Tyr Ala Pro Pro Ile Ala Gly Asn Ile Thr Cys Ile Ser Asn Ile Thr
        435                 440                 445
Gly Leu Ile Leu Thr Arg Asp Gly Gly Asp Lys Asn Gly Ser Lys Pro
    450                 455                 460
Glu Ile Phe Arg Pro Gly Gly Asn Met Lys Asp Asn Trp Arg Ser
465                 470                 475                 480
Glu Leu Tyr Lys Tyr Lys Val Val Glu Ile Lys Pro Leu Gly Leu Ala
                485                 490                 495
Pro Thr Glu Ala Lys Arg Arg Val Val Glu Arg Glu Lys Arg Ala
```

-continued

<210> SEQ ID NO 38
<211> LENGTH: 506
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Met Arg Val Met Gly Ile Gln Arg Asn Cys Gln His Leu Trp Arg Trp
1               5                   10                  15

Gly Ile Met Leu Leu Gly Met Leu Met Ile Cys Asn Ala Thr Asp Lys
            20                  25                  30

Leu Trp Val Thr Val Tyr Tyr Gly Val Pro Val Trp Arg Asp Ala Glu
        35                  40                  45

Thr Thr Leu Phe Cys Ala Ser Asp Ala Lys Gly Tyr Asp Thr Glu Ala
    50                  55                  60

His Asn Val Trp Ala Thr His Ala Cys Val Pro Thr Asp Pro Ser Pro
65                  70                  75                  80

Gln Glu Ile His Leu Glu Asn Val Thr Glu Glu Phe Asn Met Trp Lys
                85                  90                  95

Asn Asn Met Val Glu Gln Met His Thr Asp Ile Ile Ser Leu Trp Asp
            100                 105                 110

Gln Ser Leu Lys Pro Cys Val Lys Leu Thr Pro Leu Cys Val Thr Leu
        115                 120                 125

Asp Cys Thr Leu Asp Cys Asn Asn Val Thr Asn Asn Gly Thr Ser Asp
    130                 135                 140

Met Arg Glu Glu Ile Lys Asn Cys Ser Phe Asn Ile Thr Thr Glu Leu
145                 150                 155                 160

Arg Asp Lys Lys Lys Lys Val Tyr Ser Leu Phe Tyr Lys Leu Asp Ile
                165                 170                 175

Val Pro Ile Asn Gly Asp Asn Ser Thr Asn Thr Tyr Met Leu Ile Asn
            180                 185                 190

Cys Asn Thr Ser Ala Ile Thr Gln Ala Cys Pro Lys Val Thr Phe Glu
        195                 200                 205

Pro Ile Pro Ile His Phe Cys Ala Pro Ala Gly Tyr Ala Ile Leu Lys
    210                 215                 220

Cys Lys Asp Lys Glu Phe Asn Gly Thr Gly Pro Cys Lys Asn Val Ser
225                 230                 235                 240

Thr Val Gln Cys Thr His Gly Ile Lys Pro Val Val Ser Thr Gln Leu
                245                 250                 255

Leu Leu Asn Gly Ser Leu Ala Glu Glu Glu Ile Met Ile Arg Ser Glu
            260                 265                 270

Asn Ile Thr Asn Asn Ala Lys Ile Ile Ile Val Gln Leu Asn Gln Ser
        275                 280                 285

Val Val Ile Asn Cys Thr Arg Pro Gly Asn Asn Thr Arg Lys Ser Val
    290                 295                 300

Arg Ile Gly Pro Gly Gln Thr Phe Tyr Ala Thr Gly Asp Ile Ile Gly
305                 310                 315                 320

Asp Ile Arg Gln Ala His Cys Asn Val Ser Arg Ile Lys Trp Asn Thr
                325                 330                 335

Ala Leu Gln Lys Val Ala Lys Gln Leu Arg Lys Tyr Phe Arg Asn Lys
            340                 345                 350

```
Thr Ile Thr Phe Asn Gln Ser Ser Gly Gly Asp Pro Glu Ile Thr Thr
            355                 360                 365

His Thr Phe Asn Cys Gly Gly Glu Phe Phe Tyr Cys Asn Thr Ser Asn
    370                 375                 380

Leu Phe Asn Ser Thr Trp Gly Asn Gly Asn Gly Thr Asp Asn Met Gln
385                 390                 395                 400

Gly Ser Asn Ser Thr Asn Ile Thr Leu Gln Cys Arg Ile Lys Gln Ile
                405                 410                 415

Ile Asn Met Trp Gln Glu Val Gly Arg Ala Ile Tyr Ala Pro Pro Ile
            420                 425                 430

Glu Gly Asn Ile Ser Cys Ser Ser Asn Ile Thr Gly Leu Leu Leu Thr
            435                 440                 445

Arg Asp Gly Gly Asn Ser Lys Asn Ser Thr Thr Glu Glu Ile Phe Arg
    450                 455                 460

Pro Gly Gly Gly Asn Met Arg Asp Asn Trp Arg Ser Glu Leu Tyr Lys
465                 470                 475                 480

Tyr Lys Val Val Lys Ile Glu Pro Ile Gly Val Ala Pro Thr Lys Ala
                485                 490                 495

Arg Arg Arg Val Val Glu Arg Glu Lys Arg
            500                 505

<210> SEQ ID NO 39
<211> LENGTH: 510
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Met Lys Val Lys Gly Ile Gln Arg Asn Trp Pro Gln Trp Trp Ile Trp
1               5                   10                  15

Gly Ile Leu Gly Phe Trp Met Leu Met Ile Cys Asn Val Gly Gly Asn
            20                  25                  30

Leu Trp Val Thr Val Tyr Tyr Gly Val Pro Val Trp Arg Glu Ala Asn
        35                  40                  45

Thr Thr Leu Phe Cys Ala Ser Asp Ala Lys Ala Tyr Asp Thr Glu Val
    50                  55                  60

His Asn Ile Trp Ala Thr His Ala Cys Val Pro Thr Asp Pro Asn Pro
65                  70                  75                  80

Gln Glu Ile Val Leu Gly Asn Val Thr Glu Asn Phe Asn Met Trp Lys
                85                  90                  95

Asn Asn Met Val Asp Gln Met His Glu Asp Val Ile Ser Leu Trp Asp
            100                 105                 110

Glu Ser Leu Lys Pro Cys Val Lys Leu Thr Pro Leu Cys Val Thr Leu
        115                 120                 125

Glu Cys Asn Asp Ala Lys Leu Asn Ser Thr Lys Thr Asn Ser Thr Thr
    130                 135                 140

Asn Ser Thr Asp Pro Asn Asn Ser Asn Leu Gly Ile Glu Gly Glu Ile
145                 150                 155                 160

Lys Asn Cys Ser Phe Asn Thr Thr Thr Glu Ile Arg Asp Lys Lys Lys
                165                 170                 175

Arg Ala Tyr Ala Leu Phe Tyr Arg Pro Asp Val Val Pro Leu Asn Glu
            180                 185                 190

Asn Ser Ser Ser Tyr Ile Leu Ile Asn Cys Asn Ser Ser Thr Ile Thr
        195                 200                 205
```

```
Gln Ala Cys Pro Lys Val Ser Phe Glu Pro Ile Pro Ile His Tyr Cys
    210                 215                 220

Thr Pro Ala Gly Phe Ala Leu Leu Lys Cys Asn Asn Lys Thr Phe Asn
225                 230                 235                 240

Gly Ser Gly Pro Cys Thr Asn Val Ser Thr Val Gln Cys Thr His Gly
                245                 250                 255

Ile Arg Pro Val Val Ser Thr Gln Leu Leu Leu Asn Gly Ser Leu Ala
            260                 265                 270

Glu Glu Glu Ile Val Ile Arg Ser Glu Asn Phe Thr Asp Asn Ala Lys
        275                 280                 285

Thr Ile Ile Val Gln Leu Asn Glu Ser Val Glu Ile Asn Cys Thr Arg
290                 295                 300

Pro Asn Asn Thr Arg Lys Ser Ile Arg Ile Gly Pro Gly Gln Ala
305                 310                 315                 320

Phe Tyr Ala Thr Gly Glu Ile Ile Gly Asn Ile Arg Gln Ala Tyr Cys
                325                 330                 335

Asn Ile Asn Glu Ser Leu Trp Asn Glu Thr Leu Tyr Lys Val Ser Glu
            340                 345                 350

Lys Leu Lys Glu Tyr Phe Asn Thr Thr Ile Glu Phe Gln Gln Pro Ala
        355                 360                 365

Gly Gly Asp Leu Glu Ile Thr Thr His Ser Phe Asn Cys Arg Gly Glu
370                 375                 380

Phe Phe Tyr Cys Asn Thr Thr Lys Leu Phe Asn Gly Thr Tyr Ser Gln
385                 390                 395                 400

Pro Asn Ser Thr Gly Asn Thr Pro His Ser Asn Ile Thr Leu Pro Cys
                405                 410                 415

Lys Ile Lys Gln Ile Ile Asn Met Trp Gln Gly Val Gly Arg Ala Met
            420                 425                 430

Tyr Ala Pro Pro Ile Ala Gly Asn Ile Thr Cys Ile Ser Asn Ile Thr
        435                 440                 445

Gly Leu Ile Leu Thr Arg Asp Gly Gly Asp Lys Asn Gly Ser Lys Pro
450                 455                 460

Glu Ile Phe Arg Pro Gly Gly Gly Asn Met Lys Asp Asn Trp Arg Ser
465                 470                 475                 480

Glu Leu Tyr Lys Tyr Lys Val Val Glu Ile Lys Pro Leu Gly Leu Ala
                485                 490                 495

Pro Thr Glu Ala Lys Arg Arg Val Val Glu Arg Glu Lys Arg
                500                 505                 510

<210> SEQ ID NO 40
<211> LENGTH: 499
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Met Arg Val Lys Glu Thr Arg Arg Ile Trp Gln His Leu Trp Lys Trp
1               5                   10                  15

Gly Thr Met Leu Leu Gly Met Leu Met Ile Tyr Ser Ala Val Pro Val
                20                  25                  30

Trp Lys Glu Ala Thr Thr Thr Leu Phe Cys Ala Ser Asp Ala Lys Ala
            35                  40                  45

Tyr Asp Thr Glu Val His Asn Val Trp Ala Thr His Ala Cys Val Pro
```

```
            50                  55                  60
Thr Asp Pro Asn Pro Gln Glu Val Val Leu Gly Asn Val Thr Glu Asn
 65                  70                  75                  80

Phe Asn Met Trp Lys Asn Asn Met Val Glu Gln Met His Glu Asp Val
                     85                  90                  95

Ile Ser Leu Trp Asp Gln Ser Leu Lys Pro Cys Val Lys Leu Thr Pro
                100                 105                 110

Leu Cys Val Thr Leu Asn Cys Thr Asp Val Leu Gly Lys Gly Thr Ser
                115                 120                 125

Ala Asn Ala Thr Ser Ala Asn Val Thr Ser Glu Lys Gly Glu Ile Lys
                130                 135                 140

Asn Cys Ser Phe Asn Ile Thr Thr Thr Leu Arg Asp Lys Val Gln Lys
145                 150                 155                 160

Ala His Ala Leu Phe Tyr Arg Leu Asp Val Val Pro Ile Asp Asp Asn
                165                 170                 175

Asn Asp Asn Ser Ser Ser Ser Tyr Arg Leu Ile Asn Cys Asn Thr Ser
                180                 185                 190

Val Ile Thr Gln Ala Cys Pro Lys Val Ser Phe Glu Pro Ile Pro Ile
                195                 200                 205

His Phe Cys Thr Pro Ala Gly Phe Ala Leu Leu Lys Cys Asn Asn Lys
210                 215                 220

Lys Phe Asn Gly Thr Gly Pro Cys Thr Asn Val Ser Thr Val Gln Cys
225                 230                 235                 240

Thr His Gly Ile Lys Pro Val Val Ser Thr Gln Leu Leu Leu Asn Gly
                245                 250                 255

Ser Leu Ala Glu Glu Val Val Ile Arg Ser Glu Asn Phe Thr Asp
                260                 265                 270

Asn Ala Lys Thr Ile Ile Val Gln Leu Asn Asp Ser Val Val Ile Asn
                275                 280                 285

Cys Thr Arg Pro Asn Asn Asn Thr Arg Lys Gly Ile Thr Ile Gly Pro
                290                 295                 300

Gly Ser Val Phe Tyr Thr Gly Glu Ile Ile Gly Asp Ile Arg Gln Ala
305                 310                 315                 320

His Cys Asn Leu Ser Ser Ala Lys Trp Asn Asn Thr Leu Lys Gln Ile
                325                 330                 335

Val Ile Lys Leu Arg Glu Gln Phe Gly Asn Lys Thr Ile Val Phe Asn
                340                 345                 350

Gln Ser Ser Gly Gly Asp Pro Glu Ile Val Leu His Ser Phe Asn Cys
                355                 360                 365

Gly Gly Glu Phe Phe Tyr Cys Asn Thr Thr Gln Leu Phe Asn Ser Thr
                370                 375                 380

Trp Asn Ile Asn Asp Thr Arg Asn Gly Thr Thr Glu Ser Ser Lys Thr
385                 390                 395                 400

Ile Thr Leu Pro Cys Arg Ile Lys Gln Ile Ile Asn Met Trp Gln Glu
                405                 410                 415

Val Gly Lys Ala Met Tyr Ala Pro Pro Ile Arg Gly Gln Ile Arg Cys
                420                 425                 430

Ser Ser Asn Ile Thr Gly Leu Leu Leu Thr Arg Asp Gly Gly Asn Gln
                435                 440                 445

Asn Thr Ser Gly Thr Glu Ile Phe Arg Pro Gly Gly Gly Asn Met Arg
                450                 455                 460

Asp Asn Trp Arg Ser Glu Leu Tyr Lys Tyr Lys Val Val Lys Ile Glu
465                 470                 475                 480
```

-continued

```
Pro Leu Gly Ile Ala Pro Thr Lys Ala Lys Glu Arg Val Val Gln Arg
            485                 490                 495
Glu Lys Glu

<210> SEQ ID NO 41
<211> LENGTH: 492
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Met Arg Val Lys Gly Ile Arg Lys Asn Tyr Gln His Leu Trp Arg Trp
1               5                   10                  15
Gly Thr Met Leu Leu Gly Met Leu Met Ile Cys Ser Ala Val Pro Val
            20                  25                  30
Trp Lys Glu Ala Thr Thr Thr Leu Phe Cys Ala Ser Asp Ala Lys Ala
        35                  40                  45
His Asp Thr Glu Val His Asn Val Trp Ala Thr His Ala Cys Val Pro
    50                  55                  60
Thr Asp Pro Asn Pro Gln Glu Val Val Leu Glu Asn Val Thr Glu Asn
65                  70                  75                  80
Phe Asn Met Trp Lys Asn Asn Met Val Glu Gln Met Gln Glu Asp Val
                85                  90                  95
Ile Ser Leu Trp Asp Gln Ser Leu Lys Pro Cys Val Lys Leu Thr Pro
            100                 105                 110
Leu Cys Val Thr Leu Asn Cys Thr Asp Val Ser Ser Asn Ser Thr Ser
        115                 120                 125
Val Asn Ile Thr Ser Glu Lys Gly Glu Ile Lys Asn Cys Ser Phe Asn
    130                 135                 140
Val Thr Thr Ser Ile Lys Asp Lys Val Gln Lys Glu Tyr Ala Leu Phe
145                 150                 155                 160
Tyr Lys Leu Asp Val Val Pro Ile Glu Asp Asp Ser Arg Asn Asn Ser
                165                 170                 175
Tyr Arg Leu Ile Ser Cys Asn Thr Ser Val Ile Thr Gln Ala Cys Pro
            180                 185                 190
Lys Val Ser Phe Glu Pro Ile Pro Ile His Tyr Cys Thr Pro Ala Gly
        195                 200                 205
Phe Ala Ile Leu Lys Cys Asn Asp Lys Lys Phe Asn Gly Thr Gly Pro
    210                 215                 220
Cys Thr Asn Val Ser Thr Val Gln Cys Thr His Gly Ile Arg Pro Val
225                 230                 235                 240
Val Ser Thr Gln Leu Leu Leu Asn Gly Ser Leu Ala Glu Glu Glu Val
                245                 250                 255
Val Ile Arg Ser Glu Asn Phe Thr Asn Asn Ala Lys Thr Ile Ile Val
            260                 265                 270
Gln Leu Asn Glu Ser Val Glu Ile Asn Cys Thr Arg Pro Asn Asn Asn
        275                 280                 285
Thr Arg Lys Ser Ile His Ile Gly Pro Gly Arg Ala Phe Tyr Ala Thr
    290                 295                 300
Gly Asp Ile Ile Gly Asp Ile Arg Gln Ala His Cys Asn Ile Ser Arg
305                 310                 315                 320
Glu Lys Trp Asn Asn Thr Leu Lys Gln Ile Val Lys Lys Leu Arg Glu
                325                 330                 335
```

-continued

Gln Phe Gly Asn Lys Thr Ile Val Phe Asn Gln Ser Ser Gly Gly Asp
                340                 345                 350

Pro Glu Ile Val Met His Ser Phe Asn Cys Gly Gly Glu Phe Phe Tyr
            355                 360                 365

Cys Asn Thr Thr Gln Leu Phe Asn Ser Thr Trp Ser Ile Asn Gly Thr
370                 375                 380

Trp Asn Gly Thr Thr Glu Ser Asn Asp Thr Ile Thr Leu Pro Cys Arg
385                 390                 395                 400

Ile Lys Gln Ile Ile Asn Met Trp Gln Glu Val Gly Lys Ala Met Tyr
                405                 410                 415

Ala Pro Pro Ile Arg Gly Gln Ile Arg Cys Ser Ser Asn Ile Thr Gly
            420                 425                 430

Leu Leu Leu Thr Arg Asp Gly Gly Asn Ser Ser Ser Asn Asn Glu Thr
        435                 440                 445

Phe Arg Pro Gly Gly Gly Asp Met Arg Asp Asn Trp Arg Ser Glu Leu
    450                 455                 460

Tyr Lys Tyr Lys Val Val Lys Ile Glu Pro Leu Gly Val Ala Pro Thr
465                 470                 475                 480

Lys Ala Lys Glu Arg Val Val Gln Arg Glu Lys Glu
                485                 490

<210> SEQ ID NO 42
<211> LENGTH: 490
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Met Lys Val Lys Gly Ile Arg Lys Asn Cys Gln His Leu Trp Arg Trp
1               5                   10                  15

Gly Ile Met Leu Leu Gly Met Leu Met Ile Cys Ser Ala Val Pro Val
            20                  25                  30

Trp Lys Glu Ala Thr Thr Thr Leu Phe Cys Ala Ser Asp Ala Lys Ala
        35                  40                  45

His Asp Thr Glu Ala His Asn Val Trp Ala Thr His Ala Cys Val Pro
    50                  55                  60

Thr Asp Pro Asn Pro Gln Glu Ile Val Leu Glu Asn Val Thr Glu Asn
65                  70                  75                  80

Phe Asn Met Trp Lys Asn Asp Met Val Glu Gln Met Gln Glu Asp Val
                85                  90                  95

Ile Ser Leu Trp Asp Glu Ser Leu Lys Pro Cys Val Glu Leu Thr Pro
            100                 105                 110

Leu Cys Val Thr Leu Asn Cys Thr Asn Val Asn Ala Thr Asn Thr Asn
        115                 120                 125

Asn Ser Ser Gly Ile Glu Gly Gly Glu Met Lys Asn Cys Ser Phe Asn
    130                 135                 140

Val Thr Thr Ser Ile Lys Asp Lys Met Gln Lys Glu Tyr Ala Leu Phe
145                 150                 155                 160

Tyr Ser Leu Asp Val Val Gln Ile Asp Asn Asp Thr Asn Tyr Arg Leu
                165                 170                 175

Ile Asn Cys Asn Thr Ser Val Ile Thr Gln Ala Cys Pro Lys Ile Ser
            180                 185                 190

Phe Glu Pro Ile Pro Ile His Tyr Cys Thr Pro Ala Gly Phe Ala Ile

```
                195                 200                 205
Ile Lys Cys Asn Asp Lys Lys Phe Asn Gly Ser Gly Pro Cys Lys Asn
210                 215                 220

Val Ser Thr Val Gln Cys Thr His Gly Ile Lys Pro Val Ser Thr
225                 230                 235                 240

Gln Leu Leu Asn Gly Ser Leu Ala Glu Glu Ile Val Ile Arg
                245                 250                 255

Ser Glu Asn Phe Ser Asp Asn Ala Lys Thr Ile Ile Val Gln Leu Asn
                260                 265                 270

Glu Ser Val Val Ile Asn Cys Thr Arg Pro Asn Asn Asn Thr Arg Lys
            275                 280                 285

Ser Ile Ser Ile Gly Pro Gly Arg Ala Phe Tyr Ala Thr Gly Asp Ile
290                 295                 300

Ile Gly Asn Ile Arg Gln Ala His Cys Asn Leu Ser Arg Ala Lys Trp
305                 310                 315                 320

Asn Asn Thr Leu Arg Gln Ile Val Thr Lys Leu Arg Glu Gln Phe Lys
                325                 330                 335

Asn Lys Thr Ile Ala Phe Asn His Ser Ser Gly Gly Asp Pro Glu Ile
                340                 345                 350

Val Met His Thr Phe Asn Cys Gly Gly Glu Phe Phe Tyr Cys Asn Ser
            355                 360                 365

Thr Gln Leu Phe Asn Ser Thr Trp Ile Ala Asn Lys Thr Gly Asn Asp
370                 375                 380

Thr Gly Ser Asn Gly Thr Ile Thr Leu Gln Cys Arg Ile Lys Gln
385                 390                 395                 400

Ile Val Asn Arg Trp Gln Glu Val Gly Lys Ala Met Tyr Ala Pro Pro
                405                 410                 415

Ile Ser Gly Gln Ile Ser Cys Ser Ser Asn Ile Thr Gly Leu Ile Leu
            420                 425                 430

Thr Arg Asp Gly Gly Thr Asn Asn Thr Asn Gly Thr Glu Ile Phe Arg
        435                 440                 445

Pro Gly Gly Gly Asn Met Lys Asp Asn Trp Arg Ser Glu Leu Tyr Lys
450                 455                 460

Tyr Lys Val Val Arg Ile Glu Pro Leu Gly Ile Ala Pro Thr Lys Ala
465                 470                 475                 480

Arg Glu Arg Val Val Gln Arg Glu Lys Glu
                485                 490

<210> SEQ ID NO 43
<211> LENGTH: 497
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Met Arg Val Arg Gly Ile Leu Arg Asn Tyr Gln Gln Trp Trp Ile Trp
1               5                   10                  15

Gly Ile Leu Gly Phe Trp Met Leu Met Ile Cys Asn Val Val Pro Val
            20                  25                  30

Trp Lys Glu Ala Lys Thr Thr Leu Phe Cys Ala Ser Asp Ala Lys Ala
        35                  40                  45

Tyr Glu Lys Glu Val His Asn Val Trp Ala Thr His Ala Cys Val Pro
    50                  55                  60
```

```
Thr Asp Pro Asn Pro Gln Glu Met Val Leu Glu Asn Val Thr Glu Asn
 65                  70                  75                  80

Phe Asn Met Trp Lys Asn Asp Met Val Asp Gln Met His Glu Asp Ile
                 85                  90                  95

Ile Ser Leu Trp Asp Gln Ser Leu Lys Pro Cys Val Lys Leu Thr Pro
            100                 105                 110

Leu Cys Val Thr Leu Asn Cys Val Asn Ile Thr Asn Ser Thr Thr Ser
        115                 120                 125

Asn Gly Asp Gly Thr Val Thr His Ile Asn Ser Ile Lys Glu Glu Ile
    130                 135                 140

Lys Asn Cys Ser Phe Asn Ala Thr Thr Glu Leu Arg Asp Lys Lys Ser
145                 150                 155                 160

Lys Glu Tyr Ala Leu Phe Tyr Arg Leu Asp Ile Val Pro Leu Ser Ser
                165                 170                 175

Gly Asn Ser Ser Ser Asn Ser Ser Lys Tyr Arg Leu Ile Asn Cys Asn
            180                 185                 190

Thr Ser Thr Ile Thr Gln Ala Cys Pro Lys Val Ser Phe Asp Pro Ile
        195                 200                 205

Pro Ile His Tyr Cys Ala Pro Ala Gly Tyr Ala Ile Leu Lys Cys Asn
    210                 215                 220

Asn Lys Thr Phe Asn Gly Thr Gly Pro Cys Asn Asn Val Ser Thr Val
225                 230                 235                 240

Gln Cys Thr His Gly Ile Lys Pro Val Val Ser Thr Gln Leu Leu Leu
                245                 250                 255

Asn Gly Ser Leu Ala Glu Glu Ile Ile Ile Arg Ser Glu Asn Leu
            260                 265                 270

Thr Asp Asn Val Lys Thr Ile Ile Val His Leu Asn Glu Ser Val Glu
        275                 280                 285

Ile Val Cys Thr Arg Pro Asn Asn Asn Thr Arg Lys Ser Ile Arg Ile
    290                 295                 300

Gly Pro Gly Gln Thr Phe Tyr Ala Thr Gly Asp Ile Ile Gly Asp Ile
305                 310                 315                 320

Arg Gln Ala His Cys Asn Ile Ser Lys Gly Ala Trp Asn Glu Thr Leu
                325                 330                 335

Gln Trp Val Gly Lys Lys Leu Lys Glu His Phe Pro Asn Lys Thr Ile
            340                 345                 350

Lys Phe Asn Ser Ser Ser Gly Gly Asp Leu Glu Ile Thr Thr His Ser
        355                 360                 365

Phe Asn Cys Arg Gly Glu Phe Phe Tyr Cys Asn Thr Ser Gly Leu Phe
    370                 375                 380

Asn Ser Thr Tyr Arg Asn Asn Ser Thr Gly Asp Asn Ser Thr Ile Thr
385                 390                 395                 400

Leu Pro Cys Arg Ile Lys Gln Ile Ile Asn Met Trp Gln Glu Val Gly
                405                 410                 415

Arg Ala Met Tyr Ala Pro Pro Ile Ala Gly Asn Ile Thr Cys Lys Ser
            420                 425                 430

Asn Ile Thr Gly Leu Leu Leu Thr Arg Asp Gly Gly Thr Arg Asp Arg
        435                 440                 445

Asn Asp Thr Glu Thr Phe Arg Pro Gly Gly Gly Asp Met Arg Asp Asn
    450                 455                 460

Trp Arg Ser Glu Leu Tyr Lys Tyr Lys Val Val Glu Ile Lys Pro Leu
465                 470                 475                 480

Gly Ile Ala Pro Thr Lys Ala Lys Glu Arg Val Val Glu Arg Glu Lys
```

485                 490                 495

Glu

<210> SEQ ID NO 44
<211> LENGTH: 489
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Met Arg Val Met Gly Ile Gln Arg Asn Trp Pro Gln Trp Trp Ile Trp
1               5                   10                  15

Gly Ile Leu Gly Phe Trp Met Ile Ile Cys Arg Val Val Pro Val
                20                  25                  30

Trp Arg Glu Ala Lys Thr Thr Leu Phe Cys Ala Ser Asp Ala Lys Ala
            35                  40                  45

Tyr Glu Arg Glu Val His Asn Val Trp Ala Thr His Ala Cys Val Pro
50                  55                  60

Thr Asp Pro Asn Pro Gln Glu Leu Val Leu Glu Asn Val Thr Glu Asn
65                  70                  75                  80

Phe Asn Met Trp Glu Asn Asp Met Val Asp Gln Met His Glu Asp Val
                85                  90                  95

Ile Ser Leu Trp Asp Gln Ser Leu Lys Pro Cys Val Lys Leu Thr Pro
                100                 105                 110

Leu Cys Val Thr Leu Lys Cys Thr Asn Thr Thr Tyr Tyr Asn Val Ser
            115                 120                 125

Ser Lys Glu Phe Thr Asn Gly Glu Ile Lys Asn Cys Ser Phe Asn Thr
130                 135                 140

Thr Thr Glu Leu Arg Asp Lys Lys Gln Lys Val Ser Ala Leu Phe Tyr
145                 150                 155                 160

Arg Leu Asp Val Val Pro Leu Ser Lys Lys Asp Lys Thr Asn Asn Asp
                165                 170                 175

Ser Gly Glu Tyr Ile Leu Ile Asn Cys Asn Thr Ser Ala Ile Thr Gln
            180                 185                 190

Ala Cys Pro Lys Val Ser Phe Asp Pro Ile Pro Ile His Tyr Cys Thr
        195                 200                 205

Pro Ala Gly Tyr Ala Ile Leu Lys Cys Asn Asn Lys Thr Phe Asn Gly
210                 215                 220

Thr Gly Pro Cys His Asn Val Ser Thr Val Gln Cys Thr His Gly Ile
225                 230                 235                 240

Lys Pro Val Val Ser Thr Gln Leu Leu Leu Asn Gly Ser Leu Thr Glu
                245                 250                 255

Gly Glu Ile Ile Ile Arg Ser Glu Asn Leu Thr Asn Asn Ala Lys Thr
            260                 265                 270

Ile Ile Val His Leu Asn Gln Ser Val Ala Ile Val Cys Thr Arg Pro
        275                 280                 285

Gly Asn Asn Thr Arg Lys Ser Val Arg Ile Gly Pro Gly Gln Ala Phe
    290                 295                 300

Tyr Ala Thr Gly Glu Ile Ile Gly Asp Ile Arg Gln Ala Tyr Cys Asn
305                 310                 315                 320

Leu Thr Asn Trp Gln Glu Thr Leu Lys Asn Val Ser Lys Lys Leu Gln
                325                 330                 335

Glu Arg Phe Asn Lys Thr Ile Arg Phe Ala Pro Ser Ser Gly Gly Asp

```
            340                 345                 350
Leu Glu Ile Thr Thr His Ser Phe Asn Cys Gly Gly Glu Phe Phe Tyr
            355                 360                 365

Cys Asn Thr Ser Ser Leu Phe Asn Ser Ala Tyr Asn Pro Asn Gly Thr
        370                 375                 380

Lys Asp Asn Ser Asn Ser Ser Ile Thr Ile Gln Cys Lys Ile Lys Gln
385                 390                 395                 400

Ile Ile Asn Met Trp Gln Gly Val Gly Arg Ala Ile Tyr Ala Pro Pro
                405                 410                 415

Ile Ala Gly Asn Ile Thr Cys Asn Ser Asn Ile Thr Gly Ile Leu Leu
            420                 425                 430

Thr Arg Asp Gly Gly Ser Lys Asn Asn Thr Glu Glu Ile Phe Arg Pro
            435                 440                 445

Gly Gly Gly Asn Met Lys Asp Asn Trp Arg Ser Glu Leu Tyr Arg Tyr
            450                 455                 460

Lys Val Val Glu Ile Lys Pro Leu Gly Val Ala Pro Thr Glu Ala Lys
465                 470                 475                 480

Glu Arg Val Val Glu Arg Glu Lys Glu
                485

<210> SEQ ID NO 45
<211> LENGTH: 497
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Met Arg Val Lys Gly Thr Gln Met Asn Trp Pro Asn Leu Trp Arg Trp
1               5                   10                  15

Gly Thr Leu Ile Leu Gly Leu Val Ile Met Cys Ser Ala Val Pro Val
            20                  25                  30

Trp Lys Asp Ala Asp Thr Thr Leu Phe Cys Ala Ser Asp Ala Lys Ala
        35                  40                  45

His Glu Thr Glu Val His Asn Ile Trp Ala Thr His Ala Cys Val Pro
    50                  55                  60

Thr Asp Pro Asn Pro Gln Glu Ile Pro Leu Glu Asn Val Thr Glu Asn
65                  70                  75                  80

Phe Asn Met Trp Lys Asn Asn Met Ala Glu Gln Met Gln Glu Asp Val
                85                  90                  95

Ile Ser Leu Trp Asp Glu Ser Leu Lys Pro Cys Val Lys Leu Thr Pro
            100                 105                 110

Leu Cys Val Thr Leu His Cys Thr Lys Ala Asn Leu Thr His Asn Thr
        115                 120                 125

Thr Asn Asp Lys Asn Gly Thr Gly Asn Ile Thr Asp Glu Val Lys Ile
    130                 135                 140

Gly Asn Ile Thr Asp Glu Val Lys Asn Cys Ser Phe Asn Met Thr Thr
145                 150                 155                 160

Glu Ile Arg Asp Lys Lys Gln Lys Val Tyr Ala Leu Phe Tyr Lys Leu
                165                 170                 175

Asp Ile Val Gln Ile Gly Glu Asn Gly Ser Glu Tyr Arg Leu Ile Asn
            180                 185                 190

Cys Asn Thr Ser Val Ile Lys Gln Ala Cys Pro Lys Val Ser Phe Asp
        195                 200                 205
```

```
Pro Ile Pro Ile His Tyr Cys Ala Pro Ala Gly Tyr Ala Leu Leu Lys
210                 215                 220

Cys Asn Asp Lys Phe Asn Gly Thr Gly Pro Cys Arg Asn Val Ser
225                 230                 235                 240

Ser Val Gln Cys Thr His Gly Ile Lys Pro Val Val Ser Thr Gln Leu
            245                 250                 255

Leu Leu Asn Gly Ser Leu Ala Glu Glu Ile Ile Arg Ser Glu
            260                 265                 270

Asn Leu Thr Asp Asn Ala Lys Thr Ile Ile Val His Leu Asn Glu Ser
            275                 280                 285

Val Val Ile Asn Cys Thr Arg Pro Ser Asn Val Arg Ile Ser Thr
290                 295                 300

Arg Ile Gly Pro Gly Gln Val Phe Tyr Arg Thr Gly Glu Ile Ile Gly
305                 310                 315                 320

Asp Ile Arg Lys Ala Tyr Cys Glu Ile Asn Gly Thr Lys Trp Asn Lys
                325                 330                 335

Val Leu Lys Glu Val Thr Glu Lys Leu Lys Glu His Phe Asn Lys Thr
            340                 345                 350

Ile Ile Phe Gln Pro Pro Ser Gly Gly Asp Leu Glu Ile Thr Thr His
            355                 360                 365

His Phe Asn Cys Arg Gly Glu Phe Phe Tyr Cys Asn Thr Thr Lys Leu
            370                 375                 380

Phe Asn Asn Thr Cys Asn Gly Thr Met Glu Gly Phe Cys Asn Asn Ile
385                 390                 395                 400

Thr Leu Pro Cys Lys Ile Lys Gln Ile Ile Asn Met Trp Gln Gly Ala
                405                 410                 415

Gly Gln Ala Ile Tyr Ala Pro Pro Ile Ser Gly Ser Ile Lys Cys Val
            420                 425                 430

Ser Asn Ile Thr Gly Ile Ile Leu Thr Arg Asp Gly Gly Asn Asp Thr
            435                 440                 445

Gly Thr Ser Glu Ile Phe Arg Pro Gly Gly Asn Met Lys Asp Asn
            450                 455                 460

Trp Arg Asn Glu Leu Tyr Lys Tyr Lys Val Val Gln Ile Glu Pro Leu
465                 470                 475                 480

Gly Val Ala Pro Thr Lys Ala Lys Glu Arg Val Val Asp Arg Glu Lys
                485                 490                 495

Glu

<210> SEQ ID NO 46
<211> LENGTH: 499
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Met Lys Val Lys Gly Ile Gln Arg Asn Trp Pro Gln Trp Trp Ile Trp
1               5                   10                  15

Gly Ile Leu Gly Phe Trp Met Leu Met Ile Cys Asn Val Val Pro Val
            20                  25                  30

Trp Arg Glu Ala Asn Thr Thr Leu Phe Cys Ala Ser Asp Ala Lys Ala
        35                  40                  45

Tyr Asp Thr Glu Val His Asn Ile Trp Ala Thr His Ala Cys Val Pro
    50                  55                  60
```

```
Thr Asp Pro Asn Pro Gln Glu Ile Val Leu Gly Asn Val Thr Glu Asn
 65                  70                  75                  80

Phe Asn Met Trp Lys Asn Asn Met Val Asp Gln Met His Glu Asp Val
                 85                  90                  95

Ile Ser Leu Trp Asp Glu Ser Leu Lys Pro Cys Val Lys Leu Thr Pro
            100                 105                 110

Leu Cys Val Thr Leu Glu Cys Asn Asp Ala Lys Leu Asn Ser Thr Lys
        115                 120                 125

Thr Asn Ser Thr Thr Asn Ser Thr Asp Pro Asn Asn Ser Asn Leu Gly
    130                 135                 140

Ile Glu Gly Glu Ile Lys Asn Cys Ser Phe Asn Thr Thr Glu Ile
145                 150                 155                 160

Arg Asp Lys Lys Lys Arg Ala Tyr Ala Leu Phe Tyr Arg Pro Asp Val
                165                 170                 175

Val Pro Leu Asn Glu Asn Ser Ser Tyr Ile Leu Ile Asn Cys Asn
                180                 185                 190

Ser Ser Thr Ile Thr Gln Ala Cys Pro Lys Val Ser Phe Glu Pro Ile
        195                 200                 205

Pro Ile His Tyr Cys Thr Pro Ala Gly Phe Ala Leu Leu Lys Cys Asn
    210                 215                 220

Asn Lys Thr Phe Asn Gly Ser Gly Pro Cys Thr Asn Val Ser Thr Val
225                 230                 235                 240

Gln Cys Thr His Gly Ile Arg Pro Val Val Ser Thr Gln Leu Leu Leu
                245                 250                 255

Asn Gly Ser Leu Ala Glu Glu Ile Val Ile Arg Ser Glu Asn Phe
                260                 265                 270

Thr Asp Asn Ala Lys Thr Ile Ile Val Gln Leu Asn Glu Ser Val Glu
            275                 280                 285

Ile Asn Cys Thr Arg Pro Asn Asn Thr Arg Lys Ser Ile Arg Ile
            290                 295                 300

Gly Pro Gly Gln Ala Phe Tyr Ala Thr Gly Glu Ile Ile Gly Asn Ile
305                 310                 315                 320

Arg Gln Ala Tyr Cys Asn Ile Asn Glu Ser Leu Trp Asn Glu Thr Leu
                325                 330                 335

Tyr Lys Val Ser Glu Lys Leu Lys Glu Tyr Phe Asn Thr Thr Ile Glu
            340                 345                 350

Phe Gln Gln Pro Ala Gly Gly Asp Leu Glu Ile Thr Thr His Ser Phe
        355                 360                 365

Asn Cys Arg Gly Glu Phe Phe Tyr Cys Asn Thr Thr Lys Leu Phe Asn
    370                 375                 380

Gly Thr Tyr Ser Gln Pro Asn Ser Thr Gly Asn Thr Pro His Ser Asn
385                 390                 395                 400

Ile Thr Leu Pro Cys Lys Ile Lys Gln Ile Ile Asn Met Trp Gln Gly
                405                 410                 415

Val Gly Arg Ala Met Tyr Ala Pro Pro Ile Ala Gly Asn Ile Thr Cys
            420                 425                 430

Ile Ser Asn Ile Thr Gly Leu Ile Leu Thr Arg Asp Gly Gly Asp Lys
        435                 440                 445

Asn Gly Ser Lys Pro Glu Ile Phe Arg Pro Gly Gly Asn Met Lys
    450                 455                 460

Asp Asn Trp Arg Ser Glu Leu Tyr Lys Tyr Lys Val Val Glu Ile Lys
465                 470                 475                 480

Pro Leu Gly Leu Ala Pro Thr Glu Ala Lys Arg Glu Val Val Glu Arg
```

Glu Lys Glu

<210> SEQ ID NO 47
<211> LENGTH: 1482
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 47

| | |
|---|---|
| atgagagtga agggcatcag aaagaactac cagcaccttt ggagatgggg caccatgctg | 60 |
| ctgggcatgc tgatgatctg tagcgccgtg cctgtgtgga agaggccac caccacactg | 120 |
| ttctgtgcct ccgatgccaa ggcctacgat accgaggtgc acaacgtgtg gccactcac | 180 |
| gcttgcgtgc ccaccgatcc taatcctcaa gaggtggtgc tggaaaacgt gaccgagaac | 240 |
| ttcaacatgt ggaagaacaa catggtcgag cagatgcacg aggacatcat cagcctgtgg | 300 |
| gaccagagcc tgaagccttg cgtgaagctg acccctctgt gcgtgaccct gaattgcacc | 360 |
| gacgtgtcca gcaacagcac cagcgtgaac atcaccagcg agaagggcga gatcaagaac | 420 |
| tgcagcttca atatcaccac cagcatccgc gacaaggtgc agaaagagta cgccctgttc | 480 |
| tacaagctgg acgtggtgcc catcgaggac gacagcagaa acaacagcta cagactgatc | 540 |
| agctgcaaca cctccgtgat cacccaggcc tgtcctaagg tgtccttcga gcccattcct | 600 |
| atccactact gtgcccctgc cggcttcgcc atcctgaagt gcaacgacaa gaagttcaac | 660 |
| ggcacaggcc cctgcaccaa tgtgtccacc gtgcagtgta cccacggcat cagaccagtg | 720 |
| gtgtctaccc agctgctgct gaatggctct ctggccgagg aagaagtggt catcagaagc | 780 |
| gagaatttca ccaacaacgc caagaccatc atcgtgcagc tgaacgagag cgtggaaatc | 840 |
| aactgcaccc ggcctaacaa caacaccaga aagagcatcc acatcggccc tggcagagcc | 900 |
| ttttatgcca ccggcgatat catcggcgac atcagacagg cccactgtaa catcagccgg | 960 |
| gaaaagtgga caacaccct gaagcagatc gtgaagaagc tgagagagca gttcggcaac | 1020 |
| aagacgatcg tgttcaacca gagcagcgga ggcgaccccg agatcgtgat gcacagcttt | 1080 |
| aattgtggcg gcgagttctt ctactgcaac acaacccagc tgttcaactc cacctggtcc | 1140 |
| atcaatggca cctggaacgg caccaccgag agcaacgata ccatcacact gccctgccgg | 1200 |
| atcaagcaga tcattaacat gtggcaagaa gtcggcaagg ctatgtacgc ccctcctatc | 1260 |
| agaggccaga tccggtgcag cagcaacatc acaggactgc tgctcaccag agatggcggc | 1320 |
| aacagcagct ccaacaacga gacattcaga cctggcggcg gagacatgag agacaattgg | 1380 |
| agaagcgagc tgtacaagta caaggtggtc aagatcgagc ccctgggcgt cgcccctaca | 1440 |
| aaggccaaag aaagagtggt gcagcgggaa aaagagtgat ga | 1482 |

<210> SEQ ID NO 48
<211> LENGTH: 1476
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 48

| | |
|---|---|
| atgaaagtga agggcatcag aaagaactgc cagcaccttt ggagatgggg catcatgctg | 60 |
| ctgggcatgc tgatgatctg tagcgccgtg cctgtgtgga agaggccac caccacactg | 120 |

```
ttctgtgcct ccgatgccaa ggcctacgat acagaggccc ataacgtgtg ggccactcac        180
gcctgtgtgc ccaccgatcc taatcctcaa gagatcgtgc tggaaaacgt gaccgagaac        240
ttcaacatgt ggaagaacga catggtcgag cagatgcacg aggacatcat cagcctgtgg        300
gacgagagcc tgaagccttg cgtggaactg acccctctgt gcgtgaccct gaactgcacc        360
aatgtgaacg ccaccaacac caacaacagc agcggcatcg aaggcggcga tgaagaac         420 tgcagcttca acgtgaccac cagcatccgg gacaagatgc agaaagagta cgccctgttc        480
tacagcctgg acgtggtgca gatcgacaac gacaccaact accggctgat caactgcaac        540
accagcgtga tcacccaggc ctgtcctaag atcagcttcg agcccattcc tatccactac        600 tgcaccccctg ccggcttcgc catcatcaag tgcaacgaca agaagttcaa cggcagcggc        660
ccctgcaaga acgtgtccac agtgcagtgt acccacggca tcaagcccgt ggtgtctaca        720
cagctgctgc tgaatggcag cctggccgaa gaggaaatcg tgatcagaag cgagaatttc        780
agcgacaacg ccaagaccat catcgtgcag ctgaacgaga gcgtggtcat caattgcacc        840
cggcctaaca acaacacccg gaagtccatc agcatcggcc ctggcagagc cttttatgcc        900
accggcgaca tcatcggcaa catcagacag gcccactgca acctgtctcg ggccgagtgg        960
aacaataccc tgagacagat cgtgaccaag ctgcgcgagc agttcaagaa caagacaatc        1020
gccttcaacc acagctctgg cggcgacccct gagatcgtga tgcacacctt taactgtggc        1080
ggcgagttct tctactgcaa cagcacccag ctgttcaact ccacctggat cgccaacaag        1140
accggcaatg ataccggcgg cagcaacggc acaatcaccc tgcagtgccg gatcaagcag        1200
attgtgaacc ggtggcaaga agtgggcaaa gctatgtacg cccctcctat cagcggccag        1260
atcagctgca gcagcaatat caccggcctg atcctgacca gagatggcgg caccaacaat        1320
accaacggca ccgagatctt cagacccggc ggaggcaaca tgaaggacaa ttggagaagc        1380
gagctgtaca gtacaaggt cgtgcggatc gagcccctgg aatcgcccc tacaaaggcc         1440 agagaaagag tggtgcagcg ggaaaaagag tgatga                                 1476
```

<210> SEQ ID NO 49
<211> LENGTH: 1539
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 49

```
atgaaggcca aagagacacg gaagaactac cagcaccttt ggagatgggg catcaccctg        60
ctgggcatgc tgatgatctg tagcgctgtg cccgtgtgga agaggccac caccacactg         120 ttttgtgcca gcgacgccaa ggcctacgat accgaggtgc acaatgtgtg ggccactcac        180
gcctgcgtgc ccaccgatcc taatcctcaa gaggtggtgc tggaaaacgt gaccgagaac        240
ttcaacatgt ggaagaacaa catggtcgag cagatgcacg aggacatcat cagcctgtgg        300
gaccagagcc tgaagccttg cgtgaagctg acccctctgt gcgtgaccct gaactgcacc        360
gacgacctga gaatgccac cgtgaagaac gccacaaaca ccaacaacag cagctggggc        420
ggcatggaaa ggggcgagat caagaactgc agcttcaaca tcaccaccag catcagagac        480
aaggtgcaga aagagtacgc cctgttctac aagctggacg tggtgcccat cgacaacgcc        540
gacaacaaca atatcaccac cgaactacac agctaccggc tgatctcctg caacaccagc        600
gtgatcactc aggcctgtcc taaggtgtcc ttcgagccca ttcctatcca ctactgtgcc        660
```

```
cctgccggct tcgccatcct gaagtgcaac gacaagaagt tcaacggcac aggcccctgc    720
accaacgtgt ccacagtgca gtgtacccac ggcatcagac ccgtggtgtc tacacagctg    780
ctgctgaatg gaagcctggc cgagaaagaa gtggtcatca gaagcgagaa ctttaccaac    840
aacgccaaga ccatcatcgt gcagctggac gagagcgtcg tgatcaactg cacccggcct    900
aacaacaaca ccagaaagag catccacatc ggccctggca gagccttta caccaccggc    960 gagattatcg gcgacatcag acaggccac tgtaccctga accggaccga gtggaacaac   1020
accctggcca agatcaccga gaagctgaga gagcagttcg gcaacaacat cacaatcgtg   1080
ttcaaccaca gctctggcgg cgaccccgaa atcgtgatgc acagctttat ctgtggcggc   1140
gagttcttct actgcaatac cagccagctg ttcaacagca cctggaacag caccggcaac   1200
aatattagcg agagcgacaa caccgagcgg aacatcacac tgccctgccg gatcaagcag   1260
atcattaacc tgtggcaaga agtcggcaag gctatgtacg cccctcctat cagaggccag   1320
atccggtgca gcagcaacat tacaggcctg ctgctcacca gagatggcgg cagcaacacc   1380
gacgagaatc ggaccgagat ctttagaccc ggcggaggcg acatgagaga caattggaga   1440
agcgagctgt acaagtacaa ggtggtcaag atcgagcccc tgggcgtcgc ccctaccaaa   1500
gccaaagaaa gagtggtgca gcgggaaaaa gagtgatga                          1539
```

<210> SEQ ID NO 50
<211> LENGTH: 1503
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 50

```
atgagagtga aagagacacg gcggatctgg cagcacctgt ggaagtgggg aacaatgctg     60
ctgggcatgc tgatgatcta cagcgccgtg cctgtgtgga agaggccac caccacactg    120 ttctgtgcct ccgatgccaa ggcctacgat accgaggtgc acaacgtgtg ggccactcac    180
gcttgcgtgc ccaccgatcc taatcctcaa gaggtggtgc tgggcaacgt gaccgagaac    240
ttcaacatgt ggaagaacaa catggtcgag cagatgcacg aggacgtgat cagcctgtgg    300
gaccagagcc tgaagccttg cgtgaagctg acccctctgt gcgtgaccct gaactgcaca    360
gatgtgctcg gcaagggcac aagcgccaat gccacatctg ccaatgtgac cagcgagaag    420
ggcgagatca gaactgcag cttcaacatc accaccactc tgagagacaa ggtgcagaag    480
gcccacgctc tgttctacag actggacgtg gtgcccatcg acgacaacaa cgacaactcc    540
agcagcagct accggctgat caactgcaac accagcgtga tcacccaggc ctgtcctaag    600
gtgtccttcg agcctattcc tatccacttc tgtaccctg ccggcttcgc cctgctgaag    660
tgcaacaaca gaagttcaa cggcacaggc ccctgcacca acgtgtccac agtgcagtgt    720
acccacggca tcaagcccgt ggtgtctaca cagctcctgc tgaatggcag cctggccgag    780
gaagaagtgg tcatcagaag cgagaatttc accgacaacg ccaagaccat catcgtgcag    840
ctgaacgaca gcgtcgtgat caattgcacc cggcctaaca acacaccccg gaagggcatc    900
acaatcggcc ctggctccgt gttttacacc ggggagatca tcggcgacat cagacaggcc    960
cactgtaacc tgtctagcgc caagtggaac aataccctga agcagatcgt catcaagctg   1020
agagagcagt tcggcaacaa gacgatcgtg ttcaaccaga gcagcggagg cgaccctgag   1080
atcgtgctgc acagctttaa ttgtggcggc gagttcttct actgcaatac cacacagctg   1140
```

| | |
|---|---|
| ttcaacagca cctggaacat caacgacacc agaaacggca ccaccgagag cagcaagaca | 1200 |
| atcaccctgc cttgccggat caagcagatc atcaatatgt ggcaagaagt cggcaaggct | 1260 |
| atgtacgccc ctcctatcag aggccagatc agatgcagca gcaatatcac cggcctgctg | 1320 |
| ctgacaagag atggcggcaa ccagaatacc agcggcaccg agatcttcag acccggcgga | 1380 |
| ggcaacatgc gggacaattg gagaagcgag ctgtacaagt acaaggtggt caagatcgag | 1440 |
| cccctgggaa tcgcccctac caaggccaaa gaaagagtgg tgcagcggga aaagagtga | 1500 |
| tga | 1503 |

<210> SEQ ID NO 51
<211> LENGTH: 1530
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 51

| | |
|---|---|
| atgagagtga agggcatcag aaagaactgc cagcacccttt ggagatgggg caccatgctg | 60 |
| ctgggcatgt gatgatctg tagcgccgtg cctgtgtgga agaggccac caccacactg | 120 |
| ttctgtgcct ccgatgccaa ggcctacgat acagaggccc ataacgtgtg gccactcac | 180 |
| gcctgtgtgc ccaccgatcc taatcctcaa gaggtggtgc tgggcaacgt gaccgagaac | 240 |
| ttcaacatgt ggaagaacga catggtcgag cagatgcacg aggacatcat cagcctgtgg | 300 |
| gaccagagcc tgaagccttg cgtgaagctg acccctatct gcgtggccct gaactgcacc | 360 |
| gacgtgaagg acaccaacaa caccagcaac aacacgaaca ataccagctc caacaacagc | 420 |
| tccatgaccg aaggcggcga gatgaagaac tgcagcttca acatcaccac cagcatcaag | 480 |
| accaaagtga aggactacgc cctgttctac aagctggaca tcgtgcccat cgacaacgac | 540 |
| ggcgacaaca cctcctacag actgatcagc tgcaatacct ccgtgatcac ccaggcctgt | 600 |
| cctaagatca gcttcgagcc cattcctatc cactactgca cccctgccgg atacgccctg | 660 |
| ctgaagtgca acaacaagaa gttcaacggc acaggcccct gcaagaacgt gtccaccgtg | 720 |
| cagtgtaccc acggcatcag accagtggtg tctacccagc tgctgctgaa tggctctctg | 780 |
| gccgaggaag aagtggtcat cagaagcagc aacttcacca acaatgccaa agtgatcatc | 840 |
| gtgcagctga agaagccgt cgagatcaac tgcacccggc ctaacaacaa tacccggaag | 900 |
| tccatccaca tcgccctgg caaggcctgg tatacaaccg cgagatcat cggcaacatc | 960 |
| agacaggccc actgtaacat cagccggacc aagtggaaca cacctgca ccagattgtg | 1020 |
| aagaagctga aatccagtt cggcaacaag accatcatct tcaaccagag cgctggcggc | 1080 |
| gaccctgaga ttgtggtgca cagctttaac tgtggcggcg agttcttcta ctgcaacaca | 1140 |
| agccagctgt tcaacagcac ctggcggaac gacacctgga cgatacaag ccctcagatc | 1200 |
| gccaccaccg gcaacgacac aatcaccctg ccttgccgga tcagacagat cgtgaacatg | 1260 |
| tggcagcaag tgggcaaagc tatgtacgcc cctcctatcg ccggccagat cagatgcagc | 1320 |
| agcaatatca ctggcgtgct gctgaccaga gatggcggca acaatgagag caaggccaac | 1380 |
| gccaacgaga cattcagacc tgccggcgga gacatgagag acaattggag aagcgagctg | 1440 |
| tacaagtaca aggtggtcaa gatcgagccc ctgggcgtcg cccctacaaa ggccaaagaa | 1500 |
| agagtggtgc agcgggaaaa agagtgatga | 1530 |

<210> SEQ ID NO 52
<211> LENGTH: 1488
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 52

| | | | | | |
|---|---|---|---|---|---|
| atgaaagtga | agggcatcag | aaagaactac | cagcacctttt | ggagatgggg | catgatgctg | 60 |
| ctgggcatgc | tgatgatctg | tagcgccgtg | cctgtttggc | gggatgccac | caccacactg | 120 |
| ttttgtgcct | ctgacgccaa | ggcctacgag | acagagctgc | acaatgtgtg | gccactcac | 180 |
| gcctgcgtgc | ccaccgatcc | taatcctcaa | gaagtggtgc | tgggcaacgt | gaccgagaac | 240 |
| ttcaacatgt | ggaagaacga | catggtcgag | cagatgaacg | aggacatcat | cagcctgtgg | 300 |
| gacgagagcc | tgaagccttg | cgtgaagctg | accccctctgt | gcgtgacccct | gaactgcacc | 360 |
| aactacaacg | agacaaccac | caacagcacc | accaccaacg | ccacagtggt | gtctccaggc | 420 |
| gagatcaaga | actgcagctt | caatgtgacc | accggcatcc | gggacaaagt | gcggaaagat | 480 |
| cacgccctgt | tctacgccct | ggacatcgtg | cccatcgaca | acaccatcga | taataccagc | 540 |
| taccggctgg | tgtcctgcaa | caccagtgtg | ctgacacagg | cttgccccaa | ggtgtccttc | 600 |
| gagcctattc | ctatccactt | ctgtgcccct | gccggctacg | ccatcatcaa | gtgcaacaac | 660 |
| aagaccttca | cggcagcgg | cccctgcaga | aatgtgtcca | ccgtgcagtg | tacccacggc | 720 |
| atcagacccg | tggtgtctac | acagctgctg | ctgaatggca | gcctggccga | gaggaaatc | 780 |
| gtgatcagaa | gcgccaactt | cagcgacaat | accaagacca | tcatcgtgca | gctgaatgag | 840 |
| gccgtgaaga | tcaactgcac | ccggcctaac | aacaacacca | ggcggagtgt | gcacatgggc | 900 |
| cctggctctg | ccttctatac | aaccggcggc | atcatcggcg | acatcagaca | ggcccactgc | 960 |
| aacatcagcg | agagagattg | gaacggcgcc | ctgaagcaga | tcgtggaaaa | gctgggcgag | 1020 |
| cagttccaga | caagacaat | cgtgttcaag | cagagcagcg | gaggcgaccc | tgaggtggtc | 1080 |
| atgcacacct | tcaattgcag | aggcgagttc | ttctactgca | ataccaccaa | gctgttcaac | 1140 |
| tccacctggg | tcaacggcac | caagaacgat | accaaaggcg | gcaacggcac | aatcaccctg | 1200 |
| cagtgcagaa | tcaagcagat | cattaacatg | tggcagcaag | tcggcaaggc | tatgtacgcc | 1260 |
| cctcctatca | gcggccctat | cagctgcagc | agcaatatca | ccggcctgat | cctgaccaga | 1320 |
| gatggcggca | ccaacaccac | aaacgagaca | ttcagacctg | gcggcggaga | catgagagac | 1380 |
| aattggagaa | gcgagctgta | caagtacaag | gtggtcaaga | tcgagcccat | cggcgtggcc | 1440 |
| cctacaaagg | ccagagaaag | agtggtgcag | cgcgagaaag | agtgatga | | 1488 |

<210> SEQ ID NO 53
<211> LENGTH: 1485
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 53

| | | | | | |
|---|---|---|---|---|---|
| atgagagcca | aagagacacg | gaagaaatac | cagcacctgt | gggcctgggg | aacactgctg | 60 |
| ctgggaatgc | tgatgatctg | cagcgctgtg | cccgtgtgga | aggacgccaa | taccacactg | 120 |
| ttctgtgcca | gcgacgccaa | ggcctacgat | accgaggtgc | acaatgtgtg | gccactcac | 180 |
| gcctgcgtgc | caaccgatcc | atctcctcaa | gagatcgtgc | tgaagaacgt | gaccgagaac | 240 |

| | |
|---|---|
| ttcaacatgt ggaagaacaa catggtcgag cagatgcaca aggacatcat cagcctgtgg | 300 |
| gacgagagcc tgaagccttg cgtgaagctg acccctctgt gcgtgaccct gaactgcagc | 360 |
| aactacaaca gcaccaactc caccatcgat cccaacatgg aaggcgccat caagaattgc | 420 |
| agcttcaacg ccaccaccgg catccagaac aagatgaaga agagtacgc cctgttctac | 480 |
| agcctggaca tcgtgcagat cgagagcgag aacaagagca caagtccta catgctgcgg | 540 |
| agctgcaaca ccagcgtgat cactcaggcc tgtcctaaag tgaccttcga gcccattcct | 600 |
| atccactact gtgcccctgc cggcttcgcc atcctgaagt gcaacgacaa gaagttcaac | 660 |
| ggcacaggcc cctgcaagaa cgtgtccacc gtgcagtgta cccacggcat cagaccagtg | 720 |
| gtgtctaccc agctgctgct gaatggctct ctggccgagg aagagatcat catcagatcc | 780 |
| gagaacatca ccaacaacgc caagaccatc atcatccagc tgaaccggtc catcgagatc | 840 |
| aactgcaccc ggcctaacaa caacacccgg aagtccatcc acatgggctg gggcagagcc | 900 |
| ttttatgcca ccggcgatat catcggcgac atcagacagg cccactgtaa cctgagcggc | 960 |
| accaagtgga caatacccct gtaccagatc gcccggaagc tgagagagca cttcaacaat | 1020 |
| accatcgtgt tcaaccagag cagcggaggc gaccccgaga tcgtgatgca cactttaat | 1080 |
| tgtggcggcg agttcttcta ctgcaacaca cccagctgt tcaatagcac ctggcacgcc | 1140 |
| aattccacct ggaacgagac aacaggcagc ggcagcaacg ataccatctc tctgccctgc | 1200 |
| cggatcaagc agatcattaa ccggtggcaa gaagtcggca aggctatgta cgcccctcct | 1260 |
| atcggcggcc agatcagatg cagcagcaac atcacaggca tcctgctgac cagagatggc | 1320 |
| ggcaccgaga caacacaag cgagacattc agacccggcg gaggcaacat gaaggacaat | 1380 |
| tggagaagcg agctgtacaa gtacaaggtt gtgcggatcg agcccctggg cgttgcccct | 1440 |
| acaaaggcca agaaagggt cgtgcagcgc gagaaagagt gatga | 1485 |

<210> SEQ ID NO 54
<211> LENGTH: 1482
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 54

| | |
|---|---|
| atgagagtga agggcatcag aaagaactac cagcaccttt ggagatgggg caccatgctg | 60 |
| ctgggcatgc tgatgatctg tagcgccgtg cctgtgtgga agaggccac caccacactg | 120 |
| ttctgtgcca gcgacgccaa ggctcacgat accgaggtgc acaatgtgtg gccactcac | 180 |
| gcctgcgtgc ccaccgatcc taatcctcaa gaggtggtgc tggaaaacgt gaccgagaac | 240 |
| ttcaacatgt ggaagaacaa catggtcgag cagatgcaag gacgtgat cagcctgtgg | 300 |
| gaccagagcc tgaagccttg cgtgaagctg acccctctgt gcgtgaccct gaattgcacc | 360 |
| gacgtgtcca gcaacagcac cagcgtgaac atcaccagcg agagggcga gatcaagaac | 420 |
| tgcagcttca cgtgaccac cagcatcaag acaaggtgc agaaagagta cgccctgttc | 480 |
| tacaagctgg acgtggtgcc catcgaggac acagcagaa acaacagcta cagactgatc | 540 |
| agctgcaaca cctccgtgat cacccaggcc tgtcctaagg tgtccttcga gcccattcct | 600 |
| atccactact gtaccctgc cggcttcgcc atcctgaagt gcaacgacaa gaagttcaac | 660 |
| ggcacaggcc cctgcaccaa tgtgtccacc gtgcagtgta cccacggcat cagacctgtg | 720 |
| gtgtctaccc agctgctgct gaatggctct ctggccgagg aagaagtggt catcagaagc | 780 |

| | |
|---|---:|
| gagaatttca ccaacaacgc caagaccatc atcgtgcagc tgaacgagag cgtggaaatc | 840 |
| aactgcaccc ggcctaacaa caacaccaga aagagcatcc acatcggccc tggcagagcc | 900 |
| ttttatgcca ccggcgatat catcggcgac atcagacagg cccactgtaa catcagccgg | 960 |
| gaaaagtgga acaacaccct gaagcagatc gtgaagaagc tgagagagca gttcggcaac | 1020 |
| aagacgatcg tgttcaacca gagcagcgga ggcgaccccg agatcgtgat gcacagcttt | 1080 |
| aattgtggcg gcgagttctt ctactgcaac acaacccagc tgttcaactc cacctggtcc | 1140 |
| atcaatggca cctggaacgg caccaccgag agcaacgata ccatcacact gccctgccgg | 1200 |
| atcaagcaga tcattaacat gtggcaagaa gtcggcaagg ctatgtacgc ccctcctatc | 1260 |
| agaggccaga tccggtgcag cagcaatatc acaggcctgc tgctcaccag agatggcggc | 1320 |
| aatagcagct ccaacaacga cattcaga cctggcggcg agacatgag agacaattgg | 1380 |
| agaagcgagc tgtacaagta caaggtggtc aagatcgagc ccctgggcgt cgcccctaca | 1440 |
| aaggccaaag aaagagtggt gcagcgggaa aaagagtgat ga | 1482 |

<210> SEQ ID NO 55
<211> LENGTH: 1476
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 55

| | |
|---|---:|
| atgaaagtga agggcatcag aaagaactgc cagcacctttt ggagatgggg catcatgctg | 60 |
| ctgggcatgc tgatgatctg tagcgccgtg cctgtgtgga agaggccac caccacactg | 120 |
| ttctgtgcca gcgacgccaa ggctcacgat acagaggccc ataacgtgtg gccactcac | 180 |
| gcctgtgtgc ccaccgatcc taatcctcaa gagatcgtgc tggaaaacgt gaccgagaac | 240 |
| ttcaacatgt ggaagaacga catggtcgag cagatgcaag aggacgtgat cagcctgtgg | 300 |
| gacgagagcc tgaagccttg cgtggaactg accccctctgt gcgtgaccct gaactgcacc | 360 |
| aatgtgaacg ccaccaacac caacaacagc agcggcatcg aaggcggcga gatgaagaac | 420 |
| tgcagcttca acgtgaccac cagcatcaag acaagatgc agaaagagta cgccctgttc | 480 |
| tacagcctgg acgtggtgca gatcgacaac gacaccaact accggctgat caactgcaac | 540 |
| accagcgtga tcacccaggc ctgtcctaag atcagcttcg agcccattcc tatccactac | 600 |
| tgcacccctg ccggcttcgc catcatcaag tgcaacgaca agaagttcaa cggcagcggc | 660 |
| ccctgcaaga acgtgtccac agtgcagtgt acccacggca tcaagcccgt ggtgtctaca | 720 |
| cagctgctgc tgaatggcag cctggccgaa gaggaaatcg tgatcagaag cgagaatttc | 780 |
| agcgacaacg ccaagaccat catcgtgcag ctgaacgaga gcgtggtcat caattgcacc | 840 |
| cggcctaaca caacacccg aagtccatc agcatcggcc ctggcagagc cttttatgcc | 900 |
| accggcgaca tcatcggcaa catcagacag gcccactgca acctgagccg gccaagtgg | 960 |
| aacaataccc tgagacagat cgtgaccaag ctgcgcgagc agttcaagaa caagacaatc | 1020 |
| gccttcaacc acagctctgg cggcgaccct gagatcgtga tgcacacctt taactgtggc | 1080 |
| ggcgagttct tctactgcaa cagcacccag ctgttcaact ccacctggat cgccaacaag | 1140 |
| accggcaatg ataccggcgg cagcaacggc acaatcaccc tgcagtgccg gatcaagcag | 1200 |
| attgtgaacc ggtggcaaga agtgggcaaa gctatgtacg cccctcctat cagcggccag | 1260 |
| atcagctgca gcagcaatat caccggcctg atcctgacca gagatggcgg caccaacaat | 1320 |

| | |
|---|---|
| accaacggca ccgagatctt cagacccggc ggaggcaaca tgaaggacaa ttggagaagc | 1380 |
| gagctgtaca agtacaaggt cgtgcggatc gagcccctgg gaatcgcccc tacaaaggcc | 1440 |
| agagaaagag tggtgcagcg ggaaaaagag tgatga | 1476 |

<210> SEQ ID NO 56
<211> LENGTH: 1497
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 56

| | |
|---|---|
| atgagagtta gaggcatcct gcggaactac cagcagtggt ggatctgggg catcctcggc | 60 |
| ttttggatgc tgatgatctg caacgtggtg cccgtgtgga agaggccaa gaccacactg | 120 |
| ttctgtgcca gcgacgccaa ggcctacgag aaagaggtgc acaacgtctg gccacacac | 180 |
| gcctgtgtgc ccaccgatcc taatcctcaa gagatggtgc tggaaaacgt gaccgagaac | 240 |
| ttcaacatgt ggaagaacga catggtggac cagatgcacg aggacatcat cagcctgtgg | 300 |
| gaccagagcc tgaagccttg cgtgaagctg acccctctgt gcgtgaccct gaactgcgtg | 360 |
| aacatcacca acagcaccac cagcaacggc gacggcacag tgacccacat caacagcatc | 420 |
| aaagaggaaa tcaagaactg cagcttcaac gccaccaccg agctgcggga caagaagtcc | 480 |
| aaagagtacg ccctgttcta ccggctggac atcgtgcctc tgagcagcgg caatagcagc | 540 |
| agcaacagct ccaagtaccg gctgatcaac tgcaacacca gcacaatcac ccaggcctgt | 600 |
| cctaaggtgt ccttcgatcc cattcctatc cactactgtg ccctgccgg ctacgccatc | 660 |
| ctgaagtgca acaacaagac cttcaacggc acaggcccct gcaacaacgt gtccaccgtg | 720 |
| cagtgtaccc acggcatcaa gccagtggtg tctacccagc tgctgctgaa tggctctctg | 780 |
| gccgaggaag agatcatcat cagaagcgag aacctgaccg acaacgtcaa gaccatcatc | 840 |
| gtgcacctga cgagagcgt ggaaatcgtg tgcacccggc ctaacaacaa caccagaaag | 900 |
| agcatccgga tcggccctgg ccagacctt tatgccaccg gcgatatcat cggcgacatc | 960 |
| agacaggccc actgtaacat cagcaaaggc gcctggaacg aaaaccctgca gtgggtcgga | 1020 |
| aagaagctga agagcactt ccccaacaag acgatcaagt tcaacagcag ctctggcggc | 1080 |
| gacctggaaa tcaccacaca cagcttcaat tgcagaggcg agttcttcta ctgcaatacc | 1140 |
| tccggcctgt tcaactccac ctaccggaac aatagcaccg cgacaattc caccatcaca | 1200 |
| ctgccctgcc ggatcaagca gatcattaac atgtggcaag aagtcggcag ggctatgtac | 1260 |
| gcccctccta tcgccggcaa catcacatgc aagtccaaca tcaccggcct gctgctcacc | 1320 |
| agagatggcg gcaccagaga cagaaacgac accgagacat tcagacccgg cggaggcgac | 1380 |
| atgagagaca attggagaag cgagctgtac aagtacaagg tggtcgagat caagcccctg | 1440 |
| ggaatcgccc ctaccaaggc caagaaaga gtggtggaac gggaaaaaga gtgatga | 1497 |

<210> SEQ ID NO 57
<211> LENGTH: 1473
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 57

| | |
|---|---|
| atgagagtga tgggcatcca gagaaactgg ccccagtggt ggatctgggg catcctcggc | 60 |

| | |
|---|---|
| ttttggatga tcattatctg cagagtggtg cccgtgtggc gcgaggccaa gaccacactg | 120 |
| ttttgtgcct ctgacgccaa ggcctacgag cgcgaagtgc acaatgtgtg gctacccat | 180 |
| gcctgcgtgc ccaccgatcc taatcctcaa gagctggtgc tggaaaacgt gaccgagaac | 240 |
| ttcaacatgt gggagaacga catggtggac cagatgcacg aggacgtgat cagcctgtgg | 300 |
| gaccagagcc tgaagccttg cgtgaagctg accctctgt gcgtgaccct gaagtgcacc | 360 |
| aacaccacct actacaacgt gtccagcaaa gagttcacca acggcgagat caagaactgc | 420 |
| agcttcaata ccaccaccga gctgcgggac aagaaacaga aggtgtcagc cctgttctac | 480 |
| cggctggatg tggtgcccct gagcaagaag acaagaccca caacgacag cggcgagtac | 540 |
| atcctgatca actgcaacac cagcgccatc acacaggctt gccccaaggt gtccttcgat | 600 |
| cccattccta tccactactg caccctgcc ggctacgcca tcctgaagtg taacaacaag | 660 |
| accttcaacg gcacaggccc ctgccataat gtgtccaccg tgcagtgtac ccacggcatc | 720 |
| aagccagtgg tgtctaccca gctgctgctg aatggctctc tgaccgaggg cgagattatc | 780 |
| atcagaagcg agaacctgac caacaatgcc aagacaatca tcgtgcacct gaaccagagc | 840 |
| gtggccatcg tgtgtaccag acctggcaac aacaccagaa agagcgtgcg gatcggaccc | 900 |
| ggccaggcct tttatgccac cggcgaaatc atcggcgaca tcagacaggc ctactgcaat | 960 |
| ctgaccaact ggcaagagac actgaagaat gtctccaaga agctgcaaga gcggtttaac | 1020 |
| aagaccatca gattcgcccc tagctctggc ggcgacctgg aaatcaccac acacagcttt | 1080 |
| aactgtggcg gcgagttctt ctactgtaac acctccagcc tgttcaacag cgcctacaat | 1140 |
| cccaacggca ccaaggacaa cagcaacagc agcatcacca tccagtgcaa gatcaagcag | 1200 |
| atcatcaata tgtggcaagg cgtgggcaga gccatctacg cccctccaat cgccggcaac | 1260 |
| atcacctgta acagcaatat caccggcatc ctgctgacca gagatggcgg cagcaagaac | 1320 |
| aacaccgagg aaatcttcag acccggcgga ggcaacatga aggacaattg agagaagcgag | 1380 |
| ctgtaccgct acaaggtggt ggaaatcaag cccctgggag tcgcccctac cgaggccaaa | 1440 |
| gaaagagtgg tggaacggga aaaagagtga tga | 1473 |

<210> SEQ ID NO 58
<211> LENGTH: 1491
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 58

| | |
|---|---|
| atgagagtga agaaaccca gatgaactgg cccaacctgt ggaagtgggg cacactgatt | 60 |
| ctgggcctcg tgatcatctg tagcgccgtg cctgtttgga gggacgccga taccacactg | 120 |
| ttctgtgcca gcgacgccaa ggctcacgaa accgaggtgc acaatgtgtg gccactcac | 180 |
| gcctgcgtgc ccaccgatcc taatcctcaa gagatccacc tggaaaacgt gaccgagaac | 240 |
| ttcaacatgt ggaagaacaa catggtcgag cagatgcaag aggacgtgat cagcctgtgg | 300 |
| gaccagagcc tgaagccttg cgtgaagctg accctctgt gcgtgaccct gaattgcacc | 360 |
| aaggccaacc tgaccaacat caacgagaca accgccagca cggcatcgg caacatcacc | 420 |
| gacgaagtgc ggaactgcag cttcaatatg accaccgagc tgcgggacaa gaaacagaag | 480 |
| gtgcacgccc tgttctacaa gctggacatc gtgcccatcc ggaacgagag caagatgggc | 540 |
| aatgtgtcca gcgagtaccg gctgatcaac tgcaacacca gcgtgatcaa gcaggcctgt | 600 |

```
cctaagatca gcttcgaccc cattcctatc cactactgca cccctgccgg ctacgccatc    660
ctgaagtgca acgacaagaa tttcaacggc acaggcccct gcaagaacgt gtcctctgtg    720
cagtgtacac acggcatcaa gcccgtggtg tctacccagc tgctgctgaa tggaagcctg    780
gccgaggaag agatcatcat cagaagcgag aacctgacga caacgccaa gaccatcatc     840 gtgcacctga acaagagcgt ggaaatcaat tgcacccggc ctagcaacaa cacccggacc    900
agcatcacaa tcggcccagg ccaggtgttc tacagaaccg cgatatcat cggcgacatc     960 cggaaggcct actgcgagat caatggcacc aagtggaacg agacactgaa acaggtggcc   1020
ggcaagctga agagcacttt caacaagacg atcatcttcc agcctccatc tggcggcgac   1080
ctggaaatca ccatgcacca cttcaactgc agaggcgagt tcttctactg caataccacc   1140
aagctgttca acagcacctg gaacggcacc atggaaggca gaaacggcac aatcatcctg   1200
ccttgcagaa tcaagcagat catcaatatg tggcaaggcg ttggccaggc tatgtacgcc   1260
cctcctatca gcggcatcat caactgcgtg tccaatatca ccggcatcct gctgaccaga   1320
gatggcggca acaacaatgc caccaacgaa accttcagac ccggcggagg caatatcaag   1380
gacaactggc ggagcgagct gtacaagtac aaggtggtgc agatcgagcc cctgggaatc   1440
gcccctacca gagccaaaga aagagtggtg gaacgggaaa aagagtgatg a            1491

<210> SEQ ID NO 59
<211> LENGTH: 1497
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 59
atgagagtga agggcaccca gatgaactgg cccaaccttt ggagatgggg caccctgatt     60
ctgggcctcg tgatcatgtg tagcgccgtg cctgtgtgga aggacgccga taccacactg    120
ttctgtgcca gcgacgccaa ggctcacgag acagaggtgc acaacatctg gccacacac     180 gcctgcgtgc ccaccgatcc taatcctcaa gagatccctc tggaaaacgt gaccgagaac    240
ttcaacatgt ggaagaacaa catggccgag cagatgcaag aggacgtgat cagcctgtgg    300
gacgagagcc tgaagccttg cgtgaagctg acccctctgt gtgtgaccct gcactgcacc    360
aaggccaatc tgacccacaa caccaccaac gacaagaacg gcaccggcaa catcaccgac    420
gaagtgaaga tcggcaatat cacggatgaa gtcaaaaact gcagcttcaa tatgaccacc    480
gagatccggg acaagaagca gaaggtctac gccctgttct acaagctgga catcgtgcag    540
atcggcgaga acggcagcga gtacagactg atcaactgca acaccagcgt gatcaagcag    600
gcctgtccta aggtgtcctt cgatcccatt cctatccact actgtgcccc tgccggatac    660
gccctgctga gtgcaacga taagaagttc aacggcacag gccctgcag aaacgtgtcc      720 agcgtgcagt gtacccacgg catcaagcct gtggtgtcta cccagctgct gctgaatggc    780
tctctggccg aggaagagat catcatcaga agcgagaacc tgaccgacaa cgccaagacc    840
atcatcgtgc acctgaacga gagcgtggtc atcaattgca cccggcctag caacaacgtg    900
cggatcagca caagaatcgg cccaggccag gtgttctaca gaaccggcga gatcatcggc    960
gacatccgga aggcctactg cgagatcaat ggcaccaagt ggaacaaggt gctgaaagaa   1020
gtgacagaga agctgaaaga gcacttcaac aagacgatca tcttccagcc tccatctggc   1080
ggcgacctgg aaatcaccac acaccacttc aactgcagag gcgagttctt ctactgcaat   1140
```

```
accaccaagc tgttcaacaa tacctgcaac ggcaccatgg aagggttctg caacaacatc   1200
acactgccct gcaagattaa gcagatcatc aatatgtggc aaggcgccgg acaggccatc   1260
tacgcccctc caatcagcgg cagcattaag tgcgtgtcca atatcaccgg catcatcctg   1320
accagagatg cggcaatga taccggcacc agcgagatct ttagacccgg cggaggcaac   1380
atgaaggaca actggcggaa cgagctgtac aagtacaagg tggtgcagat tgagcccctg   1440
ggcgtcgccc ctacaaaggc caaagaaaga gtggtggacc gggaaaaaga gtgatga      1497

<210> SEQ ID NO 60
<211> LENGTH: 1491
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 60
atgagagtga tgggcatcca gagaaactgc cagcaccttt ggagatgggg catcatgctg     60
ctgggcatgc tgatgatctg caacgccgtg cctgtttgga gggacgccga dacaacactg   120
ttctgtgcct ctgacgccaa gggctacgat acagaggccc ataacgtgtg gccactcac    180 gcctgtgtgc ccacagatcc atctccacaa gagatccacc tggaaaacgt gaccgaggaa   240
ttcaacatgt ggaagaacaa catggtcgag cagatgcaca ccgacatcat cagcctgtgg   300
gaccagagcc tgaagccttg cgtgaagctg accctctgt gcgtgaccct ggactgtacc    360
ctggattgca acaacgtgac caacaacggc accagcgaca tgcgggaaga gatcaagaac   420
tgcagcttca acatcaccac cgagctgcgg gacaagaaaa agaaggtgta cagcctgttc   480
tacaagctgg acatcgtgcc catcaacggc gacaacagca ccaacaccta catgctgatc   540
aattgcaaca ccagcgccat cacacaggct tgccccaaag tgaccttcga gcctattcct   600
atccacttct gtgcccctgc cggctacgcc atcctgaagt gcaaggacaa agagttcaac   660
ggcacaggcc cctgcaagaa cgtgtccacc gtgcagtgta ccacggcat caagccagtg   720 gtgtctaccc agctgctgct gaatggctct ctggccgaag aggaaatcat gatcagaagc   780
gagaatatca cgaacaacgc caagatcatc atcgtgcagc tgaaccagag cgtggtcatc   840
aactgcaccc ggcctggcaa caacaccaga agtctgtgc ggatcggccc tggccagacc   900
ttttatgcca ccggcgatat catcggcgac atcagacagg cccactgtaa cgtgtcccgg   960
atcaagtgga acacagccct gcagaaggtg gccaagcagc tgagaaagta cttccggaac   1020
aagaccatca ccttcaacca gagcagcgga ggcgaccccg agatcaccac acaccctttt   1080
aattgtggcg gcgagttctt ctactgcaac acctccaacc tgttcaactc cacctggggc   1140
aacggcaatg gcaccgacaa tatgcagggc agcaatagca ccaatatcac cctgcagtgc   1200
cgcatcaagc agatcattaa catgtggcaa gaagtcggca gggccatcta cgcccctcca   1260
atcgagggca atatcagctg cagcagcaac attaccggcc tgctgctcac cagagatggc   1320
ggcaacagca agaactccac caccgaagag atcttcagac ccggcggagg caacatgaga   1380
gacaattgga gaagcgagct gtacaagtac aaggtggtca gatcgagcc catcggcgtg   1440 gcccctacaa aggccagaga aagagtggtg aacgggaaa aagagtgatg a             1491

<210> SEQ ID NO 61
<211> LENGTH: 1503
<212> TYPE: DNA
<213> ORGANISM: Artificial Sequence
```

```
<220> FEATURE:
<223> OTHER INFORMATION: Description of Artificial Sequence: Synthetic
      polynucleotide

<400> SEQUENCE: 61
atgaaagtga agggcatcca gagaaactgg ccccagtggt ggatctgggg catcctcgga     60
ttctggatgc tgatgatctg caacgtggtg cccgtgtggc gggaagccaa taccacactg    120
ttttgtgcca cgacgccaa ggcctacgat accgaggtgc acaacatctg gccacacac     180
gcctgcgtgc ccaccgatcc taatcctcaa gagatcgtgc tgggcaacgt gaccgagaac    240
ttcaacatgt ggaagaacaa catggtggac cagatgcacg aggacgtgat cagcctgtgg    300
gacgagagcc tgaagccttg cgtgaagctg acccctctgt gcgtgaccct ggaatgcaac    360
gatgccaagc tgaacagcac caagaccaac tccaccacca acagcacaga ccccaacaac    420
agcaacctgg gcatcgaggg cgagatcaag aactgcagct tcaacaccac caccgagatc    480
cgggacaaga agaagagagc ctacgctctg ttctacagac ccgatgtggt gcccctgaac    540
gagaacagca gcagctacat cctgatcaac tgcaacagct ccaccatcac acaggcttgc    600
cccaaggtgt ccttcgagcc cattcctatc cactactgta ccctgccgg cttcgccctg    660
ctgaagtgca caacaagac cttcaacggc agcggcccct gcaccaatgt gtctaccgtg    720
cagtgtaccc acggcatcag acccgtggtg tctacacagc tcctgctgaa tggcagcctg    780
gccgaagagg aaatcgtgat cagaagcgag aatttcaccg acaacgccaa gaccatcatc    840
gtgcagctga acgagtccgt ggaaatcaat tgcaccccggc ctaacaacaa caccagaaag    900
agcatccgga tcggcccagg ccaggccttt tatgccaccg gcgagattat cggcaacatc    960
cggcaggcct actgcaacat caacgagtcc ctgtggaacg aaaccctgta aggtgtcc    1020
gagaagctga aagagtactt taataccacc atcgagttcc agcagcctgc cggcggagat   1080
ctggaaatca ccacacacag cttcaattgc aggggcgagt tcttctactg taacacgacc   1140
aagctgttca acgggaccta cagccagcct aacagcaccg caataccccc tcacagcaac   1200
atcaccctgc cttgcaagat caagcagatc attaacatgt ggcaaggcgt gggcagagct   1260
atgtacgccc ctcctatcgc cggcaacatt acctgcatca gcaatatcac cggcctgatc   1320
ctgaccagag atggcggcga caagaacggc agcaagcccg agatttttcag acccggcgga   1380
ggcaacatga aggacaattg gagaagcgag ctgtacaagt acaaggtggt cgagattaag   1440
cccctggggc tcgctcctac agaggccaag agagaagtgg tcgagcgcga aaagagtga   1500
tga                                                                 1503

<210> SEQ ID NO 62
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Leu Arg Asp Lys Lys Gln Lys Val His Ala Leu Phe Tyr Lys Leu Asp
1               5                   10                  15

Ile Val Pro Ile Glu Asp
            20

<210> SEQ ID NO 63
<211> LENGTH: 22
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 63

Leu Arg Asp Lys Lys Gln Lys Val His Ala Leu Phe Tyr Lys Leu Asp
1               5                   10                  15

Ile Val Pro Ile Glu Asp
            20

<210> SEQ ID NO 64
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Leu Arg Asp Lys Lys Gln Lys Val His Ala Leu Phe Tyr Lys Leu Asp
1               5                   10                  15

Ile Val Pro Ile Glu Asp
            20

<210> SEQ ID NO 65
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Leu Arg Asp Lys Lys Gln Lys Val His Ala Leu Phe Tyr Lys Leu Asp
1               5                   10                  15

Ile Val Pro Ile Glu Asp
            20

<210> SEQ ID NO 66
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Leu Arg Asp Lys Lys Gln Lys Val His Ala Leu Phe Tyr Lys Leu Asp
1               5                   10                  15

Ile Val Pro Ile Glu Asp
            20

<210> SEQ ID NO 67
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Leu Arg Asp Lys Lys Gln Lys Val His Ala Leu Phe Tyr Lys Leu Asp
1               5                   10                  15

Ile Val Pro Ile Glu Asp
```

20

<210> SEQ ID NO 68
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Leu Arg Asp Lys Lys Gln Lys Val His Ala Leu Phe Tyr Lys Leu Asp
1               5                   10                  15

Ile Val Pro Ile Glu Asp
            20

<210> SEQ ID NO 69
<211> LENGTH: 80
<212> TYPE: PRT
<213> ORGANISM: Human immunodeficiency virus 1

<400> SEQUENCE: 69

Cys Val Thr Leu His Cys Thr Asn Ala Asn Leu Thr Lys Ala Asn Leu
1               5                   10                  15

Thr Asn Val Asn Asn Arg Thr Asn Val Ser Asn Ile Ile Gly Asn Ile
                20                  25                  30

Thr Asp Glu Val Arg Asn Cys Ser Phe Asn Met Thr Thr Glu Leu Arg
            35                  40                  45

Asp Lys Lys Gln Lys Val His Ala Leu Phe Tyr Lys Leu Asp Ile Val
        50                  55                  60

Pro Ile Glu Asp Asn Asn Asp Ser Ser Glu Tyr Arg Leu Ile Asn Cys
65                  70                  75                  80

<210> SEQ ID NO 70
<211> LENGTH: 80
<212> TYPE: PRT
<213> ORGANISM: Human immunodeficiency virus 1

<400> SEQUENCE: 70

Ser Leu Lys Cys Thr Asp Leu Lys Asn Asp Thr Asn Thr Asn Ser Ser
1               5                   10                  15

Ser Gly Arg Met Ile Met Glu Lys Gly Glu Ile Lys Asn Cys Ser Phe
                20                  25                  30

Asn Ile Ser Thr Ser Ile Arg Gly Lys Val Gln Lys Glu Tyr Ala Phe
            35                  40                  45

Phe Tyr Lys Leu Asp Ile Ile Pro Ile Asp Asn Asp Thr Thr Ser Tyr
        50                  55                  60

Lys Leu Thr Ser Cys Asn Thr Ser Val Ile Thr Gln Ala Cys Pro Lys
65                  70                  75                  80

<210> SEQ ID NO 71
<211> LENGTH: 79
<212> TYPE: PRT
<213> ORGANISM: Human immunodeficiency virus 1

<400> SEQUENCE: 71

Thr Leu Asn Cys Thr Asn Ala Asn Leu Thr Asn Thr Asn Asn Thr Thr
1               5                   10                  15

Ser Asn Thr Ile Gly Asn Ile Thr Asp Glu Val Arg Asn Cys Ser Phe
                20                  25                  30

Asn Met Thr Thr Glu Leu Arg Asp Lys Lys Gln Lys Val His Ala Leu
            35                  40                  45

Phe Tyr Lys Leu Asp Ile Val Gln Ile Gly Asn Ser Ser Glu Tyr Arg
    50                  55                  60

Leu Ile Asn Cys Asn Thr Ser Val Ile Lys Gln Ala Cys Pro Lys
65                  70                  75

<210> SEQ ID NO 72
<211> LENGTH: 110
<212> TYPE: PRT
<213> ORGANISM: Human immunodeficiency virus 1

<400> SEQUENCE: 72

Thr Leu His Cys Thr Lys Ala Asn Ala Thr Val Arg Asn Ala Thr Ser
1               5                   10                  15

Asn Val Thr Thr Thr Val Ser Pro Val Leu Gly Asn Ile Thr Asp Asp
                20                  25                  30

Val Lys Asn Cys Thr Phe Asn Met Thr Thr Glu Leu Arg Asp Lys Glu
            35                  40                  45

Gln Gln Ala Tyr Ala Leu Phe Tyr Lys Leu Asp Ile Val Lys Ile Gly
    50                  55                  60

Asp Asn Lys Asn Asn Asn Ser Ser Ser Asn Asn Ser Glu Thr Ser
65                  70                  75                  80

Asn Arg Gln Asn Asn Thr Ser Ser Asp Asp Ser Gly Glu Tyr Met Leu
                85                  90                  95

Ile Asn Cys Asn Thr Ser Val Ile Lys Gln Ala Cys Pro Lys
            100                 105                 110

<210> SEQ ID NO 73
<211> LENGTH: 103
<212> TYPE: PRT
<213> ORGANISM: Human immunodeficiency virus 1

<400> SEQUENCE: 73

Thr Leu Asn Cys Thr Glu Ala Phe Lys Val Ala Asn Thr Thr Asn Val
1               5                   10                  15

Asn Ala Thr Ile Ala Pro Thr Thr Ser Ser Thr Val Thr Gly Ser
                20                  25                  30

Thr Arg Pro Thr Ala Thr Val Pro Asn Leu Leu Lys Asn Ile Thr Asp
            35                  40                  45

Glu Val Lys Asn Cys Thr Phe Asn Met Thr Thr Glu Leu Arg Asp Lys
    50                  55                  60

Lys Gln Gln Ala Tyr Ala Leu Phe Tyr Lys Leu Asp Leu Val Pro Ile
65                  70                  75                  80

Asn Lys Thr Leu Lys Thr Tyr Arg Leu Ile Asn Cys Asn Thr Ser Val
                85                  90                  95

Ile Lys Gln Ala Cys Pro Lys
            100

<210> SEQ ID NO 74
<211> LENGTH: 94
<212> TYPE: PRT
<213> ORGANISM: Human immunodeficiency virus 1

<400> SEQUENCE: 74

Thr Leu Asn Cys Thr Asn Thr Thr Val Lys Asn Phe Thr Lys Ser Ser
1               5                   10                  15

Gln Asp Glu Val Phe Asn Ile Glu Gly Asn Thr Thr Asp Glu Ile Lys

```
                   20                  25                  30

Asn Cys Ser Phe Asn Met Thr Thr Glu Leu Lys Asp Lys Gln Lys
            35                  40                  45

Ala Phe Ala Leu Phe Tyr Lys Leu Asp Ile Met Pro Ile Val Asn Asn
     50                  55                  60

Gly Glu Asn Lys Glu Asn Gly Asn Asn Lys His Glu Tyr Arg Leu
 65                  70                  75                  80

Ile Asn Cys Asn Thr Ser Val Ile Lys Gln Ala Cys Pro Lys
                85                  90
```

<210> SEQ ID NO 75
<211> LENGTH: 83
<212> TYPE: PRT
<213> ORGANISM: Human immunodeficiency virus 1

<400> SEQUENCE: 75

```
Thr Leu Gln Cys Arg Asn Asn Val Thr Leu Asn His Thr Thr Ile Asn
 1               5                  10                  15

Asn Asn Tyr Ser Asn Ile Val Gly Asn Ile Thr Asp Glu Ile Arg Asn
                20                  25                  30

Cys Ser Phe Asn Met Thr Thr Glu Leu Arg Asp Lys Arg Gln Thr Val
            35                  40                  45

Tyr Ala Leu Phe Tyr Lys Leu Asp Val Val Pro Ile Lys Asn Asn Ser
     50                  55                  60

Asp Glu Tyr Arg Leu Ile Asn Cys Asn Thr Ser Val Ile Lys Gln Ala
 65                  70                  75                  80

Cys Pro Lys
```

<210> SEQ ID NO 76
<211> LENGTH: 89
<212> TYPE: PRT
<213> ORGANISM: Human immunodeficiency virus 1

<400> SEQUENCE: 76

```
Thr Leu Asn Cys Thr Glu Ala Asn Phe Thr Lys Val Asn Asn Asp Thr
 1               5                  10                  15

Asp Thr Ile Lys Leu Gly Asn Ile Thr Asp Glu Val Lys Asn Cys Ser
                20                  25                  30

Phe Asn Met Thr Thr Glu Ile Ile Asp Lys Lys Gln Lys Phe Tyr Ala
            35                  40                  45

Leu Phe Tyr Lys Leu Asp Ile Ile Gln Ile Glu Asn Gly Asn Asp Asn
     50                  55                  60

Asn Ser Asn Ser Thr Ser Arg Glu Tyr Arg Leu Ile Asn Cys Asn Thr
 65                  70                  75                  80

Ser Ala Ile Lys Gln Ala Cys Pro Lys
                85
```

<210> SEQ ID NO 77
<211> LENGTH: 79
<212> TYPE: PRT
<213> ORGANISM: Human immunodeficiency virus 1

<400> SEQUENCE: 77

```
Thr Leu Asn Cys Thr Asn Val Asn Leu Val Asn Thr Thr His Gly Thr
 1               5                  10                  15

Asp Ser Ile Gly Asn Ile Thr Asp Glu Val Arg Asn Cys Ser Phe Asn
                20                  25                  30
```

```
Met Thr Thr Glu Ile Arg Asp Lys Lys Gln Lys Val His Ala Leu Phe
            35                  40                  45

Tyr Arg Leu Asp Ile Val Pro Ile Glu Asn Asn Ser Ser Glu Tyr Arg
 50                  55                  60

Leu Ile Asn Cys Asn Thr Ser Val Ile Lys Gln Ala Cys Pro Lys
 65                  70                  75

<210> SEQ ID NO 78
<211> LENGTH: 85
<212> TYPE: PRT
<213> ORGANISM: Human immunodeficiency virus 1

<400> SEQUENCE: 78

Thr Leu Asp Cys Thr Asn Asn Val Asn Ile Thr Thr Asn Gly Thr Lys
 1               5                  10                  15

Leu Ala Asn Asp Ser Asn Thr Ile Gly Asn Ile Thr Asp Glu Val Arg
             20                  25                  30

Asn Cys Thr Phe Asn Thr Thr Thr Glu Leu Arg Asp Lys Lys Gln Gln
             35                  40                  45

Val Tyr Ala Leu Phe Tyr Lys Leu Asp Ile Val Gln Ile Gly Asp Asn
 50                  55                  60

Asn Ser Ser Glu Tyr Arg Leu Ile Asn Cys Asn Thr Ser Val Ile Lys
 65                  70                  75                  80

Gln Ala Cys Pro Lys
             85

<210> SEQ ID NO 79
<211> LENGTH: 82
<212> TYPE: PRT
<213> ORGANISM: Human immunodeficiency virus 1

<400> SEQUENCE: 79

Thr Leu Asn Cys Thr Asn Ala Val Ala Lys Asn Ile Ile Ser Pro Asn
 1               5                  10                  15

Thr Asn Ser Val Gly Asn Val Thr Asp Glu Val Lys Asn Cys Thr Phe
             20                  25                  30

Asn Met Thr Thr Glu Val Gln Asp Lys Lys Gln Glu Val His Ala Leu
             35                  40                  45

Phe Tyr Glu Leu Asp Ile Val Gln Ile Thr Gly Ser Asp Ser Asn Thr
 50                  55                  60

Ser Tyr Arg Leu Ile Asn Cys Asn Thr Ser Val Ile Lys Gln Ala Cys
 65                  70                  75                  80

Pro Lys

<210> SEQ ID NO 80
<211> LENGTH: 85
<212> TYPE: PRT
<213> ORGANISM: Human immunodeficiency virus 1

<400> SEQUENCE: 80

Thr Leu Asn Cys Ser Asn Ala Thr Leu Lys Ser Asn Ile Thr Ser Asp
 1               5                  10                  15

Pro Asn Ile Gly Asn Met Thr Asp Glu Val Arg Asn Cys Ser Phe Asn
             20                  25                  30

Met Thr Thr Glu Leu Arg Asp Lys Lys His Gln Val Tyr Ala Leu Phe
             35                  40                  45

Tyr Lys Leu Asp Ile Val Pro Ile Lys Glu Asp Ser Asp Lys Ala Asn
 50                  55                  60
```

```
Asn Ser Glu Phe Tyr Arg Leu Ile Asn Cys Asn Thr Ser Val Ile Lys
 65                  70                  75                  80

Gln Ala Cys Pro Lys
                85
```

```
<210> SEQ ID NO 81
<211> LENGTH: 81
<212> TYPE: PRT
<213> ORGANISM: Human immunodeficiency virus 1

<400> SEQUENCE: 81
```

```
Thr Leu Asn Cys Thr Asn Ala Asn Leu Ser Thr Asn Ala Asn Arg Thr
  1               5                  10                  15

Asn Asp Pro Thr Ile Gly Asn Ile Thr Asp Glu Val Lys Asn Cys Thr
                20                  25                  30

Phe Asn Met Thr Thr Glu Leu Arg Asp Lys Gln Lys Val His Ala
             35                  40                  45

Leu Phe Tyr Arg Leu Asp Ile Val Gln Leu Asn Asn Ser Glu Glu
         50                  55                  60

Tyr Arg Leu Ile Asn Cys Asn Thr Ser Val Ile Lys Gln Ala Cys Pro
 65                  70                  75                  80

Lys
```

```
<210> SEQ ID NO 82
<211> LENGTH: 91
<212> TYPE: PRT
<213> ORGANISM: Human immunodeficiency virus 1

<400> SEQUENCE: 82
```

```
Thr Leu Asn Cys Thr Asn Ala Asn Leu Thr Asn Ala Arg Leu Thr Thr
  1               5                  10                  15

Asn Asn Thr Phe Pro Ser Phe Asn Ile Thr Gly Asn Ile Thr Glu Glu
                20                  25                  30

Val Arg Asn Cys Ser Phe Asn Met Thr Thr Glu Leu Arg Asp Lys Gln
             35                  40                  45

Gln Lys Val Tyr Ala Leu Phe Tyr Lys Leu Asp Ile Val Pro Ile Asp
         50                  55                  60

Arg Asp Lys Asn Asn Ser Ser Asn Ser Glu Tyr Arg Leu Ile Asn Cys
 65                  70                  75                  80

Asn Thr Ser Val Ile Lys Gln Ala Cys Pro Lys
                85                  90
```

```
<210> SEQ ID NO 83
<211> LENGTH: 81
<212> TYPE: PRT
<213> ORGANISM: Human immunodeficiency virus 1

<400> SEQUENCE: 83
```

```
Ile Leu Asn Cys Thr Asp Leu Thr Asn Gly Thr Lys Thr Ser Asn Gly
  1               5                  10                  15

Ser Glu Thr Lys Gly Asn Ile Lys Asp Glu Val Ser Asn Cys Thr Phe
                20                  25                  30

Ser Met Thr Thr Glu Leu Ala Asp Arg Lys Gln Lys Val Tyr Ala Leu
             35                  40                  45

Phe Tyr Lys Leu Asp Ile Val Pro Val Gly Lys Asp Ser Ser Asn Gly
         50                  55                  60

Tyr Arg Leu Ile Asn Cys Asn Thr Ser Val Ile Lys Gln Ala Cys Pro
```

```
            65                  70                  75                  80

Lys

<210> SEQ ID NO 84
<211> LENGTH: 89
<212> TYPE: PRT
<213> ORGANISM: Human immunodeficiency virus 1

<400> SEQUENCE: 84

Thr Leu Asn Cys Thr Glu Ala Lys Leu Ser Gln Thr Ala Asn Asn Gln
1               5                   10                  15

Thr Gly Asn Ile Thr Asp Gly Gly Asp Ile Gly Lys Ile Thr Glu Glu
            20                  25                  30

Val Lys Asn Cys Thr Phe Asn Met Thr Thr Glu Leu Arg Asp Lys Gln
        35                  40                  45

Gln Lys Val His Ala Leu Phe Tyr Arg Leu Asp Ile Val Gln Ile Asn
    50                  55                  60

Ser Asn Asp Asn Asn Ser Arg Glu Tyr Arg Leu Ile Asn Cys Asn Thr
65                  70                  75                  80

Ser Val Ile Lys Gln Ala Cys Pro Lys
                85

<210> SEQ ID NO 85
<211> LENGTH: 82
<212> TYPE: PRT
<213> ORGANISM: Human immunodeficiency virus 1

<400> SEQUENCE: 85

Thr Leu Asn Cys Ser Asn Ala Lys Leu Asn Gly Thr Thr Asp Asn Asp
1               5                   10                  15

Ser Glu Thr Ile Gly Asn Leu Thr Asp Glu Ile Arg Asn Cys Thr Phe
            20                  25                  30

Asn Val Ala Thr Glu Leu Arg Asp Arg Lys Lys Gln Val Tyr Ala Leu
        35                  40                  45

Phe Tyr Lys Leu Asp Ile Val Pro Ile Glu Asp Ala Asn Ser Ser Ser
    50                  55                  60

Val Tyr Arg Leu Ile Asn Cys Asn Thr Ser Val Ile Lys Gln Ala Cys
65                  70                  75                  80

Pro Lys

<210> SEQ ID NO 86
<211> LENGTH: 83
<212> TYPE: PRT
<213> ORGANISM: Human immunodeficiency virus 1

<400> SEQUENCE: 86

Thr Leu Ser Cys Ala Ser Val Asn Leu Thr Lys Val Asn Thr Met Thr
1               5                   10                  15

Asn Val Pro Asn Ile Gly Asn Ile Thr Asp Glu Val Lys Asn Cys Ser
            20                  25                  30

Phe Asn Met Thr Thr Glu Val Arg Asp Lys Lys Gln Lys Val His Ala
        35                  40                  45

Leu Phe Tyr Lys Leu Asp Ile Val Gln Ile Gly Asn Asn Asn Asn Ser
    50                  55                  60

Ser Glu Tyr Arg Leu Ile Asn Cys Asn Thr Ser Val Ile Lys Gln Ala
65                  70                  75                  80

Cys Pro Lys
```

<210> SEQ ID NO 87
<211> LENGTH: 83
<212> TYPE: PRT
<213> ORGANISM: Human immunodeficiency virus 1

<400> SEQUENCE: 87

Thr Leu Asn Cys Thr Asn Ala Asn Leu Thr Arg Ser Asn Ser Thr Thr
1               5                   10                  15

Val Gly Asp Ala Asn Ile Gly Asn Val Thr Asp Glu Val Arg Asn Cys
                20                  25                  30

Thr Phe Asn Val Thr Thr Glu Leu Lys Asp Lys Lys Gln Gln Val Tyr
            35                  40                  45

Ala Leu Phe Tyr Lys Pro Asp Ile Val Pro Ile Gly Asn Ser Asn Ser
        50                  55                  60

Ser Glu Tyr Arg Leu Ile Asn Cys Asn Thr Ser Val Ile Lys Gln Ala
65                  70                  75                  80

Cys Pro Lys

<210> SEQ ID NO 88
<211> LENGTH: 103
<212> TYPE: PRT
<213> ORGANISM: Human immunodeficiency virus 1

<400> SEQUENCE: 88

Thr Leu Asn Cys Ser Asn Ala Lys Leu Asn Thr Ser Asn Thr Asn Asn
1               5                   10                  15

Val Pro Asn Asn Ile Gly Asn Ile Thr Asp Glu Val Arg Asn Cys Thr
                20                  25                  30

Phe Asn Met Thr Thr Glu Leu Arg Asp Lys Lys Arg Lys Val His Ala
            35                  40                  45

Leu Phe Tyr Lys Leu Asp Ile Ile Gln Ile Lys Asn Asp Glu Ser Ser
        50                  55                  60

Asn Ser Asn Ile Thr Ser Asp Gly Ser Asn Ser Asn Ser Asn Gly
65                  70                  75                  80

Ser Thr Ser Ser Asp Tyr Tyr Arg Leu Ile Asn Cys Asn Thr Ser Val
                85                  90                  95

Ile Lys Gln Ala Cys Pro Lys
            100

<210> SEQ ID NO 89
<211> LENGTH: 81
<212> TYPE: PRT
<213> ORGANISM: Human immunodeficiency virus 1

<400> SEQUENCE: 89

Thr Leu Asn Cys Ser Asn Ala Thr Phe Ser Gly Asn Thr Thr Ser Ser
1               5                   10                  15

Asn Met Thr Thr Thr Val Gly Thr Ile Thr Asn Glu Val Lys Asn Cys
                20                  25                  30

Ser Phe Asn Ile Thr Thr Glu Ile Lys Asp Arg Lys Lys Lys Val His
            35                  40                  45

Ala Leu Phe Tyr Arg Leu Asp Ile Val Gln Leu Asp Asn Ser Ala Glu
        50                  55                  60

Tyr Arg Leu Ile Asn Cys Asn Thr Ser Val Ile Lys Gln Ala Cys Pro
65                  70                  75                  80

Lys

<210> SEQ ID NO 90
<211> LENGTH: 97
<212> TYPE: PRT
<213> ORGANISM: Human immunodeficiency virus 1

<400> SEQUENCE: 90

Thr Leu Asn Cys Thr Asn Ala Thr Val Thr Asn Pro Asn Asn Ala Thr
1               5                   10                  15

Thr Asp His Ser Thr Ile Gly Asn Ile Thr Asp Glu Val Arg Asn Cys
            20                  25                  30

Ser Phe Asn Met Thr Thr Val Ile Arg Asp Lys Gln Gln Ile His
        35                  40                  45

Ala Leu Phe Tyr Lys Leu Asp Ile Val Pro Ile Lys Asp Asn Asn Asn
    50                  55                  60

Asn Ser Asn Lys Ser Asn Ser Ser Asn Glu Ser Asp Ser Ser Met
65                  70                  75                  80

Tyr Arg Leu Ile Asn Cys Asn Thr Ser Val Ile Lys Gln Ala Cys Pro
                85                  90                  95

Lys

<210> SEQ ID NO 91
<211> LENGTH: 93
<212> TYPE: PRT
<213> ORGANISM: Human immunodeficiency virus 1

<400> SEQUENCE: 91

Thr Leu Asn Cys Thr Ser Ala Asn Leu Thr Thr Ser Ala Asn Leu Thr
1               5                   10                  15

Asn Val Asn Thr Thr Asn Asp Ile Asn Leu Gly Asn Met Thr Glu Glu
            20                  25                  30

Val Arg Asn Cys Ser Phe Ser Val Thr Thr Glu Leu Lys Asp Lys Lys
        35                  40                  45

Gln Lys Val His Ala Leu Phe Tyr Arg Leu Asp Ile Val Gln Met Glu
    50                  55                  60

Asn Ala Asn Asn Asn Gly Ser Thr Gly Tyr Asn Glu Tyr Arg Leu Ile
65                  70                  75                  80

Asn Cys Asn Thr Ser Val Ile Lys Gln Ala Cys Pro Lys
                85                  90

<210> SEQ ID NO 92
<211> LENGTH: 86
<212> TYPE: PRT
<213> ORGANISM: Human immunodeficiency virus 1

<400> SEQUENCE: 92

Thr Leu Asn Cys Ala Ile Ala Asn Leu Thr Asn Ala Asn Ala Asn Leu
1               5                   10                  15

Thr Asn Ile Asn Leu Asn Ile Thr Gly Asn Ile Thr Asp Glu Val Arg
            20                  25                  30

Asn Cys Thr Phe Asn Met Thr Thr Glu Ile Arg Asp Lys Lys Gln Lys
        35                  40                  45

Ala Tyr Ala Leu Phe Tyr Lys Leu Asp Leu Val Gln Leu Lys Asp Ser
    50                  55                  60

Asn Asp Ser Asn Arg Tyr Met Leu Ile Asn Cys Asn Thr Ser Val Ile
65                  70                  75                  80

Lys Gln Ala Cys Pro Lys

<210> SEQ ID NO 93
<211> LENGTH: 87
<212> TYPE: PRT
<213> ORGANISM: Human immunodeficiency virus 1

<400> SEQUENCE: 93

Thr Leu Lys Cys Thr Lys Ala Asn Phe Thr Thr Asn Thr Thr Asn Val
1               5                   10                  15

Asn Asn Thr Thr Asn Val Pro Lys Gly Ile Gly Asn Leu Thr Asp Glu
            20                  25                  30

Val Arg Asn Cys Thr Phe Asn Val Thr Thr Glu Ile Arg Asp Lys Lys
        35                  40                  45

Lys Asn Val Tyr Ala Leu Phe Tyr Lys Leu Asp Leu Val Gln Met Gly
    50                  55                  60

Asp Lys Asn Asp Ser Leu Tyr Arg Leu Ile Asn Cys Asn Thr Ser Val
65                  70                  75                  80

Ile Lys Gln Ala Cys Pro Lys
                85

<210> SEQ ID NO 94
<211> LENGTH: 81
<212> TYPE: PRT
<213> ORGANISM: Human immunodeficiency virus 1

<400> SEQUENCE: 94

Thr Leu Asn Cys Ser Ile Glu Thr Lys Trp Leu Asn Val Thr Asn Met
1               5                   10                  15

Ala Asn Ala Ser Asp Ile Ile Gly Asn Ile Thr Asp Glu Val Arg Asn
            20                  25                  30

Cys Ser Phe Asn Met Thr Thr Glu Leu Arg Asp Lys Lys Gln Lys Val
        35                  40                  45

Tyr Ala Leu Phe Tyr Lys Leu Asp Ile Val Pro Ile Glu Thr Gly Glu
    50                  55                  60

Tyr Arg Leu Ile Asn Cys Asn Thr Ser Val Ile Lys Gln Ala Cys Pro
65                  70                  75                  80

Lys

<210> SEQ ID NO 95
<211> LENGTH: 83
<212> TYPE: PRT
<213> ORGANISM: Human immunodeficiency virus 1

<400> SEQUENCE: 95

Thr Leu Asn Cys Thr Asn Ala Thr Val Thr Pro Thr Asn Ala Thr Val
1               5                   10                  15

Thr Pro Ile Asn Ala Ala Asp Glu Met Lys Asn Cys Ser Phe Asn Met
            20                  25                  30

Thr Thr Glu Leu Arg Asp Lys Lys Gln Lys Val His Ala Leu Phe Tyr
        35                  40                  45

Lys Leu Asp Ile Val Gln Met Gly Asn Glu Asn Ser Asn Tyr Ser Tyr
    50                  55                  60

Ser Glu Tyr Arg Leu Ile Asn Cys Asn Thr Ser Val Ile Lys Gln Ala
65                  70                  75                  80

Cys Pro Lys

```
<210> SEQ ID NO 96
<211> LENGTH: 82
<212> TYPE: PRT
<213> ORGANISM: Human immunodeficiency virus 1

<400> SEQUENCE: 96

Thr Leu Ile Cys Thr Asp Ala Asn Leu Thr Asn Ala Asn Pro Thr Lys
1               5                   10                  15

Glu Gly Val Asn Ile Gly Asn Ile Thr Asp Glu Val Lys Asn Cys Ser
            20                  25                  30

Tyr Asn Met Thr Thr Glu Ile Lys Asp Lys Lys Gln Lys Val His Ser
        35                  40                  45

Leu Phe Tyr Arg Leu Asp Ile Val Pro Ile Lys Asp Glu Asn Ser Ser
    50                  55                  60

Glu Tyr Arg Leu Ile Asn Cys Asn Thr Ser Val Ile Lys Gln Ala Cys
65                  70                  75                  80

Pro Lys

<210> SEQ ID NO 97
<211> LENGTH: 93
<212> TYPE: PRT
<213> ORGANISM: Human immunodeficiency virus 1

<400> SEQUENCE: 97

Thr Leu Asn Cys Ala Asn Ala Asn Phe Thr Ile Gly Asn Asn Thr Thr
1               5                   10                  15

Asn Asn Asn Thr Thr Asn Asp Pro Ser Thr Gly Thr Ile Gly Asn Ile
            20                  25                  30

Thr Asp Glu Val Lys Asn Cys Ser Phe Asn Ile Thr Thr Glu Ile Lys
        35                  40                  45

Asp Lys Lys Gln Lys Ile Tyr Ala Leu Phe Tyr Arg Leu Asp Ile Val
    50                  55                  60

Pro Ile Lys Glu Asn Asn Ser Thr Ser Gly Glu Tyr Arg Leu Ile
65                  70                  75                  80

Asn Cys Asn Thr Ser Val Ile Lys Gln Ala Cys Pro Lys
                85                  90

<210> SEQ ID NO 98
<211> LENGTH: 102
<212> TYPE: PRT
<213> ORGANISM: Human immunodeficiency virus 1

<400> SEQUENCE: 98

Thr Leu Asn Cys Thr Ala Ala Lys Phe Asn Asn Thr Asn Ala Gln Gly
1               5                   10                  15

Asn Asn Thr Ser Thr Gln Ser Asn Thr Thr Ala Asn Lys Thr Asp Glu
            20                  25                  30

Val Asn Ile Gly Asp Ile Thr Asp Glu Val Lys Asn Cys Ser Phe Asn
        35                  40                  45

Val Thr Thr Glu Leu Arg Asp Lys Gln Lys Gln Ile His Ala Leu Phe
    50                  55                  60

Tyr Met Leu Asp Ile Val Ser Ile Glu Glu Gly Asn Ser Ser Lys Asp
65                  70                  75                  80

Ser Asn Ser Ser Met Tyr Arg Leu Ile Asn Cys Asn Thr Ser Val Ile
                85                  90                  95

Lys Gln Ala Cys Pro Lys
            100
```

<210> SEQ ID NO 99
<211> LENGTH: 71
<212> TYPE: PRT
<213> ORGANISM: Human immunodeficiency virus 1

<400> SEQUENCE: 99

Thr Leu Asn Cys Ser Asn Lys Val Glu Leu Pro Asn Ile Thr Asp Glu
1               5                   10                  15

Ile Lys Asn Cys Thr Phe Asn Met Thr Thr Asp Leu Lys Asp Lys Lys
            20                  25                  30

Arg Lys Val His Ala Leu Phe Tyr Thr Leu Asp Ile Val Gln Ile Ser
        35                  40                  45

Asn Ser Asn Asn Asn Glu Tyr Arg Leu Val Ser Cys Asn Thr Ser Val
    50                  55                  60

Ile Lys Gln Ala Cys Pro Lys
65                  70

<210> SEQ ID NO 100
<211> LENGTH: 79
<212> TYPE: PRT
<213> ORGANISM: Human immunodeficiency virus 1

<400> SEQUENCE: 100

Thr Leu Asn Cys Thr Asn Ala Lys Trp Asn Glu Ser Thr Thr Thr Ile
1               5                   10                  15

Thr Pro Asp Asn Asn Thr Gln Glu Val Lys Asn Cys Ser Phe Lys
            20                  25                  30

Ile Thr Thr Glu Leu Arg Asp Lys Gln Gln Lys Val Tyr Ala Leu Phe
        35                  40                  45

Tyr Lys Leu Asp Ile Val Gln Met Glu Asn Ser Ser Asn Glu Tyr Arg
    50                  55                  60

Leu Ile Asn Cys Asn Thr Ser Val Ile Lys Gln Ala Cys Pro Lys
65                  70                  75

<210> SEQ ID NO 101
<211> LENGTH: 78
<212> TYPE: PRT
<213> ORGANISM: Human immunodeficiency virus 1

<400> SEQUENCE: 101

Thr Leu Asn Cys Val Asn Ala Asn Ile Thr Ser Lys Glu Lys Ile Ser
1               5                   10                  15

Gly Glu Asn Ile Thr Asp Glu Ile Arg Asn Cys Thr Phe Asn Met Thr
            20                  25                  30

Thr Glu Ile Arg Asp Lys Lys Gln Glu Thr Tyr Ala Leu Phe Tyr Lys
        35                  40                  45

Leu Asp Ile Val Pro Ile Lys Asn Asn Lys Ser Ser Glu Tyr Arg Leu
    50                  55                  60

Ile Asn Cys Asn Thr Ser Val Ile Lys Gln Ala Cys Pro Lys
65                  70                  75

<210> SEQ ID NO 102
<211> LENGTH: 88
<212> TYPE: PRT
<213> ORGANISM: Human immunodeficiency virus 1

<400> SEQUENCE: 102

Thr Leu Asn Cys Thr Thr Ala Lys Leu Asn Val Ser Thr Ser Ser
1               5                   10                  15

```
Thr Asn Asn Thr Leu Leu Asn Ala Asp Ile Gly Asn Val Thr Asp
                20                  25                  30

Glu Val Arg Asn Cys Thr Phe Asn Met Thr Thr Glu Ile Arg Asp Lys
            35                  40                  45

Gln His Lys Val His Ala Leu Phe Tyr Lys Leu Asp Ile Val Gln Met
        50                  55                  60

Gly Asn Asn Asn Ser Ser Glu Tyr Arg Leu Ile Asn Cys Asn Thr Ser
65                  70                  75                  80

Val Ile Lys Gln Ala Cys Pro Lys
                85

<210> SEQ ID NO 103
<211> LENGTH: 95
<212> TYPE: PRT
<213> ORGANISM: Human immunodeficiency virus 1

<400> SEQUENCE: 103

Thr Leu Asn Cys Asn Asn Lys Val Ile Val Asn Asn Lys Thr Asn
1               5                   10                  15

Tyr Thr Asp Lys Ile Gly Asn Ile Thr Ile Gly Asn Ile Thr Asp Glu
                20                  25                  30

Val Arg Asn Cys Ser Phe Asn Met Thr Thr Val Leu Arg Asp Gln Arg
            35                  40                  45

Gln Lys Val Tyr Ala Leu Phe Tyr Lys Leu Asp Ile Val Gln Ile Asn
        50                  55                  60

Ser Asp Ser Asn Asn Ser Asn Asn Ser Asp Asn Gly Met Tyr Arg
65                  70                  75                  80

Leu Ile Asn Cys Asn Thr Ser Val Ile Lys Gln Ala Cys Pro Lys
                85                  90                  95

<210> SEQ ID NO 104
<211> LENGTH: 86
<212> TYPE: PRT
<213> ORGANISM: Human immunodeficiency virus 1

<400> SEQUENCE: 104

Thr Leu Asn Cys Thr Asn Ala Asn Leu Thr Asn Gly Asn Thr Thr Thr
1               5                   10                  15

Thr Asn Pro Thr Asn Val Pro Lys Thr Val Gly Asn Leu Thr Asp Asp
                20                  25                  30

Ile Arg Asn Cys Thr Phe Asn Met Thr Thr Glu Leu Lys Asp Lys Lys
            35                  40                  45

Gln Lys Val His Ala Leu Phe Tyr Lys Leu Asp Ile Val Gln Met Gly
        50                  55                  60

Asp Asn Ser Ser Glu Tyr Arg Leu Ile Asn Cys Asn Thr Ser Val Ile
65                  70                  75                  80

Lys Gln Ala Cys Pro Lys
                85

<210> SEQ ID NO 105
<211> LENGTH: 82
<212> TYPE: PRT
<213> ORGANISM: Human immunodeficiency virus 1

<400> SEQUENCE: 105

Thr Leu Asn Cys Thr Gln Ala Asn Leu Lys Ser Asn Ala Thr Glu Asn
1               5                   10                  15
```

Thr Thr Ala Thr Val Glu Ser Leu Lys Glu Val Arg Asn Cys Ser
            20                  25                  30

Phe Asn Met Thr Thr Glu Leu Arg Asp Lys Lys Gln Lys Val His Ala
            35                  40                  45

Leu Phe Tyr Arg Leu Asp Leu Val Gln Met Gly Asn Asp Asn Ser Thr
            50                  55                  60

Glu Tyr Arg Leu Ile Asn Cys Asn Thr Ser Val Ile Lys Gln Ala Cys
65                  70                  75                  80

Pro Lys

<210> SEQ ID NO 106
<211> LENGTH: 85
<212> TYPE: PRT
<213> ORGANISM: Human immunodeficiency virus 1

<400> SEQUENCE: 106

Thr Leu Asn Cys Thr Thr Ala Lys Leu Asn Ser Thr Ser Thr Thr Asn
1               5                   10                  15

Val Ser Asn Ile Val Gly Asn Leu Thr Asp Glu Val Arg Asn Cys Ser
            20                  25                  30

Phe Asn Met Thr Thr Glu Leu Arg Asp Lys Lys Gln Lys Phe Tyr Ala
            35                  40                  45

Leu Phe Tyr Lys Leu Asp Ile Val Ser Ile Glu Asp Asp Arg Asn Asn
            50                  55                  60

Ser Asp Asn Arg Tyr Arg Leu Ile Asn Cys Asn Thr Ser Val Ile Lys
65                  70                  75                  80

Gln Ala Cys Pro Lys
                85

<210> SEQ ID NO 107
<211> LENGTH: 91
<212> TYPE: PRT
<213> ORGANISM: Human immunodeficiency virus 1

<400> SEQUENCE: 107

Thr Leu Asn Cys Thr Asn Val Asn Ile Thr His Thr Ser Ser Asn Val
1               5                   10                  15

Thr Thr Arg Pro Pro Ile Thr Gln Leu Asn Thr Ser Tyr Asp Gln Asp
            20                  25                  30

Ser Met Asn Cys Thr Phe Asn Met Thr Thr Glu Ile Lys Asp Lys Lys
            35                  40                  45

Thr Lys Val Asn Ala Leu Phe Tyr Lys Leu Asp Ile Val Gln Met Glu
            50                  55                  60

Asn Glu Asn Asn Asn Ser Tyr Asn Ser Tyr Arg Leu Ile Asn Cys
65                  70                  75                  80

Asn Thr Ser Val Ile Lys Gln Ala Cys Pro Lys
                85                  90

<210> SEQ ID NO 108
<211> LENGTH: 87
<212> TYPE: PRT
<213> ORGANISM: Human immunodeficiency virus 1

<400> SEQUENCE: 108

Thr Leu Ser Cys Thr Asn Ala Ile Val Asn Tyr Val Thr Asn Thr Thr
1               5                   10                  15

Asn Val Pro Asn Ile Ile Gly Asn Ile Thr Asp Glu Met Lys Asn Cys
            20                  25                  30

Ser Phe Asn Met Thr Thr Glu Leu Lys Asp Lys Lys Gln Lys Val His
        35                  40                  45

Ala Leu Phe Tyr Glu Leu Asp Ile Val Gln Ile Gly Lys Asn Glu Asn
 50                  55                  60

Asn Ser Ala Tyr Asn Thr Tyr Arg Leu Ile Asn Cys Asn Thr Ser Val
 65                  70                  75                  80

Ile Lys Gln Ala Cys Pro Lys
                85

<210> SEQ ID NO 109
<211> LENGTH: 73
<212> TYPE: PRT
<213> ORGANISM: Human immunodeficiency virus 1

<400> SEQUENCE: 109

Thr Leu Asn Cys Thr Lys Ile Ser Thr Asn Asn Tyr Thr Ala Asp Glu
 1               5                  10                  15

Val Arg Asn Cys Ser Phe Asn Met Thr Thr Val Ile Arg Asp Lys Lys
                20                  25                  30

Gln Gln Val His Ala Leu Phe Tyr Lys Leu Asp Ile Val Pro Ile Asn
        35                  40                  45

Ser Ser Asp His Asn Asn Thr Glu Tyr Arg Leu Ile Asn Cys Asn Thr
 50                  55                  60

Ser Val Ile Lys Gln Ala Cys Pro Lys
 65                  70

<210> SEQ ID NO 110
<211> LENGTH: 81
<212> TYPE: PRT
<213> ORGANISM: Human immunodeficiency virus 1

<400> SEQUENCE: 110

Thr Leu Asn Cys Thr Asn Ala Asn Pro Thr Asn Val Thr Tyr Thr Asn
 1               5                  10                  15

Val Thr Ala Ala Ile Gly Asn Ile Thr Asp Glu Ile Arg Asn Cys Ser
                20                  25                  30

Phe Asn Met Thr Thr Glu Leu Lys Asp Arg Lys Gln Lys Val Tyr Ala
        35                  40                  45

Leu Phe Tyr Lys Pro Asp Ile Val Pro Leu Asn Asp Asn Ser Ser Glu
 50                  55                  60

Tyr Arg Leu Ile Asn Cys Asn Thr Ser Ile Ile Lys Gln Ala Cys Pro
 65                  70                  75                  80

Lys

<210> SEQ ID NO 111
<211> LENGTH: 90
<212> TYPE: PRT
<213> ORGANISM: Human immunodeficiency virus 1

<400> SEQUENCE: 111

Thr Leu Asn Cys Thr His Thr Val Thr Val Lys Asn Ile Thr Asn Trp
 1               5                  10                  15

Asn Asn Met Asn Asn Ile Thr Glu Glu Val Asn Ile Gly Asn Ile Thr
                20                  25                  30

Asn Glu Val Lys Asn Cys Ser Phe Ile Met Thr Thr Glu Leu Arg Asp
        35                  40                  45

Lys Lys Gln Lys Ala Tyr Ala Leu Phe Tyr Met Leu Asp Ile Val Pro

```
                50                  55                  60

Ile Gly Gln Asn Asn Ser Gln Asp Glu Tyr Arg Leu Ile Asn Cys Asn
 65                  70                  75                  80

Thr Ser Val Ile Lys Gln Ala Cys Pro Lys
                 85                  90

<210> SEQ ID NO 112
<211> LENGTH: 79
<212> TYPE: PRT
<213> ORGANISM: Human immunodeficiency virus 1

<400> SEQUENCE: 112

Thr Leu Asp Cys Thr Lys Thr Asn Trp Glu Val Gly Asn Val Thr Asp
  1               5                  10                  15

Gly Ile Gly Asn Ile Thr Asp Glu Val Arg Asn Cys Thr Phe Asn Met
                 20                  25                  30

Thr Thr Glu Ile Arg Asp Lys Lys Gln Lys Val Gln Ala Leu Phe Tyr
             35                  40                  45

Arg Leu Asp Ile Val Pro Ile Lys Asn Glu Ser Tyr Lys Glu Tyr Arg
         50                  55                  60

Leu Ile Asn Cys Asn Thr Ser Val Ile Lys Gln Ala Cys Pro Lys
 65                  70                  75

<210> SEQ ID NO 113
<211> LENGTH: 93
<212> TYPE: PRT
<213> ORGANISM: Human immunodeficiency virus 1

<400> SEQUENCE: 113

Thr Leu Asn Cys Ser Thr Ala Lys Leu Ile Asn Ala Thr Met Ser Asn
  1               5                  10                  15

Asp Thr Asn Ile Arg Asn Ser Asp Ile Gly Asn Ile Thr Asp Glu Ile
                 20                  25                  30

Arg Asn Cys Thr Phe Asn Met Thr Thr Glu Ile Arg Asp Lys Gln His
             35                  40                  45

Lys Val His Ala Leu Phe Tyr Lys Leu Asp Ile Val Glu Ile Gly Ser
         50                  55                  60

Asn Asn Asn Asn Asn Ser Tyr Lys Asp Tyr Lys Asp Tyr Arg Leu Ile
 65                  70                  75                  80

Asn Cys Asn Thr Ser Val Ile Lys Gln Ala Cys Pro Lys
                 85                  90

<210> SEQ ID NO 114
<211> LENGTH: 90
<212> TYPE: PRT
<213> ORGANISM: Human immunodeficiency virus 1

<400> SEQUENCE: 114

Thr Leu Asn Cys Thr Asn Ala Asn Leu Thr Asn Val Asn Ile Asn Ala
  1               5                  10                  15

Thr Leu Ala Asn Arg Ala Lys Asp Leu Lys Asn Val Thr Glu Asp Ile
                 20                  25                  30

Arg Asn Cys Thr Phe Asn Met Thr Thr Glu Val Thr Asp Lys Lys Gln
             35                  40                  45

Lys Val His Ala Leu Phe Tyr Lys Leu Asp Ile Val Pro Met Gly Asn
         50                  55                  60

Ser Ser Asn Ser Ser Glu Tyr Asn Glu Tyr Arg Leu Ile Asn Cys Asn
 65                  70                  75                  80
```

Thr Ser Val Ile Lys Gln Ala Cys Pro Lys
            85                  90

<210> SEQ ID NO 115
<211> LENGTH: 89
<212> TYPE: PRT
<213> ORGANISM: Human immunodeficiency virus 1

<400> SEQUENCE: 115

Thr Leu Asn Cys Thr Asn Ala Asn Phe Thr Lys Asp Gln Gly Thr Thr
1               5                   10                  15

Gly Thr Asn Ile Thr Thr Pro Thr Val Pro Ala Glu Val Gly Asn Leu
            20                  25                  30

Thr Asp Glu Ile Arg Asn Cys Ser Phe Asn Met Thr Thr Glu Leu Lys
        35                  40                  45

Asp Lys Lys Gln Lys Val Tyr Ala Leu Phe Tyr Lys Leu Asp Val Val
    50                  55                  60

Gln Ile Asn Asn Ser Ser Glu Tyr Arg Ile Ile Asn Cys Asn Thr
65                  70                  75                  80

Ser Val Ile Lys Gln Ala Cys Pro Lys
            85

<210> SEQ ID NO 116
<211> LENGTH: 87
<212> TYPE: PRT
<213> ORGANISM: Human immunodeficiency virus 1

<400> SEQUENCE: 116

Thr Leu Asn Cys Ile Asn Ala Asn Phe Thr Gly Asn Asn Thr Thr Lys
1               5                   10                  15

Val Asn Ile Thr Pro Ile Tyr Asn Thr Thr Glu Asp Leu Thr Gly Glu
            20                  25                  30

Ile Arg Asn Cys Ser Phe Asn Ile Thr Thr Glu Ile Ile Asp Lys Lys
        35                  40                  45

Lys Gln Val Tyr Ala Leu Phe Tyr Lys Leu Asp Thr Val Gln Ile Gly
    50                  55                  60

Asp Glu Asn Ser Thr Met Tyr Arg Leu Ile Asn Cys Asn Thr Ser Val
65                  70                  75                  80

Ile Lys Gln Ala Cys Pro Lys
            85

<210> SEQ ID NO 117
<211> LENGTH: 82
<212> TYPE: PRT
<213> ORGANISM: Human immunodeficiency virus 1

<400> SEQUENCE: 117

Thr Leu Asn Cys Thr Ile Ala Thr Leu Thr Lys Ala Asn Glu Thr Lys
1               5                   10                  15

Val Asn Val Thr Val Ser Ile Gly Asn Leu Thr Asp Glu Val Arg
            20                  25                  30

Asn Cys Ser Phe Asn Val Thr Thr Glu Leu Lys Asp Lys Lys Lys Asn
        35                  40                  45

Val His Ala Leu Phe Tyr Lys Leu Asp Leu Val Gln Met Glu Asn Ser
    50                  55                  60

Lys Tyr Arg Leu Ile Asn Cys Asn Thr Ser Val Ile Lys Gln Ala Cys
65                  70                  75                  80

Pro Lys

<210> SEQ ID NO 118
<211> LENGTH: 85
<212> TYPE: PRT
<213> ORGANISM: Human immunodeficiency virus 1

<400> SEQUENCE: 118

Thr Leu Asn Cys Thr Lys Ala Thr Phe Lys Ser Asn Tyr Thr Thr Lys
1               5                   10                  15

Val Pro Asn Thr Val Gly Asn Leu Thr Asp Glu Val Lys Asn Cys Thr
            20                  25                  30

Phe Asn Met Thr Thr Glu Ile Arg Asp Lys Lys Gln Arg Val His Ala
        35                  40                  45

Leu Phe Tyr Lys Leu Asp Ile Val Pro Leu Ser Asp Asn Ser Asn Ser
    50                  55                  60

Ser Asn Thr Glu Tyr Arg Leu Ile Asn Cys Asn Thr Ser Val Ile Lys
65                  70                  75                  80

Gln Ala Cys Pro Lys
                85

<210> SEQ ID NO 119
<211> LENGTH: 100
<212> TYPE: PRT
<213> ORGANISM: Human immunodeficiency virus 1

<400> SEQUENCE: 119

Thr Leu Asn Cys Gly His Asn Val Thr Val Thr Asp Ser Ile Ser Pro
1               5                   10                  15

Ala Asn Gly Ser Thr Ile Ile Gly Asn Arg Thr Glu Asp Val His Gly
            20                  25                  30

Ile Ser Pro Ala Asn Gly Ser Thr Ile Ile Gly Asn Ile Thr Glu Asp
        35                  40                  45

Val Arg Asn Cys Ser Phe Asn Met Thr Thr Glu Leu Lys Asp Arg Lys
    50                  55                  60

Lys Gln Val Tyr Ala Leu Phe Tyr Lys Leu Asp Thr Val Gln Val Ser
65                  70                  75                  80

Asn Glu Thr Tyr Arg Leu Ile Asn Cys Asn Thr Ser Val Ile Lys Gln
                85                  90                  95

Ala Cys Pro Lys
            100

<210> SEQ ID NO 120
<211> LENGTH: 100
<212> TYPE: PRT
<213> ORGANISM: Human immunodeficiency virus 1

<400> SEQUENCE: 120

Thr Leu Asn Cys Thr Asp Ser Ile His Ile Thr Asn Lys Ile Tyr Ile
1               5                   10                  15

Lys Glu Asn Asn Thr Ile Gly Asn Met Thr Asp Glu Val Arg Asn Cys
            20                  25                  30

Thr Phe Asn Val Thr Thr Glu Ile Arg Asp Lys Met Lys Lys Val His
        35                  40                  45

Ala Leu Phe Tyr Lys Leu Asp Ile Val Gln Ile Asn Asn Ser Asp Ser
    50                  55                  60

Asn Ser Thr Val Ser Ile Asn Asn Ser Ser Asn Ser Asn Ser Glu
65                  70                  75                  80

```
Tyr Lys Thr Tyr Arg Leu Ile Asn Cys Asn Thr Ser Ala Ile Lys Gln
                85                  90                  95

Ala Cys Pro Lys
            100

<210> SEQ ID NO 121
<211> LENGTH: 100
<212> TYPE: PRT
<213> ORGANISM: Human immunodeficiency virus 1

<400> SEQUENCE: 121

Thr Leu Lys Cys Ser Asn Ala Thr Phe Gly Asn Thr Lys Thr Ser Ala
1               5                   10                  15

Asn Ser Ser Glu Ile Gly Asp Leu Lys Asp Glu Val Lys Asn Cys Ser
                20                  25                  30

Phe Asn Ile Thr Thr Glu Leu Arg Asp Lys Lys Gln Gln Val Tyr Ala
                35                  40                  45

Leu Phe Tyr Lys Leu Asp Ile Val Pro Ile Asp Asn Asn Asp Lys Asn
            50                  55                  60

Ser Ser Ser Ser Asn Asn Ser Asn Arg Asn Asn Ser Ser Ser Glu Tyr
65                  70                  75                  80

Gly Ser Glu Tyr Arg Leu Ile Asn Cys Asn Thr Ser Val Ile Lys Gln
                85                  90                  95

Ala Cys Pro Lys
            100

<210> SEQ ID NO 122
<211> LENGTH: 85
<212> TYPE: PRT
<213> ORGANISM: Human immunodeficiency virus 1

<400> SEQUENCE: 122

Thr Leu Asn Cys Ser Asn Ala Asn Leu Thr Asn Ile Asn Asn Thr Ile
1               5                   10                  15

Thr Asp Lys Ile Gly Asn Leu Thr Ile Gly Asn Ile Thr Asp Asp Ile
                20                  25                  30

Lys Asn Cys Ser Phe Asn Met Thr Thr Glu Leu Arg Asp Lys Lys Lys
                35                  40                  45

Lys Ala Tyr Ala Leu Phe Tyr Lys Leu Asp Ile Val Ser Ile Glu Lys
            50                  55                  60

Asn Thr Ser Glu Tyr Arg Leu Ile Asn Cys Asn Ser Ser Val Ile Lys
65                  70                  75                  80

Gln Ala Cys Pro Lys
            85

<210> SEQ ID NO 123
<211> LENGTH: 80
<212> TYPE: PRT
<213> ORGANISM: Human immunodeficiency virus 1

<400> SEQUENCE: 123

Val Trp Lys Asp Ala Asp Thr Thr Leu Phe Cys Ala Ser Asp Ala Lys
1               5                   10                  15

Ala His Glu Thr Glu Val His Asn Val Trp Ala Thr His Ala Cys Val
                20                  25                  30

Pro Thr Asp Pro Asn Pro Gln Glu Ile His Leu Glu Asn Val Thr Glu
                35                  40                  45
```

```
Asn Phe Asn Met Trp Lys Asn Asn Met Val Glu Gln Met Gln Glu Asp
 50                  55                  60

Val Ile Ser Leu Trp Asp Gln Ser Leu Gln Pro Cys Val Lys Leu Thr
 65                  70                  75                  80

<210> SEQ ID NO 124
<211> LENGTH: 80
<212> TYPE: PRT
<213> ORGANISM: Human immunodeficiency virus 1

<400> SEQUENCE: 124

Val Trp Lys Asp Ala Asp Thr Thr Leu Phe Cys Ala Ser Asp Ala Lys
 1               5                  10                  15

Ala His Glu Thr Glu Val His Asn Val Trp Ala Thr His Ala Cys Val
                 20                  25                  30

Pro Thr Asp Pro Asn Pro Gln Glu Ile His Leu Glu Asn Val Thr Glu
             35                  40                  45

Asn Phe Asn Met Trp Lys Asn Asn Met Val Glu Gln Met Gln Glu Asp
 50                  55                  60

Val Ile Ser Leu Trp Asp Gln Ser Leu Gln Pro Cys Val Lys Leu Thr
 65                  70                  75                  80

<210> SEQ ID NO 125
<211> LENGTH: 80
<212> TYPE: PRT
<213> ORGANISM: Human immunodeficiency virus 1

<400> SEQUENCE: 125

Val Trp Lys Asp Ala Asp Thr Thr Leu Phe Cys Ala Ser Asp Ala Lys
 1               5                  10                  15

Ala His Glu Thr Glu Val His Asn Val Trp Ala Thr His Ala Cys Val
                 20                  25                  30

Pro Thr Asp Pro Asn Pro Gln Glu Ile His Leu Glu Asn Val Thr Glu
             35                  40                  45

Asn Phe Asn Met Trp Lys Asn Asn Met Val Glu Gln Met Gln Glu Asp
 50                  55                  60

Val Ile Ser Leu Trp Asp Gln Ser Leu Gln Pro Cys Val Lys Leu Thr
 65                  70                  75                  80

<210> SEQ ID NO 126
<211> LENGTH: 80
<212> TYPE: PRT
<213> ORGANISM: Human immunodeficiency virus 1

<400> SEQUENCE: 126

Val Trp Lys Glu Ala Thr Thr Thr Leu Phe Cys Ala Ser Asp Ala Lys
 1               5                  10                  15

Ala Tyr Asp Thr Glu Val His Asn Val Trp Ala Thr His Ala Cys Val
                 20                  25                  30

Pro Thr Asp Pro Asn Pro Gln Glu Val Val Leu Gly Asn Val Thr Glu
             35                  40                  45

Asn Phe Asn Met Trp Lys Asn Asn Met Val Asp Gln Met His Glu Asp
 50                  55                  60

Ile Ile Ser Leu Trp Asp Glu Ser Leu Lys Pro Cys Val Lys Leu Thr
 65                  70                  75                  80

<210> SEQ ID NO 127
<211> LENGTH: 58
<212> TYPE: PRT
```

<213> ORGANISM: Human immunodeficiency virus 1

<400> SEQUENCE: 127

Ser Val Ile Lys Gln Ala Cys Pro Lys Ile Ser Phe Asp Pro Ile Pro
1               5                   10                  15

Ile His Tyr Cys Thr Pro Ala Gly Tyr Val Ile Leu Lys Cys Asn Asp
            20                  25                  30

Lys Asn Phe Asn Gly Thr Gly Pro Cys Lys Asn Val Ser Ser Val Gln
        35                  40                  45

Cys Thr His Gly Ile Lys Pro Val Val Ser
    50                  55

<210> SEQ ID NO 128
<211> LENGTH: 58
<212> TYPE: PRT
<213> ORGANISM: Human immunodeficiency virus 1

<400> SEQUENCE: 128

Ser Val Ile Lys Gln Ala Cys Pro Lys Ile Ser Phe Asp Pro Ile Pro
1               5                   10                  15

Ile His Tyr Cys Thr Pro Ala Gly Tyr Val Ile Leu Lys Cys Asn Asp
            20                  25                  30

Lys Asn Phe Asn Gly Thr Gly Pro Cys Lys Asn Val Ser Ser Val Gln
        35                  40                  45

Cys Thr His Gly Ile Lys Pro Val Val Ser
    50                  55

<210> SEQ ID NO 129
<211> LENGTH: 58
<212> TYPE: PRT
<213> ORGANISM: Human immunodeficiency virus 1

<400> SEQUENCE: 129

Ser Val Ile Lys Gln Ala Cys Pro Lys Ile Ser Phe Asp Pro Ile Pro
1               5                   10                  15

Ile His Tyr Cys Thr Pro Ala Gly Tyr Val Ile Leu Lys Cys Asn Asp
            20                  25                  30

Lys Asn Phe Asn Gly Thr Gly Pro Cys Lys Asn Val Ser Ser Val Gln
        35                  40                  45

Cys Thr His Gly Ile Lys Pro Val Val Ser
    50                  55

<210> SEQ ID NO 130
<211> LENGTH: 58
<212> TYPE: PRT
<213> ORGANISM: Human immunodeficiency virus 1

<400> SEQUENCE: 130

Ser Val Ile Thr Gln Ala Cys Pro Lys Val Ser Phe Gln Pro Ile Pro
1               5                   10                  15

Ile His Tyr Cys Val Pro Ala Gly Phe Ala Met Leu Lys Cys Asn Asn
            20                  25                  30

Lys Thr Phe Asn Gly Ser Gly Pro Cys Thr Asn Val Ser Thr Val Gln
        35                  40                  45

Cys Thr His Gly Ile Arg Pro Val Val Ser
    50                  55

<210> SEQ ID NO 131
<211> LENGTH: 20

```
<212> TYPE: PRT
<213> ORGANISM: Human immunodeficiency virus 1

<400> SEQUENCE: 131

Gly Asn Ile Lys Asp Asn Trp Arg Ser Glu Leu Tyr Lys Tyr Lys Val
1               5                   10                  15

Val Gln Ile Glu
            20

<210> SEQ ID NO 132
<211> LENGTH: 20
<212> TYPE: PRT
<213> ORGANISM: Human immunodeficiency virus 1

<400> SEQUENCE: 132

Gly Asn Ile Lys Asp Asn Trp Arg Ser Glu Leu Tyr Lys Tyr Lys Val
1               5                   10                  15

Val Gln Ile Glu
            20

<210> SEQ ID NO 133
<211> LENGTH: 20
<212> TYPE: PRT
<213> ORGANISM: Human immunodeficiency virus 1

<400> SEQUENCE: 133

Gly Asn Ile Lys Asp Asn Trp Arg Ser Glu Leu Tyr Lys Tyr Lys Val
1               5                   10                  15

Val Gln Ile Glu
            20

<210> SEQ ID NO 134
<211> LENGTH: 20
<212> TYPE: PRT
<213> ORGANISM: Human immunodeficiency virus 1

<400> SEQUENCE: 134

Gly Asp Met Arg Asp Asn Trp Arg Ser Glu Leu Tyr Lys Tyr Lys Val
1               5                   10                  15

Val Lys Ile Glu
            20

<210> SEQ ID NO 135
<211> LENGTH: 504
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 135

Met Arg Val Lys Gly Ile Arg Lys Asn Tyr Gln His Leu Trp Arg Trp
1               5                   10                  15

Gly Thr Met Leu Leu Gly Met Leu Met Ile Cys Ser Ala Ala Glu Gln
                20                  25                  30

Leu Trp Val Thr Val Tyr Tyr Gly Val Pro Val Trp Lys Glu Ala Thr
            35                  40                  45

Thr Thr Leu Phe Cys Ala Ser Asp Ala Lys Ala Tyr Asp Thr Glu Val
        50                  55                  60

His Asn Val Trp Ala Thr His Ala Cys Val Pro Thr Asp Pro Asn Pro
65                  70                  75                  80
```

```
Gln Glu Val Val Leu Glu Asn Val Thr Glu Asn Phe Asn Met Trp Lys
             85                  90                  95

Asn Asn Met Val Glu Gln Met His Glu Asp Ile Ile Ser Leu Trp Asp
            100                 105                 110

Gln Ser Leu Lys Pro Cys Val Lys Leu Thr Pro Leu Cys Val Thr Leu
            115                 120                 125

Asn Cys Thr Asp Val Ser Ser Asn Ser Thr Ser Val Asn Ile Thr Ser
            130                 135                 140

Glu Lys Gly Glu Ile Lys Asn Cys Ser Phe Asn Ile Thr Thr Ser Ile
145                 150                 155                 160

Arg Asp Lys Val Gln Lys Glu Tyr Ala Leu Phe Tyr Lys Leu Asp Val
            165                 170                 175

Val Pro Ile Glu Asp Asp Ser Arg Asn Asn Ser Tyr Arg Leu Ile Ser
            180                 185                 190

Cys Asn Thr Ser Val Ile Thr Gln Ala Cys Pro Lys Val Ser Phe Glu
            195                 200                 205

Pro Ile Pro Ile His Tyr Cys Ala Pro Ala Gly Phe Ala Ile Leu Lys
            210                 215                 220

Cys Asn Asp Lys Lys Phe Asn Gly Thr Gly Pro Cys Thr Asn Val Ser
225                 230                 235                 240

Thr Val Gln Cys Thr His Gly Ile Arg Pro Val Val Ser Thr Gln Leu
            245                 250                 255

Leu Leu Asn Gly Ser Leu Ala Glu Glu Val Val Ile Arg Ser Glu
            260                 265                 270

Asn Phe Thr Asn Asn Ala Lys Thr Ile Ile Val Gln Leu Asn Glu Ser
            275                 280                 285

Val Glu Ile Asn Cys Thr Arg Pro Asn Asn Asn Thr Arg Lys Ser Ile
290                 295                 300

His Ile Gly Pro Gly Arg Ala Phe Tyr Ala Thr Gly Asp Ile Ile Gly
305                 310                 315                 320

Asp Ile Arg Gln Ala His Cys Asn Ile Ser Arg Glu Lys Trp Asn Asn
            325                 330                 335

Thr Leu Lys Gln Ile Val Lys Lys Leu Arg Glu Gln Phe Gly Asn Lys
            340                 345                 350

Thr Ile Val Phe Asn Gln Ser Ser Gly Gly Asp Pro Glu Ile Val Met
            355                 360                 365

His Ser Phe Asn Cys Gly Gly Glu Phe Phe Tyr Cys Asn Thr Thr Gln
            370                 375                 380

Leu Phe Asn Ser Thr Trp Ser Ile Asn Gly Thr Trp Asn Gly Thr Thr
385                 390                 395                 400

Glu Ser Asn Asp Thr Ile Thr Leu Pro Cys Arg Ile Lys Gln Ile Ile
            405                 410                 415

Asn Met Trp Gln Glu Val Gly Lys Ala Met Tyr Ala Pro Pro Ile Arg
            420                 425                 430

Gly Gln Ile Arg Cys Ser Ser Asn Ile Thr Gly Leu Leu Leu Thr Arg
            435                 440                 445

Asp Gly Gly Asn Ser Ser Asn Asn Glu Thr Phe Arg Pro Gly Gly
            450                 455                 460

Gly Asp Met Arg Asp Asn Trp Arg Ser Glu Leu Tyr Lys Tyr Lys Val
465                 470                 475                 480

Val Lys Ile Glu Pro Leu Gly Val Ala Pro Thr Lys Ala Lys Arg Arg
            485                 490                 495

Val Val Gln Arg Glu Lys Arg Val
```

-continued

```
                500

<210> SEQ ID NO 136
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Thr Asp Val Ser Ser Asn Ser Thr Ser Val Asn Ile Thr Ser Glu
1               5                   10                  15

<210> SEQ ID NO 137
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Glu Asp Asp Ser Arg Asn Asn Ser
1               5

<210> SEQ ID NO 138
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Ser Ile Asn Gly Thr Trp Asn Gly Thr Thr Glu Ser
1               5                   10

<210> SEQ ID NO 139
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139

Asn Ser Ser Ser Asn Asn
1               5

<210> SEQ ID NO 140
<211> LENGTH: 502
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 140

Met Lys Val Lys Gly Ile Arg Lys Asn Cys Gln His Leu Trp Arg Trp
1               5                   10                  15

Gly Ile Met Leu Leu Gly Met Leu Met Ile Cys Ser Ala Thr Glu Lys
                20                  25                  30

Leu Trp Val Thr Val Tyr Tyr Gly Val Pro Val Trp Lys Glu Ala Thr
            35                  40                  45

Thr Thr Leu Phe Cys Ala Ser Asp Ala Lys Ala Tyr Asp Thr Glu Ala
```

-continued

```
                50                  55                  60
His Asn Val Trp Ala Thr His Ala Cys Val Pro Thr Asp Pro Asn Pro
 65                  70                  75                  80

Gln Glu Ile Val Leu Glu Asn Val Thr Glu Asn Phe Asn Met Trp Lys
                 85                  90                  95

Asn Asp Met Val Glu Gln Met His Glu Asp Ile Ile Ser Leu Trp Asp
                100                 105                 110

Glu Ser Leu Lys Pro Cys Val Glu Leu Thr Pro Leu Cys Val Thr Leu
                115                 120                 125

Asn Cys Thr Asn Val Asn Ala Thr Asn Thr Asn Asn Ser Ser Gly Ile
            130                 135                 140

Glu Gly Gly Glu Met Lys Asn Cys Ser Phe Asn Val Thr Thr Ser Ile
145                 150                 155                 160

Arg Asp Lys Met Gln Lys Glu Tyr Ala Leu Phe Tyr Ser Leu Asp Val
                165                 170                 175

Val Gln Ile Asp Asn Asp Thr Asn Tyr Arg Leu Ile Asn Cys Asn Thr
                180                 185                 190

Ser Val Ile Thr Gln Ala Cys Pro Lys Ile Ser Phe Glu Pro Ile Pro
            195                 200                 205

Ile His Tyr Cys Thr Pro Ala Gly Phe Ala Ile Ile Lys Cys Asn Asp
210                 215                 220

Lys Lys Phe Asn Gly Ser Gly Pro Cys Lys Asn Val Ser Thr Val Gln
225                 230                 235                 240

Cys Thr His Gly Ile Lys Pro Val Val Ser Thr Gln Leu Leu Leu Asn
                245                 250                 255

Gly Ser Leu Ala Glu Glu Ile Val Ile Arg Ser Glu Asn Phe Ser
            260                 265                 270

Asp Asn Ala Lys Thr Ile Ile Val Gln Leu Asn Glu Ser Val Val Ile
            275                 280                 285

Asn Cys Thr Arg Pro Asn Asn Asn Thr Arg Lys Ser Ile Ser Ile Gly
            290                 295                 300

Pro Gly Arg Ala Phe Tyr Ala Thr Gly Asp Ile Ile Gly Asn Ile Arg
305                 310                 315                 320

Gln Ala His Cys Asn Leu Ser Arg Ala Glu Trp Asn Asn Thr Leu Arg
                325                 330                 335

Gln Ile Val Thr Lys Leu Arg Glu Gln Phe Lys Asn Lys Thr Ile Ala
            340                 345                 350

Phe Asn His Ser Ser Gly Gly Asp Pro Glu Ile Val Met His Thr Phe
            355                 360                 365

Asn Cys Gly Gly Glu Phe Phe Tyr Cys Asn Ser Thr Gln Leu Phe Asn
370                 375                 380

Ser Thr Trp Ile Ala Asn Lys Thr Gly Asn Asp Thr Gly Gly Ser Asn
385                 390                 395                 400

Gly Thr Ile Thr Leu Gln Cys Arg Ile Lys Gln Ile Val Asn Arg Trp
                405                 410                 415

Gln Glu Val Gly Lys Ala Met Tyr Ala Pro Pro Ile Ser Gly Gln Ile
                420                 425                 430

Ser Cys Ser Ser Asn Ile Thr Gly Leu Ile Leu Thr Arg Asp Gly Gly
            435                 440                 445

Thr Asn Asn Thr Asn Gly Thr Glu Ile Phe Arg Pro Gly Gly Gly Asn
            450                 455                 460

Met Lys Asp Asn Trp Arg Ser Glu Leu Tyr Lys Tyr Lys Val Val Arg
465                 470                 475                 480
```

```
Ile Glu Pro Leu Gly Ile Ala Pro Thr Lys Ala Arg Arg Val Val
                485                 490                 495

Gln Arg Glu Lys Arg Ile
            500

<210> SEQ ID NO 141
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

Thr Asn Val Asn Ala Thr Asn Thr Asn Asn Ser Ser Gly Ile Glu
1               5                   10                  15

<210> SEQ ID NO 142
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Asp Asn Asp Thr Asn
1               5

<210> SEQ ID NO 143
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

Ile Ala Asn Lys Thr Gly Asn Asp Thr Gly Gly Ser
1               5                   10

<210> SEQ ID NO 144
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Thr Asn Asn Thr Asn Gly Thr
1               5

<210> SEQ ID NO 145
<211> LENGTH: 35
<212> TYPE: PRT
<213> ORGANISM: Human immunodeficiency virus 1

<400> SEQUENCE: 145

Cys Thr Arg Pro Ser Asn Asn Thr Arg Lys Ser Ile His Ile Gly Pro
1               5                   10                  15

Gly Arg Ala Phe Tyr Thr Thr Gly Glu Ile Ile Gly Asp Ile Arg Gln
            20                  25                  30

Ala His Cys
        35
```

<210> SEQ ID NO 146
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

Gly Arg Cys Arg
1

<210> SEQ ID NO 147
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

Gly Pro Gly Arg Ala Phe
1               5

<210> SEQ ID NO 148
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Gly Pro Gly Arg
1

<210> SEQ ID NO 149
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

Gly Pro Gly Arg Ala Phe His Thr Thr Gly Arg Ile Ile
1               5                   10

<210> SEQ ID NO 150
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

Gly Pro Gly Arg Ala Phe Tyr Thr
1               5

<210> SEQ ID NO 151
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 151

Gly Pro Gly Arg Ala Phe Val Thr
1               5

<210> SEQ ID NO 152
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Gly Pro Gly Arg Ala Phe Val Thr
1               5

<210> SEQ ID NO 153
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 153

Gly Pro Gly Arg Val Leu Tyr Thr
1               5

<210> SEQ ID NO 154
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 154

Gly Pro Gly Arg Ala Phe Val Thr
1               5

<210> SEQ ID NO 155
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 155

Gly Pro Gly Arg Ala Phe Val Thr Ile Gly Lys Ile
1               5                   10

<210> SEQ ID NO 156
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 156

Gly Pro Gly Arg Ala Phe Val Thr
1               5

<210> SEQ ID NO 157
<211> LENGTH: 33
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 157

Thr Arg Pro Asn Asn Asn Thr Arg Lys Ser Ile His Ile Gly Pro Gly
1               5                   10                  15

Arg Ala Phe Tyr Ala Thr Gly Asp Ile Ile Gly Asp Ile Arg Gln Ala
            20                  25                  30

His

<210> SEQ ID NO 158
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 158

Thr Arg Pro Asn Asn Asn Thr Arg Lys Ser Ile His Ile Gly Pro Gly
1               5                   10                  15

Arg Ala Phe Tyr Ala Thr Gly Asp Ile Ile Gly Asp Ile Arg Gln Ala
            20                  25                  30

His

<210> SEQ ID NO 159
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 159

Thr Arg Pro Asn Asn Asn Thr Arg Lys Ser Ile Ser Ile Gly Pro Gly
1               5                   10                  15

Arg Ala Phe Tyr Ala Thr Gly Asp Ile Ile Gly Asn Ile Arg Gln Ala
            20                  25                  30

His

<210> SEQ ID NO 160
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 160

Thr Arg Pro Asn Asn Asn Thr Arg Lys Ser Ile Ser Ile Gly Pro Gly
1               5                   10                  15

Arg Ala Phe Tyr Ala Thr Gly Asp Ile Ile Gly Asn Ile Arg Gln Ala
            20                  25                  30

His

<210> SEQ ID NO 161
<211> LENGTH: 33
<212> TYPE: PRT
<213> ORGANISM: Artificial Sequence
<220> FEATURE:
```

<223> OTHER INFORMATION: Description of Artificial Sequence: Synthetic
      polypeptide

<400> SEQUENCE: 161

Thr Arg Pro Asn Asn Asn Thr Arg Arg Ser Val His Met Gly Pro Gly
1               5                   10                  15

Ser Ala Phe Tyr Thr Thr Gly Gly Ile Ile Gly Asp Ile Arg Gln Ala
            20                  25                  30

His

<210> SEQ ID NO 162
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 162

Thr Arg Pro Asn Asn Asn Thr Arg Lys Ser Ile His Met Gly Trp Gly
1               5                   10                  15

Arg Ala Phe Tyr Ala Thr Gly Asp Ile Ile Gly Asp Ile Arg Gln Ala
            20                  25                  30

His

<210> SEQ ID NO 163
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 163

Thr Arg Pro Ser Asn Asn Thr Arg Thr Ser Ile Thr Ile Gly Pro Gly
1               5                   10                  15

Gln Val Phe Tyr Arg Thr Gly Asp Ile Ile Gly Asp Ile Arg Lys Ala
            20                  25                  30

Tyr

<210> SEQ ID NO 164
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 164

Thr Arg Pro Ser Asn Asn Val Arg Ile Ser Thr Arg Ile Gly Pro Gly
1               5                   10                  15

Gln Val Phe Tyr Arg Thr Gly Glu Ile Ile Gly Asp Ile Arg Lys Ala
            20                  25                  30

Tyr

<210> SEQ ID NO 165
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

```
<400> SEQUENCE: 165

Thr Arg Pro Asn Asn Asn Thr Arg Lys Ser Ile Arg Ile Gly Pro Gly
1               5                   10                  15

Gln Thr Phe Tyr Ala Thr Gly Asp Ile Ile Gly Asp Ile Arg Gln Ala
            20                  25                  30

His

<210> SEQ ID NO 166
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 166

Thr Arg Pro Gly Asn Asn Thr Arg Lys Ser Val Arg Ile Gly Pro Gly
1               5                   10                  15

Gln Ala Phe Tyr Ala Thr Gly Glu Ile Ile Gly Asp Ile Arg Gln Ala
            20                  25                  30

Tyr

<210> SEQ ID NO 167
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 167

Thr Arg Pro Asn Asn Asn Thr Arg Lys Ser Ile His Ile Gly Pro Gly
1               5                   10                  15

Lys Ala Trp Tyr Thr Thr Gly Glu Ile Ile Gly Asn Ile Arg Gln Ala
            20                  25                  30

His

<210> SEQ ID NO 168
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 168

Thr Arg Pro Asn Asn Asn Thr Arg Lys Ser Ile His Ile Gly Pro Gly
1               5                   10                  15

Arg Ala Phe Tyr Thr Thr Gly Glu Ile Ile Gly Asp Ile Arg Gln Ala
            20                  25                  30

His

<210> SEQ ID NO 169
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 169

Thr Arg Pro Asn Asn Asn Thr Arg Lys Gly Ile Thr Ile Gly Pro Gly
```

```
                1               5                  10                 15
Ser Val Phe Tyr Thr Gly Glu Ile Ile Gly Asp Ile Arg Gln Ala His
                20                 25                 30
```

<210> SEQ ID NO 170
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (12)..(12)
<223> OTHER INFORMATION: His, Ser, Thr or Arg

<400> SEQUENCE: 170

```
Thr Arg Pro Asn Asn Asn Thr Arg Lys Ser Ile Xaa Ile Gly Pro Gly
1               5                  10                 15

Arg Ala Phe Tyr Ala Thr Gly Asp Ile Ile Gly Asp Ile Arg Gln Ala
                20                 25                 30

His
```

<210> SEQ ID NO 171
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 171

```
Thr Arg Pro Asn Asn Asn Thr Arg Lys Ser Ile Arg Ile Gly Pro Gly
1               5                  10                 15

Gln Thr Phe Tyr Ala Thr Gly Asp Ile Ile Gly Asn Ile Arg Gln Ala
                20                 25                 30

His
```

<210> SEQ ID NO 172
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 172

```
Thr Arg Pro Asn Asn Asn Thr Arg Lys Ser Ile Arg Ile Gly Pro Gly
1               5                  10                 15

Gln Thr Phe Tyr Ala Thr Gly Asp Ile Ile Gly Asp Ile Arg Gln Ala
                20                 25                 30

His
```

<210> SEQ ID NO 173
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 173

```
Thr Arg Pro Asn Asn Asn Thr Arg Lys Gly Ile His Ile Gly Leu Gly
1               5                  10                 15
```

Arg Ala Leu Tyr Ala Thr Gly Asp Ile Ile Gly Asp Ile Arg Gln Ala
            20                  25                  30

His

<210> SEQ ID NO 174
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 174

Thr Arg Pro Asn Asn Asn Thr Arg Lys Ser Ile Arg Ile Gly Pro Gly
1               5                   10                  15

Gln Thr Phe Tyr Ala Thr Gly Glu Ile Ile Gly Asn Ile Arg Gln Ala
            20                  25                  30

His

<210> SEQ ID NO 175
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 175

Thr Arg Pro Asn Asn Asn Thr Arg Lys Ser Ile His Ile Gly Pro Gly
1               5                   10                  15

Arg Ala Phe Tyr Ala Thr Gly Glu Thr Ile Gly Asn Ile Arg Gln Ala
            20                  25                  30

His

<210> SEQ ID NO 176
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 176

Thr Arg Pro Asn Asn Asn Thr Arg Lys Ser Met Ile Gly Pro Gly Gln
1               5                   10                  15

Thr Phe Tyr Ala Thr Gly Glu Thr Ile Gly Asp Ile Arg Arg Ala His
            20                  25                  30

<210> SEQ ID NO 177
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 177

Thr Arg Pro Gly Asn Asn Thr Arg Lys Ser Ile His Ile Ala Pro Gly
1               5                   10                  15

Arg Thr Phe Tyr Ala Thr Gly Glu His Gly Asp Ile Arg Arg Ala His
            20                  25                  30

```
<210> SEQ ID NO 178
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (12)..(12)
<223> OTHER INFORMATION: His, Arg or absent

<400> SEQUENCE: 178

Thr Arg Pro Asn Asn Asn Thr Arg Lys Ser Ile Xaa Ile Gly Pro Gly
1               5                   10                  15

Gln Thr Phe Tyr Ala Thr Gly Glu Ile Ile Gly Asp Ile Arg Gln Ala
            20                  25                  30

His

<210> SEQ ID NO 179
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 179

Gly Pro Gly Gln
1

<210> SEQ ID NO 180
<211> LENGTH: 9
<212> TYPE: PRT
<213> ORGANISM: Human immunodeficiency virus 1

<400> SEQUENCE: 180

Arg Arg Val Val Glu Arg Glu Lys Arg
1               5

<210> SEQ ID NO 181
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 181

Glu Arg Val Val Glu Arg Glu Lys Glu
1               5

<210> SEQ ID NO 182
<211> LENGTH: 4
<212> TYPE: PRT
<213> ORGANISM: Human immunodeficiency virus 1

<400> SEQUENCE: 182

Arg Glu Lys Arg
1

<210> SEQ ID NO 183
<211> LENGTH: 4
<212> TYPE: PRT
<213> ORGANISM: Artificial Sequence
<220> FEATURE:
<223> OTHER INFORMATION: Description of Artificial Sequence: Synthetic
```

-continued peptide

<400> SEQUENCE: 183

Ser Glu Lys Ser
1

<210> SEQ ID NO 184
<211> LENGTH: 24
<212> TYPE: PRT
<213> ORGANISM: Homo sapiens

<400> SEQUENCE: 184

Met Pro Met Gly Ser Leu Gln Pro Leu Ala Thr Leu Tyr Leu Leu Gly
1               5                   10                  15

Met Leu Val Ala Ser Val Leu Ala
            20

<210> SEQ ID NO 185
<211> LENGTH: 868
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 185

Met Lys Ala Lys Glu Thr Arg Lys Asn Tyr Gln His Leu Trp Arg Trp
1               5                   10                  15

Gly Ile Thr Leu Leu Gly Met Leu Met Ile Cys Ser Ala Ala Glu Gln
            20                  25                  30

Leu Trp Val Thr Val Tyr Tyr Gly Val Pro Val Trp Lys Glu Ala Thr
        35                  40                  45

Thr Thr Leu Phe Cys Ala Ser Asp Ala Lys Ala Tyr Asp Thr Glu Val
    50                  55                  60

His Asn Val Trp Ala Thr His Ala Cys Val Pro Thr Asp Pro Asn Pro
65                  70                  75                  80

Gln Glu Val Val Leu Glu Asn Val Thr Glu Asn Phe Asn Met Trp Lys
                85                  90                  95

Asn Asn Met Val Glu Gln Met His Glu Asp Ile Ile Ser Leu Trp Asp
            100                 105                 110

Gln Ser Leu Lys Pro Cys Val Lys Leu Thr Pro Leu Cys Val Thr Leu
        115                 120                 125

Asn Cys Thr Asp Asp Leu Lys Asn Ala Thr Val Lys Asn Ala Thr Asn
    130                 135                 140

Thr Asn Asn Ser Ser Trp Gly Gly Met Glu Arg Gly Glu Ile Lys Asn
145                 150                 155                 160

Cys Ser Phe Asn Ile Thr Thr Ser Ile Arg Asp Lys Val Gln Lys Glu
                165                 170                 175

Tyr Ala Leu Phe Tyr Lys Leu Asp Val Val Pro Ile Asp Asn Ala Asp
            180                 185                 190

Asn Asn Asn Ile Thr Thr Asn Tyr Thr Ser Tyr Arg Leu Ile Ser Cys
        195                 200                 205

Asn Thr Ser Val Ile Thr Gln Ala Cys Pro Lys Val Ser Phe Glu Pro
    210                 215                 220

Ile Pro Ile His Tyr Cys Ala Pro Ala Gly Phe Ala Ile Leu Lys Cys
225                 230                 235                 240

Asn Asp Lys Lys Phe Asn Gly Thr Gly Pro Cys Thr Asn Val Ser Thr
                245                 250                 255

```
Val Gln Cys Thr His Gly Ile Arg Pro Val Ser Thr Gln Leu Leu
            260                 265                 270

Leu Asn Gly Ser Leu Ala Glu Lys Glu Val Val Ile Arg Ser Glu Asn
        275                 280                 285

Phe Thr Asn Asn Ala Lys Thr Ile Ile Val Gln Leu Asp Glu Ser Val
    290                 295                 300

Val Ile Asn Cys Thr Arg Pro Asn Asn Asn Thr Arg Lys Ser Ile His
305                 310                 315                 320

Ile Gly Pro Gly Arg Ala Phe Tyr Thr Thr Gly Glu Ile Ile Gly Asp
                325                 330                 335

Ile Arg Gln Ala His Cys Thr Leu Asn Arg Thr Glu Trp Asn Asn Thr
            340                 345                 350

Leu Ala Lys Ile Thr Glu Lys Leu Arg Glu Gln Phe Gly Asn Asn Ile
        355                 360                 365

Thr Ile Val Phe Asn His Ser Ser Gly Gly Asp Pro Glu Ile Val Met
    370                 375                 380

His Ser Phe Ile Cys Gly Gly Glu Phe Phe Tyr Cys Asn Thr Ser Gln
385                 390                 395                 400

Leu Phe Asn Ser Thr Trp Asn Ser Thr Gly Asn Asn Ile Ser Glu Ser
                405                 410                 415

Asp Asn Thr Glu Arg Asn Ile Thr Leu Pro Cys Arg Ile Lys Gln Ile
            420                 425                 430

Ile Asn Leu Trp Gln Glu Val Gly Lys Ala Met Tyr Ala Pro Pro Ile
        435                 440                 445

Arg Gly Gln Ile Arg Cys Ser Ser Asn Ile Thr Gly Leu Leu Leu Thr
    450                 455                 460

Arg Asp Gly Gly Ser Asn Thr Asp Glu Asn Arg Thr Glu Ile Phe Arg
465                 470                 475                 480

Pro Gly Gly Gly Asp Met Arg Asp Asn Trp Arg Ser Glu Leu Tyr Lys
                485                 490                 495

Tyr Lys Val Val Lys Ile Glu Pro Leu Gly Val Ala Pro Thr Lys Ala
            500                 505                 510

Lys Arg Arg Val Val Gln Arg Glu Lys Arg Ala Val Gly Thr Ile Gly
        515                 520                 525

Ala Met Phe Leu Gly Phe Leu Gly Ala Ala Gly Ser Thr Met Gly Ala
    530                 535                 540

Ala Ser Met Thr Leu Thr Val Gln Ala Arg Leu Leu Leu Ser Gly Ile
545                 550                 555                 560

Val Gln Gln Gln Asn Asn Leu Leu Arg Ala Ile Glu Ala Gln Gln His
                565                 570                 575

Leu Leu Gln Leu Thr Val Trp Gly Ile Lys Gln Leu Gln Ala Arg Val
            580                 585                 590

Leu Ala Val Glu Arg Tyr Leu Lys Asp Gln Gln Leu Leu Gly Ile Trp
        595                 600                 605

Gly Cys Ser Gly Lys Leu Ile Cys Thr Thr Ala Val Pro Trp Asn Ala
    610                 615                 620

Ser Trp Ser Asn Lys Ser Leu Asp Glu Ile Trp Asp Asn Met Thr Trp
625                 630                 635                 640

Met Glu Trp Glu Arg Glu Ile Asp Asn Tyr Thr Asn Leu Ile Tyr Thr
                645                 650                 655

Leu Ile Glu Glu Tyr Arg Asn Gln Gln Glu Lys Asn Glu Gln Ala Leu
            660                 665                 670
```

```
Leu Glu Leu Asp Lys Trp Ala Ser Leu Trp Asn Trp Phe Asn Ile Thr
            675                 680                 685

Asn Trp Leu Trp Tyr Ile Lys Ile Phe Ile Met Ile Val Gly Gly Leu
        690                 695                 700

Val Gly Leu Arg Ile Val Phe Thr Val Leu Ser Ile Val Asn Arg Val
705                 710                 715                 720

Arg Lys Gly Tyr Ser Pro Leu Ser Phe Gln Thr Arg Leu Pro Thr Pro
                725                 730                 735

Arg Gly Pro Asp Arg Pro Glu Gly Ile Glu Glu Glu Gly Gly Glu Arg
            740                 745                 750

Asp Arg Asp Arg Ser Gly Leu Leu Val Asp Gly Phe Leu Ala Leu Ile
            755                 760                 765

Trp Val Asp Leu Arg Ser Leu Cys Leu Phe Ser Tyr His Arg Leu Arg
770                 775                 780

Asp Leu Leu Leu Ile Val Ala Arg Ile Val Glu Leu Leu Gly Arg Arg
785                 790                 795                 800

Gly Trp Glu Val Leu Lys Tyr Trp Trp Asn Leu Leu Gln Tyr Trp Ser
                805                 810                 815

Gln Glu Leu Lys Asn Ser Ala Val Ser Leu Leu Asn Ala Thr Ala Ile
            820                 825                 830

Ala Val Ala Glu Gly Thr Asp Arg Val Ile Glu Val Leu Gln Arg Ala
            835                 840                 845

Cys Arg Ala Ile Leu His Ile Pro Thr Arg Ile Arg Gln Gly Leu Glu
        850                 855                 860

Arg Ala Leu Leu
865

<210> SEQ ID NO 186
<211> LENGTH: 856
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 186

Met Arg Val Lys Glu Thr Arg Arg Ile Trp Gln His Leu Trp Lys Trp
1               5                   10                  15

Gly Thr Met Leu Leu Gly Met Leu Met Ile Tyr Ser Ala Ala Glu Asn
            20                  25                  30

Leu Trp Val Thr Val Tyr Tyr Gly Val Pro Val Trp Lys Glu Ala Thr
        35                  40                  45

Thr Thr Leu Phe Cys Ala Ser Asp Ala Lys Ala Tyr Asp Thr Glu Val
    50                  55                  60

His Asn Val Trp Ala Thr His Ala Cys Val Pro Thr Asp Pro Asn Pro
65                  70                  75                  80

Gln Glu Val Val Leu Gly Asn Val Thr Glu Asn Phe Asn Met Trp Lys
                85                  90                  95

Asn Asn Met Val Glu Gln Met His Glu Asp Val Ile Ser Leu Trp Asp
            100                 105                 110

Gln Ser Leu Lys Pro Cys Val Lys Leu Thr Pro Leu Cys Val Thr Leu
        115                 120                 125

Asn Cys Thr Asp Val Leu Gly Lys Gly Thr Ser Ala Asn Ala Thr Ser
    130                 135                 140

Ala Asn Val Thr Ser Glu Lys Gly Glu Ile Lys Asn Cys Ser Phe Asn
145                 150                 155                 160
```

```
Ile Thr Thr Thr Leu Arg Asp Lys Val Gln Lys Ala His Ala Leu Phe
            165                 170                 175

Tyr Arg Leu Asp Val Val Pro Ile Asp Asn Asn Asp Asn Ser Ser
            180                 185                 190

Ser Ser Tyr Arg Leu Ile Asn Cys Asn Thr Ser Val Ile Thr Gln Ala
            195                 200                 205

Cys Pro Lys Val Ser Phe Glu Pro Ile Pro Ile His Phe Cys Thr Pro
210                 215                 220

Ala Gly Phe Ala Leu Leu Lys Cys Asn Asn Lys Lys Phe Asn Gly Thr
225                 230                 235                 240

Gly Pro Cys Thr Asn Val Ser Thr Val Gln Cys Thr His Gly Ile Lys
            245                 250                 255

Pro Val Val Ser Thr Gln Leu Leu Asn Gly Ser Leu Ala Glu Glu
            260                 265                 270

Glu Val Val Ile Arg Ser Glu Asn Phe Thr Asp Asn Ala Lys Thr Ile
            275                 280                 285

Ile Val Gln Leu Asn Asp Ser Val Val Ile Asn Cys Thr Arg Pro Asn
            290                 295                 300

Asn Asn Thr Arg Lys Gly Ile Thr Ile Gly Pro Gly Ser Val Phe Tyr
305                 310                 315                 320

Thr Gly Glu Ile Ile Gly Asp Ile Arg Gln Ala His Cys Asn Leu Ser
            325                 330                 335

Ser Ala Lys Trp Asn Asn Thr Leu Lys Gln Ile Val Ile Lys Leu Arg
            340                 345                 350

Glu Gln Phe Gly Asn Lys Thr Ile Val Phe Asn Gln Ser Ser Gly Gly
            355                 360                 365

Asp Pro Glu Ile Val Leu His Ser Phe Asn Cys Gly Gly Glu Phe Phe
            370                 375                 380

Tyr Cys Asn Thr Thr Gln Leu Phe Asn Ser Thr Trp Asn Ile Asn Asp
385                 390                 395                 400

Thr Arg Asn Gly Thr Thr Glu Ser Ser Lys Thr Ile Thr Leu Pro Cys
            405                 410                 415

Arg Ile Lys Gln Ile Ile Asn Met Trp Gln Glu Val Gly Lys Ala Met
            420                 425                 430

Tyr Ala Pro Pro Ile Arg Gly Gln Ile Arg Cys Ser Ser Asn Ile Thr
            435                 440                 445

Gly Leu Leu Leu Thr Arg Asp Gly Gly Asn Gln Asn Thr Ser Gly Thr
450                 455                 460

Glu Ile Phe Arg Pro Gly Gly Gly Asn Met Arg Asp Asn Trp Arg Ser
465                 470                 475                 480

Glu Leu Tyr Lys Tyr Lys Val Val Lys Ile Glu Pro Leu Gly Ile Ala
            485                 490                 495

Pro Thr Lys Ala Lys Arg Arg Val Val Gln Arg Glu Lys Arg Ala Val
            500                 505                 510

Gly Thr Ile Gly Ala Met Phe Leu Gly Phe Leu Gly Ala Ala Gly Ser
            515                 520                 525

Thr Met Gly Ala Ala Ser Ile Thr Leu Thr Val Gln Ala Arg Leu Leu
            530                 535                 540

Leu Ser Gly Ile Val Gln Gln Asn Asn Leu Met Arg Ala Ile Glu
545                 550                 555                 560

Ala Gln Gln His Met Leu Gln Leu Thr Val Trp Gly Ile Lys Gln Leu
            565                 570                 575
```

-continued

```
Gln Ala Arg Val Leu Ala Val Glu Arg Tyr Leu Arg Asp Gln Gln Leu
            580                 585                 590

Leu Gly Ile Trp Gly Cys Ser Gly Lys Leu Ile Cys Thr Thr Thr Val
        595                 600                 605

Pro Trp Asn Ala Ser Trp Ser Asn Lys Ser Val Asp Tyr Ile Trp Asp
    610                 615                 620

Asn Met Thr Trp Met Gln Trp Asp Arg Glu Ile Asn Asn Tyr Thr Asn
625                 630                 635                 640

Tyr Ile Tyr Thr Leu Leu Glu Asp Ala Gln Asn Gln Gln Glu Lys Asn
                645                 650                 655

Glu Gln Glu Leu Leu Glu Leu Asp Lys Trp Ala Ser Leu Trp Asn Trp
            660                 665                 670

Phe Asp Ile Thr Lys Trp Leu Trp Tyr Ile Lys Ile Phe Ile Met Ile
        675                 680                 685

Val Gly Gly Leu Ile Gly Leu Arg Ile Val Phe Ala Val Leu Ser Ile
    690                 695                 700

Val Asn Arg Val Lys Gln Gly Tyr Ser Pro Leu Ser Phe Gln Thr His
705                 710                 715                 720

Leu Pro Ala Arg Arg Glu Pro Asp Arg Pro Glu Gly Ile Glu Gly Glu
                725                 730                 735

Gly Gly Glu Lys Asp Lys Asp Arg Ser Ile Arg Leu Val His Gly Leu
            740                 745                 750

Leu Ala Leu Ile Trp Asp Asp Leu Arg Ser Leu Cys Leu Phe Ser Tyr
        755                 760                 765

His His Leu Arg Asp Leu Leu Leu Ile Val Thr Arg Ile Val Glu Thr
    770                 775                 780

Leu Gly Arg Arg Gly Trp Glu Ala Leu Lys Tyr Trp Trp Asn Leu Leu
785                 790                 795                 800

Gln Tyr Trp Ser Gln Glu Leu Lys Asn Ser Ala Val Ser Leu Phe Asp
                805                 810                 815

Ala Ile Ala Ile Ala Val Ala Glu Gly Thr Asp Arg Val Ile Glu Val
            820                 825                 830

Val Arg Arg Ile Phe Arg Ala Val Leu His Ile Pro Thr Arg Ile Arg
        835                 840                 845

Gln Gly Leu Glu Arg Ala Leu Leu
    850                 855

<210> SEQ ID NO 187
<211> LENGTH: 865
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 187

Met Arg Val Lys Gly Ile Arg Lys Asn Cys Gln His Leu Trp Arg Trp
1               5                   10                  15

Gly Thr Met Leu Leu Gly Met Leu Met Ile Cys Ser Ala Ala Glu Asn
            20                  25                  30

Leu Trp Val Thr Val Tyr Tyr Gly Val Pro Val Trp Lys Glu Ala Thr
        35                  40                  45

Thr Thr Leu Phe Cys Ala Ser Asp Ala Lys Ala Tyr Asp Thr Glu Ala
    50                  55                  60

His Asn Val Trp Ala Thr His Ala Cys Val Pro Thr Asp Pro Asn Pro
65                  70                  75                  80
```

-continued

```
Gln Glu Val Val Leu Gly Asn Val Thr Glu Asn Phe Asn Met Trp Lys
                85                  90                  95

Asn Asp Met Val Glu Gln Met His Glu Asp Ile Ile Ser Leu Trp Asp
            100                 105                 110

Gln Ser Leu Lys Pro Cys Val Lys Leu Thr Pro Ile Cys Val Ala Leu
        115                 120                 125

Asn Cys Thr Asp Val Lys Asp Thr Asn Asn Thr Ser Asn Asn Thr Asn
    130                 135                 140

Asn Thr Ser Ser Asn Asn Ser Ser Met Thr Glu Gly Glu Met Lys
145                 150                 155                 160

Asn Cys Ser Phe Asn Ile Thr Thr Ser Ile Lys Thr Lys Val Lys Asp
                165                 170                 175

Tyr Ala Leu Phe Tyr Lys Leu Asp Ile Val Pro Ile Asp Asn Asp Gly
            180                 185                 190

Asp Asn Thr Ser Tyr Arg Leu Ile Ser Cys Asn Thr Ser Val Ile Thr
        195                 200                 205

Gln Ala Cys Pro Lys Ile Ser Phe Glu Pro Ile Pro Ile His Tyr Cys
    210                 215                 220

Thr Pro Ala Gly Tyr Ala Leu Leu Lys Cys Asn Asn Lys Lys Phe Asn
225                 230                 235                 240

Gly Thr Gly Pro Cys Lys Asn Val Ser Thr Val Gln Cys Thr His Gly
                245                 250                 255

Ile Arg Pro Val Val Ser Thr Gln Leu Leu Leu Asn Gly Ser Leu Ala
            260                 265                 270

Glu Glu Glu Val Val Ile Arg Ser Ser Asn Phe Thr Asn Asn Ala Lys
        275                 280                 285

Val Ile Ile Val Gln Leu Lys Glu Ala Val Glu Ile Asn Cys Thr Arg
    290                 295                 300

Pro Asn Asn Asn Thr Arg Lys Ser Ile His Ile Gly Pro Gly Lys Ala
305                 310                 315                 320

Trp Tyr Thr Thr Gly Glu Ile Ile Gly Asn Ile Arg Gln Ala His Cys
                325                 330                 335

Asn Ile Ser Arg Thr Lys Trp Asn Asn Thr Leu His Gln Ile Val Lys
            340                 345                 350

Lys Leu Arg Ile Gln Phe Gly Asn Lys Thr Ile Ile Phe Asn Gln Ser
        355                 360                 365

Ala Gly Gly Asp Pro Glu Ile Val Val His Ser Phe Asn Cys Gly Gly
    370                 375                 380

Glu Phe Phe Tyr Cys Asn Thr Ser Gln Leu Phe Asn Ser Thr Trp Arg
385                 390                 395                 400

Asn Asp Thr Trp Asn Asp Thr Ser Pro Gln Ile Ala Thr Thr Gly Asn
                405                 410                 415

Asp Thr Ile Thr Leu Pro Cys Arg Ile Arg Gln Ile Val Asn Met Trp
            420                 425                 430

Gln Gln Val Gly Lys Ala Met Tyr Ala Pro Ile Ala Gly Gln Ile
        435                 440                 445

Arg Cys Ser Ser Asn Ile Thr Gly Val Leu Leu Thr Arg Asp Gly Gly
    450                 455                 460

Asn Asn Glu Ser Lys Ala Asn Ala Asn Glu Thr Phe Arg Pro Ala Gly
465                 470                 475                 480

Gly Asp Met Arg Asp Asn Trp Arg Ser Glu Leu Tyr Lys Tyr Lys Val
                485                 490                 495
```

Val Lys Ile Glu Pro Leu Gly Val Ala Pro Thr Lys Ala Lys Arg Arg
        500                 505                 510

Val Val Gln Arg Glu Lys Arg Ala Val Gly Thr Leu Gly Ala Met Phe
        515                 520                 525

Leu Gly Phe Leu Gly Ala Ala Gly Ser Thr Met Gly Ala Ala Ser Ile
        530                 535                 540

Thr Leu Thr Val Gln Ala Arg Gln Leu Leu Ser Gly Ile Val Gln Gln
545                 550                 555                 560

Gln Arg Asn Leu Leu Arg Ala Ile Glu Ala Gln Gln His Leu Leu Gln
                565                 570                 575

Leu Thr Val Trp Gly Ile Lys Gln Leu Gln Ala Arg Val Leu Ala Val
            580                 585                 590

Glu Arg Tyr Leu Gln Asp Gln Gln Leu Leu Gly Ile Trp Gly Cys Ser
            595                 600                 605

Gly Lys Leu Ile Cys Thr Thr Thr Val Pro Trp Asn Val Ser Trp Ser
        610                 615                 620

Asn Lys Ser Leu Gly Glu Ile Trp Asp Asn Met Thr Trp Met Glu Trp
625                 630                 635                 640

Glu Arg Glu Ile Ser Asn Tyr Thr Gly Gln Ile Tyr Thr Leu Ile Glu
                645                 650                 655

Gln Ser Gln Asn Gln Gln Glu Lys Asn Glu Leu Glu Leu Leu Glu Leu
            660                 665                 670

Asp Lys Trp Ala Ser Leu Trp Asn Trp Phe Asp Ile Ser Asn Trp Leu
        675                 680                 685

Trp Tyr Ile Lys Ile Phe Ile Met Ile Val Gly Gly Leu Val Gly Leu
690                 695                 700

Arg Ile Ile Phe Ala Val Leu Ser Ile Val Asn Arg Val Arg Gln Gly
705                 710                 715                 720

Tyr Ser Pro Leu Ser Leu Gln Thr Arg Phe Pro Ala Gln Arg Gly Pro
                725                 730                 735

Gly Arg Pro Glu Gly Ile Glu Glu Glu Gly Gly Glu Gln Asp Arg Asp
            740                 745                 750

Arg Ser Glu Arg Leu Val Asn Gly Phe Leu Thr Leu Phe Trp Val Asp
        755                 760                 765

Leu Arg Ser Leu Cys Leu Phe Ser Tyr His Ser Leu Arg Asp Leu Leu
770                 775                 780

Leu Ile Val Ala Arg Ile Val Glu Leu Leu Gly Arg Arg Gly Trp Glu
785                 790                 795                 800

Ala Leu Lys Tyr Leu Trp Asn Leu Leu Gln Tyr Trp Ile Gln Glu Leu
                805                 810                 815

Lys Asn Ser Ala Val Ser Leu Leu Asn Ala Thr Ala Ile Ala Val Ala
            820                 825                 830

Glu Gly Thr Asp Arg Ile Ile Glu Leu Ala Gln Arg Ala Phe Arg Ala
        835                 840                 845

Phe Leu Asn Ile Pro Thr Arg Ile Arg Gln Gly Leu Glu Arg Ala Leu
        850                 855                 860

Leu
865

<210> SEQ ID NO 188
<211> LENGTH: 851
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 188

```
Met Lys Val Lys Gly Ile Arg Lys Asn Tyr Gln His Leu Trp Arg Trp
1               5                   10                  15

Gly Met Met Leu Leu Gly Met Leu Met Ile Cys Ser Ala Thr Glu Lys
            20                  25                  30

Leu Trp Val Thr Val Tyr Tyr Gly Val Pro Val Trp Arg Asp Ala Thr
        35                  40                  45

Thr Thr Leu Phe Cys Ala Ser Asp Ala Lys Ala Tyr Glu Thr Glu Leu
    50                  55                  60

His Asn Val Trp Ala Thr His Ala Cys Val Pro Thr Asp Pro Asn Pro
65                  70                  75                  80

Gln Glu Val Val Leu Gly Asn Val Thr Glu Asn Phe Asn Met Trp Lys
                85                  90                  95

Asn Asp Met Val Glu Gln Met Asn Glu Asp Ile Ile Ser Leu Trp Asp
            100                 105                 110

Glu Ser Leu Lys Pro Cys Val Lys Leu Thr Pro Leu Cys Val Thr Leu
        115                 120                 125

Asn Cys Thr Asn Tyr Asn Glu Thr Thr Asn Ser Thr Thr Thr Asn
130                 135                 140

Ala Thr Val Val Ser Pro Gly Glu Ile Lys Asn Cys Ser Phe Asn Val
145                 150                 155                 160

Thr Thr Gly Ile Arg Asp Lys Val Arg Lys Asp His Ala Leu Phe Tyr
                165                 170                 175

Ala Leu Asp Ile Val Pro Ile Asp Asn Thr Ile Asp Asn Thr Ser Tyr
            180                 185                 190

Arg Leu Val Ser Cys Asn Thr Ser Val Leu Thr Gln Ala Cys Pro Lys
        195                 200                 205

Val Ser Phe Glu Pro Ile Pro Ile His Phe Cys Ala Pro Ala Gly Tyr
    210                 215                 220

Ala Ile Ile Lys Cys Asn Asn Lys Thr Phe Asn Gly Ser Gly Pro Cys
225                 230                 235                 240

Arg Asn Val Ser Thr Val Gln Cys Thr His Gly Ile Arg Pro Val Val
                245                 250                 255

Ser Thr Gln Leu Leu Leu Asn Gly Ser Leu Ala Glu Glu Ile Val
            260                 265                 270

Ile Arg Ser Ala Asn Phe Ser Asp Asn Thr Lys Thr Ile Ile Val Gln
        275                 280                 285

Leu Asn Glu Ala Val Lys Ile Asn Cys Thr Arg Pro Asn Asn Asn Thr
    290                 295                 300

Arg Arg Ser Val His Met Gly Pro Gly Ser Ala Phe Tyr Thr Thr Gly
305                 310                 315                 320

Gly Ile Ile Gly Asp Ile Arg Gln Ala His Cys Asn Ile Ser Glu Arg
                325                 330                 335

Asp Trp Asn Gly Ala Leu Lys Gln Ile Val Glu Lys Leu Gly Glu Gln
            340                 345                 350

Phe Gln Asn Lys Thr Ile Val Phe Lys Gln Ser Ser Gly Gly Asp Pro
        355                 360                 365

Glu Val Val Met His Thr Phe Asn Cys Arg Gly Glu Phe Phe Tyr Cys
    370                 375                 380

Asn Thr Thr Lys Leu Phe Asn Ser Thr Trp Val Asn Gly Thr Lys Asn
385                 390                 395                 400
```

```
Asp Thr Lys Gly Gly Asn Gly Thr Ile Thr Leu Gln Cys Arg Ile Lys
                405                 410                 415

Gln Ile Ile Asn Met Trp Gln Gln Val Gly Lys Ala Met Tyr Ala Pro
            420                 425                 430

Pro Ile Ser Gly Pro Ile Ser Cys Ser Ser Asn Ile Thr Gly Leu Ile
        435                 440                 445

Leu Thr Arg Asp Gly Gly Thr Asn Thr Thr Asn Glu Thr Phe Arg Pro
    450                 455                 460

Gly Gly Gly Asp Met Arg Asp Asn Trp Arg Ser Glu Leu Tyr Lys Tyr
465                 470                 475                 480

Lys Val Val Lys Ile Glu Pro Ile Gly Val Ala Pro Thr Lys Ala Arg
                485                 490                 495

Arg Arg Val Val Gln Arg Glu Lys Arg Ala Val Gly Ile Gly Ala Phe
            500                 505                 510

Phe Leu Gly Phe Leu Gly Ala Ala Gly Ser Thr Met Gly Ala Ala Ser
        515                 520                 525

Ile Thr Leu Thr Val Gln Ala Arg Leu Leu Ser Gly Ile Val Gln
    530                 535                 540

Gln Gln Ser Asn Leu Leu Arg Ala Ile Glu Ala Gln Gln His Leu Leu
545                 550                 555                 560

Gln Leu Thr Val Trp Gly Ile Lys Gln Leu Gln Ala Arg Val Leu Ala
                565                 570                 575

Val Glu Ser Tyr Leu Arg Asp Gln Gln Leu Leu Gly Ile Trp Gly Cys
            580                 585                 590

Pro Gly Lys Leu Ile Cys Thr Thr Asn Val Pro Trp Asn Asn Ser Trp
        595                 600                 605

Ser Lys Asn Lys Ser Tyr Asn Gln Ile Trp Asp Asn Met Thr Trp Met
    610                 615                 620

Glu Trp Glu Arg Glu Ile Asn Asn Tyr Thr Asp Tyr Ile Tyr Ser Leu
625                 630                 635                 640

Ile Glu Ile Ser Gln Arg Gln Gln Glu Lys Asn Glu Gln Glu Leu Leu
                645                 650                 655

Glu Leu Asp Lys Trp Ala Asn Leu Trp Thr Trp Phe Asp Ile Thr Asn
            660                 665                 670

Trp Leu Trp Tyr Ile Lys Ile Phe Ile Met Ile Val Gly Gly Leu Ile
        675                 680                 685

Gly Leu Arg Ile Val Phe Ser Val Leu Ser Ile Val Asn Arg Val Arg
    690                 695                 700

Gln Gly Tyr Ser Pro Leu Ser Phe Gln Thr Arg Leu Pro Thr Gln Arg
705                 710                 715                 720

Gly Pro Asp Arg Pro Glu Glu Ile Glu Glu Gly Gly Glu Arg Asp
                725                 730                 735

Arg Asp Arg Ser Ser Gly Leu Ala Asp Gly Phe Leu Thr Leu Ile Trp
            740                 745                 750

Val Asp Leu Arg Ser Leu Cys Leu Phe Ser Tyr His Arg Leu Arg Asp
        755                 760                 765

Leu Leu Leu Ile Val Thr Arg Ile Val Glu Leu Leu Gly Arg Arg Gly
    770                 775                 780

Trp Glu Ala Leu Lys Tyr Trp Trp Asn Leu Leu Gln Tyr Trp Ser Gln
785                 790                 795                 800

Glu Leu Lys Ser Ser Ala Ile Ser Leu Leu Asn Thr Ile Ala Ile Val
                805                 810                 815

Val Ala Glu Gly Thr Asp Arg Ile Ile Glu Val Ala Gln Arg Ala Cys
```

-continued

```
                820                 825                 830
Gly Ala Ile Leu His Ile Pro Arg Arg Ile Arg Gln Gly Phe Glu Arg
            835                 840                 845

Ile Leu Val
        850

<210> SEQ ID NO 189
<211> LENGTH: 841
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (673)..(673)
<223> OTHER INFORMATION: Any amino acid

<400> SEQUENCE: 189

Met Arg Ala Lys Glu Thr Arg Lys Lys Tyr Gln His Leu Trp Ala Trp
1               5                   10                  15

Gly Thr Leu Leu Leu Gly Met Leu Met Ile Cys Ser Ala Thr Glu Gln
            20                  25                  30

Leu Trp Val Thr Val Tyr Tyr Gly Val Pro Val Trp Lys Asp Ala Asn
        35                  40                  45

Thr Thr Leu Phe Cys Ala Ser Asp Ala Lys Ala Tyr Asp Thr Glu Val
    50                  55                  60

His Asn Val Trp Ala Thr His Ala Cys Val Pro Thr Asp Pro Ser Pro
65                  70                  75                  80

Gln Glu Ile Val Leu Lys Asn Val Thr Glu Asn Phe Asn Met Trp Lys
                85                  90                  95

Asn Asn Met Val Glu Gln Met His Lys Asp Ile Ile Ser Leu Trp Asp
            100                 105                 110

Glu Ser Leu Lys Pro Cys Val Lys Leu Thr Pro Leu Cys Val Thr Leu
        115                 120                 125

Asn Cys Ser Asn Tyr Asn Ser Thr Asn Ser Thr Ile Asp Pro Asn Met
    130                 135                 140

Glu Gly Ala Ile Lys Asn Cys Ser Phe Asn Ala Thr Thr Gly Ile Gln
145                 150                 155                 160

Asn Lys Met Lys Lys Glu Tyr Ala Leu Phe Tyr Ser Leu Asp Ile Val
                165                 170                 175

Gln Ile Glu Ser Glu Asn Lys Ser Asn Lys Ser Tyr Met Leu Arg Ser
            180                 185                 190

Cys Asn Thr Ser Val Ile Thr Gln Ala Cys Pro Lys Val Thr Phe Glu
        195                 200                 205

Pro Ile Pro Ile His Tyr Cys Ala Pro Ala Gly Phe Ala Ile Leu Lys
    210                 215                 220

Cys Asn Asp Lys Lys Phe Asn Gly Thr Gly Pro Cys Lys Asn Val Ser
225                 230                 235                 240

Thr Val Gln Cys Thr His Gly Ile Arg Pro Val Val Ser Thr Gln Leu
                245                 250                 255

Leu Leu Asn Gly Ser Leu Ala Glu Glu Ile Ile Ile Arg Ser Glu
            260                 265                 270

Asn Ile Thr Asn Asn Ala Lys Thr Ile Ile Ile Gln Leu Asn Arg Ser
        275                 280                 285

Ile Glu Ile Asn Cys Thr Arg Pro Asn Asn Asn Thr Arg Lys Ser Ile
    290                 295                 300
```

```
His Met Gly Trp Gly Arg Ala Phe Tyr Ala Thr Gly Asp Ile Ile Gly
305                 310                 315                 320

Asp Ile Arg Gln Ala His Cys Asn Leu Ser Gly Thr Lys Trp Asn Asn
            325                 330                 335

Thr Leu Tyr Gln Ile Ala Arg Lys Leu Arg Glu His Phe Asn Asn Thr
        340                 345                 350

Ile Val Phe Asn Gln Ser Ser Gly Gly Asp Pro Glu Ile Val Met His
    355                 360                 365

Thr Phe Asn Cys Gly Gly Glu Phe Phe Tyr Cys Asn Thr Thr Gln Leu
370                 375                 380

Phe Asn Ser Thr Trp His Ala Asn Ser Thr Trp Asn Glu Thr Thr Gly
385                 390                 395                 400

Ser Gly Ser Asn Asp Thr Ile Ser Leu Pro Cys Arg Ile Lys Gln Ile
            405                 410                 415

Ile Asn Arg Trp Gln Glu Val Gly Lys Ala Met Tyr Ala Pro Pro Ile
        420                 425                 430

Gly Gly Gln Ile Arg Cys Ser Ser Asn Ile Thr Gly Ile Leu Leu Thr
    435                 440                 445

Arg Asp Gly Gly Thr Glu Asn Asn Thr Ser Glu Thr Phe Arg Pro Gly
450                 455                 460

Gly Gly Asn Met Lys Asp Asn Trp Arg Ser Glu Leu Tyr Lys Tyr Lys
465                 470                 475                 480

Val Val Arg Ile Glu Pro Leu Gly Val Ala Pro Thr Lys Ala Lys Arg
            485                 490                 495

Arg Val Val Gln Arg Glu Lys Arg Ala Val Thr Phe Gly Ala Phe Phe
        500                 505                 510

Leu Gly Phe Leu Gly Thr Ala Gly Ser Thr Met Gly Ala Ala Ser Ile
    515                 520                 525

Thr Leu Thr Val Gln Ala Arg Gln Leu Leu Ser Gly Ile Val Gln Gln
    530                 535                 540

Gln Ser Asn Leu Leu Arg Ala Ile Glu Ala Gln Gln Arg Met Leu Gln
545                 550                 555                 560

Leu Thr Val Trp Gly Ile Lys Gln Leu Gln Ala Arg Val Leu Ala Val
            565                 570                 575

Glu Arg Tyr Leu Lys Asp Gln Gln Leu Leu Gly Ile Trp Gly Cys Ser
        580                 585                 590

Gly Arg Leu Ile Cys Thr Thr Ala Val Pro Trp Asn Ala Ser Trp Ser
    595                 600                 605

Asn Lys Ser Leu Asn Glu Ile Trp Asp Asn Met Thr Trp Met Gln Trp
610                 615                 620

Glu Arg Glu Ile Asp Asn Tyr Thr Asn Leu Ile Tyr Thr Leu Ile Glu
625                 630                 635                 640

Glu Ser Gln Tyr Gln Gln Glu Lys Asn Glu Gln Glu Leu Leu Glu Leu
            645                 650                 655

Asp Lys Trp Ala Ser Leu Trp Ser Trp Phe Asn Ile Thr Asn Trp Leu
        660                 665                 670

Xaa Val Gly Gly Leu Val Gly Leu Arg Ile Ile Phe Ala Val Leu Ser
    675                 680                 685

Ile Val Lys Arg Val Gly Gln Gly Tyr Ser Pro Leu Ser Phe Gln Ile
    690                 695                 700

Arg Pro Pro Ala Arg Arg Gly Pro Asp Arg Pro Glu Gly Ile Asp Glu
705                 710                 715                 720
```

```
Glu Gly Gly Glu Arg Asp Arg Asp Arg Ser Asn Arg Leu Val Asp Gly
                725                 730                 735

Phe Leu Ala Leu Ile Trp Asp Asp Leu Arg Ser Leu Cys Leu Phe Ser
            740                 745                 750

Tyr His Arg Leu Arg Asp Leu Leu Ser Ile Leu Thr Arg Ile Val Glu
        755                 760                 765

Leu Leu Gly Arg Arg Gly Trp Glu Ala Leu Arg Tyr Cys Trp Asn Leu
    770                 775                 780

Leu Lys Tyr Trp Asn Gln Glu Leu Lys Asn Gly Ala Val Gly Leu Leu
785                 790                 795                 800

Gly Ala Thr Ala Ile Ala Val Ala Gly Gly Thr Asp Gly Ile Ile Glu
            805                 810                 815

Ala Val Arg Gly Leu Cys Gly Ala Ile Leu Asn Ile Pro Gly Arg Ile
        820                 825                 830

Arg Gln Gly Leu Glu Arg Ala Leu Leu
    835                 840

<210> SEQ ID NO 190
<211> LENGTH: 504
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 190

Met Arg Val Lys Gly Ile Arg Lys Asn Tyr Gln His Leu Trp Arg Trp
1               5                   10                  15

Gly Thr Met Leu Leu Gly Met Leu Met Ile Cys Ser Ala Ala Glu Gln
            20                  25                  30

Leu Trp Val Thr Val Tyr Tyr Gly Val Pro Val Trp Lys Glu Ala Thr
        35                  40                  45

Thr Thr Leu Phe Cys Ala Ser Asp Ala Lys Ala His Asp Thr Glu Val
    50                  55                  60

His Asn Val Trp Ala Thr His Ala Cys Val Pro Thr Asp Pro Asn Pro
65                  70                  75                  80

Gln Glu Val Val Leu Glu Asn Val Thr Glu Asn Phe Asn Met Trp Lys
                85                  90                  95

Asn Asn Met Val Glu Gln Met Gln Glu Asp Val Ile Ser Leu Trp Asp
            100                 105                 110

Gln Ser Leu Lys Pro Cys Val Lys Leu Thr Pro Leu Cys Val Thr Leu
        115                 120                 125

Asn Cys Thr Asp Val Ser Ser Asn Ser Thr Ser Val Asn Ile Thr Ser
    130                 135                 140

Glu Lys Gly Glu Ile Lys Asn Cys Ser Phe Asn Val Thr Thr Ser Ile
145                 150                 155                 160

Lys Asp Lys Val Gln Lys Glu Tyr Ala Leu Phe Tyr Lys Leu Asp Val
                165                 170                 175

Val Pro Ile Glu Asp Asp Ser Arg Asn Asn Ser Tyr Arg Leu Ile Ser
            180                 185                 190

Cys Asn Thr Ser Val Ile Thr Gln Ala Cys Pro Lys Val Ser Phe Glu
        195                 200                 205

Pro Ile Pro Ile His Tyr Cys Thr Pro Ala Gly Phe Ala Ile Leu Lys
    210                 215                 220

Cys Asn Asp Lys Lys Phe Asn Gly Thr Gly Pro Cys Thr Asn Val Ser
225                 230                 235                 240
```

```
Thr Val Gln Cys Thr His Gly Ile Arg Pro Val Ser Thr Gln Leu
            245                 250                 255

Leu Leu Asn Gly Ser Leu Ala Glu Glu Val Val Ile Arg Ser Glu
            260                 265                 270

Asn Phe Thr Asn Asn Ala Lys Thr Ile Ile Val Gln Leu Asn Glu Ser
            275                 280                 285

Val Glu Ile Asn Cys Thr Arg Pro Asn Asn Asn Thr Arg Lys Ser Ile
    290                 295                 300

His Ile Gly Pro Gly Arg Ala Phe Tyr Ala Thr Gly Asp Ile Ile Gly
305                 310                 315                 320

Asp Ile Arg Gln Ala His Cys Asn Ile Ser Arg Glu Lys Trp Asn Asn
                325                 330                 335

Thr Leu Lys Gln Ile Val Lys Lys Leu Arg Glu Gln Phe Gly Asn Lys
            340                 345                 350

Thr Ile Val Phe Asn Gln Ser Ser Gly Gly Asp Pro Glu Ile Val Met
            355                 360                 365

His Ser Phe Asn Cys Gly Gly Glu Phe Phe Tyr Cys Asn Thr Thr Gln
            370                 375                 380

Leu Phe Asn Ser Thr Trp Ser Ile Asn Gly Thr Trp Asn Gly Thr Thr
385                 390                 395                 400

Glu Ser Asn Asp Thr Ile Thr Leu Pro Cys Arg Ile Lys Gln Ile Ile
                405                 410                 415

Asn Met Trp Gln Glu Val Gly Lys Ala Met Tyr Ala Pro Pro Ile Arg
            420                 425                 430

Gly Gln Ile Arg Cys Ser Ser Asn Ile Thr Gly Leu Leu Leu Thr Arg
            435                 440                 445

Asp Gly Gly Asn Ser Ser Ser Asn Asn Glu Thr Phe Arg Pro Gly Gly
450                 455                 460

Gly Asp Met Arg Asp Asn Trp Arg Ser Glu Leu Tyr Lys Tyr Lys Val
465                 470                 475                 480

Val Lys Ile Glu Pro Leu Gly Val Ala Pro Thr Lys Ala Lys Arg Arg
                485                 490                 495

Val Val Gln Arg Glu Lys Arg Val
            500

<210> SEQ ID NO 191
<211> LENGTH: 502
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 191

Met Lys Val Lys Gly Ile Arg Lys Asn Cys Gln His Leu Trp Arg Trp
1               5                   10                  15

Gly Ile Met Leu Leu Gly Met Leu Met Ile Cys Ser Ala Thr Glu Lys
            20                  25                  30

Leu Trp Val Thr Val Tyr Tyr Gly Val Pro Val Trp Lys Glu Ala Thr
        35                  40                  45

Thr Thr Leu Phe Cys Ala Ser Asp Ala Lys Ala His Asp Thr Glu Ala
    50                  55                  60

His Asn Val Trp Ala Thr His Ala Cys Val Pro Thr Asp Pro Asn Pro
65                  70                  75                  80

Gln Glu Ile Val Leu Glu Asn Val Thr Glu Asn Phe Asn Met Trp Lys
```

```
                        85                  90                  95
Asn Asp Met Val Glu Gln Met Gln Glu Asp Val Ile Ser Leu Trp Asp
                100                 105                 110
Glu Ser Leu Lys Pro Cys Val Glu Leu Thr Pro Leu Cys Val Thr Leu
            115                 120                 125
Asn Cys Thr Asn Val Asn Ala Thr Asn Thr Asn Asn Ser Ser Gly Ile
        130                 135                 140
Glu Gly Gly Glu Met Lys Asn Cys Ser Phe Asn Val Thr Thr Ser Ile
145                 150                 155                 160
Lys Asp Lys Met Gln Lys Glu Tyr Ala Leu Phe Tyr Ser Leu Asp Val
                165                 170                 175
Val Gln Ile Asp Asn Asp Thr Asn Tyr Arg Leu Ile Asn Cys Asn Thr
            180                 185                 190
Ser Val Ile Thr Gln Ala Cys Pro Lys Ile Ser Phe Glu Pro Ile Pro
        195                 200                 205
Ile His Tyr Cys Thr Pro Ala Gly Phe Ala Ile Ile Lys Cys Asn Asp
    210                 215                 220
Lys Lys Phe Asn Gly Ser Gly Pro Cys Lys Asn Val Ser Thr Val Gln
225                 230                 235                 240
Cys Thr His Gly Ile Lys Pro Val Val Ser Thr Gln Leu Leu Leu Asn
                245                 250                 255
Gly Ser Leu Ala Glu Glu Ile Val Ile Arg Ser Glu Asn Phe Ser
            260                 265                 270
Asp Asn Ala Lys Thr Ile Ile Val Gln Leu Asn Glu Ser Val Val Ile
        275                 280                 285
Asn Cys Thr Arg Pro Asn Asn Asn Thr Arg Lys Ser Ile Ser Ile Gly
    290                 295                 300
Pro Gly Arg Ala Phe Tyr Ala Thr Gly Asp Ile Ile Gly Asn Ile Arg
305                 310                 315                 320
Gln Ala His Cys Asn Leu Ser Arg Ala Lys Trp Asn Asn Thr Leu Arg
                325                 330                 335
Gln Ile Val Thr Lys Leu Arg Glu Gln Phe Lys Asn Lys Thr Ile Ala
            340                 345                 350
Phe Asn His Ser Ser Gly Gly Asp Pro Glu Ile Val Met His Thr Phe
        355                 360                 365
Asn Cys Gly Gly Glu Phe Phe Tyr Cys Asn Ser Thr Gln Leu Phe Asn
    370                 375                 380
Ser Thr Trp Ile Ala Asn Lys Thr Gly Asn Asp Thr Gly Gly Ser Asn
385                 390                 395                 400
Gly Thr Ile Thr Leu Gln Cys Arg Ile Lys Gln Ile Val Asn Arg Trp
                405                 410                 415
Gln Glu Val Gly Lys Ala Met Tyr Ala Pro Pro Ile Ser Gly Gln Ile
            420                 425                 430
Ser Cys Ser Ser Asn Ile Thr Gly Leu Ile Leu Thr Arg Asp Gly Gly
        435                 440                 445
Thr Asn Asn Thr Asn Gly Thr Glu Ile Phe Arg Pro Gly Gly Gly Asn
    450                 455                 460
Met Lys Asp Asn Trp Arg Ser Glu Leu Tyr Lys Tyr Lys Val Val Arg
465                 470                 475                 480
Ile Glu Pro Leu Gly Ile Ala Pro Thr Lys Ala Arg Arg Val Val
                485                 490                 495
Gln Arg Glu Lys Arg Ile
            500
```

<210> SEQ ID NO 192
<211> LENGTH: 509
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 192

```
Met Arg Val Arg Gly Ile Leu Arg Asn Tyr Gln Gln Trp Trp Ile Trp
1               5                   10                  15

Gly Ile Leu Gly Phe Trp Met Leu Met Ile Cys Asn Val Val Gly Asn
            20                  25                  30

Leu Trp Val Thr Val Tyr Tyr Gly Val Pro Val Trp Lys Glu Ala Lys
        35                  40                  45

Thr Thr Leu Phe Cys Ala Ser Asp Ala Lys Ala Tyr Glu Lys Glu Val
    50                  55                  60

His Asn Val Trp Ala Thr His Ala Cys Val Pro Thr Asp Pro Asn Pro
65                  70                  75                  80

Gln Glu Met Val Leu Glu Asn Val Thr Glu Asn Phe Asn Met Trp Lys
                85                  90                  95

Asn Asp Met Val Asp Gln Met His Glu Asp Ile Ile Ser Leu Trp Asp
            100                 105                 110

Gln Ser Leu Lys Pro Cys Val Lys Leu Thr Pro Leu Cys Val Thr Leu
        115                 120                 125

Asn Cys Val Asn Ile Thr Asn Ser Thr Thr Ser Asn Gly Asp Gly Thr
130                 135                 140

Val Thr His Ile Asn Ser Ile Lys Glu Ile Lys Asn Cys Ser Phe
145                 150                 155                 160

Asn Ala Thr Thr Glu Leu Arg Asp Lys Lys Ser Lys Glu Tyr Ala Leu
                165                 170                 175

Phe Tyr Arg Leu Asp Ile Val Pro Leu Ser Ser Gly Asn Ser Ser Ser
            180                 185                 190

Asn Ser Ser Lys Tyr Arg Leu Ile Asn Cys Asn Thr Ser Thr Ile Thr
        195                 200                 205

Gln Ala Cys Pro Lys Val Ser Phe Asp Pro Ile Pro Ile His Tyr Cys
    210                 215                 220

Ala Pro Ala Gly Tyr Ala Ile Leu Lys Cys Asn Asn Lys Thr Phe Asn
225                 230                 235                 240

Gly Thr Gly Pro Cys Asn Asn Val Ser Thr Val Gln Cys Thr His Gly
                245                 250                 255

Ile Lys Pro Val Val Ser Thr Gln Leu Leu Leu Asn Gly Ser Leu Ala
            260                 265                 270

Glu Glu Glu Ile Ile Ile Arg Ser Glu Asn Leu Thr Asp Asn Val Lys
        275                 280                 285

Thr Ile Ile Val His Leu Asn Glu Ser Val Gln Ile Val Cys Thr Arg
    290                 295                 300

Pro Asn Asn Asn Thr Arg Lys Ser Ile Arg Ile Gly Pro Gly Gln Thr
305                 310                 315                 320

Phe Tyr Ala Thr Gly Asp Ile Ile Gly Asp Ile Arg Gln Ala His Cys
                325                 330                 335

Asn Ile Ser Lys Gly Ala Trp Asn Glu Thr Leu Gln Trp Val Gly Lys
            340                 345                 350

Lys Leu Lys Glu His Phe Pro Asn Lys Thr Ile Lys Phe Asn Ser Ser
```

```
                355                 360                 365
Ser Gly Gly Asp Leu Glu Ile Thr Thr His Ser Phe Asn Cys Arg Gly
        370                 375                 380

Glu Phe Phe Tyr Cys Asn Thr Ser Gly Leu Phe Asn Ser Thr Tyr Arg
385                 390                 395                 400

Asn Asn Ser Thr Gly Asp Asn Ser Thr Ile Thr Leu Pro Cys Arg Ile
                405                 410                 415

Lys Gln Ile Ile Asn Met Trp Gln Glu Val Gly Arg Ala Met Tyr Ala
        420                 425                 430

Pro Pro Ile Ala Gly Asn Ile Thr Cys Lys Ser Asn Ile Thr Gly Leu
            435                 440                 445

Leu Leu Thr Arg Asp Gly Gly Thr Arg Asp Arg Asn Asp Thr Glu Thr
        450                 455                 460

Phe Arg Pro Gly Gly Gly Asp Met Arg Asp Asn Trp Arg Ser Glu Leu
465                 470                 475                 480

Tyr Lys Tyr Lys Val Val Glu Ile Lys Pro Leu Gly Ile Ala Pro Thr
                485                 490                 495

Lys Ala Lys Arg Arg Val Val Glu Arg Glu Lys Arg Val
            500                 505

<210> SEQ ID NO 193
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 193

Val Asn Ile Thr Asn Ser Thr Thr Ser Asn Gly Asp Gly Thr Val Thr
1               5                   10                  15

His Ile Asn Ser Ile
            20

<210> SEQ ID NO 194
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 194

Ser Ser Gly Asn Ser Ser Ser Asn Ser Ser Lys
1               5                   10

<210> SEQ ID NO 195
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 195

Arg Asn Asn Ser Thr Gly Asp
1               5

<210> SEQ ID NO 196
<211> LENGTH: 7
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 196

Thr Arg Asp Arg Asn Asp Thr
1               5

<210> SEQ ID NO 197
<211> LENGTH: 501
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 197

Met Arg Val Met Gly Ile Gln Arg Asn Trp Pro Gln Trp Trp Ile Trp
1               5                   10                  15

Gly Ile Leu Gly Phe Trp Met Ile Ile Ile Cys Arg Val Val Gly Asn
            20                  25                  30

Leu Trp Val Thr Val Tyr Tyr Gly Val Pro Val Trp Arg Glu Ala Lys
        35                  40                  45

Thr Thr Leu Phe Cys Ala Ser Asp Ala Lys Ala Tyr Glu Arg Glu Val
    50                  55                  60

His Asn Val Trp Ala Thr His Ala Cys Val Pro Thr Asp Pro Asn Pro
65                  70                  75                  80

Gln Glu Leu Val Leu Glu Asn Val Thr Glu Asn Phe Asn Met Trp Glu
                85                  90                  95

Asn Asp Met Val Asp Gln Met His Glu Asp Val Ile Ser Leu Trp Asp
            100                 105                 110

Gln Ser Leu Lys Pro Cys Val Lys Leu Thr Pro Leu Cys Val Thr Leu
        115                 120                 125

Lys Cys Thr Asn Thr Thr Tyr Tyr Asn Val Ser Ser Lys Glu Phe Thr
    130                 135                 140

Asn Gly Glu Ile Lys Asn Cys Ser Phe Asn Thr Thr Thr Glu Leu Arg
145                 150                 155                 160

Asp Lys Lys Gln Lys Val Ser Ala Leu Phe Tyr Arg Leu Asp Val Val
                165                 170                 175

Pro Leu Ser Lys Lys Asp Lys Thr Asn Asn Asp Ser Gly Glu Tyr Ile
            180                 185                 190

Leu Ile Asn Cys Asn Thr Ser Ala Ile Thr Gln Ala Cys Pro Lys Val
        195                 200                 205

Ser Phe Asp Pro Ile Pro Ile His Tyr Cys Thr Pro Ala Gly Tyr Ala
    210                 215                 220

Ile Leu Lys Cys Asn Asn Lys Thr Phe Asn Gly Thr Gly Pro Cys His
225                 230                 235                 240

Asn Val Ser Thr Val Gln Cys Thr His Gly Ile Lys Pro Val Val Ser
                245                 250                 255

Thr Gln Leu Leu Leu Asn Gly Ser Leu Thr Glu Gly Glu Ile Ile Ile
            260                 265                 270

Arg Ser Glu Asn Leu Thr Asn Asn Ala Lys Thr Ile Ile Val His Leu
        275                 280                 285

Asn Gln Ser Val Ala Ile Val Cys Thr Arg Pro Gly Asn Asn Thr Arg
    290                 295                 300

Lys Ser Val Arg Ile Gly Pro Gly Gln Ala Phe Tyr Ala Thr Gly Glu
305                 310                 315                 320
```

Ile Ile Gly Asp Ile Arg Gln Ala Tyr Cys Asn Leu Thr Asn Trp Gln
                    325                 330                 335

Glu Thr Leu Lys Asn Val Ser Lys Lys Leu Gln Glu Arg Phe Asn Lys
                340                 345                 350

Thr Ile Arg Phe Ala Pro Ser Ser Gly Gly Asp Leu Glu Ile Thr Thr
            355                 360                 365

His Ser Phe Asn Cys Gly Gly Glu Phe Phe Tyr Cys Asn Thr Ser Ser
        370                 375                 380

Leu Phe Asn Ser Ala Tyr Asn Pro Asn Gly Thr Lys Asp Asn Ser Asn
385                 390                 395                 400

Ser Ser Ile Thr Ile Gln Cys Lys Ile Lys Gln Ile Ile Asn Met Trp
                405                 410                 415

Gln Gly Val Gly Arg Ala Ile Tyr Ala Pro Pro Ile Ala Gly Asn Ile
                420                 425                 430

Thr Cys Asn Ser Asn Ile Thr Gly Ile Leu Leu Thr Arg Asp Gly Gly
                435                 440                 445

Ser Lys Asn Asn Thr Glu Glu Ile Phe Arg Pro Gly Gly Gly Asn Met
            450                 455                 460

Lys Asp Asn Trp Arg Ser Glu Leu Tyr Arg Tyr Lys Val Val Glu Ile
465                 470                 475                 480

Lys Pro Leu Gly Val Ala Pro Thr Glu Ala Lys Arg Arg Val Val Glu
                485                 490                 495

Arg Glu Lys Arg Ala
            500

<210> SEQ ID NO 198
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 198

Thr Asn Thr Thr Tyr Tyr Asn Val Ser Ser Lys Glu
1               5                   10

<210> SEQ ID NO 199
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 199

Ser Lys Lys Asp Lys Thr Asn Asn Asp Ser Gly Glu
1               5                   10

<210> SEQ ID NO 200
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 200

Asn Pro Asn Gly Thr Lys Asp Asn Ser
1               5

<210> SEQ ID NO 201
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 201

Ser Lys Asn Asn Thr Glu
1               5

<210> SEQ ID NO 202
<211> LENGTH: 507
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 202

Met Arg Val Lys Glu Thr Gln Met Asn Trp Pro Asn Leu Trp Lys Trp
1               5                   10                  15

Gly Thr Leu Ile Leu Gly Leu Val Ile Ile Cys Ser Ala Ser Asp Asn
            20                  25                  30

Leu Trp Val Thr Val Tyr Tyr Gly Val Pro Val Trp Arg Asp Ala Asp
        35                  40                  45

Thr Thr Leu Phe Cys Ala Ser Asp Ala Lys Ala His Glu Thr Glu Val
    50                  55                  60

His Asn Val Trp Ala Thr His Ala Cys Val Pro Thr Asp Pro Asn Pro
65                  70                  75                  80

Gln Glu Ile His Leu Glu Asn Val Thr Glu Asn Phe Asn Met Trp Lys
                85                  90                  95

Asn Asn Met Val Glu Gln Met Gln Glu Asp Val Ile Ser Leu Trp Asp
            100                 105                 110

Gln Ser Leu Lys Pro Cys Val Lys Leu Thr Pro Leu Cys Val Thr Leu
        115                 120                 125

Asn Cys Thr Lys Ala Asn Leu Thr Asn Ile Asn Glu Thr Thr Ala Ser
    130                 135                 140

Asn Gly Ile Gly Asn Ile Thr Asp Glu Val Arg Asn Cys Ser Phe Asn
145                 150                 155                 160

Met Thr Thr Glu Leu Arg Asp Lys Lys Gln Lys Val His Ala Leu Phe
                165                 170                 175

Tyr Lys Leu Asp Ile Val Pro Ile Arg Asn Glu Ser Lys Met Gly Asn
            180                 185                 190

Val Ser Ser Glu Tyr Arg Leu Ile Asn Cys Asn Thr Ser Val Ile Lys
        195                 200                 205

Gln Ala Cys Pro Lys Ile Ser Phe Asp Pro Ile Pro Ile His Tyr Cys
    210                 215                 220

Thr Pro Ala Gly Tyr Ala Ile Leu Lys Cys Asn Asp Lys Asn Phe Asn
225                 230                 235                 240

Gly Thr Gly Pro Cys Lys Asn Val Ser Ser Val Gln Cys Thr His Gly
                245                 250                 255

Ile Lys Pro Val Val Ser Thr Gln Leu Leu Leu Asn Gly Ser Leu Ala
            260                 265                 270

Glu Glu Glu Ile Ile Ile Arg Ser Glu Asn Leu Thr Asn Asn Ala Lys
        275                 280                 285

```
Thr Ile Ile Val His Leu Asn Lys Ser Val Glu Ile Asn Cys Thr Arg
    290                 295                 300

Pro Ser Asn Asn Thr Arg Thr Ser Ile Thr Ile Gly Pro Gly Gln Val
305                 310                 315                 320

Phe Tyr Arg Thr Gly Asp Ile Ile Gly Asp Ile Arg Lys Ala Tyr Cys
                325                 330                 335

Glu Ile Asn Gly Thr Lys Trp Asn Glu Thr Leu Lys Gln Val Ala Gly
            340                 345                 350

Lys Leu Lys Glu His Phe Asn Lys Thr Ile Ile Phe Gln Pro Pro Ser
        355                 360                 365

Gly Gly Asp Leu Glu Ile Thr Met His His Phe Asn Cys Arg Gly Glu
    370                 375                 380

Phe Phe Tyr Cys Asn Thr Thr Lys Leu Phe Asn Ser Thr Trp Asn Gly
385                 390                 395                 400

Thr Met Glu Gly Arg Asn Gly Thr Ile Ile Leu Pro Cys Arg Ile Lys
                405                 410                 415

Gln Ile Ile Asn Met Trp Gln Gly Val Gly Gln Ala Met Tyr Ala Pro
            420                 425                 430

Pro Ile Ser Gly Ile Ile Asn Cys Val Ser Asn Ile Thr Gly Ile Leu
        435                 440                 445

Leu Thr Arg Asp Gly Gly Asn Asn Asn Ala Thr Asn Glu Thr Phe Arg
    450                 455                 460

Pro Gly Gly Gly Asn Ile Lys Asp Asn Trp Arg Ser Glu Leu Tyr Lys
465                 470                 475                 480

Tyr Lys Val Val Gln Ile Glu Pro Leu Gly Ile Ala Pro Thr Arg Ala
                485                 490                 495

Lys Arg Arg Val Val Glu Arg Glu Lys Arg Val
                500                 505

<210> SEQ ID NO 203
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 203

Thr Lys Ala Asn Leu Thr Asn Ile Asn Glu Thr Thr Ala Ser Asn Gly
1               5                   10                  15

Ile Gly Asn Ile
            20

<210> SEQ ID NO 204
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 204

Arg Asn Glu Ser Lys Met Gly Asn Val Ser Ser Glu
1               5                   10

<210> SEQ ID NO 205
<211> LENGTH: 7
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 205

Asn Gly Thr Met Glu Gly Arg
1               5

<210> SEQ ID NO 206
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 206

Asn Asn Asn Ala Thr Asn
1               5

<210> SEQ ID NO 207
<211> LENGTH: 509
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 207

Met Arg Val Lys Gly Thr Gln Met Asn Trp Pro Asn Leu Trp Arg Trp
1               5                   10                  15

Gly Thr Leu Ile Leu Gly Leu Val Ile Met Cys Ser Ala Ser Asp Asn
            20                  25                  30

Leu Trp Val Thr Val Tyr Tyr Gly Val Pro Val Trp Lys Asp Ala Asp
        35                  40                  45

Thr Thr Leu Phe Cys Ala Ser Asp Ala Lys Ala His Glu Thr Glu Val
    50                  55                  60

His Asn Ile Trp Ala Thr His Ala Cys Val Pro Thr Asp Pro Asn Pro
65                  70                  75                  80

Gln Glu Ile Pro Leu Glu Asn Val Thr Glu Asn Phe Asn Met Trp Lys
                85                  90                  95

Asn Asn Met Ala Glu Gln Met Gln Glu Asp Val Ile Ser Leu Trp Asp
            100                 105                 110

Glu Ser Leu Lys Pro Cys Val Lys Leu Thr Pro Leu Cys Val Thr Leu
        115                 120                 125

His Cys Thr Lys Ala Asn Leu Thr His Asn Thr Thr Asn Asp Lys Asn
    130                 135                 140

Gly Thr Gly Asn Ile Thr Asp Glu Val Lys Ile Gly Asn Ile Thr Asp
145                 150                 155                 160

Glu Val Lys Asn Cys Ser Phe Asn Met Thr Thr Glu Ile Arg Asp Lys
                165                 170                 175

Lys Gln Lys Val Tyr Ala Leu Phe Tyr Lys Leu Asp Ile Val Gln Ile
            180                 185                 190

Gly Glu Asn Gly Ser Glu Tyr Arg Leu Ile Asn Cys Asn Thr Ser Val
        195                 200                 205

Ile Lys Gln Ala Cys Pro Lys Val Ser Phe Asp Pro Ile Pro Ile His
    210                 215                 220

Tyr Cys Ala Pro Ala Gly Tyr Ala Leu Leu Lys Cys Asn Asp Lys Lys
225                 230                 235                 240

Phe Asn Gly Thr Gly Pro Cys Arg Asn Val Ser Ser Val Gln Cys Thr 245                 250                 255
His Gly Ile Lys Pro Val Val Ser Thr Gln Leu Leu Asn Gly Ser
            260                 265                 270

Leu Ala Glu Glu Ile Ile Ile Arg Ser Glu Asn Leu Thr Asp Asn
        275                 280                 285

Ala Lys Thr Ile Ile Val His Leu Asn Glu Ser Val Ile Asn Cys
    290                 295                 300

Thr Arg Pro Ser Asn Asn Val Arg Ile Ser Thr Arg Ile Gly Pro Gly
305                 310                 315                 320

Gln Val Phe Tyr Arg Thr Gly Glu Ile Ile Gly Asp Ile Arg Lys Ala
                325                 330                 335

Tyr Cys Glu Ile Asn Gly Thr Lys Trp Asn Lys Val Leu Lys Glu Val
                340                 345                 350

Thr Glu Lys Leu Lys Glu His Phe Asn Lys Thr Ile Ile Phe Gln Pro
                355                 360                 365

Pro Ser Gly Gly Asp Leu Glu Ile Thr Thr His His Phe Asn Cys Arg
370                 375                 380

Gly Glu Phe Phe Tyr Cys Asn Thr Thr Lys Leu Phe Asn Asn Thr Cys
385                 390                 395                 400

Asn Gly Thr Met Glu Gly Phe Cys Asn Asn Ile Thr Leu Pro Cys Lys
                405                 410                 415

Ile Lys Gln Ile Ile Asn Met Trp Gln Gly Ala Gly Gln Ala Ile Tyr
                420                 425                 430

Ala Pro Pro Ile Ser Gly Ser Ile Lys Cys Val Ser Asn Ile Thr Gly
                435                 440                 445

Ile Ile Leu Thr Arg Asp Gly Gly Asn Asp Thr Gly Thr Ser Glu Ile
450                 455                 460

Phe Arg Pro Gly Gly Asn Met Lys Asp Asn Trp Arg Asn Glu Leu
465                 470                 475                 480

Tyr Lys Tyr Lys Val Val Gln Ile Glu Pro Leu Gly Val Ala Pro Thr
                485                 490                 495

Lys Ala Lys Arg Arg Val Val Asp Arg Glu Lys Arg Val
                500                 505

<210> SEQ ID NO 208
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 208

Thr Lys Ala Asn Leu Thr His Asn Thr Thr Asn Asp Lys Asn Gly Thr
1               5                   10                  15

Gly Asn Ile Thr Asp Glu Val Lys Ile Gly Asn Ile
            20                  25

<210> SEQ ID NO 209
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 209

Gly Glu Asn Gly Ser Glu

<210> SEQ ID NO 210
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 210

Asn Gly Thr Met Glu Gly Phe
1               5

<210> SEQ ID NO 211
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 211

Asn Asp Thr Gly Thr Ser
1               5

<210> SEQ ID NO 212
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 212

Thr Leu Asp Cys Asn Asn Val Thr Asn Asn Gly Thr Ser Asp Met
1               5                   10                  15

<210> SEQ ID NO 213
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 213

Asn Gly Asp Asn Ser Thr Asn Thr
1               5

<210> SEQ ID NO 214
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 214

Gly Asn Gly Asn Gly Thr Asp Asn Met Gln Gly Ser Asn
1               5                   10

<210> SEQ ID NO 215
<211> LENGTH: 8
<212> TYPE: PRT
<213> ORGANISM: Artificial Sequence
<220> FEATURE:
<223> OTHER INFORMATION: Description of Artificial Sequence: Synthetic

```
                                      peptide

<400> SEQUENCE: 215

Asn Ser Lys Asn Ser Thr Thr Glu
1               5

<210> SEQ ID NO 216
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 216

Asn Asp Ala Lys Leu Asn Ser Thr Lys Thr Asn Ser Thr Thr Asn Ser
1               5                   10                  15

Thr Asp Pro Asn Asn Ser Asn Leu Gly Ile
            20                  25

<210> SEQ ID NO 217
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 217

Asn Glu Asn Ser Ser Ser
1               5

<210> SEQ ID NO 218
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 218

Ser Gln Pro Asn Ser Thr Gly Asn Thr Pro
1               5                   10

<210> SEQ ID NO 219
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 219

Asp Lys Asn Gly Ser Lys Pro
1               5
```

MOSAIC HIV-1 ENVELOPES TO INDUCE ADCC RESPONSES

This application is a National Stage Entry of PCT/US18/53994 filed on Oct. 2, 2018 which claims priority to U.S. Ser. No. 62/566,928 filed Oct. 2, 2017 and U.S. Ser. No. 62/672,158 filed May 16, 2018, the contents of which are incorporated by reference herein in their entireties.

All patents, patent applications and publications cited herein are hereby incorporated by reference in their entirety. The disclosures of these publications in their entireties are hereby incorporated by reference into this application in order to more fully describe the state of the art as known to those skilled therein as of the date of the invention described and claimed herein.

This patent disclosure contains material that is subject to copyright protection. The copyright owner has no objection to the facsimile reproduction by anyone of the patent document or the patent disclosure as it appears in the U.S. Patent and Trademark Office patent file or records, but otherwise reserves any and all copyright rights.

SEQUENCE LISTING

The instant application contains a Sequence Listing which has been submitted electronically in ASCII format and is hereby incorporated by reference in its entirety. Said ASCII copy, created on Nov. 16, 2018, is named 2933311-038-WO1_SL.txt and is 380,186 bytes in size.

FIELD OF THE INVENTION

The invention is directed to mosaic HIV-1 envelopes, and methods of using the same to induce ADCC responses.

BACKGROUND OF THE INVENTION

Antibody (Ab)—dependent cellular cytotoxicity (ADCC) plays a role in vaccine-induced protection from HIV-1. See Bradley et al. (2017) Nature Communications, vol. 8, p. 1571; DOI 10.1038/ncomms15711.

SUMMARY OF THE INVENTION

In some aspects the invention provides new mosaic HIV-1 envelope designs, selection of HIV-1 envelopes and combinations thereof. In some aspects the invention is directed to methods of using these envelopes to induce antibody responses. In some aspects, these antibody responses include without limitation protective antibody responses, T-cells responses, or the combination thereof. Without being bound by theory, in some embodiments, these protective responses are associated with ADCC activity.

In certain embodiments, the invention provides a new strategy to decrease number of Envs needed while retraining good epitope diversity coverage—these new envelopes are referred to as "ADCC structural mosaics."

In some aspects the invention provides immunogenic compositions comprising any one of the envelopes listed in Table 1, for example as nucleic acids, proteins or combination thereof. In some embodiments these immunogens are designed to as gp120 envelopes. In some embodiments these immunogens are designed as immunogens which do not have closed envelope trimer structure. The invention provides that sets are complementary. They are solved simultaneously or serially. In some embodiments, these sets are serial. In some embodiments, the first members of sets can be used alone. In certain embodiments, while the second or subsequent member is complementary, in certain embodiments, is not to be used alone In certain aspects, the invention provides an immunogenic composition comprising a recombinant polypeptide of any one of the envelopes listed in Table 1 or FIG. 2, a nucleic acid encoding any one of the envelopes listed in Table 1 or FIG. 2, or a combination thereof. Non-limiting selections and rationale for selections and combinations are described in Example 1, and FIG. 1. In non-limiting embodiments, the recombinant envelope is ADCC-StrMos.B. 1+1.1Δ11gp120. In non-limiting embodiments, the recombinant envelope is ADCC-StrNat.B1Δ11gp120.

In certain embodiments, the composition comprises a recombinant envelopes in group GP502, ADCC-StrMos.B.1+1.1Δ11gp120 (SEQ ID NO: 12) and ADCC-StrMos.B.1+1.2Δ11gp120 (SEQ ID NO: 13), or a nucleic acids encoding these.

In certain embodiments, the composition comprises a recombinant envelopes in group GP503, ADCC-StrNat.B1Δ11gp120 (SEQ ID NO: 14) and ADCC-StrNat.B5Δ11gp120 (SEQ ID NO: 15), or nucleic acids encoding these.

In certain embodiments, wherein the composition comprises a recombinant envelope envelopes in group GP504, ADCC-StrNat.B1Δ11gp120 (SEQ ID NO: 14), ADCC-StrNat.B2Δ11gp120 (SEQ ID NO: 116), ADCC-StrNat.B3Δ11gp120 (SEQ ID NO: 17), ADCC-StrNat.B4Δ11gp120 (SEQ ID NO: 18), and ADCC-StrNat.B5Δ11gp120 (SEQ ID NO: 15), or nucleic acids encoding these.

In certain embodiments, the composition comprises recombinant envelopes in group GP505, ADCC-StrMos.M.3+2.4 Δ11gp120 (SEQ ID NO: 19) and ADCC-StrMos.M.3+2.5 Δ11gp120 (SEQ ID NO: 20), or nucleic acids encoding these.

In certain embodiments, the composition comprises a recombinant envelopes in group GP506, ADCC-StrMos.B.1+1.1Δ11gp120 (SEQ ID NO: 12), ADCC.StrMos.C.1+1.1Δ11gp120 (SEQ ID NO:21) and ADCC.StrMos.AE.1+1.1Δ11gp120 (SEQ ID NO: 22), or nucleic acids encoding these.

In certain aspects, the invention provides nucleic acid enocoding any one of the recombinant envelopes in the preceding claims wherein the nucleic acid is a modified mRNA.

In certain aspects, the invention provides nucleic acid enocoding any one of the recombinant envelopes in the preceding claims wherein the nucleic acid is operably linked to a promoter.

In certain embodiments, the compositions further comprise an adjuvant, and/or a carrier.

In certain aspects, the invention provides methods of inducing an immune response in a subject comprising administering to the subject an amount of the composition of the invention an amount sufficient to effect such induction. In certain embodiments the methods further comprise administering an adjuvant.

In certain embodiments the compositions are administered as a prime.

In certain embodiments the compositions are administered as a boost or multiple boosts.

In certain aspects the invention provides an isolated and purified recombinant envelope listed in Table 1 or FIG. 2, or a nucleic acid encoding the same.

In certain embodiments, the invention provides compositions comprising recombinant envelopes from GP502, ADCC-StrMos.B.1+1.1 and ADCC-StrMos.B.1+1.2, or a nucleic acids encoding these. In certain embodiments, the invention provides compositions comprising recombinant envelopes in group GP506, ADCC-StrMos.B.1+1.1, ADCC-.StrMos.C.1+1.1Δ11 and ADCC.StrMos.AE.1+1.1, or nucleic acids encoding these. In certain embodiments the nucleic acids are mRNAs.

The invention provides compositions immunogens and methods for inducing antibodies to the HIV-1 envelope, wherein in some embodiments, the compositions induce protective responses which in some embodiments are associated with ADCC activity.

In certain embodiments, the compositions comprise nucleic acid, as DNA and/or RNA, or proteins immunogens, for example either alone or in any combination. In certain embodiments, the methods comprise genetic, as DNA and/or RNA, immunization, for example alone or in combination with envelope protein(s). The method and/or compositions, whether comprising nucleic acids or recombinant proteins can further comprise any suitable adjuvant. In certain embodiments the invention provides that the immunogens are administered as stabilized mRNAs. See e.g. Pardi et al. Zika virus protection by a single low-dose nucleoside-modified mRNA vaccination. *Nature*, 2017; DOI: 10.1038/nature21428.

In certain embodiments the nucleic acid encoding an envelope is operably linked to a promoter inserted an expression vector. In certain aspects the compositions comprise a suitable carrier. In certain aspects the compositions comprise a suitable adjuvant.

In certain embodiments the induced immune response includes induction of antibodies, including but not limited to ADCC responses, autologous and/or cross-reactive (broadly) neutralizing antibodies against HIV-1 envelope. Various assays that analyze whether an immunogenic composition induces an immune response, and the type of antibodies induced are known in the art and are also described herein. Methods and assays to determine correlates of protection are known in the art.

In certain aspects the invention provides an expression vector comprising any of the nucleic acid sequences of the invention, wherein the nucleic acid is operably linked to a promoter. In certain aspects the invention provides an expression vector comprising a nucleic acid sequence encoding any of the polypeptides of the invention, wherein the nucleic acid is operably linked to a promoter. In certain embodiments, the nucleic acids are codon optimized for expression in a mammalian cell, in vivo or in vitro. In certain aspects the invention provides nucleic acids comprising any one of the nucleic acid sequences of invention. In certain aspects the invention provides nucleic acids consisting essentially of any one of the nucleic acid sequences of invention. In certain aspects the invention provides nucleic acids consisting of any one of the nucleic acid sequences of invention. In certain embodiments the nucleic acid of the invention, is operably linked to a promoter and is inserted in an expression vector. In certain aspects the invention provides an immunogenic composition comprising the expression vector.

In certain aspects the invention provides a composition comprising at least one of the nucleic acid sequences of the invention. In certain aspects the invention provides a composition comprising any one of the nucleic acid sequences of invention. In certain aspects the invention provides a composition comprising at least one nucleic acid sequence encoding any one of the polypeptides of the invention.

The envelope used in the compositions and methods of the invention can be in any suitable form: a gp160, gp150, gp145, any suitable form of a trimer, for example but not limited to SOSIP trimers, gp140 (including but not limited to gp140C, gp140CF, gp140CFI), gp120, gp41, N-terminal deletion variants (e.g. delta 11 deletions) as described herein, cleavage resistant variants, or codon optimized sequences thereof.

The polypeptide described herein can be a polypeptide comprising any one of the polypeptides described herein. The polypeptide can be a polypeptide consisting essentially of any one of the polypeptides described herein. The polypeptide described herein can be a polypeptide consisting of any one of the polypeptides described herein. In certain embodiments, the polypeptide is recombinantly produced. In certain embodiments, the polypeptides and nucleic acids of the invention are suitable for use as an immunogen, for example to be administered in a human subject.

The envelope used in the compositions and methods of the invention can be a gp160, gp150, gp145, gp140, gp120, gp41, N-terminal deletion variants as described herein, cleavage resistant variants as described herein, or codon optimized sequences thereof. In certain embodiments the composition comprises envelopes as trimers. In certain embodiments, envelope proteins are multimerized, for example envelopes are attached to a particle such that multiple copies are attached and the multimerized envelope is prepared and formulated for immunization in a human. In certain embodiments, the compositions comprise envelopes, as particulate, high-density array on liposomes or other particles, for example but not limited to nanoparticles. In some embodiments, the envelopes are in a well ordered, near native like or closed conformation.

In certain embodiments, where the nucleic acids are operably linked to a promoter and inserted in a vector, wherein the vector is any suitable vector. Non-limiting examples, include, the VSV, replicating rAdenovirus type 4, MVA, Chimp adenovirus vectors, pox vectors, and the like. In certain embodiments, the nucleic acids are administered in NanoTaxi block polymer nanospheres. In certain embodiments, the composition and methods comprise an adjuvant. Non-limiting examples include, 3M052, AS01 B, AS01 E, Gla/SE, alum, Poly I poly C (in any form, including but not limited to PolyIC/long chain (LC)), TLR agonists, TLR7/8 and 9 agonists, or a combination of TLR7/8 and TLR9 agonists (see Moody et al. (2014) J. Virol. March 2014 vol. 88 no. 6 3329-3339), or any other adjuvant. Non-limiting examples of TLR7/8 agonist include TLR7/8 ligands, Gardiquimod, Imiquimod and R848 (resiquimod). A non-limiting embodiment of a combination of TLR7/8 and TLR9 agonist comprises R848 and oCpG in STS (see Moody et al. (2014) J. Virol. March 2014 vol. 88 no. 6 3329-3339).

In certain aspects, the invention provides a kit comprising a combination/selection of immunogens, for example but not limited to combination of immunogens as described herein.

BRIEF DESCRIPTION OF THE FIGURES

FIGS. 1A-1K show embodiments of envelopes of the invention. SEQ ID Nos: 1-11 are the listed amino acid sequences. SEQ ID Nos: 12-22 the amino acid sequence without the leader peptide. These are envelopes used in the animal study described in Ex. 4, and corresponding figures. FIG. 1A illustrates SEQ ID NO. 1. FIG. 1B illustrates SEQ ID NO. 2. FIG. 1C illustrates SEQ ID NO. 3. FIG. 1D illustrates SEQ ID NO. 4. FIG. 1E illustrates SEQ ID NO.

5. FIG. 1F illustrates SEQ ID NO. 6. FIG. 1G illustrates SEQ ID NO. 7. FIG. 1H illustrates SEQ ID NO. 8. FIG. 1I illustrates SEQ ID NO. 9. FIG. 1J illustrates SEQ ID NO. 10. FIG. 1K illustrates SEQ ID NO. 11.

FIGS. 2A-2S show embodiments of envelopes of the invention. SEQ ID NOS. 23-35 and 32-37, respectively, in order of appearance.

FIG. 3-3S show embodiments of envelopes of the invention. Underlined are amino acids in the N-terminus which are deleted to generate deltaN variants. SEQ ID NOS. 23-35, 32-35 and 38-39, respectively, in order of appearance.

FIGS. 4A-4O show embodiments of envelopes of the invention. Delta N variants of a selection of the sequences in FIG. 3. SEQ ID NOS. 1-3, 40, 6-7, 4, 41-44, 11, 45, 8 and 46, respectively, in order of appearance.

FIGS. 5A-5O show embodiments of envelopes of the invention. Non-limiting embodiments of codon optimized nucleic acid sequences. SEQ ID NOS. 47-61, respectively, in order of appearance.

FIGS. 6A-6O show embodiments of envelopes of the invention. These sequences are a translation of the sequences of FIG. 5. SEQ ID NOS. 1-3, 40, 6-7, 4, 41-44, 11, 45, 8 and 46, respectively, in order of appearance.

Figure 7B:
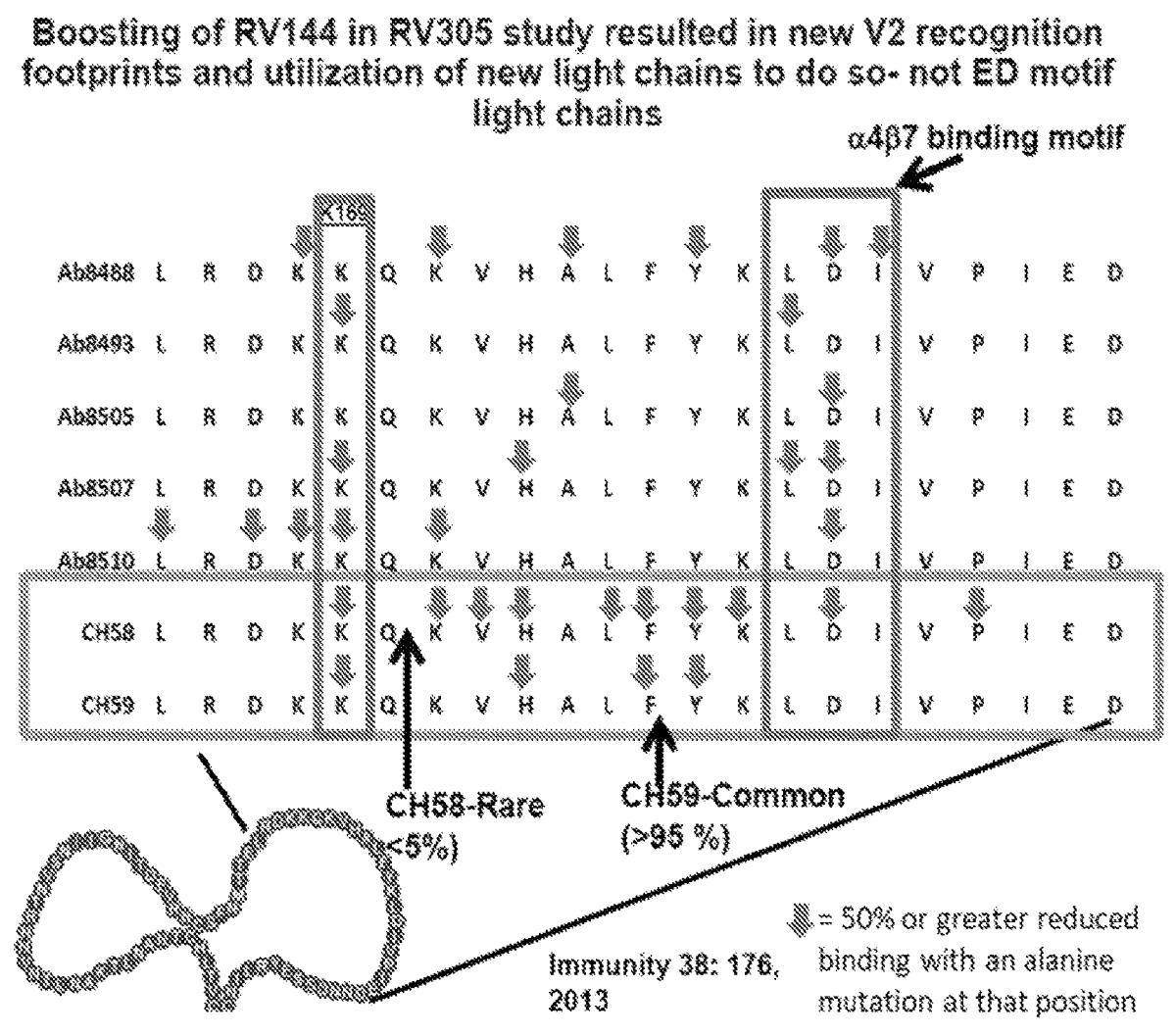
Figure 7C:
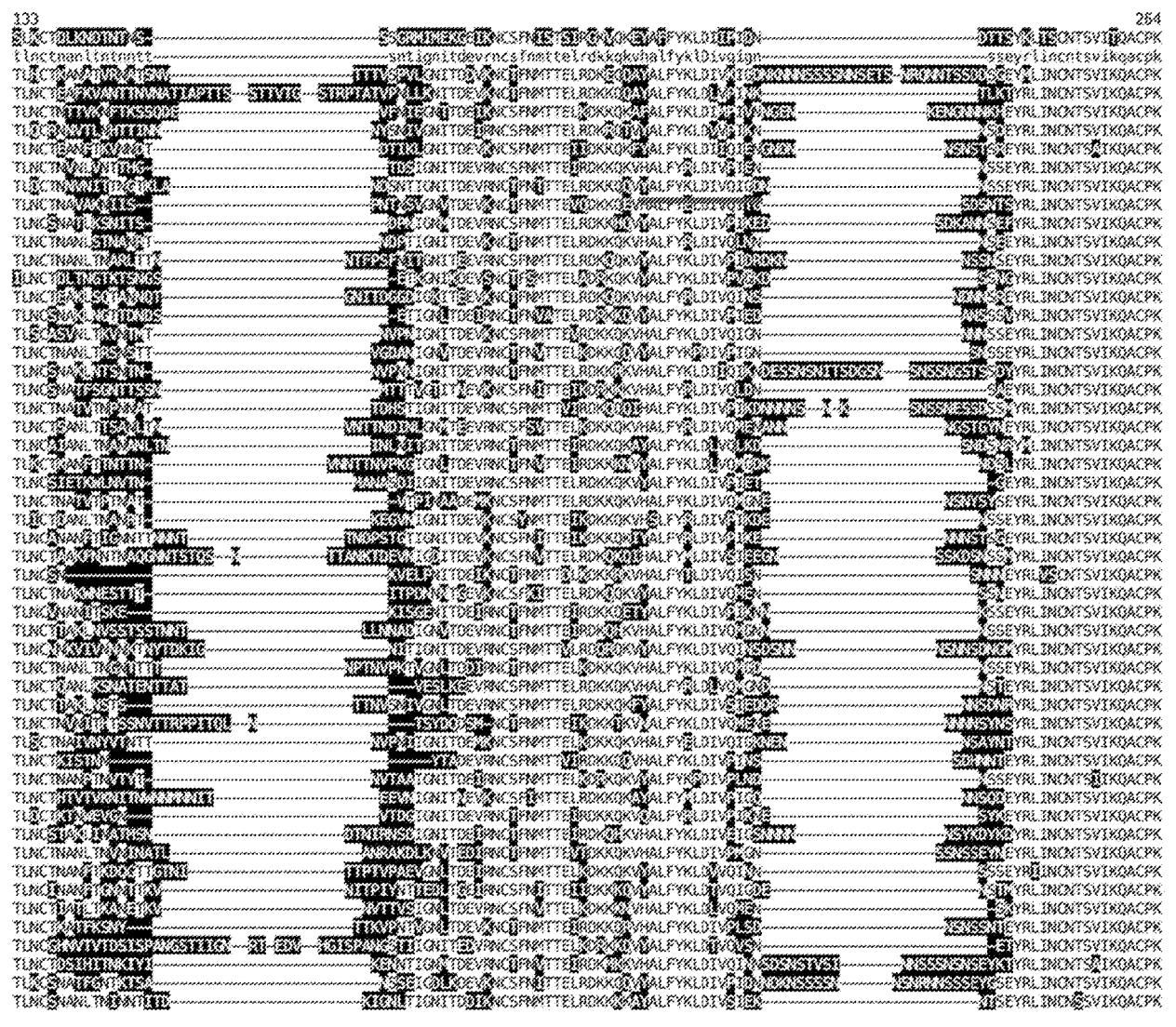

FIG. 7B shows that boosting RV144 participants in RV305 clinical trial resulted in a new V2 recognition footprints. FIG. 7B discloses SEQ ID NOS 62-69, respectively, in order of appearance. FIG. 7C shows that the V2 region that is highly variable, including V2 contacts (underlined in red). FIG. 7C discloses SEQ ID NOS 70-122, respectively, in order of appearance.

Figure 8:
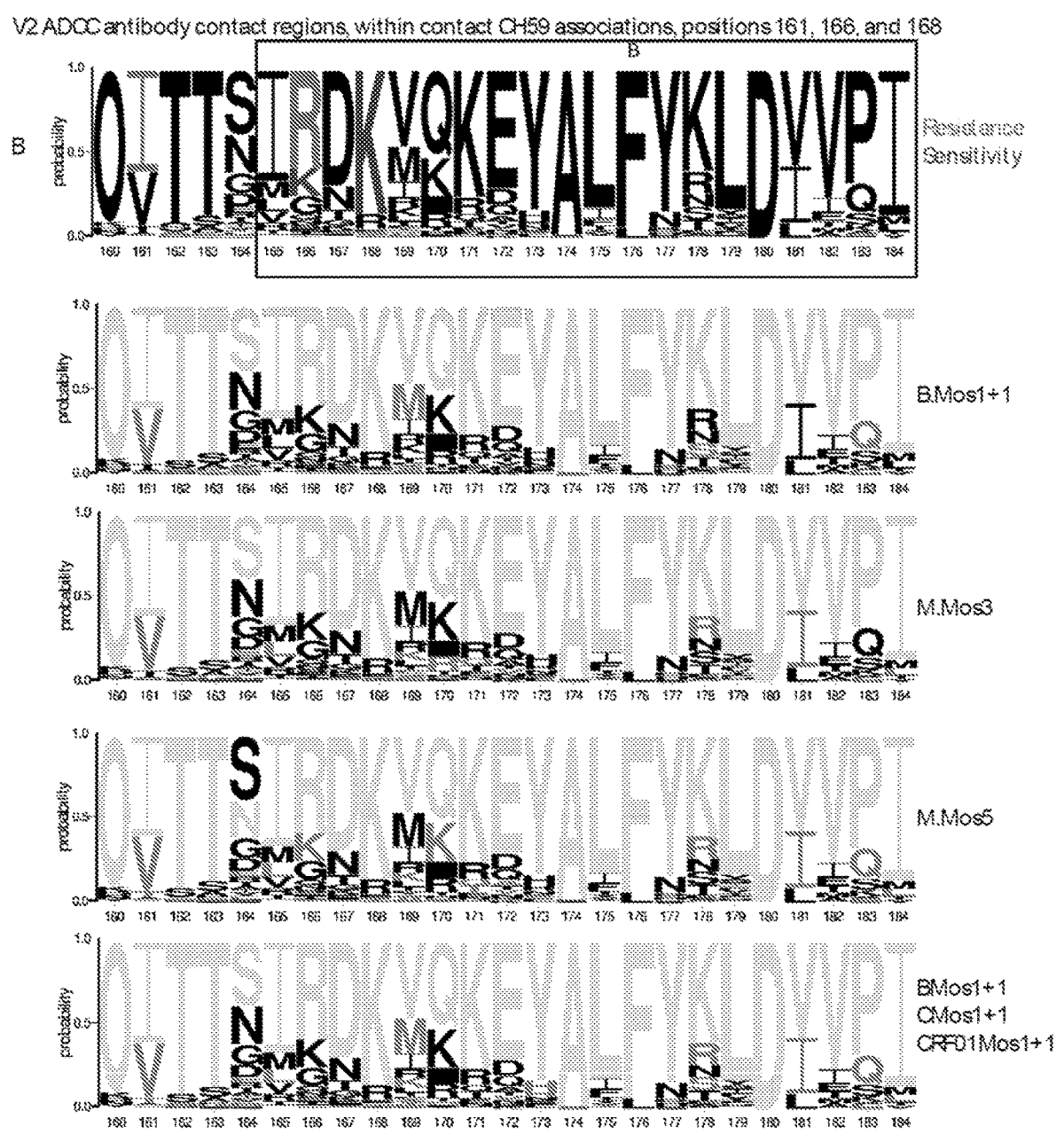

FIG. 8 is a schematic showing coverage of V2 epitopes and CH59 signatures in the B Glade by different epitope options. V2 ADCC antibody contact regions, within contact CH59 associations, positions 161, 166, and 168.

FIG. 10 discloses SEQ ID NOS 123-134, respectively, in order of appearance.

Figure 11:
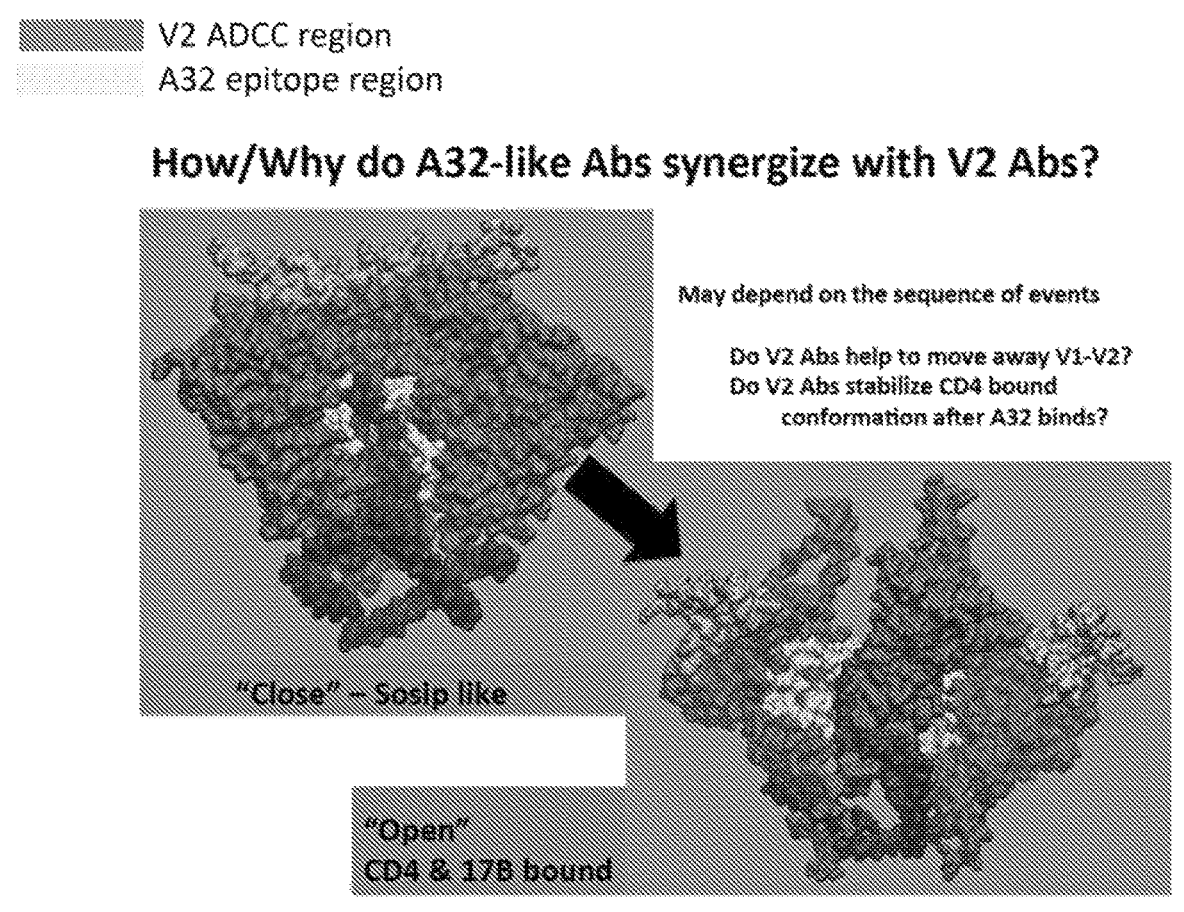

FIG. 11 shows structures of the A32 epitope. To incorporate structure, a single monomer from a CD4 bound open trimer was used.

FIG. 16 shows amino acids sequences, where V2 regions are "woven" in, no structures, unalignable. FIG. 16 discloses SEQ ID NOS 135-144, respectively, in order of appearance.

FIG. 17A discloses SEQ ID NOS 145-156, respectively, in order of appearance. FIG. 17B show embodiments of V3 sequences of ADCC mosaic envelopes of the invention. FIG. 17B discloses SEQ ID NOS 157-170, respectively, in order of appearance.

FIG. 17C shows embodiments of V3 sequences of the designated envelopes. "mutC" sequences have amino acid changes designed to reduce cleavage of the V3 loop during recombinant expression. FIG. 17C discloses SEQ ID NOS 171-173, 171, 174-175, 171 and 176-178, respectively, in order of appearance.

FIG. 18A shows a design of an animal study of ADCC mosaics versus natural Env gp120s. FIG. 18B shows immunization timeline for an animal study. In some embodiments, Gr. XX is Gr. 502, Gr. 503, Gr. 504, Gr. 505, or Gr. 506.

FIG. 30 shows Binding of guinea pig pre-bleed sera from the indicated groups (GP502-GP506) to gp120 protein was determined by indirect ELISA. Plates were coated with protein at 2 ug/ml and sera were tittered in 3 fold serial dilutions. Each titration was expressed as the log of area under the curve (Log AUC). Each symbol represents an individual animal within each group of six animals. Higher Log AUC represents greater binding to the test protein.

DETAILED DESCRIPTION OF THE INVENTION

Abbreviations and Definitions

Figure 7A:
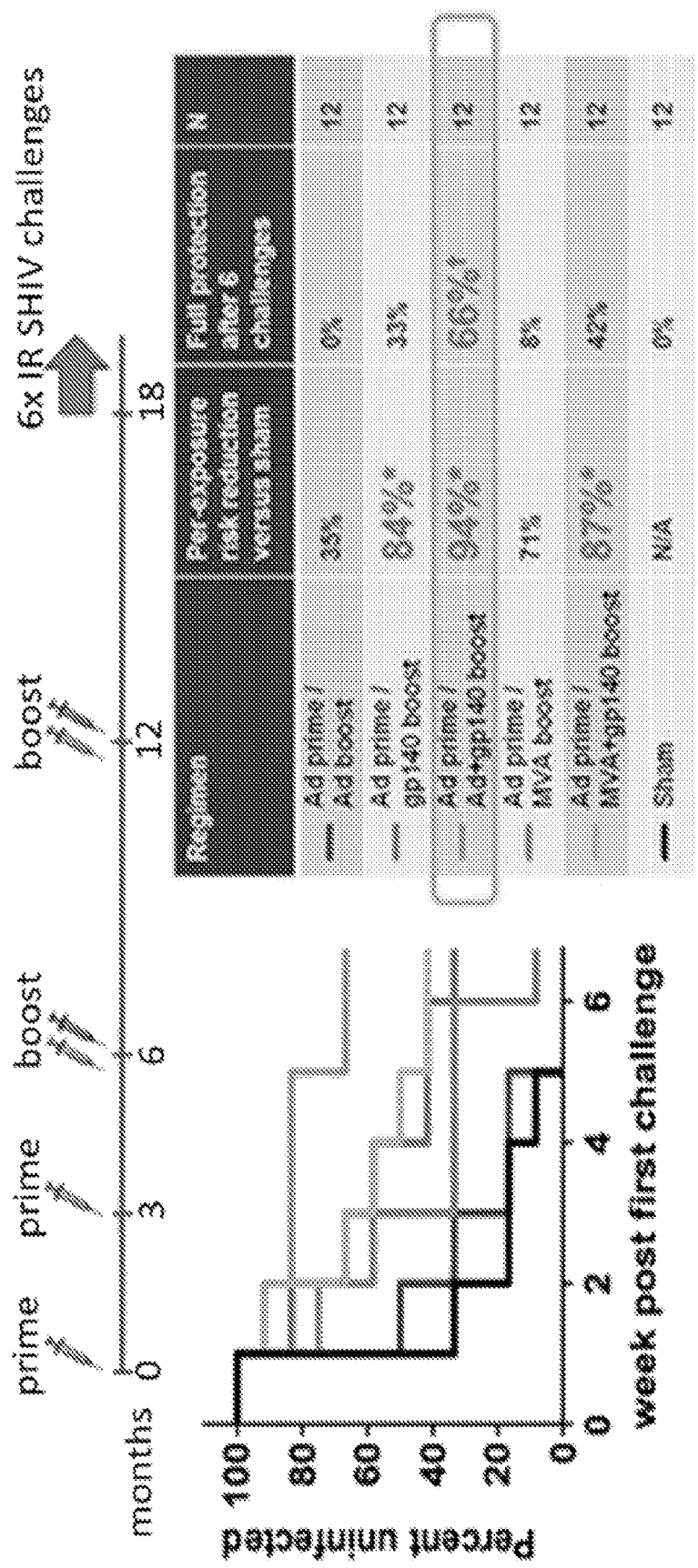
FIG. 7A shows a table adapted from an IAS presentation on Jul. 24, 2017 in Paris, France, entitled "Evaluation of lead HIV-1 vaccine regimen in APPROACH: Phase 1/2a study testing heterologous prime boost regimens using mosaic Ad26 and MVA vectors combined with Env protein" and an IAS presentation on Jul. 25, 2017 entitled "The Ad26/Ad26+ gp140 HIV Vaccine Regimen Provided Sigificant Protection against SHIV$_{SF162P3}$ Challenges in NHP (study 13-19*). After completion of TRAVERSE, proof of concept: HPX2008/HVTN 705. Correlates: Elisa, Elispot, ADCP: not tier 2 bNAbs.
Figure 9:
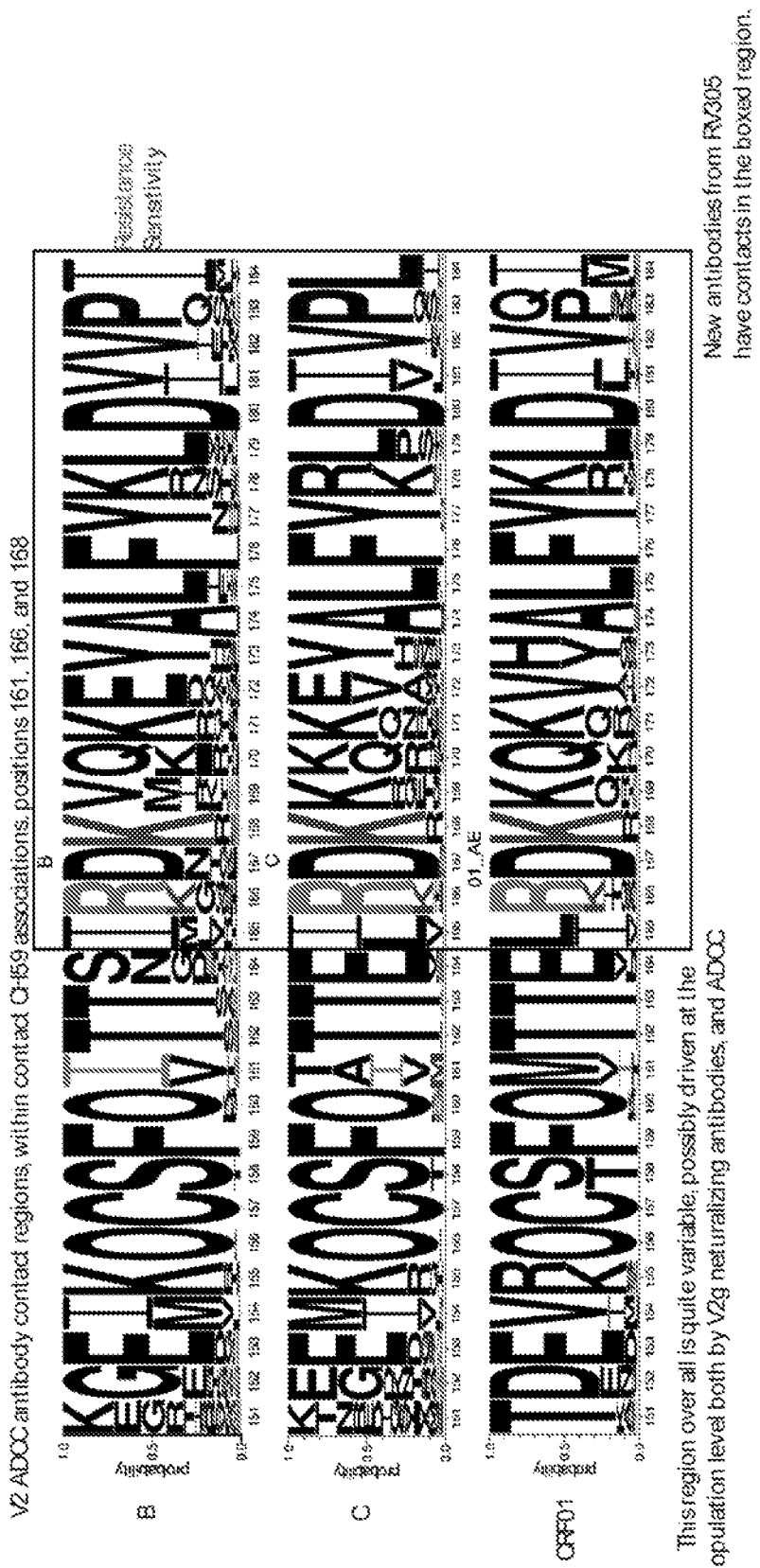
FIG. 9 is a schematic showing that V2 Ab CH59 has sensitivity signatures in the A32 contacts. These sensitivity signatures are also enriched in CRF01. Without being bound by theory, these A32 contacts enable V2 epitope exposure, similarly to H375 enabling A32 exposure in CRF01.
Figure 10:
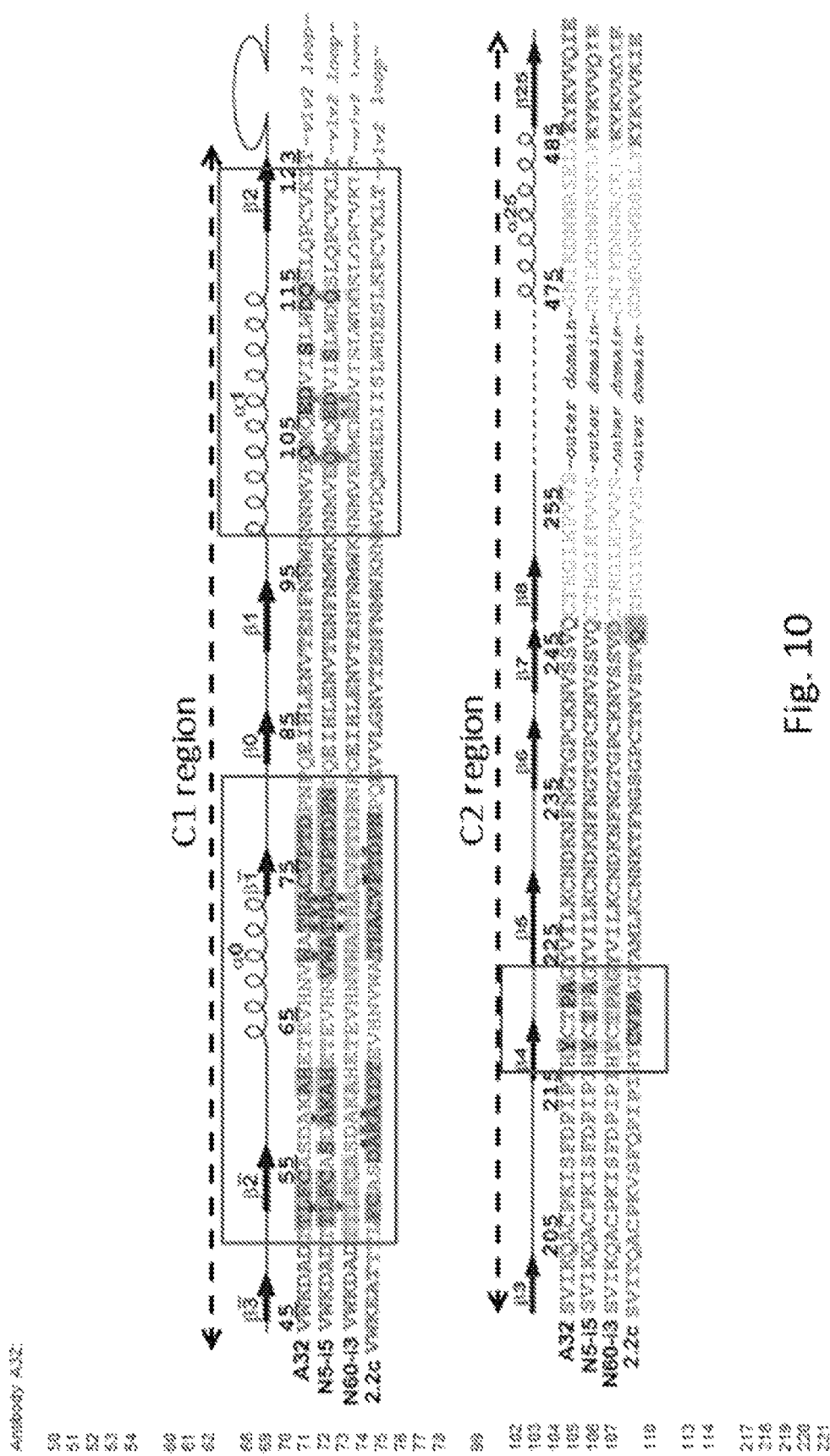
FIG. 10 is a schematic of the A32 maps to the C1-C2 regions of gp120. See also, Tolbert W D, Gohain N at al.(2016) Structure, 2016, 24(5):697-709; Gohain N, Tolbert at al. (2015) J Virol. 89(17):8840-54; and Acharya P, Tolbert at al. (2014) J Virol. 88(21):12895-906.
Figure 12:
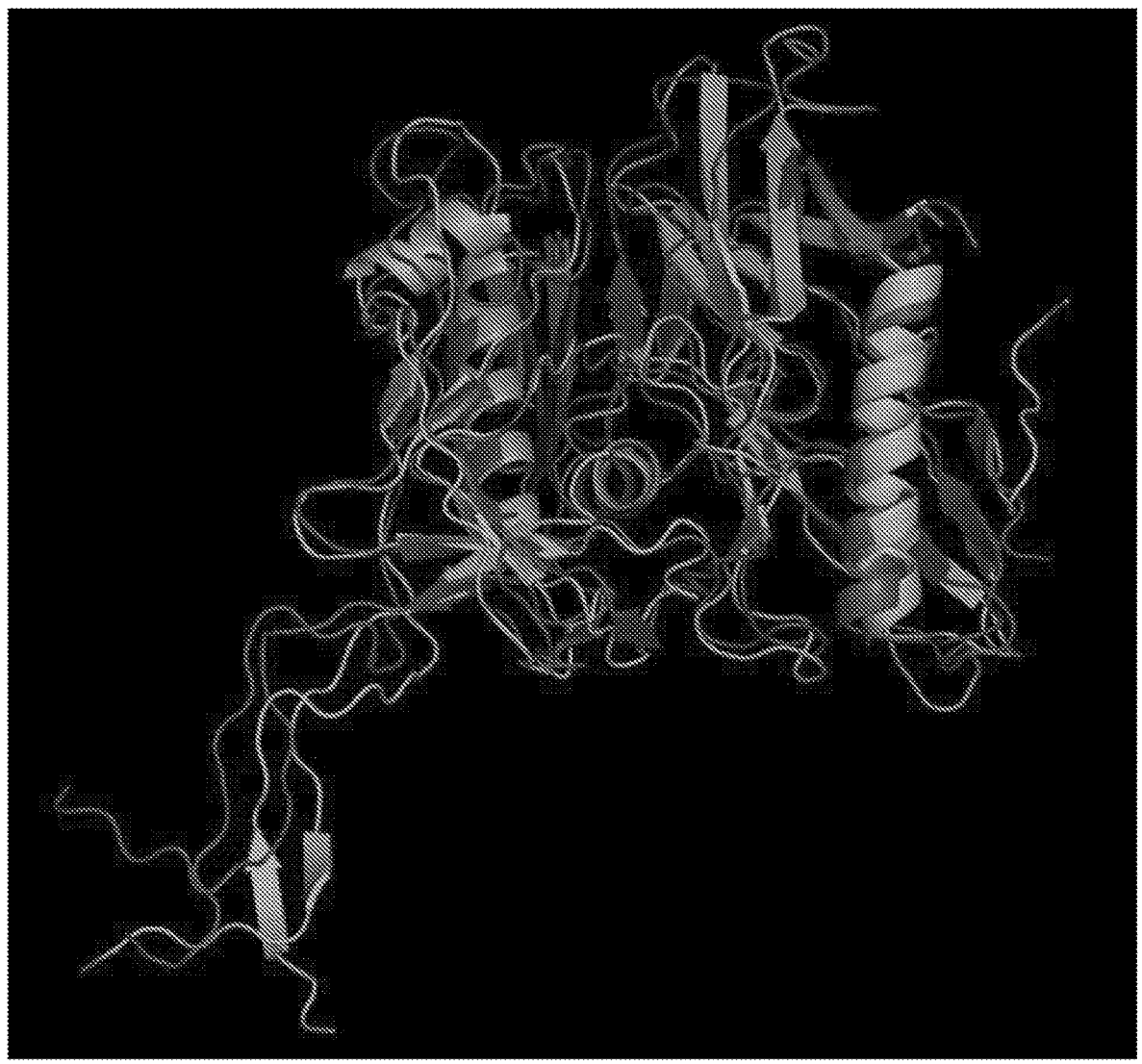
FIG. 12 shows a protein ribbon structure of the A32 epitope. A new CD4 bound open structure is shown in green, with a higher resolution, and more structural features. A similar trace in red is shown, but with less detail.
Figure 13:
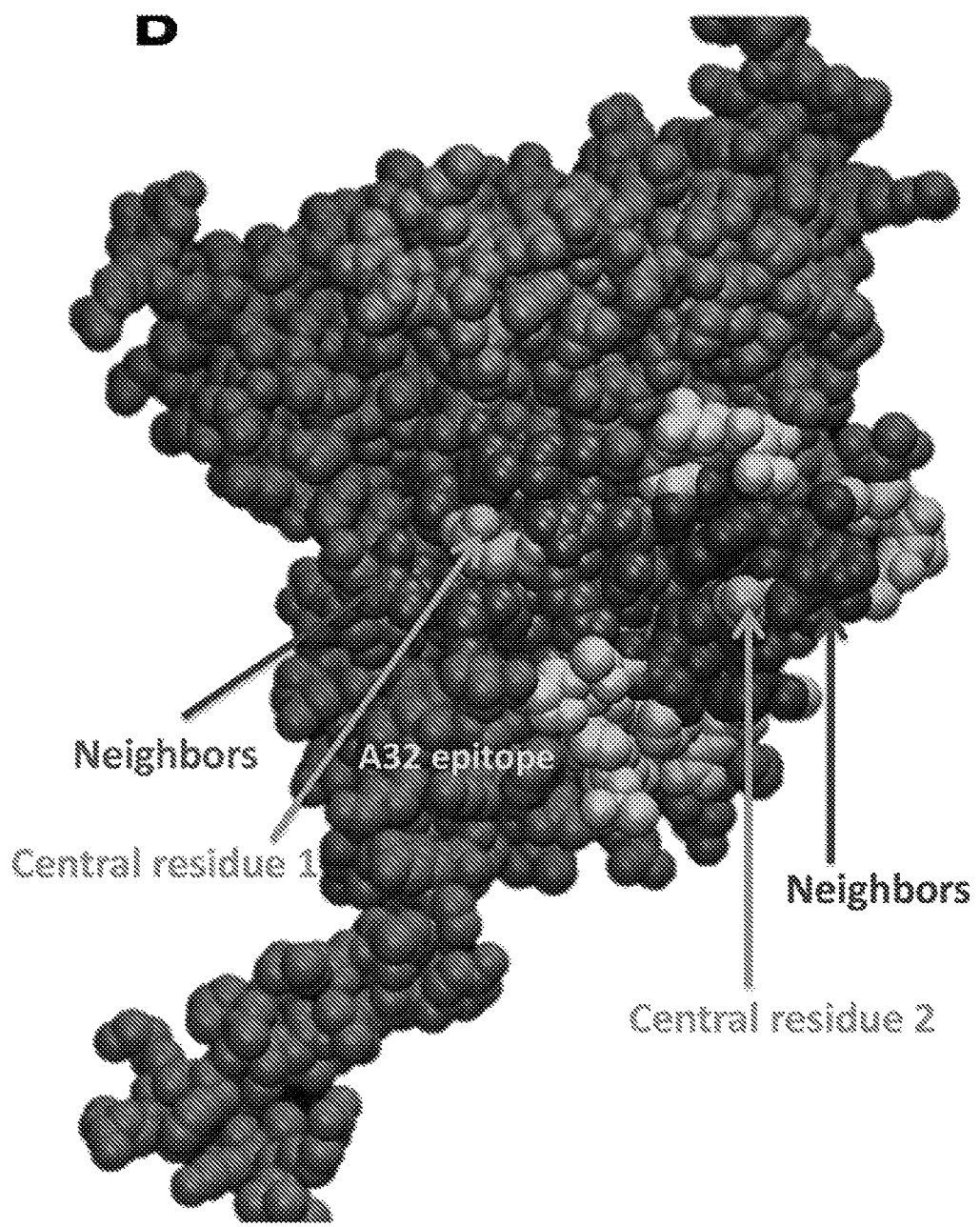
FIG. 13 shows a model of an HIV-1 envelope used for design of structural mosaics. Local regions: 8 closest amino acids defined for each amino acid in the structure: "local spheres." Any given amino acid is involved in many local spheres. Genetic algorithm: Maximize 3 dimensional potential epitope (=local sphere) coverage, choosing from among vast pools in silico recombinants that resemble natural proteins. Genetic algorithm solves for immunogen proteins that in combination yield the best population coverage of all local spheres in the structure. The whole structure is solved simultaneously, not just the A32 epitope in isolation. Sets are complementary, valency=2, 3, 5, or 6.
Figure 14:
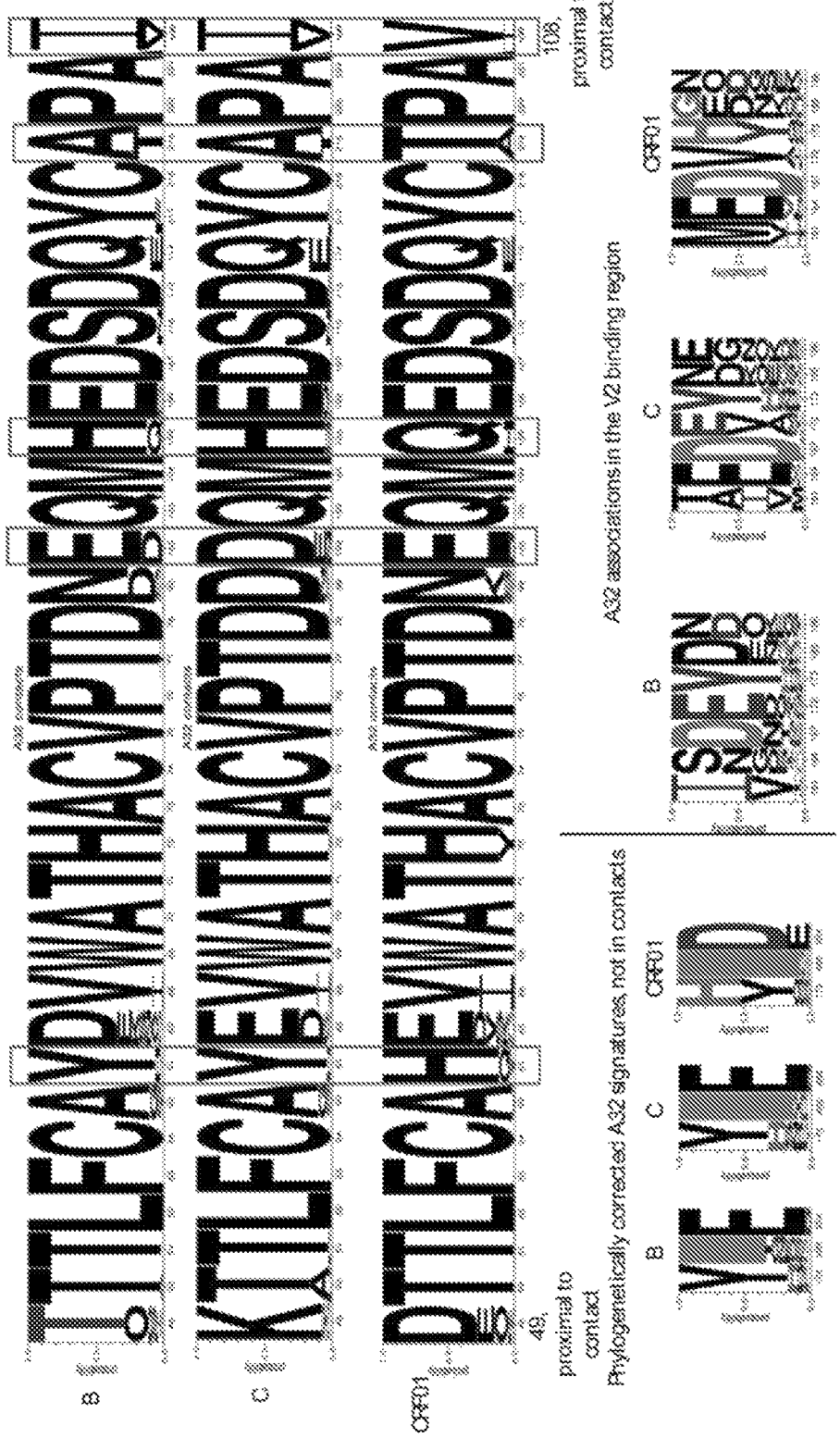
FIG. 14 shows a schematic of a signature analysis, A32 contacts.
Figure 15:
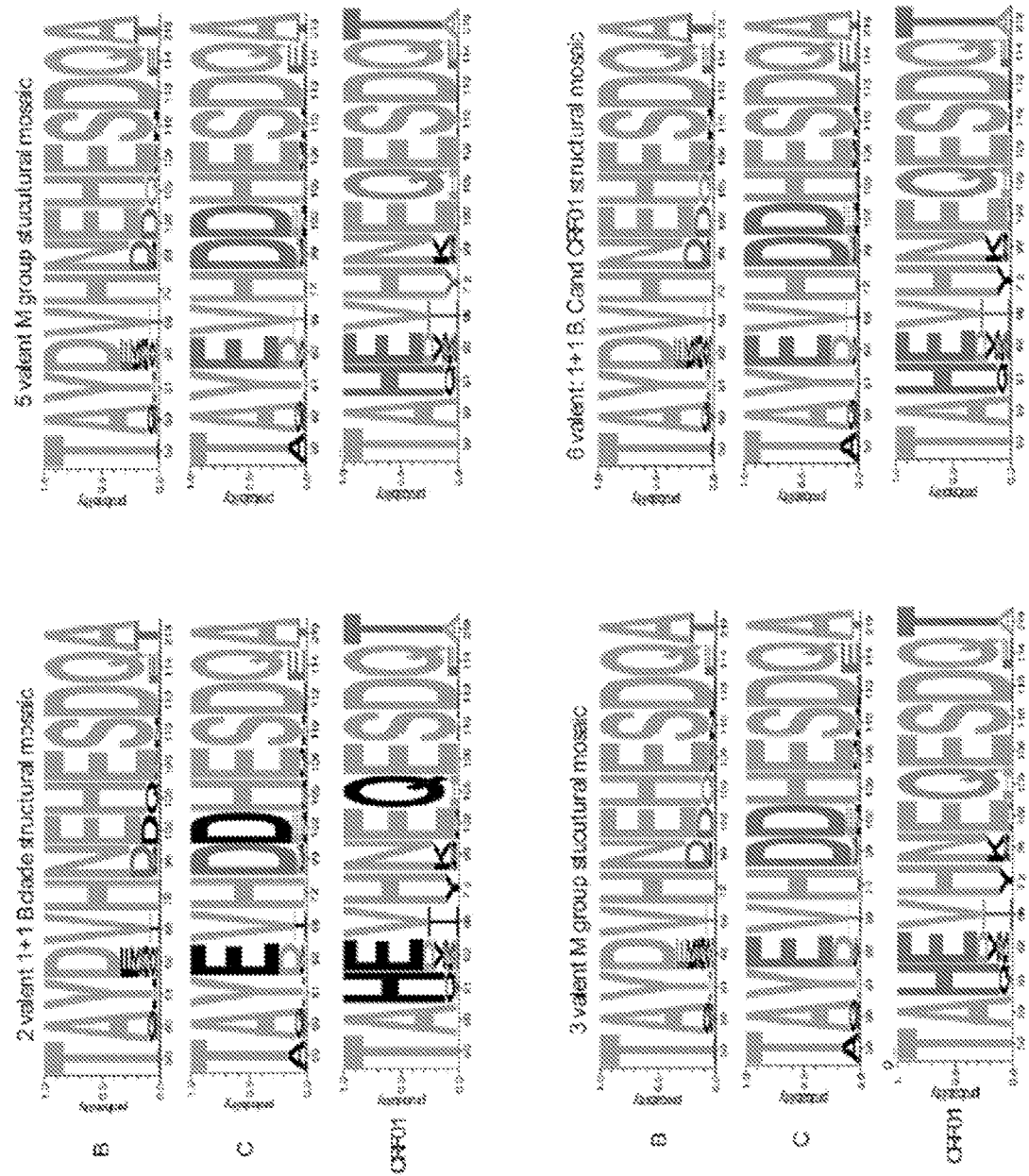
FIG. 15 shows a schematic of variable position in the A32 contacts and vaccine coverage. Variable positions in the A32 contact surface.—coverage of different clades by different vaccine options. The green text represents B Glade consensus amino acids. The pink text represents other amino acids in the vaccine. The coverage of A32 contact diversity is improved considerably by going to an M group vaccine, even with the B Glade.

Detailed descriptions of one or more embodiments are provided herein. It is to be understood, however, that the invention can be embodied in various forms. Therefore, specific details disclosed herein are not to be interpreted as limiting, but rather as a basis for the claims and as a representative basis for teaching one skilled in the art to employ the invention in any appropriate manner.

The singular forms "a", "an" and "the" include plural reference unless the context clearly dictates otherwise. The use of the word "a" or "an" when used in conjunction with the term "comprising" in the claims and/or the specification can mean "one," but it is also consistent with the meaning of "one or more," "at least one," and "one or more than one."

Wherever any of the phrases "for example," "such as," "including" and the like are used herein, the phrase "and without limitation" is understood to follow unless explicitly stated otherwise. Similarly "an example," "exemplary" and the like are understood to be non-limiting.

The term "substantially" allows for deviations from the descriptor that do not negatively impact the intended purpose. Descriptive terms are understood to be modified by the term "substantially" even if the word "substantially" is not explicitly recited.

The terms "comprising" and "including" and "having" and "involving" (and similarly "comprises", "includes," "has," and "involves") and the like are used interchangeably and have the same meaning. Specifically, each of the terms is defined consistent with the common United States patent law definition of "comprising" and is therefore interpreted to be an open term meaning "at least the following," and is also interpreted not to exclude additional features, limitations, aspects, etc. Thus, for example, "a process involving steps a, b, and c" means that the process includes at least steps a, b and c. Wherever the terms "a" or "an" are used, "one or more" is understood, unless such interpretation is nonsensical in context.

As used herein the term "about" is used herein to mean approximately, roughly, around, or in the region of. When the term "about" is used in conjunction with a numerical range, it modifies that range by extending the boundaries above and below the numerical values set forth. In general, the term "about" is used herein to modify a numerical value above and below the stated value by a variance of 20 percent up or down (higher or lower).

In certain embodiment, the invention provides a composition comprising any one of the inventive proteins, wherein the composition comprises purified homogenously glycosylated protein. In certain embodiments, about 70%, 75%, 80%, 85%, 90%, 95%, 99%, or 99.9% of the proteins in the composition are homogenously glycosylated. In certain embodiments, 70%, 75%, 80%, 85%, 90%, 95%, 99%, or 99.9% of the proteins in the composition are homogenously glycosylated. In certain embodiments, 70%-75%, 75.1%-80%, 80.1%-85%, 85.1%-90%, 90.1%-95%, 95.1%-99%, 96%-99%, 97%-99%, 98%-99% or 99.9% of the proteins in the composition are homogenously glycosylated.

Various methods of determining the glycosylation pattern on a peptide are known in the art. In certain embodiments, glycosylation pattern on the peptides and % homogeneity can be determined by Liquid chromatography—mass spectrometry (LC-MS, or alternatively HPLC-MS).

The immunogens can be formulated with appropriate carriers using standard techniques to yield compositions suitable for administration. The compositions can include an adjuvant, such as, for example, alum, poly IC, poly IC/LC, MF-59 or other squalene-based adjuvant, ASO1B or other liposomal based adjuvant suitable for protein immunization. Suitable vaccine strategies include without limitation, e.g., those described in the Examples that follow.

Nucleic acid sequences (e.g., DNA sequences) encoding the immunogens can also be administered to a subject (e.g., a human) under conditions such that the immunogen is expressed in vivo and BNAbs are produced. The DNA can be naked DNA with a potent promoter such as the CMV promoter as used in the pCMVr plasmid (Churchyard et al, PLoS One 6:e21225 (2011)) or as an insert in a vector, such as a rAdenoviral (Barouch, et al. Nature Med. 16: 319-23 (2010), recombinant mycobacterial (i.e., BCG or *M smegmatis*) (Yu et al. Clinical Vaccine Immunol. 14: 886-093 (2007); ibid 13: 1204-11 (2006), or recombinant vaccinia type of vector (Santra S. Nature Med. 16: 324-8 (2010)).

Immunogens of the invention, and nucleic acids (e.g., DNAs) encoding same, are suitable for use in generating an immune response (e.g., BNAbs) in a patient (e.g., a human patient) to HIV-1. The V3 N301, N332 peptide glycan can optimally be administered as a peptide-glycan formulated in a squalene based adjuvant such as MF 59, or GLA-SE (Alving et al, Current Opinion in Immunology 24:310 (2012)). The mode of administration of the immunogen, or encoding sequence, can vary with the immunogen to be administered, the patient and the effect sought, similarly, the dose administered. For example, the administration route is intramuscular or subcutaneous injection (intravenous and intraperitoneal can also be used). Additionally, the formulations can be administered via the intranasal route, or intrarectally or vaginally as a suppository-like vehicle. Optimum dosing regimens can be readily determined by one skilled in the art. The immunogens (and nucleic acids encoding same) are for use prophylactically, however, their administration to infected individuals can reduce viral load.

The invention includes the specific protein immunogens disclosed herein and nucleic acids comprising nucleotide sequences encoding same. The proteins can be expressed, for example, in 293T cells, 293F cells or CHO cells (Liao et al, Virology 353:268-82 (2006)).

In some embodiments the antigens are nucleic acids, including but not limited to mRNAs which could be modified and/or unmodified. See US Pub 20180028645A1, US Pub 20170369532, US Pub 20090286852, US Pub 20130111615, US Pub 20130197068, US Pub 20130261172, US Pub 20150038558, US Pub 20160032316, US Pub 20170043037, US Pub 20170327842, each content is incorporated by reference in its entirety.

In certain embodiments, where the composition comprises nucleic acids such as mRNA, whether modified or unmodified, the mRNAs could be formulated in lipid nanoparticles (LNPs). See US Pub 20180028645A1 and WO 2015/164674), where the content is incorporated by reference in its entirety. mRNAs delivered in LNP formulations have advantages over non-LNPs formulations. See US Pub 20180028645A1.

In some aspects the invention provides vectors comprising the nucleic acids of the invention. In some aspects, the invention provides a host cell, cell cultures or plurality of host cells comprising the nucleic acids of the invention.

Sequences/Clones

Described herein are nucleic and amino acids sequences of HIV-1 envelopes. The sequences for use as immunogens are in any suitable form. In certain embodiments, the described HIV-1 envelope sequences are gp160s. In certain embodiments, the described HIV-1 envelope sequences are gp120s. Other sequences, for example but not limited to stable SOSIP trimer designs, gp145s, gp140s, both cleaved and uncleaved, gp140 Envs with the deletion of the cleavage (C) site, fusion (F) and immunodominant (I) region in gp41—named as gp140ΔCFI (gp140CFI), gp140 Envs with the deletion of only the cleavage (C) site and fusion (F) domain—named as gp140ΔCF (gp140CF), gp140 Envs with the deletion of only the cleavage (C)—named gp140ΔC (gp140C) (See e.g. Liao et al. Virology 2006, 353, 268-282), gp150s, gp41s, which are readily derived from the nucleic acid and amino acid gp160 sequences. In certain embodiments the nucleic acid sequences are codon optimized for optimal expression in a host cell, for example a mammalian cell, a rBCG cell or any other suitable expression system.

An HIV-1 envelope has various structurally defined fragments/forms: gp160; gp140—including cleaved gp140 and uncleaved gp140 (gp140C), gp140CF, or gp140CFI; gp120 and gp41. A skilled artisan appreciates that these fragments/forms are defined not necessarily by their crystal structure, but by their design and bounds within the full length of the gp160 envelope. While the specific consecutive amino acid sequences of envelopes from different strains are different, the bounds and design of these forms are well known and characterized in the art.

For example, it is well known in the art that during its transport to the cell surface, the gp160 polypeptide is processed and proteolytically cleaved to gp120 and gp41 proteins. Cleavages of gp160 to gp120 and gp41 occurs at a conserved cleavage site "REKR." See Chakrabarti et al. Journal of Virology vol. 76, pp. 5357-5368 (2002) see for example FIG. 1, and Second paragraph in the Introduction on p. 5357; Binley et al. Journal of Virology vol. 76, pp. 2606-2616 (2002) for example at Abstract; Gao et al. Journal of Virology vol. 79, pp. 1154-1163 (2005); Liao et al. Virology vol. 353(2): 268-282 (2006).

The role of the furin cleavage site is well understood both in terms of improving cleave efficiency, see Binley et al. supra, and eliminating cleavage, see Bosch and Pawlita, Virology 64 (5):2337-2344 (1990); Guo et al. Virology 174: 217-224 (1990); McCune et al. Cell 53:55-67 (1988); Liao et al. J Virol. Apr; 87(8):4185-201 (2013).

Likewise, the design of gp140 envelope forms is also well known in the art, along with the various specific changes which give rise to the gp140C (uncleaved envelope), gp140CF and gp140CFI forms. Envelope gp140 forms are designed by introducing a stop codon within the gp41 sequence. See Chakrabarti et al. at FIG. 1.

Envelope gp140C refers to a gp140 HIV-1 envelope design with a functional deletion of the cleavage (C) site, so that the gp140 envelope is not cleaved at the furin cleavage site. The specification describes cleaved and uncleaved forms, and various furin cleavage site modifications that prevent envelope cleavage are known in the art. In some embodiments of the gp140C form, two of the R residues in and near the furin cleavage site are changed to E, e.g., RRVVEREKR (SEQ ID NO: 180) is changed to ERVVEREKE (SEQ ID NO: 181), and is one example of an uncleaved gp140 form. Another example is the gp140C form which has the REKR site (SEQ ID NO: 182) changed to SEKS (SEQ ID NO: 183). See supra for references.

Envelope gp140CF refers to a gp140 HIV-1 envelope design with a deletion of the cleavage (C) site and fusion (F) region. Envelope gp140CFI refers to a gp140 HIV-1 envelope design with a deletion of the cleavage (C) site, fusion (F) and immunodominant (I) region in gp41. See Chakrabarti et al. Journal of Virology vol. 76, pp. 5357-5368 (2002) see for example FIG. 1, and Second paragraph in the Introduction on p. 5357; Binley et al. Journal of Virology vol. 76, pp. 2606-2616 (2002) for example at Abstract; Gao et al. Journal of Virology vol. 79, pp. 1154-1163 (2005); Liao et al. Virology vol. 353(2): 268-282 (2006).

In certain embodiments, the envelope design in accordance with the invention involves deletion of residues (e.g., 5-11, 5, 6, 7, 8, 9, 10, or 11 amino acids) at the N-terminus. For delta N-terminal design, amino acid residues ranging from 4 residues or even fewer to 14 residues or even more are deleted. These residues are between the maturation (signal peptide, for example ending with CXX, X can be any amino acid) and "VPVXXXX . . . ". In certain embodiments, the invention comprises an immunogen, gp160, gp120 or gp140, without an N-terminal Herpes Simplex gD tag substituted for amino acids of the N-terminus of gp120, with an HIV leader sequence (or other leader sequence), and without the original about 4 to about 25, for example 4, 5, 6, 7, 8, 9, 10, 11, 12, 13, 14, 15, 16, 17, 18, 19, 20, 21, 22, 23, 24, 25 amino acids of the N-terminus of the envelope (e.g. gp120). See WO2013/006688, e.g. at pages 10-12, the contents of which publication is hereby incorporated by reference in its entirety.

The general strategy of deletion of N-terminal amino acids of envelopes results in proteins, for example gp120s, expressed in mammalian cells that are primarily monomeric, as opposed to dimeric, and, therefore, solves the production and scalability problem of commercial gp120 Env vaccine production. In other embodiments, the amino acid deletions at the N-terminus result in increased immunogenicity of the envelopes.

In certain embodiments, the invention provides envelope sequences, amino acid sequences and the corresponding nucleic acids, and in which the V3 loop is substituted with the following V3 loop sequence TRPNNNTRKSIRIGPGQTFY ATGDIIGNIRQAH (SEQ ID NO: 171). This substitution of the V3 loop reduced product cleavage and improves protein yield during recombinant protein production in CHO cells. Other strategies for eliminating cleavage during recombinant production can be used.

Within the sequences disclosed herein, the deltaN is deletion of amino acids (whatever number) immediately after signal peptide and up to the sequences VPV.

Figure 17A:
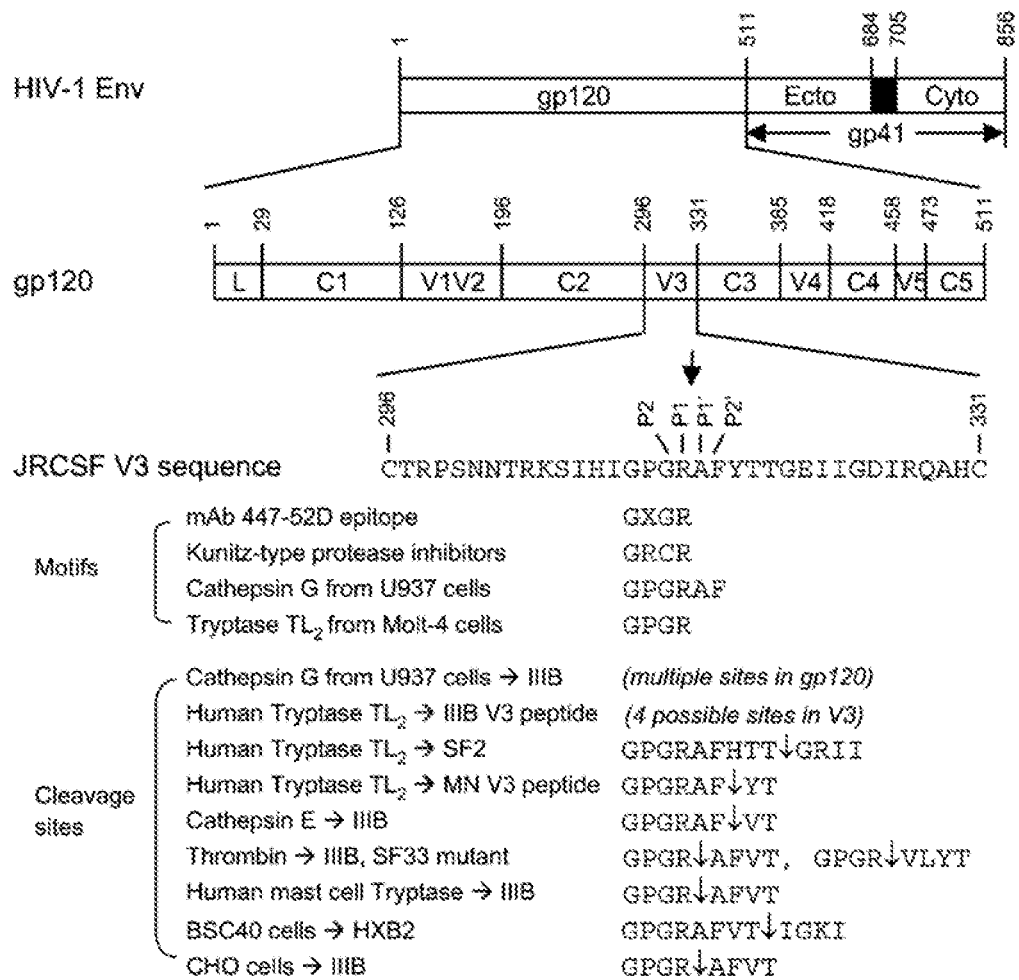
FIG. 17A shows a schematic where the V3 loop can be fixed to prevent cleavage during recombinant production for example, by taking GPGR/S/K and making it into GPGQ (SEQ ID NO: 179), and also taking the Ala after the R/S/K and making it into T to prevent cleavage during recombinant production. In some embodiments, protease inhibitors also work, other mutations can also be made to reduce or eliminate the cleavage of the protein during recombinant production.
Figure 19:
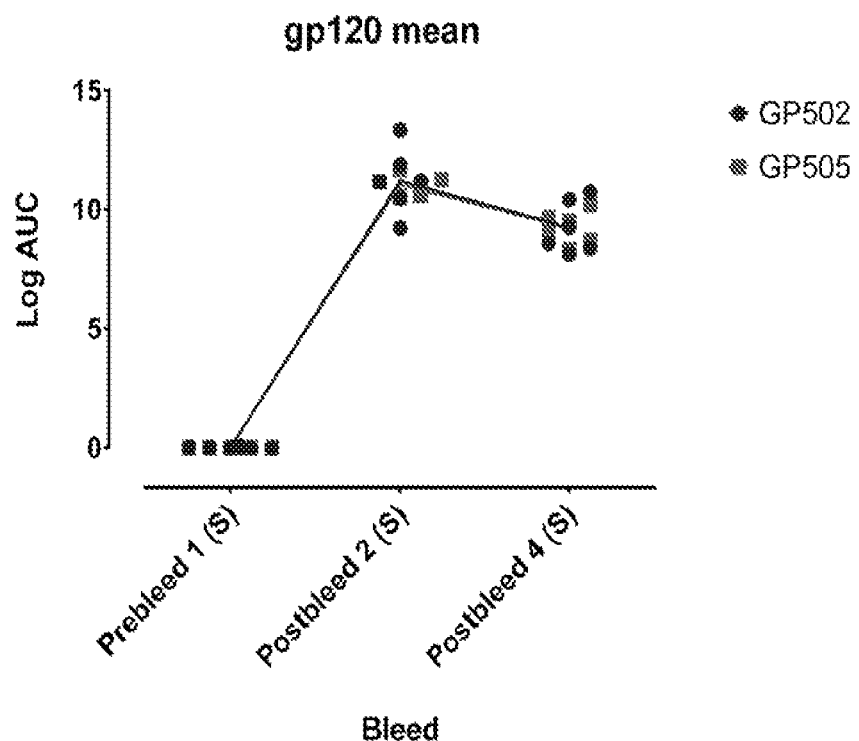
FIG. 19 shows the gp120 average score for the entire gp120 panel (all the members of the panel listed on the next slide). Compares the key groups with each other. Mean binding of guinea pig sera from the indicated groups (GP502-GP506) to eight different gp120's from multiple clades was determined by indirect ELISA at pre-bleed and post bleeds 2 and 4. Plates were coated with protein at 2 ug/ml and sera were tittered in 3 fold serial dilutions. Each titration was expressed as the log of area under the curve (Log AUC). Each symbol represents the average data for an individual animal within each group of six animals. Higher Log AUC represents greater binding to the test protein.
Figure 19:
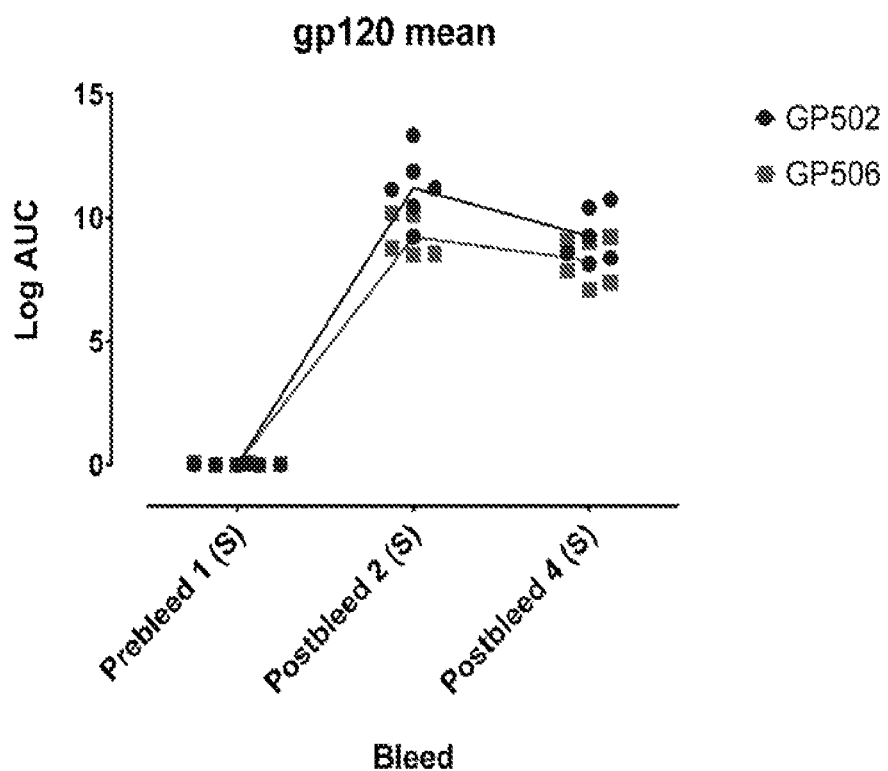
Figure 19:
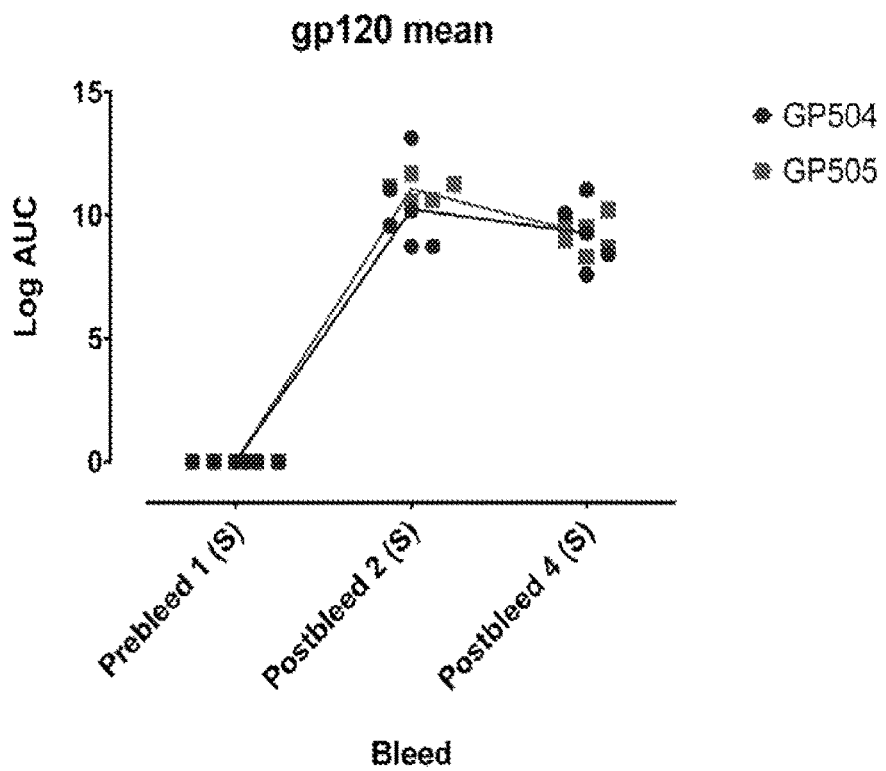
Figure 19:
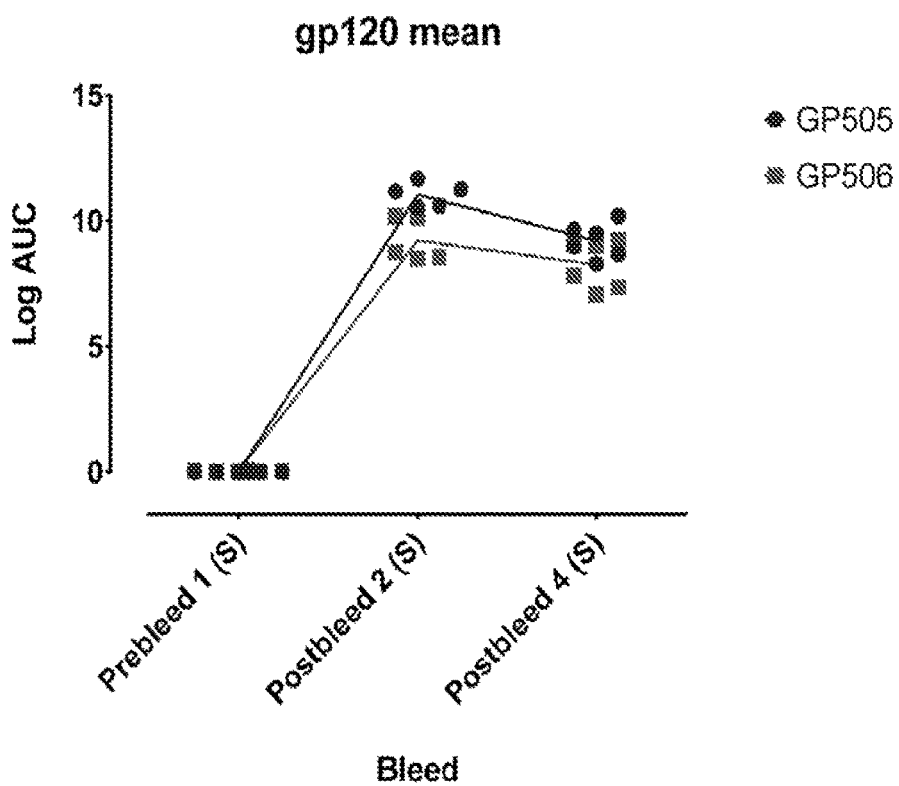
Figure 20:
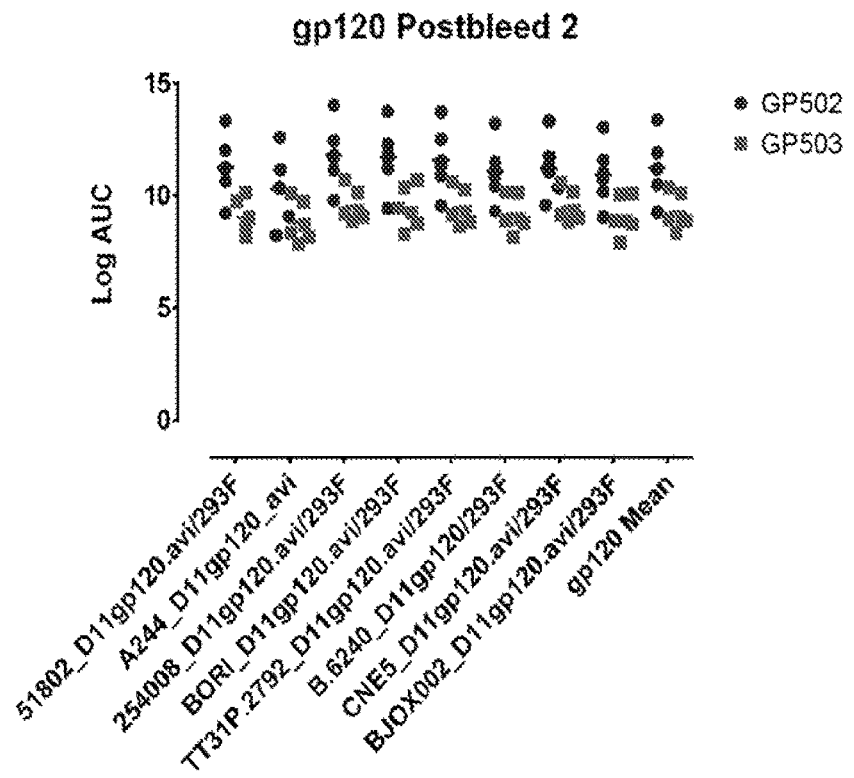
FIG. 20 shows the reactivity of postbleed 2 of the indicated groups for the entire gp120 panel. Compares the key groups with each other to give a visual of how the groups did on each env. Binding of post bleed 2 guinea pig sera from the indicated groups (GP502-GP506) to gp120 was determined by indirect ELISA. Plates were coated with protein at 2 ug/ml and sera were tittered in 3 fold serial dilutions. Each titration was expressed as the log of area under the curve (Log AUC). Each symbol represents an individual animal within each group of six animals. Higher Log AUC represents greater binding to the test protein.
Figure 20:
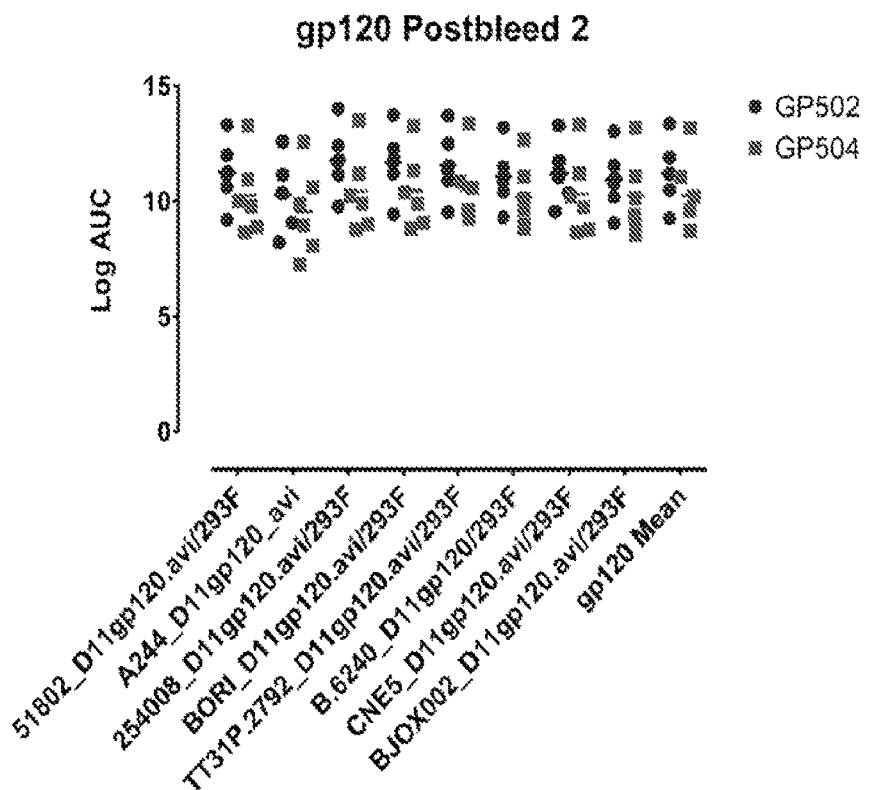
Figure 20:
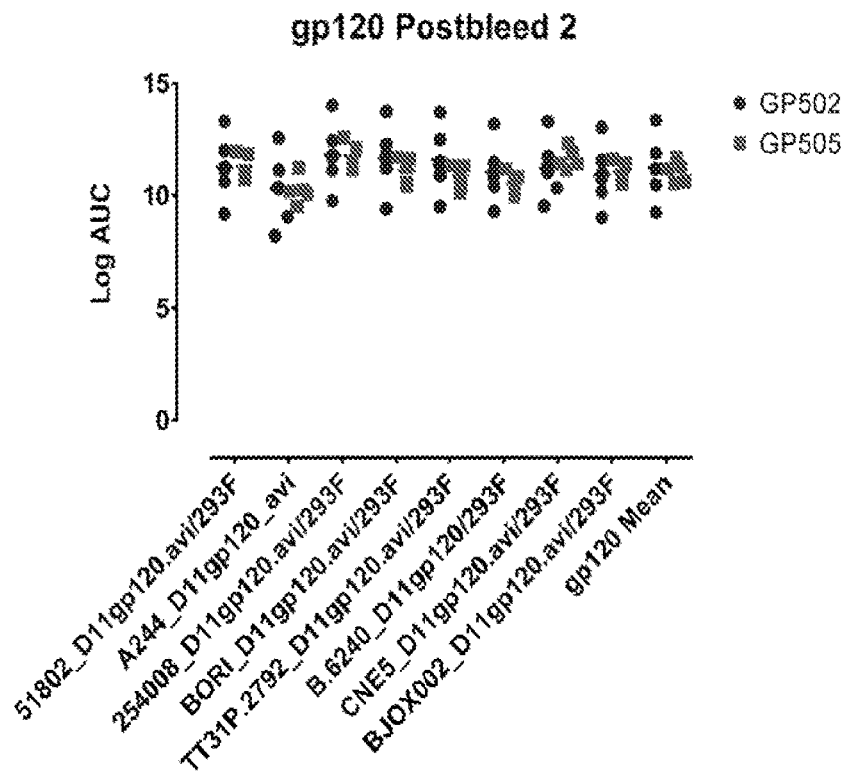
Figure 20:
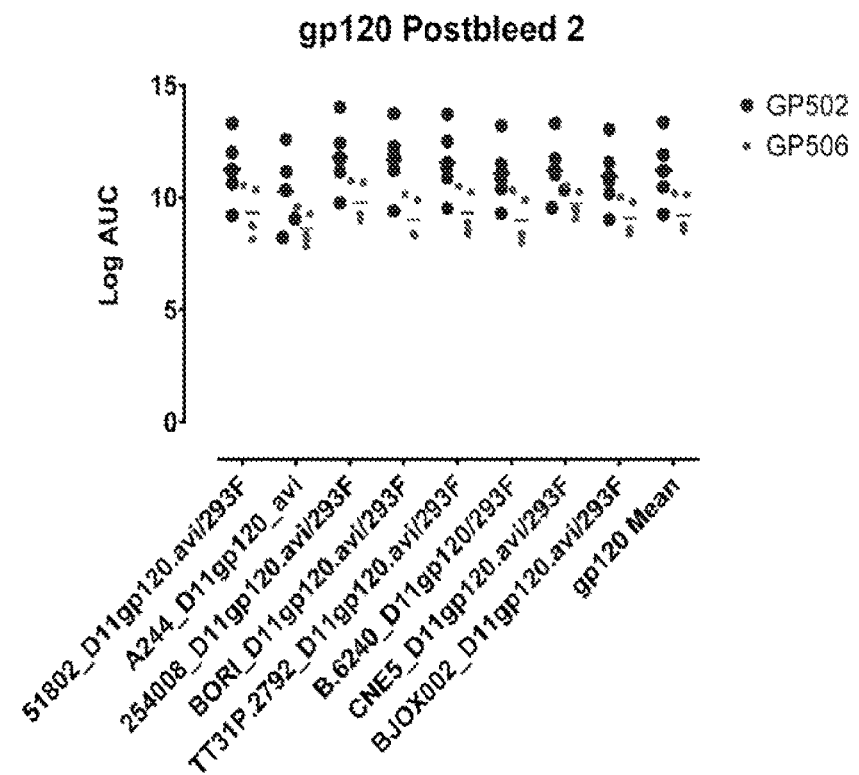
Figure 20:
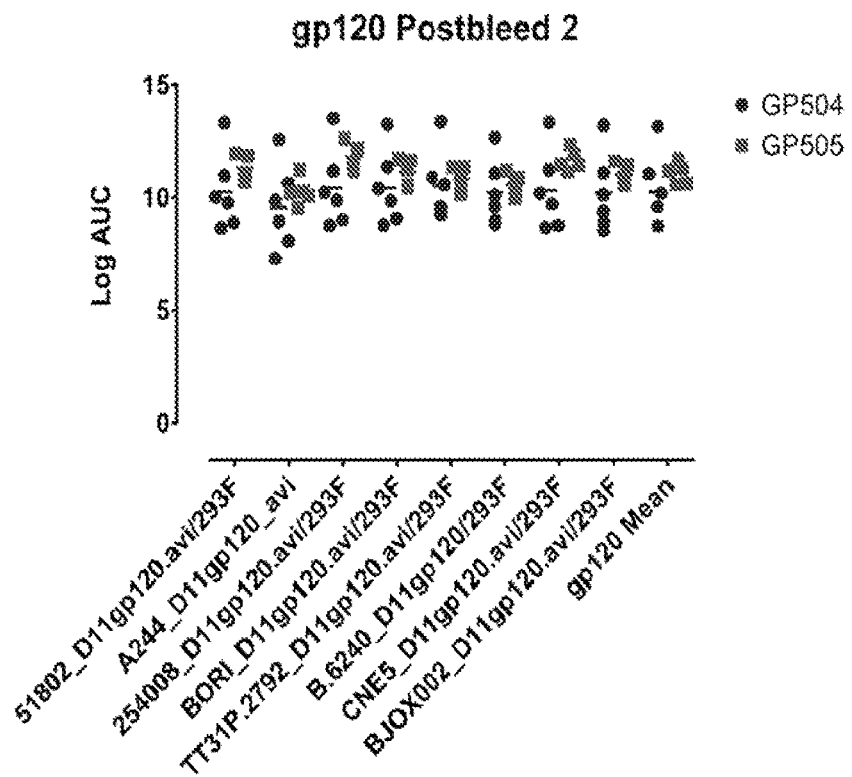
Figure 20:
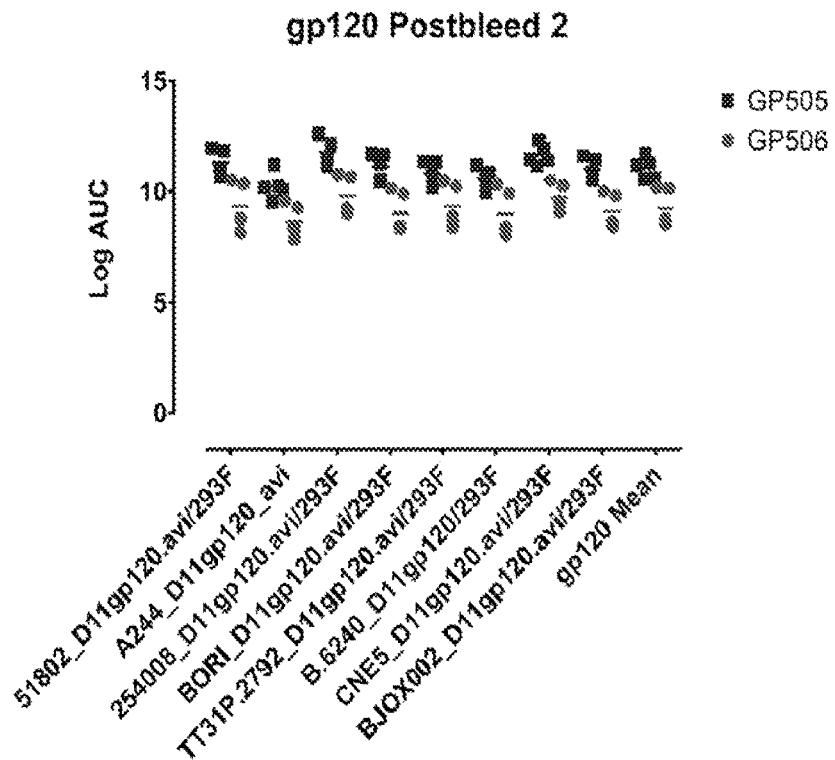
Figure 21:
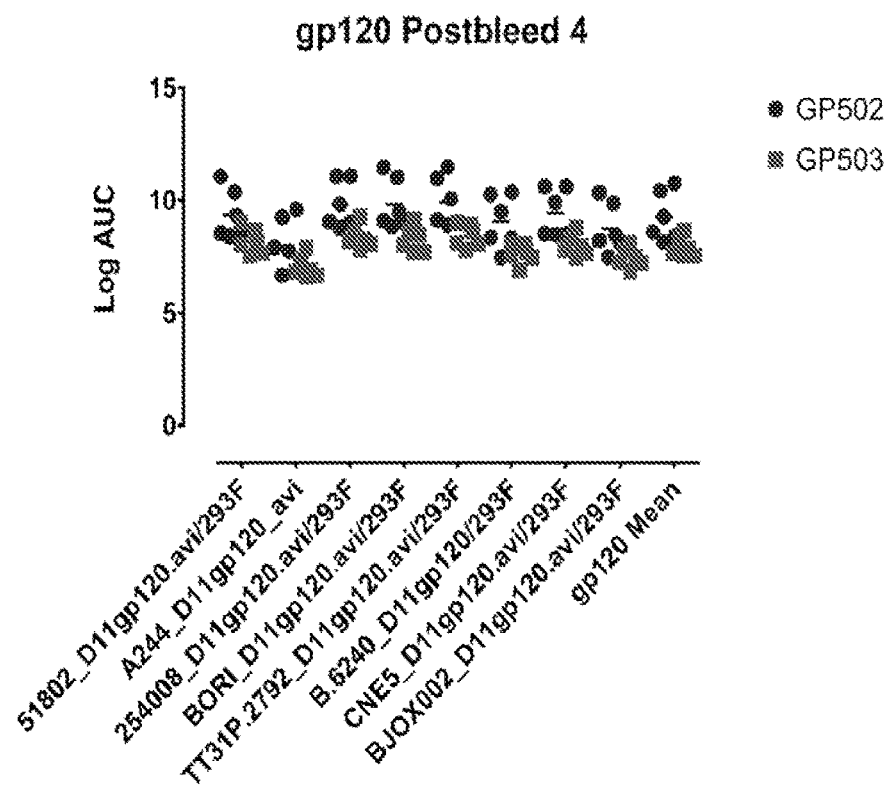
FIG. 21 shows the reactivity of postbleed 4 of the indicated groups for the entire gp120 panel. Compares the key groups with each other to give a visual of how the groups did on each env. Binding of post bleed 4 guinea pig sera from the indicated groups (GP502-GP506) to gp120 was determined by indirect ELISA. Plates were coated with protein at 2 ug/ml and sera were tittered in 3 fold serial dilutions. Each titration was expressed as the log of area under the curve (Log AUC). Each symbol represents an individual animal within each group of six animals. Higher Log AUC represents greater binding to the test protein.
Figure 21:
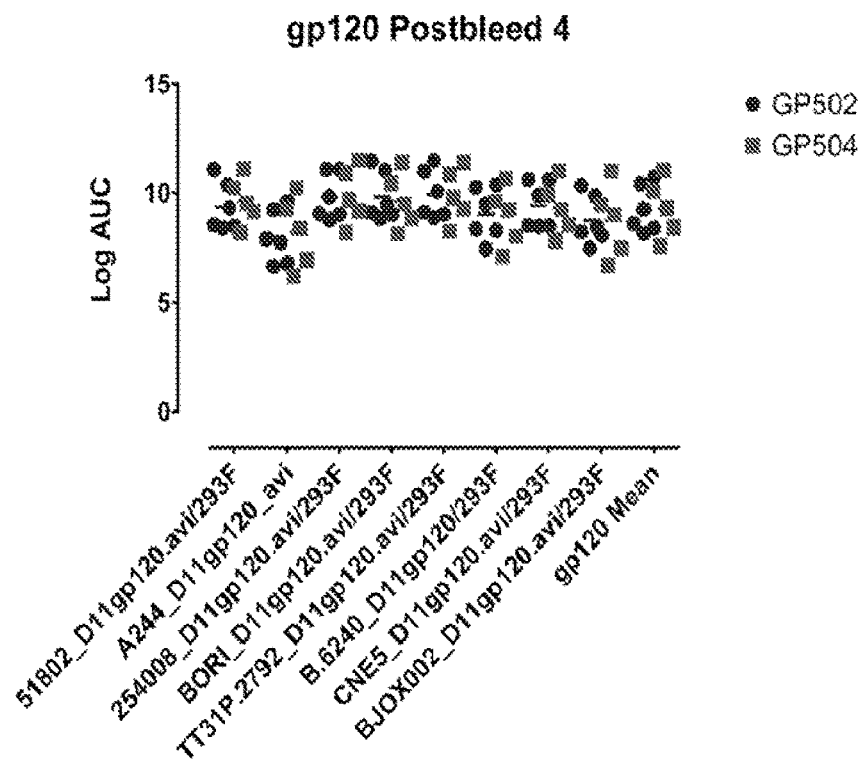
Figure 21:
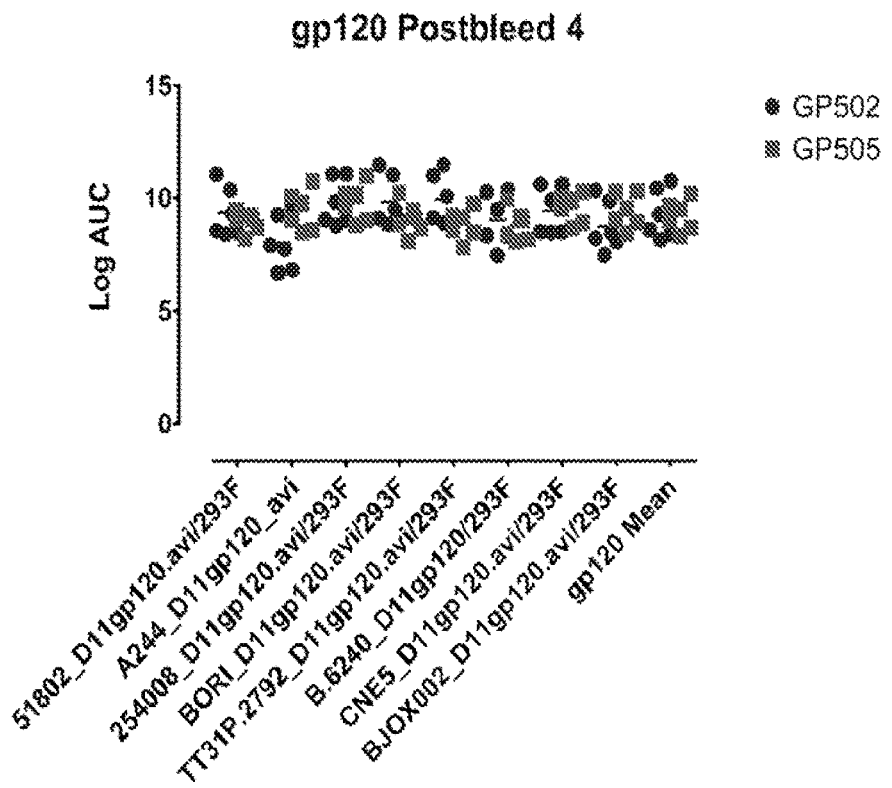
Figure 21:
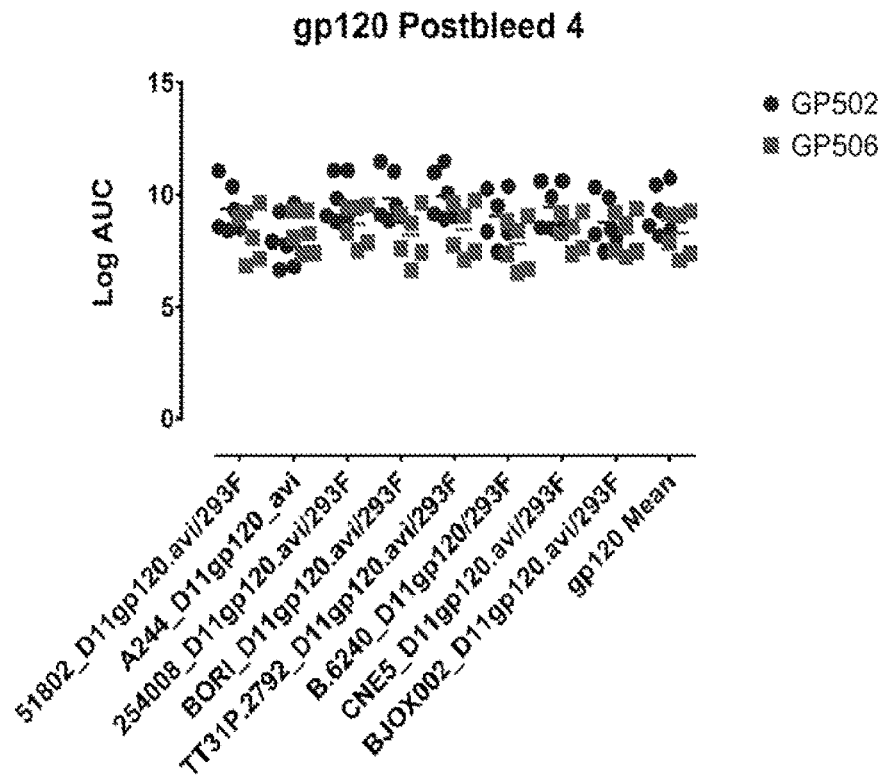
Figure 21:
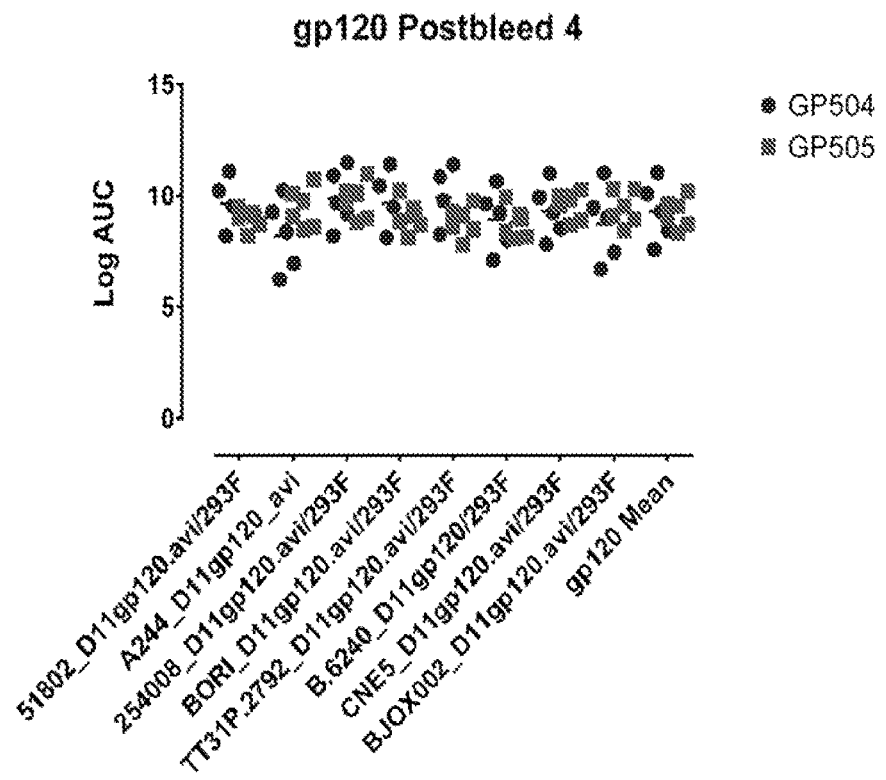
Figure 21:
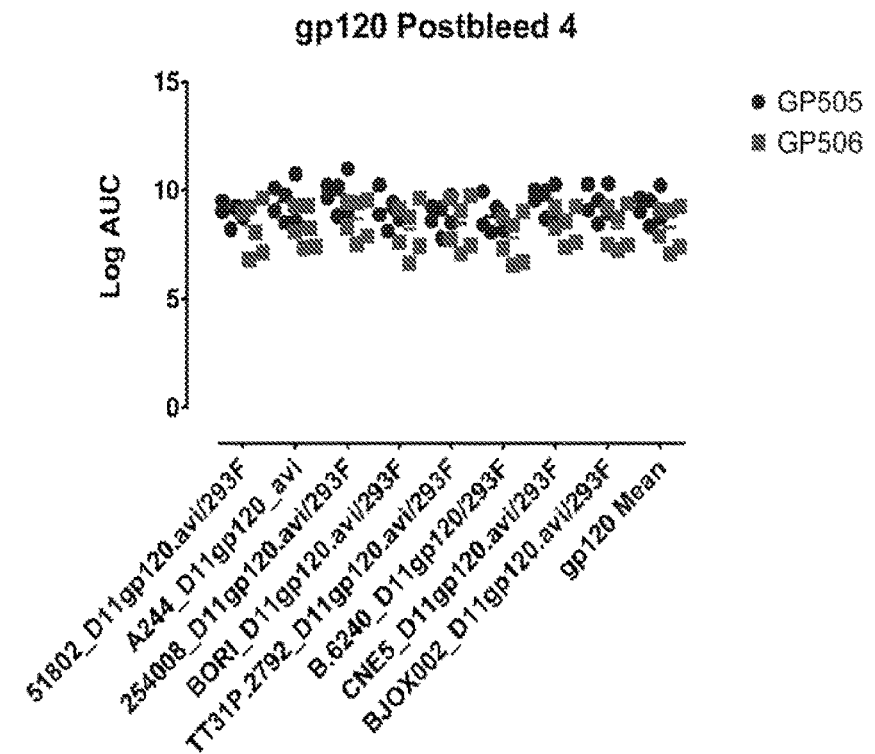
Figure 22:
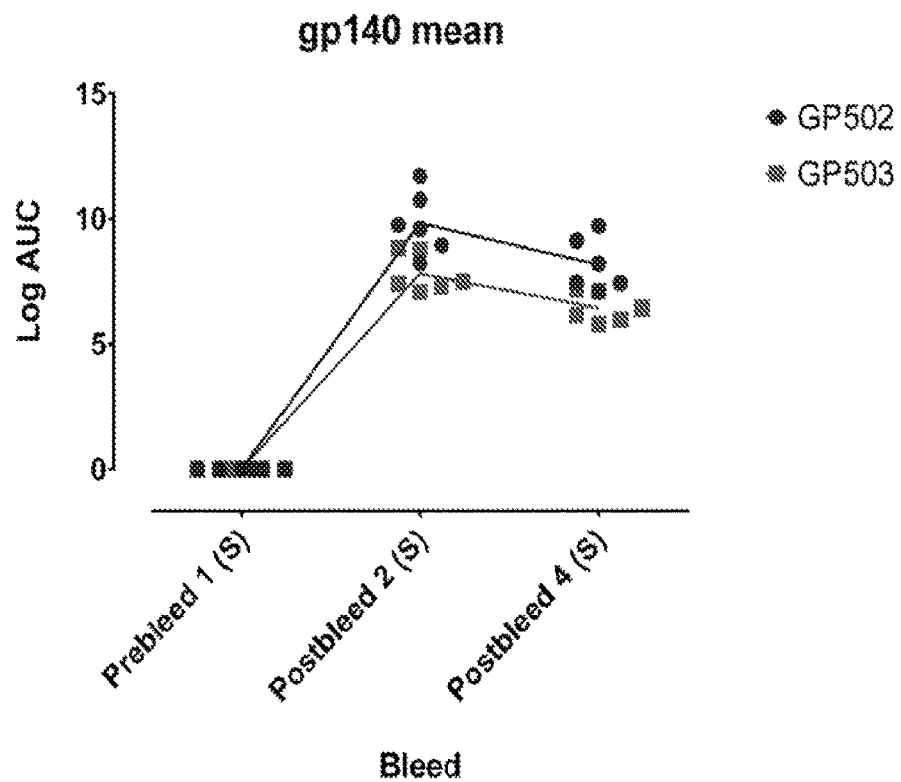
FIG. 22 shows the gp140 average score for the entire gp140 panel (all the members of the panel listed on the next slide). Compares the key groups with each other. Mean binding of guinea pig sera from the indicated groups (GP502-GP506) to eight different gp140's from multiple clades was determined by indirect ELISA at pre-bleed and post bleeds 2 and 4. Plates were coated with protein at 2 ug/ml and sera were tittered in 3 fold serial dilutions. Each titration was expressed as the log of area under the curve (Log AUC). Each symbol represents the average data for an individual animal within each group of six animals. Higher Log AUC represents greater binding to the test protein.
Figure 22:
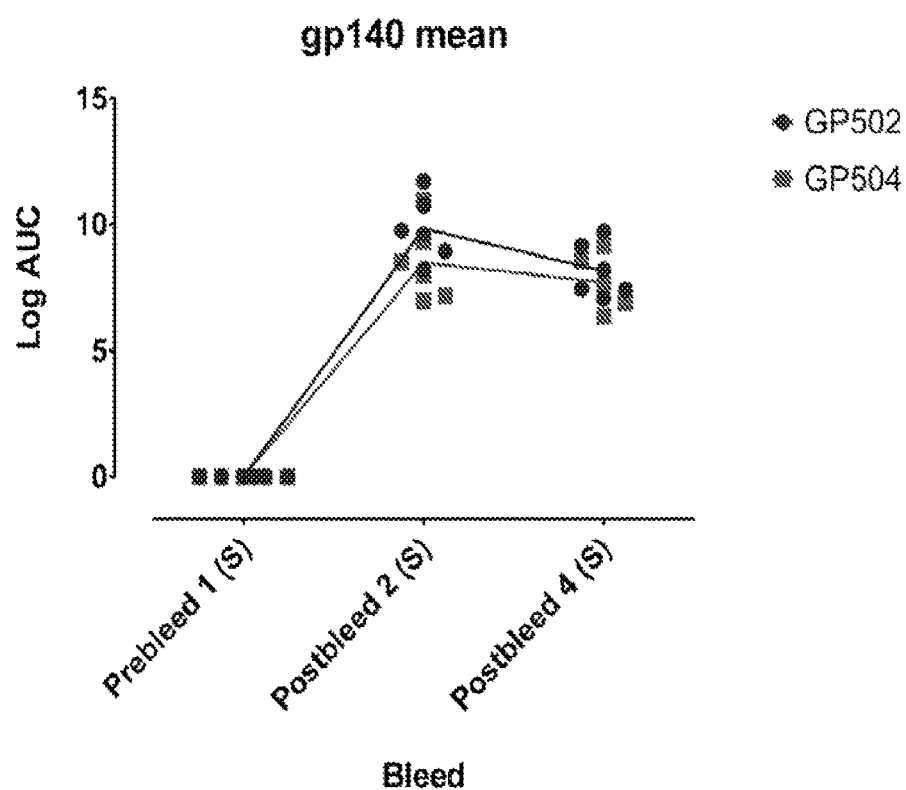
Figure 22:
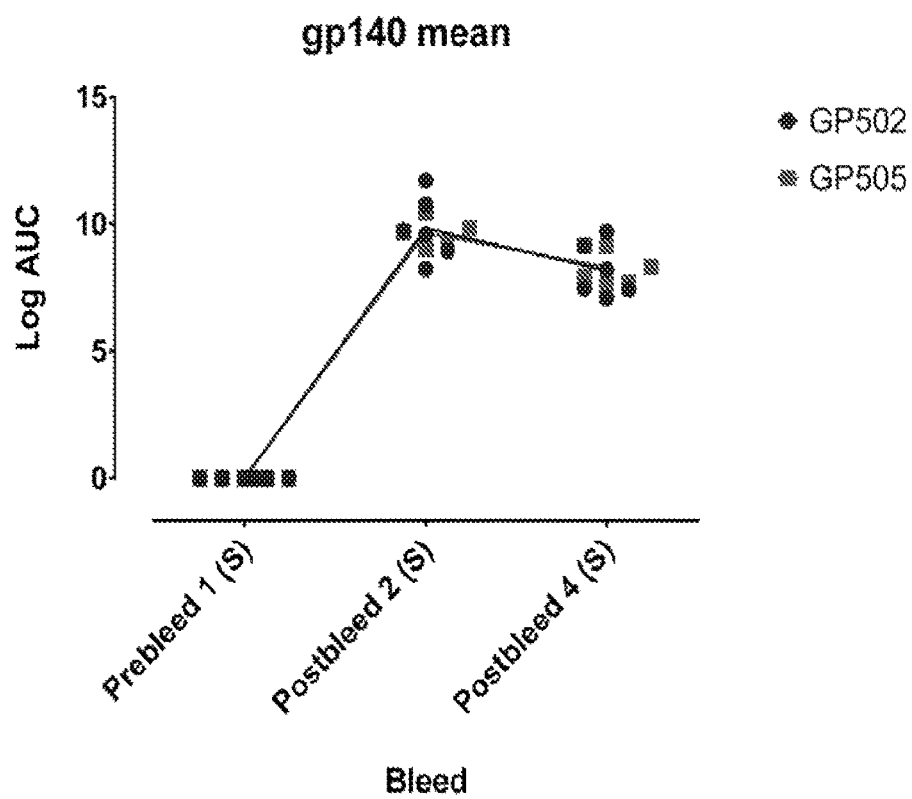
Figure 22:
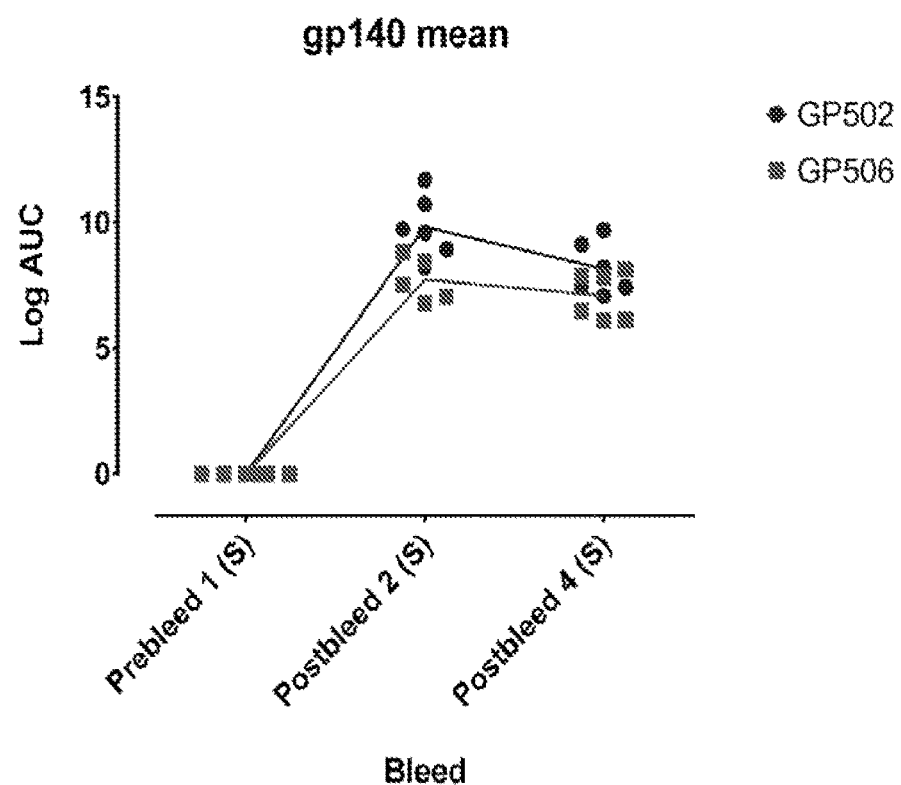
Figure 22:
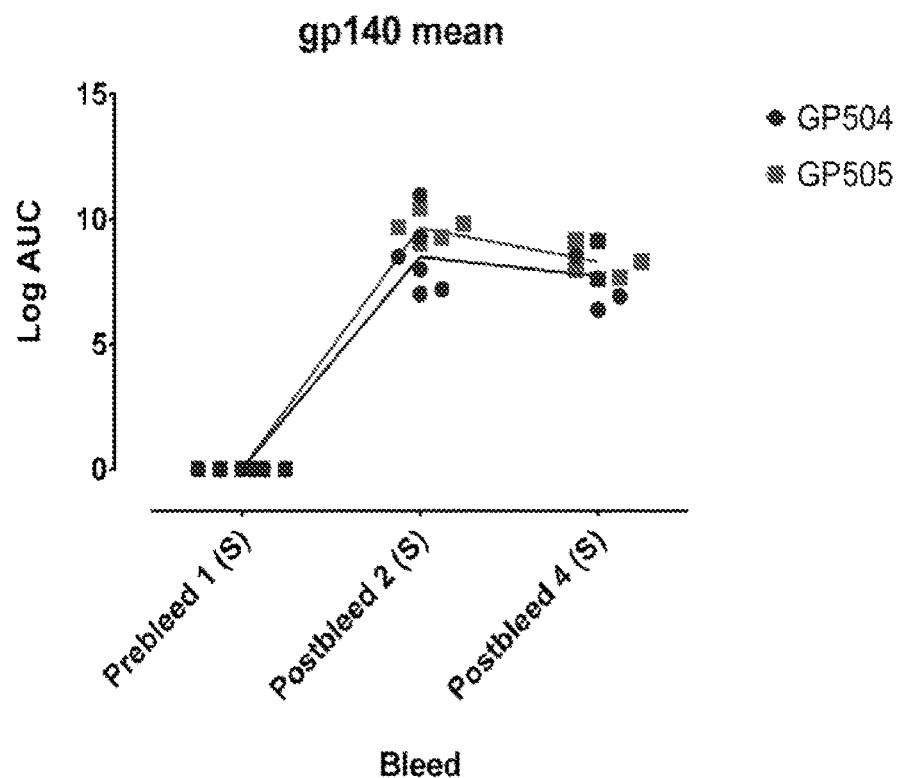
Figure 22:
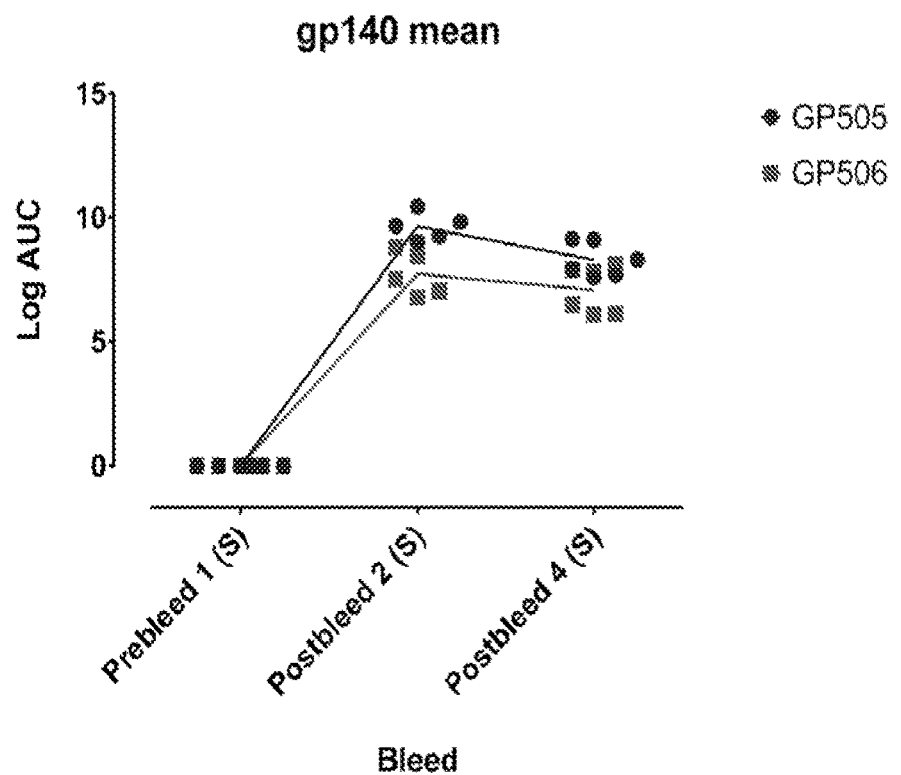
Figure 23:
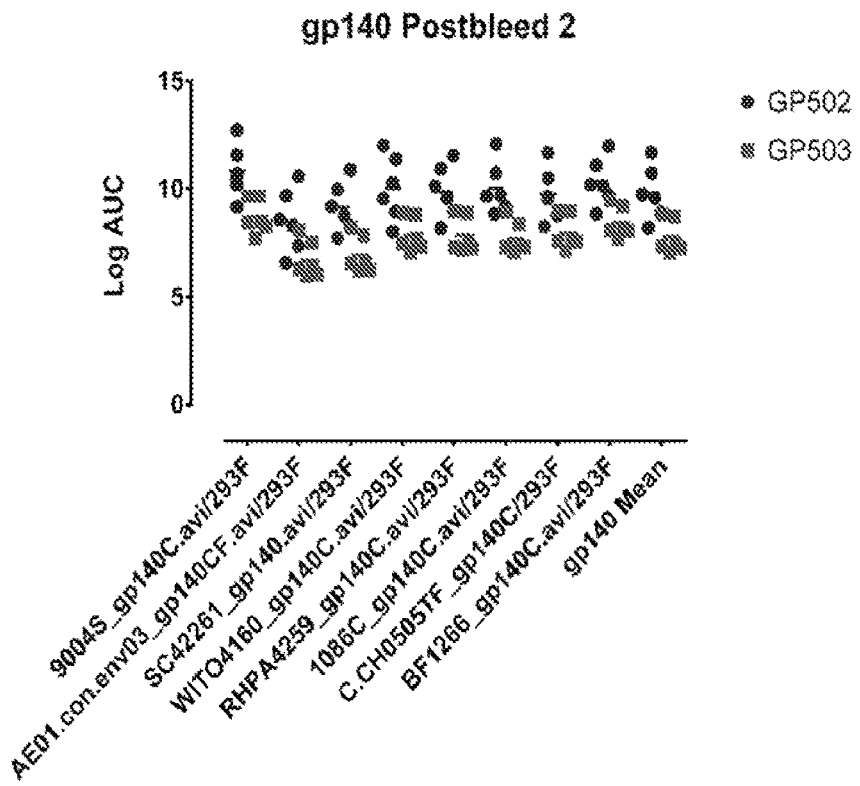
FIG. 23 shows the reactivity of postbleed 2 of the indicated groups for the entire gp140 panel. Compares the key groups with each other to give a visual of how the groups did on each env. Binding of post bleed 2 guinea pig sera from the indicated groups (GP502-GP506) to gp140 was determined by indirect ELISA. Plates were coated with protein at 2 ug/ml and sera were tittered in 3 fold serial dilutions. Each titration was expressed as the log of area under the curve (Log AUC). Each symbol represents an individual animal within each group of six animals. Higher Log AUC represents greater binding to the test protein.
Figure 23:
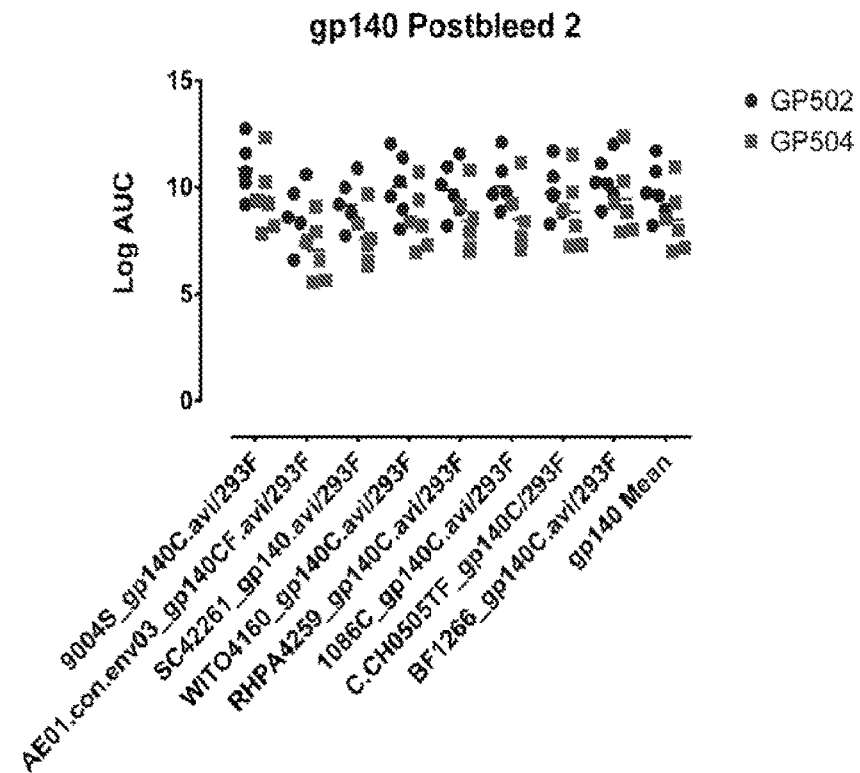
Figure 23:
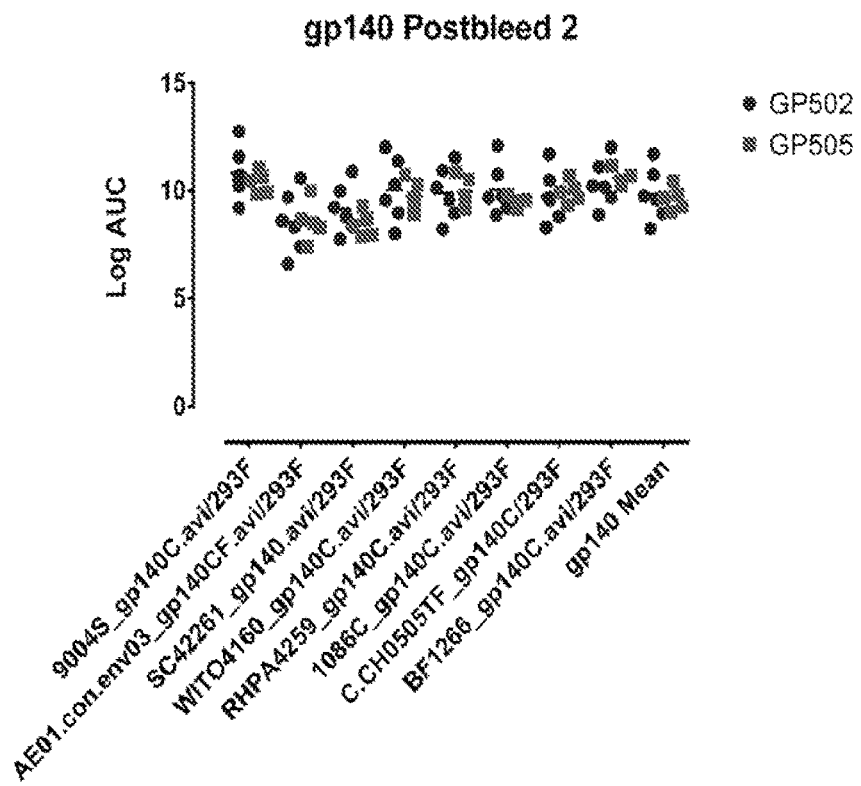
Figure 23:
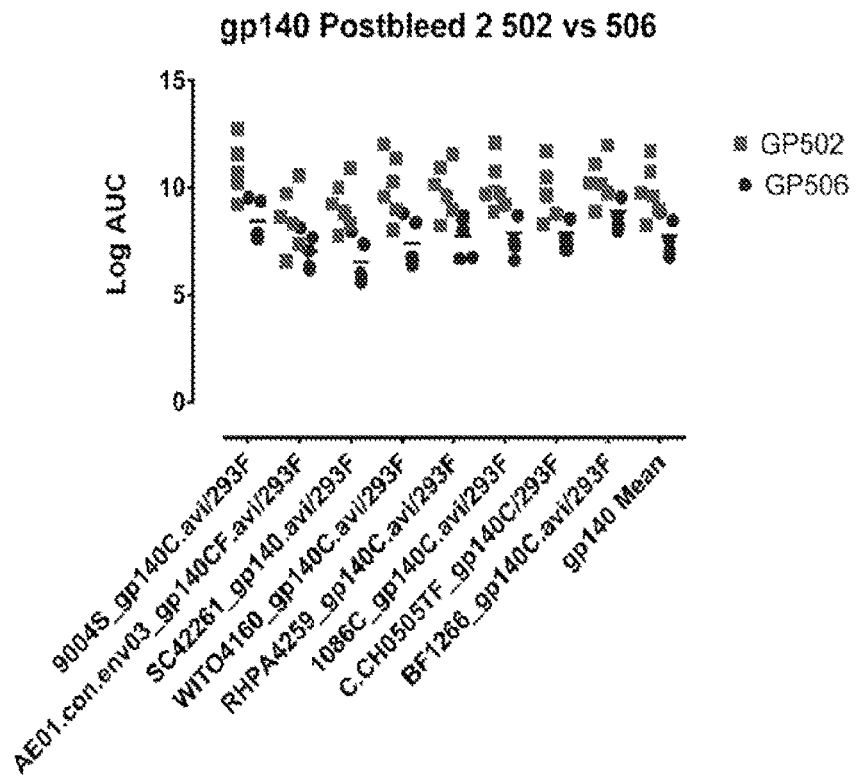
Figure 23:
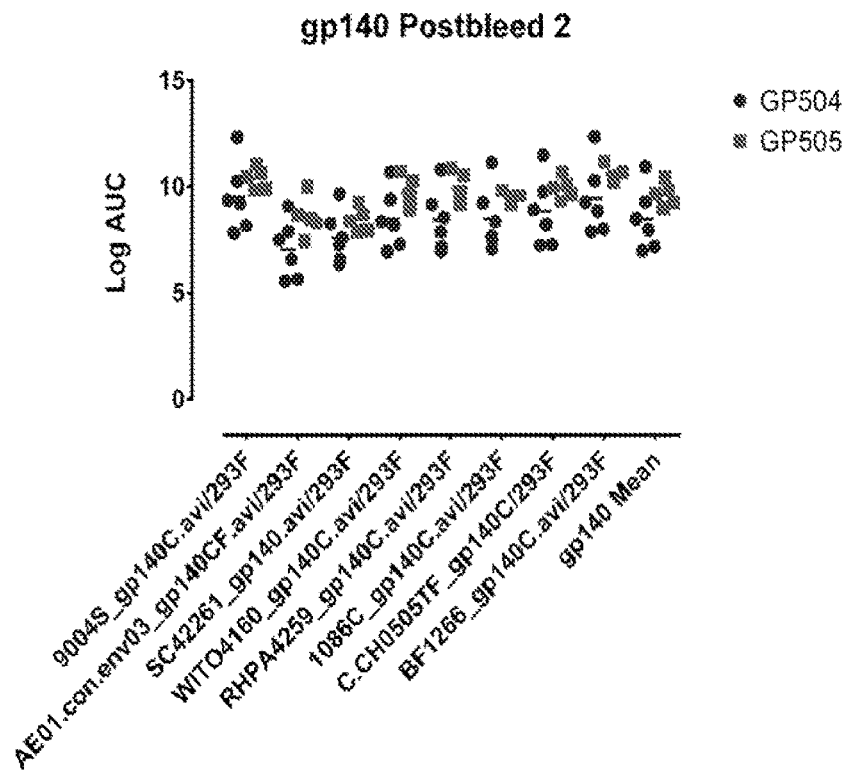
Figure 23:
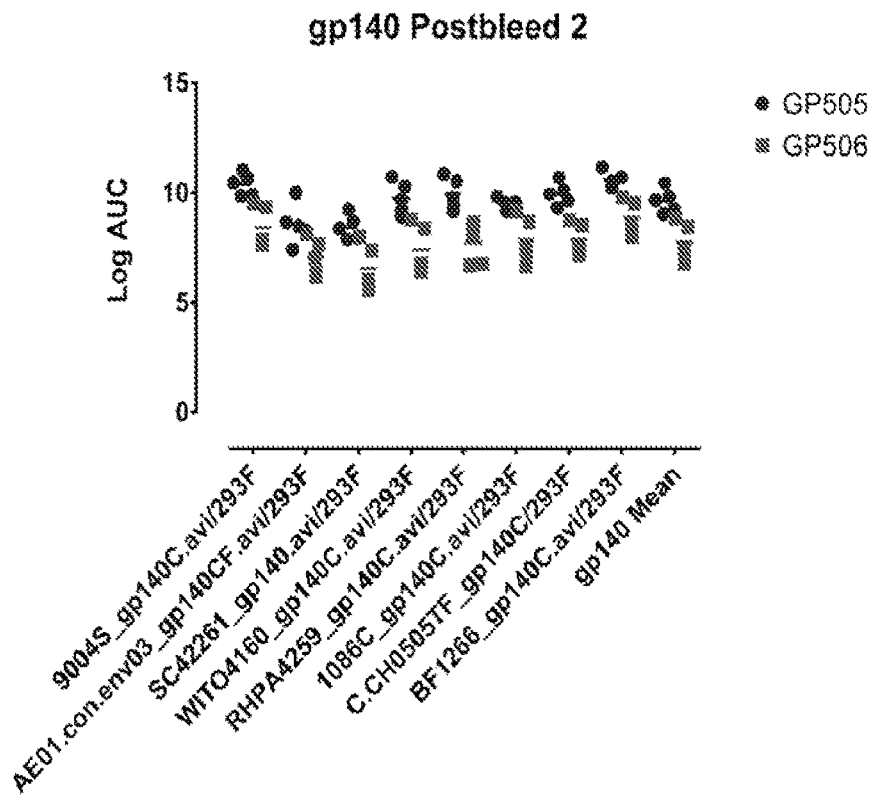
Figure 24:
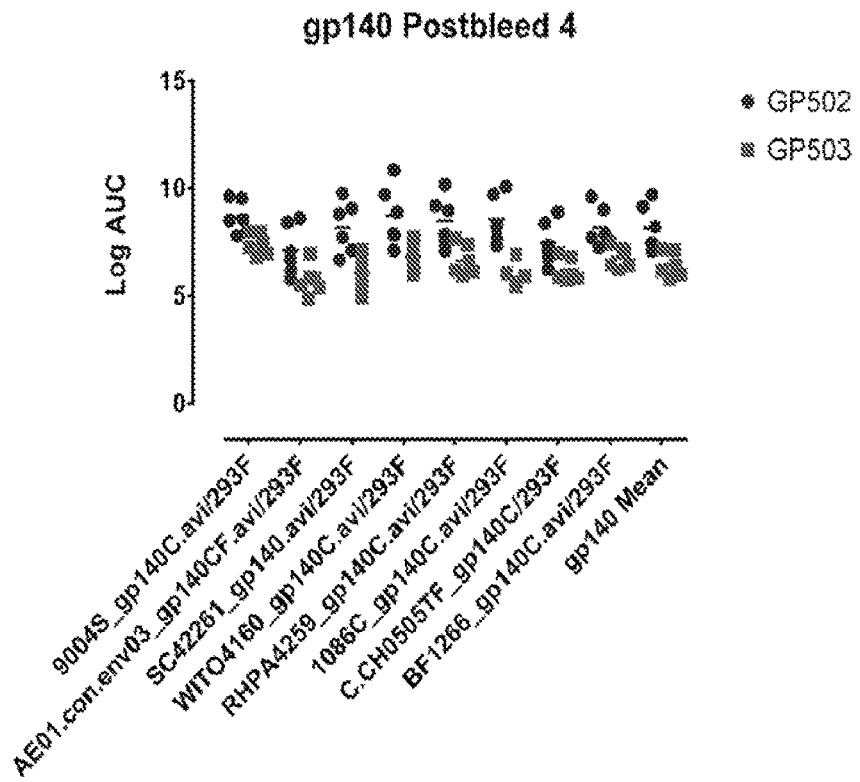
FIG. 24 shows reactivity of postbleed 4 of the indicated groups for the entire gp140 panel. Compares the key groups with each other to give a visual of how the groups did on each env. Binding of post bleed 4 guinea pig sera from the indicated groups (GP502-GP506) to gp140 was determined by indirect ELISA. Plates were coated with protein at 2 ug/ml and sera were tittered in 3 fold serial dilutions. Each titration was expressed as the log of area under the curve (Log AUC). Each symbol represents an individual animal within each group of six animals. Higher Log AUC represents greater binding to the test protein.
Figure 24:
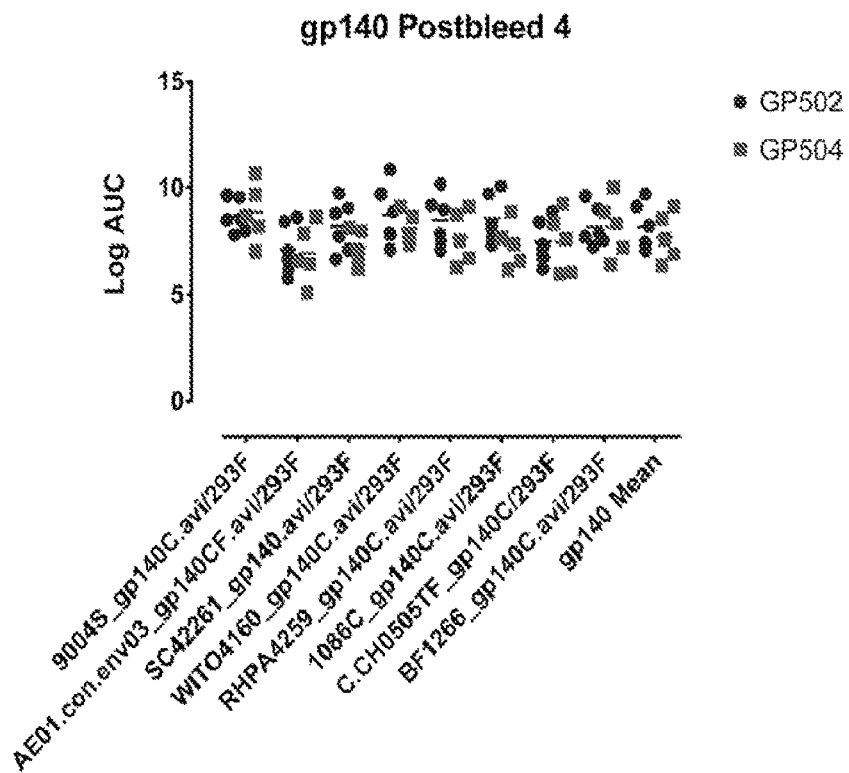
Figure 24:
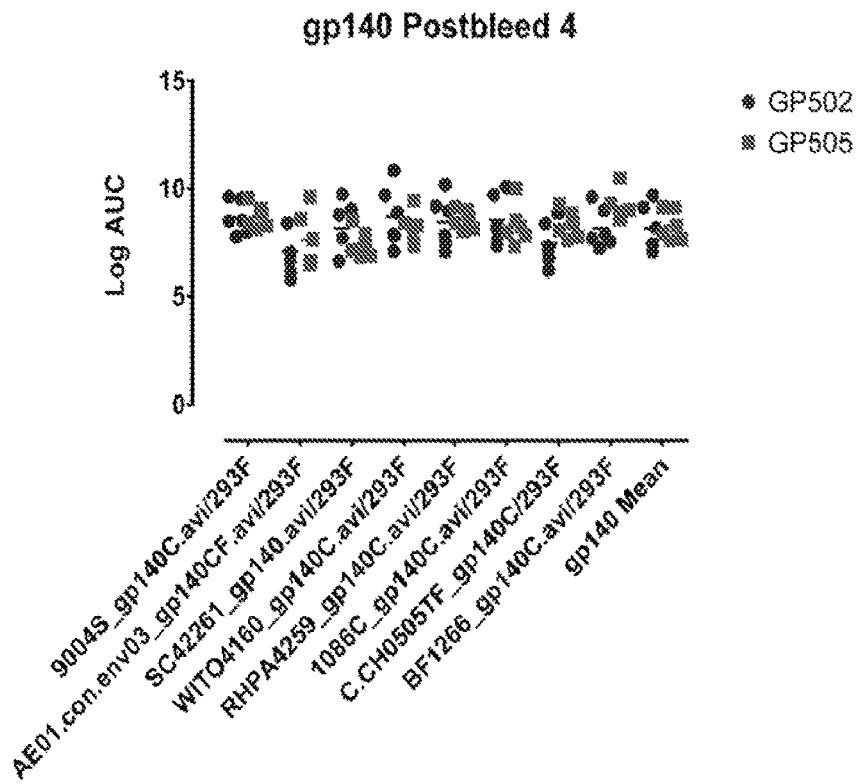
Figure 24:
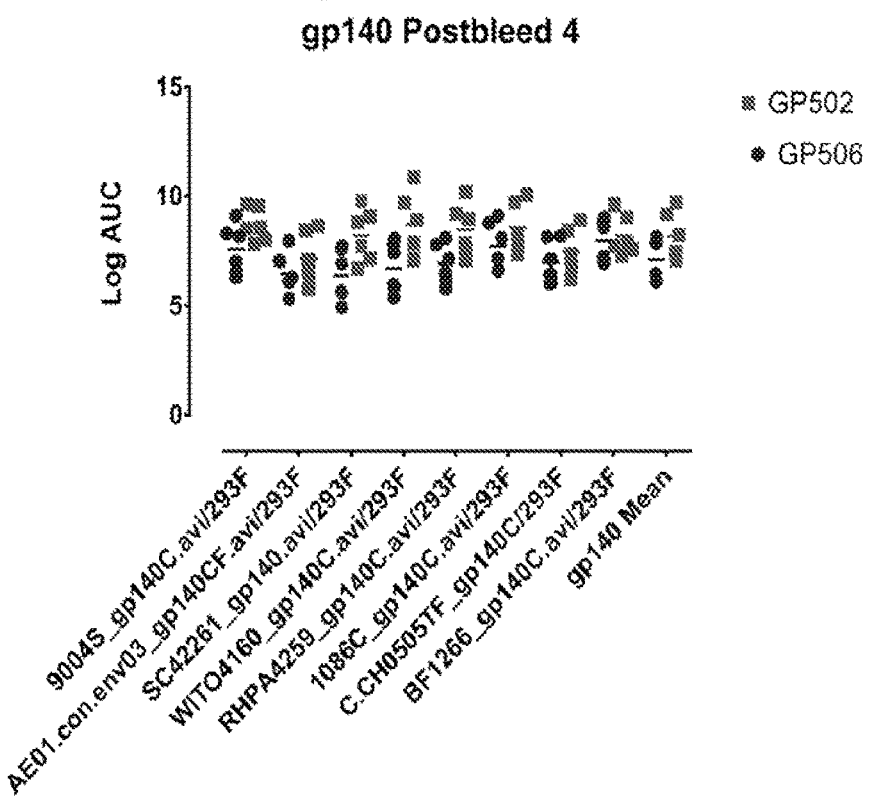
Figure 24:
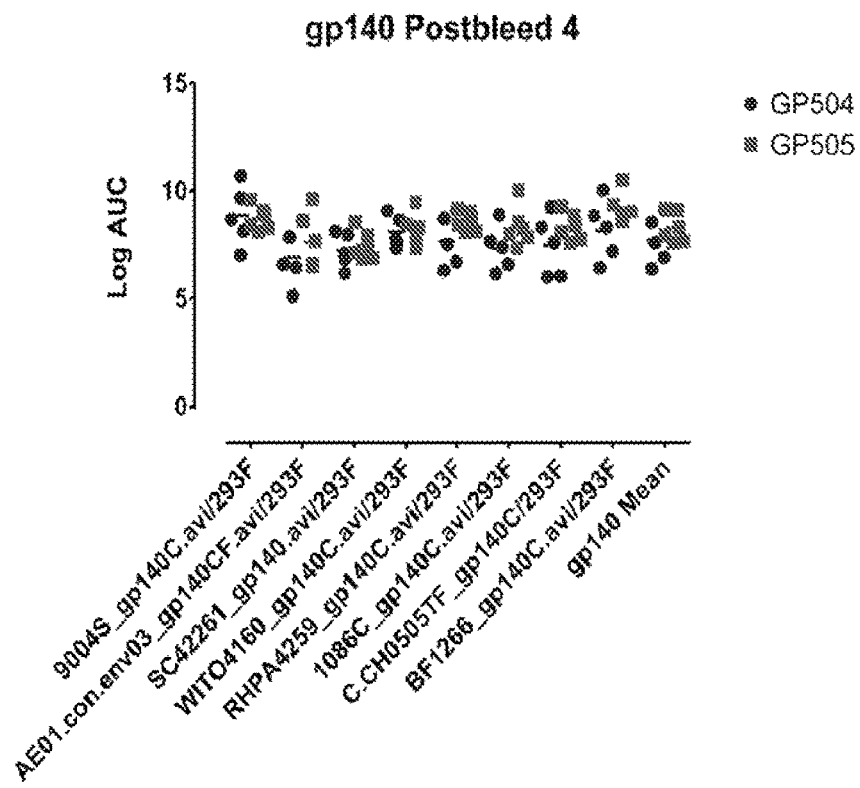
Figure 24:
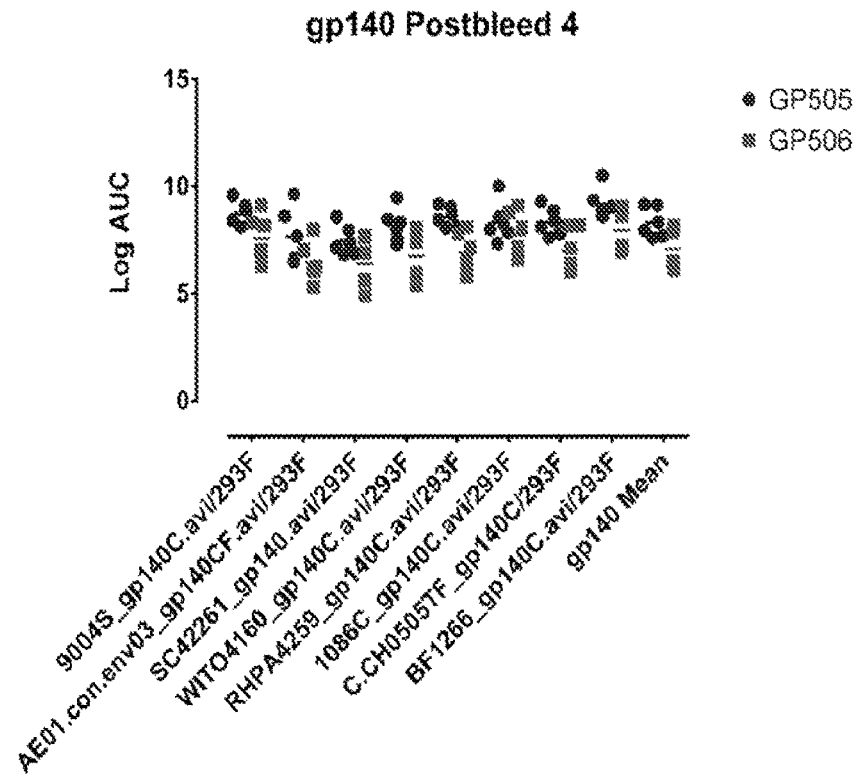
Figure 25:
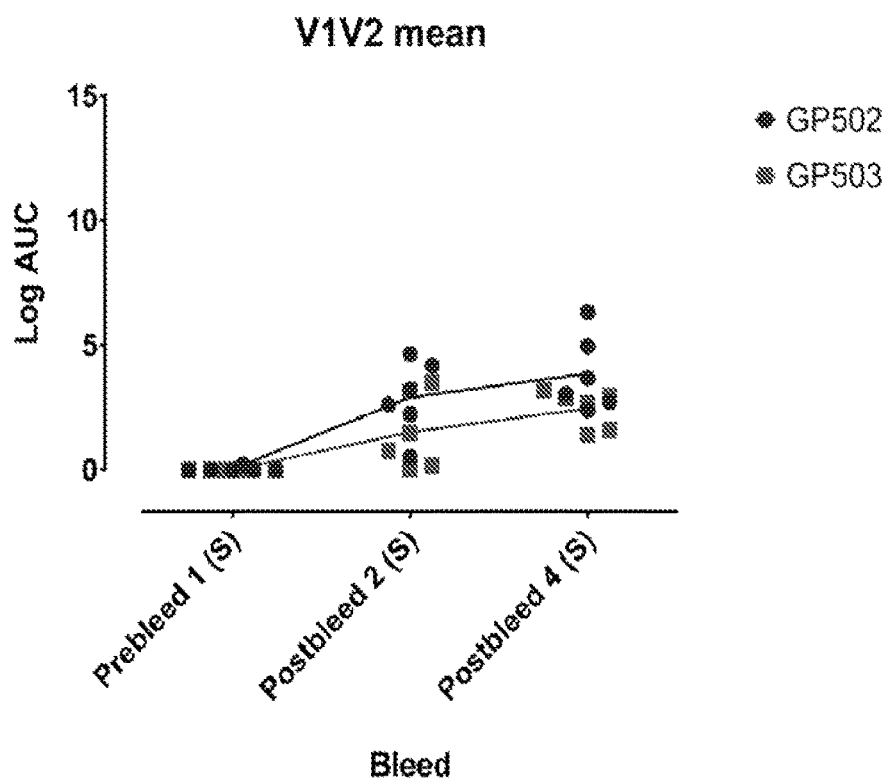
FIG. 25 shows the gp70 V1V2 average score for the entire V1V2 panel (all the members of the panel listed on the next slide). Compares the key groups with each other. Mean binding of guinea pig sera from the indicated groups (GP502-GP506) to sixteen different V1V2 proteins from multiple clades was determined by indirect ELISA at pre-bleed and post bleeds 2 and 4. Plates were coated with protein at 2 ug/ml and sera were tittered in 3 fold serial dilutions. Each titration was expressed as the log of area under the curve (Log AUC). Each symbol represents the average data for an individual animal within each group of six animals. Higher Log AUC represents greater binding to the test protein.
Figure 25:
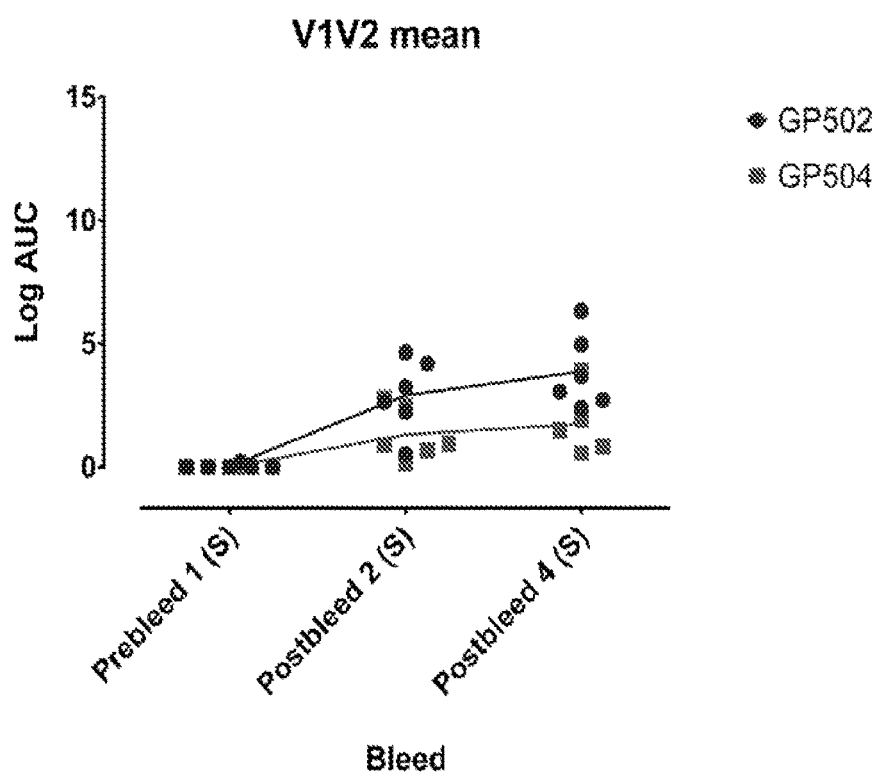
Figure 25:
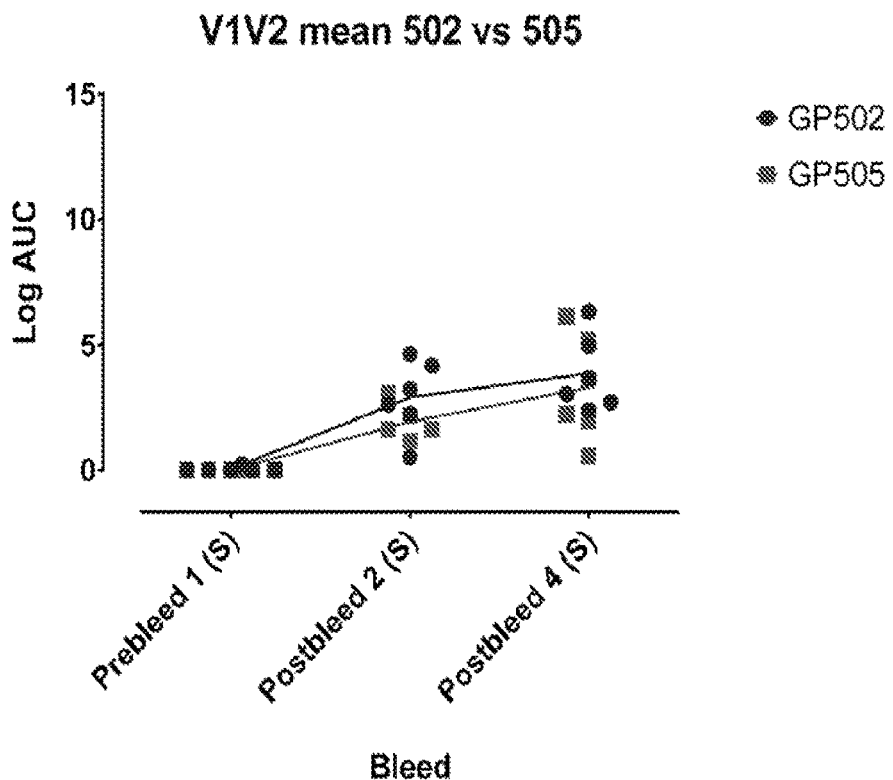
Figure 25:
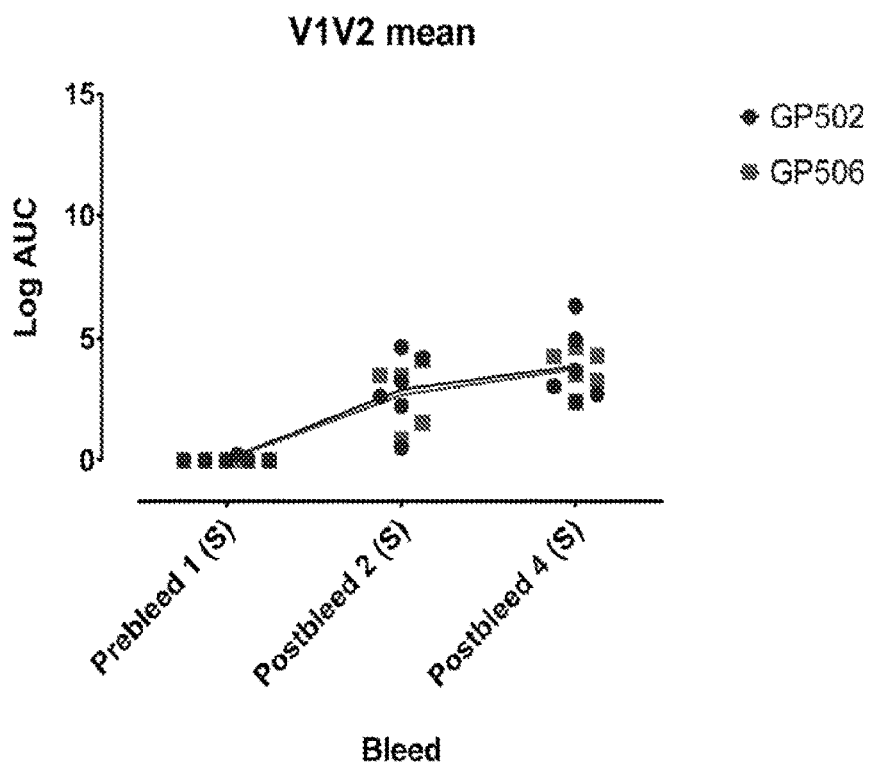
Figure 25:
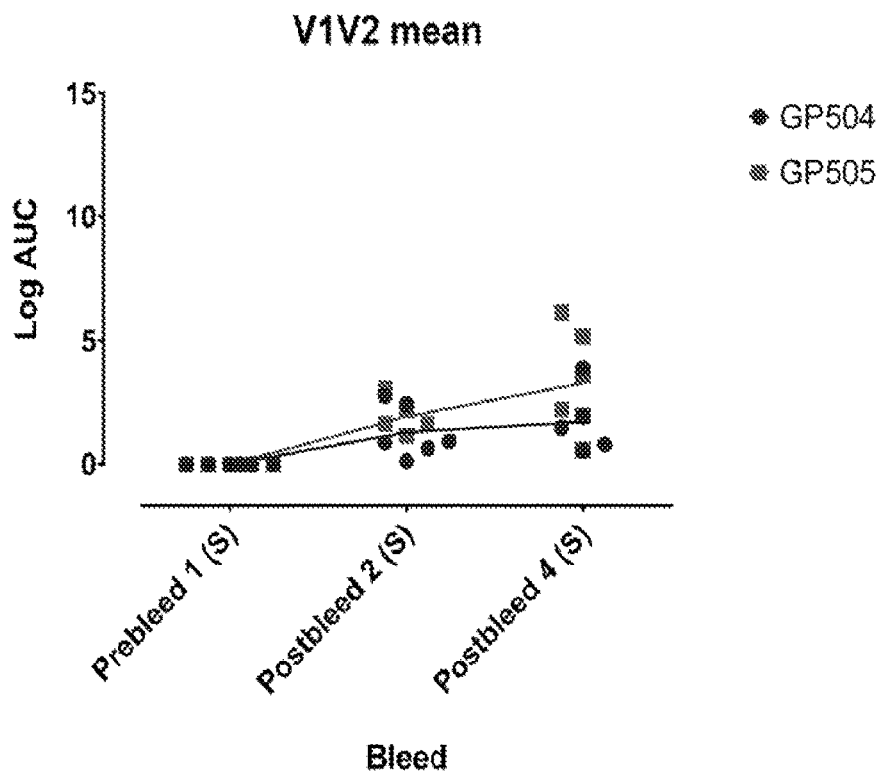
Figure 25:
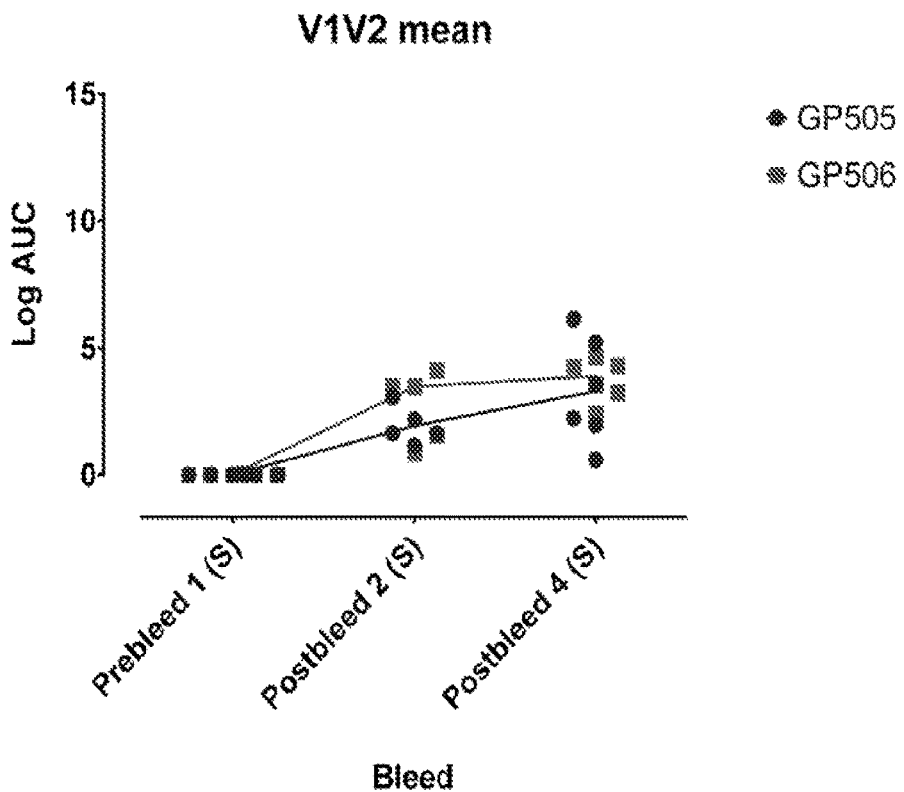
Figure 26:
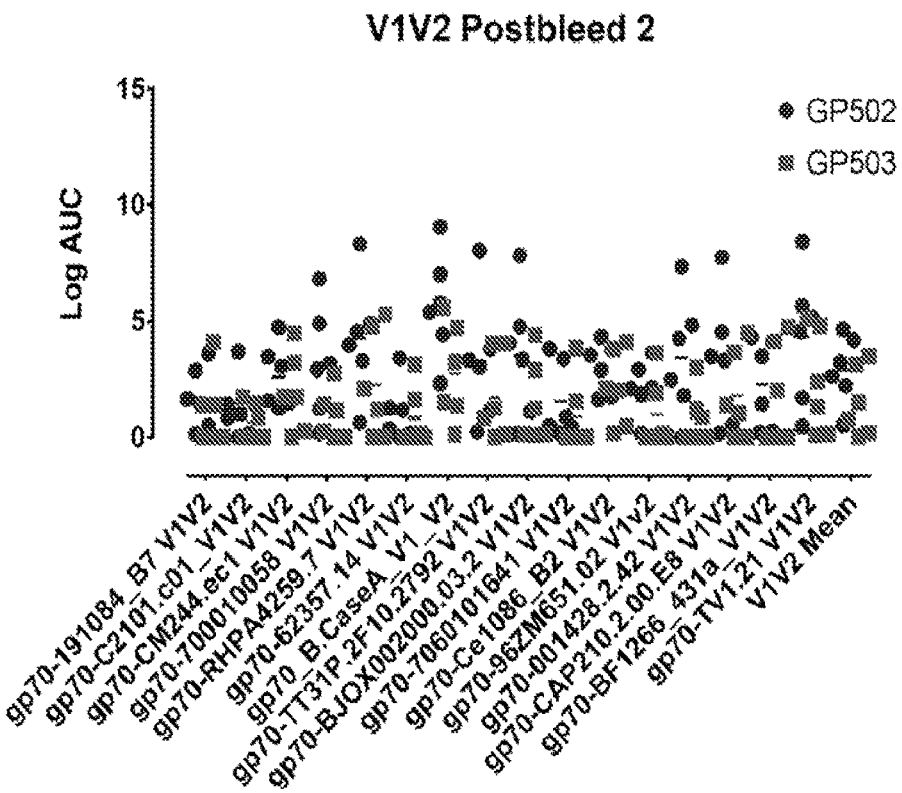
FIG. 26 shows the reactivity of postbleed 2 of the indicated groups for the entire V1V2 panel post bleed 2. Compares the key groups with each other to give a visual of how the groups did on each env. Binding of post bleed 2 guinea pig sera from the indicated groups (GP502-GP506) to V1V2 protein was determined by indirect ELISA. Plates were coated with protein at 2 ug/ml and sera were tittered in 3 fold serial dilutions. Each titration was expressed as the log of area under the curve (Log AUC). Each symbol represents an individual animal within each group of six animals. Higher Log AUC represents greater binding to the test protein.
Figure 26:
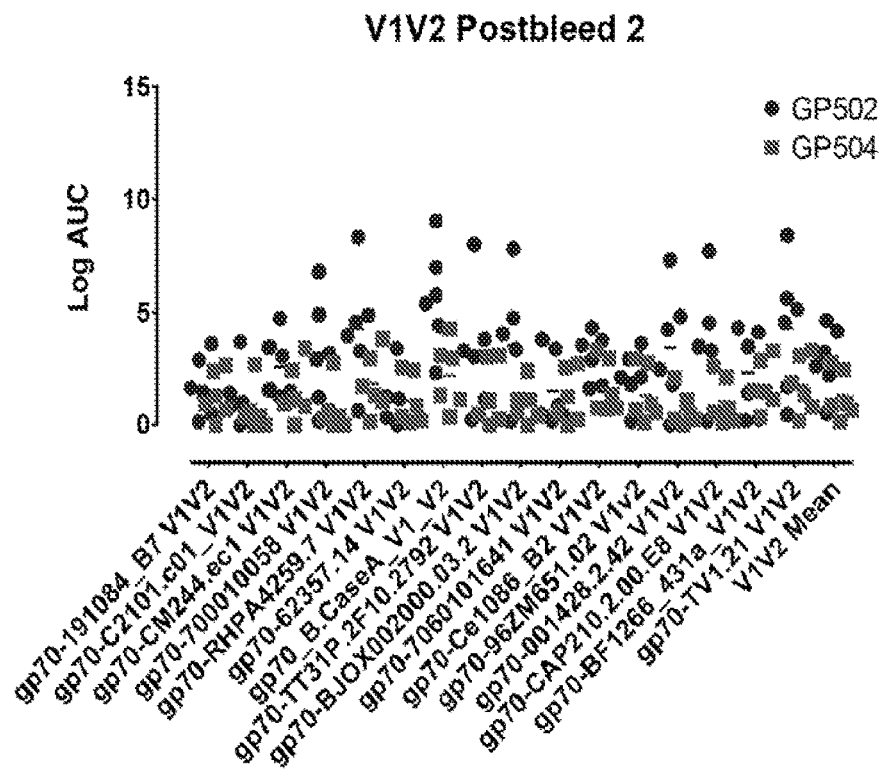
Figure 26:
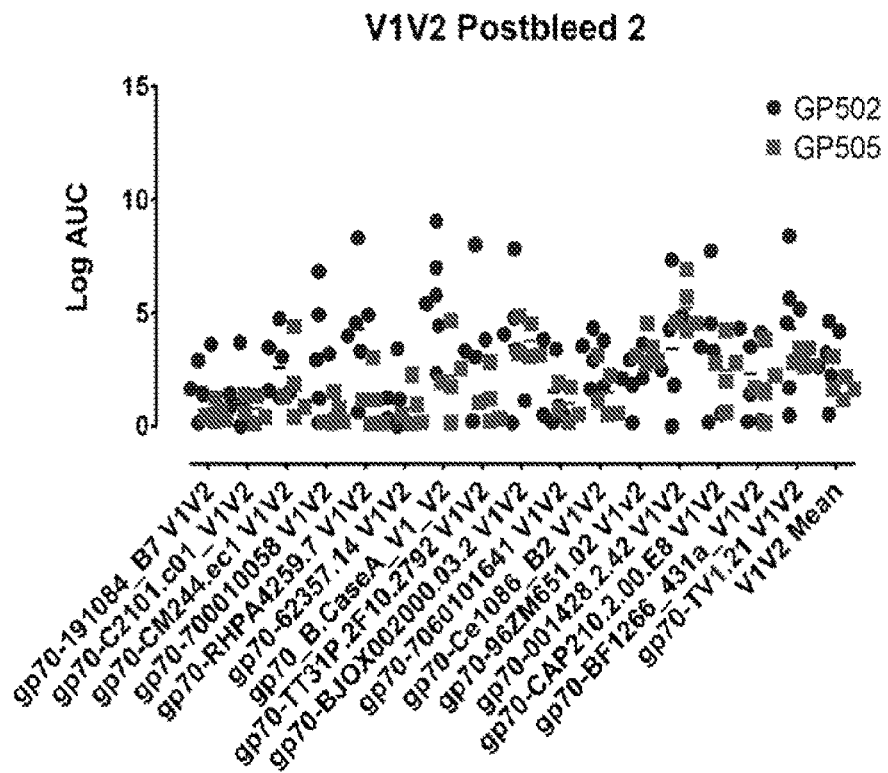
Figure 26:
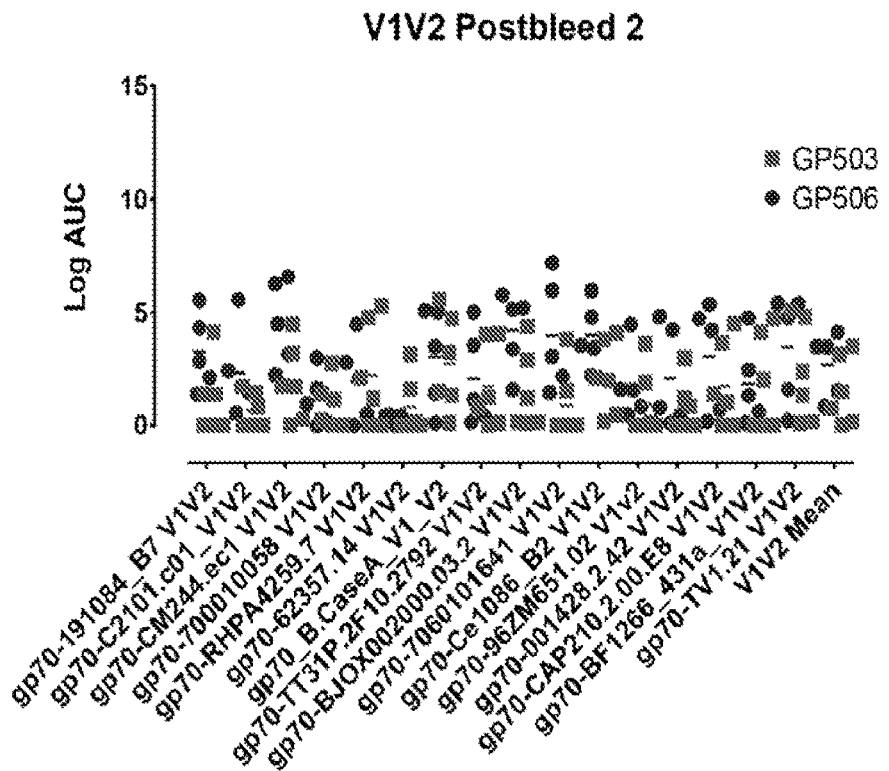
Figure 26:
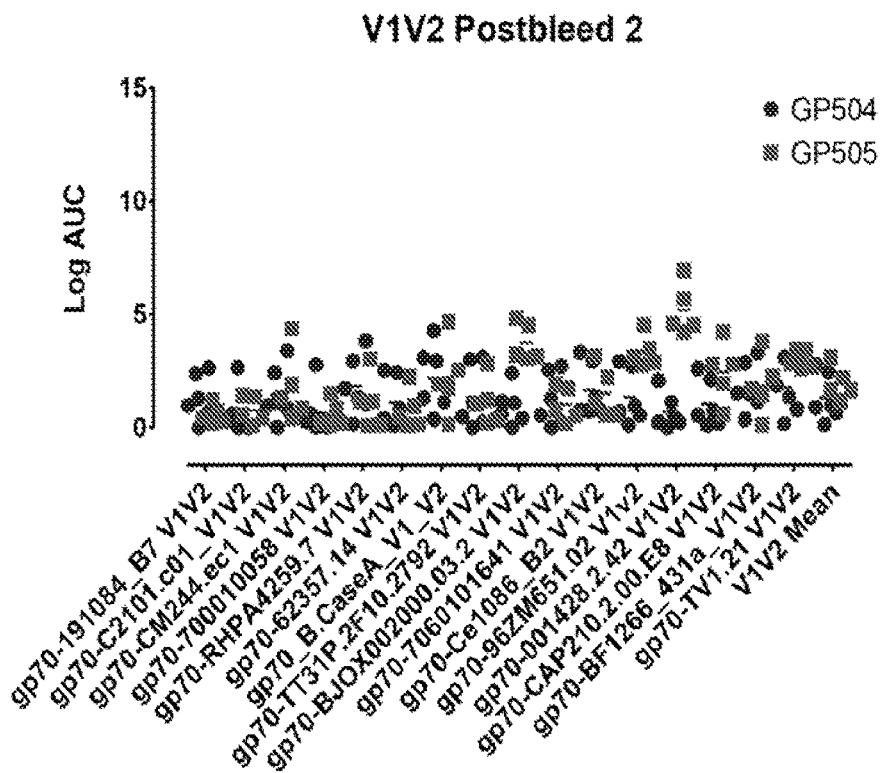
Figure 26:
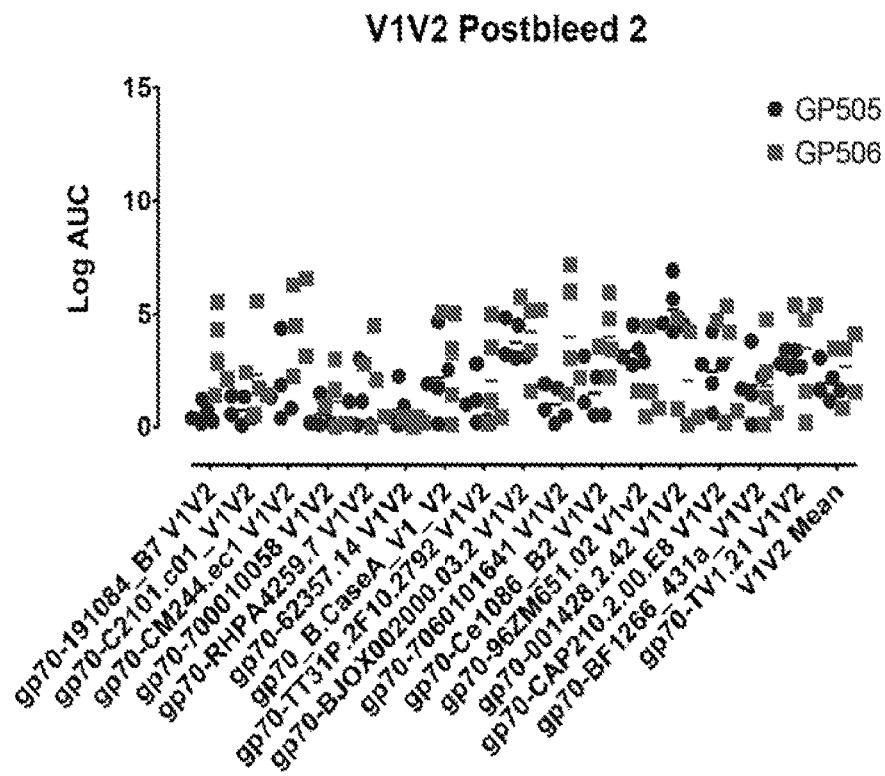
Figure 27:
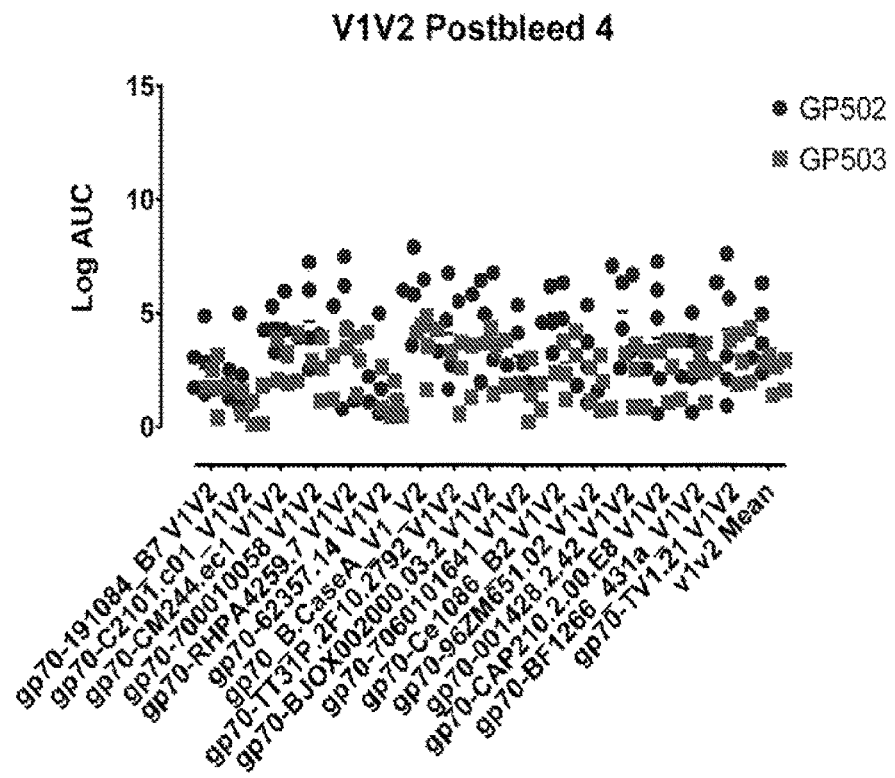
FIG. 27 shows the reactivity of the indicated groups for the entire V1V2 panel post bleed 4. Compares the key groups with each other to give a visual of how the groups did on each env. Binding of post bleed 4 guinea pig sera from the indicated groups (GP502-GP506) to V1V2 protein was determined by indirect ELISA. Plates were coated with protein at 2 ug/ml and sera were tittered in 3 fold serial dilutions. Each titration was expressed as the log of area under the curve (Log AUC). Each symbol represents an individual animal within each group of six animals. Higher Log AUC represents greater binding to the test protein.
Figure 27:
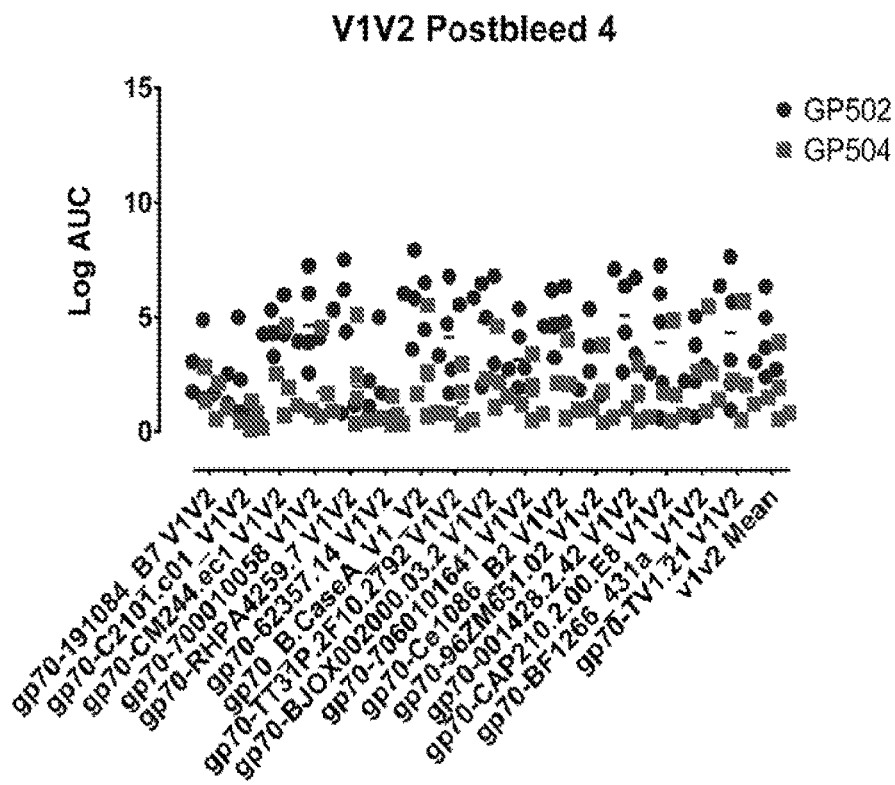
Figure 27:
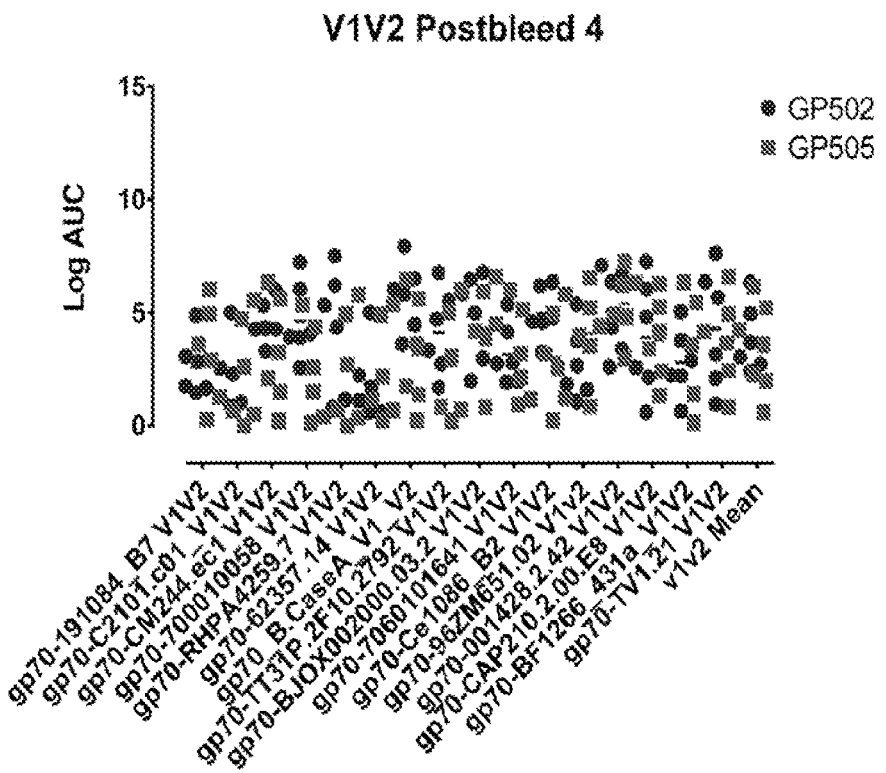
Figure 27:
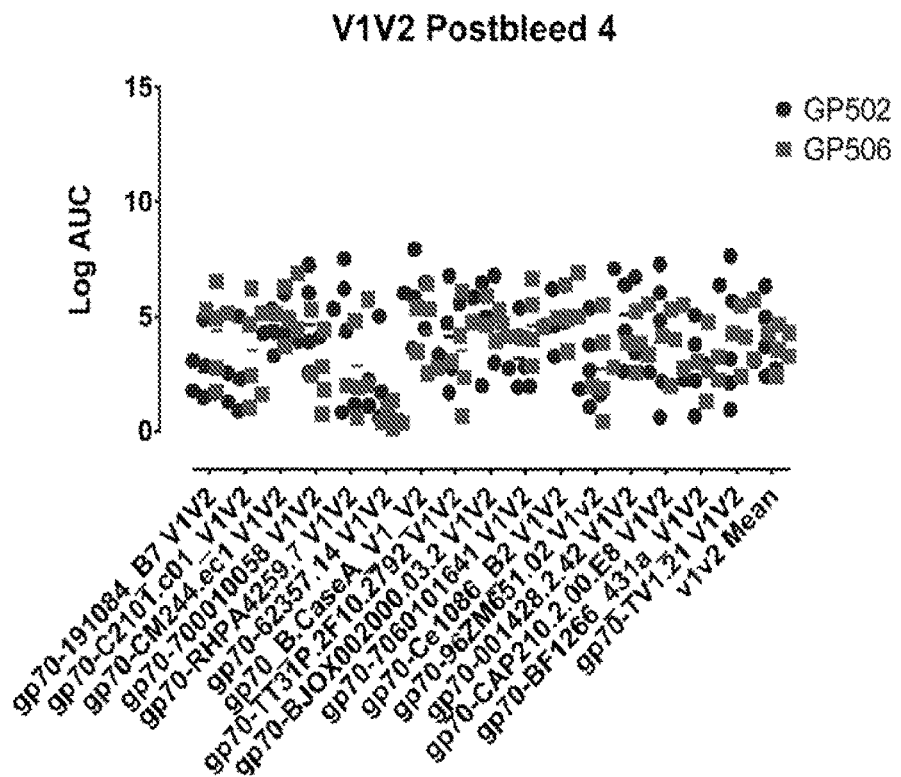
Figure 27:
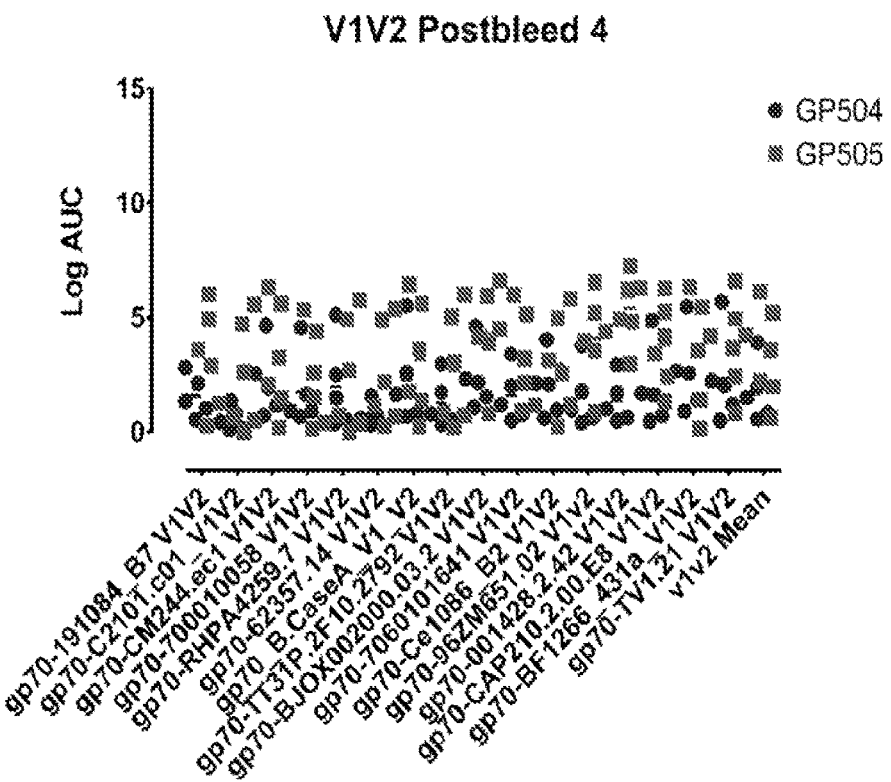
Figure 27:
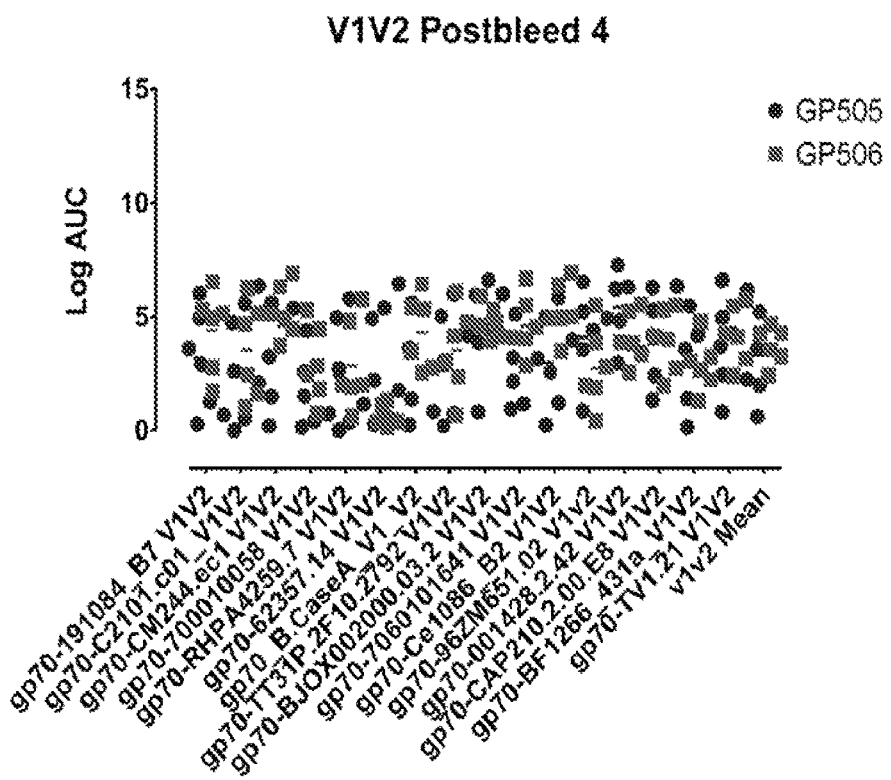
Figure 28A:
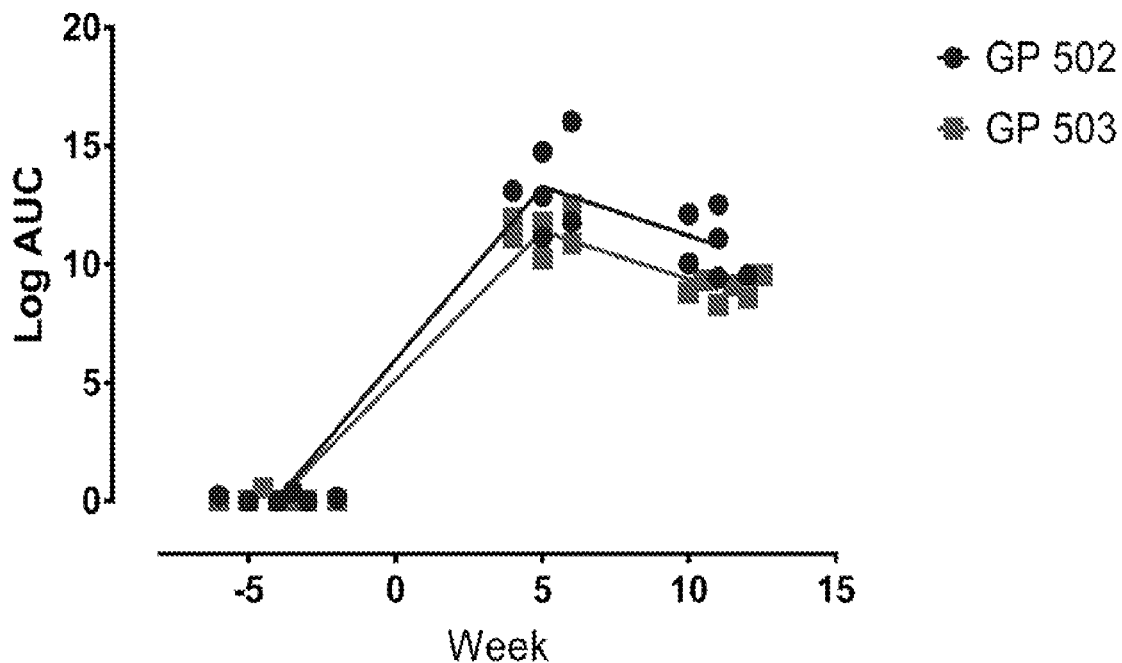
FIG. 28A-28C shows the reactivity of the indicated groups for some mutants that knockout either A32, or C11 epitope ADCC binding. Binding of guinea pig sera from the indicated groups (GP502 and GP503) to wild type A244 gp120 and two mutant forms was determined by indirect ELISA. Plates were coated with protein at 2 ug/ml and sera were tittered in 3 fold serial dilutions. Each titration was expressed as the log of area under the curve (Log AUC). Each symbol represents an individual animal within each group of six animals. Higher Log AUC represents greater binding to the test protein.
Figure 28B:
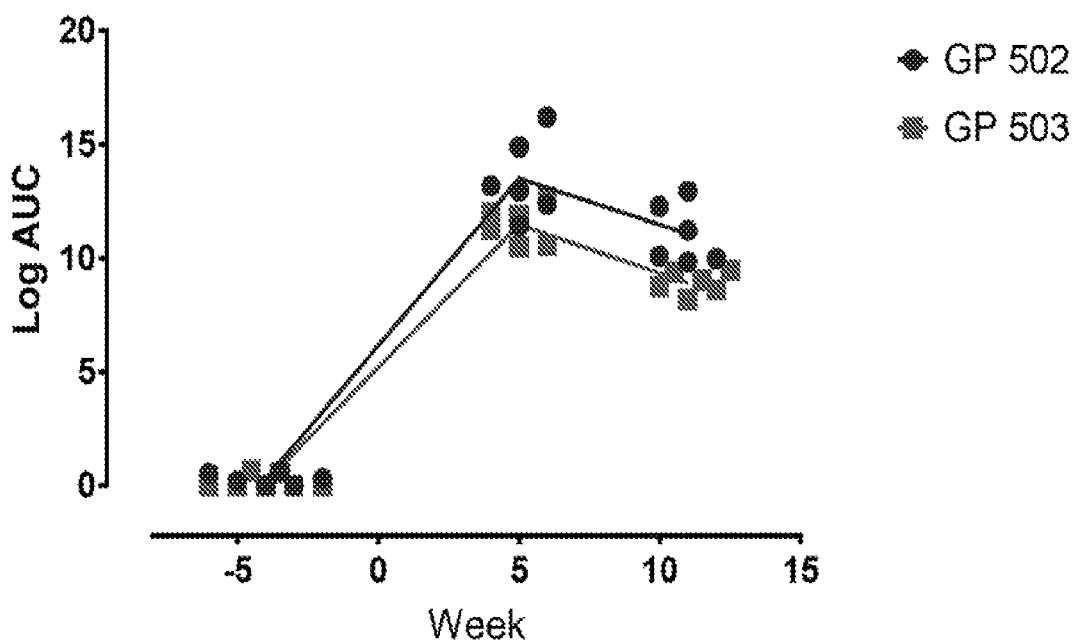
Figure 28C:
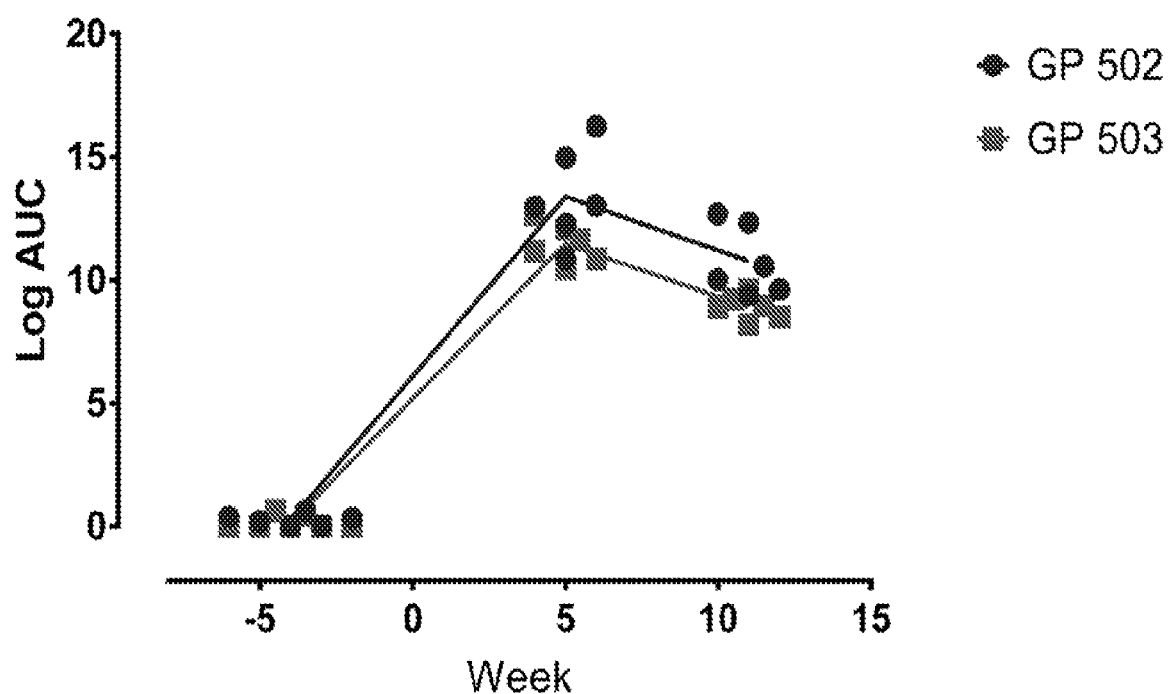
Figure 29A:
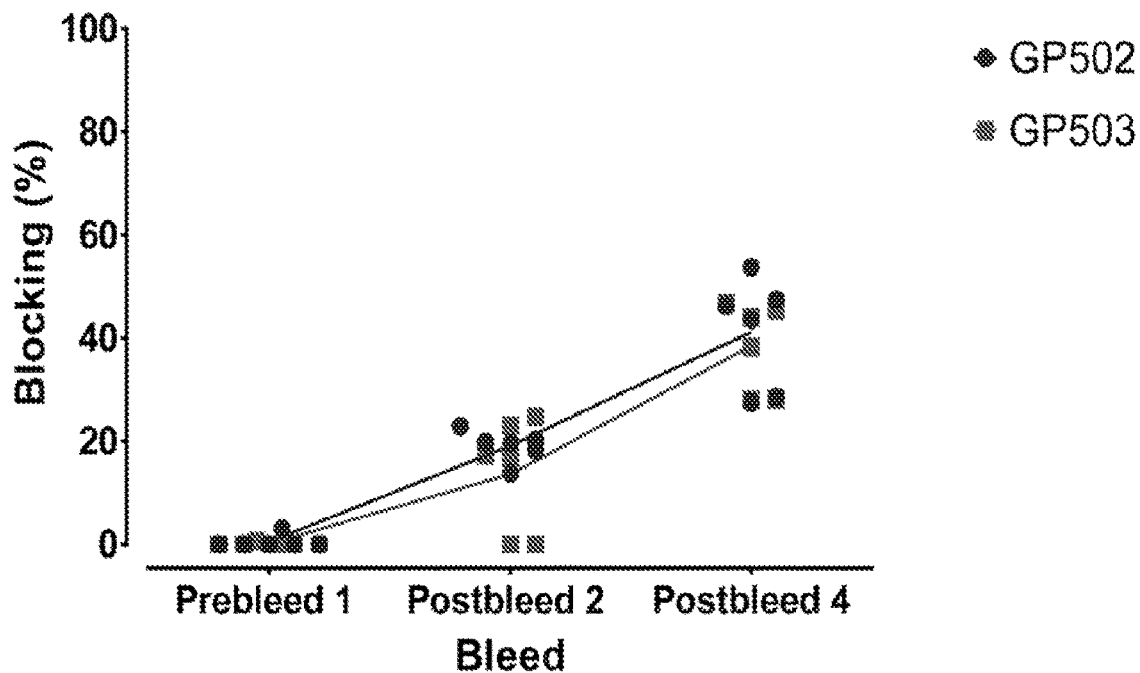
FIG. 29A-29F shows the blocking assays average score for the entire panel of blocking assays (all the assays of the blocking panel listed on the next figure). Compares the key groups with each other. Mean blocking activity of post bleed guinea pig sera from the indicated groups (GP502-GP506) was measured by ELISA. The mean was calculated from the results of blocking across seven different antibody specificities. Plates were coated with protein at 2 ug/ml. Sera were added at a 1:50 dilution, washed and a biotinylated epitope specific monoclonal antibody was added at an amount equivalent to the EC50. Reduction in binding of the biotinylated antibody was compared to a full binding control and expressed as % Blocking. Each symbol represents an individual animal within each group of six animals. Higher % Blocking suggests greater binding of the sera to specific epitopes on the test protein.
Figure 29B:
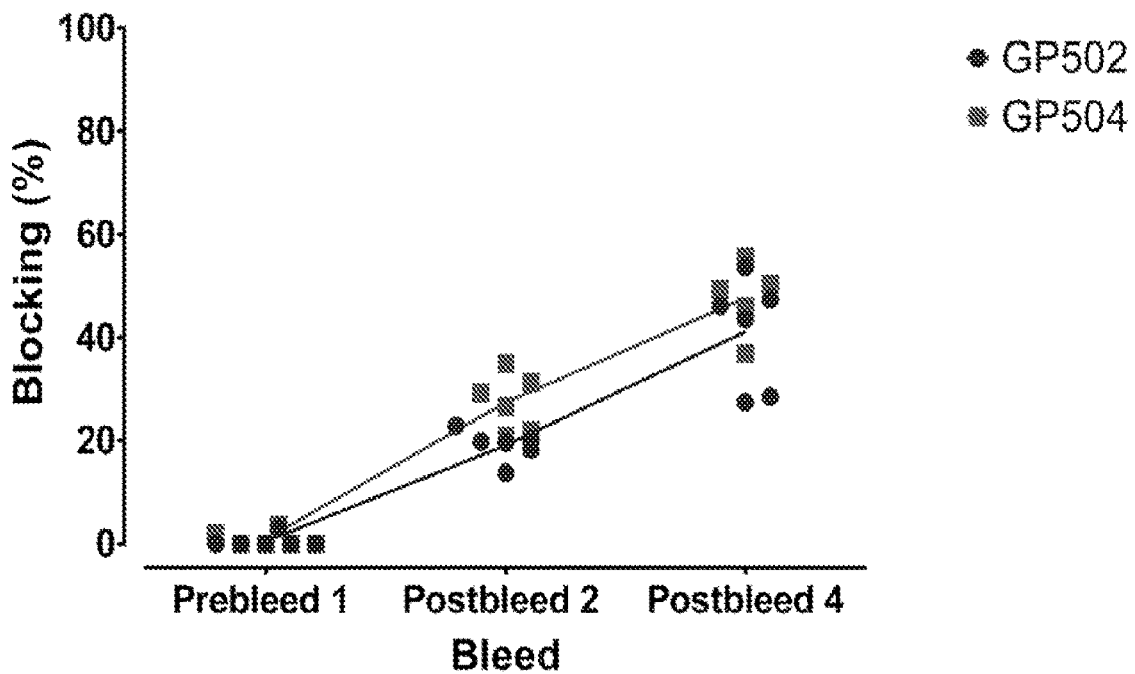
Figure 29C:
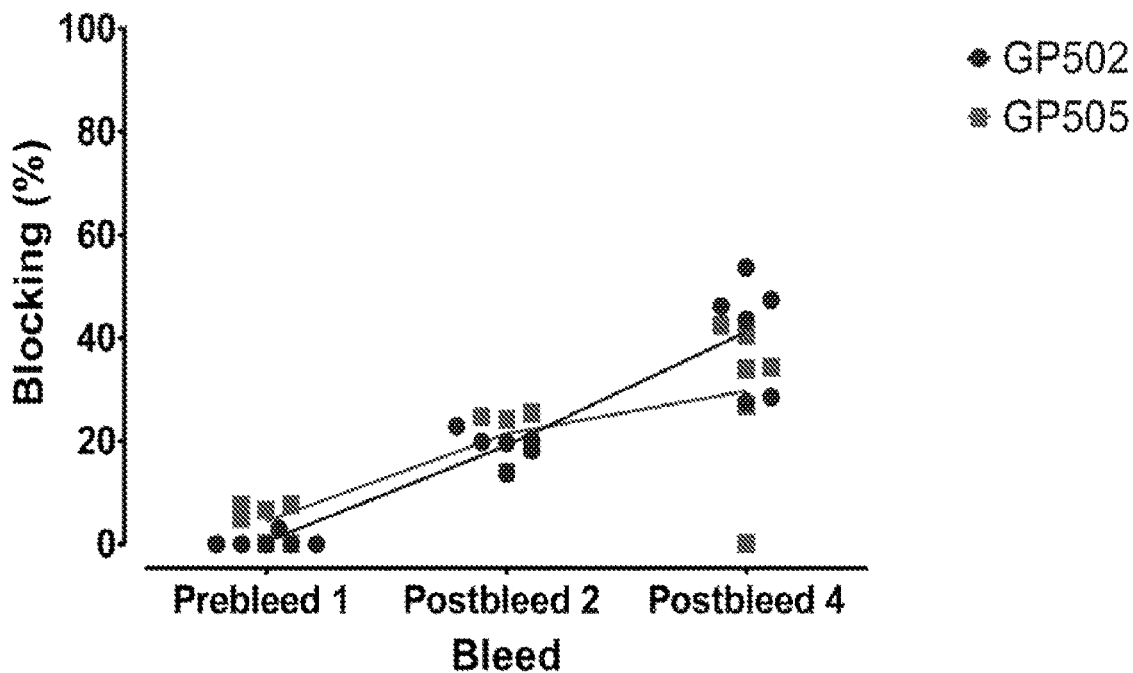
Figure 29D:
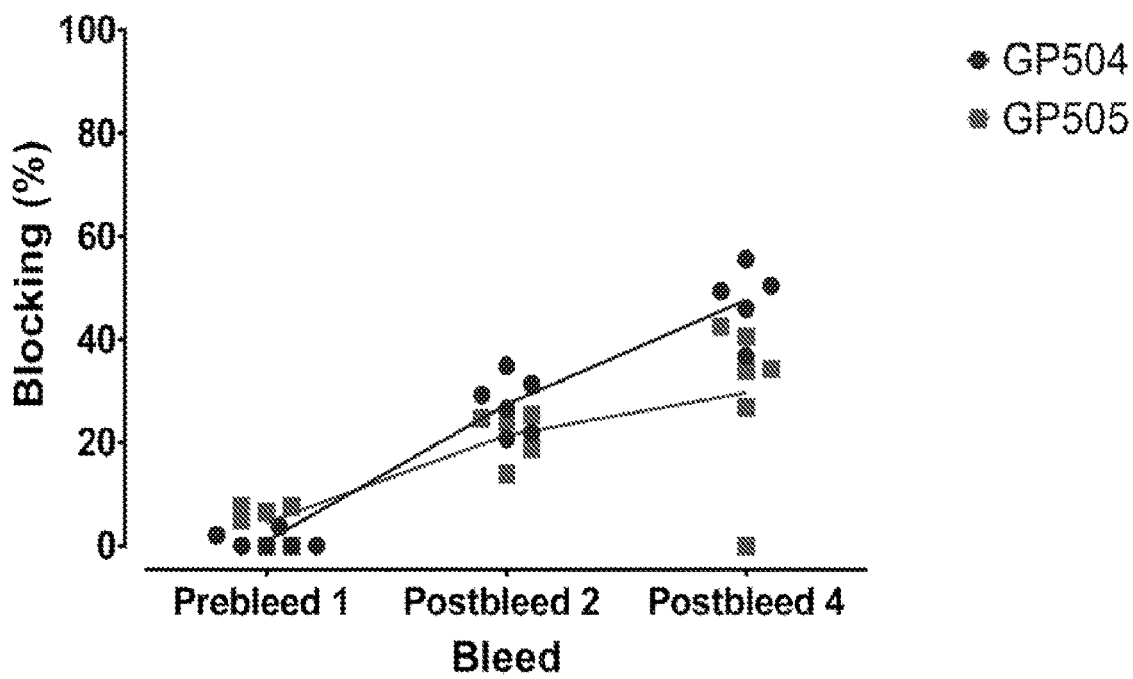
Figure 29E:
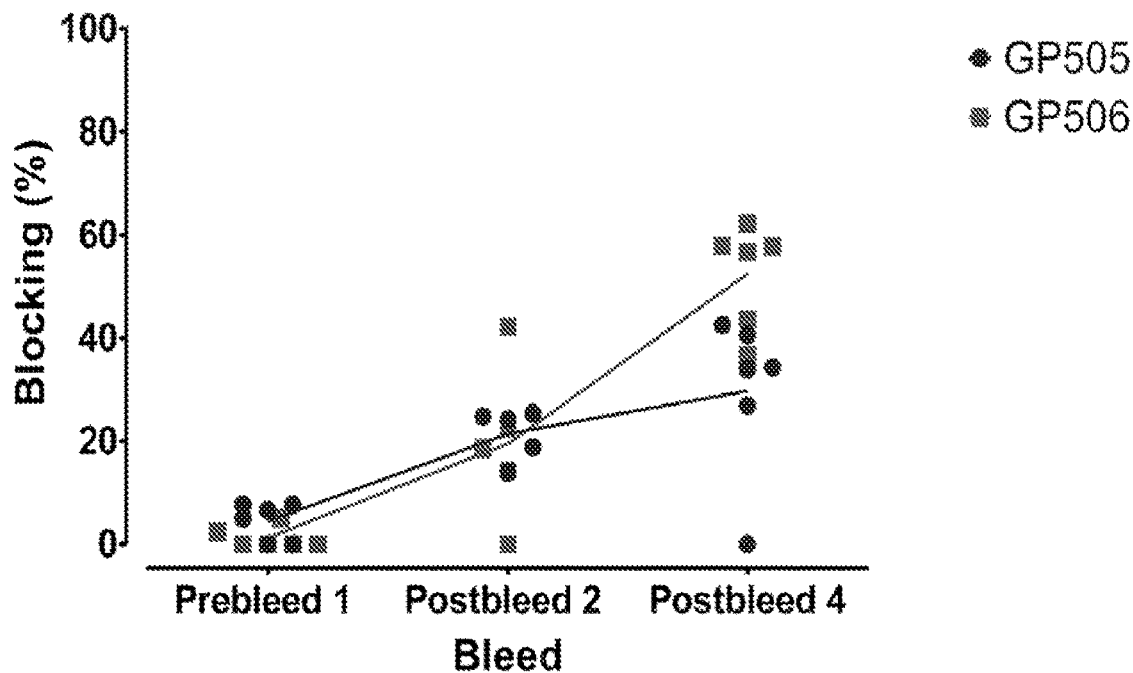
Figure 29F:
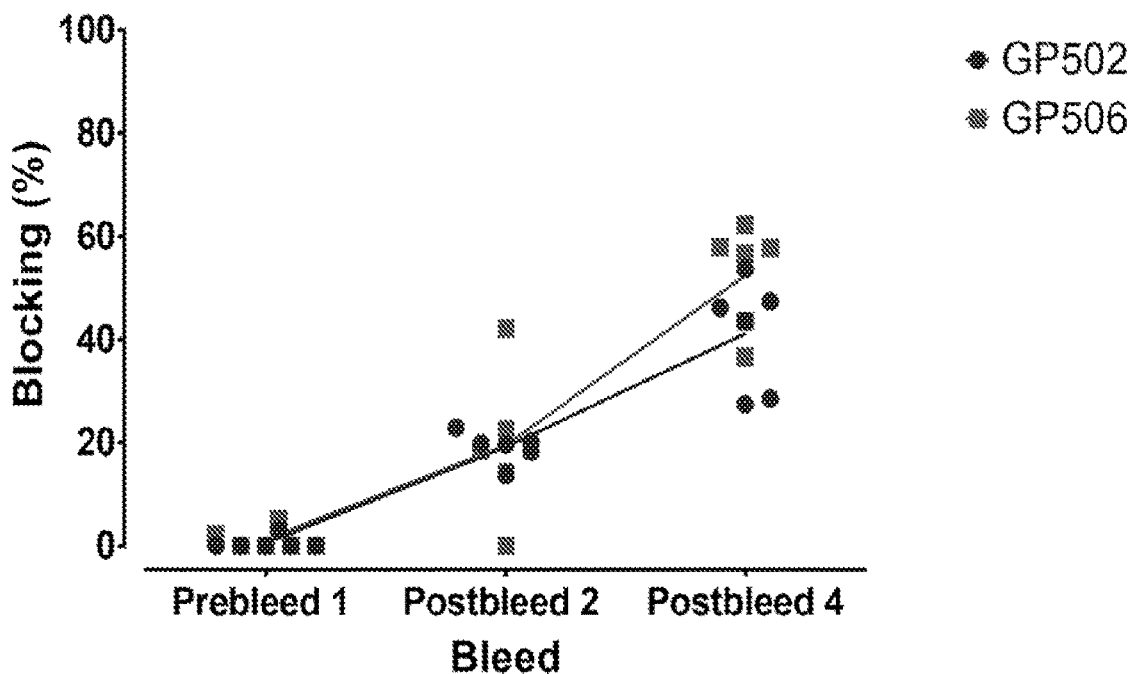
Figure 29G:
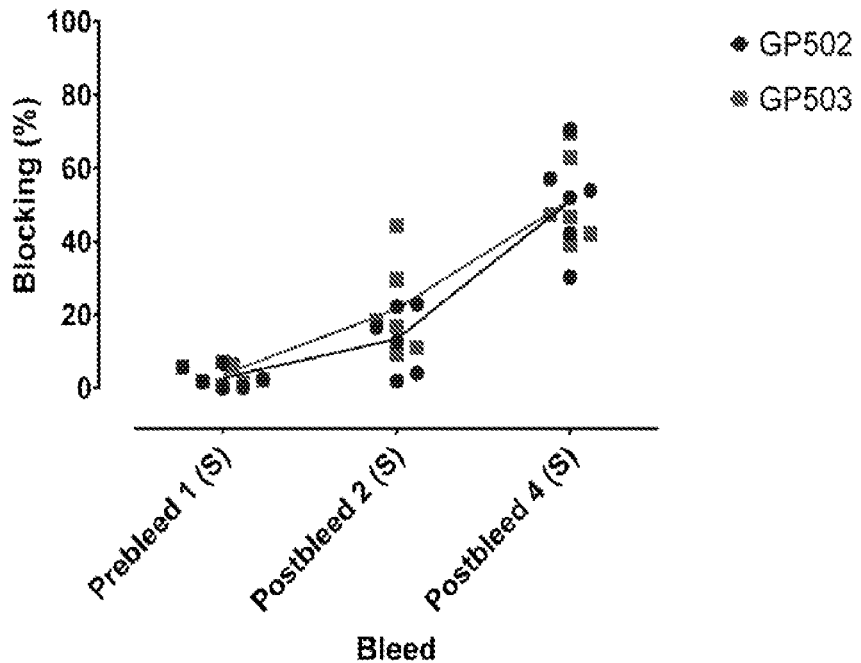
FIG. 29G shows Epitope specific blocking activity of guinea pig sera from the indicated groups (GP502 and GP503) was measured by ELISA.
Figure 29G:
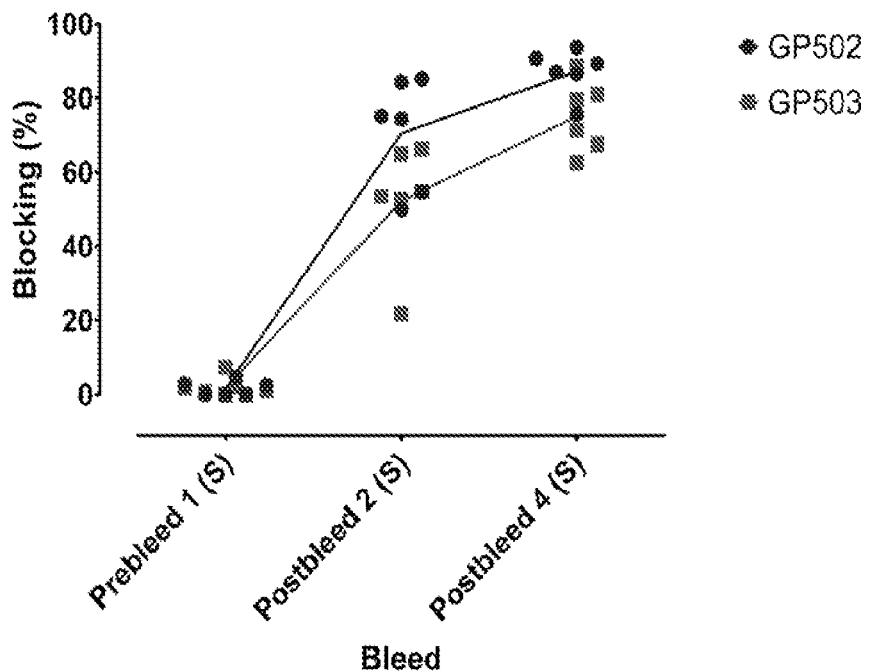
Figure 29G:
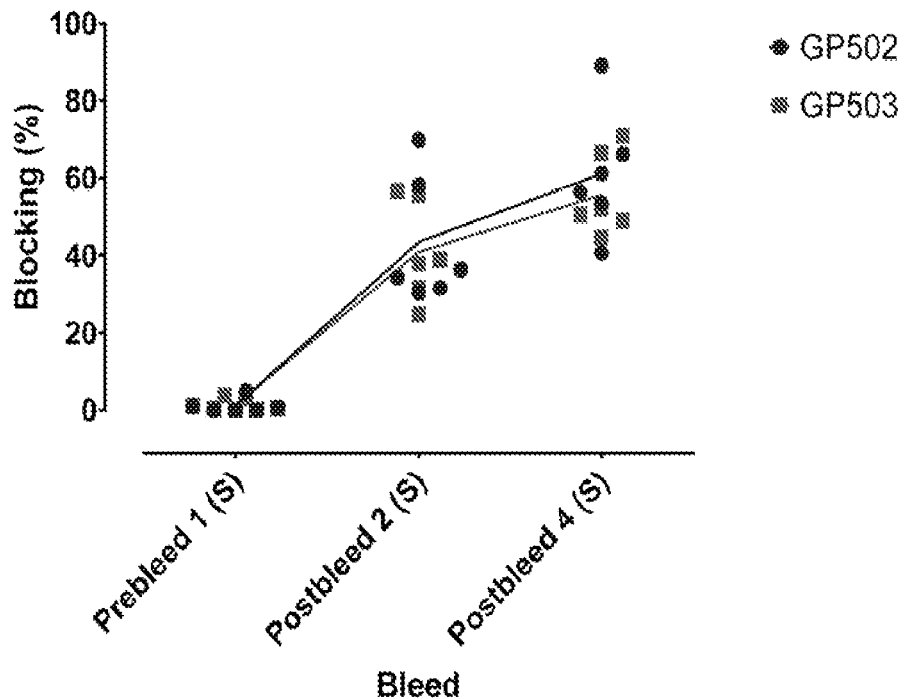
Figure 29:
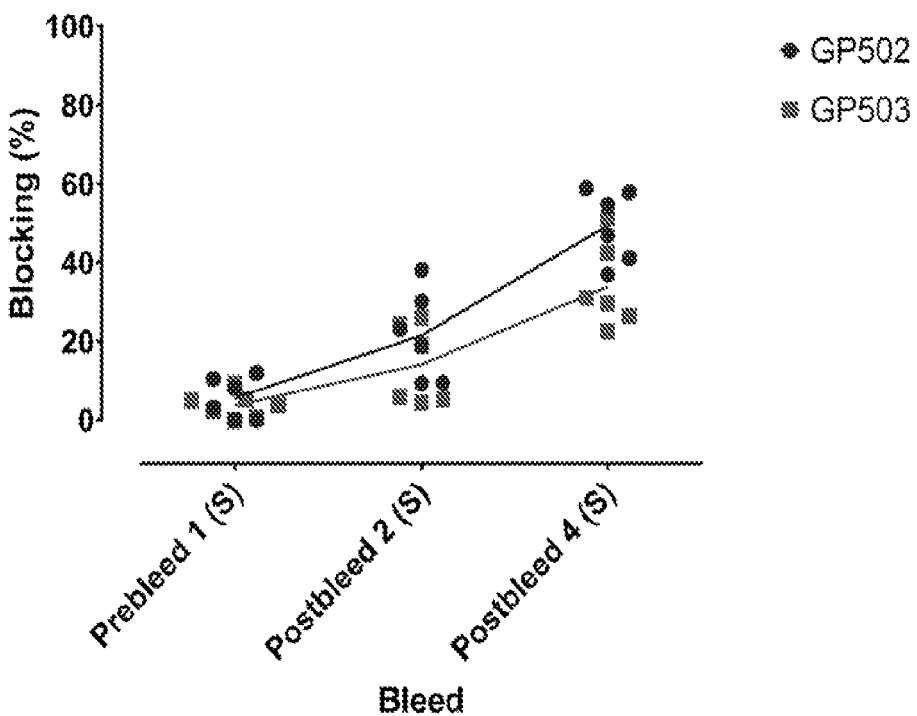
FIG. 29H shows Epitope specific blocking activity of guinea pig sera from the indicated groups (GP502 and GP504) was measured by ELISA.
FIG. 29I shows Epitope specific blocking activity of guinea pig sera from the indicated groups (GP502 and GP505) was measured by ELISA.
FIG. 29J shows Epitope specific blocking activity of guinea pig sera from the indicated groups (GP502 and GP506) was measured by ELISA.
FIG. 29K shows Epitope specific blocking activity of guinea pig sera from the indicated groups (GP504 and GP505) was measured by ELISA.
FIG. 29L shows Epitope specific blocking activity of guinea pig sera from the indicated groups (GP505 and GP506) was measured by ELISA.
Figure 29G:
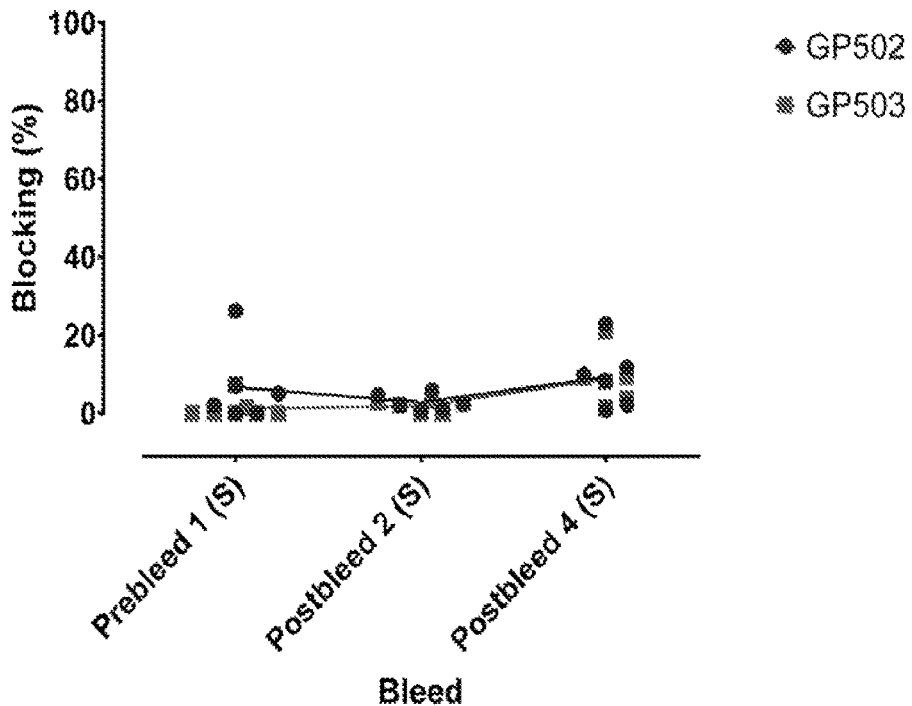
Figure 29G:
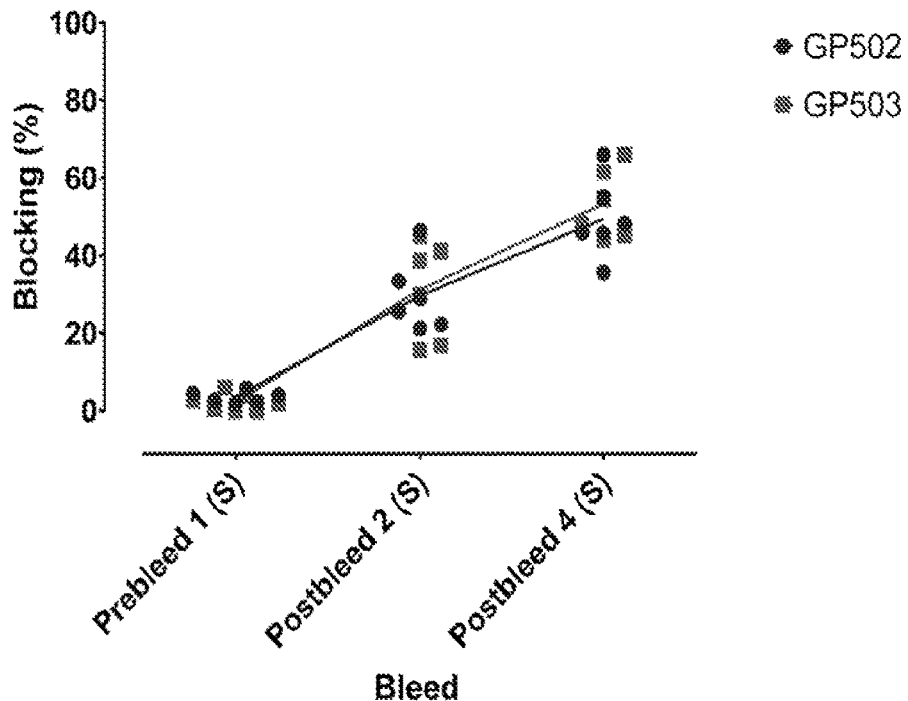
Figure 29G:
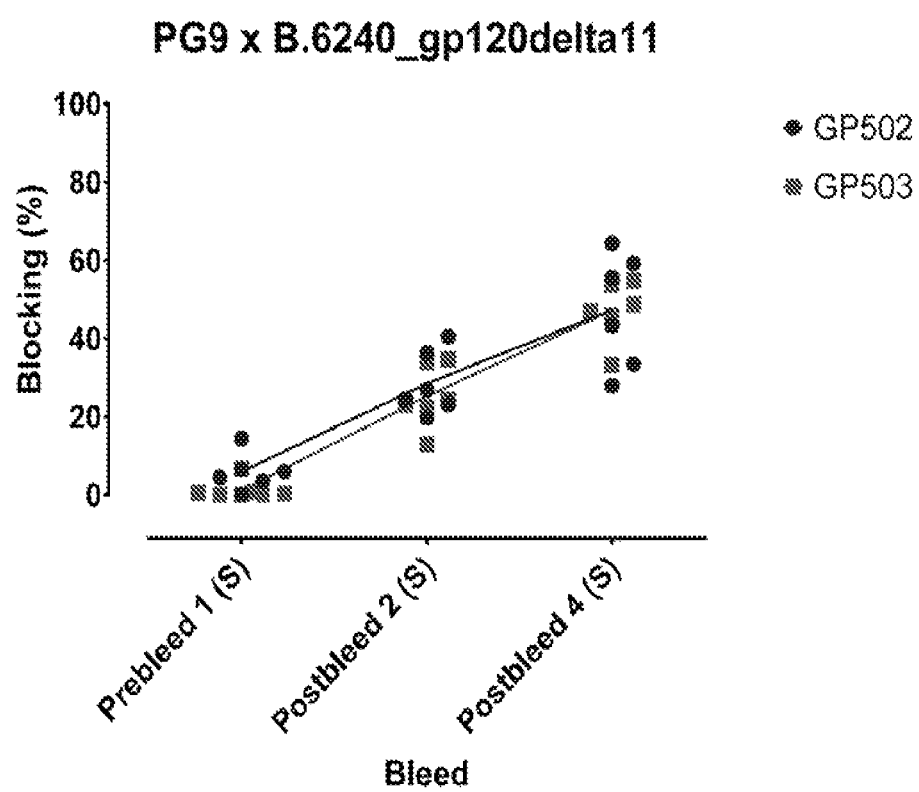
Figure 29H:
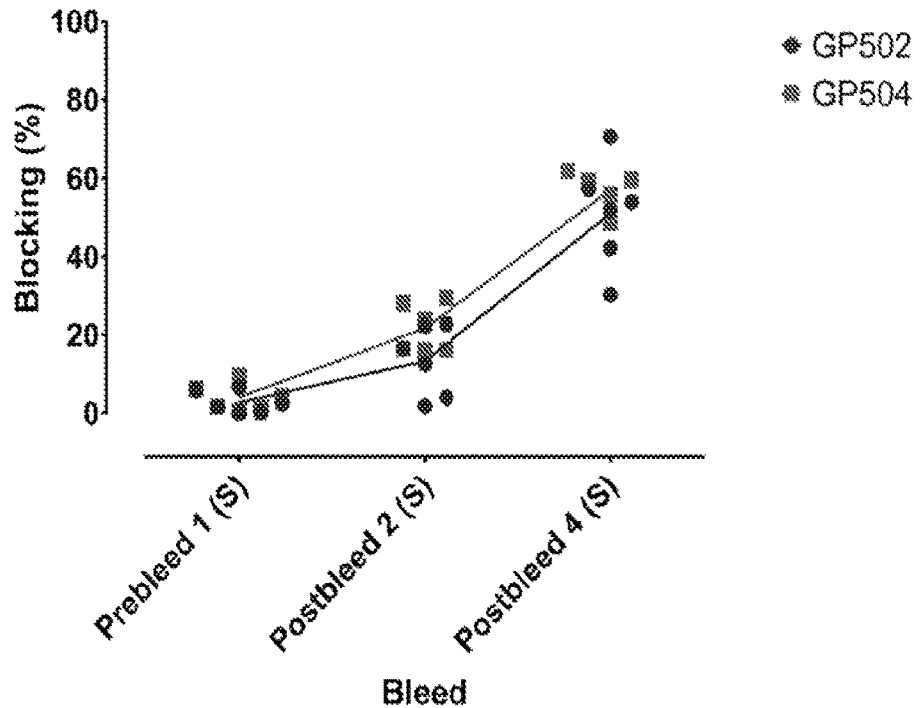
Figure 29H:
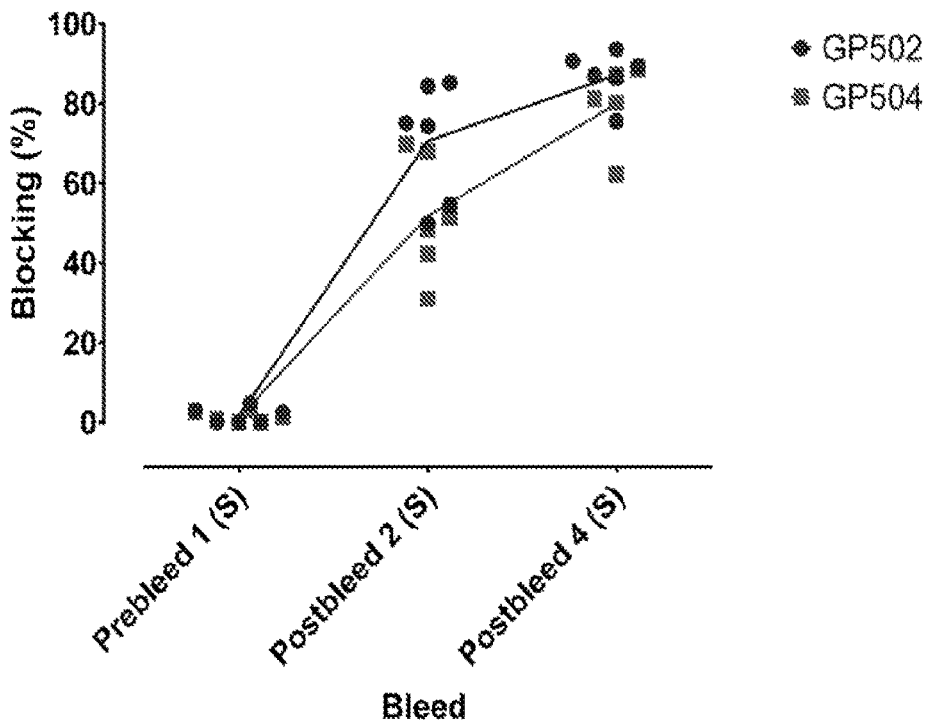
Figure 29H:
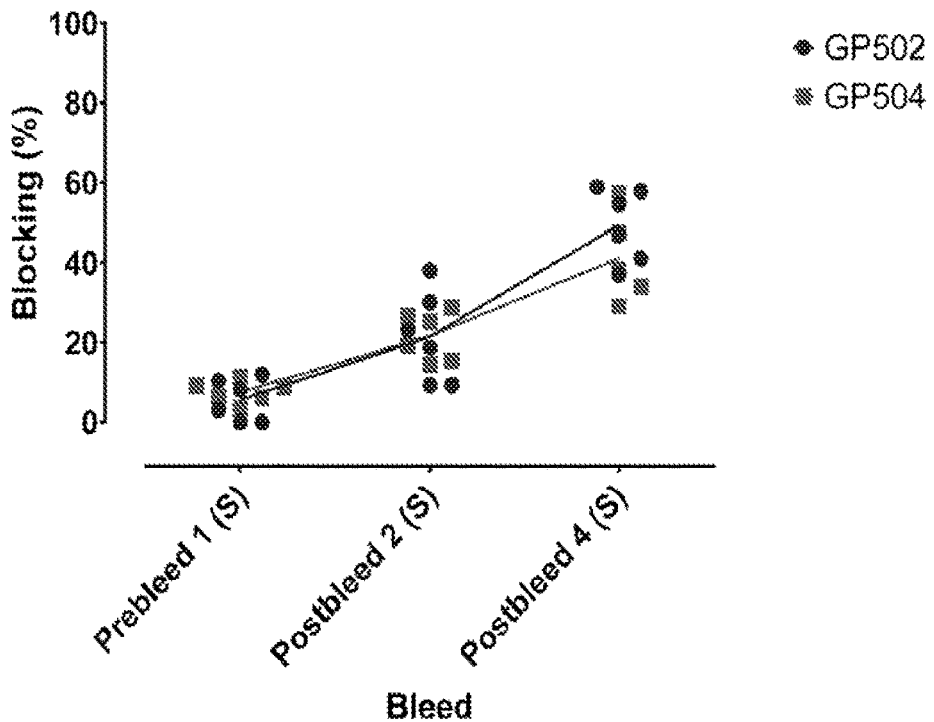
Figure 29H:
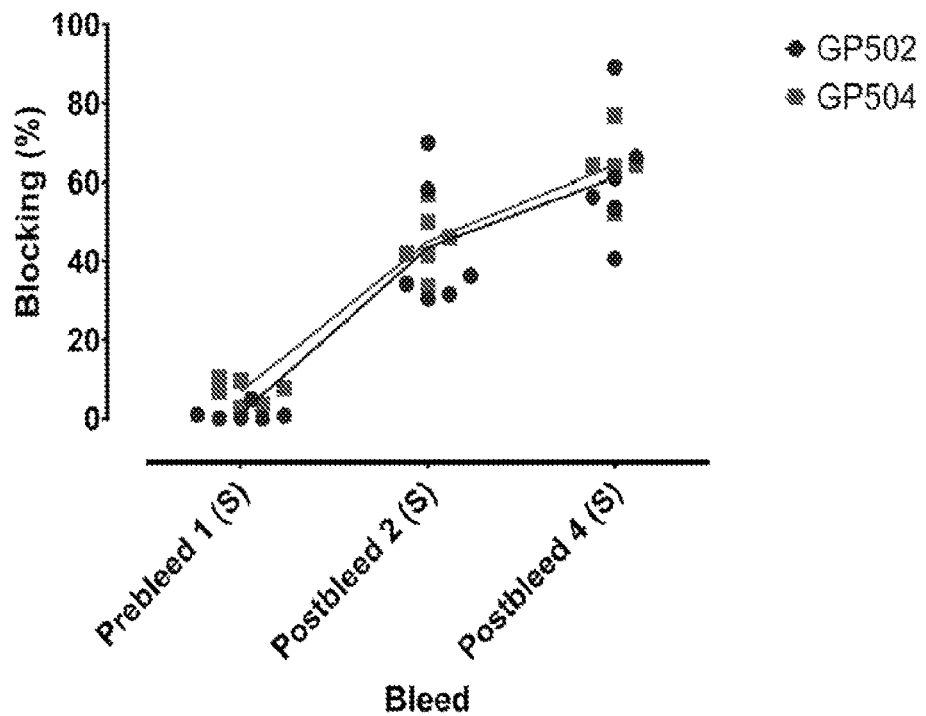
Figure 29H:
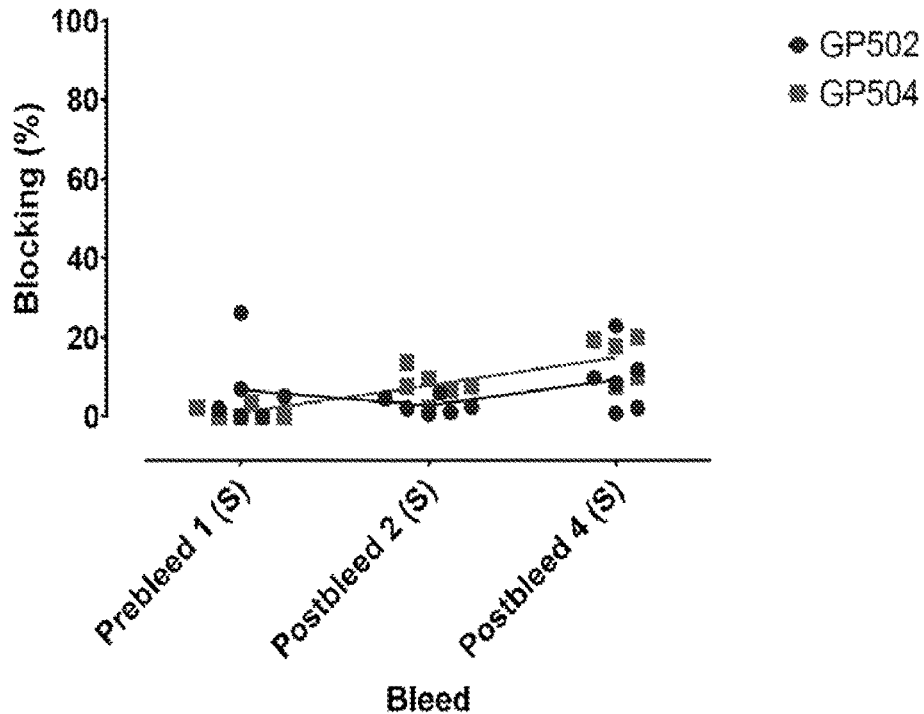
Figure 29H:
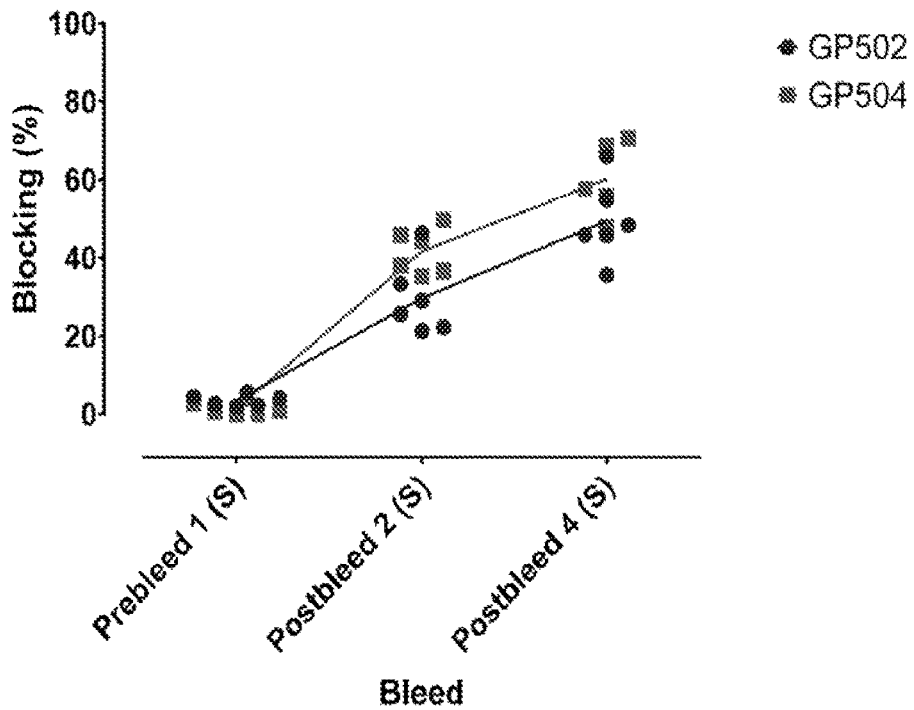
Figure 29H:
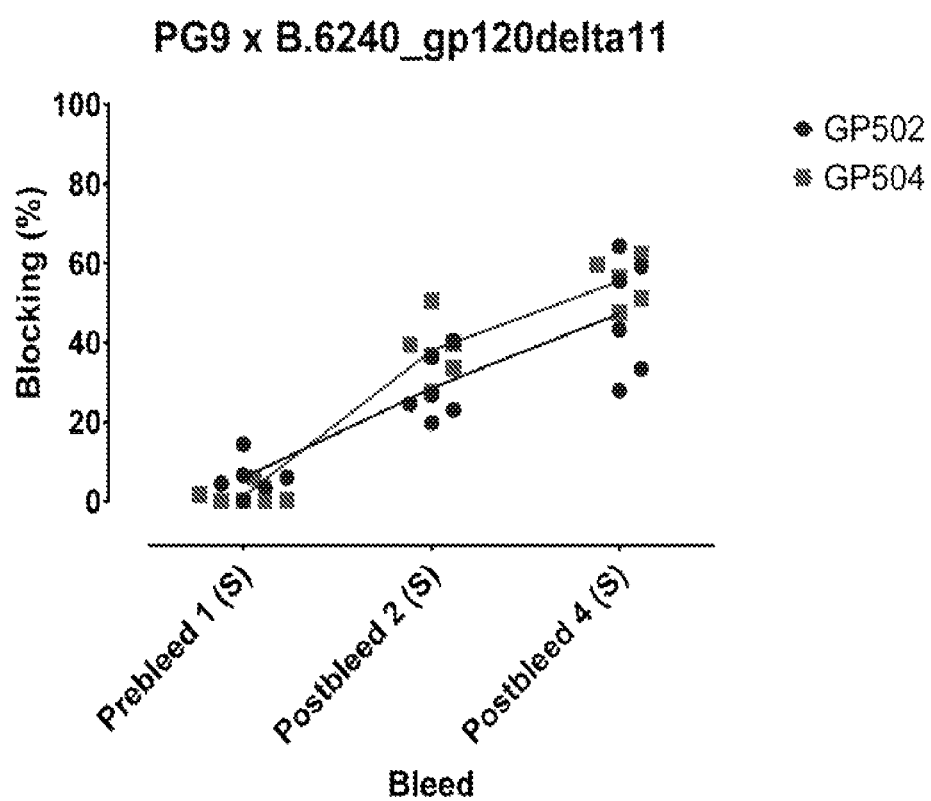
Figure 29I:
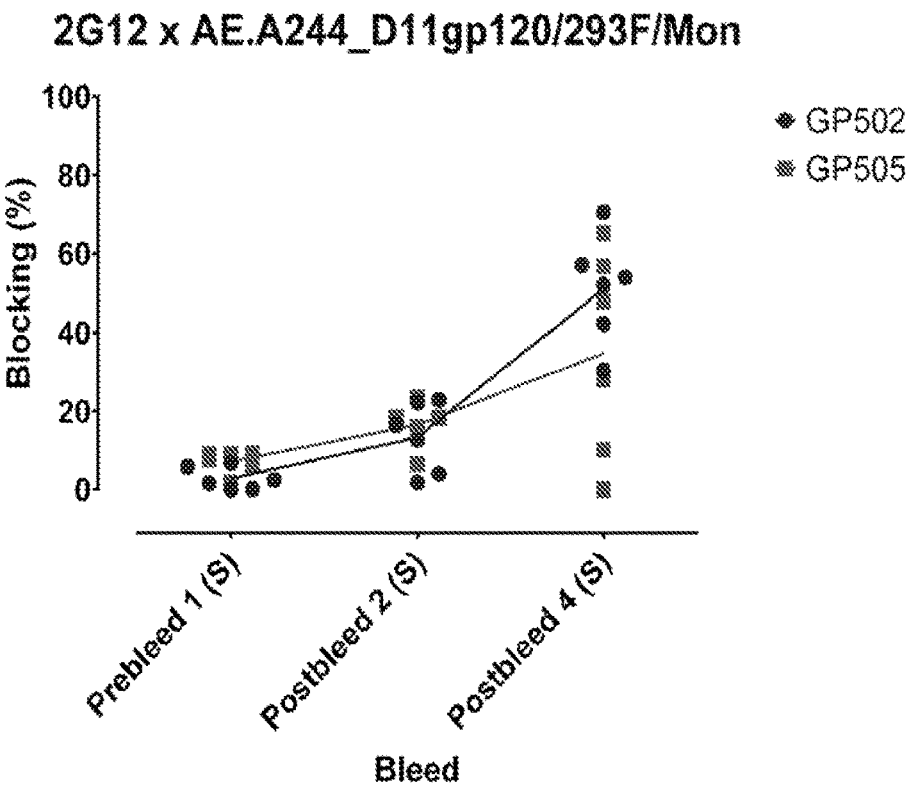
Figure 29I:
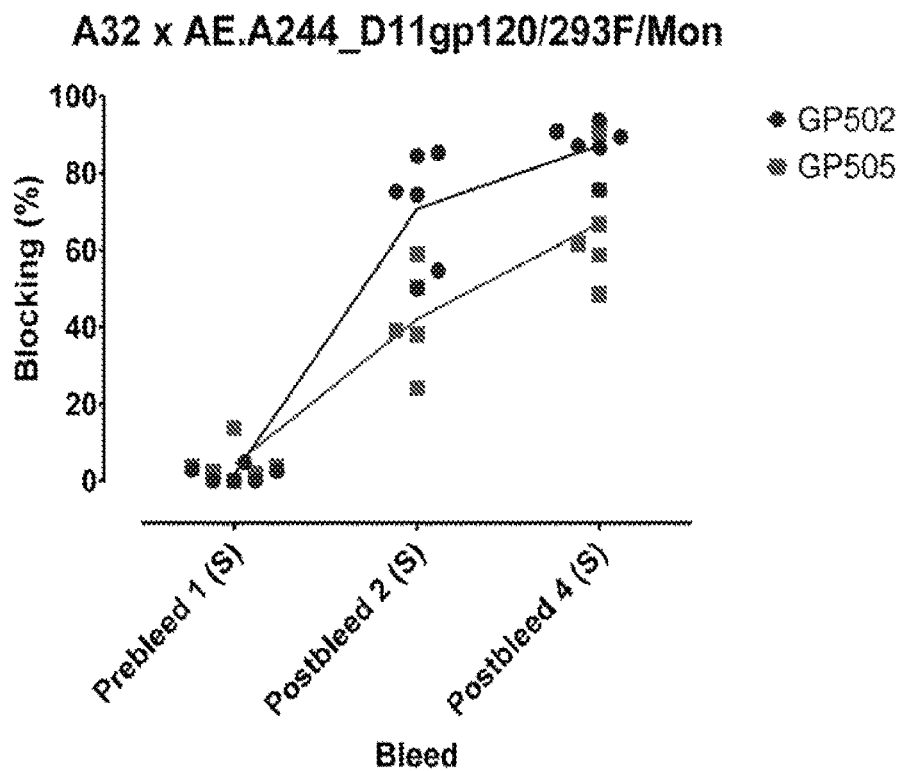
Figure 29I:
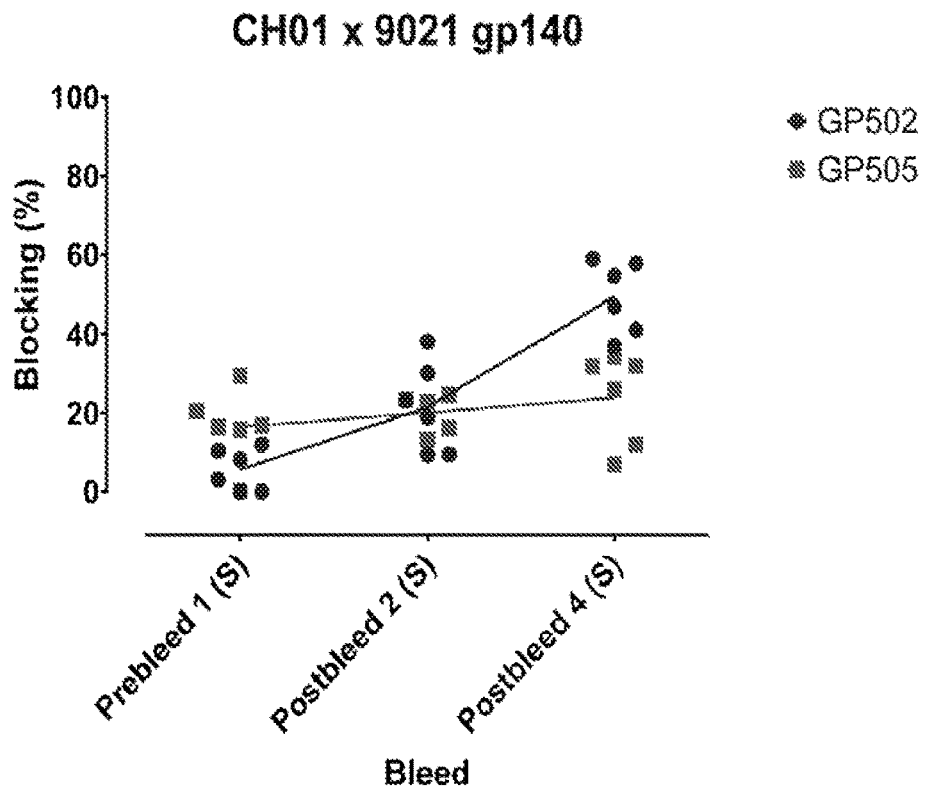
Figure 29I:
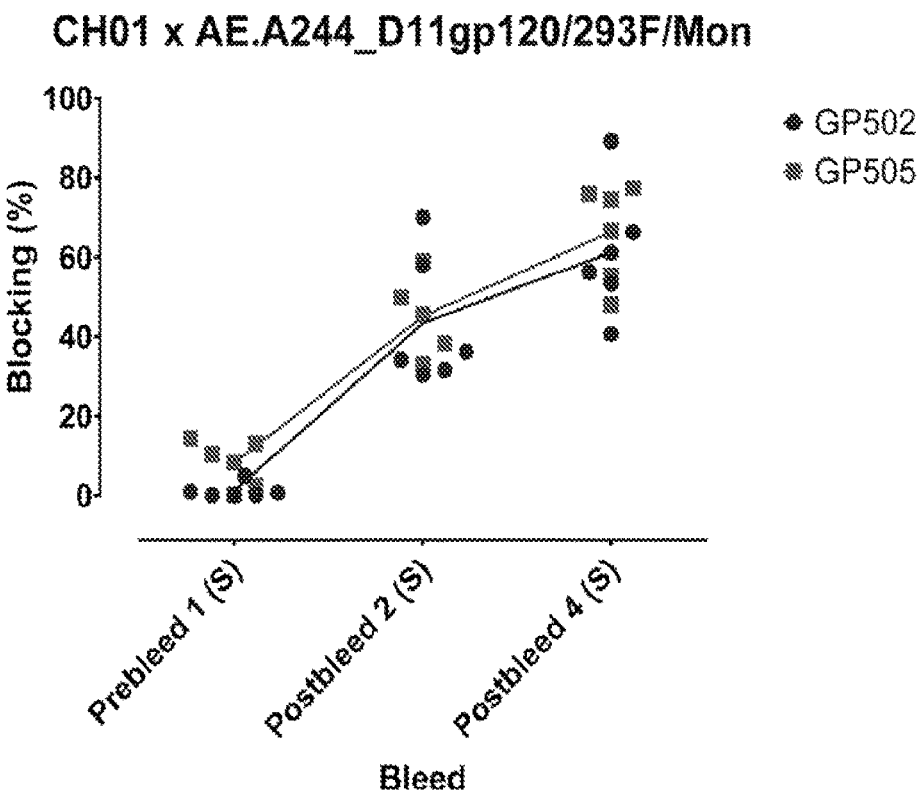
Figure 29I:
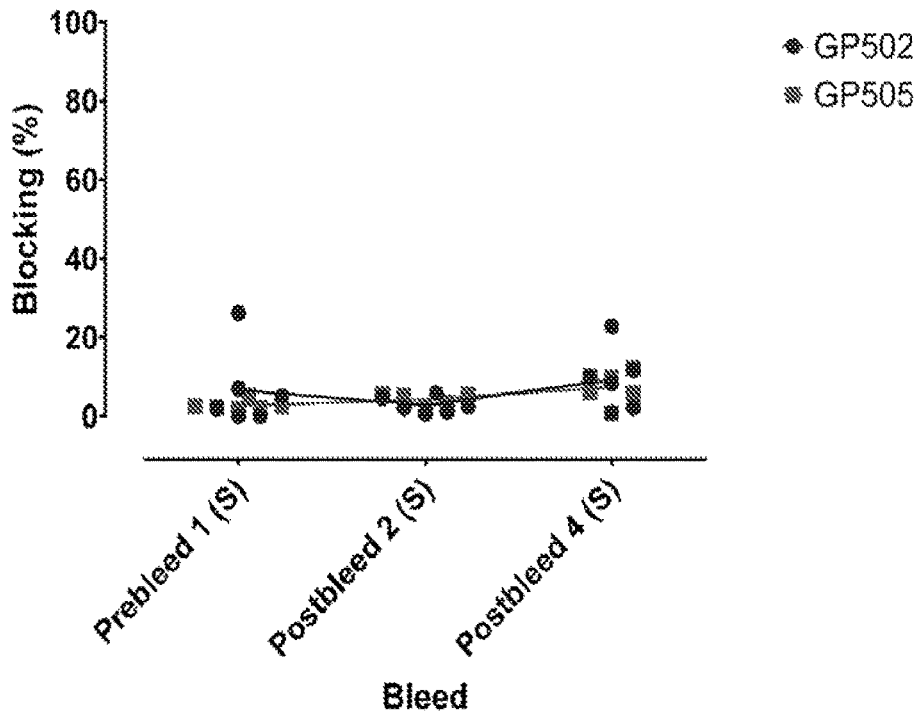
Figure 29I:
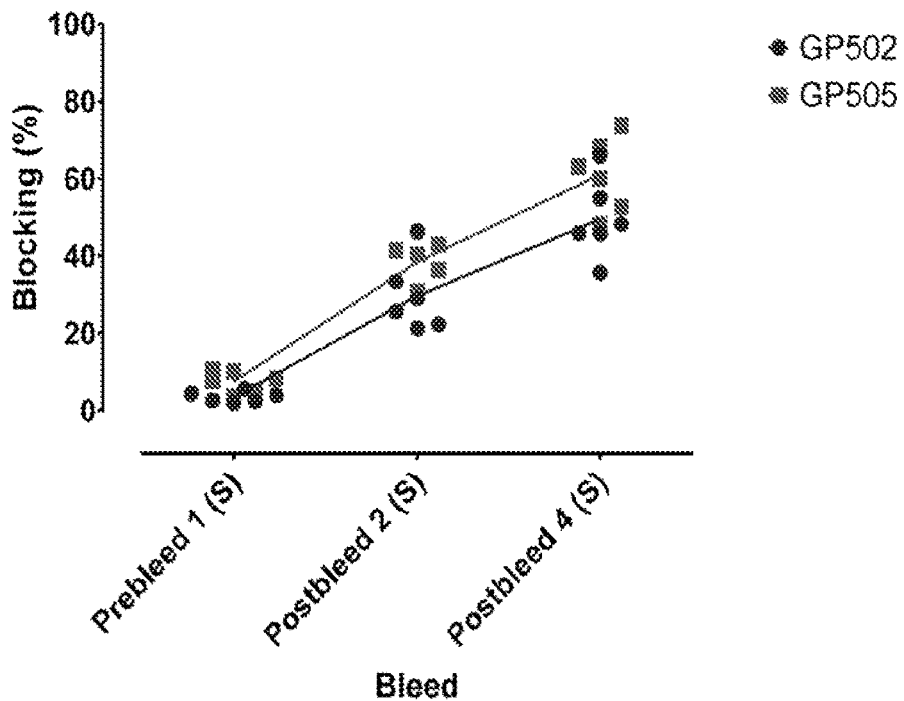
Figure 29I:
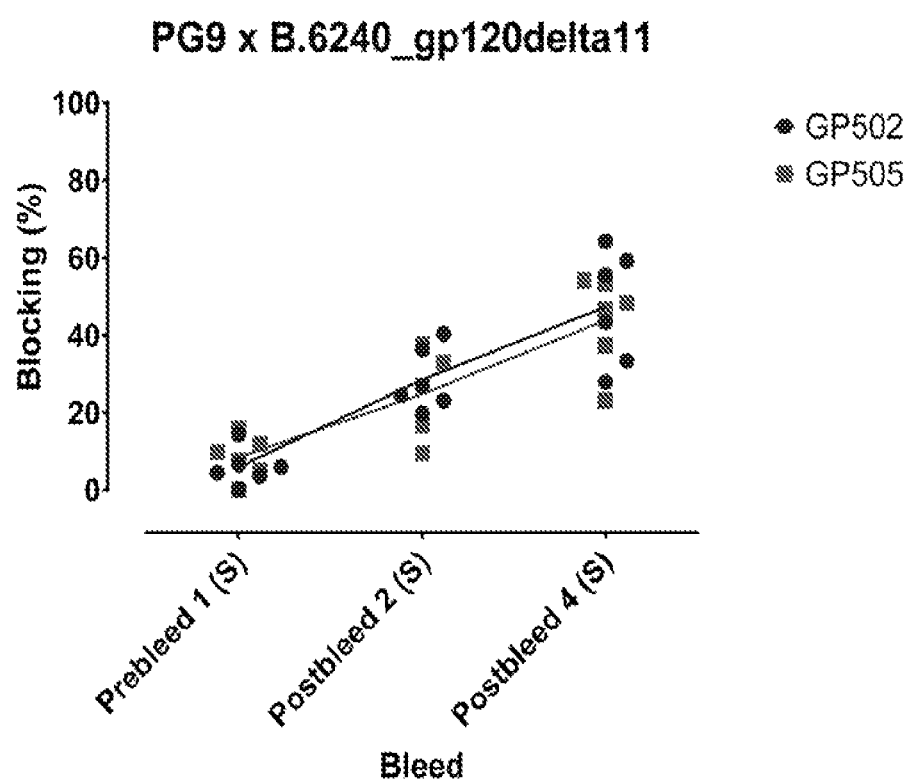
Figure 29J:
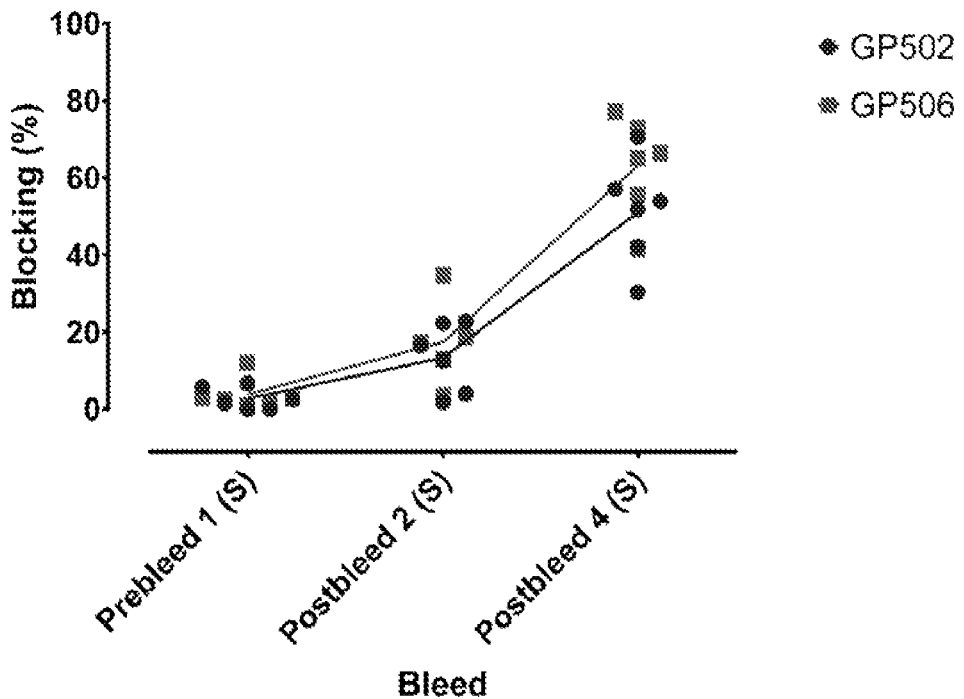
Figure 29J:
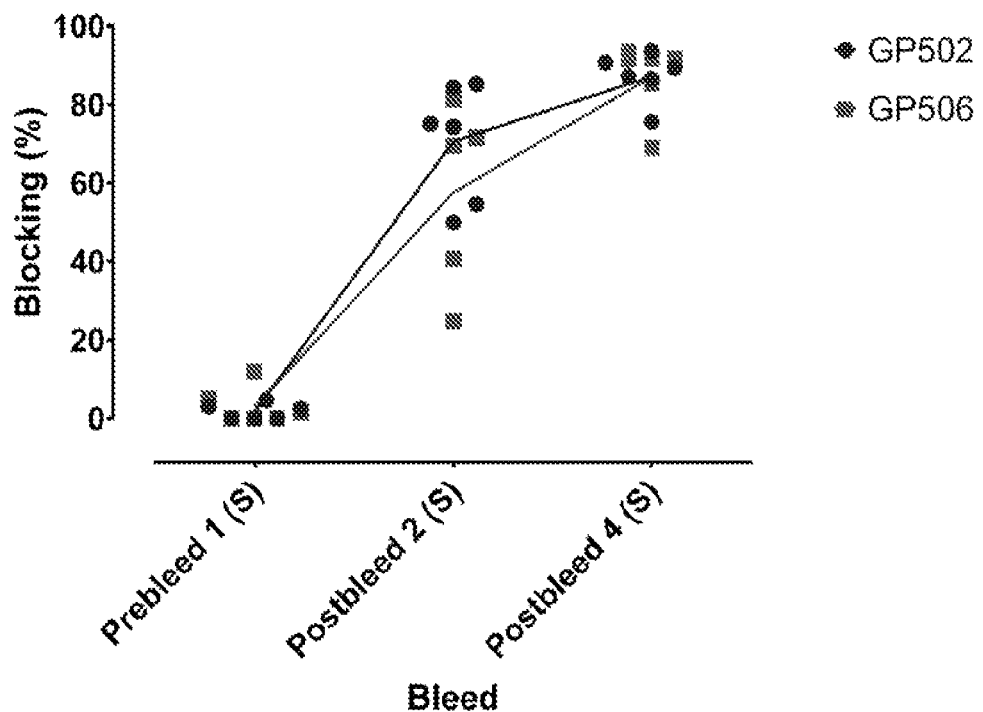
Figure 29J:
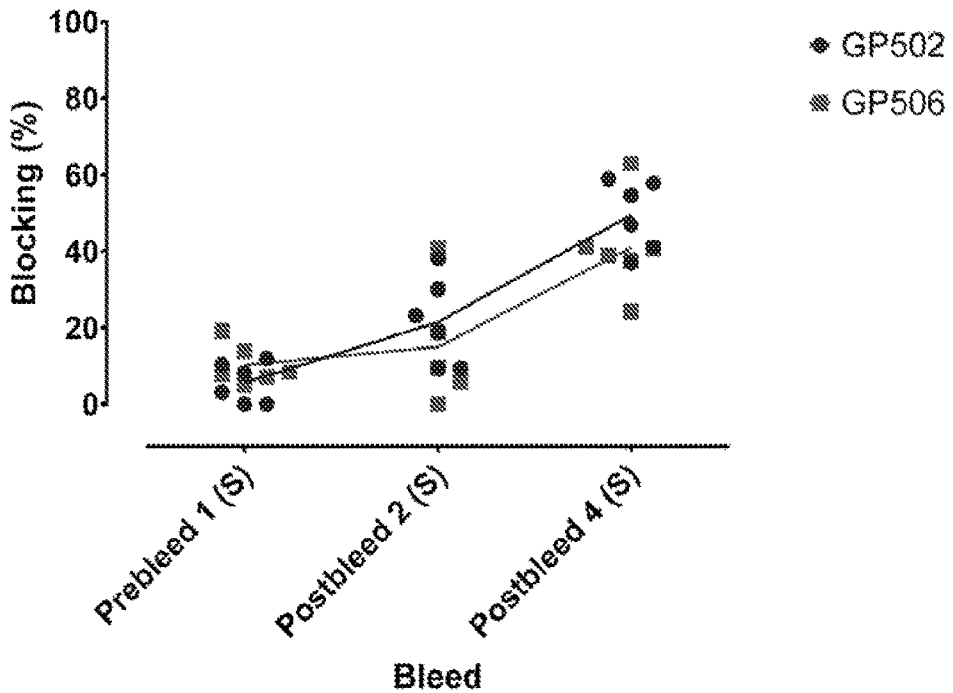
Figure 29J:
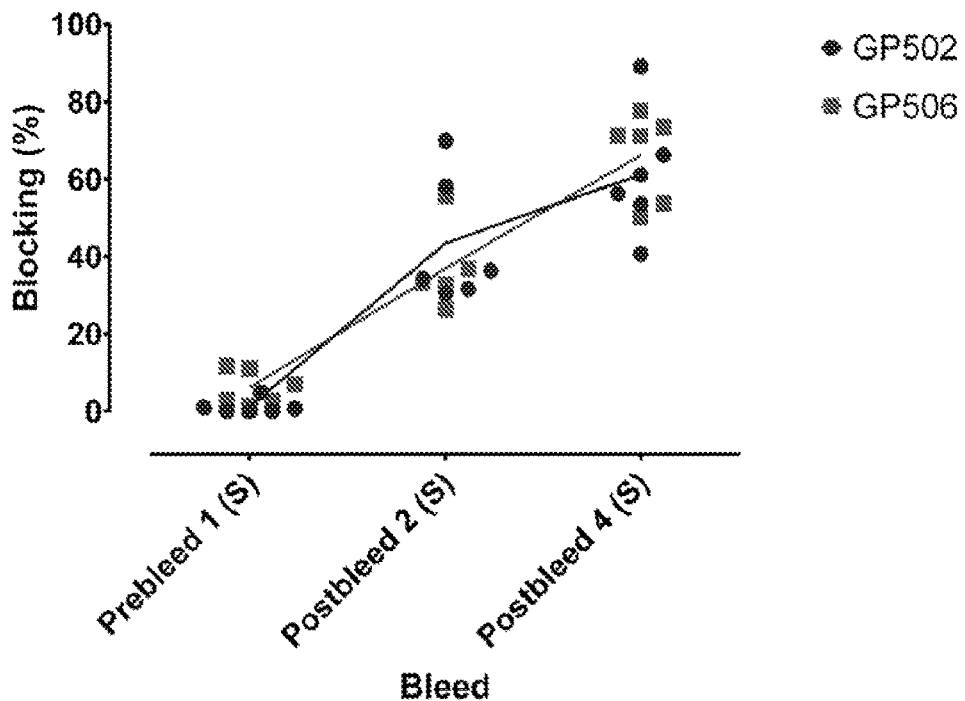
Figure 29J:
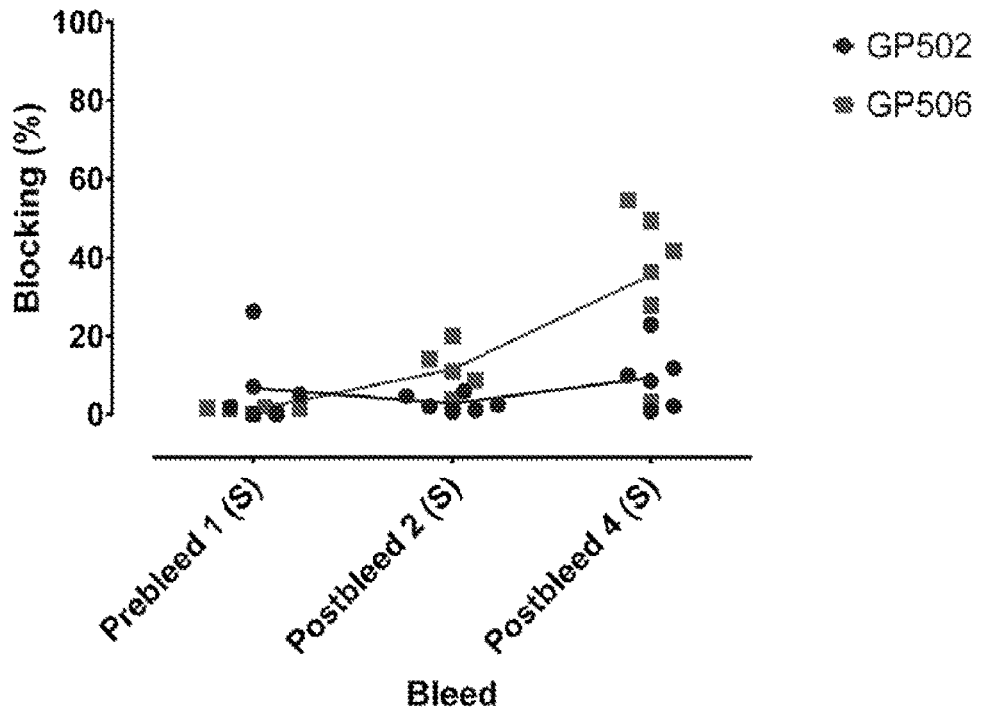
Figure 29J:
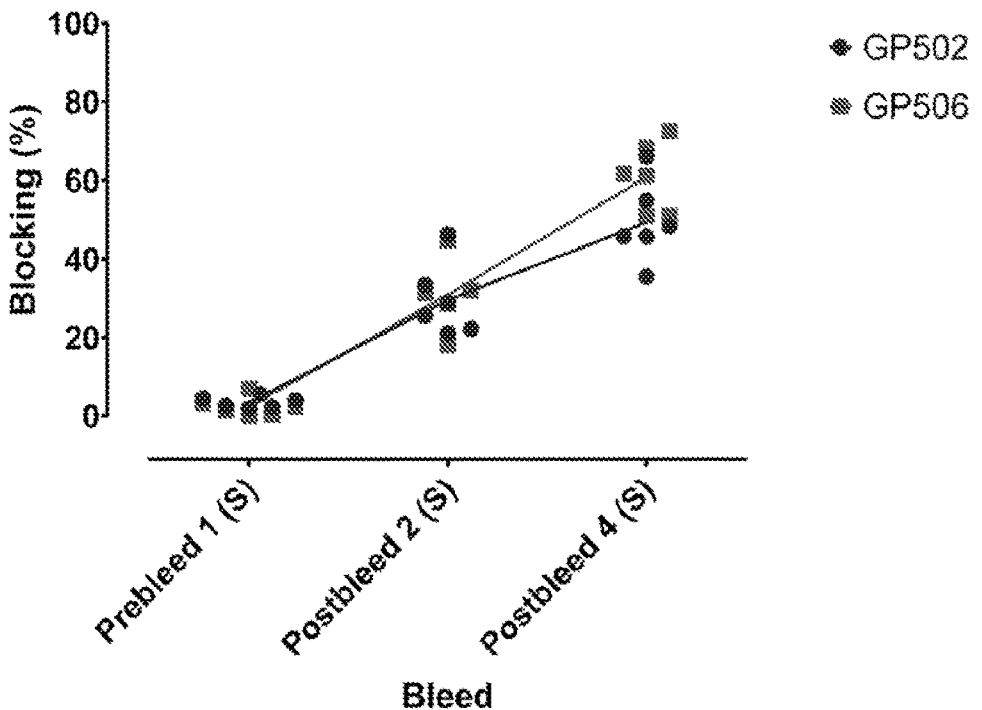
Figure 29J:
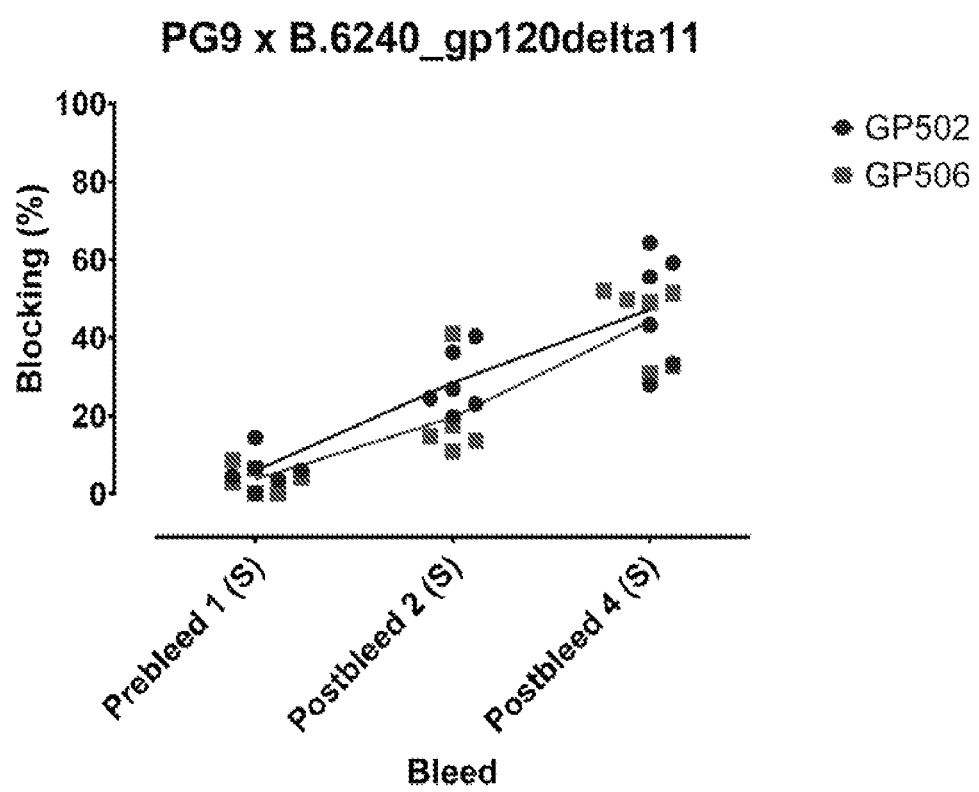
Figure 29K:
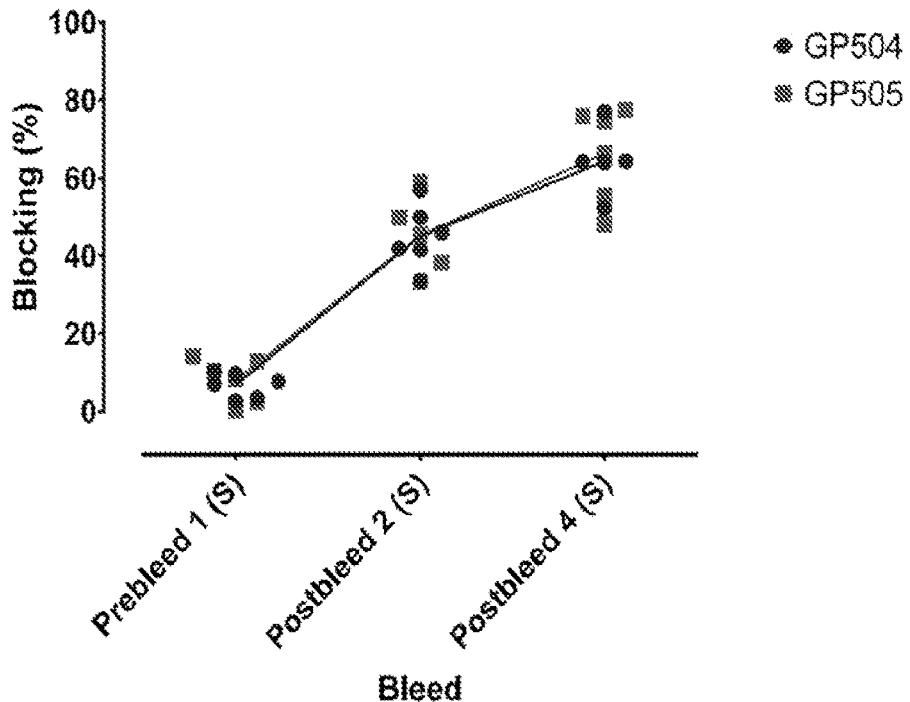
Figure 29K:
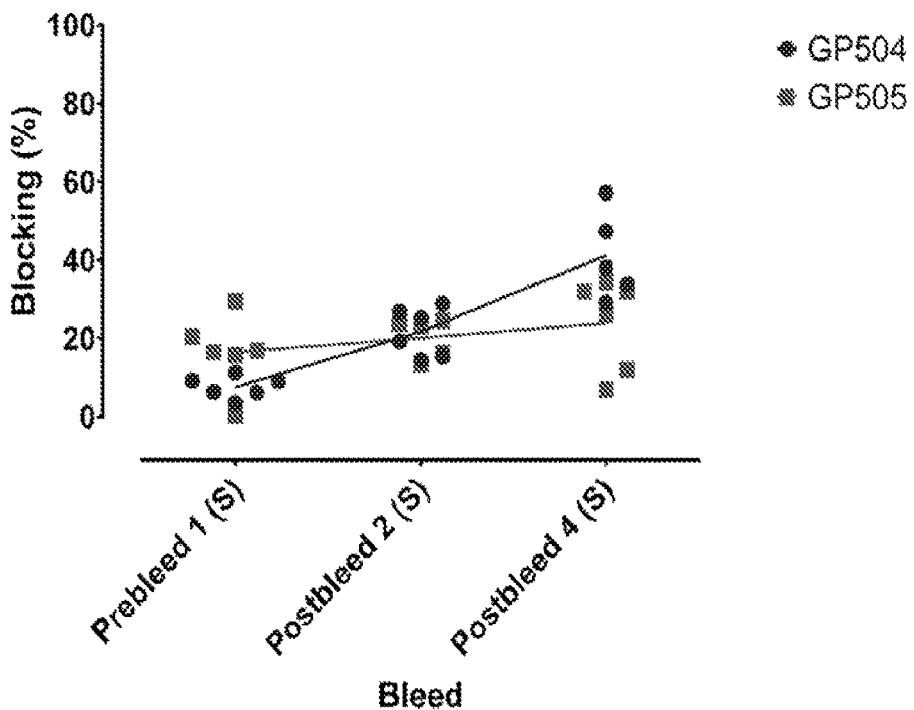
Figure 29K:
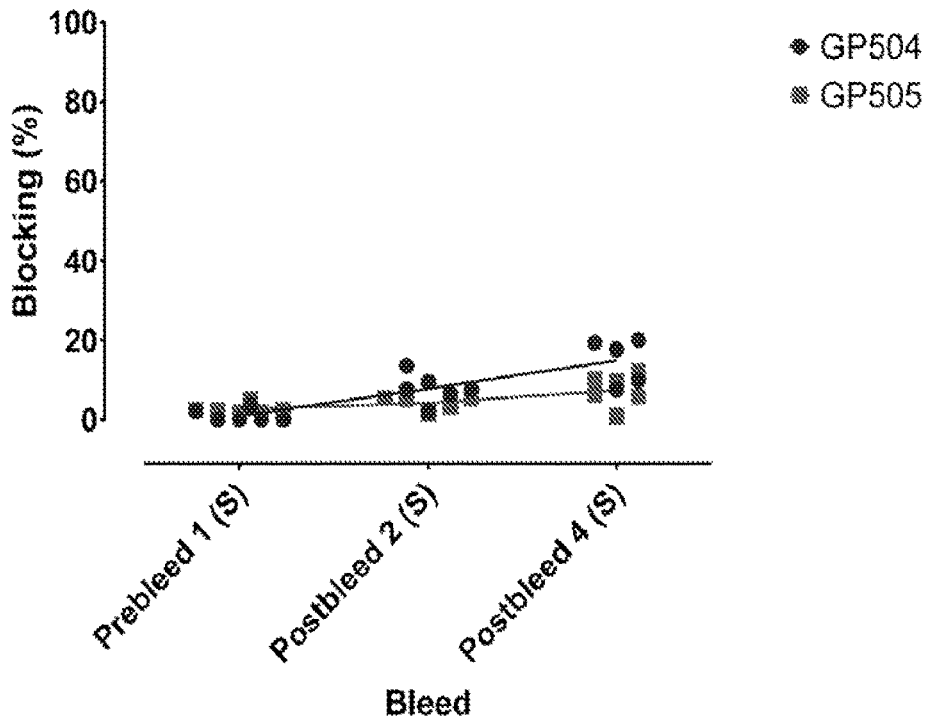
Figure 29K:
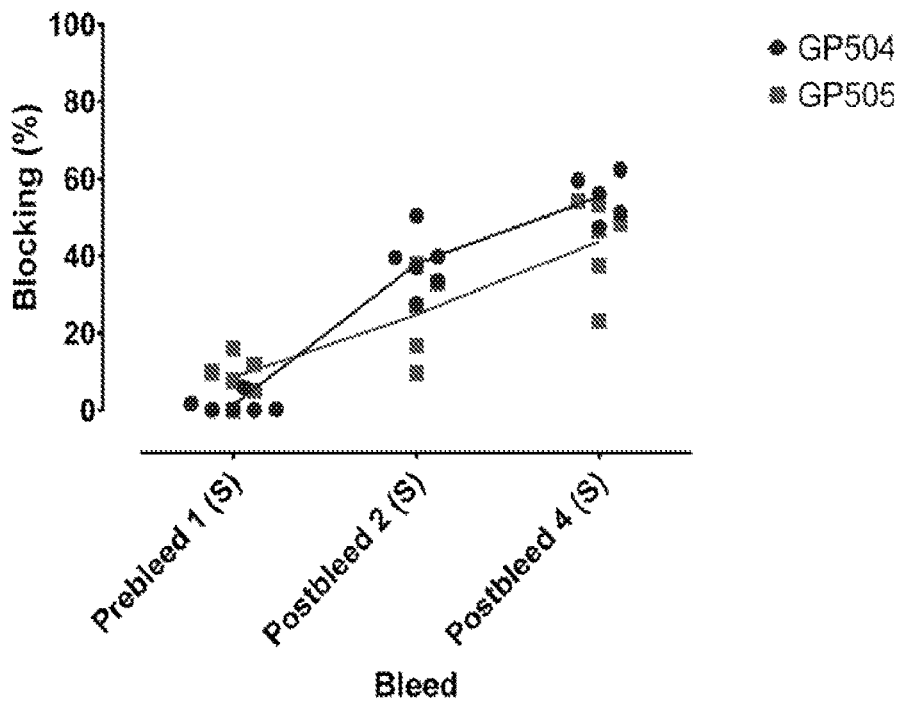
Figure 29K:
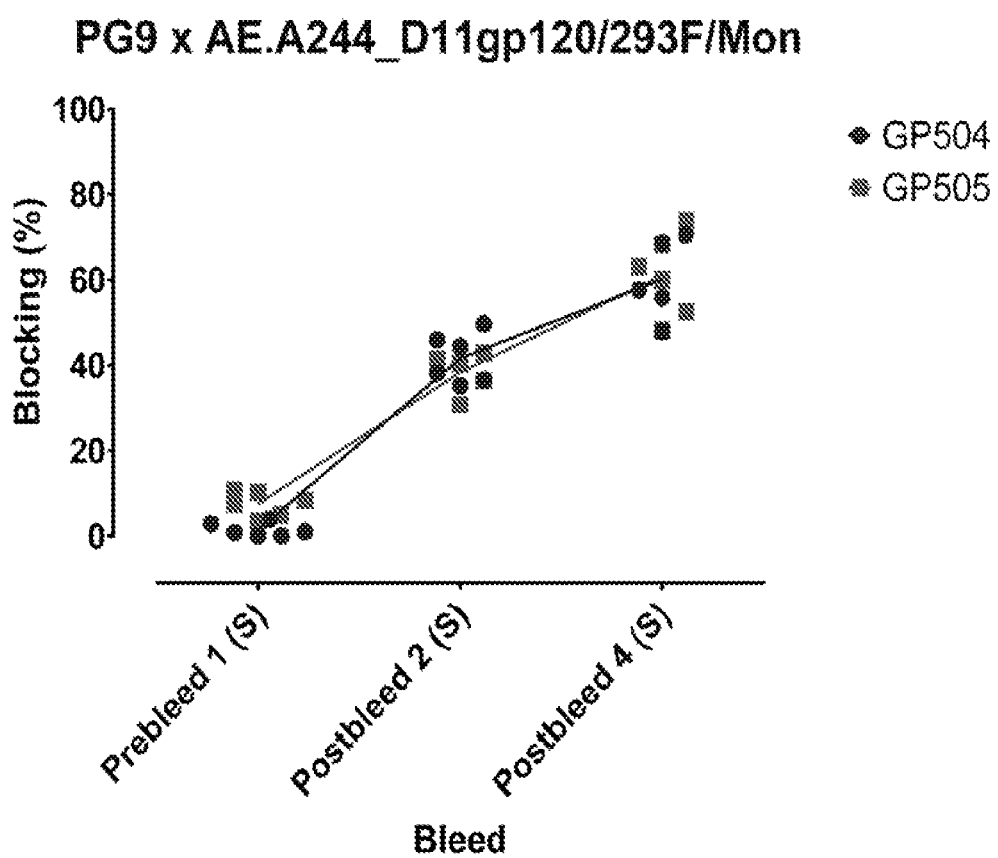
Figure 29L:
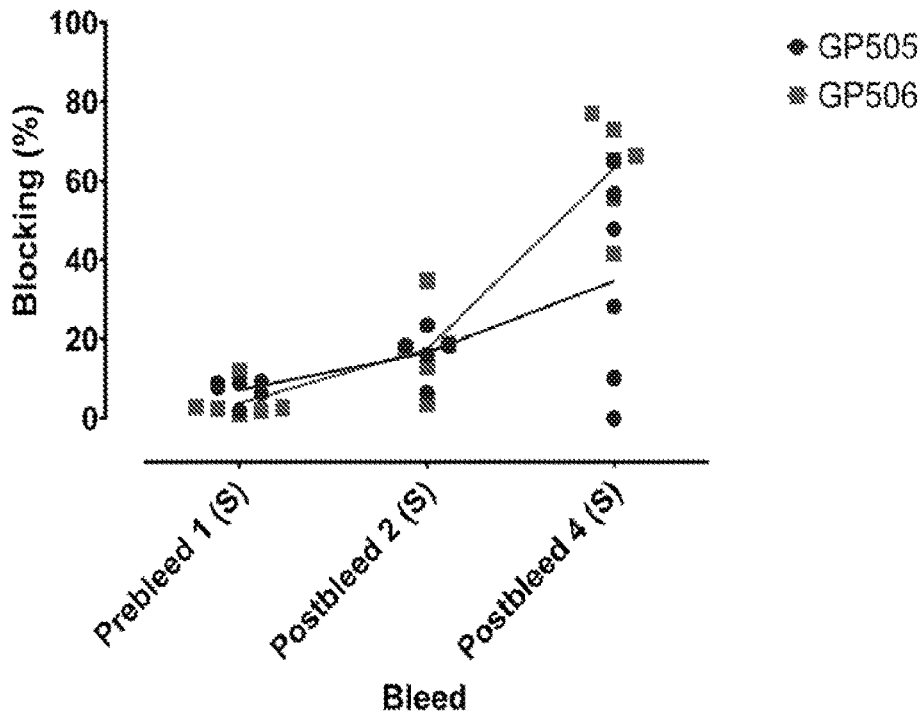
Figure 29L:
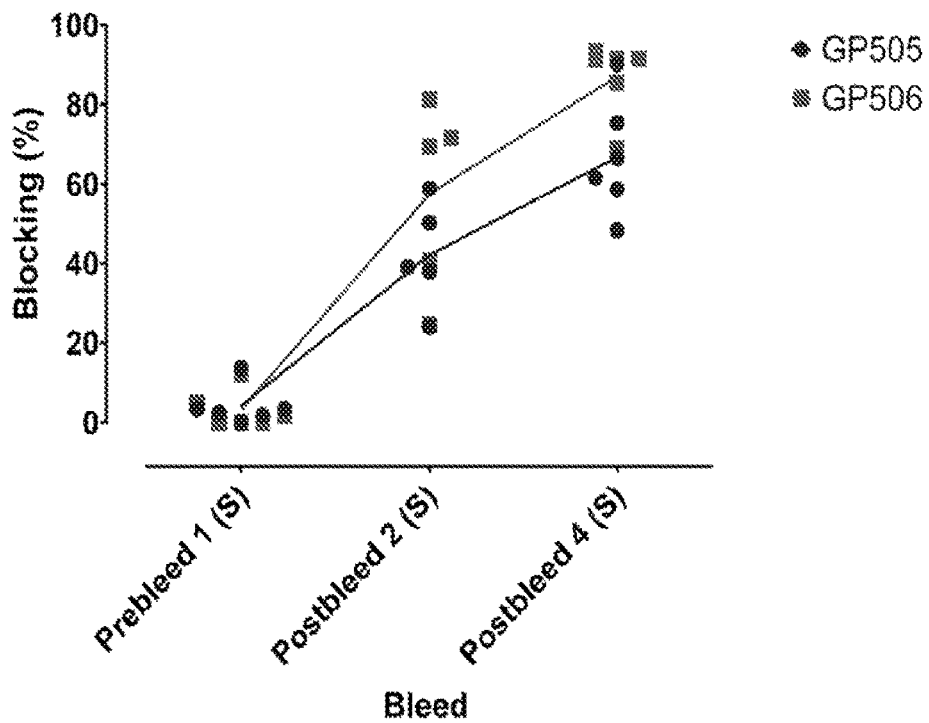
Figure 29L:
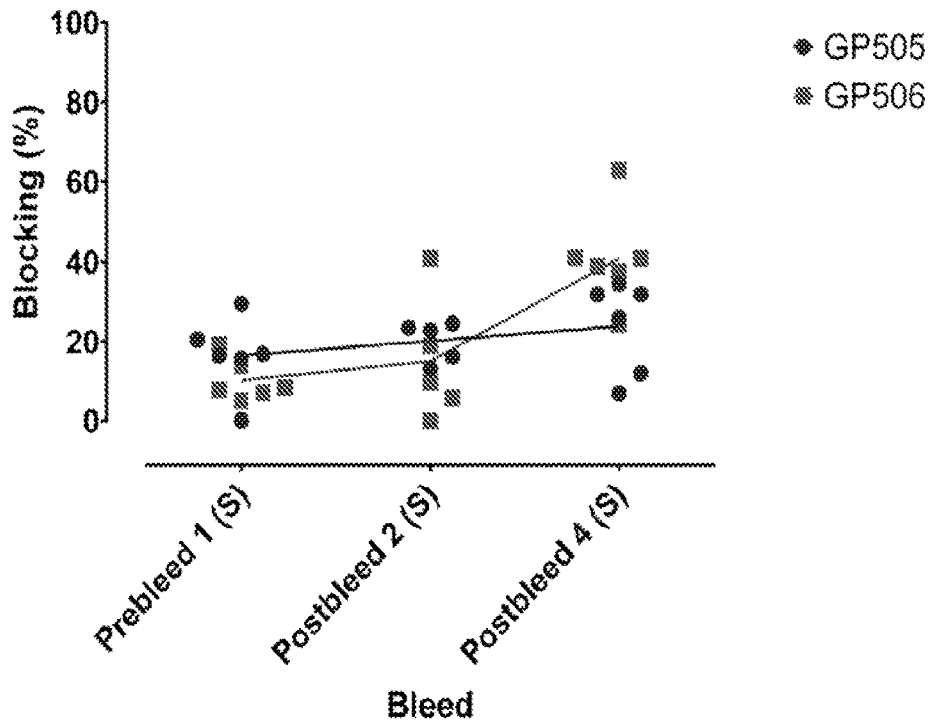
Figure 29L:
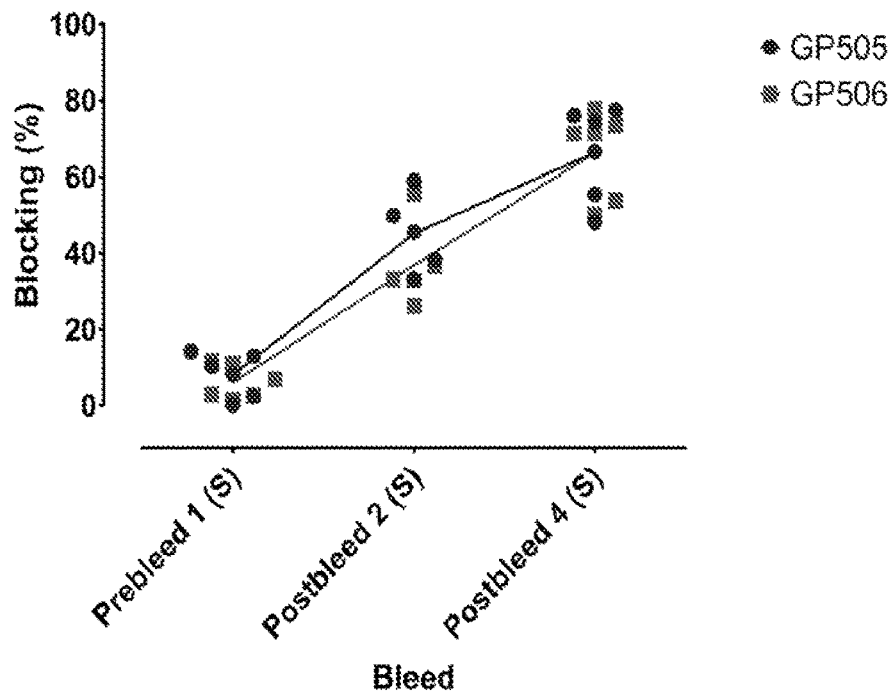
Figure 29L:
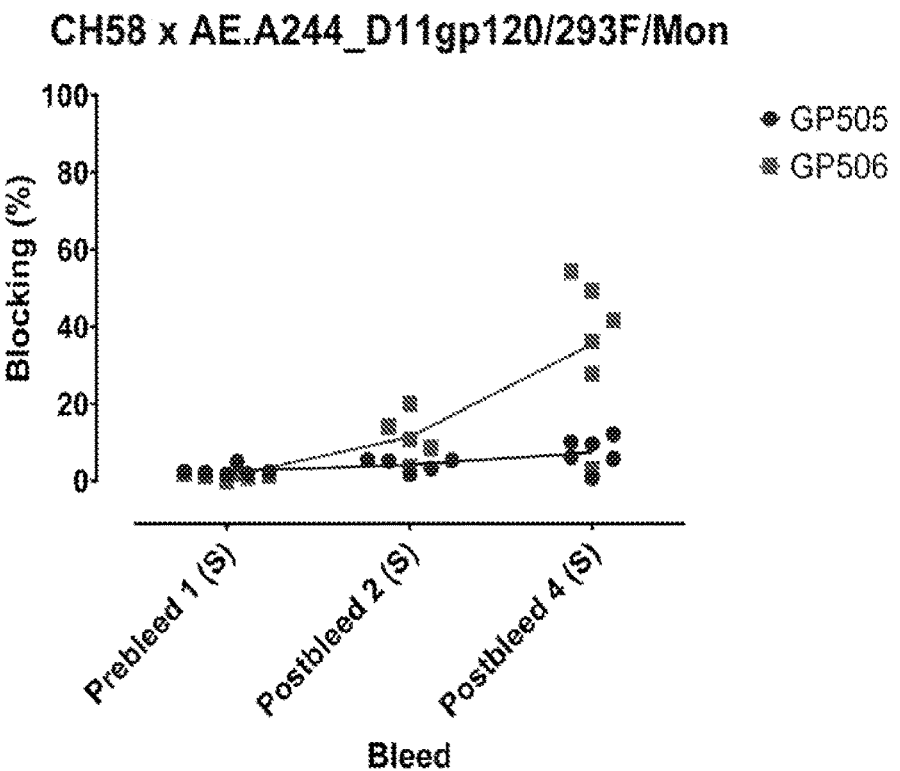
Figure 29L:
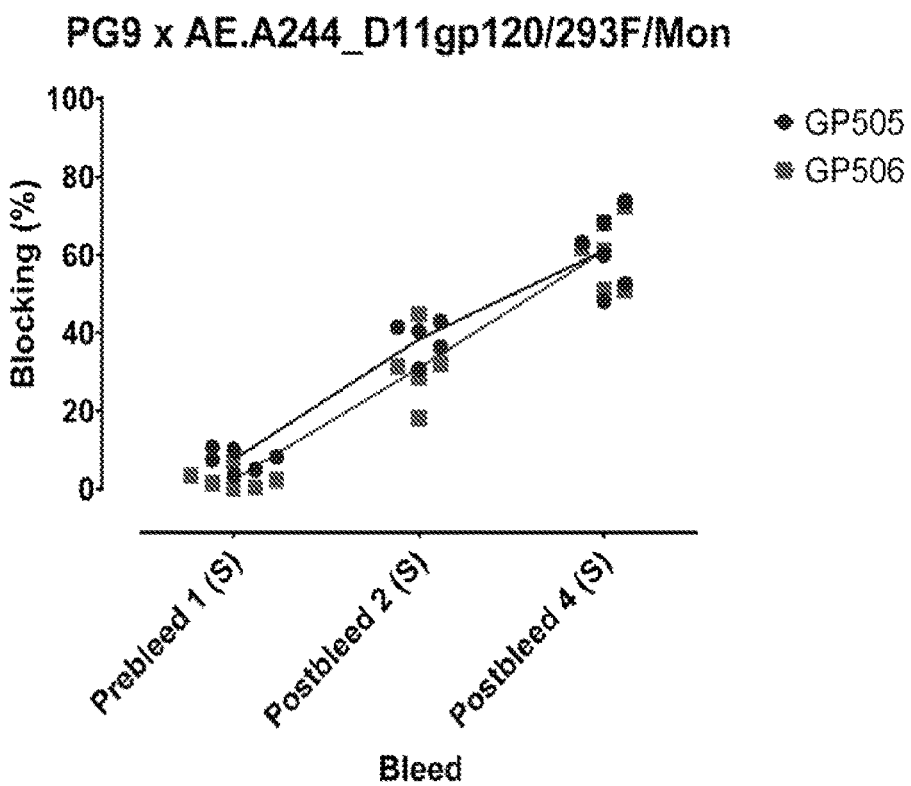
Figure 29L:
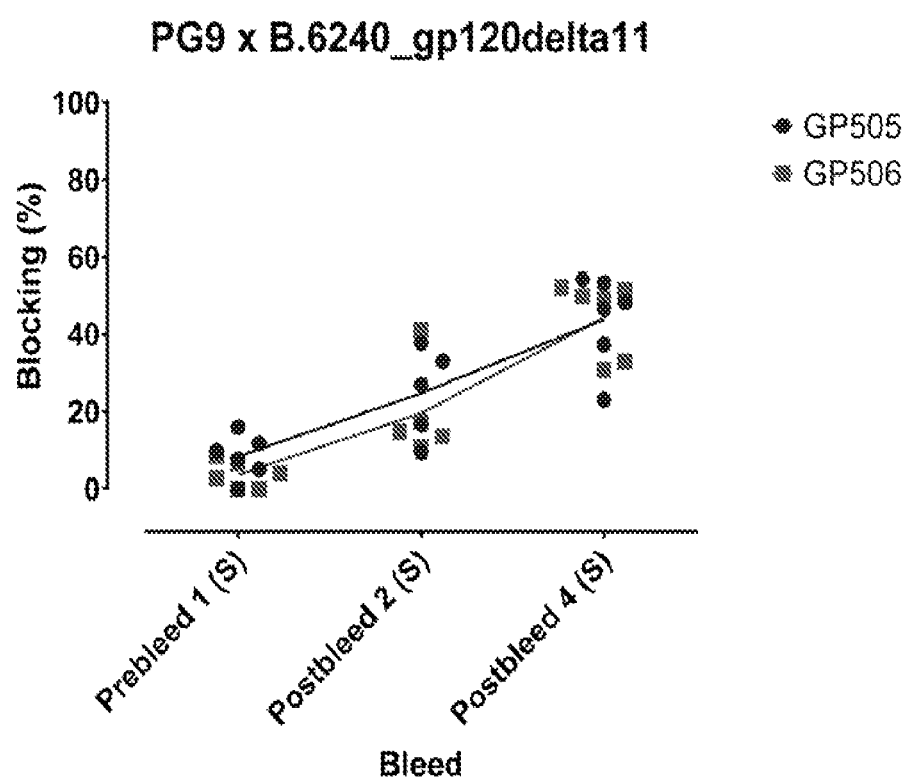
Figure 30:
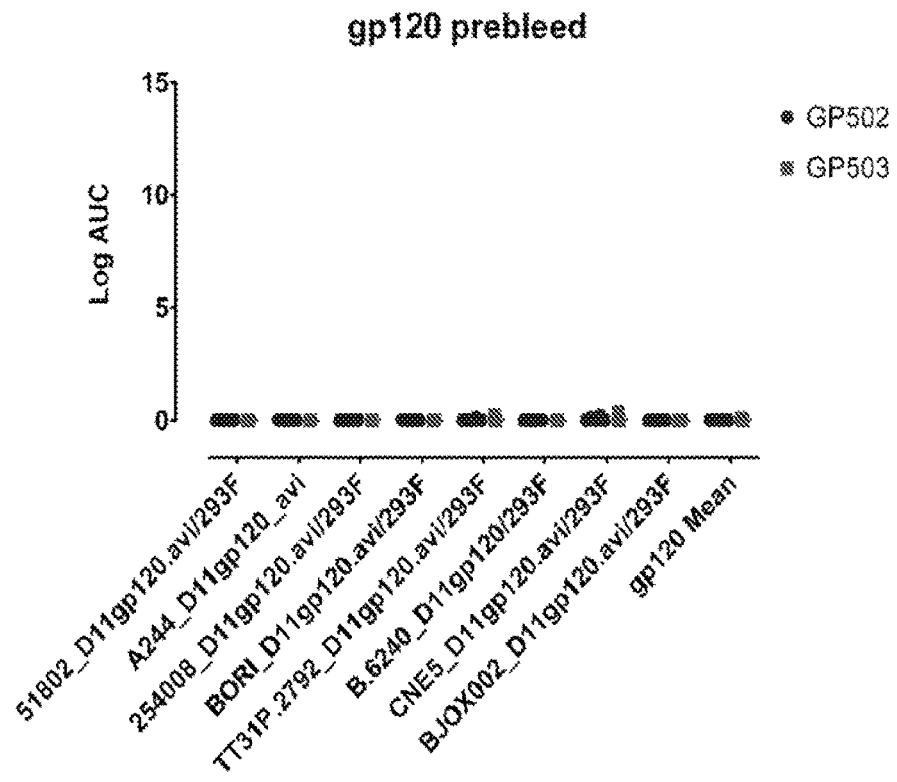
FIGS. 30-XX show mean serum blocking activity of GP sera to V2, Glycan and ADCC mediating epitopes by ELISA.
Figure 30:
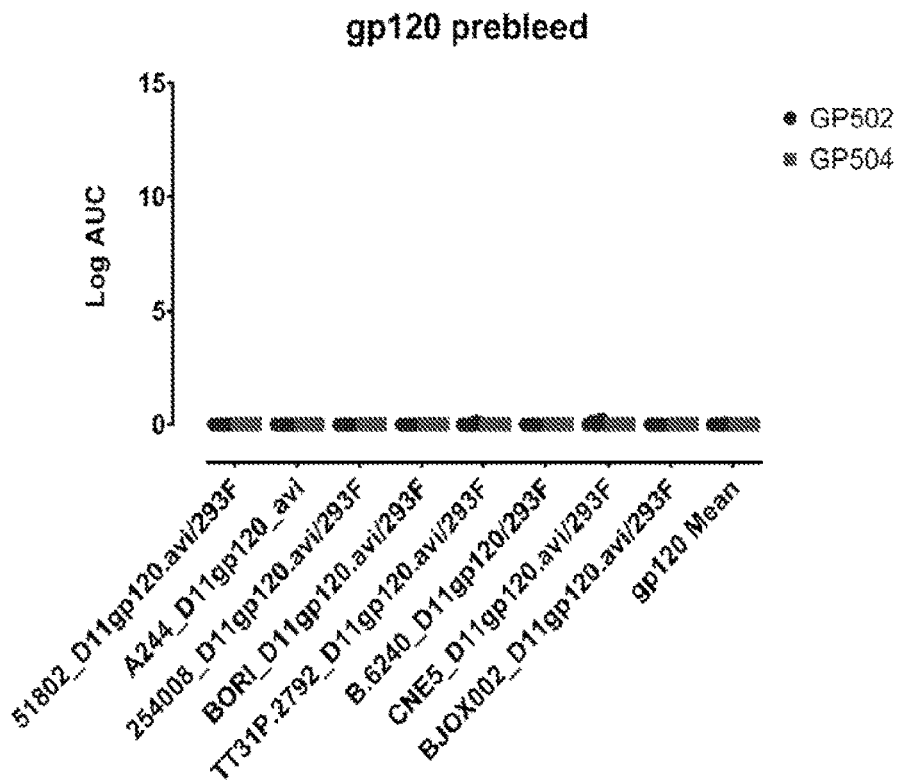
Figure 30:
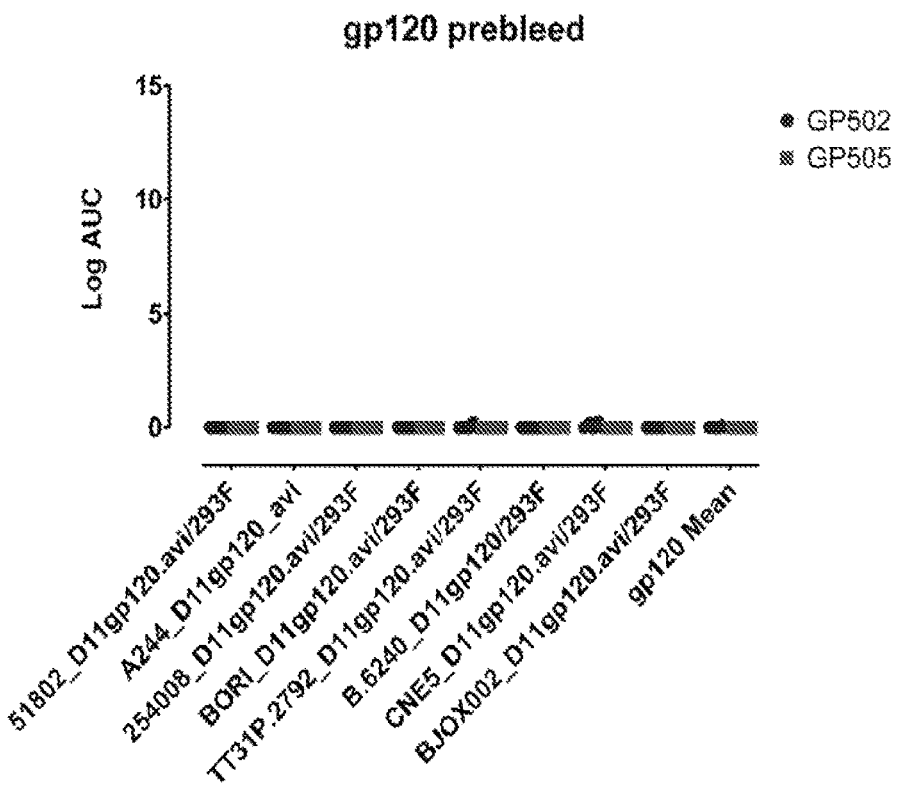
Figure 30:
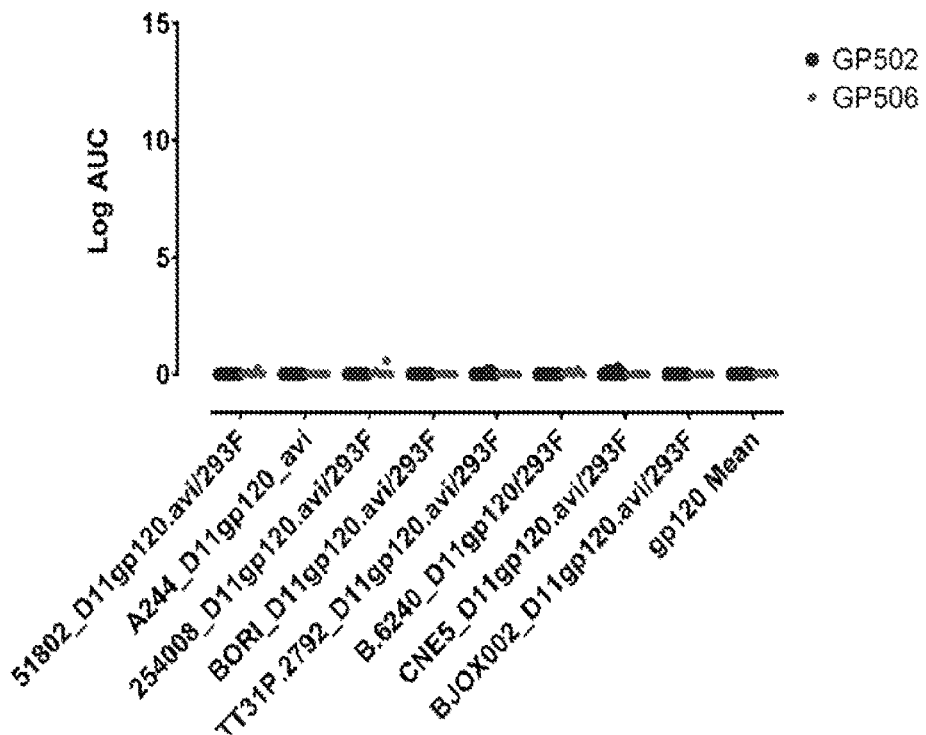
Figure 30:
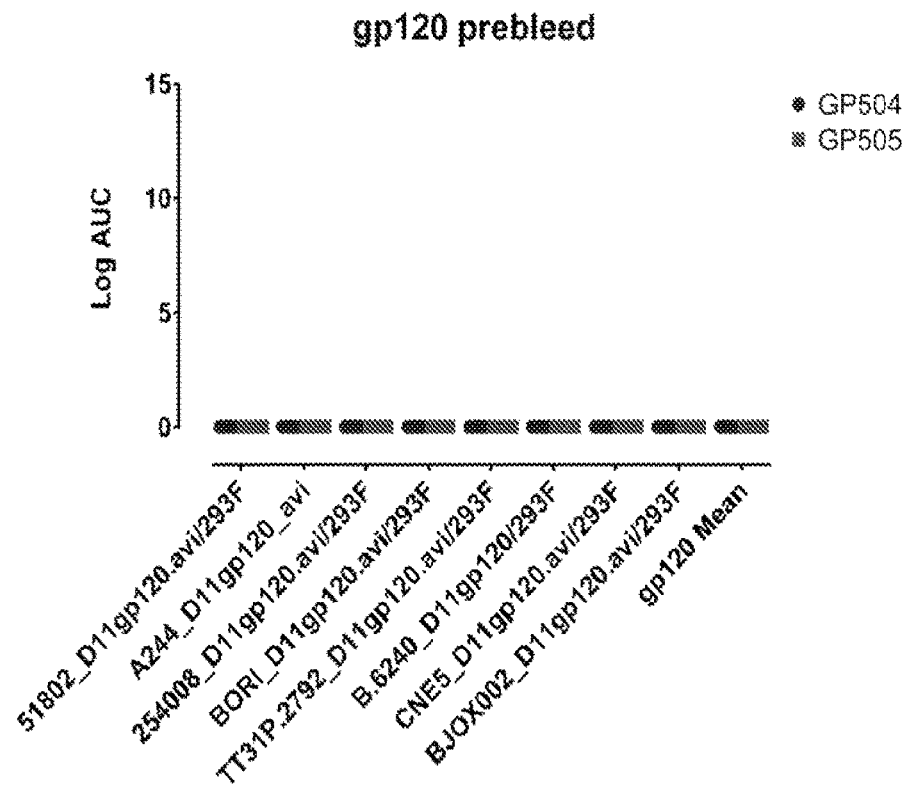
Figure 30:
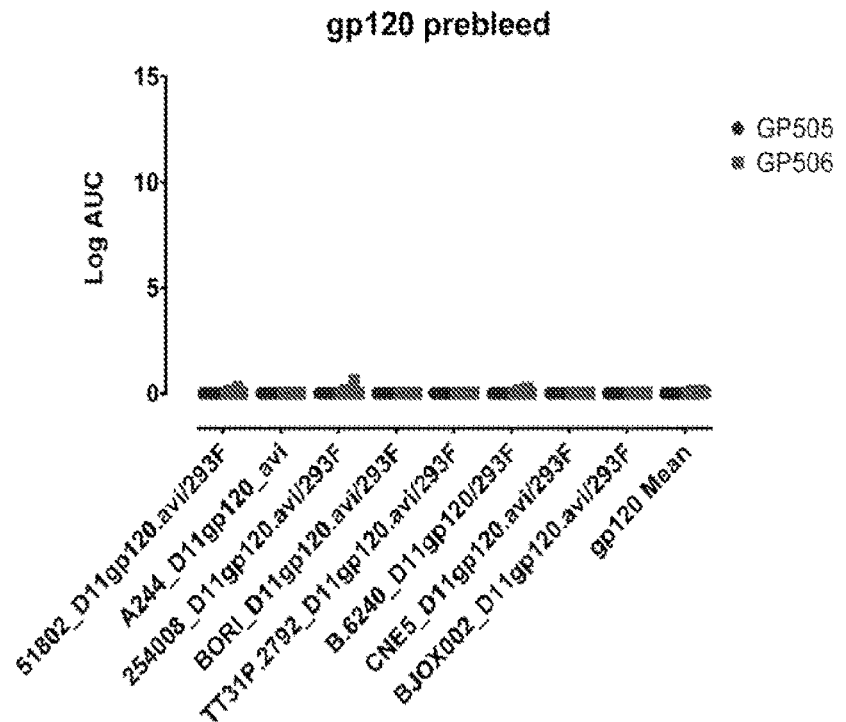
Figure 31:
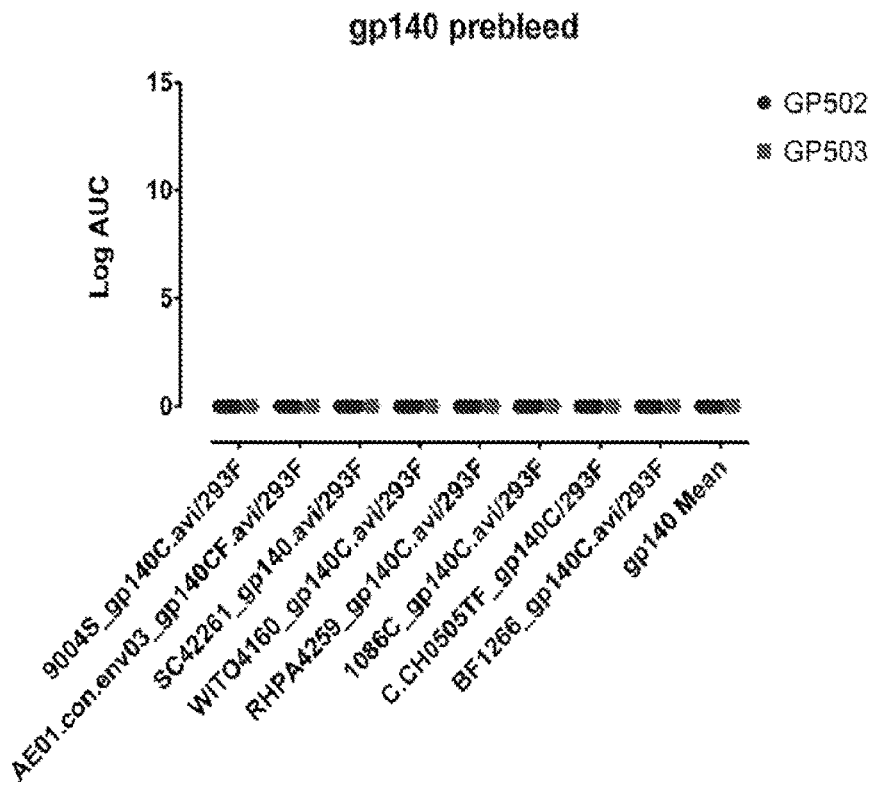
FIG. 31 shows Binding of guinea pig pre-bleed sera from the indicated groups (GP502-GP506) to gp140 protein was determined by indirect ELISA. Plates were coated with protein at 2 ug/ml and sera were tittered in 3 fold serial dilutions. Each titration was expressed as the log of area under the curve (Log AUC). Each symbol represents an individual animal within each group of six animals. Higher Log AUC represents greater binding to the test protein.
Figure 31:
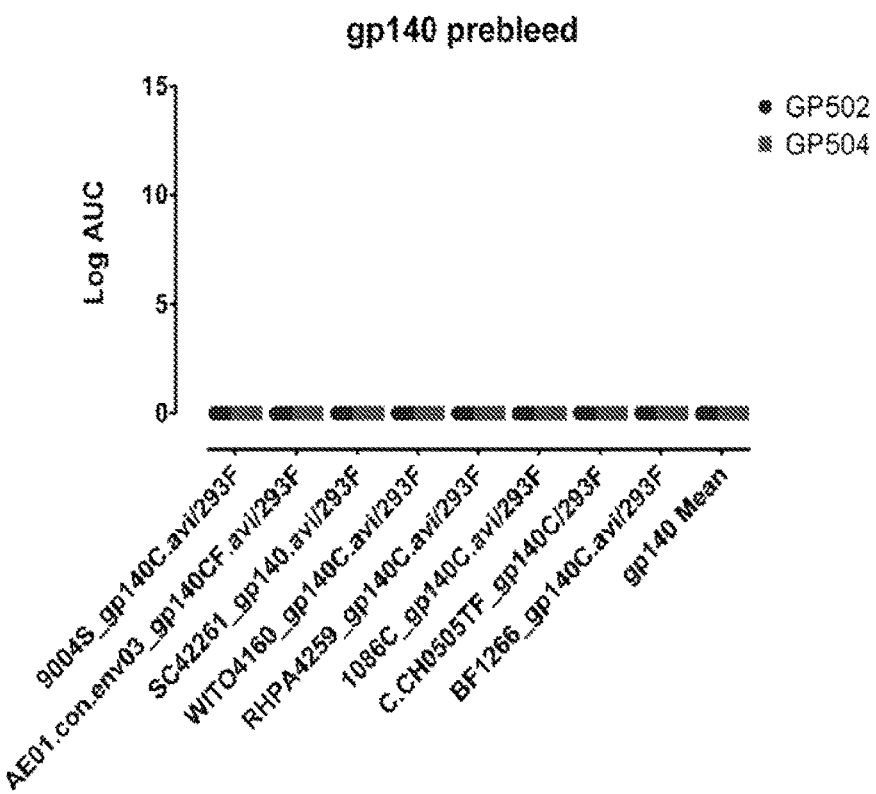
Figure 31:
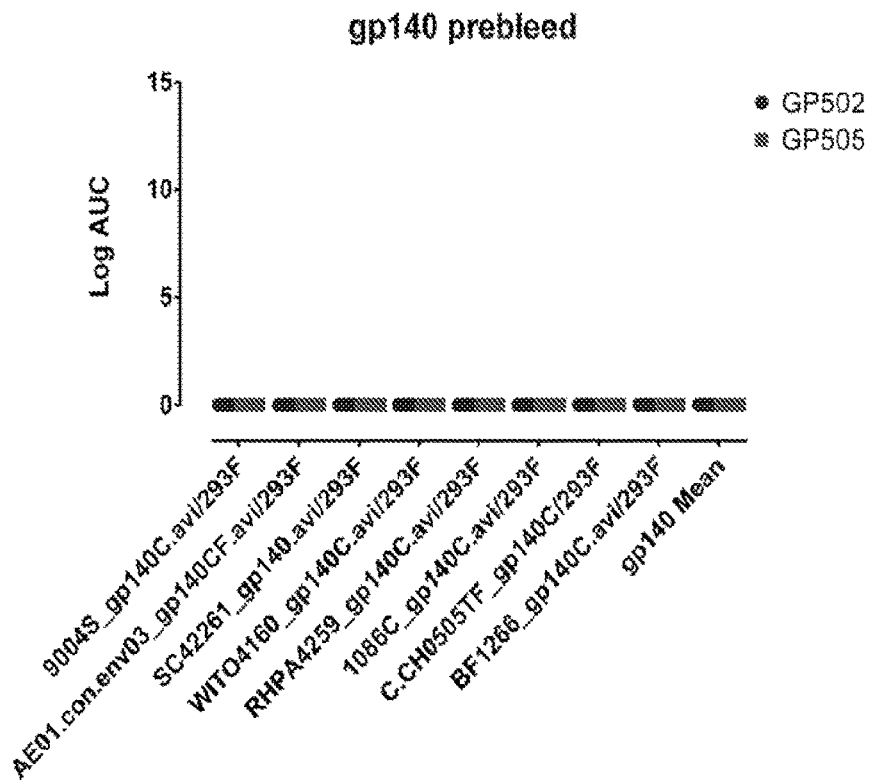
Figure 31:
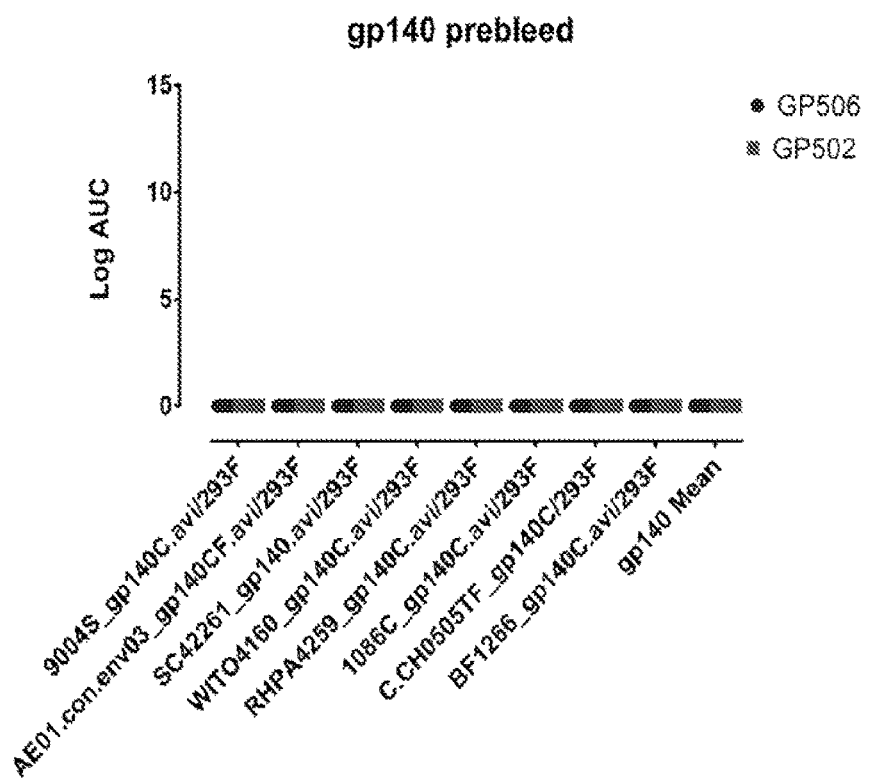
Figure 31:
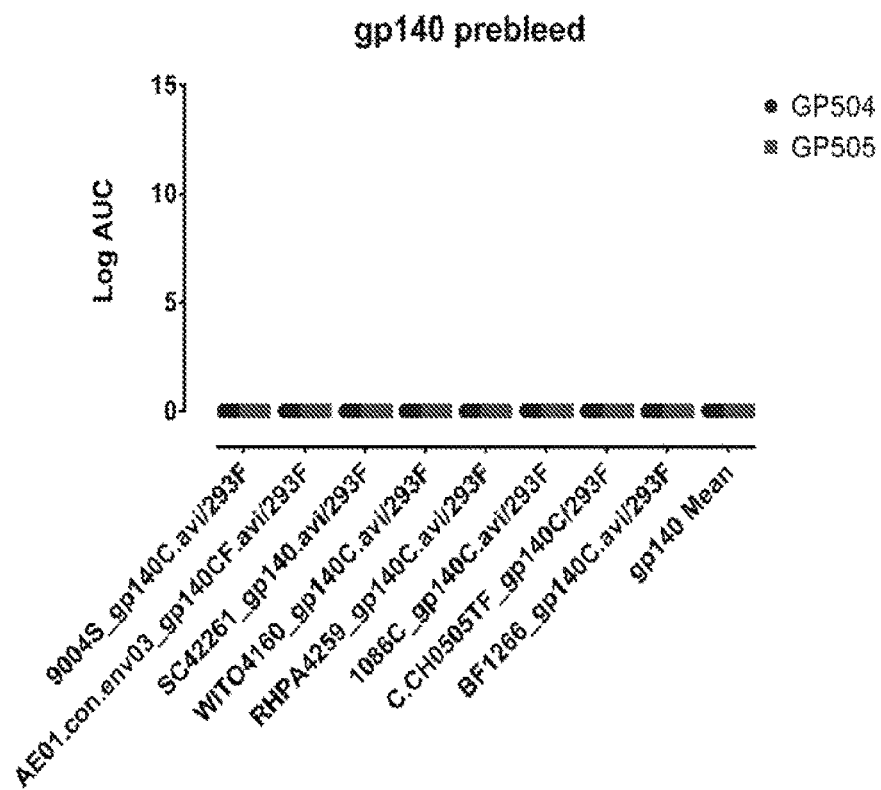
Figure 31:
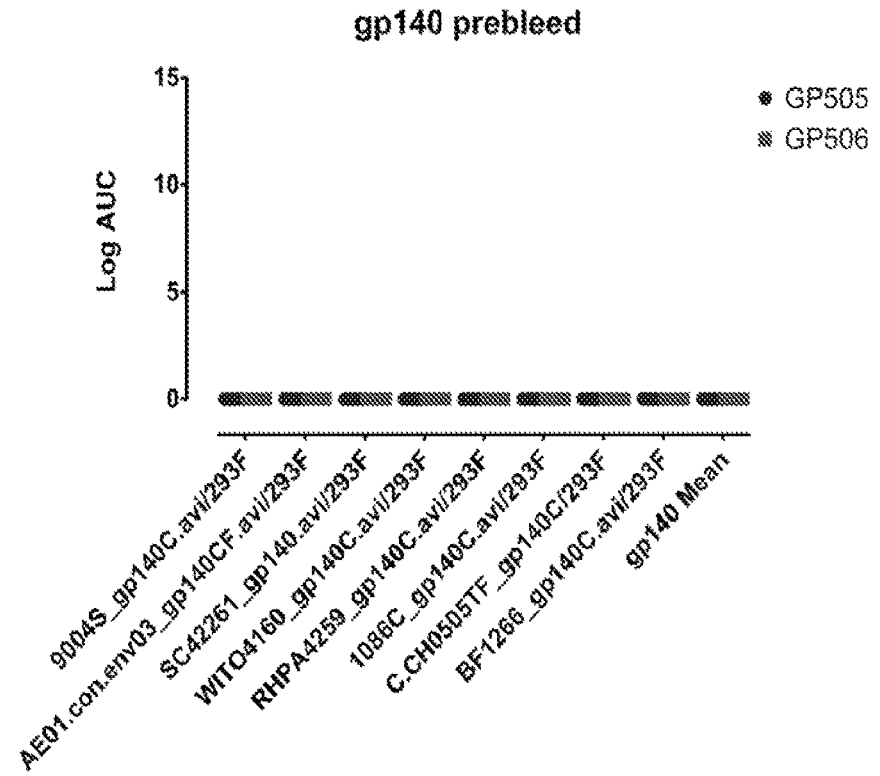
Figure 32:
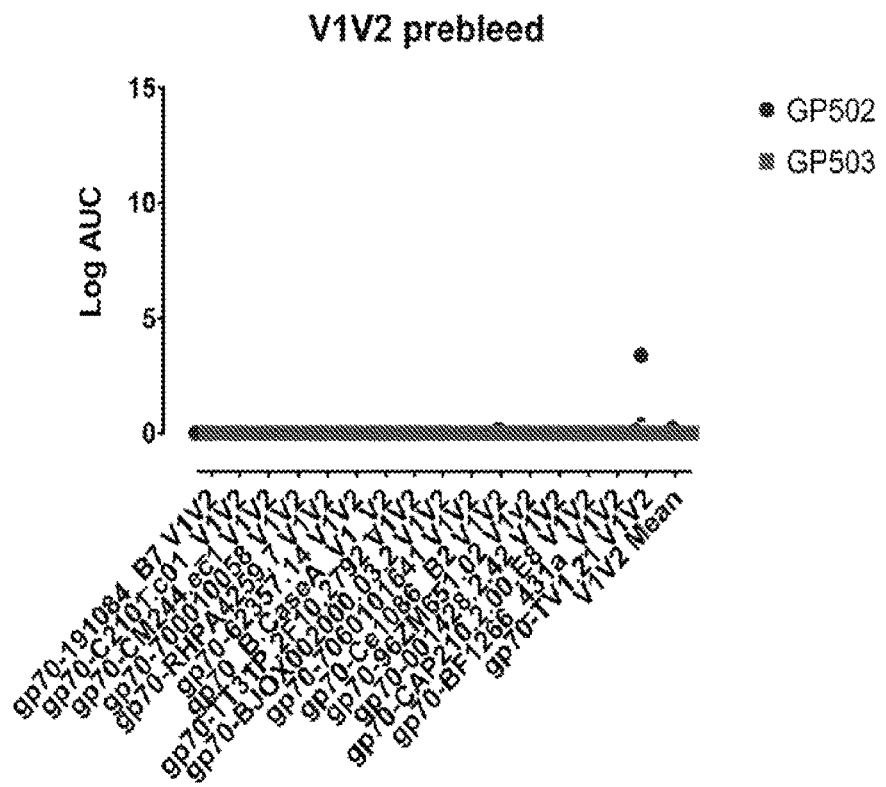
FIG. 32 shows Binding of guinea pig pre-bleed sera from the indicated groups (GP502-GP506) to V1V2 proteins was determined by indirect ELISA. Plates were coated with protein at 2 ug/ml and sera were tittered in 3 fold serial dilutions. Each titration was expressed as the log of area under the curve (Log AUC). Each symbol represents an individual animal within each group of six animals. Higher Log AUC represents greater binding to the test protein.
Figure 32:
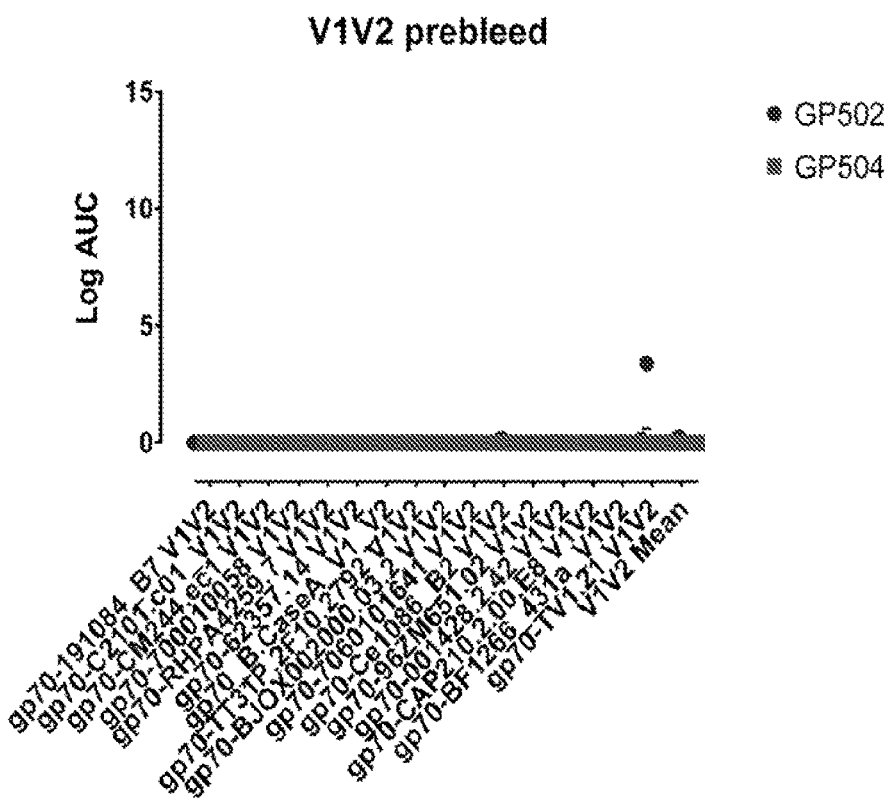
Figure 32:
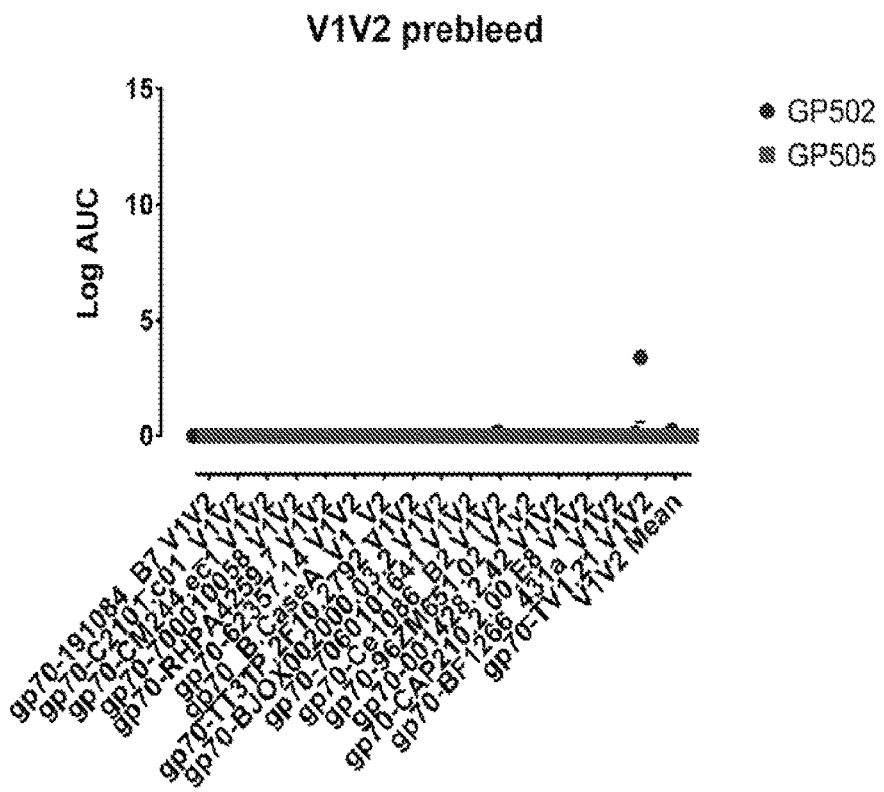
Figure 32:
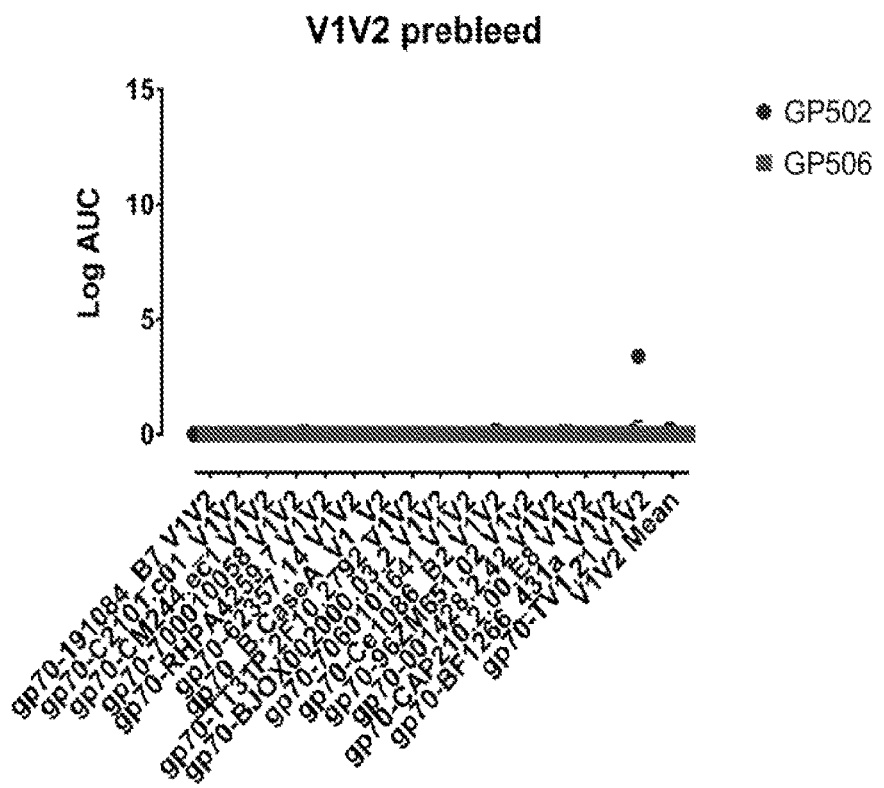
Figure 32:
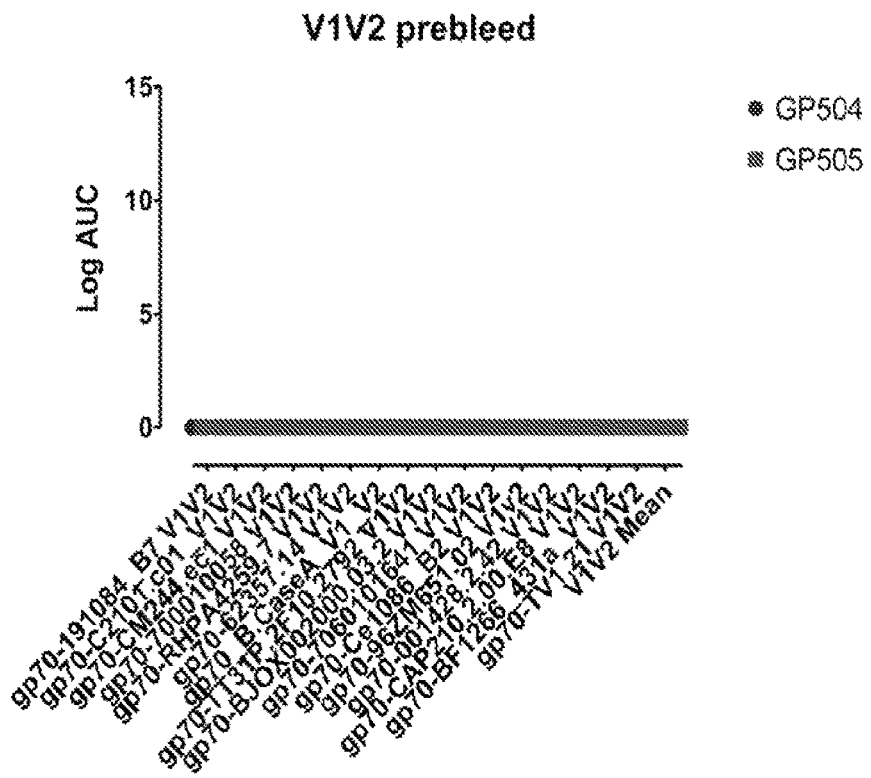
Figure 32:
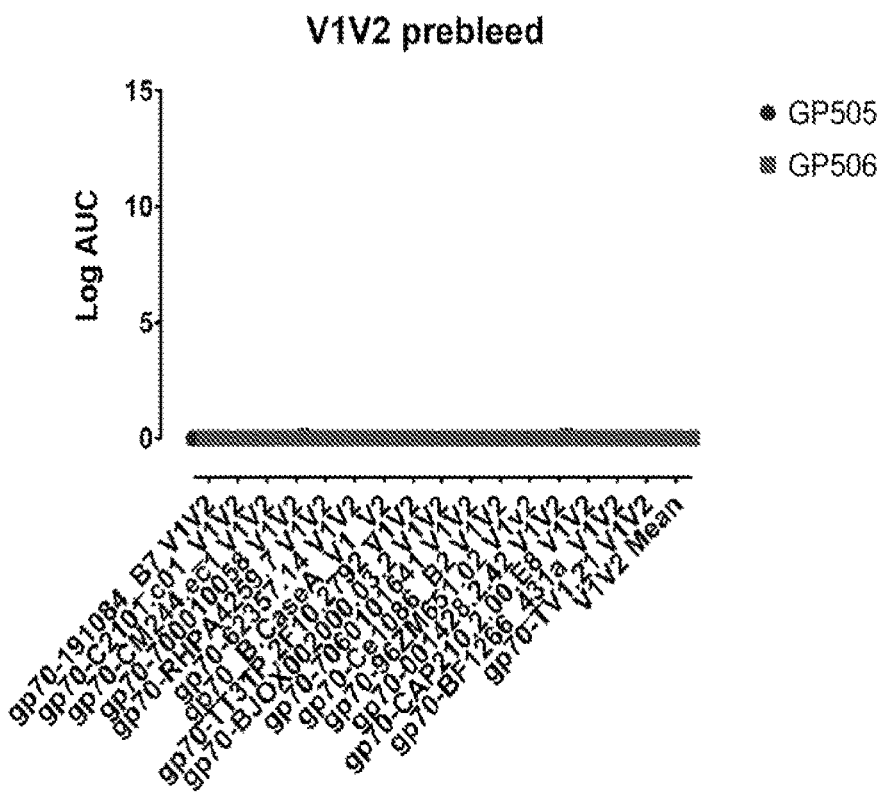

In some embodiments, the sequences include modification such that the furin cleavage sites are eliminated. Eliminates the site for furin because we change it in gp140C but we match the gp120s Fixing the V3 loop to prevent cleavage during recombinant production—in some embodiments, taking the GPGR/S/K is made into GPGQ (SEQ ID NO: 179), and also the Ala after the R/S/K is made into T to prevent cleavage during recombinant production. In some embodiments, protease inhibitors also work, other mutations can also be made to reduce or eliminate the cleavage of the protein during recombinant production. See, for example, FIG. 17.

In certain aspects the invention comprises using immunogenic compositions wherein immunogens are delivered as DNA or RNA in suitable formulations. Various technologies which comprise using DNA or RNA, or can use complexes of nucleic acid molecules and other entities to be used in immunization. In certain embodiments, DNA or RNA is administered as nanoparticles consisting of low dose antigen-encoding DNA formulated with a block copolymer (amphiphilic block copolymer 704). See Cany et al., Journal of Hepatology 2011 vol. 54 j 115-121; Arnaoty et al., Chapter 17 in Yves Bigot (ed.), Mobile Genetic Elements: Protocols and Genomic Applications, Methods in Molecular Biology, vol. 859, pp 293-305 (2012); Arnaoty et al. (2013) Mol Genet Genomics. 2013 August; 288(7-8):347-63. Nanocarrier technologies called Nanotaxi® for immunogenic macromolecules (DNA, RNA, Protein) delivery are under development. See for example technologies developed by Incellart. In certain embodiments, the nucleic acids, for e.g. mRNAs encoding immunogens of the invention, are delivered by a lipid nanoparticle (LNP) technology. In non-limiting embodiments, the LNPs can comprise four different lipids that can self-assemble to 80-100 nm size particles.

In certain aspects the invention comprises using immunogenic compositions wherein immunogens are delivered as recombinant proteins. Various methods for production and purification of recombinant proteins suitable for use in immunization are known in the art. In certain embodiments recombinant proteins are produced in CHO cells.

The immunogenic envelopes can also be administered as a protein boost in combination with a variety of nucleic acid envelope primes (e.g., HIV −1 Envs delivered as DNA expressed in viral or bacterial vectors).

Dosing of proteins and nucleic acids can be readily determined by a skilled artisan. A single dose of nucleic acid can range from a few nanograms (ng) to a few micrograms (µg) or milligram of a single immunogenic nucleic acid. Recombinant protein dose can range from a few µg micrograms to a few hundred micrograms, or milligrams of a single immunogenic polypeptide.

Administration: The compositions can be formulated with appropriate carriers using known techniques to yield compositions suitable for various routes of administration. In certain embodiments the compositions are delivered via intramascular (IM), via subcutaneous, via intravenous, via nasal, via mucosal routes, or any other suitable route of immunization.

The compositions can be formulated with appropriate carriers and adjuvants using techniques to yield compositions suitable for immunization. The compositions can include an adjuvant, such as, for example but not limited to, alum, poly IC, MF-59 or other squalene-based adjuvant, ASO1B, or other liposomal based adjuvant suitable for protein or nucleic acid immunization. In certain embodiments, the adjuvant is GSK AS01E adjuvant containing MPL and QS21. This adjuvant has been shown by GSK to be as potent as the similar adjuvant AS01B but to be less reactogenic using HBsAg as vaccine antigen [Leroux-Roels et al., IABS Conference, Apr. 2013, 9]. In certain embodiments, TLR agonists are used as adjuvants. In other embodiment, adjuvants which break immune tolerance are included in the immunogenic compositions.

In certain embodiments, the compositions are formulated such that the immunogens are comprises in nanoparticles. In some embodiments, these are lipid nanoparticle immunogens. In some embodiments, these are liposomes comprising immunogens. In some embodiments these are lipid nanodiscs. The immunogens can be arranged as particulate, high-density array on liposomes or other particles, for example but not limited to nanoparticles. In non-limiting embodiment, the liposome comprises cholesterol, PC, PE, PA, or any combination thereof. See Alam et al. J Immunol. 2007 Apr. 1; 178(7):4424-35; Alam et al. J Virol. 2008 January; 82(1):115-25; Alam et al. Proc Natl Acad Sci USA. 2009 Dec. 1; 106(48):20234-9. doi: 10.1073/pnas.0908713106; Dennison et al. J Virol. 2009 October; 83(19):10211-23. doi: 10.1128/JVI.00571-09; Dennison et al. PLoS One. 2011; 6 (11):e27824. doi: 10.1371/journal-.pone.0027824. In some embodiments, the lipid composition of lipid nanoparticle comprises cholesterol, POPC, sphingomyelin, or any combination thereof. In some embodiments, the lipids can comprise POPC, POPE, DMPA, cholesterol, or any combination thereof. In some embodiments, the ratio is POPC:POPE:DMPA:Cholesterol 45:25:20:1.33. In some embodiments, the protein to lipid ratio is about 1:3000. In some embodiments, the peptide to lipid ratio used provides 50-100 mer V3 peptide units per 100-200 nm lipid nanoparticle. In some embodiments the peptide:lipid ratio is 1:100. A skilled artisan can readily determine conditions and lipids to achieve different desired ratios.

In certain embodiments, the compositions and methods comprise any suitable agent or immune modulation which can modulate mechanisms of host immune tolerance and release of the induced antibodies. In non-limiting embodiments modulation includes PD-1 blockade; T regulatory cell depletion; anti-CD25 antibodies; CD40L hyperstimulation; anti-CTLA4 antibodies; soluble antigen administration, wherein the soluble antigen is designed such that the soluble agent eliminates B cells targeting dominant epitopes, or a combination thereof. In certain embodiments, an immunomodulatory agent is administered in at time and in an amount sufficient for transient modulation of the subject's immune response so as to induce an immune response which comprises broad neutralizing antibodies against HIV-1 envelope. Non-limiting examples of such agents is any one of the agents described herein: e.g. chloroquine (CQ), PTP1B Inhibitor-CAS 765317-72-4-Calbiochem or MSI 1436 clodronate or any other bisphosphonate; a Foxol inhibitor, e.g. 3443551Foxol Inhibitor, AS1842856-Calbiochem; Gleevac, anti-CD25 antibody, anti-CCR4 Ab, an agent which binds to a B cell receptor for a dominant HIV-1 envelope epitope, or any combination thereof. In non-limiting embodiments, the modulation includes administering an anti-CTLA4 antibody, OX-40 agonists, or a combination thereof. Non-limiting examples are ipilimumab and tremelimumab. In certain embodiments, the methods comprise administering a second immunomodulatory agent, wherein the second and first immunomodulatory agents are different.

One of skill in the art understands that the envelope glycoproteins referenced in various examples and figures can comprise a signal/leader sequence. It is well known in the art that HIV-I envelope glycoprotein is a secretory protein with a signal or leader peptide sequence that is removed during processing and recombinant expression (without removal of the signal peptide, the protein is not secreted). See for example Li et al. Control of expression, glycosylation, and secretion of HIV-I gp120 by homologous and heterologous signal sequences. Virology 204(1):266-78 (1994) ("Li et al. 1994"), at first paragraph, and Li et al. Effects of inefficient cleavage of the signal sequence of HIV-1 gp120 on its association with calnexin, folding, and intracellular transport. PNAS 93:9606-9611 (1996) ("Li et al. 1996"), at 9609. Any suitable signal sequence can be used. In some embodiments the leader sequence is the endogenous leader sequence. Most of the gp120 and gp160 amino acid sequences include the endogenous leader sequence. In other non-limiting examples the leaders sequence is human Tissue Plasminogen Activator (TPA) sequence, human CDS leader sequence (e.g. MPMGSLQ-PLATLYLLGMLVASVLA (SEQ ID NO: 184). Most of the chimeric designs include CDS leader sequence. A skilled artisan appreciates that when used as immunogens, and for example when recombinantly produced, the amino acid sequences of these proteins do not comprise the leader peptide sequences.

tion is not limited to specific embodiments disclosed in these Examples, which are for purposes of illustration only, since alternative methods can be utilized to obtain similar results.

In the below examples and throughout the specification ADCC and structural mosaics are used interchangeably.

Example 1—ADCC Vaccine Design Strategies

Improving results of RV144 Foundations
Previous studies for example in Pollara et al. J Virol. 88(14):7715 (2014):
    RV305: a boost of RV144 expanded the ADCC repertoire, and drove affinity maturation of ADCC-mediating Abs
    C1 and V2 ADCC Abs can act synergistically: A32 and V2 antibodies have synergistic ADCC. HIV-1 vaccine-induced C1 and V2 Env-specific antibodies synergize for increased antiviral activities.
Previous studied for example Finzi et al. J Virol. 91(7): e02452-16 (2017):
    These studies show uniqueness of CRF01_AE viruses in terms of ADCC susceptibility. And also showed S375HW induction of A32 C1 Ab ADCC sensitivity

TABLE 1 shows various combinations (sets) of immunogens

| Envelope Names | Clade B | | | | | Global | | | |
| --- | --- | --- | --- | --- | --- | --- | --- | --- | --- |
| | Set1 (2 Valent) Structural mosaics | Set2 (2 Valent) Natural strains chosen serially | Set 3 (5 Valent) 5 Natural strains | Set 4 (5 Valent) 4 Natural strains | Set 5 (2 valent) Variants of Set 1 Vaccine mosaics) | Set 6 (6 valent) To compare with (Structural) Str.Mos.M5 (Structural) | Set 6a Alternative to Set 6 (Structural) (X or XX) | Set 6b Alternative to Set 6 (Structural) | Set 7 fill out M group coverage (Structural Mosaic) |
| ADCC-StrMos.B.1 + 1.1 | X | | | | | X | | X | X |
| ADCC-StrMos.B.1 + 1.2 | X | | | | | X | | | |
| ADCC.StrNat.B.1 | | X | X | X | | | | | |
| ADCC.StrNat.B.2 | X | X | X | X | | | | | |
| Str.Nat.B3 | | | X | X | | | | | |
| Str.Nat.B4 | | | X | X | | | | | |
| Str.Nat.B5 | | | X | | | | | | |
| A244 (see WO/2013/006688, which is incorporated by reference in its entirety) | | | | | X | | | | |
| ADCC-StrMos-Modified.B.1 + 1.1 | | | | | | X | | | |
| ADCC-StrMos-Modified.B.1 + 1.2 | | | | | | X | | | |
| ADCC.StrMos.C.1 + 1.1 | | | | | | X | X | X | X |
| ADCC.StrMos.C.1 + 1.2 | | | | | | X | X | | |
| ADCC.StrMos.AE.1 + 1.1 | | | | | | X | XX | X | X |
| ADCC.StrMos.AE.1 + 1.2 | | | | | | X | XX | | |
| ADCC-StrMos.M.3 + 2.4 | | | | | | | | | X |
| ADCC-StrMos.M.3 + 2.5 | | | | | | | | | X |

EXAMPLES

The following examples are given for the purpose of illustrating various embodiments of the invention and are not meant to limit the present invention in any fashion. One skilled in the art will appreciate readily that the present invention is well adapted to carry out various embodiments of the invention. Changes therein and other uses which are encompassed within the spirit of the invention as defined by the scope of the claims will occur to those skilled in the art.

Examples are provided herein to facilitate a more complete understanding of the invention. The following examples illustrate the exemplary modes of making and practicing the invention. However, the scope of the invenfor clades B, C, and D. Importance of uniqueness of AE viruses in being susceptible to ADCC. Influence of the Envelope gp120 Phe 43 Cavity on HIV-1 Sensitivity to Antibody-Dependent Cell-Mediated Cytotoxicity Responses.

Bradley et al. Nat Commun 2017 8:15711 (2017) showed that:
    a designed pentavalent AE that improved protection in NHPs;
    Adding diversity to the CRF01 cocktail improves Ab mediated protection in NHPs. Pentavalent HIV-1 vaccine protects against simian-human immunodeficiency virus challenge.

Weissman et al. "Zika virus protection by a single low-dose nucleoside-modified mRNA vaccination." *Nature*, 2017; DOI: 10.1038/nature21428:

mRNAs are just as good or better than proteins in inducing anti-Env Abs

Next generation vaccines to induce ADCC Abs could be mRNAs, and we could compare within-clade to global panels of ADCC mosaics and natural strains RV305 boosting of RV144 vaccinees after 6-8 years Broadened the number of V2 epitopes recognized New V2 ADCC epitopes recognized Expanded the C1 ADCC clonal lineages Increased ADCC breadth (against clades CRF01, B and C) and potency.

A32 and V2 antibodies have synergistic ADCC

HIV-1 vaccine-induced C1 and V2 Env-specific antibodies synergize for increased antiviral activities (see Pollara J . . . Ferrari G J Virol. 88(14):7715 (2014)):

ALVAC/AIDSVax vaccine induced (ADCC) via antibodies against the Env V2 (CH58 & CH59 entered on K169) and constant 1 (C1) regions Prebinding with RV144 C1 Abs increased binding of V2 Ab CH58, suggesting binding of the C1 Ab induced a conformation change that increased V2 epitope accessibility C1 and V2 antibodies combined increased ADCC: Increased the HIV-1 ADCC activity of V2 Ab CH58 at concentrations similar to that observed in plasma of RV144 vaccinee For Vaccine Design: Without wishing to be bound by theory, the ADCC responses against natural variants can be more effective if the diversity of both of these epitopes were better represented in the vaccine. Without wishing to be bound by theory, the synergy that results from C1 region antibody binding can enhance access to the V2 epitope be mimicked in a vaccine, and improve the V2 epitope response.

Importance of uniqueness of AE viruses in being susceptible to ADCC

Influence of the Envelope gp120 Phe 43 Cavity on HIV-1 Sensitivity to Antibody-Dependent Cell-Mediated Cytotoxicity Responses (see Prevost J . . . Finzi A J Virol. 91(7): e02452-16 (2017)):

CD4-bound HIV Env is preferentially targeted by ADCC (Veillette J Virol. 2015 89:545). HIV has evolved to down-regulate CD4, and limit Env on the cell surface, consistent with evading ADCC.

HIV typically has a Ser at position 375 (ST375>90% of non-CRF01 viruses). 375 is in the "CD4 Phe 43 cavity" of Env, a CD4 contact region.

CRF01_AE has an H375, in 99% of viruses. S375H/W—>spontaneous sampling of an Env conformation closer to the CD4-bound state, and increased ADCC senstivity. The H375 enhances the exposure of the C1, cluster A (A32) antibody epitope. The A244 CRF01 RV144 vaccine may have enabled better targeting of the A32 epitope region. Concern: The CRF01 circulating virus in Thailand may be more susceptible to such ADCC antibodies.

For Vaccine Design: Without wishing to be bound by theory, CRF01 A244 RV144 strain can be included, that has the A32 epitope naturally more exposed, improve responses to this region. Without wishing to be bound by theory, the vaccine triggered response can translate to protection against other variants in a vaccine cocktail that spend less time in the CD4-bound like state.

Adding diversity to the CRF01 cocktail improves Ab mediated protection in NHPs

Pentavalent HIV-1 vaccine protects against simian-human immunodeficiency virus challenge (see Bradley T . . . Haynes B, Nat Commun 2017 8:15711 (2017)):

The two CRF01 strains used in RV144 (92TH023 and A244) are highly similar, and identical in the important V2 region.

A Pentavalent gp120 boost was designed to optimize the diversity of CRF01 V2 motifs.

8 weekly low-dose intrarectal challenges with SHIV-1157 (QNE)Y173H (subtype C tier 2, with V2 modifications).

Immunization of 9 rhesus macaques showed a difference ($p=0.02$ KM log rank).

ALVAC-AE+bivalent (B/E) 4×'s—only 1/9 uninfected at the week 8 challenge

ALVAC-AE+pentavalent (B/E/E/E)—5/9 uninfected

ALVAC-AE+pentavalent (B/E/E/E)—5/9 uninfected

Four immunological parameters predicted decreased infection risk: (1) plasma Ab binding to HIV-infected cells; (2) peak ADCC antibody titers; (3) NK cell-mediated ADCC; and (4) Ab-mediated activation of MIP-1β in NK cells.

Design of ADCC/Structural Mosaics

Considers all structural contacts of every amino acid in the structure. Start with CD4-bound structures that expose Ab epitopes of antibodies thought to be involved in protective ADCC responses: C1 and V2.

Optimize for breadth in silico, for coverage of sequence and conformational epitope diversity.

Using a genetic algorithm, recombines natural proteins to maximize 3 dimensional potential epitope coverage:

No sequential regions in the sequence spanning 8 amino acids are not found in nature.

No spheres are not found in nature.

Solves to generate proteins that should be able to yield the best coverage of spheres in a population.

Sets are complementary. They are solved simultaneously or serially; In some embodiments, these sets are serial. The first members can be used alone, while the second member is complementary but in certain embodiments, is not to be used alone. See also Ex 2A.

The full database is used—M group is enriched for B, C and CRF01.

Animal studies to resolve the fewest Envs to include in an polyvalent Env boost regimen.

Three mosaic sets have members that are "B-like", "C-like" as "CRF01 like" as a consequence, but once a particular local variant is present, it doesn't need to be covered again New ADCC Designs Without being bound by theory, mRNAs can be just as good or better than proteins in inducing anti-Env Abs.

The new ADCC designs disclosed herein co-optimize vaccine coverage of CD4 bound gp120 including C1 and V2 epitopes. As the combination can result in ADCC synergy, and Abs against both targets would require breadth.

Structural mosaics were used as a foundation for this design, working from the new CD4-bound structure having PDB accession No. 5VN3, and considering just the gp120 monomer, the vaccine delivery form.

Designs under current development:

Previously designed V2 C Glade pentavalent, with or without CRF01 A244 "trigger"

B Clade optimized for Merlin Robb's testing:
  Bivalent: 2 structural mosaics, vs 2 best naturals for epitope coverage
  Bivalent: 2 structural mosaic above, but modified to capture V2 sensitivity signatures
  Pentavalent: 5 best natural B Clade, serial design
  Pentavlent: 4 best natural B Clade, with CRF01 A244 "trigger"
Global mosaics: 3 valent is included in both of the other two:
  3 valent: Best mosaics for B, C, and CRF01 (CRF01 mosaic can be a surrogate for A244)
  6 valent: Best 2 structural mosaics for B, C, and CRF01
  5 valent: Best mosaics for B, C, and CRF01 fixed, and add two more complementary mosaics for optimal M group coverage
Vaccine Strategies and SHIV Challenge Experiments
Challenge: one B Clade SHIV that represent transmitted variants: (a) Compare all vaccines, 7 groups—too many so small animal immunogenicity; (b) Immunogenicity vs protection: this would be staged—only challenge using vaccine that gives the best response.
take best B Clade option, and the best global options and test with three challenges, 2×3 groups, 6 total
C clade and CRF01 pentavlent: (a) 1 B clade SHIVs; (b) 1 CRF01; (c) 1 C clade Example 2: ADCC Vaccine Design glycosylation sites. There were not picked to be extremely short, just on the smaller side of natural variation, and that were not highly negatively charged.

4) Inventors made the paired sets (1+1) distinctive so we can have some diversity in these regions.

One of skill in the art understands that these designs are called "ADCC" because they were optimized with what is known about ADCC functionalities and good epitopes from RV144 in mind, the label is to distinguish them from the other T cell mosaics, and the trimer structure-based designed mosaic that were created using Joe Sodroski's s early model structure. This does not mean that these proteins are not useful for other immune responses. In non-limiting they can elicit good T cell responses, and can be useful for augmenting breadth of gp120 directed bNAbs.

Clade B

| | |
|---|---|
| Set 1: Synthesize 2: ADCC-StrMos.B.1 + 1.1 + ADCC-StrMos.B.1 + 1.2 Structural mosaics | 2 valent |
| Set 2: Synthesize 2: ADCC.StrNat.B.1 + ADCC.StrNat.B.2 2 Natural strains chosen serially to maximize coverage | 2 valent |
| Set 3: Synthesize 3: Set 2 + 3 more, Str.Nat.B3, Str.Nat.B4, Str.Nat.B5. pentavalent 5 Natural strains, 3 additional added serially to Set 2 to maximize coverage | 5 valent |
| Set 4: Str. Nat. B pentavalent (Set 3, but Str.Nat.B5 is replaced with A244 gp120) 4 Natural strains to present B clade variation with A244 to trigger responses | 5 valent |
| Set 5: Synthesize 2: | 2 valent |

| | Clade | Valency | B.tbl B-0off | B.tbl B-1off | C.tbl C-0off | C.tbl C-1off | 01.tbl 01-0off | 01.tbl 01-1off | others 0off | others 1off |
|---|---|---|---|---|---|---|---|---|---|---|
| Vaccine-2B.StrMos.1 + 1 | B | 2 | 0.5093 | 0.7735 | 0.3085 | 0.5603 | 0.2894 | 0.5318 | 0.3281 | 0.5801 |
| Vaccine-2C.StrMos.1 + 1 | C | 2 | 0.2868 | 0.5527 | 0.5157 | 0.7675 | 0.3061 | 0.5586 | 0.4249 | 0.6787 |
| Vaccine-2CRF01.StrMos.1 + 1 | CRF01 | 2 | 0.2512 | 0.5052 | 0.2795 | 0.5385 | 0.6088 | 0.8561 | 0.2823 | 0.5431 |
| Vaccine-MosB.C.CRF01.best1 | M | 3 | 0.4793 | 07587 | 0.4785 | 0.7523 | 0.5656 | 0.8292 | 0.4419 | 0.7195 |
| Vaccine-StrMosM.3 | M | 3 | 0.4904 | 0.7632 | 0.4854 | 0.7509 | 0.5644 | 0.8241 | 0.4523 | 0.7231 |
| Vaccine-StrMosM.5 | M | 5 | 0.5266 | 0.7901 | 0.5532 | 0.7977 | 0.5716 | 0.8280 | 0.5105 | 0.7583 |
| Vaccine-MosB.C.CRF01.best1 + 2 | M | 5 | 0.5300 | 0.7891 | 0.5463 | 0.7946 | 0.5877 | 0.8426 | 0.5126 | 0.7658 |
| Vaccine-StrNat.Bpenta | B | 5 | 0.5437 | 0.8051 | 0.3380 | 0.6104 | 0.3256 | 0.5877 | 0.3560 | 0.6240 |
| Vaccine-StrNat. B4 | B | 4 | 0.5212 | 0.7897 | 0.3246 | 0.5967 | 0.3013 | 0.5611 | 0.3390 | 0.6062 |
| Vaccine-StrNat. B3 | B | 3 | 0.4945 | 0.7658 | 0.3022 | 0.5727 | 0.2878 | 0.5327 | 0.3181 | 0.7645 |
| Vaccine-StrNat. B2 | B | 2 | 0.4567 | 0.7265 | 0.2865 | 0.5366 | 0.2587 | 0.5053 | 0.2991 | 0.7365 |
| Vaccine-StrNat. B1 | B | 1 | 0.3835 | 0.6614 | 0.2241 | 0.4716 | 0.1917 | 0.4322 | 0.2383 | 0.4907 |
| Vaccine-V2Nat.Cpenta | C | 5 | 0.2980 | 0.5873 | 0.S242 | 0.7835 | 0.3252 | 0.5987 | 0.4383 | 0.7045 |
| Vaccine-SouthAfrica | C | 3 | 0.2719 | 0.5490 | 0.4499 | 0.7223 | 0.2884 | 0.5512 | 0.3829 | 0.6531 |
| Vaccine-1B.4CRF01.penta | CRF01 + B | 5 | 0.9781 | 0.6816 | 0.3232 | 0.6104 | 0.6071 | 0.8605 | 0.3387 | 0.6284 |
| Vaccine-RV144 | CRF01 + B | 3 | 0.3817 | 0.5881 | 0.2777 | 0.5055 | 0.4699 | 0.7170 | 0.2850 | 0.5164 |
| Vaccine-Mos2B.2C.2CRF01.best1 + 1 | M | 6 | 0.5392 | 0.8016 | 0.5539 | 0.7992 | 0.6314 | 0.8708 | 0.5083 | 0.7665 |

The mosaic envelopes are designed using the same strategy to insert hypervariable regions designed to be used for the original structural mosaics, as those full Env proteins were highly biologically active, but not the same inserts. In that similar context they worked well. The same guiding principles for hypervariable loop characteristics make sense here. In brief:

1) Inventors restricted themselves to Clade matched acute infection Env sequences, as hypervariable loops tend to be selected to shorter at transmission.
2) Inventors characterized all hypervariable regions, looked for short repeated pattern in hypervariable regions that were repeated based on search strings of varying length. Repeated motifs of 5 or 6 amino acids or longer are infrequent, and favored natural hypervariable regions that carried repeated motifs.
3) Inventors picked hypervariable stretches that were of modest length, with only one or two potential N-linked Modified versions of Set 1 are also contemplated. Without wishing to be bound by theory, we can enhance induction of V2 targeting antibodies by including external signatures, such as those in, a strategy to try as an alternative to the addition of A244.

Global

| | |
|---|---|
| Vaccine-Mos 2B. 2C. 2CRF01 Best 1 + 1 (6 valent), To compare with Vaccine Str.Mos.M5 (5 valent). | |
| Set 6: Synthesize 4: 2 B + 2 C + 2 CRF01 structural mosaic | 6 valent |
| Set 1: ADCC-StrMos.B.1 + 1.1 + ADCC-StrMos.B.1 + 1.2 + Add: ADCC-StrMos.C.1 + 1.1 + ADCC-StrMos.C.1 + 1.2 + ADCC-StrMos.AE.1 + 1.1 + ADCC-StrMos.AE.1 + 1.2 | |
| Subset alternatives with these same set 6 proteins: | |
| 6A. 2 C or 2 CRF01 can be used as a stand-alone pair if desired analogous to Set 1, but optimized for other clades: [C.1 + 1.1 + C.1 + 1.2] or [AE.1 + 1.1 + AE.1 + 1.2] | 2 valent clade focused |
| 6B. A trivalent combination of the best three can also be | 3 valent |

-continued

```
tested:
[B.1 + 1.1 + C.1 + 1.1 + AE.1 + 1]
Set 7: Synthesize 2: 5 valent: The best of the 3 clades, [B.1 +
1.1 + C.1+ 1.1 + AE.1 + 1] Set as fixed input, then solve the
two best complements to these to fill out M group coverage.
```

In some embodiments, we can compare Set 6 (the 3 best pairs for B, C, and CRF01, hexavalent), versus Set 6B (the single best for B, C and CRF01, trivalent), versus set 6B plus the two best M group complements to Set 6B, pentavalent).

Example 2A: Sequence of ADCC Vaccine Designs

Set 1:
B.ADCC-StrMos.1+1, coverage: 0.509261
Note These are serial, 1+1.1 is the best single gp120 for the B Glade and can be used alone, and 1+1.2 is its best complement, both designed to maximize coverage while maintaining "real" and common structural spheres throughout the monomer.

Set 2 and Set 3: 2 or 5 valent B Glade structural mosaics:

B naturals, picked serially to be optimal using the structural mosaic code, to be used in series and combination. Either the first 2 can be used as bivalent pair, or all 5 as pentavalent, or the first 4 coupled with the CRF01 A244 as a pentavalent.

For the natural proteins, optimization was not done on the hypervariable loops, which are noted in red, and only gp120 was considered, gp41 is in blue. The red is needed for a full protein (pointing out that inventors did not use the hypervariable stretches in the optimization). In the black section, where no structure is available, inventors optimized across linear peptides.

```
ADCC-StrMos.B.1+1.1 (SEQ ID NO: 135)
MRVKGIRKNYQHLWRWGTMLLGMLMICSAAEQLWVTVYYGVPVWKEATTTLFCASDAKAYDTEVHNVWATHACVPT

DPNPQEVVLENVTENFNMWKNNMVEQMHEDIISLWDQSLKPCVKLTPLCVTLNCTDVSSNSTSVNITSEKGEIKN

CSFNITTSIRDKVQKEYALFYKLDVVPIEDDSKNNSYRLISCNTSVITQACPKVSFEPIPIHYCAPAGFAILKCND

KKFNGTGOCTNVSTVQCTHGIRPVVSTQLLLNGSLAEEEVVIRSENFTNNAKTIIVQLNESVEINCTRPNNNTRKS

IHIGPGRAFYATGDIIGDIRQAHCNISREKWNNTLKQIVKKLREQFGNKTIVFNQSSGGDPEIVMHSFNCGGEFFY

CNTTQLFNSTWSINGTWNGTTESNDTITLPCRIKQIINMWQEVGKAMYAPPIRGQIRCSSNITGLLLTRDGCNSSS

NNETFRPGGGDMRDNWRSELYKYKVVKIEPLGVAPTKAKRRWQREKRV

V1 B acute Con SC31  TDVSSNSTSVNITSE  (SEQ ID NO: 136)

V2 B acute Con 9077  EDDSKNNS  (SEQ ID NO: 137)

V4 B acute Con TT31P SINGTWNGTTES  (SEQ ID NO: 138)

V5 B acute Con 6247  NSSSNN  (SEQ ID NO: 139)

ADCC-StrMos.B.1+1.2 (SEQ ID NO: 140)
MKVKGIRKNCQHLWRWGIMLLGMLMICSATEKLWVTVYYGVPVWKEATTTLFCASDAKAYDTEAHNVWATHACVPT

DPNPQEIVLENVTENFNMWKNDMVEQMHEDIISLWDESLKPCVELTPLCVTLNCTNVNATNTNNSSGIEGGEMKNC

SFNVTTSIRDKMQKEYALFYSLDVVQIDNDTNYRLINCNTSVITQACPKISFEPIPIHYCTPAGFAIKCNDKKFN

GSGPCKNVSTVQCTHGIKPVVSTQLLLNGSLAEEEIVIRSENFSDNAKTIIVQLNESVVINCTRPNNNTRKSISIG

PGRAFYATGDIIGNIRQAHCNLSRAEWNNTLRQIVTKLREQFKNKTIAFNHSSGGDPEIVMHTFNCGGEFFYCNST

QLFNSTWIANKTGNDTGGSNGTITLQCRIKQIVNRWQEVGKAMYAPPISGQISCSSNITGLILTRDGGINNTNGTE

IFRPGGGNMKDNWRSELYKYKVVRIEPLGIAPTKARRRVVQREKRI
Which has coverage: 0.509261

V1 B acute Con 63215  TNVNATNTNNSSGIE  (SEQ ID NO: 141)

V2 B acute Con Z85    DNDTN  (SEQ ID NO: 142)

V4 B acute Con 61792  IANKTGNDTGGS  (SEQ ID NO: 143)

V5 B acute Con SC20   INNTNGT  (SEQ ID NO: 144)
```

ADCC-StrNat.B1--B.US.85.WCIPR.U69584 (SEQ ID NO: 185)
MKAKETRKNYQHLWRWGITLLGMLMICSAAEQLWVTVYYGVPVWKEATTTLFCASDAKAYDTEVHNVWATHAC

VPTDPNPQEVVLENVTENFNMWKNNMVEQMHEDIISLWDQSLKPCVKLTPLCVTLNCTDDLKNATVKNATNTN

NSSWGGMERGEIKNCSFNITTSIRDKVQKEYALFYKLDVVPIDNADNNHTTNYTSYRLISCNTSVITQACPK

VSFEPIPIHYCAPAGFAILKCNDKKFNGTGPCTNVSTVQCTHGIRPVVSTQLLLNGSLAEKEVVIRSENFTNN

AKTIIVQLDESVVINCTRPNNNTRKSIHIGPGRAFYTTGEIIGDIRQAHCTLNRTEWNNTLAKITEKLREQFG

NNITIVFNHSSGGDPEIVMHSFICGGEFFYCNTSQLFNSTWNSTWNSTGNNISESDNTERNITLPCRIKQIINLWQE

VGKAMYAPPIRGQIRCSSNITGLLLTRDGGSNTDENRTEIFRPGGGDMRDNWRSELYKYKVVKIEPLGVAPTK

AKRRVVQREKRAVGTIGAMFLGFLGAAGSTMGAASMTLTVQARLLLSGIVQQQNNLLRAIEAQQHLLQLTVWG

IKQLQARVLAVERYLKDQQLLGIWGCSGKLICTTAVPWNASWSNKSLDEIWDNMTWMEWEREIDNYTNLIYTL

IEEYRNQQEKNEQALLELDKWASLWNWFNITNWLWYIKIFIMIVGGLVGLRIVFTVLSIVNRVRKGYSPLSFQ

TRLPTPRGPDRPEGIEEEGGERDRDRSGLLVDGFLALIWVDLRSLCLFSYHRLRDLLLIVARIVELLGRRGWE

VLKYWWNLLQYWSQELKNSAVSLLNATAIAVAEGTDRVIEVLQRACRAILHIPTRIRQGLERALL

ADCC-StrNat.B2--B.TT.93.QH0065_M.AF277060 (SEQ ID NO: 186)
MRVKETRRIWQHLWKWGTMLLGMLMIYSAAENLWVTVYYGVPVWKEATTTLFCASDAKAYDTEVHNVWATHAC

VPTDPNPQEVVLGNVTENFNMWKNNMVEQMHEDVISLWDQSLKPCVKLTPLCVTLNCTDVLGKGTSANATSAN

VTSEKGEIKNCSFNITTTLRDKVQKAHALFYRLDVVPIDENKDNESSGYRLINCNTSVITQACPKVSFEPIPI

HFCTPAGFALLKCNNKKFNGTGPCTNVSTVQCTHGIKPVVSTQLLLNGSLAEEEVVIRSENFTDNAKTIIVQL

NDSVVINCTRPNNNTRKGITIGPGSVFYTGEIIGDIRQAHCNLSSAKWNNTLKQIVIKLREQFGNKTIVFNQS

SGGDPEIVLHSFNCGGEFFYCNTTQLFNSTWNINDTRNGTTESSKTITLPCRIKQIINMWQEVGKAMYAPPIR

GQIRCSSNITGLLLTRDGGNQNTSGTEIFRPGGGNMRDNWRSELYKYKVVKIEPLGIAPTKAKRRVVQREKRA

VGTIGAMFLGFLGAAGSTMGAASITLTVQARLLLSGIVQQQNNLMRAIEAQQHMLQLTVWGIKQLQARVLAVE

RYLRDQQLLGIWGCSGKLICTTTVPWNASWSNKSVDYIWDNMTWMQWDREINNYTNYIYTLLEDAQNQQEKNE

QELLELDKWASLWNWFDITKWLWYIKIFIMIVGGLIGLRIVFAVLSIVNRVKQGYSPLSFQTHLPARREPDRP

EGIEGEGGEKDKDRSIRLVHGLLALIWDDLRSLCLFSYHHLRDLLLIVTRIVETLGRRGWEALKYWWNLLQYW

SQELKNSAVSLFDAIAIAVAEGTDRVIEWRRIFRAVLHIPTRIRQGLERALL

ADCC-StrNat.B3--B.CN.12.2039_2_13.KX693556 (SEQ ID NO: 187)
MRVKGIRKNCQHLWRWGTMLLGMLMICSAAENLWVTVYYGVPVWKEATTTLFCASDAKAYDTEAHNVWATHACVPT

DPNPQEVVLGNVTENFNMWKNDMVEQMHEDIISLWDQSLKPCVKLTPICVALNCTDVKDTNNTSKNTERNTSSNSS

NTEGGEMKNCSFNITTSIKTKVKDYALFYKLDIVPIDNDGDNTSYRLISCNTSVITQACPKISFEPIPIHYCTPAG

YALLKCNNKKFNGTGPCKNVSTVQCTHGIRPVVSTQLLLNGSLAEEEVVIRSSNFTNNAKVIIVQLKEAVEINCTR

PNNNTRKSIHIGPGKAWYTTGEIIGNIRQAHCNISRTKWNNTLHQIVKKLRIQFGNKTIIFNQSAGGDPEIVVHSF

NCGGEFFYCNTSQLFNSTWRNDTWNLTSEQIATTCNDTITLPCRIRQIVNMWQQVGKAMYAPPIAGQIRCSSNITG

VLLTRDGNNESKANANETFRPAGGDMRDNWRSELYKYKVVKIEPLGVAPTKAKRRVVQREKRAVGTLGAMFLGFL

GAAGSTMGAASITLTVQARQLLSGIVQQQRNLLRAIEAQQHLLQLTVWGIKQLQARVLAVERYLQDQQLLGIWGCS

GKLICTTTVPWNVSWSNKSLGEIWDNMTWMEWEREISNYTGQIYTLIEQSQNQQEKNELELLELDKWASLWNWFDI

SNWLWYIKIFIMIVGGLVGLRIIFAVLSIVNRVRQGYSPLSQTRFPAQRGPGRPEGIEEEGGEQDRDRSERLVNG

FLTLFWVDLRSLCLFSYHSLRDLLLIVARIVELLGRRGWEALKYLWNLLQYWIQELKNSAVSLLNATAIAVAEGTD

RIIELAQRAFAFLNIPTRIRQGLERALL

ADCC-StrNat.B4--B.US.05.1444_A22.HQ216584 (SEQ ID NO: 188)
MKVKGIRKNYQHLWRWGMMLLGMLMICSATEKLWVTVYYGVPVWRDATTTLFCASDAKAYETELHNVWATHACVPT

DPNPQEVVLGNVTENFNMWKNDMVEQMNEDIISLWDESLKPCVKLTPLCVTLNC TNYNETTTNGTTTNATVVS PGE

IKNCSFNVTTGIRDKVRKDHALFYALDIVPI DNTIDNTS YRLVSCNTSVLTQACPKVFEPIPIHFCAPAGYAIIK

CNNKTFNGSGPCRNVSTVQCTHGIRPVVSTQLLLNGSLAEEEIVIRSANFSDNTKTIIVQLNEAVKINCTRPNNNT

RRSVHMGPGSAFYTTGGIIGDIRQAHCNISERDWNGALKQIVEKLGEQFQNKTIVFKQSSGGDPEWMHTFNCRGE

FFYCNTTKLFNSTW VNGTKNDTKGG NGTITLQCRIKQIINMWQQVGKAMYAPPISGPISCSSNITGLILTRDGC IN

TTN ETFRPGGGDMRDNWRSELYKYKVVKIEPIGVAPTKARRRVVQREKRA VGIGAFFLGFLGAAGSTMGAASITLT

VQARLLLSGIVQQQSNLLRAIEAQQHLLQLTVWGIKQLQARVLAVESYLRDQQLLGIWGCPGKLICTTNVPWNNSW

SKNKSYNQIWDNMTWMEWEREINNYTDYIYSLIEISQRQQEKNEQELLELDKWANLWTWFDITNWLWYIKIFIMIV

GGLIGLRIVFSVLSIVNRVRQGYSPLSFQTRLPTQRGPDRPEEIEEEGGERDRDRSSGLADGFLTLIWVDLRSLCL

FSYHRLRDLLLIVTRIVELLGRRGWEALKYWWNLLQYWSQELKSSAISLLNTIAIWAEGTDRIIEVAQRACGAIL

HIPRRIRQGFERILV

ADCC-StrNat.B5--B.BR.10.10BR_SP062.KT427799 (SEQ ID NO: 189)
MRAKETRKKYQHLWAWGTLLLGMLMICSATEQLWVTVYYGVPVWKDANTTLFCASDAKAYDTEVHNVWATHACVPT

DPSPQEIVLKNVTENFNMWKNNMVEQMHKDIISLWDESLKPCVKLTPLCVTLNC SNYNSTNSTIDPNM EGAIKNCS

FNATTGIQNKMKKEYALFYSLDIVQI ESENESNKT YMLRSCNTSVITQACPKVTFEPIPIHYCAPAGFAILKCNDK

KFNGTGPCKNVSTVQCTHGIRPVVSTQLLLNGSLAEEEIIIRSENITNNAKTIIQLNRSIEINCTRPNNNTRKSI

HMGWGRAFYATGDIIGDIRQAHCNLSGTKWNNTLYQIARKLREHFNNTIVFNQSSGGDPEIVMHTFNCGGEFFYCN

TTQLFNSTW KANSTWNETTGSGS NDTISLPCRIKQIINRWQEVGKAMYAPPIGGQIRCSSNITGILLTRDGC TENN

TS ETFRPGGGNMKDNWRSELYKYKVVRIEPLGVAPTKAKRRVVQREKRA VTFGAFFLGFLGTAGSTMGAASITLTV

QARQLLSGIVQQQSNLLRAIEAQQRMLQLTVWGIKQLQARVLAVERYLKDQQLLGIWGCSGRLICTTAVPWNASWS

NKSLNEIWDNMTWMQWEREIDNYTNLIYTLIEESQYQQEKNEQELLELDKWASLWSWFNITNWL#VGGLVGLRIIF

AVLSIVKRVGQGYSPLSFQIRPPARRGPDRPEGIDEEGGERDRDRSNRLVDGFLALIWDDLRSLCLFSYHRLRDLL

SILTRIVELLGRRGWEALRYCWNLLKYWNQELKNGAVGLLGATAIAVAGGTDGIIEAVRGLCGAILNIPGRIRQGL

ERALL

Set 5:

Modified versions of Set 1, without wishing to be bound by theory, we can enhance induction of V2 targeting antibodies by including external signatures, such as those in, a strategy to try as an alternative to the addition of A244. These can be compared to Set 1 to see if they alter the antigenicity, and sensitivity to V2 antibodies like CH58 and CH59 first.

ADCC-StrMos-Modified.B.1+1.1 *Y61N E102E H105Q I108V I161V R166K K168K A219T K337K* (SEQ ID NO: 190)
MRVKGIRKNYQHLWRWGTMLLGMLMICSAAEQLWVTVYYGVPVWKEATTTLFCASDAKAN DTEVHNVWATHACVPT

DPNPQEVVLENVTENFNMWKNNMVEQMN EL ISLWDQSLKPCVKLTPLCVTLNC TDVSSNSTSVNITSE KGEIKN

CSFNVTTSI DKVQKEYALFYKLDVVPI EDDSRNNS YRLISCNTSVITQACPKVSFEPIPIHYC PAGFAILKCND

KKFNGTGPCTNVSTVQCTHGIRPVVSTQLLLNGSLAEEEVVIRSENFTNNAKTIIVQLNESVEINCTRPNNNTRKS

IHIGPGRAFYATGDIIGDIRQAHCNISREKWNNTLKQIVKKLREQFGNKTIVFNQSSGGDPEIVMHSFNCGGEFFY

CNTTQLFNSTW SINGTWNGTTES NDTITLPCRIKQIINMWQEVGKAMYAPPIRGQIRCSSNITGLLLTRDGC NESS

NN ETFRPGGGDMRDNWRSELYKYKWKIEPLGVAPTKAKRRWQREKRV

ADCC-StrMos-Modified.B.1+1.2 changes: *Y61N E102E H105Q I108V V161V R166K K168K T219T E337K* (SEQ ID NO: 191)
MKVKGIRKNCQHLWRWGIMLLGMLMICSATEKLWVTVYYGVPVWKEATTTLFCASDAKAoDTEAHNVWATHACVPT

DPNPQEIVLENVTENFNMWKNDMVEQMN EL ISLWDESLKPCVELTPLCVTLNC TNVNATNTNNSSGIE GGEMKNC

SFNVTTSI DKMQKEYALFYSLDWQI DNDTN YRLINCNTSVITQACPKISFEPIPIHYCTPAGFAIIKCNDKKFN

-continued

```
GSGPCKNVSTVQCTHGIKPVVSTQLLLNGSLAEEEIVIRSENFSDNAKTIIVQLNESVVINCTRPNNNTRKSISIG

PGRAFYATGDIIGNIRQAHCNLSRAKWNNTLRQIVTKLREQFKNKTIAFNHSSGGDPEIVMHTFNCGGEFFYCNST

QLFNSTWIANKTGNDTGGSNGTITLQCRIKQIVNRWQEVGKAMYAPPISGQISCSSNITGLILTRDGCTNNTNGTE

IFRPGGGNMKDNWRSELYKYKVVRIEPLGIAPTKARRRVVQREKRI

Set 6:
ADCC-StrMos.C.1+1.1 + ADCC-StrMos.C.1+1.2
ADCC.StrMos.C.1+1.1 (SEQ ID NO: 192)
MRV-
RGILRNYQQWWIWGILGFWMLMICNVVGNLWVTVYYGVPVWKEAKTTLFCASDAKAYEKEVHNVWATHACVPT

DPNPQEMVLENVTENFNMWKNDMVDQMHEDIISLWDQSLKPCVKLTPLCVTLNCVNITNSTTSNGDGTVTHIN

SIKEEIKNCSFNATTELRDKKSKEYALFYRLDIVPLSSGNSSSNSSKYRLINCNTSTITQACPKVSFDPIPIH

YCAPAGYAILKCNNKTFNGTGPCNNVSTVQCTHGIKPVVSTQLLLNGSLAEEEIIIRSENLTDNVKTIIVHLN

ESVEIVCTRPNNNTRKSIRIGPGQTFYATGDIIGDIRQAHCNISKGAWNETLQWVGKKLKEHFPNKTIKFNSS

SGGDLEITTHSFNCRGEFFYCNTSGLFNSTYRNNSTGLNSTITLPCRIKQIINMWQEVGRAMYAPPIAGNITC

KSNITGLLLTRDGCTRDKNDTETFRPGGGDMRDNWRSELYKYKVVEIKPLGIAPTKAKRRVVEREKRV

V1 C ZA NA N Y Y NA 705010198acute VNITNSTTSNGDGTVTHINSI (SEQ ID NO: 193)

V2 C acute Con 703010054 SSGNSSSNSSK (SEQ ID NO: 194)

V4 C ZA JN681249 N Y Y 3 So706 T10b 3acute RNNSTGL (SEQ ID NO: 195)

V5 C acute Con 703010193 TRDRNDT (SEQ ID NO: 196)

ADCC.StrMos.C.1+1.2 (SEQ ID NO: 197)
MRVMGIQRNWPQWWIWGILGFWMIICRVVGNLWVTVYYGVPVWREAKTTLFCASDAKAYEREVHNVWATHAC

VPTDPNPQELVLENVTENFNMWENDMVDQMHEDVISLWDQSLKPCVKLTPLCVTLKCTNTTYYNVSSKEFTNG

EIKNCSFNTTTELRDKKQKVSALFYRLDVVPLSKKDKTNNDSGEYILINCNTSAITQACPKVSFDPIPIHYCT

PAGYAILKCNNKTFNGTGPCHNVSTVQCTHGIKPVVSTQLLLNGSLTEGEIIIRSENLTNNAKTIIVHLNQSV

AIVCTRPGNNTRKSVRIGPGQAFYATGEIIGDIRQAYCNLTNWQETLKNVSKKLQERFNKTIRFAPSSGGDLE

ITTHSFNCGGEFFYCNTSSLFNSAYNPNGTKDNSSSITIQCKIKQIINMWQGVGRAIYAPPIAGNITCNSNI

TGILLTRDGCSKNNTESKNNTEEIFRPGGGNMKDNWRSELYRYKVVEIKPLGVAPTEAKRRVVEREKRA

V1 C acute Con CAP177 TNTTYYNVSSKE (SEQ ID NO: 198)

V2 C acute Con 703010010 SKKDKTNNDSGE (SEQ ID NO: 199)

V4 C acute Con 703010200 NPNGTKDNS (SEQ ID NO: 200)

V5 C ZM EU166866 Y Y Y 2 249Macute SKNNTE (SEQ ID NO: 201)

ADCC-StrMos.AE.1+1.1 + ADCC-StrMos.AE.1+1.2
ADCC.StrMos.AE.1+1.1 (SEQ ID NO: 202)
MRVKETQMNWPNLWKWGTLILGLVIICSASDNLWVTVYYGVPVWRDADTTLFCASDAKAHETEVHNVWATHAC

VPTDPNPQEIHLENVTENFNMWKNNMVEQMQEDVISLWDQSLKPCVKLTPLCVTLNCTKANLNINENTTASNG

IGNIIGNITDEVRNCSFNMTTELRDKKQKVHALFYKLDIVPISNESKAGNVSSEYRLINCNTSVIKQACPKISFDPI

PIHYCTPAGYAILKCNDKNFNGTGPCKNVSSVQCTHGIKPVVSTQLLLNGSLAEEEIIIRSENLTNNAKTIIV

HLNKSVEINCTRPSNNTRTSITIGPGQVFYRTGDIIGDIRKAYCEINGTKWNETLKQVAGKLKEHFNKTIIFQ
```

PPSGGDLEITMHHFNCRGEFFYCNTTKLFNSTW<u>NGTMEGR</u>NGTIILPCRIKQIINMWQGVGQAMYAPPISGII

NCVSNITGILLTRDGGM<u>NNNATN</u>ETFRPGGGNIKDNWRSELYKYKVVQIEPLGIAPTRAKRRVVEREKRV

V1 01 AE CN HM215386 Y Y NA BJOX025000 01 1acute <u>TKANLTNINETTASNGIGNI</u>
(SEQ ID NO: 203)

V2 01 AE TH NA N Y Y 2 254008P00Re 1acute <u>RNESKMGNVSSE</u>(SEQ ID NO: 204)

V4 01 AE CN NA N Y Y NA BJMSM2249 13 21 2acute <u>NGTMEGR</u>(SEQ ID NO: 205)

V5 01 AE CN HM215394 N Y Y NA BJOX031000 02 2acute <u>NNNATN</u>(SEQ ID NO: 206)

ADCC.StrMos.AE.1+1.2 (SEQ ID NO: 207)
MRVKGTQMNWPNLWRWGTLILGLVIMCSASDNLWVTVYYGVPVWKDADTTLFCASDAKAHETEVHNIWATHAC

VPTDPNPQEIPLENVTENFNMWKNNMAEQMQEDVISLWDESLKPCVKLTPLCVTLHC<u>TKANLTENTTNDKNGT</u>

<u>GNITDEVKIGNI</u>TDEVKNCSFNMTTEIRDKKQKVYALFYKLDIVQI<u>GENGSE</u>YRLINCNTSVIKQACPKVSFD

PIPIHYCAPAGYALLKCNDKKFNGTGPCRNVSSVQCTHGIKPVVSTQLLLNGSLAEEEIIRSENLTDNAKTI

IVHLNESVVINCTRPSNNVRISTRIGPGQVFYRTGEIIGDIRKAYCEINGTKWNKVLKEVTEKLKEHFNKTIIFQP

PSGGDLEITTHHFNCRGEFFYCNTTKLFNNTC<u>NGTMEGE</u>CNNITLPCKIKQIINMWQGAGQAIYAPPISGSIKCVS

NITGIILTRDGG<u>NDTGTS</u>EIFRPGGGNMKDNWRNELYKYKVVQIEPLGVAPTKAKRRVVDREKRV

V1 01 AE CN HM215379 N Y Y NA BJOX018000 02 3

<u>TKANLTENTTNDKNGTGNITDEVKIGNI</u>(SEQ ID NO: 208)

V2 01 AE CN NA N Y Y NA BJMSM2249 13 21 2acute <u>GENGSE</u>(SEQ ID NO: 209)

V4 01 AE CN HM215394 N Y Y NA BJOX031000 02 2acute <u>NGTMEGE</u>(SEQ ID NO: 210)

V5 01 AE CN HM215390 N Y Y NA BJOX028000 34 2acute <u>NDTGTS</u>(SEQ ID NO: 211)

Set 7

Includes two complements to ADCC-StrMos.B.1+1.1 from Set 1 described herein, ADCC.StrMos.C.1+1.1 from Set 6 described herein, and ADCC.StrMos.AE.1+1.1 from Set 6 described herein. To these, add ADCC-StrMos.M.3+2.4 and ADCC-StrMos.M.3+2.5 to give an M group pentavalent.

ADCC-StrMos.M.3+2.4 (SEQ ID NO: 36)
MRVMGIQRNCQHLWRWGIMLLGMLMICNATDKLWVTVYYGVPVWRDAETTLFCASDAKGYDTEAHNVWATHAC

VPTDPSPQEIHLENVTEEFNMWKNNMVEQMHTDIISLWDQSLKPCVKLTPLCVTLDC<u>TLDCNNVTNNGTSDM</u>R

EEIKNCSFNITTELRDKKKKVYSLFYKLDIVPI<u>NGDNSTNI</u>YMLINCNTSAITQACPKVTFEPIPIHFCAPAG

YAILKCKDKEFNGTGPCKNVSTVQCTHGIKPVVSTQLLLNGSLAEEEIMIRSENITNNAKIIIVQLNQSVVIN

CTRPGNNTRKSVRIGPGQTFYATGDIIGDIRQAHCNVSRIKWNTALQKVAKQLRKYFRNKTITFNQSSGGDPE

ITTHTFNCGGEFFYCNTSNLFNSTW<u>GKGNGTDNMQGSN</u>STNITLQCRIKQIINMWQEVGRAIYAPPIEGNISC

SSNITGLLLTRDGGN<u>NGKNSTTE</u>EIFRPGGGNMRDNWRSELYKYKVVKIEPIGVAPTKARRRVVEREKRI

ADCC-StrMos.M.3+2.4 is mostly subtype A1 with a little bit of D.

V1 A1.KE.94.Q842 d16.AF407162 <u>TLDCNNVTNNGTSDM</u>(SEQ ID NO: 212)

V2 A1.CM.08.886 24.KP718928 <u>HGDNSTNT</u>(SEQ ID NO: 213)

V4 CD.KE.x.BK184 W6M ENV D2.DQ208491 <u>GNGNGTDNMQGSN</u>(SEQ ID NO: 214)

```
V5 A1.KE.06.06KECst 005.FJ623481 NSKNSTTS (SEQ ID NO: 215)

ADCC-StrMos.M.3+2.5 (SEQ ID NO: 37)
MKVKGIQRNWPQWWIWGILGFWMLMICNVGGNLWVTVYYGVPVWREANTTLFCASDAKAYDTEVHNIWATHAC

VPTDPNPQEIVLGNVTENFNMWKNNMVDQMHEDVISLWDESLKPCVKLTPLCVTLEC NDAKLNSTKTNSTTNS

TDPNNSNLSI EGEIKNCSFNTTTEIRDKKKRAYALFYRPDVVPL NENSSS YILINCNSSTITQACPKVSFEPI

PIHYCTPAGFALLKCNNKTFNGSGPCTNVSTVQCTHGIRPVVSTQLLLNGSLAEEEIVIRSENFTDNAKTIIV

QLNESVEINCTRPNNNTRKSIRIGPGQAFYATGEIIGNIRQAYCNINESLWNETLYKVSEKLKEYFNTTIEFQ

QPAGGDLEITTHSFNCRGEFFYCNTTKLFNGTY SQFNSTGNTP HSNITLPCKIKQIINMWQGVGRAMYAPPIA

GNITCISNITGLILTRDGC DKNGSKP EIFRPGGGNMKDNWRSELYKYKVVEIKPLGLAPTEAKRRVVEREKRA

ADCC-StrMos.M.3+2.5 is a subtype B/C recombinant.

V1 B.BR.03.03BR1020.JN692445 NDAKLNSTKTNSTTNS (SEQ ID NO: 216)

V2 C.ZA.98.DU123 6.DQ411850 NENSSS (SEQ ID NO: 217)

V4 C.BW.98.98BWMC134.AF443077 SQFNSTGNTP (SEQ ID NO: 218)

V5 C acute Con 089 DKNGSKP (SEQ ID NO: 219)
```

Example 3: Animal Studies

Table 1 shows several different sets of immunogens based on different designs and combinations of envelopes. The immunological properties of these sets will be tested in various animal studies including mouse models, guinea pigs, non-human primates, or any other suitable model. These animal studies will be designed to test overall immune response, type of antibodies induced, durability of the induced immune response, and can include challenge with SIV or SHIV virus of a desired HIV-1 Glade to determine whether the immune response provides protection.

In non-limiting embodiments, the parameters analyzed in these studies are as described in Bradley et al (2017). In a non-limiting example, four immunological parameters predicted decreased infection risk: plasma Ab binding to HIV-infected cells; peak ADCC antibody titers; NK cell-mediated ADCC; Ab-mediated activation of MIP-1β in NK cells.

Any other suitable assay or correlates can be used to analyze the immune responses induced by the different sets of immunogens and the determine if the sets induce protective responses to SIV and SHIV challenge. Non-limiting examples correlates which can be analyzed include without limitation: antibody responses to C1C2 epitopes of the HIV-1 envelope, antibodies responses to V2 epitopes, antibody responses to V3 epitopes, alpha4 beta7 binding, ADCC activity, binding responses to virus infected cells (can also be used as proxy for ADCC activity), etc. Without limitation, antibody responses analyses include analyses for neutralizing and non-neutralizing antibodies, magnitude, durability, types, etc. of the induced antibody responses. Analyses can be done on any suitable sample, including without limitation plasma, serum, blood, urine, mucosal samples, etc.

Animal studies will be followed up by human clinical trials.

Example 4: Comparison of Combinations of ADCC Structural Mosaic Envs with Natural Envs for Induction of Env Binding Antibodies—Guinea Pig Studies This example described a guinea pig study testing the following immunogens in Groups 502-506 (See also FIGS. 18, 19-35). All groups were adjuvanated with Rehydragel (MHRP autoclaved @ 5 mg/ml). Every individual protein was administered at a 100 ug dose at three week intervals. Postbleeds were collected two weeks after each immunization.

GP502: Immunization #1-5 with Immunogen:
ADCC-StrMos.B.1+1.1Δ11gp120/293F/Mon (100 ug), and
ADCC-StrMos.B.1+1.2Δ11gp120/293F/Mon (100 ug)

GP503: Immunization #1-5 with Immunogen:
ADCC-StrNat.B1Δ11gp120/293F/Mon (100 ug), and
ADCC-StrNat.B5Δ11gp120/293F/Mon (100 ug)

GP504: Immunization #1-5 with Immunogen:
ADCC-StrNat.B1Δ11 gp120/293F/Mon (100 ug)
ADCC-StrNat.B2Δ11gp120_CD5ss/293F/Mon (100 ug)
ADCC-StrNat.B3Δ11gp120/293F/Mon (100 ug)
ADCC-StrNat.B4Δ11gp120/293F/Mon (100 ug)
ADCC-StrNat.B5Δ11gp120/293F/Mon (100 ug).

GP505: Immunization #1-5 with Immunogen:
ADCC-StrMos.M.3+2.4/293F/Mon (100 ug)
ADCC-StrMos.M.3+2.5_TPAss/293F/Mon (100 ug).

GP506: Immunization #1-5 with Immunogen:
ADCC-StrMos.B.1+1.1Δ11gp120/293F/Mon (100 ug)
ADCC.StrMos.C.1+1.1Δ11gp120_TPAss/293F/Mon (100 ug)
ADCC.StrMos.AE.1+1.1Δ11gp120/293F/Mon (100 ug).

Preliminary data from this study, Figures XX-XX, show that in some embodiments, bivalent Glade B str. ADCC mosaics (Group 502) are better than Group 503, and not performing worse than other groups in binding or blocking assays; in some embodiments bivalent M str. Mos Group 505 are better or not performing worse than Group 506 (trivalent A, B, AE mos).

Additional neutralization assays testing neutralization of other viruses is in process.

Specificity of sera is epitope mapped by linear peptide arrays—experiments are in progress.

Comparison of immunogenicity of new Glade B ADCC bivalent mosaic group 1/group 502 with original "pentavalent Envs" of Bradley et al Nature Comm. 8: 15711, 2017 will be conducted.

Additional studies will include ADCP, binding to surface of virus infected cells.

EQUIVALENTS

Those skilled in the art will recognize, or be able to ascertain, using no more than routine experimentation, numerous equivalents to the specific substances and procedures described herein. Such equivalents are considered to be within the scope of this invention, and are covered by the following claims.

What is claimed:

1. An immunogenic composition comprising a recombinant polypeptide ADCC-StrMos.B.1+1.1.DELTA.11gp120 (SEQ ID NO: 12), or a nucleic acid encoding said recombinant polypeptide.

2. The immunogenic composition of claim 1 wherein the composition further comprises a recombinant polypeptide ADCC-StrMos.B.1+1.2.DELTA.11gp120 (SEQ ID NO: 13), or a nucleic acid encoding said recombinant polypeptide.

3. The immunogenic composition of any one of claims 1 or 2 wherein the nucleic acid is a modified mRNA.

4. The immunogenic composition of claim 3 wherein the nucleic acid is operably linked to a promoter.

5. The immunogenic composition of any one of claims 1 or 2 further comprising an adjuvant.

6. The immunogenic composition of any one of claims 1 or 2 further comprising a carrier.

7. A method of inducing an immune response in a subject comprising administering to the subject an amount of the composition of any one of claims 1 or 2 in an amount sufficient to effect such induction.

8. The method of claim 7 further comprising administering an adjuvant.

9. The method of claim 7, wherein the composition is administered as a prime.

10. The method of claim 7, wherein the composition is administered as a boost.

11. A recombinant envelope ADCC-StrMos.B.1+1.1.DELTA.11gp120 (SEQ ID NO: 12) or a nucleic acid encoding the same.

12. A composition comprising the recombinant envelope of claim 11 and a carrier.

13. A nucleic acid encoding the recombinant envelope of claim 11.

14. A composition comprising the nucleic acid of claim 13 and a carrier.

15. A method of inducing an immune response in a subject comprising administering to the subject an amount of the composition of any one of claim 12 or 14 in an amount sufficient to effect such induction.

* * * * *